US012643879B2

(12) United States Patent
Zawadzka et al.

(10) Patent No.: US 12,643,879 B2

(45) Date of Patent: Jun. 2, 2026

(54) FUNCTIONALIZED HETEROCYCLIC COMPOUNDS AS MODULATORS OF STIMULATOR OF INTERFERON GENES (STING)

(71) Applicant: RYVU THERAPEUTICS S.A., Cracow (PL)

(72) Inventors: Magdalena Izabela Zawadzka, Gdansk (PL); Luigi Piero Stasi, Monza (IT); Maciej Krzysztof Rogacki, Cracow (PL); Grzegorz Wojciech Cwiertnia, Kamesznica (PL); Lukasz Piotr Dudek, Wieliczka (PL); Agnieszka Justyna Gibas, Cracow (PL); Anna Rajda, Wroclaw (PL); Charles-Henry Fabritius, Poznan (PL); Adam Radzimierski, Cracow (PL); Tushar Ravindra Mahajan, Cracow (PL); Marcin Wojciech Les, Mielec (PL); Karol Zuchowicz, Gnojnik (PL); Marek Wronowski, Debowa Góra (PL); David Jörg Synak, Cracow (PL); Sundara Raghuram Tangirala, Cracow (PL)

(73) Assignee: Ryvu Therapeutics S.A., Cracow (PL)

( * ) Notice: Subject to any disclaimer, the term of this patent is extended or adjusted under 35 U.S.C. 154(b) by 744 days.

(21) Appl. No.: 17/783,940

(22) PCT Filed: Dec. 11, 2020

(86) PCT No.: PCT/EP2020/085833

§ 371 (c)(1),
(2) Date: Jun. 9, 2022

(87) PCT Pub. No.: WO2021/116446

PCT Pub. Date: Jun. 17, 2021

(65) Prior Publication Data

US 2023/0055741 A1 Feb. 23, 2023

(30) Foreign Application Priority Data

Dec. 11, 2019 (EP) .................................... 19460066

(51) Int. Cl.

| | |
|---|---|
| ***C07D 401/14*** | (2006.01) |
| ***A61K 47/54*** | (2017.01) |
| ***A61P 37/02*** | (2006.01) |
| ***C07D 405/14*** | (2006.01) |
| ***C07D 413/14*** | (2006.01) |
| ***C07D 471/04*** | (2006.01) |

(52) U.S. Cl.

CPC .......... *C07D 401/14* (2013.01); *A61K 47/545* (2017.08); *A61P 37/02* (2018.01); *C07D 405/14* (2013.01); *C07D 413/14* (2013.01); *C07D 471/04* (2013.01); *C07B 2200/07* (2013.01)

(58) Field of Classification Search

None

See application file for complete search history.

(56) References Cited

U.S. PATENT DOCUMENTS

| | | | | |
|---|---|---|---|---|
| 3,410,851 | A | 11/1968 | Stauffer | |
| 12,162,863 | B2 * | 12/2024 | Dobrzanska ......... | C07D 473/00 |
| 12,344,606 | B2 * | 7/2025 | Zawadzka ............ | C07D 405/14 |
| 2008/0139558 | A1 | 6/2008 | Smith et al. | |
| 2011/0212946 | A1 | 9/2011 | Barrow et al. | |
| 2022/0251082 | A1 | 8/2022 | Zawadzka et al. | |
| 2022/0402898 | A1 | 12/2022 | Dobrzanska et al. | |
| 2023/0076506 | A1 * | 3/2023 | Zawadzka ............ | C07D 413/14 |
| 2025/0313561 | A1 | 10/2025 | Zawadzka et al. | |

FOREIGN PATENT DOCUMENTS

| | | | | |
|---|---|---|---|---|
| EP | 3807264 A1 * | 4/2021 | ............. | A61K 39/39 |
| GB | 2563642 A | 12/2018 | | |
| WO | WO-2004042083 A2 | 5/2004 | | |
| WO | WO-2007128568 A1 | 11/2007 | | |
| WO | WO 2014/002053 | 1/2014 | | |
| WO | WO 2018/234805 | 6/2017 | | |
| WO | WO 2018/234808 | 6/2017 | | |
| WO | WO 2019/100061 | 11/2017 | | |
| WO | WO-2019023635 A1 | 1/2019 | | |
| WO | WO-2019182886 A1 | 9/2019 | | |
| WO | WO-2019238786 A1 | 12/2019 | | |
| WO | WO 2020/228637 | 11/2020 | | |
| WO | WO-2020249773 A1 * | 12/2020 | ............. | C07D 13/14 |
| WO | WO-2021116451 A1 | 6/2021 | | |

OTHER PUBLICATIONS

Abdel-Aal et al. Arch Pharm Chem Life Sci. 2019;352:1800376 (Year: 2019).*

G.-F. Zhang et al. Ciprofloxacin derivatives and their antibacterial activities. European Journal of Medicinal Chemistry, 2018, 146, 599e612 (Year: 2018).*

Climova, A. et al. New Coordination Compounds Based on a Pyrazine Derivative: Design, Characterization, and Biological Study. Molecules 2022, 27, 3467. (Year: 2022).*

Fedorowicz, J. et al. Modifications of quinolones and fluoroquinolones: hybrid compounds and dual-action molecules. Monatshefte flr Chemie—Chemical Monthly, 2018, 149:1199-1245. (Year: 2018).*

International Search Report and Written Opinion for International Application No. PCT/EP2020/066370, European Patent Office, Netherlands (Year: 2021).*

Goswami, L. et al. Efficient synthesis of diverse heterobifunctionalized clickable oligo(ethylene glycol) linkers: potential applications in bioconjugation and targeted drug delivery. Org. Biomol. Chem., 2013, 11, 1116 (Year: 2013).*

(Continued)

*Primary Examiner* — Clinton A Brooks

*Assistant Examiner* — Nicola Maria Bauer

(74) *Attorney, Agent, or Firm* — Knobbe, Martens, Olson & Bear, LLP

(57) ABSTRACT

The present invention relates to compound-linker constructs and antibody-drug-conjugates of compounds of formula (I) that are useful as modulators of STING (Stimulator of Interferon Genes).

28 Claims, 4 Drawing Sheets

(56) References Cited

OTHER PUBLICATIONS

Chau, C. et al. Antibody-drug conjugates for cancer. Lancet 2019; 394: 793-804 (Year: 2019).*
Chau, C et al. Lancet 2019; 394: 793-804 (Year: 2019).*
Goswami, L et al. Org. Biomol. Chem., 2013, 11, 1116 (Year: 2013).*
G .- F. Zhang et al. European Journal of Medicinal Chemistry, 2018, 146, 599e612 (Year: 2018).*
Climova, A. et al. Molecules 2022, 27, 3467 (Year: 2022).*
Fedorowicz, J. et al. Monatshefte für Chemie—Chemical Monthly, 2018, 149: 1199-1245 (Year: 2018).*
Aguirre, S., et al., "DENV Inhibits Type I IFN Production in Infected Cells by Cleaving Human STING," PloS Pathog. 8(10):e1002934, PLOS, United States (2012).
Bargh, J.D., et al., "Cleavable linkers in antibody-drug conjugates," Chem. Soc. Rev. 10.1039/c8cs00676h, Royal Society of Chemistry, United Kingdom, (Jul. 2019), 14 pages.
Beck, A., et al., "Strategies and challenges for the next generation of antibody-drug conjugates," Nature Reviews Drug Discovery 16(5):315-337, Springer Nature, Germany (2017).
Chen, X., et al., "SARS coronavirus papain-like protease inhibits the type I interferon signaling pathway through interaction with the STING-TRAF3-TBK1 complex," Protein Cell 5(5):369-381, Oxford University Press, United Kingdom (2014).
Cirulli, E., et al., "Exome sequencing in amyotrophic lateral sclerosis identifies risk genes and pathways," Science 347(6229):1436-1441, American Association for the Advancement of Science, United States (2015).
Collins, A.C., et al., "Cyclic GMP-AMP Synthase is an Innate Immune DNA Sensor for *Mycobacterium tuberculosis*," Cell Host Microbe 17(6):820-828, Cell Press, United States (2015).
Corrales, L., and Gajewski, T.F., "Molecular Pathways: Targeting the Stimulator of Interferon Genes (STING) in the Immunotherapy of Cancer," Clin. Cancer Res. 21(21):4774-4779, American Association for Cancer Research, United States (2015).
Corrales, L., et al., "Direct Activation of STING in the Tumor Microenvironment Leads to Potent and Systemic Tumor Regression and Immunity," Cell Rep. 11(7):1018-1030, Cell Press, United States (2015).
Corrales, L., et al., "Extremely potent immunotherapeutic activity of a STING agonist in the B16 melanoma model in vivo," J. Immunother. Cancer 2013, 1 (Suppl 1):O15, BMJ Publishing Group Ltd, United Kingdom (2013).
Crow, Y.J., et al., "Mutations in the gene encoding the 3'-5' DNA exonuclease TREX1 cause Aicardi-Goutières syndrome at the *AGS1* locus," Nat. Genet. 38(8):917-920, Springer, Germany (2006).
Ding, Q., et al., "Hepatitis C virus NS4B blocks the interaction of STING and TBK1 to evade host innate immunity," J. Hepatol. 59(1):52-58, Elsevier, Netherlands (2013).
Dubensky, T.W., et al., "Rationale, progress and development of vaccines utilizing STING-activating cyclic dinucleotide adjuvants," Ther. Adv. Vaccines 1(4):131-143, Sage Publications, United States (2013).
Freischmidt, A., et al., "Haploinsufficiency of *TBK1* causes familial ALS and fronto-temporal dementia," Nat. Neurosci. 18(5):631-636, Springer, Germany (2015).
Fu, J., et al., "STING agonist formulated cancer vaccines can cure established tumors resistant to PD-1 blockade," Sci. Transl. Med. 7(283):283ra52, American Association for the Advancement of Science, United States (2015).
Gao, D., et al., "Cyclic GMP-AMP synthase is an innate immune sensor of HIV and other retroviruses," Science 341(6148):903-906, American Association for the Advancement of Science, United States (2013).
Gao, P., et al., "Cyclic [G(2',5')pA(3',5')p] is the metazoan second messenger produced by DNA-activated cyclic GMP-AMP synthase," Cell 153:1094-1107, Cell Press, United States (2013).
Herzner, A.-M., et al., "Sequence-specific activation of the DNA sensor cGAS by Y-form DNA structures as found in primary HIV-1 cDNA," Nat. Immunol. 16(10):1025-1033, Springer, Germany (2015).
Holm, C.K., et al., "Influenza A virus targets a cGAS-independent STING pathway that controls enveloped RNA viruses," Nat Comm. 7:10680, Springer, Netherlands (2016).
Huber, J.P., et al., "Cutting Edge: Type I IFN Reverses Human Th2 Commitment and Stability by Suppressing GATA3," J. Immunol. 185:813-817, American Association of Immunologists, United States (2010).
International Search Report and Written Opinion for International Application No. PCT/EP2020/085833, European Patent Office, Netherlands, mailed Feb. 10, 2021, 14 pages.
Ishikawa, H., and Barber, G.N., "STING is an Endoplasmic Reticulum Adaptor that Facilitates Innate Immune Signaling," Nature 455 (7213):674-678, Springer, Netherlands (2008).
Ishikawa, H., et al., "STING regulates intracellular DNA-mediated, type I interferon-dependent innate immunity," Nature 461(7265):788-792, Springer, Netherlands (2009).
Jin, L., et al., "MPYS is required for IRF3 Activation and Type I IFN production in the response of cultured phagocytes to bacterial second messengers c-di-AMP and c-di-GMP," J. Immunol. 187(5):2595-2601, American Association of Immunologists, United States (2011).
Lau, L., et al., "DNA tumor virus oncogenes antagonize the cGAS-STING DNA sensing pathway," Science 350(6260):568-571, American Association for the Advancement of Science, Untied States (2015).
Lemos, H., et al., "Activation of the STING Adaptor Attenuates Experimental Autoimmune Encephalitis," J. Immunol. 192(12):5571-5578, American Association of Immunologists, United States (2014).
Liu, Y., et al., "RIG-I-Mediated STING Upregulation Restricts Herpes Simplex Virus 1 Infection," J. Virol. 90(20):9406-9419, American Society for Microbiology, United States (2016).
Ma, Z., and Damania, B., "The cGAS-STING Defense Pathway and Its Counteraction by Viruses," Cell Host & Microbe 19(2):150-158, Cell Press, United States (2016).
Ma, Z., et al., "Modulation of the cGAS-STING DNA sensing pathway by gammaherpesviruses," PNAS 112(31):E4306-E4315, National Academy of Sciences, United States (2015).
McNab, F., et al., "Type I interferons in infectious disease," Nat. Rev. Immunol. 15(2):87-103, Springer, Germany (2015).
Moisan, J., et al., "TLR7 ligand prevents allergen-induced airway hyperresponsiveness and eosinophilia in allergic asthma by a MYD88-dependent and MK2-independent pathway," Am. J. Physiol. Lung Cell Mol. Physiol. 290:L987-L995, American Physiological Society, United States (2005).
Mousavizadeh, A., et al., "Cell targeting peptides as smart ligands for targeting of therapeutic or diagnostic agents: a systematic review," Colloids Surfaces B. 158:507-517, Elsevier, Netherlands (2017).
Nitta, S., et al., "Hepatitis C Virus NS4B Protein Targets STING and Abrogates RIG-I-Mediated Type I Interferon-Dependent Innate Immunity," Hepatology 57(1):46-58, Wiley, United States (2013).
Orava, E.W., et al., "Delivering cargoes into cancer cells using DNA aptamers targeting internalized surface portals," Biochimica Biophys. Acta 1798:2190-2200, Elsevier, Netherlands (2010).
Pedley, R.B., et al., "The potential for enhanced tumour localisation by poly(ethylene glycol) modification of anti-CEA antibody," Br. J. Cancer 70:1126-1130, Macmillan Press Ltd, Great Britain (1994).
Persing, D.H., et al., "Taking toll: lipid A mimetics as adjuvants and immunomodulators," Trends Microbiol. 10(10 Suppl):S32-S37, Elsevier, Netherlands (2002).
Polakis, P., "Antibody Drug Conjugates for Cancer Therapy," Pharmacol. Revs. 68(1):3-19, American Society for Pharmacology and Experimental Therapeutics, United States (2016).
Prantner, D., et al., "Stimulator of IFN Gene is Critical for Induction of IFN-β during *Chlamydia muridarum* Infection," J. Immunol. 184(5):2551-2560, American Association of Immunologists, United States (2010).
Rakoff-Nahoum, S., et al., "Recognition of Commensal Microflora by Toll-Like Receptors is Required for Intestinal Homeostasis," Cell 118(2):229-241, Cell Press, United States (2004).

(56) References Cited

OTHER PUBLICATIONS

Sharma, S., et al., "Innate immune recognition of an AT-rich stem-loop DNA motif in the *Plasmodium falciparum* genome," Immunity 35(2):194-207, Cell Press, United States (2011).
Stetson, D.B., et al., "Trex1 Prevents Cell-Intrinsic Initiation of Autoimmunity," Cell 134(4):587-598, Cell Press, United States (2008).
Storek, K.Ḿ., et al., "cGAS and Ifi204 Cooperate to Produce Type I IFNs in Response to *Francisella* Infection," J. Immunol. 194(7):3236-3245, American Association of Immunologists, Inc., United States (2015).
Sun, L., et al., "Coronavirus Papain-like Proteases Negatively Regulate Antiviral Innate Immune Response through Disruption of STING-Mediated Signaling," PloS One 7(2): e30802, PLOS, United States (2012).
Sun, L., et al., "Cyclic GMP-AMP Synthase is a Cytosolic DNA Sensor that Activates the Type I Interferon Pathway," Science 339(6161):786-791, American Association for the Advancement of Science, United States (2013).
Turner, A., et al., "Comparative biodistributions of indium-111-labelled macrocycle chimeric B72.3 antibody conjugates in tumour-bearing mice," Br. J. Cancer 70:35-41, Macmillan Press Ltd, Great Britain (1994).
Wassermann, R., et al., "*Mycobacterium tuberculosis* Differentially Activates cGAS- and Inflammasome-Dependent Intracellular Immune Responses through ESX-1," Cell Host & Microbe 17(6):799-810, Cell Press, United States (2015).
Watson, R.O., et al., "The cytosolic sensor cGAS detects *Mycobacterium tuberculosis* DNA to induce type I interferons and activate autophagy," Cell Host & Microbe 17(6):811-819, Cell Press, United States (2015).
Woo, S.-R., et al., "The STING pathway and the T cell-inflamed tumor microenvironment," Trends Immunol. 36(4):250-256, Elsevier, Netherlands (2015).
Wu, J.-J., et al.,, "Inhibition of cGAS DNA Sensing by a Herpes-virus Virion Protein," Cell Host & Microbe 18(3):333-344, Cell Press, United States (2015).
Zitvogel, L., et al., "Type I interferons in anticancer immunity," Nature Reviews Immunology 15(7):405-414, Springer, Germany (2015).
Todorov, A.R., et al., "Tautomeric Switching and Metal-Cation Sensing of Ligand-Equipped 4-Hydroxy-/4-oxo-1,4-dihydroquinolines," Chemistry: A European Journal 18(23):7269-7277, Wiley-VCH, Germany (2012).
International Search Report and Written Opinion for International Application No. PCT/EP2020/085840, European Patent Office, Netherlands, mailed Feb. 11, 2021, 10 pages.
Aguzzi, A., et al., "The immunobiology of prion diseases," Nature Reviews Immunology, 13(12):888-902, Springer Nature, Germany (Nov. 2013).
An, X., et al., "An Analysis of the Expression and Association with Immune Cell Infiltration of the cGAS/STING Pathway in Pan-Cancer," Molecular Therapy: Nucleic Acids 14:80-89, CellPress, United States (Mar. 2019).
Bakhoum, S.F., et al., "Chromosomal instability drives metastasis through a cytosolic DNA response," Nature 553(7689):467-472, Springer Nature, Germany (Jan. 2018).
Database Registry [online], Chemical Abstracts Service, Database Accession No. 1011381-60-4, Columbus, Ohio, United States (Apr. 1, 2008), 11 pages, assessed Aug. 7, 2018.
Database Registry [online], Chemical Abstracts Service, Database Accession No. 1244927-19-2, Columbus, Ohio, United States (Oct. 3, 2010), 3 pages, assessed Aug. 7, 2018.
Demaria, O., et al., "STING activation of tumor endothelial cells initiates spontaneous and therapeutic antitumor immunity," PNAS 112(50):15408-15413, National Academy of Sciences, United States (Dec. 2015).
File Registry on STN, Document No. 70:77793 (1969), 2 pages.
Guo, F., et al., "STING Agonists Induce an Innate Antiviral Immune Response against Hepatitis B Virus," Antimicrobial Agents and Chemotherapy 59(2):1273-1281, American Society for Microbiology, United States (Feb. 2015).
Madhun, A.S., et al., "Intranasal c-di-GMP-adjuvanted plant-derived HS influenza vaccine induces multifunctional Th1 CD4+ cells and strong mucosal and systemic antibody responses in mice," Vaccine 29:4973-4982, Elsevier, Netherlands (Jul. 2011).
Misra, P.S., et al., "Synthesis of 2-phenyl benzimidazole derivatives and their Schiff bases as possible antimicrobial agents," Rasayan J. Chem. 3(1):51-54, Rasayan Journal of Chemistry, India (Mar. 2010).
Office Action mailed Sep. 30, 2024, in U.S. Appl. No. 17/618,007, Zawadzka, M.I., et al., § 371(c) Date: Dec. 10, 2021, 29 pages.
Notice of Allowance mailed Feb. 19, 2025, in U.S. Appl. No. 17/618,007, Zawadzka, M.I., et al., § 371(c) Date: Dec. 10, 2021, 14 pages.
Wang, T., et al., "Salts, Cocrystals, and Ionic Cocrystals of a "Simple" Tautomeric Compound," Crystal Growth and Design 18(11):6973-6983, American Chemical Society, United States (Oct. 2018).
Zhang, B., et al., "Molecular Design, Synthesis and Biological Research of Novel Pyridyl Acridones as Potent DNA-binding and Apoptosis-inducing Agents," European Journal of Medicinal Chemistry 93:214-226, Elsevier Masson SAS, France (Mar. 2015).
Zhang, Z., et al., "Peptide nanotube loaded with a STING agonist, c-di-GMP, enhance cancer immunotherapy against melanoma," Nano Research 16(4):5206-5215, Springer Nature, Germany (Apr. 2023).

* cited by examiner

Example 31, 7 mg/kg, E5Dx3

Example 31, 15 mg/kg, E5Dx3

Example 57, 10 mg/kg, E5Dx3

Example 57, 20 mg/kg, E5Dx3

FUNCTIONALIZED HETEROCYCLIC COMPOUNDS AS MODULATORS OF STIMULATOR OF INTERFERON GENES (STING)

FIELD OF THE INVENTION

The present invention relates to functionalized compounds of formula (I) in the form of compound-linker constructs and conjugates that are useful as modulators of STING (Stimulator of Interferon Genes). The present invention further relates to the functionalized compounds of formula (I) for use as a medicament and to a pharmaceutical composition comprising said compounds.

BACKGROUND OF THE INVENTION

The cellular innate immune system is essential for recognizing pathogen infection and for establishing effective host defense. The adaptor protein STING (Stimulator of Interferon Genes), also known as TMEM 173, MPYS, MITA and ERIS, has been identified as a central signaling molecule in the innate immune response to cytosolic nucleic acids (H. Ishikawa, G. N. Barber, Nature, 2008, vol. 455, pp. 674-678). STING inter alia induces type I interferon (IFN) production when cells are infected with intracellular pathogens, such as viruses, mycobacteria and intracellular parasites.

Activation of STING promotes IRF3 and NFkB-dependent signaling leading in consequence to production of proinflammatory cytokines and interferons, including type I and type III interferons and TNF α of particular importance in cancer immunotherapy. STING is responsible for sensing of cytoplasmic nucleic acids and their derivatives called cyclic dinucleotides (CDN), both of pathogen or host origin (e.g. double stranded DNA from bacteria or viruses and cytoplasmic self-DNA).

Endogenous STING direct agonist 2',3'-cGAMP (2',3'-cyclic guanosine monophosphate-adenosine monophosphate) is produced in mammalian cells by enzyme cGAS (cyclic GMP-AMP synthase, MB21D1 or C6orf150) (P. Gao et al., Cell, 2013, 153, pp. 1094-1107, Wu et al. Science, 2013, 339, pp. 786-791) and has proven activity in modulating STING-dependent pathway, together with its derivatives (L. Corrales et al., J Immunother Cancer, 2013, 1(Suppl 1): O15, L. Corrales et al., Cell Rep., 2015, May 19; 11(7), pp. 1018-30, S-R. Woo et al., Trends Immunol., 2015, 36 (4), 250, J. Fu et al., Sci. Trans. Med., Vol. 7, Issue 283, pp. 283ra52).

Recent evidence supports findings that once STING is activated by CDN within tumor microenvironment, preferably in tumor-resident dendritic cells, it promotes type I IFN and TNF α release which results in immunity-mediated anti-tumor response. STING-dependent activation of antigen-presenting cells (APC) efficiently drives highly specific T-cell priming against neoantigens (L. Corrales and T F. Gajewski, Clin Cancer Res, 2015, 21 (21), pp. 4774-9). STING activation not only provides generation of tumor-specific killer T cells, which directly eradicate tumors, but also results in vaccine-like long-lasting immunity protecting from cancer recurrence.

Thus, synthetic STING agonists are of special interest as potential anticancer agents. The activation or inhibition of type I interferon production is an important strategy for the treatment or prevention of human diseases including viral infections and autoimmune disease. It has been found that compounds activating or inhibiting type I interferon production may be useful not only in infectious disease innate immunity, but also in cancer (L. Zitvogel et al., Nature Reviews Immunology, 2015, vol. 15(7), pp. 405-414), allergic diseases (J. Moisan et al., Am. J. Physiol. Lung Cell Mol. Physiol., 2006, vol. 290, L987-995), neurodegenerative diseases such as amyotrophic lateral sclerosis and multiple sclerosis (H. Lemos et al., J. Immunol, 2014, vol. 192(12), pp. 5571-8; E. Cirulli et al., Science, 2015, vol. 347(6229), pp. 1436-41; A. Freischmidt et al., Nat Neurosci., vol. 18(5), 631-6), other inflammatory conditions such as irritable bowel disease (S. Rakoff-Nahoum, Cell, 2004, 23, 118(2), pp. 229-41), and as vaccine adjuvants (Persing et al., Trends Microbiol. 2002, 10(10 Suppl), S32-7; Dubensky et al, Therapeutic Advances in Vaccines, published online Sep. 5, 2013).

STING is essential for antimicrobial host defense, including protection against a range of DNA and RNA viruses and bacteria (reviewed in Barber et al., Nat. Rev. Immunol., 2015, vol. 15(2), pp. 87-103, Ma and Damania, Cell Host & Microbe, 2016, vol. 19(2), pp. 150-158). Herpesviridae, Flaviviridae, Coronaviridae, Papillomaviridae, Adenoviridae, Hepadnaviridae, ortho- and paramyxoviridae and rhabdoviridae have evolved mechanisms to inhibit STING mediated Type I interferon production and evade host immune control (Holm et al., Nat Comm., 2016, vol. 7, p. 10680; Ma et al., PNAS 2015, vol. 112(31) E4306-E4315; Wu et al., Cell Host Microbe, 2015, vol. 18(3), pp. 333-44; Liu et al., J Virol, 2016, vol. 90(20), pp. 9406-19; Chen et al., Protein Cell 2014, vol. 5(5), pp. 369-81; Lau et al., Science, 2013, vol. 350(6260), pp. 568-71; Ding et al., J Hepatol, 2013, vol. 59(1), pp. 52-8; Nitta et al., Hepatology, 2013, vol. 57(1), pp. 46-58; Sun et al., PloS One, 2012, vol. 7(2), e30802; Aguirre et al., PloS Pathog, 2012, vol. 8(10), e1002934; Ishikawa et al., Nature, 2009, vol. 461(7265), pp. 788-92). Thus, drug activation of STING is considered to be beneficial for treatment of these infectious diseases.

In contrast, increased and prolonged type I IFN production is associated with a variety of chronic infections, including Mycobacteria (Collins et al., Cell Host Microbe, 2015, vol. 17(6), pp. 820-8); Wassermann et al., Cell Host Microbe, 2015, vol. 17(6), pp. 799-810; Watson et al., Cell Host Microbe, 2015, vol. 17(6), pp. 811-9), Franciscella (Storek et al., J Immunol., 2015, vol. 194(7), pp. 3236-45; Jin et al., J Immunol., 2011, vol. 187(5), pp. 2595-601), Chlamydia (Prantner et al., J Immunol, 2010, vol. 184(5), pp. 2551-60), Plasmodium (Sharma et al., Immunity, 2011, vol. 35(2), pp. 194-207), and HIV (Herzner et al., Nat Immunol, 2015, vol. 16(10), pp. 1025-33; Gao et al., Science, 2013, vol. 341(6148), pp. 903-6). Similarly, excess type I interferon production is found among patients with complex forms of autoimmune disease. Genetic evidence in humans and support from studies in animal models support the hypothesis that inhibition of STING results in reduced type I interferon that drives autoimmune disease (Y. J. Crow et al., Nat. Genet, 2006, vol. 38(8), pp. 38917-920, D. B. Stetson et al., Cell, 2008, pp. 134587-598). Therefore, inhibitors of STING provide a treatment to patients with chronic type I interferon and proinflammatory cytokine production associated with infections or complex autoimmune diseases. Allergic diseases are associated with a Th2-based immune-response to allergens. Th2 responses are associated with raised levels of IgE, which, via its effects on mast cells, promotes a hypersensitivity to allergens, resulting in the symptoms seen, for example, in allergic rhinitis and asthma. In healthy individuals the immune-response to allergens is more balanced with a mixed Th2/Th1 and regulatory T cell response. Induction of Type 1 interferons have been shown to result in reduction of Th2-type cytokines in the local environment and promote Th1/Treg responses. In this context, induction of type 1 interferons by, for example, activation of STING, may offer benefit in treatment of allergic diseases such as asthma and allergic rhinitis (J. P. Huber et al., J Immunol, 2010, vol. 185, pp. 813-817).

The covalent attachment of small molecule compounds to a linker and optionally additionally to a targeting moiety can mask the compound from the host's immune system (reducing immunogenicity and antigenicity), and increase its hydrodynamic size (size in solution), which prolongs its circulation time by reducing renal clearance. Furthermore, the water solubility of the compound can be positively influenced by the use of a suitable linker with hydrophilic groups.

Conjugates of small molecule compounds with targeting moieties, in particular antibody-drug conjugates (ADC), combine the targeting capabilities of, e.g., a monoclonal antibody, with the pharmacological activity of the attached compounds (also referred to as payloads). In particular, the targeting moiety may specifically target a certain tumor antigen (e.g. a protein that, ideally, is only to be found in or on tumor cells) or immune cells antigen and attach itself to the antigens on the surface of cancerous cells or immune cells. The biochemical reaction between the targeting moiety, preferably an antibody, and the target protein (antigen) can trigger a signal in the tumor cell or immune cells, which then absorbs or internalizes the antibody together with the linked compound (payload). After the ADC is internalized (endocytosis), the linked compound will exhibit its pharmacological activity within the cell. This targeting limits side effects and gives a wider therapeutic window than other chemotherapeutic agents. In some cases, the payload may be sufficiently membrane-permeable to diffuse out of the cell and act in bystander cells. In another approach, a non-internalising mechanism of action is also possible. In this case, linker cleavage and payload release occur in the extracellular tumor microenvironment. Thus, ADC endocytosis is not required and non-internalising antigens may be selected as targets.

Overall, ADCs therefore aim to combine the favorable aspects of systemic administration of small molecular weight active compounds with targeted delivery via e.g. monoclonal antibodies therapies, thereby creating highly active and selective therapeutics with long plasma half-lives.

Linkers in connection with ADCs link the small molecule compound (payload) with the targeting moiety, e.g., the antibody. ADC linkers can be classified as "cleavable" or "non-cleavable", with cleavable linkers being the preferred choice (J. D. Bargh et al., Chem. Soc. Rev., 2019, DOI: 10.1039/c8cs00676h).

In view of the above, drugs modulating STING are useful for treating one or more diseases selected from the group consisting of inflammatory, allergic, and autoimmune diseases, infectious diseases, cancer, pre-cancerous syndromes, and/or as immunogenic composition or vaccine adjuvants. Of particular relevance is the immunotherapy of cancer and viral infections, in particular prostate cancer, renal carcinoma, melanoma, pancreatic cancer, cervical cancer, ovarian cancer, colon cancer, head and neck cancer, lung cancer, fibrosarcoma, and breast cancer. Furthermore, activation of local immune response to the lesions is considered to be preferably parenteral or non-parenteral therapeutic approach.

Accordingly, there is a need for drugs modulating the activity of STING, and accordingly, provide a therapeutic impact in the treatment of diseases, in which the modulation of STING is beneficial.

In this context, it is another object of the present invention to provide functionalized compounds, e.g. in the form of compound-linker constructs or conjugates with targeting moieties such as antibodies.

OBJECTS AND SUMMARY OF THE INVENTION

It is therefore an object of the present invention to provide functionalized compounds, which modulate STING, in particular functionalized compounds, which act as STING agonists, thereby activating STING. In particular, there is an interest in providing functionalized compounds, which have high activity as STING agonists.

It is another object of the present invention to provide functionalized compounds, which are suitable for use as a medicament. It is another object of the present invention to provide functionalized compounds, which are suitable for use in the treatment of one or more diseases, which are linked to STING modulation. It is yet another object to provide functionalized compounds, which are suitable for use in the treatment of one or more diseases selected from the group consisting of inflammatory diseases, allergic diseases, autoimmune diseases, infectious diseases, cancer, and pre-cancerous syndromes. In particular, it is an object to provide functionalized compounds, which are suitable for the treatment of cancer, in particular prostate cancer, lung cancer, breast cancer, head and neck cancer, bladder cancer, and/or melanoma. It is yet another object to provide functionalized compounds, which are suitable for use in immunogenic compositions and as vaccine adjuvants.

It is another object of the present invention to provide functionalized compounds, which are beneficial in that they contain a group masking the compound from the host's immune system and/or increasing its hydrodynamic size, and/or improving the water solubility, or functionalized compounds, which are beneficial in that they contain a moiety with targeting capabilities such that a tumor antigen or immune cell may specifically be targeted, so that the functionalized compounds will be absorbed or internalized in a tumor cell or immune cell to provide their pharmacological activity.

The above objects can be achieved by the compound-linker constructs and conjugates as defined herein as well as pharmaceutical compositions comprising the same, and by the medical uses thereof.

The inventors of the present invention inter alia surprisingly found that the compounds of formula (I) as defined herein modulate STING, in particular act as STING agonists, and can be attached to a linker to form a compound-linker construct. Said construct may then be used as such or be further modified to provide a conjugate, wherein the compound is covalently linked to a targeting moiety. The functionalized compounds of the invention, i.e. the compound-linker constructs and conjugates as described herein, can be used as a medicament, in particular for the treatment of one or more diseases selected from the group consisting of inflammatory diseases, allergic diseases, autoimmune diseases, infectious diseases, cancer, and pre-cancerous syndromes. In particular, the functionalized compounds of the invention are suitable for the treatment of cancer, in particular prostate cancer, lung cancer, breast cancer, head and neck cancer, bladder cancer, and/or melanoma. Further, the functionalized compounds are suitable for use in immunogenic compositions and as vaccine adjuvants.

In a first aspect, the present invention therefore relates to a compound-linker construct comprising (i) a compound of formula (I); and (ii) a linker $L^1$ wherein the compound of formula (I) is a compound of the following formula (I)

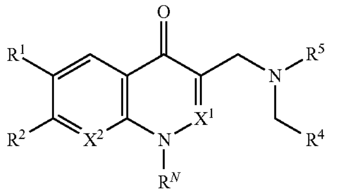

or a salt, stereoisomer, tautomer, or N-oxide thereof, wherein $X^1$ is CH or N;

$X^2$ is $CR^3$ or N;

$R^1$, $R^2$ and $R^3$ are independently H, OH, $NR^CR^D$, CN, halogen, $C_1$-$C_4$-alkyl, $NR^CR^D$—$C_1$-$C_4$-alkyl, $C_1$-$C_4$-alkoxy, aryloxy, benzyloxy, C(═O)$R^E$, $NR^F$C(═O)$R^E$, $NR^F$—($C_1$-$C_4$-alkylene) C(═O)$R^E$, $NR^F$—($C_1$-$C_4$-alkylene)-$NR^CR^D$, O—($C_1$-$C_4$-alkylene)-$NR^CR^D$, or 4- to 6-membered saturated, partially or fully unsaturated, or aromatic carbocyclyl, carbocyclyl-$C_1$-$C_2$-alkyl, heterocyclyl, heterocyclyloxy, or heterocyclyl-$C_1$-$C_2$-alkyl, or 8- to 10-membered saturated, partially or fully unsaturated, or aromatic carbobicyclyl or heterobicyclyl, wherein the aforementioned heterocyclic or heterobicyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents $R^X$;

$R^5$ is a 5- or 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents $R^Y$;

and wherein $R^N$ is H, $C_1$-$C_4$-alkyl, HO(C═O)—$C_1$-$C_4$-alkyl, $NR^CR^D$—$C_1$-$C_4$-alkyl, $C_1$-$C_2$alkoxy-$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, $NR^CR^D$—$C_1$-$C_4$-alkyl, phenyl, benzyl, $OR^G$, or $NR^HR^I$; or a 5- or 6-membered saturated, partially or fully unsaturated heterocyclyl, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^F$;

$R^F$ is H, $C_1$-$C_2$-alkyl, $C_3$-$C_6$-cycloalkyl, phenyl, benzyl, or C(═O)$NR^HR^I$;

$R^G$ is H, $C_1$-$C_2$-alkyl, or 5- or 6-membered aromatic carbocyclyl, carbocyclyl-$C_1$-$C_2$alkyl, heterocyclyl, or heterocyclyl-$C_1$-$C_2$alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is OH, $NR^CR^D$, halogen, CN, $NO_2$, $C_1$-$C_2$-alkyl, $C_1$-$C_2$haloalkyl, $NR^CR^D$—$C_1$-$C_4$-alkyl, $R^C$O—$C_1$-$C_4$-alkyl, $C_1$-$C_2$-alkoxy, C(═O)$R^E$, or two $R^X$ form ═O, or two $R^X$ together with the carbon atom to which they are bonded form a 3- to 5-membered saturated, partially or fully unsaturated, or aromatic carbocyclic ring;

$R^Y$ is halogen, CN, OH, $C_1$-$C_2$-alkyl, HO—$C_1$-$C_2$-alkyl, $C_3$-$C_6$-cycloalkyl, $C_1$-$C_2$-alkoxy, $NR^CR^D$, S(═O)$_2$ $NR^CR^D$, C(═O)$R^E$, or 5- or 6-membered saturated, partially or fully unsaturated, or aromatic carbocyclyl, carbocyclyl-$C_1$-$C_2$-alkyl, heterocyclyl, and heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form ═O; or two $R^Y$ attached to identical or neighboring carbon atoms may form a 3-membered carbocyclic ring;

with the proviso that either any one of $R^1$, $R^2$, or $R^3$ is $NR^CR^D$, $NR^CR^D$—$C_1$-$C_4$-alkyl, $NR^F$—($C_1$-$C_4$-alkylene)-$NR^CR^D$, O—($C_1$-$C_4$-alkylene)-$NR^CR^D$, or 8- to 10-membered saturated, partially or fully unsaturated, or aromatic carbobicyclyl or heterobicyclyl, wherein the aforementioned heterobicyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or any one of $R^1$, $R^2$, or $R^3$ is $NR^FC(═O)R^E$, wherein $R^E$ is $NR^CR^D$—$C_1$-$C_4$-alkyl;

or $R^N$ is $NR^CR^D$—$C_1$-$C_4$-alkyl, or $C_1$-$C_2$-alkoxy-$C_1$-$C_4$-alkyl;

or any one of the substituents $R^1$, $R^2$, $R^3$, $R^4$, $R^5$, $R^N$ carries a substituent $R^X$, wherein $R^X$ is OH, $NR^CR^D$, $NR^CR^D$—$C_1$-$C_4$-alkyl, or $R^CO$—$C_1$-$C_4$-alkyl.

Preferably, the compound of formula (I) is covalently bonded to the linker $L^1$, wherein the linker $L^1$ may be cleavable or non-cleavable. The above defined provisos regarding the compound of formula (I) define functional groups, which preferably form the covalent bond to the linker $L^1$. In connection with the provisos it is to be understood that, although it is sufficient that one of the given alternatives is fulfilled, this does not exclude that more than one of the given alternatives are fulfilled by the compounds of formula (I). Therefore, the term "any one of" also includes the option "at least one of". In other words, if, e.g., $R^2$ is selected according to the proviso, this does not exclude that $R^1$ or $R^3$ is selected according to the proviso. Similarly, if, e.g., $R^2$ is selected according to the proviso, this does not exclude that $R^N$ is selected according to the proviso, and/or that any one of the substituents $R^1$, $R^2$, $R^3$, $R^4$, $R^5$, $R^N$ carries a substituent $R^X$ according to the proviso. As used in connection with the proviso, the term "carries a substituent $R^X$" means that the mentioned substituent may carry the substituent $R^X$ at any position, which also includes the option that $R^X$ is attached to $R^Y$, wherein $R^Y$ is attached to the mentioned substituent. This is particularly relevant in connection with the substituent $R^5$. In connection with $R^5$, the term "carries a substituent $R^X$" preferably means that $R^5$ represents a 5- or 6-membered saturated heterocyclic ring as defined herein, which is substituted by $R^Y$, wherein $R^Y$, which is preferably a pyridine, is further substituted by $R^X$. On the other hand, in connection with the remaining substituents, e.g., $R^4$, the term "carries a substituent $R^X$" preferably means that $R^4$ represents a 5- or 6-membered aromatic carbocyclic or heterocyclic ring, or a 9- or 10-membered aromatic carbobicyclic or heterobicyclic ring, wherein a substitutable carbon or heteroatom in the aforementioned cyclic rings is substituted with a substituent $R^X$.

In one embodiment, the present invention relates to a compound-linker construct as defined above, wherein a covalent bond between the compound of formula (I) and the linker $L^1$ is established by the reaction of a functional group of the compound of formula (I) with a functional group handle of the linker $L^1$; and wherein preferably the functional group of the compound of formula (I) is attached to or part of the substituents $R^2$, $R^4$, $R^5$, or $R^N$ so that the linker $L^1$ will be covalently bonded to the compound of formula (I) according to any one of the following structures:

($I$-$R^2$-$L^1$)

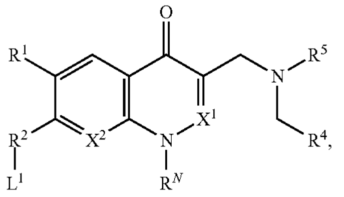

($I$-$R^N$-$L^1$)

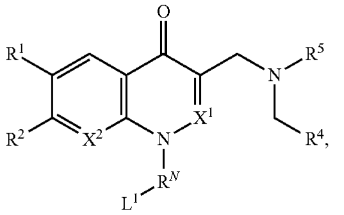

($I$-$R^4$-$L^1$)

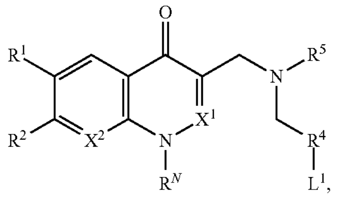

($I$-$R^5$-$L^1$)

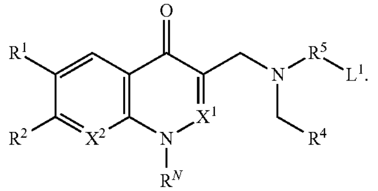

In another embodiment, the present invention relates to a compound-linker construct as defined above, wherein the linker $L^1$ comprises (i) a chain $L^C$ of 2 to 100 atoms selected from carbon, nitrogen, oxygen, and sulfur atoms, which may be interrupted by 5- to 10-membered aryl and heteroaryl groups and/or 3- to 8-membered saturated carbocyclyl or heterocyclyl groups, wherein the aforementioned heteroaryl and heterocyclic groups comprise one or more, same or different heteroatoms selected from O, N or S, wherein said N- and/or S-atoms are independently oxidized or non-oxidized, and wherein each substitutable carbon or heteroatom in the chain is independently unsubstituted or substituted with one or more same or different substituents selected from halogen, OH, ═O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

and preferably a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

(ii) a functional group handle $H^{1A}$, which is covalently bonded to the compound of formula (I);

(iii) a functional group handle $H^{1B}$ suitable for forming a covalent bond to a targeting moiety T.

In another embodiment, the present invention relates to a compound-linker construct as defined above, wherein the linker $L^1$ has the structure $H^{1A}L^C$-$H^{1B}$ and is selected from the group consisting of:

($L^1$-1)

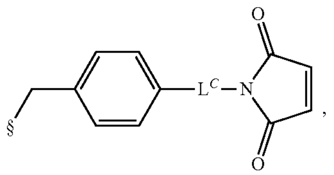

($L^1$-2)

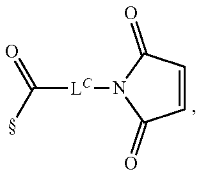

($L^1$-3)

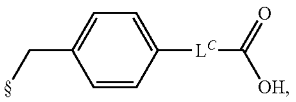

($L^1$-4)

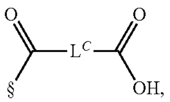

($L^1$-5)

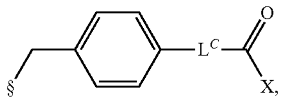

($L^1$-6)

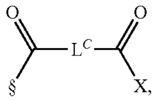

($L^1$-7)

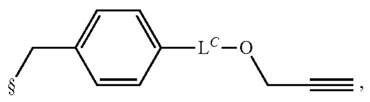

-continued ($L^1$-8)

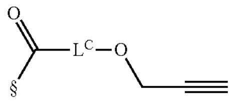

($L^1$-9)

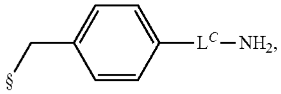

($L^1$-10)

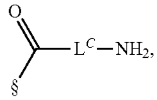

($L^1$-11)

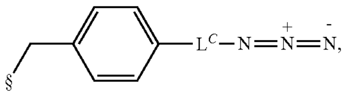

($L^1$-12)

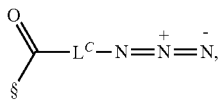

($L^1$-13)

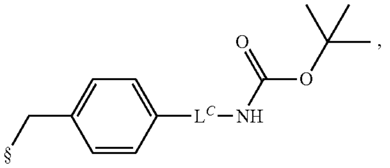

($L^1$-14)

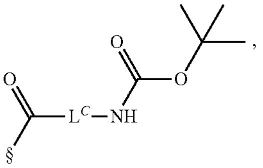

($L^1$-15)

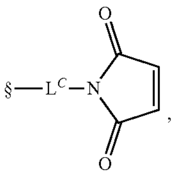

($L^1$-16)

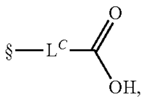

($L^1$-17)

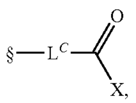

($L^1$-18)

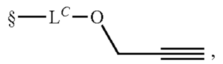

-continued (L[1]-19)

§—$L^C$—$NH_2$, (L[1]-20)

§—$L^C$—$N{=}\overset{+}{N}{=}\overset{-}{N}$ , (L[1]-21)

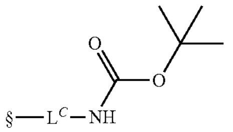

;

and wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$- haloalkyl, $C_3$-$C_6$-cycloalkyl, $C_3$-$C_6$-halocycloalkyl, $C_1$-$C_6$-alkoxy, and $C_1$-$C_6$-haloalkoxy; and § marks the connection to the compound of formula (I); and X represents a leaving group selected from (X-1)

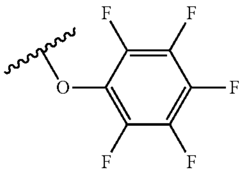

and (X-2)

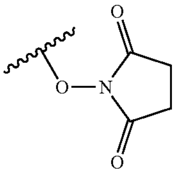

and wherein preferably $L^C$ is selected from the group consisting of ($L^c$-1)

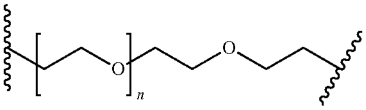

, ($L^c$-2)

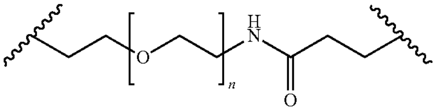

, ($L^c$-3)

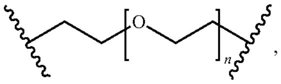

, ($L^c$-4)

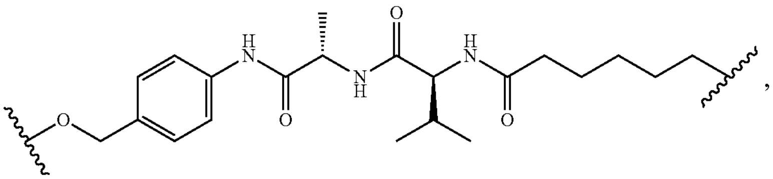

, ($L^c$-5)

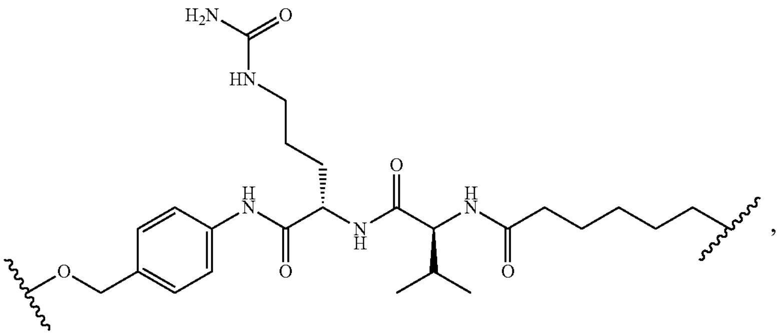

,

-continued
($L^c$-6)
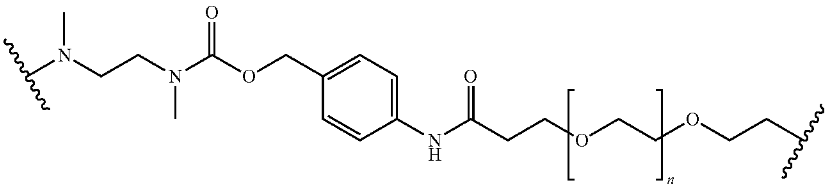
,
($L^c$-7)
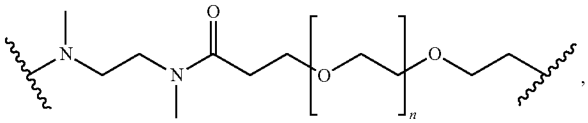
,
($L^c$-8)
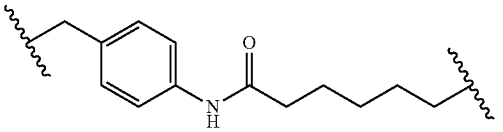
,
($L^c$-9)
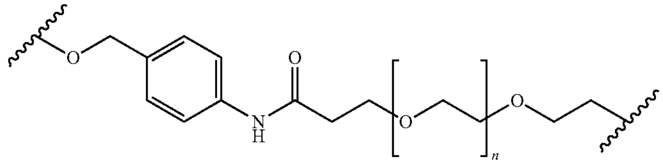
,
($L^c$-10)
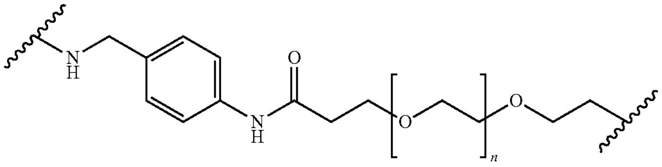
, and
($L^c$-11)
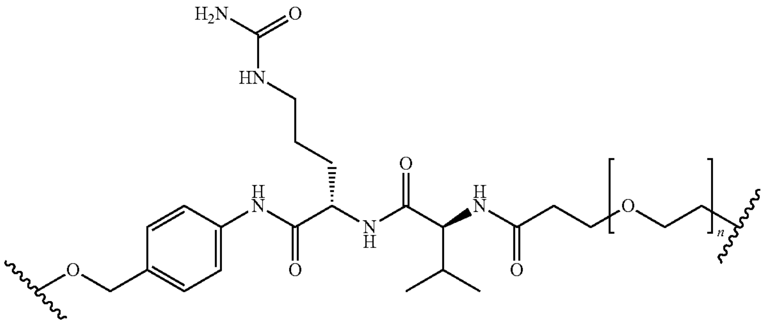
;
wherein n is 0, 1, 2, 3, 4, 5, 6, 7, or 8.

In another embodiment, the present invention relates to a compound-linker construct as defined above, wherein the linker $L^1$ has the structure $H^{1A}L^C\text{-}H^{1B}$ and is selected from the group consisting of:

($L^1$-1)

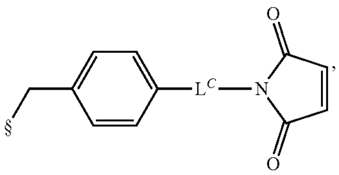

($L^1$-2)

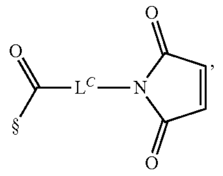

($L^1$-3)

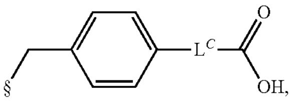

($L^1$-4)

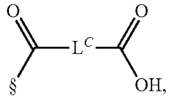

($L^1$-5)

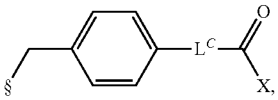

and ($L^1$-6)

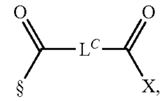

wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy; and § marks the connection to the compound of formula (I); and X represents a leaving group selected from (X-1)

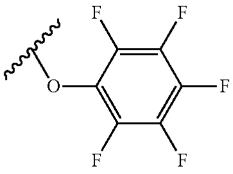

and (X-2)

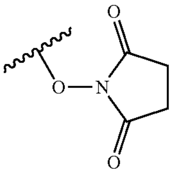

and wherein preferably $L^C$ is selected from the group consisting of ($L^c$-1)

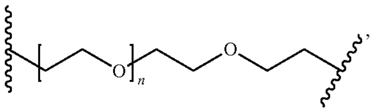

($L^c$-2)

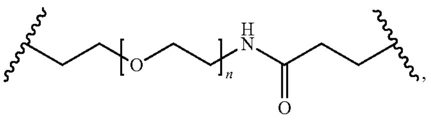

($L^c$-3)

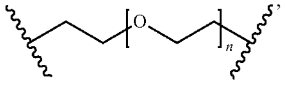

($L^c$-4)

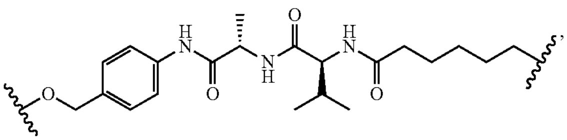

-continued
(L^c-5)
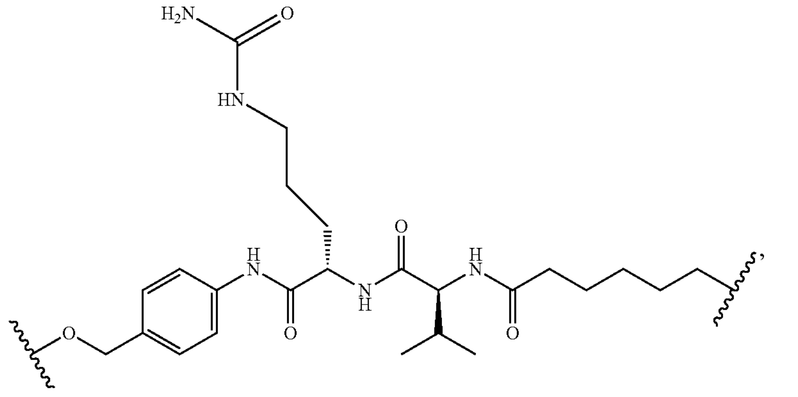
(L^c-6)
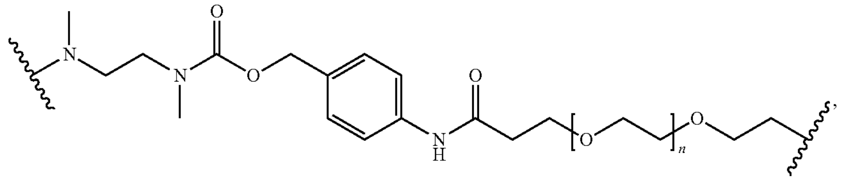
(L^c-7)
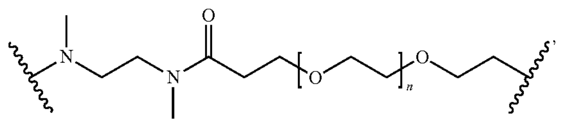
(L^c-8)
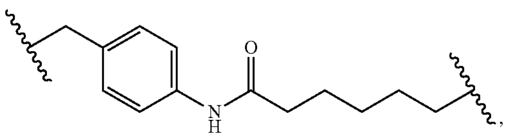
and
(L^c-9)
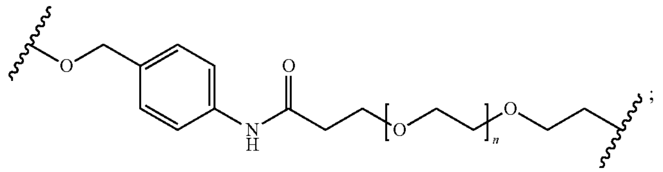
wherein n is 0, 1, 2, 3, 4, 5, 6, 7, or 8.
In another embodiment, the present invention relates to a compound-linker construct as defined above,
wherein the linker $L^1$ is selected from the group consisting of:
($L^1$-a)
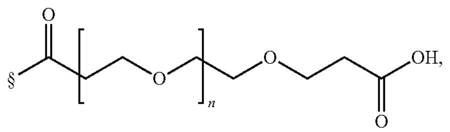
($L^1$-b)
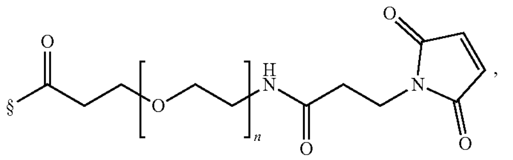

-continued
(L1-c)
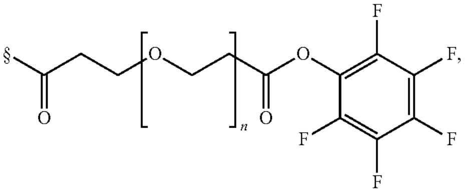
(L1-d)
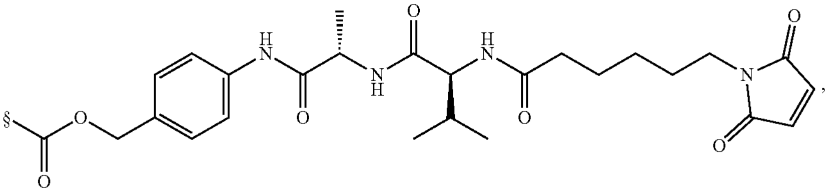
(L1-e)
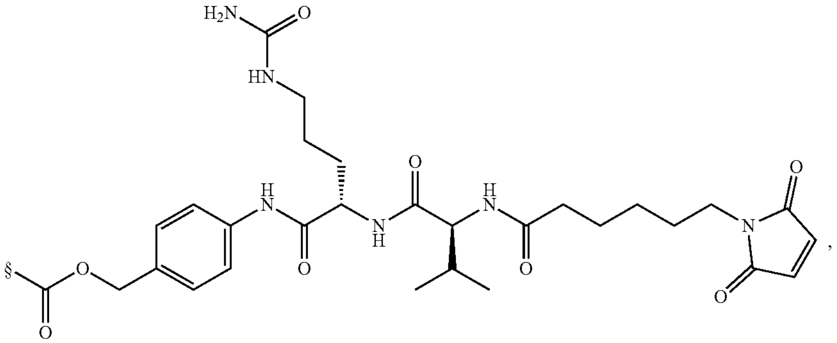
(L1-f)
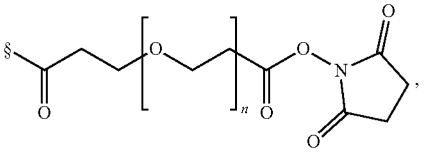
(L1-g)
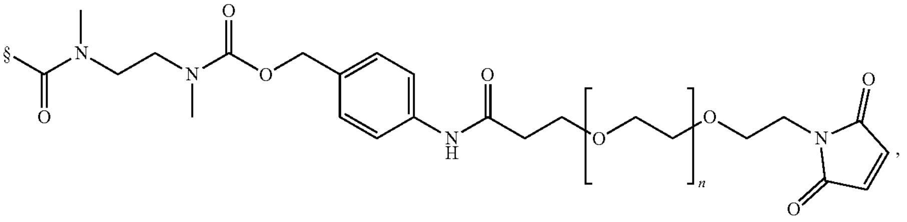
(L1-h)
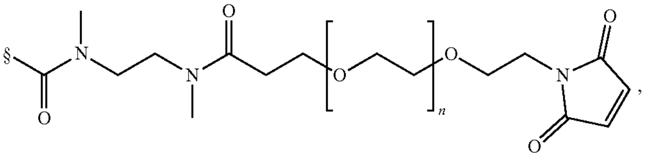

-continued (L$^1$-i)

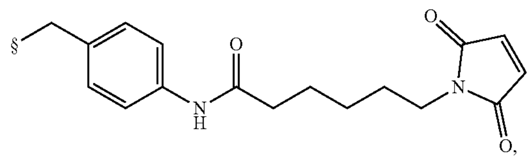

wherein

§ marks the connection to the compound of formula (I); and wherein n is 0, 1, 2, 3, 4, 5, 6, 7, or 8.

In a second aspect, the present invention relates to a conjugate comprising (i) a compound of formula (I);

(ii) a linker $L^2$; and (iii) a targeting moiety T wherein the compound of formula (I) is a compound of the following formula (I)

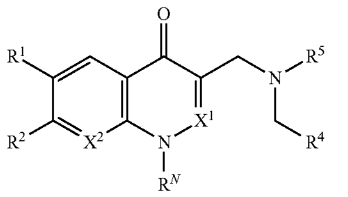

or a salt, stereoisomer, tautomer, or N-oxide thereof, wherein $X^1$ is CH or N;

$X^2$ is $CR^3$ or N;

$R^1$, $R^2$ and $R^3$ are independently H, OH, $NR^CR^D$, CN, halogen, $C_1$-$C_4$-alkyl, $NR^CR^D$—$C_1$-$C_4$-alkyl, $C_1$-$C_4$-alkoxy, aryloxy, benzyloxy, C(=O)$R^E$, $NR^F$C(=O)$R^E$, $NR^F$—($C_1$-$C_4$-alkylene) C(=O)$R^E$, $NR^F$—($C_1$-$C_4$-alkylene)-$NR^CR^D$, O—($C_1$-$C_4$-alkylene)-$NR^CR^D$, or 4- to 6-membered saturated, partially or fully unsaturated, or aromatic carbocyclyl, carbocyclyl-$C_1$-$C_2$-alkyl, heterocyclyl, heterocyclyloxy, or heterocyclyl-$C_1$-$C_2$-alkyl, or 8- to 10-membered saturated, partially or fully unsaturated, or aromatic carbobicyclyl or heterobicyclyl, wherein the aforementioned heterocyclic or heterobicyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents $R^X$;

$R^5$ is a 5- or 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents $R^Y$;

and wherein $R^N$ is H, $C_1$-$C_4$-alkyl, HO(C=O)—$C_1$-$C_4$-alkyl, $NR^CR^D$—$C_1$-$C_4$-alkyl, $C_1$-$C_2$alkoxy-$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, $NR^CR^D$—$C_1$-$C_4$-alkyl, phenyl, benzyl, $OR^G$, or $NR^HR^I$; or a 5- or 6-membered saturated, partially or fully unsaturated heterocyclyl, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^F$;

$R^F$ is H, $C_1$-$C_2$-alkyl, $C_3$-$C_6$-cycloalkyl, phenyl, benzyl, or C(=O)$NR^HR^I$;

$R^G$ is H, $C_1$-$C_2$-alkyl, or 5- or 6-membered aromatic carbocyclyl, carbocyclyl-$C_1$-$C_2$alkyl, heterocyclyl, or heterocyclyl-$C_1$-$C_2$alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is OH, $NR^CR^D$, halogen, CN, $NO_2$, $C_1$-$C_2$-alkyl, $C_1$-$C_2$haloalkyl, $NR^CR^D$—$C_1$-$C_4$-alkyl, $R^CO$—$C_1$-$C_4$-alkyl, $C_1$-$C_2$-alkoxy, C(=O)$R^E$, or two $R^X$ form =O, or two $R^X$ together with the carbon atom to which they are bonded form a 3- to 5-membered saturated, partially or fully unsaturated, or aromatic carbocyclic ring;

$R^Y$ is halogen, CN, OH, $C_1$-$C_2$-alkyl, HO—$C_1$-$C_2$-alkyl, $C_3$-$C_6$-cycloalkyl, $C_1$-$C_2$-alkoxy, $NR^CR^D$, S(=O)$_2$ $NR^CR^D$, C(=O)$R^E$, or 5- or 6-membered saturated, partially or fully unsaturated, or aromatic carbocyclyl, carbocyclyl-$C_1$-$C_2$-alkyl, heterocyclyl, and heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form =O; or two $R^Y$ attached to identical or neighboring carbon atoms may form a 3-membered carbocyclic ring;

with the proviso that either any one of $R^1$, $R^2$, or $R^3$ is $NR^CR^D$, $NR^CR^D$—$C_1$-$C_4$-alkyl, $NR^F$—($C_1$-$C_4$-alkylene)-$NR^CR^D$, O—($C_1$-$C_4$-alkylene)-$NR^CR^D$, or 8- to 10-membered saturated, partially or fully unsaturated, or aromatic carbobicyclyl or heterobicyclyl, wherein the aforementioned heterobicyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or any one of $R^1$, $R^2$, or $R^3$ is $NR^F$C(=O)$R^E$, wherein $R^E$ is $NR^CR^D$—$C_1$-$C_4$-alkyl;

or $R^N$ is $NR^CR^D$—$C_1$-$C_4$-alkyl, or $C_1$-$C_2$-alkoxy-$C_1$-$C_4$-alkyl;

or any one of the substituents $R^1$, $R^2$, $R^3$, $R^4$, $R^5$, $R^N$ carries a substituent $R^X$, wherein $R^X$ is OH, $NR^CR^D$, $NR^CR^D$—$C_1$-$C_4$-alkyl, or $R^CO$—$C_1$-$C_4$-alkyl.

Preferably, the compound of formula (I) and the targeting moiety T are covalently bonded to the linker $L^2$, so that the linker $L^2$ links the compound of formula (I) to the targeting moiety T. Optionally, the targeting moiety may be linked to one or more, preferably 1 to 30, compounds of formula (I) via the linker $L^2$. Thus, the conjugate may be represented by the following formula:

$$[(I)\text{-}L^2]_a\text{-}T$$

wherein (I) refers to the compound of formula (I), $L^2$ is the linker $L^2$,

T is the targeting moiety T, and a is an integer of from 1 to 30.

The linker $L^2$ may be bonded to the compound of formula (I) and the targeting moiety such that it is cleavable or non-cleavable.

The above defined provisos regarding the compound of formula (I) define functional groups, which preferably form the covalent bond to the linker $L^2$. In connection with the provisos it is to be understood that, although it is sufficient that one of the given alternatives is fulfilled, this does not exclude that more than one of the given alternatives are fulfilled by the compounds of formula (I). Therefore, the term “any one of” also includes the option “at least one of”. In other words, if, e.g., $R^2$ is selected according to the proviso, this does not exclude that $R^1$ or $R^3$ is selected according to the proviso. Similarly, if, e.g., $R^2$ is selected according to the proviso, this does not exclude that $R^N$ is selected according to the proviso, and/or that any one of the substituents $R^1$, $R^2$, $R^3$, $R^4$, $R^5$, $R^N$ carries a substituent $R^X$ according to the proviso. As used in connection with the proviso, the term “carries a substituent $R^X$” means that the mentioned substituent may carry the substituent $R^X$ at any position, which also includes the option that $R^X$ is attached to $R^Y$, wherein $R^Y$ is attached to the mentioned substituent. This is particularly relevant in connection with the substituent $R^5$. In connection with $R^5$, the term “carries a substituent $R^X$” preferably means that $R^5$ represents a 5- or 6-membered saturated heterocyclic ring as defined herein, which is substituted by $R^Y$, wherein $R^Y$, which is preferably a pyridine, is further substituted by $R^X$. On the other hand, in connection with the remaining substituents, e.g., $R^4$, the term “carries a substituent $R^X$” preferably means that $R^4$ represents a 5- or 6-membered aromatic carbocyclic or heterocyclic ring, or a 9- or 10-membered aromatic carbobicyclic or heterobicyclic ring, wherein a substitutable carbon or heteroatom in the aforementioned cyclic rings is substituted with a substituent $R^X$.

In one embodiment, the present invention relates to a conjugate as defined above, wherein a covalent bond between the compound of formula (I) and the linker $L^2$ is established by the reaction of a functional group of the compound of formula (I) with a functional group handle of the linker $L^2$ and wherein a covalent bond between the targeting moiety T and the linker $L^2$ is established by the reaction of a functional group of the targeting moiety T with a functional group handle of the linker $L^2$; and wherein preferably the functional group of the compound of formula (I) is attached to or part of the substituents $R^2$, $R^4$, $R^5$, or $R^N$ so that the linker $L^2$, to which the targeting moiety is covalently bonded on one end, will on the other end be covalently bonded to the compound of formula (I) according to any one of the following structures:

(I-$R^2$-$L^2$-T)

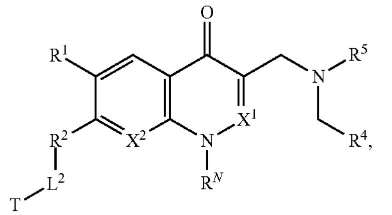

(I-$R^N$-$L^2$-T)

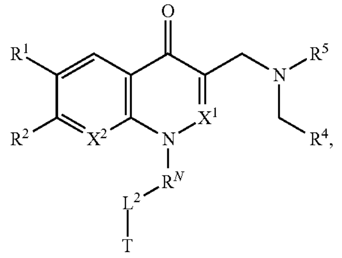

(I-$R^4$-$L^2$-T)

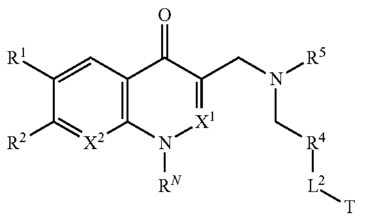

(I-$R^5$-$L^2$-T)

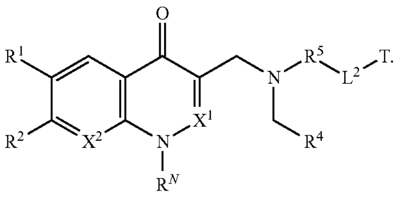

In another embodiment, the present invention relates to a conjugate as defined above, wherein the linker $L^2$ comprises (i) a chain $L^C$ of 2 to 100 atoms selected from carbon, nitrogen, oxygen, and sulfur atoms, which may be interrupted by 5- to 10-membered aryl and heteroaryl groups and/or 3- to 8-membered saturated carbocyclyl or heterocyclyl groups, wherein the aforementioned heteroaryl and heterocyclic groups comprise one or more, same or different heteroatoms selected from O, N or S, wherein said N- and/or S-atoms are independently oxidized or non-oxidized, and wherein each substitutable carbon or heteroatom in the chain is independently unsubstituted or substituted with one or more same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

and preferably a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_5$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$haloalkoxy;

(ii) a functional group handle $H^{1A}$, which is covalently bonded to the compound of formula (I);

(iii) a functional group handle $H^{2B}$, which is covalently bonded to the targeting moiety T.

In one embodiment of the conjugate, the linker $L^2$ has the structure $H^{1A}$-$L^C$-$H^{2B}$ and is selected from the group consisting of:

($L^2$-1)

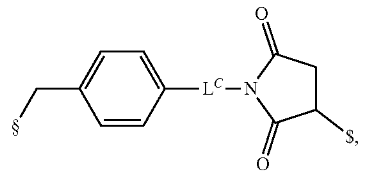

($L^2$-2)

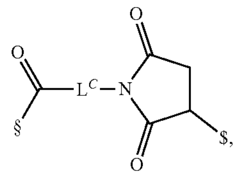

($L^2$-3)

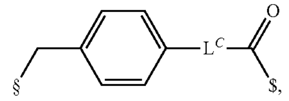

($L^2$-4)

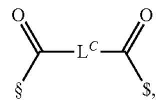

($L^2$-5)

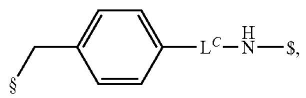

($L^2$-6)

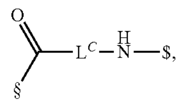

($L^2$-7)

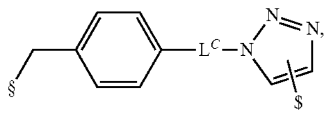

($L^2$-8)

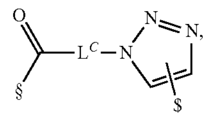

($L^2$-9)

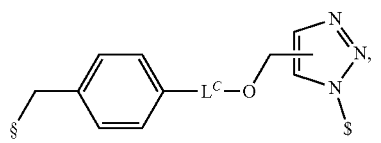

-continued (L$^2$-10)

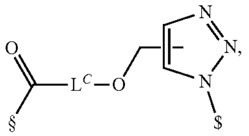

(L$^2$-11)

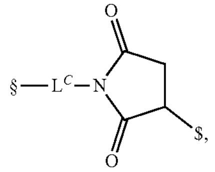

(L$^2$-12)

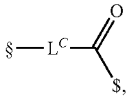

(L$^2$-13)

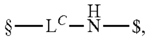

(L$^2$-14)

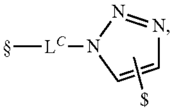

and

-continued (L$^2$-15)

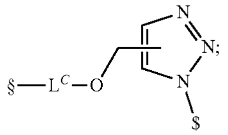

wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy; and § marks the connection to the compound of formula (I); and $ marks the connection to the targeting moiety T; and and wherein preferably $L^C$ is selected from the group consisting of (L$^C$-1)

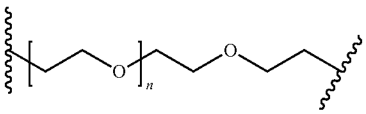

, (L$^C$-2)

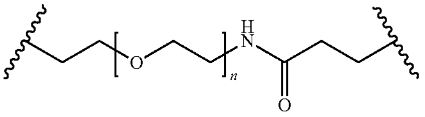

, (L$^C$-3)

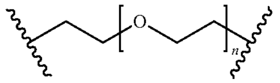

, (L$^C$-4)

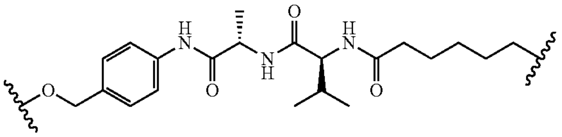

, (L$^C$-5)

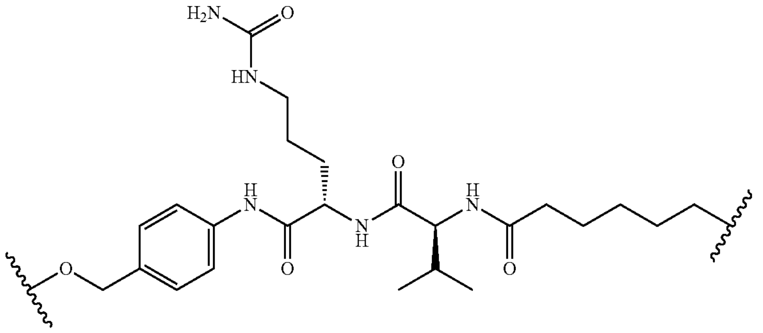

, (L$^C$-6)

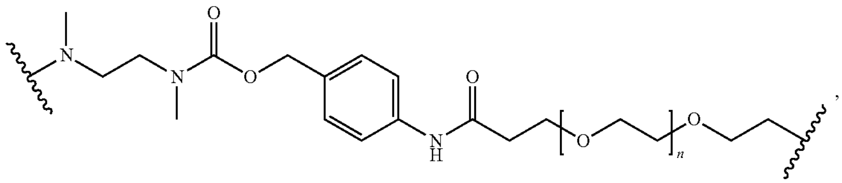

,

-continued ($L^C$-7)

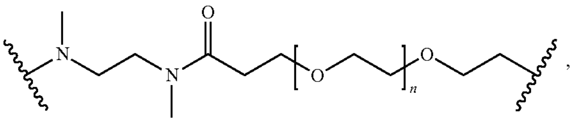

, ($L^C$-8)

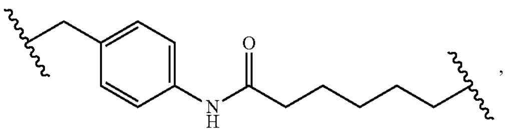

, ($L^C$-9)

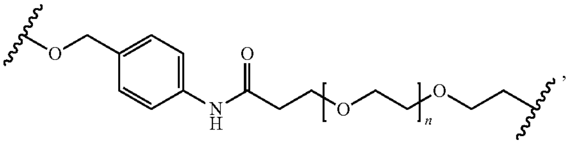

, ($L^C$-10)

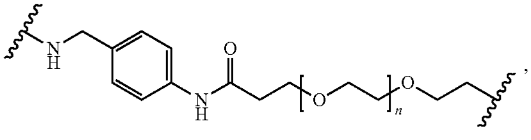

, and ($L^C$-11)

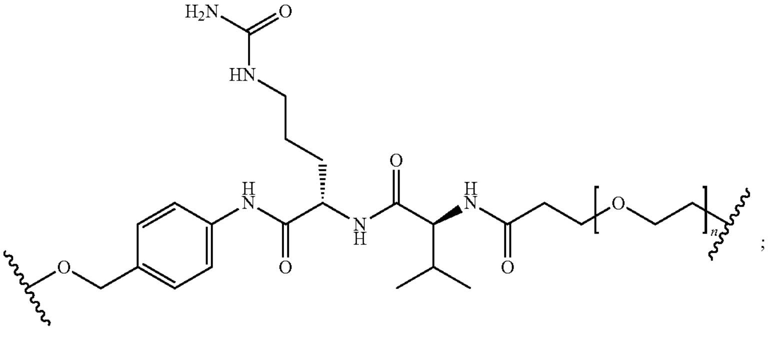

;

wherein n is 0, 1, 2, 3, 4, 5, 6, 7, or 8.

In another embodiment, the present invention relates to a conjugate as defined above, wherein the linker $L^2$ has the structure $H^{1A}$-$L^C$-$H^{2B}$ and is selected from the group consisting of:

($L^2$-1)

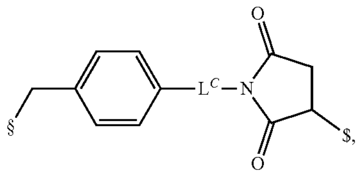

($L^2$-2)

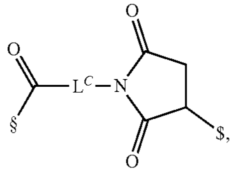

($L^2$-3)

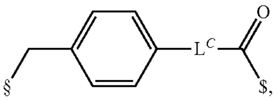

and

-continued ($L^2$-4)

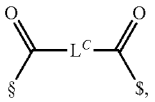

wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$haloalkoxy;

§ marks the connection to the compound of formula (I); and $ marks the connection to the targeting moiety T.

and wherein preferably $L^C$ is selected from the group consisting of ($L^C$-1)

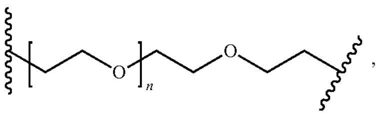

, ($L^C$-2)

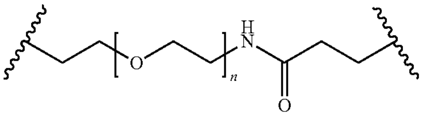

,

-continued ($L^C$-3)

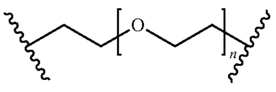
, ($L^C$-4)

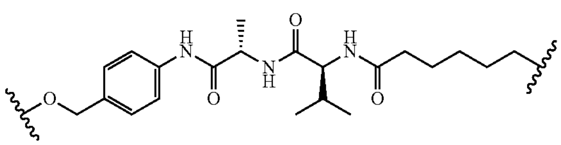
, ($L^C$-5)

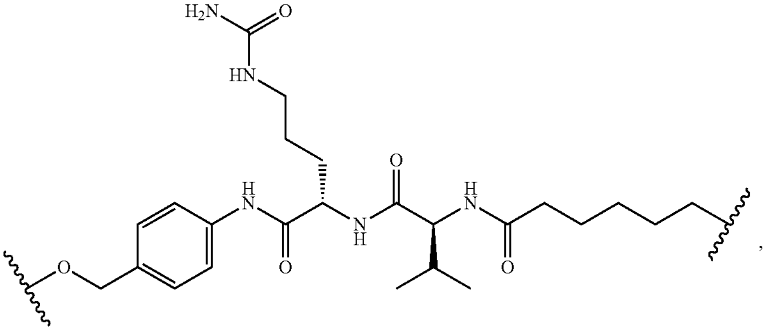
, ($L^C$-6)

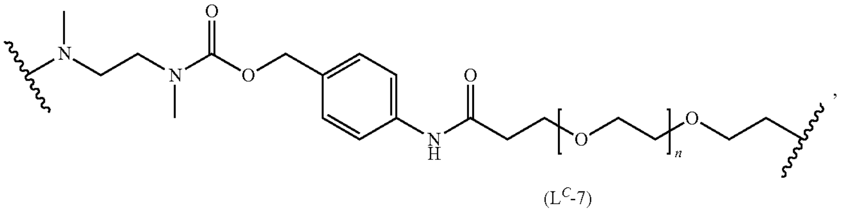
, ($L^C$-7)

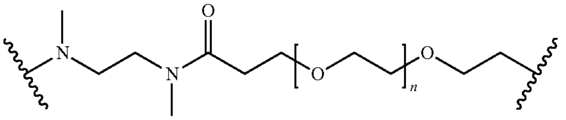
, ($L^C$-8)

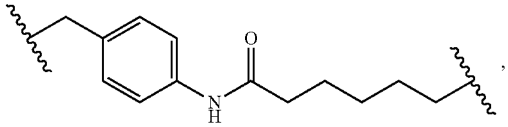
, and ($L^C$-9)

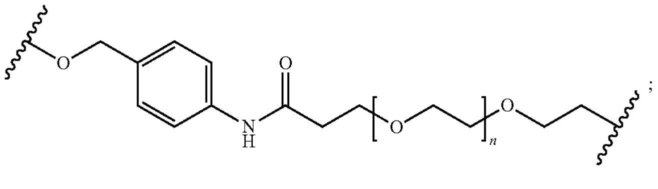
;

wherein n is 0, 1, 2, 3, 4, 5, 6, 7, or 8.

In another embodiment, the present invention relates to a conjugate as defined above, wherein the targeting moiety T comprises an antibody, an antibody fragment, a nucleic acid based molecule, a carbohydrate, a peptide, or a modified peptide, in particular an antibody or an antigen-binding fragment, which is designed to target the Human Epidermal Growth Factor Receptor (EGFR), a plasminogen activator, a cytotoxic T-lymphocyte associated antigen (CTLA) such as CTLA-4, PD-1, PD-L1, KIR, TIM3, VISTA, TIGIT, LAG3, OX40, ROR1, ROR2, vascular endothelial growth factor (VEGF), fibroblast growth factor receptor (FGFR), platelet-derived growth factor (PDGF), transforming growth factor (TGF), neurotrophic factors, a nerve growth factor, platelet-derived growth factor (PDGF), interleukin receptors, transforming growth factor (TGF), estrogen receptor, progesterone receptor, c-Kit, cMET, ErbB2/Her2, ErbB3/Her3, ErbB4/Her4, CD3, CD20, CD22, CD30, CD33, CD40, CD47, CD79, CD123, CD133, CD166, CD137, the mesothelin protein, EpCAM, FLT3, PSMA, PSCA, STEAP, CEA, folate receptor, the CD39/CD73 receptors, adenosine receptors, SLC34A2 gene product, the EphA2 tyrosine kinase, the Muc1/Muc16 cell-surface antigens, ALK, AFP, bcr-Abl, PAP.

In another embodiment, the present invention relates to a compound-linker construct or a conjugate as defined herein, wherein the functional group of the compound of formula (I), which is attached to or part of the substituents $R^2$, $R^4$, $R^5$, or $R^N$, and which forms the covalent bond to the functional group handle $H^{1A}$ of the linker $L^1$ or $L^2$, is selected from the following options: either $R^2$ is $NHR^D$, $NHR^D$—$C_1$-$C_4$-alkyl, NH—($C_1$-$C_4$-alkylene)-$NR^CR^D$, $NR^F$—($C_1$-$C_4$-alkylene)-$NHR^D$, O—($C_1$-$C_4$-alkylene)-$NHR^D$, or 8- to 10-membered saturated heterobicyclyl, wherein the aforementioned heterobicyclic ring comprises at least one nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or $R^2$ is $NR^FC(=O)R^E$, wherein $R^E$ is $NHR^D$—$C_1$-$C_4$-alkyl;

or $R^N$ is $NHR^D$—$C_1$-$C_4$-alkyl;

or any one of the substituents $R^2$, $R^4$, $R^5$, $R^N$ carries a substituent $R^X$, wherein $R^X$ is OH, $NHR^D$, $NHR^D$—$C_1$-$C_4$-alkyl, or HO—$C_1$-$C_4$-alkyl;

and preferably either $R^2$ is $NH_2$, $NH_2$—$C_1$-$C_2$-alkyl, NH—($C_1$-$C_3$-alkylene)-$NH_2$, NH—($C_1$-$C_3$-alkylene)-$NHCH_3$, NH—($C_1$-$C_3$-alkylene)-$N(CH_3)_2$, O—($C_1$-$C_3$-alkylene)-$NH_2$, or O—($C_1$-$C_3$-alkylene)-$NHCH_3$;

or $R^2$ is $NHC(=O)R^E$, wherein $R^E$ is $NH_2$—$C_1$-$C_4$-alkyl;

or $R^N$ is $NH_2$—$C_1$-$C_3$-alkyl;

or any one of the substituents $R^2$, $R^4$, or $R^5$ carries a substituent $R^X$, wherein $R^X$ is OH, $NH_2$, $NHCH_3$, $NH_2$—$C_1$-$C_2$-alkyl, or HO—$C_1$-$C_2$-alkyl.

In another embodiment, the present invention relates to a compound-linker construct or a conjugate as defined herein, wherein in the compound of formula (I)

$X^1$ is CH;

$X^2$ is $CR^3$ with $R^3$ being H;

$R^1$ is H or F;

$R^2$ is H, OH, $NR^CR^D$, CN, halogen, $NR^CR^D$—$C_1$-$C_4$-alkyl, $NR^FC(=O)R^E$, $NR^F$—($C_1$-$C_4$-alkylene) C(=O) $R^E$, $NR^F$—($C_1$-$C_4$-alkylene)-$NR^CR^D$, O—($C_1$-$C_4$-alkylene)-$NR^CR^D$, or 4- to 6-membered saturated heterocyclyl, or 8- to 10-membered saturated heterobicyclyl, wherein the aforementioned heterocyclic or heterobicyclic rings comprise a nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is pyridinyl, wherein each substitutable carbon atom in the cyclic ring is independently unsubstituted or substituted by one or more, same or different substituents $R^X$;

$R^5$ is piperidine, wherein each substitutable carbon or heteroatom in the piperidine ring is independently unsubstituted or substituted by one or more, same or different substituents $R^Y$; and $R^N$ is H, $C_1$-$C_4$-alkyl, HO(C=O)—$C_1$-$C_3$-alkyl, $NHR^D$—$C_1$-$C_3$-alkyl, $C_1$-$C_2$alkoxy-$C_1$-$C_3$-alkyl, or cyclopropyl;

wherein preferably $R^C$ is H or $C_1$-$C_2$-alkyl;

$R^D$ is H or $C_1$-$C_2$-alkyl;

$R^E$ is $NH_2$—$C_1$-$C_4$-alkyl;

$R^F$ is H;

$R^X$ is halogen, OH, $NH_2$, $NHCH_3$, $C_1$-$C_2$-alkyl, $C_1$-$C_2$alkoxy, $NH_2$—$C_1$-$C_2$-alkyl, HO—$C_1$-$C_2$-alkyl, or two $R^X$ together with the carbon atom to which they are bonded form a 3-membered saturated carbocyclic ring;

$R^Y$ is halogen, OH, $NH_2$, or a 5- or 6-membered aromatic heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

with the proviso that either $R^2$ is $NH_2$, $NH_2$—$C_1$-$C_2$-alkyl, NH—($C_1$-$C_3$-alkylene)-$NH_2$, NH—($C_1$-$C_3$-alkylene)-$NHCH_3$, NH—($C_1$-$C_3$-alkylene)-$N(CH_3)_2$, O—($C_1$-$C_3$-alkylene)-$NH_2$, or O—($C_1$-$C_3$-alkylene)-$NHCH_3$;

or $R^2$ is $NHC(=O)R^E$, wherein $R^E$ is $NH_2$—$C_1$-$C_4$-alkyl;

or $R^N$ is $NH_2$—$C_1$-$C_3$-alkyl;

or any one of the substituents $R^2$, $R^4$, or $R^5$ carries a substituent $R^X$, wherein $R^X$ is OH, $NH_2$, $NHCH_3$, $NH_2$—$C_1$-$C_2$-alkyl, or HO—$C_1$-$C_2$-alkyl.

In a further aspect, the present invention relates to a pharmaceutical composition comprising a pharmaceutically effective amount of the compound-linker construct as defined herein or the conjugate as defined herein, and optionally a pharmaceutically acceptable carrier, diluent or excipient.

In yet another aspect, the present invention relates to a compound-linker construct as defined herein or a conjugate as defined herein, or a pharmaceutical composition comprising the compound-linker construct or the conjugate as defined herein for use in medicine. In particular, the present invention relates to a compound-linker construct as defined herein or a conjugate as defined herein, or a pharmaceutical composition comprising the compound-linker construct or the conjugate as defined herein for use in modulating STING, in particular activating STING.

In yet another aspect, the present invention relates to a compound-linker construct as defined herein or a conjugate as defined herein, or a pharmaceutical composition comprising the compound-linker construct or the conjugate as defined herein for use in a method of treating a disease, in which the modulation of STING, in particular the activation of STING, is beneficial.

In one embodiment, the compound-linker construct as defined herein or the conjugate as defined herein, or the pharmaceutical composition comprising the compound-linker construct or the conjugate as defined herein is for use in the treatment of a disease selected from the group consisting of cancer, pre-cancerous syndromes, and infectious diseases; or for use in an immunogenic composition or as vaccine adjuvant.

In another embodiment, the compound-linker construct as defined herein or the conjugate as defined herein, or the pharmaceutical composition comprising the compound-linker construct or the conjugate as defined herein is for use in the treatment of a disease selected from the group consisting of inflammatory diseases, allergic diseases, and autoimmune diseases.

In a further aspect, the present invention relates to methods of treatment comprising the administration of the compound-linker construct as defined herein or the conjugate as defined herein, or the pharmaceutical composition comprising the compound-linker construct or the conjugate as defined herein to a human or animal body.

DETAILED DESCRIPTION

Figure 1A:
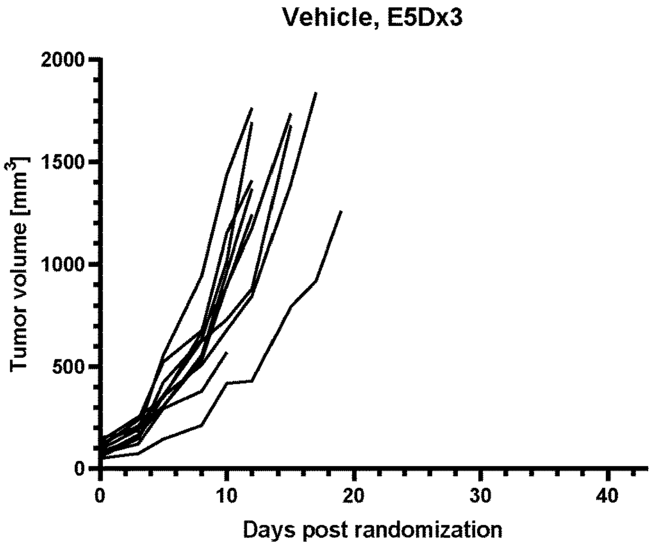
FIG. 1A-FIG. 1C show the efficacy of Example 4 in CT26 murine colon carcinoma allograft in Balb/C female mice.

In the following, preferred embodiments of the compound-linker construct as defined herein and the conjugate as defined herein as well as in this connection preferred embodiments of the substituents in the compounds of formula (I), preferred embodiments of the linkers $L^1$ and $L^2$ and preferred embodiments of the targeting moieties are described in further detail. It is to be understood that each preferred embodiment is relevant on its own as well as in combination with other preferred embodiments.

As indicated above, the present invention relates to compound-linker constructs and conjugates comprising a compound of formula (I). The compound of formula (I) will be described in further detail hereinafter.

As explained in further detail below, it is to be understood that in the compound-linker construct or the conjugate of the invention, the covalent bond between the compound of formula (I) and the linker $L^1$ or $L^2$ is established by the reaction of a functional group of the compound of formula (I) with a functional group handle of the linker $L^1$ or $L^2$. Preferred functional groups for forming the covalent bond to the linker $L^1$ and $L^2$ will be defined further below. These groups preferably comprise amino or hydroxy groups. It is to be understood that upon reaction with the linker $L^1$ or $L^2$, a hydrogen atom of these groups will be replaced by $L^1$ or $L^2$, so that e.g. O-$L^1$, O-$L^2$, N-$L^1$ or N-$L^2$ bonds will be formed. Thus, when defining the compounds of formula (I) hereinafter, it is to be understood that at one of the defined substituents, especially at a hydroxyl or amino group, a hydrogen atom will be replaced by $L^1$ or $L^2$ in the compound-linker constructs and conjugates comprising the compound of formula (I). For ease of reference, this replaced hydrogen atom is not considered in the subsequent definition of the compound of formula (I), but a skilled person will understand that in the claimed compound-linker constructs and conjugates, one hydrogen atom is nevertheless missing and replaced by the linker $L^1$.

The compound of formula (I) being part of the compound-linker constructs and conjugates of the invention has the following formula:

(I)

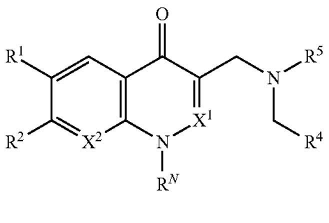

wherein $X^1$ is CH or N; and

Accordingly, the compound of formula (I) may therefore be a compound of formula (Ia), (Ib), (Ic) or (Id) as shown below:

(Ia)

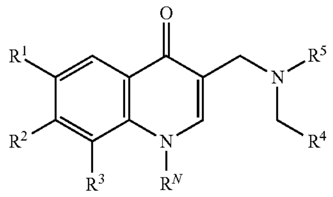

(Ib)

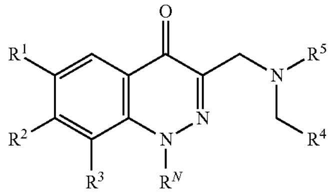

(Ic)

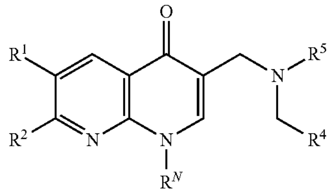

(Id)

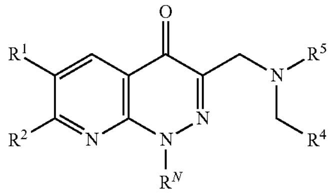

In a preferred embodiment, the compound of formula (I) is a compound of formula (Ia) or (Ib), in particular a compound of formula (Ia).

In another preferred embodiment of the compound of formula (I), $X^2$ is $CR^3$ with $R^3$ being H.

Accordingly, the compound of formula (I) is preferably a compound of formula (Ia) or (Ib), wherein $R^3$ is H.

In one embodiment of the invention, the compound of formula (I) is a compound of formula (Ia), wherein $R^3$ is H. These compounds are referred to as compounds of formula (Ia*) as shown below:

(Ia*)

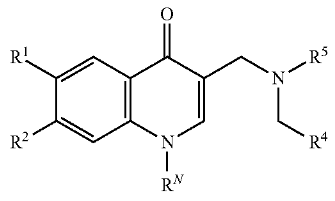

In connection with the compounds according to formula (Ia), (Ib), (Ic) and (Id) as well as (Ia*), it is to be understood that the substituents $R^1$, $R^2$, $R^3$, $R^4$, $R^5$, and $R^N$ are as defined above in formula (I). Further preferred embodiments regarding these substituents are provided further below.

As indicated above, any one of the substituents $R^1$, $R^2$, $R^3$, $R^4$, $R^5$, or $R^N$ either represents or carries a functional group that is suitable for further functionalization, wherein the functionalization includes the formation of a compound-linker construct or a conjugate according to the present invention. In particular, either any one of $R^1$, $R^2$, or $R^3$ is $NR^CR^D$, $NR^CR^D$—$C_1$-$C_4$-alkyl, $NR^F$—($C_1$-$C_4$-alkylene)-$NR^CR^D$, O—($C_1$-$C_4$-alkylene)-$NR^CR^D$, or 8- to 10-membered saturated, partially or fully unsaturated, or aromatic carbobicyclyl or heterobicyclyl, wherein the aforementioned heterobicyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or any one of $R^1$, $R^2$, or $R^3$ is $NR^FC$(═O)$R^E$, wherein $R^E$ is $NR^CR^D$—$C_1$-$C_4$-alkyl;

or $R^N$ is $NR^CR^D$—$C_1$-$C_4$-alkyl, or $C_1$-$C_2$-alkoxy-$C_1$-$C_4$-alkyl;

or any one of the substituents $R^1$, $R^2$, $R^3$, $R^4$, $R^5$, $R^N$ carries a substituent $R^X$, wherein $R^X$ is OH, $NR^CR^D$, $NR^CR^D$—$C_1$-$C_4$-alkyl, or $R^C$O—$C_1$-$C_4$-alkyl.

Preferably, either any one of $R^1$, $R^2$, or $R^3$ is $NR^CR^D$, $NR^CR^D$—$C_1$-$C_4$-alkyl, $NR^F$—($C_1$-$C_4$-alkylene)-$NR^CR^D$, O—($C_1$-$C_4$-alkylene)-$NR^CR^D$, or 8- to 10-membered saturated, partially or fully unsaturated, or aromatic carbobicyclyl or heterobicycly, wherein the aforementioned heterobicyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or any one of $R^1$, $R^2$, or $R^3$ is $NR^FC$(═O)$R^E$, wherein $R^E$ is $NR^CR^D$—$C_1$-$C_4$-alkyl;

or $R^N$ is $NR^CR^D$—$C_1$-$C_4$-alkyl;

or any one of the substituents $R^1$, $R^2$, $R^3$, $R^4$, $R^5$, $R^N$ carries a substituent $R^X$, wherein $R^X$ is OH, $NR^CR^D$, $NR^CR^D$—$C_1$-$C_4$-alkyl, or $R^C$O—$C_1$-$C_4$-alkyl.

Preferably, either any one of $R^1$, $R^2$, or $R^3$ is $NHR^D$, $NR^CR^D$—$C_1$-$C_4$-alkyl, $NR^F$—($C_1$-$C_4$-alkylene)-$NR^CR^D$, O—($C_1$-$C_4$-alkylene)-$NR^CR^D$, or 8- to 10-membered saturated, partially or fully unsaturated, or aromatic carbobicyclyl or heterobicyclyl, wherein the aforementioned heterobicyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or any one of $R^1$, $R^2$, or $R^3$ is $NR^FC$(═O)$R^E$, wherein $R^E$ is $NR^CR^D$—$C_1$-$C_4$-alkyl;

or $R^N$ is $NR^CR^D$—$C_1$-$C_4$-alkyl;

or any one of the substituents $R^1$, $R^2$, $R^3$, $R^4$, $R^5$, $R^N$ carries a substituent $R^X$, wherein $R^X$ is OH, $NR^CR^D$, $NR^CR^D$—$C_1$-$C_4$-alkyl, or $R^C$O—$C_1$-$C_4$-alkyl.

Preferably, any one of $R^2$, $R^4$, $R^5$, or $R^N$ either represents or carries a functional group that is suitable for further functionalization. In particular, either $R^2$ is $NHR^D$, $NHR^D$—$C_1$-$C_4$-alkyl, NH—($C_1$-$C_4$-alkylene)-$NR^CR^D$, $NR^F$—($C_1$-$C_4$-alkylene)-$NHR^D$, O—($C_1$-$C_4$-alkylene)-$NHR^D$, or 8- to 10-membered saturated heterobicyclyl, wherein the aforementioned heterobicyclic ring comprises at least one nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or $R^2$ is $NR^FC$(═O)$R^E$, wherein $R^E$ is $NHR^D$—$C_1$-$C_4$-alkyl;

or $R^N$ is $NHR^D$—$C_1$-$C_4$-alkyl;

or any one of the substituents $R^2$, $R^4$, $R^5$, $R^N$ carries a substituent $R^X$, wherein $R^X$ is OH, $NHR^D$, $NHR^D$—$C_1$-$C_4$-alkyl, or HO—$C_1$-$C_4$-alkyl.

More preferably, any one of $R^2$, $R^4$, or $R^5$ either represents or carries a functional group that is suitable for further functionalization. In particular, either $R^2$ is $NH_2$, $NH_2$—$C_1$-$C_2$-alkyl, NH—($C_1$-$C_3$-alkylene)-$NH_2$, NH—($C_1$-$C_3$-alkylene)-$NHCH_3$, NH—($C_1$-$C_3$-alkylene)-$N(CH_3)_2$, O—($C_1$-$C_3$-alkylene)-$NH_2$, or O—($C_1$-$C_3$-alkylene)-$NHCH_3$;

or $R^2$ is NHC(═O)$R^E$, wherein $R^E$ is $NH_2$—$C_1$-$C_4$-alkyl;

or $R^N$ is $NH_2$—$C_1$-$C_3$-alkyl;

or any one of the substituents $R^2$, $R^4$, or $R^5$ carries a substituent $R^X$, wherein $R^X$ is OH, $NH_2$, $NHCH_3$, $NH_2$—$C_1$-$C_2$-alkyl, or HO—$C_1$-$C_2$-alkyl.

Most preferably, $R^2$ either represents or carries a functional group that is suitable for further functionalization. In particular, either $R^2$ is $NH_2$, $NH_2$—$C_1$-$C_2$-alkyl, NH—($C_1$-$C_3$-alkylene)-$NH_2$, NH—($C_1$-$C_3$-alkylene)-$NHCH_3$, NH—($C_1$-$C_3$-alkylene)-$N(CH_3)_2$, O—($C_1$-$C_3$-alkylene)-$NH_2$, or O—($C_1$-$C_3$-alkylene)-$NHCH_3$;

or $R^2$ is NHC(=O)$R^E$, wherein $R^E$ is $NH_2$—$C_1$-$C_4$-alkyl;

or any $R^2$ carries a substituent $R^X$, wherein $R^X$ is OH, $NH_2$, $NHCH_3$, $NH_2$—$C_1$-$C_2$-alkyl, or HO—$C_1$-$C_2$-alkyl.

In connection with the above options for the functional groups, it is to be understood that, although it is sufficient that one of the given alternatives is fulfilled, this does not exclude that more than one of the given alternatives are fulfilled by the compounds of formula (I). As used in connection with the above options, the term "carries a substituent $R^X$" means that the mentioned substituent may carry the substituent $R^X$ at any position, which also includes the option that $R^X$ is attached to $R^Y$, wherein $R^Y$ is attached to the mentioned substituent. This is particularly relevant in connection with the substituent $R^5$. In connection with $R^5$, the term "carries a substituent $R^X$" preferably means that $R^5$ represents a 5- or 6-membered saturated heterocyclic ring as defined herein, which is substituted by $R^Y$, wherein $R^Y$, which is preferably a pyridine, is further substituted by $R^X$. On the other hand, in connection with the remaining substituents, e.g., $R^4$, the term "carries a substituent $R^X$" preferably means that $R^4$ represents a 5- or 6-membered aromatic carbocyclic or heterocyclic ring, or a 9- or 10-membered aromatic carbobicyclic or heterobicyclic ring, wherein a substitutable carbon or heteroatom in the aforementioned cyclic rings is substituted with a substituent $R^X$.

The following substituents are preferred in connection with the compound of formula (I), as well as in connection with the compounds of formula (Ia), (Ib), (Ic) and (Id), especially in connection with the compounds of formula (Ia) and (Ib), and in particular in connection with the compounds according to formula (Ia), and in connection with the compounds according to formula (Ia*).

In one preferred embodiment, $R^1$ is H or F.

Accordingly, if the compound of formula (I) is a compound of formula (Ia*) as defined above, it may be represented by the formula (Ia*.1) or (Ia*.2) as shown below:

(Ia*.1)

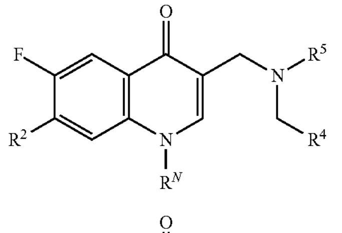

(Ia*.2)

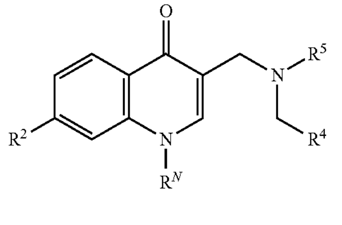

Thus, in a particularly preferred embodiment according to the present invention, the compound of formula (I) is a compound of formula (Ia*.1) or (Ia*.2).

The following substituents are therefore not only preferred in connection with the compound of formula (I) as well as in connection with the compounds of (la), (Ib), (Ic) and (Id), especially in connection with the compounds of formula (Ia) and (Ib), and in particular in connection with the compounds according to formula (Ia), and in connection with the compounds according to formula (Ia*), but especially preferably in connection with the compounds of formula (Ia*.1) and (Ia*.2).

In one preferred embodiment, $R^2$ is H, OH, $NR^CR^D$, CN, halogen, $NR^CR^D$—$C_1$-$C_4$-alkyl, $C_1$-$C_4$-alkoxy, $NR^F$C(=O)$R^E$, $NR^F$—($C_1$-$C_4$-alkylene)-C(=O)$R^E$, $NR^F$—($C_1$-$C_4$-alkylene)-$NR^CR^D$, O—($C_1$-$C_4$-alkylene)-$NR^CR^D$, or 4- to 6-membered saturated, partially or fully unsaturated, or aromatic heterocyclyl or 8- to 10-membered saturated, partially or fully unsaturated, or aromatic heterobicyclyl, wherein the aforementioned heterocyclic or heterobicyclic rings comprise a nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In one preferred embodiment, $R^2$ is H, OH, $NR^CR^D$, CN, halogen, $NR^CR^D$—$C_1$-$C_4$-alkyl, $NR^F$C(=O)$R^E$, $NR^F$—($C_1$-$C_4$-alkylene) C(=O) $R^E$, $NR^F$—($C_1$-$C_4$-alkylene)-$NR^CR^D$, O—($C_1$-$C_4$-alkylene)-$NR^CR^D$, or 4- to 6-membered saturated heterocyclyl, or 8- to 10-membered saturated heterobicyclyl, wherein the aforementioned heterocyclic or heterobicyclic rings comprise a nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In a more preferred embodiment, $R^2$ is H, $NHR^D$, halogen, $NHR^D$—$C_1$-$C_4$-alkyl, NHC(=O)$R^E$, NH—($C_1$-$C_4$-alkylene)-C(=O)$R^E$, NH—($C_1$-$C_4$-alkylene)-$NR^CR^D$, O—($C_1$-$C_4$-alkylene)-$NR^CR^D$, or 4- to 6-membered saturated heterocyclyl, or 8- to 10-membered saturated heterobicyclyl, wherein the aforementioned heterocyclic or heterobicyclic rings comprise a nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In an even more preferred embodiment, $R^2$ is H, $NHR^D$, halogen, $NHR^D$—$C_1$-$C_4$-alkyl, NHC(=O)$R^E$, NH—($C_1$-$C_4$-alkylene)-$NR^CR^D$, O—($C_1$-$C_4$-alkylene)-$NR^CR^D$, or 4- to 6-membered saturated heterocyclyl, or 9- to 10-membered saturated heterobicyclyl, wherein the aforementioned heterocyclic or heterobicyclic rings comprise one or two nitrogen atoms, wherein said N-atoms are independently oxidized or non-oxidized, and wherein each substitutable carbon or heteroatom in the aforementioned groups is independently unsubstituted or substituted with one or more, same or different substituents $R^X$.

If an $R^X$ group is present at $R^2$, it is preferred that $R^X$ is halogen, OH, $NH_2$, $NHCH_3$, $C_1$-$C_2$alkyl, $C_1$-$C_2$alkoxy, $NH_2$—$C_1$-$C_2$-alkyl, HO—$C_1$-$C_2$alkyl, or two $R^X$ together with the carbon atom to which they are bonded form a 3-membered saturated carbocyclic ring.

In particular, it is preferred if an $R^X$ group is present at $R^2$ that at least one $R^X$ is OH, $NH_2$, $NHCH_3$, $NH_2$—$C_1$-$C_2$-alkyl, HO—$C_1$-$C_2$alkyl. Such groups are particularly suitable as functional groups to facilitate covalent attachment of the compound of formula (I) to a suitable carrier or to a linker establishing a bond to a suitable carrier.

Furthermore, the following substituent definitions are preferred in connection with the above definition of $R^2$:

$R^C$ is H or $C_1$-$C_2$alkyl;

$R^D$ is H or $C_1$-$C_2$-alkyl;

$R^E$ is $NH_2$—$C_1$-$C_4$-alkyl;

$R^F$ is H.

Preferred $R^2$ groups are selected from the group consisting of H, Br, F, Cl, $NH_2$, ($R^2$-1)

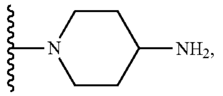

($R^2$-2)

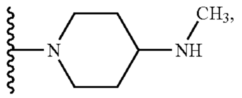

($R^2$-3)

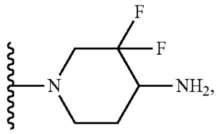

($R^2$-4)

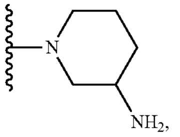

($R^2$-5)

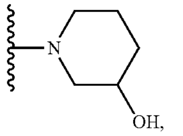

($R^2$-6)

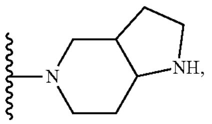

($R^2$-7)

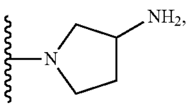

($R^2$-8)

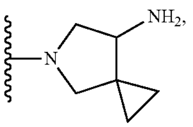

($R^2$-9)

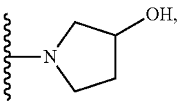

-continued ($R^2$-10)

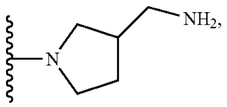

($R^2$-11)

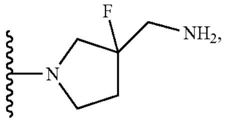

($R^2$-12)

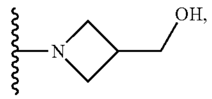

($R^2$-13)

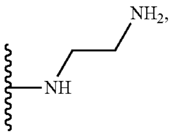

($R^2$-14)

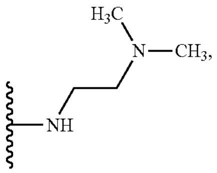

($R^2$-15)

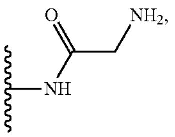

($R^2$-16)

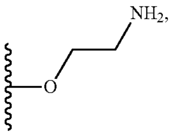

($R^2$-17)

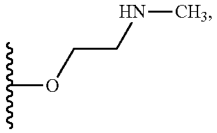

($R^2$-18)

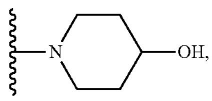

($R^2$-19)

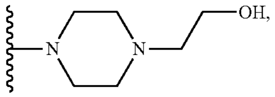

($R^2$-20)

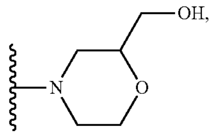

-continued
($R^2$-21)
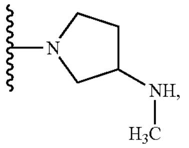
($R^2$-22)
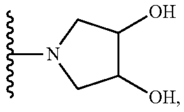
($R^2$-23)
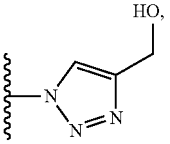
($R^2$-24)
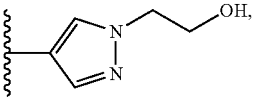
($R^2$-25)
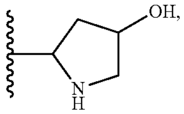
($R^2$-26)
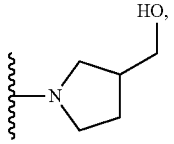
($R^2$-27)
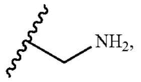
($R^2$-28)
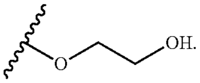
Particularly preferred $R^2$ groups are selected from the group consisting of H, Br, F, $NH_2$,
($R^2$-1)
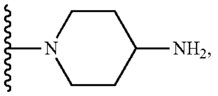
($R^2$-2)
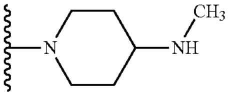
($R^2$-3)
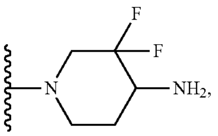
-continued
($R^2$-4)
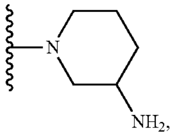
($R^2$-5)
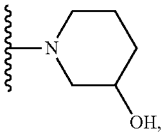
($R^2$-6)
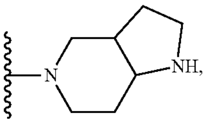
($R^2$-7)
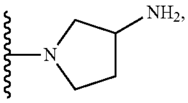
($R^2$-8)
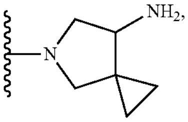
($R^2$-9)
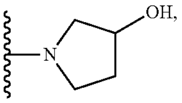
($R^2$-10)
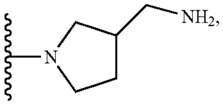
($R^2$-11)
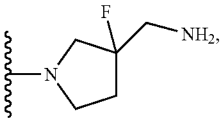
($R^2$-12)
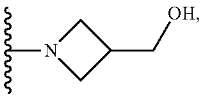
($R^2$-13)
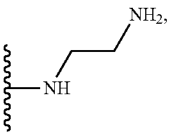
($R^2$-14)
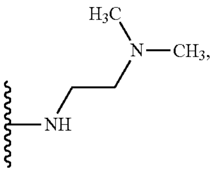

-continued ($R^2$-15)

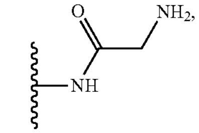

($R^2$-16)

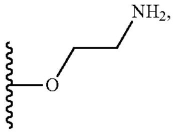

and ($R^2$-17)

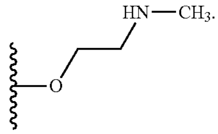

In one preferred embodiment, $R^N$ is H, $C_1$-$C_4$-alkyl, HO(C═O)—$C_1$-$C_3$-alkyl, $NHR^D$—$C_1$-$C_3$-alkyl, $C_1$-$C_2$-alkoxy-$C_1$-$C_3$-alkyl, cyclopropyl or a 4-membered saturated heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$.

If a $R^X$ group is present at $R^N$, it is preferred that $R^X$ is OH or two $R^X$ form ═O.

In connection with the above embodiment with regard to $R^N$ it is preferred that $R^D$ is H.

In one preferred embodiment, $R^N$ is H, $C_1$-$C_4$-alkyl, HO(C═O)—$C_1$-$C_3$-alkyl, $NHR^D$—$C_1$-$C_3$-alkyl, $C_1$-$C_2$-alkoxy-$C_1$-$C_3$-alkyl, or cyclopropyl.

In a more preferred embodiment, $R^N$ is H, $C_1$-$C_3$-alkyl, HO(C═O)—$C_1$-alkyl, or cyclopropyl.

In a more preferred embodiment, $R^N$ is H, $CH_3$, isopropyl or cyclopropyl.

In another more preferred embodiment, $R^N$ is H, $C_1$-$C_2$-alkyl, HO(C═O)—$C_1$-alkyl, or cyclopropyl.

In a more preferred embodiment, $R^N$ is H, $CH_3$ or cyclopropyl.

In one particularly preferred embodiment, $R^N$ is $CH_3$.

In another particularly preferred embodiment, $R^N$ is cyclopropyl.

In one preferred embodiment, $R^4$ is pyridinyl, wherein each substitutable carbon atom in the cyclic ring is independently unsubstituted or substituted by one or more, same or different substituents $R^X$.

If at least one $R^X$ group is present at $R^4$, it is preferred that $R^X$ is $NH_2$, $NHCH_3$, $NH_2$—$C_1$-$C_2$-alkyl, $C_1$-$C_2$-alkyl, or $C_1$-$C_2$-alkoxy.

It is preferred that the pyridinyl is substituted by one or more, same or different substituents $R^X$ as defined above.

Thus, in a more preferred embodiment, $R^4$ is methylpyridinyl, aminopyridinyl or methoxypyridinyl.

Preferably, $R^4$ is any one of the following substituted pyridinyl rings:

($R^4$-1)

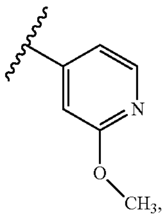

($R^4$-2)

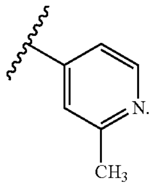

In a particularly preferred embodiment, $R^4$ is methylpyridinyl.

Particularly preferably, $R^4$ is:

($R^4$-2)

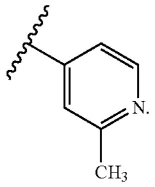

In one embodiment, $R^5$ is a 5- or 6-membered saturated heterocyclic ring, wherein said heterocyclic ring comprises one or more nitrogen atoms, wherein said N-atoms are independently oxidized or non-oxidized, and wherein each substitutable carbon or heteroatom is independently unsubstituted or substituted with one or more, same or different substituents $R^Y$.

In a more preferred embodiment, $R^5$ is a 6-membered saturated heterocyclic ring, wherein said heterocyclic ring comprises one or more nitrogen atoms, wherein said N-atoms are independently oxidized or non-oxidized, and wherein each substitutable carbon or heteroatom is independently unsubstituted or substituted with one or more, same or different substituents $R^Y$.

In a yet more preferred embodiment, $R^5$ is piperidine, wherein each substitutable carbon or heteroatom in the piperidine ring is independently unsubstituted or substituted by one or more, same or different substituents $R^Y$.

If at least one $R^Y$ group is present at $R^5$, it is preferred that $R^Y$ is halogen, OH, $NH_2$, or a 5- or 6-membered aromatic heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

It is preferred that the nitrogen atom of the piperidinyl group is substituted by a substituent $R^Y$, wherein $R^Y$ is a 5- or 6-membered aromatic heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

If at least one $R^X$ group is present at $R^Y$, it is preferred that $R^X$ is F, Cl, $NH_2$, $NHCH_3$, $N(CH_3)_2$, $NH_2$—$C_1$-$C_2$-alkyl, HO—$C_1$-$C_4$-alkyl, $C_1$-$C_2$-alkyl, $C_1$-$C_2$-haloalkyl, or $C_1$-$C_2$-alkoxy.

In one particularly preferred embodiment, $R^5$ is piperidine, wherein each substitutable carbon or heteroatom in the piperidine ring is independently unsubstituted or substituted by one or more, same or different substituents $R^Y$; and wherein the nitrogen atom of the piperidine group is substituted by $R^Y$ being a 5- or 6-membered aromatic heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned heterocyclic ring is independently unsubstituted or substituted with one or more, same or different substituents $R^X$, wherein preferably $R^X$ is F, Cl, $NH_2$, $NHCH_3$, $N(CH_3)_2$, $NH_2$—$C_1$-$C_2$-alkyl, HO—$C_1$-$C_4$-alkyl, $C_1$-$C_2$-alkyl, $C_1$-$C_2$-haloalkyl, or $C_1$-$C_2$-alkoxy.

Accordingly, particularly preferred $R^5$ groups are selected from the group consisting of ($R^5$-1)

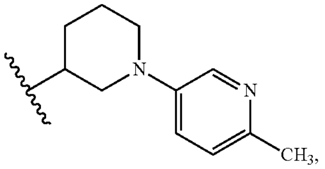

($R^5$-2)

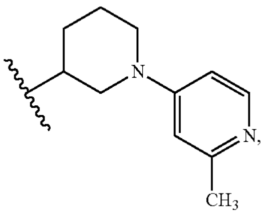

($R^5$-3)

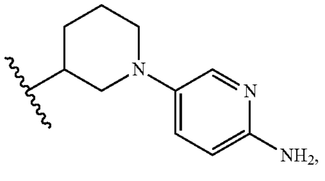

-continued ($R^5$-4)

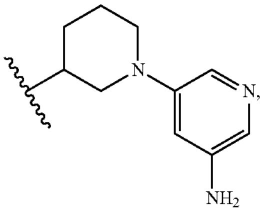

($R^5$-5)

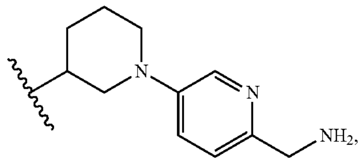

($R^5$-6)

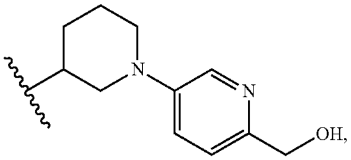

($R^5$-7)

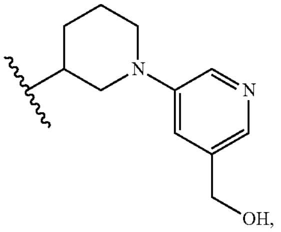

($R^5$-8)

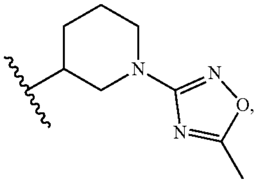

($R^5$-9)

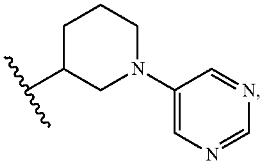

($R^5$-10)

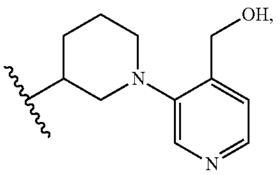

($R^5$-11)

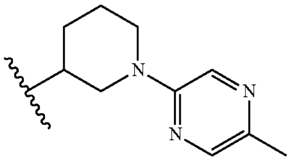

,

-continued
($R^5$-12)
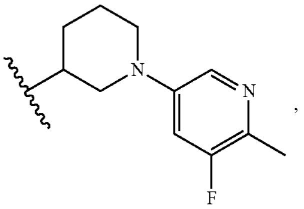
($R^5$-13)
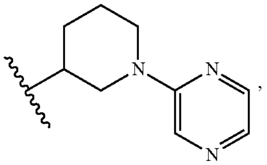
($R^5$-14)
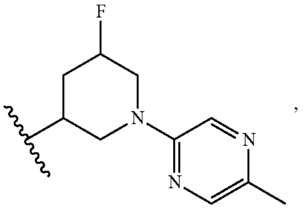
($R^5$-15)
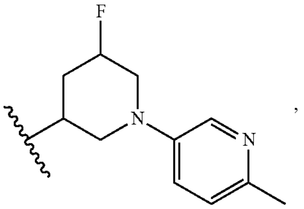
($R^5$-16)
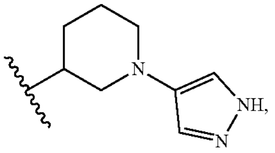
($R^5$-17)
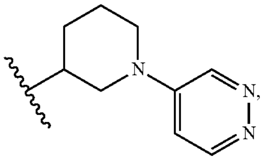
($R^5$-18)
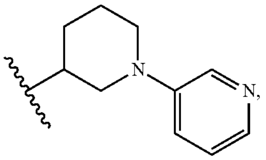
($R^5$-19)
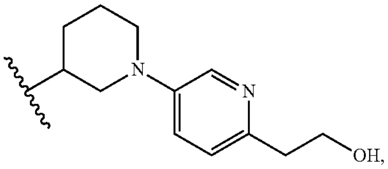
-continued
($R^5$-20)
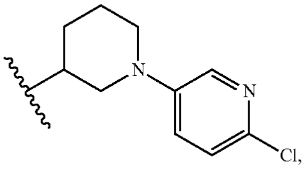
($R^5$-21)
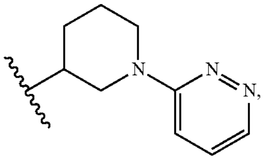
($R^5$-22)
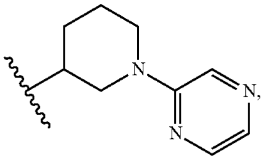
($R^5$-23)
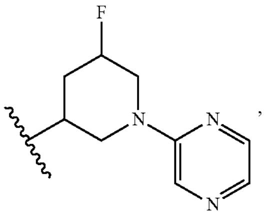
($R^5$-24)
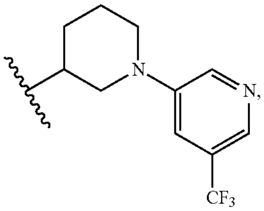
($R^5$-25)
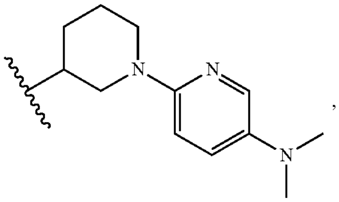
($R^5$-26)
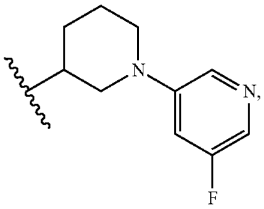

-continued (R5-27)

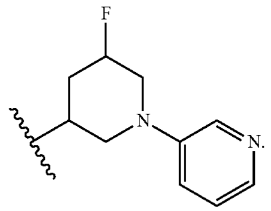

In one preferred embodiment, $R^5$ is a 5- or 6-membered saturated heterocyclic ring, wherein said heterocyclic ring comprises one or more nitrogen atoms, wherein said N-atoms are independently oxidized or non-oxidized, and wherein each substitutable carbon or heteroatom is independently unsubstituted or substituted with one or more, same or different substituents $R^Y$.

In a more preferred embodiment, $R^5$ is a 6-membered saturated heterocyclic ring, wherein said heterocyclic ring comprises one or more nitrogen atoms, wherein said N-atoms are independently oxidized or non-oxidized, and wherein each substitutable carbon or heteroatom is independently unsubstituted or substituted with one or more, same or different substituents $R^Y$.

In a yet more preferred embodiment, $R^5$ is piperidine, wherein each substitutable carbon or heteroatom in the piperidine ring is independently unsubstituted or substituted by one or more, same or different substituents $R^Y$.

If at least one $R^Y$ group is present at $R^5$, it is preferred that $R^Y$ is halogen, OH, $NH_2$, or a 5- or 6-membered aromatic heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

It is preferred that the nitrogen atom of the piperidinyl group is substituted by a substituent $R^Y$, wherein $R^Y$ is a 6-membered aromatic heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

It is more preferred that the nitrogen atom of the piperidinyl group is substituted by a substituent $R^Y$, wherein $R^Y$ is pyridinyl, wherein each substitutable carbon atom is independently unsubstituted or substituted with one or more, same or different substituents $R^X$.

If at least one $R^X$ group is present at $R^Y$, it is preferred that $R^X$ is $NH_2$, $NHCH_3$, $NH_2$—$C_1$-$C_2$-alkyl, $C_1$-$C_2$-alkyl, or $C_1$-$C_2$-alkoxy.

In one particularly preferred embodiment, $R^5$ is piperidine, wherein each substitutable carbon or heteroatom in the piperidine ring is independently unsubstituted or substituted by one or more, same or different substituents $R^Y$; and wherein the nitrogen atom of the piperidine group is substituted by a substituent $R^Y$ being pyridinyl, which is unsubstituted or substituted with one or more, same or different substituents $R^X$, wherein preferably $R^X$ is $NH_2$, $NHCH_3$, $NH_2$—$C_1$-alkyl, or $C_1$-alkyl.

In another particularly preferred embodiment, $R^5$ is piperidine, wherein the nitrogen atom of the piperidine group is substituted by a substituent $R^Y$ being pyridinyl, which is unsubstituted or substituted with one or more, same or different substituents $R^X$, wherein preferably $R^X$ is $NH_2$, $NHCH_3$, $NH_2$—$C_1$-alkyl, or $C_1$-alkyl.

It is especially preferred that $R^5$ is (R5-a)

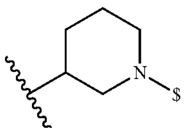

wherein $ marks the connection to the substituent $R^Y$. As indicated above, $R^Y$ is preferably pyridinyl, which is unsubstituted or substituted with one or more, same or different substituents $R^X$, wherein $R^X$ is $NH_2$, $NHCH_3$, $NH_2$—$C_1$-alkyl, or $C_1$-alkyl. In particular, $R^Y$ is (RY-1)

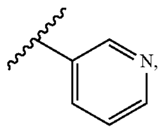

or (RY-2)

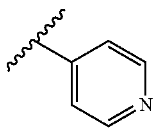

wherein $R^Y$-1 and $R^Y$-2 may be unsubstituted or substituted with one or more, same or different substituents $R^X$, wherein $R^X$ is $NH_2$, $NHCH_3$, $NH_2$—$C_1$-alkyl, or $C_1$-alkyl, in particular $CH_3$.

Accordingly, particularly preferred $R^5$ groups are selected from the group consisting of (R5-1)

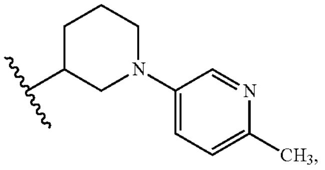

(R5-2)

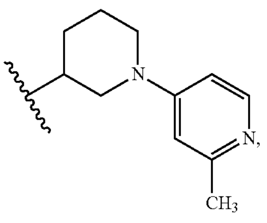

-continued ($R^5$-3)

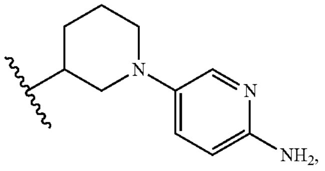

($R^5$-4)

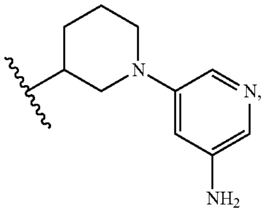

($R^5$-5)

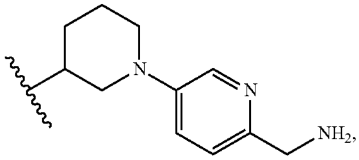

Thus, particularly preferred compounds in connection with the compound-linker constructs and the conjugates according to the present invention are compounds of formula (Ia*) as compiled in the tables below.

Table 1

Compounds of the formula (Ia*.1), in which $R^N$ is $CH_3$, $R^4$ is $R^4$-1, and $R^2$ and $R^5$ correspond in each case to one row of Table A Table 2

Compounds of the formula (Ia*.1), in which $R^N$ is $CH_3$, $R^4$ is $R^4$-2, and $R^2$ and $R^5$ correspond in each case to one row of Table A.

Table 3

Compounds of the formula (Ia*.1), in which $R^N$ is cyclopropyl, $R^4$ is $R^4$-1, and $R^2$ and $R^5$ correspond in each case to one row of Table A.

Table 4

Compounds of the formula (Ia*.1), in which $R^N$ is cyclopropyl, $R^4$ is $R^4$-2, and $R^2$ and $R^5$ correspond in each case to one row of Table A.

Table 5

Compounds of the formula (Ia*.2), in which $R^N$ is $CH_3$, $R^4$ is $R^4$-1, and $R^2$ and $R^5$ correspond in each case to one row of Table A Table 6

Compounds of the formula (Ia*.2), in which $R^N$ is $CH_3$, $R^4$ is $R^4$-2, and $R^2$ and $R^5$ correspond in each case to one row of Table A.

Table 7

Compounds of the formula (Ia*.2), in which $R^N$ is cyclopropyl, $R^4$ is $R^4$-1, and $R^2$ and $R^5$ correspond in each case to one row of Table A.

Table 8

Compounds of the formula (Ia*.2), in which $R^N$ is cyclopropyl, $R^4$ is $R^4$-2, and $R^2$ and $R^5$ correspond in each case to one row of Table A.

TABLE A

| No. | $R^2$ | $R^5$ |
|---|---|---|
| A-1 | H | $R^5$-1 |
| A-2 | H | $R^5$-2 |
| A-3 | H | $R^5$-3 |
| A-4 | H | $R^5$-4 |
| A-5 | H | $R^5$-5 |
| A-6 | Br | $R^5$-1 |
| A-7 | Br | $R^5$-2 |
| A-8 | Br | $R^5$-3 |
| A-9 | Br | $R^5$-4 |
| A-10 | Br | $R^5$-5 |
| A-11 | F | $R^5$-1 |
| A-12 | F | $R^5$-2 |
| A-13 | F | $R^5$-3 |
| A-14 | F | $R^5$-4 |
| A-15 | F | $R^5$-5 |
| A-16 | $NH_2$ | $R^5$-1 |
| A-17 | $NH_2$ | $R^5$-2 |
| A-18 | $NH_2$ | $R^5$-3 |
| A-19 | $NH_2$ | $R^5$-4 |
| A-20 | $NH_2$ | $R^5$-5 |
| A-21 | $R^2$-1 | $R^5$-1 |
| A-22 | $R^2$-1 | $R^5$-2 |
| A-23 | $R^2$-1 | $R^5$-3 |
| A-24 | $R^2$-1 | $R^5$-4 |
| A-25 | $R^2$-1 | $R^5$-5 |
| A-26 | $R^2$-2 | $R^5$-1 |
| A-27 | $R^2$-2 | $R^5$-2 |
| A-28 | $R^2$-2 | $R^5$-3 |
| A-29 | $R^2$-2 | $R^5$-4 |
| A-30 | $R^2$-2 | $R^5$-5 |
| A-31 | $R^2$-3 | $R^5$-1 |
| A-32 | $R^2$-3 | $R^5$-2 |
| A-33 | $R^2$-3 | $R^5$-3 |
| A-34 | $R^2$-3 | $R^5$-4 |
| A-35 | $R^2$-3 | $R^5$-5 |
| A-36 | $R^2$-4 | $R^5$-1 |
| A-37 | $R^2$-4 | $R^5$-2 |
| A-38 | $R^2$-4 | $R^5$-3 |
| A-39 | $R^2$-4 | $R^5$-4 |
| A-40 | $R^2$-4 | $R^5$-5 |
| A-41 | $R^2$-5 | $R^5$-1 |
| A-42 | $R^2$-5 | $R^5$-2 |
| A-43 | $R^2$-5 | $R^5$-3 |
| A-44 | $R^2$-5 | $R^5$-4 |
| A-45 | $R^2$-5 | $R^5$-5 |
| A-46 | $R^2$-6 | $R^5$-1 |
| A-47 | $R^2$-6 | $R^5$-2 |
| A-48 | $R^2$-6 | $R^5$-3 |
| A-49 | $R^2$-6 | $R^5$-4 |
| A-50 | $R^2$-6 | $R^5$-5 |
| A-51 | $R^2$-7 | $R^5$-1 |
| A-52 | $R^2$-7 | $R^5$-2 |
| A-53 | $R^2$-7 | $R^5$-3 |
| A-54 | $R^2$-7 | $R^5$-4 |
| A-55 | $R^2$-7 | $R^5$-5 |
| A-56 | $R^2$-8 | $R^5$-1 |
| A-57 | $R^2$-8 | $R^5$-2 |
| A-58 | $R^2$-8 | $R^5$-3 |
| A-59 | $R^2$-8 | $R^5$-4 |
| A-60 | $R^2$-8 | $R^5$-5 |
| A-61 | $R^2$-9 | $R^5$-1 |
| A-62 | $R^2$-9 | $R^5$-2 |
| A-63 | $R^2$-9 | $R^5$-3 |
| A-64 | $R^2$-9 | $R^5$-4 |
| A-65 | $R^2$-9 | $R^5$-5 |
| A-66 | $R^2$-10 | $R^5$-1 |
| A-67 | $R^2$-10 | $R^5$-2 |
| A-68 | $R^2$-10 | $R^5$-3 |
| A-69 | $R^2$-10 | $R^5$-4 |
| A-70 | $R^2$-10 | $R^5$-5 |
| A-71 | $R^2$-11 | $R^5$-1 |
| A-72 | $R^2$-11 | $R^5$-2 |
| A-73 | $R^2$-11 | $R^5$-3 |
| A-74 | $R^2$-11 | $R^5$-4 |
| A-75 | $R^2$-11 | $R^5$-5 |
| A-76 | $R^2$-12 | $R^5$-1 |
| A-77 | $R^2$-12 | $R^5$-2 |
| A-78 | $R^2$-12 | $R^5$-3 |

TABLE A-continued

| No. | $R^2$ | $R^5$ |
|---|---|---|
| A-79 | $R^2$-12 | $R^5$-4 |
| A-80 | $R^2$-12 | $R^5$-5 |
| A-81 | $R^2$-13 | $R^5$-1 |
| A-82 | $R^2$-13 | $R^5$-2 |
| A-83 | $R^2$-13 | $R^5$-3 |
| A-84 | $R^2$-13 | $R^5$-4 |
| A-85 | $R^2$-13 | $R^5$-5 |
| A-86 | $R^2$-14 | $R^5$-1 |
| A-87 | $R^2$-14 | $R^5$-2 |
| A-88 | $R^2$-14 | $R^5$-3 |
| A-89 | $R^2$-14 | $R^5$-4 |
| A-90 | $R^2$-14 | $R^5$-5 |
| A-91 | $R^2$-15 | $R^5$-1 |
| A-92 | $R^2$-15 | $R^5$-2 |
| A-93 | $R^2$-15 | $R^5$-3 |
| A-94 | $R^2$-15 | $R^5$-4 |
| A-95 | $R^2$-15 | $R^5$-5 |
| A-96 | $R^2$-16 | $R^5$-1 |
| A-97 | $R^2$-16 | $R^5$-2 |
| A-98 | $R^2$-16 | $R^5$-3 |
| A-99 | $R^2$-16 | $R^5$-4 |
| A-100 | $R^2$-16 | $R^5$-5 |
| A-101 | $R^2$-17 | $R^5$-1 |
| A-102 | $R^2$-17 | $R^5$-2 |
| A-103 | $R^2$-17 | $R^5$-3 |
| A-104 | $R^2$-17 | $R^5$-4 |
| A-105 | $R^2$-17 | $R^5$-5 |

It has been found that the compounds as defined in the above tables are particularly advantageous as STING agonists to be used in connection with the compound-linker constructs and conjugates according to the present invention as well as pharmaceutical compositions and medical uses thereof. Therefore, the compound-linker constructs and conjugates according to the present invention preferably comprise a compound according to any one of tables 1-8.

Particularly preferred compound-linker constructs and conjugates according to the present invention comprise a compound of formula (I), which is selected from the group consisting of 3-({[(3S)-1-(6-aminopyridin-3-yl)piperidin-3-yl][(2-methylpyridin-4-yl)methyl]amino}methyl)-1-methyl-1,4-dihydroquinolin-4-one; 3-({[(3S)-1-(6-aminopyridin-3-yl)piperidin-3-yl][(2-methoxypyridin-4-yl)methyl]amino}methyl)-1-cyclopropyl-6,7-difluoro-1,4-dihydroquinolin-4-one; 7-[(3R)-3-aminopyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 7-[(3S)-3-aminopyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one; 7-[(3R)-3-(aminomethyl)pyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 7-[(3S)-3-aminopiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 7-[(3R)-3-aminopiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 3-({[(2-aminopyridin-4-yl)methyl][(3S)-1-(6-methylpyridin-3-yl)piperidin-3-yl]amino}methyl)-1-cyclopropyl-6,7-difluoro-1,4-dihydroquinolin-4-one; 7-amino-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-7-{[2-(dimethylamino)ethyl]amino}-6-fluoro-3-({[(3S)-1-(6-methylpyridin-3-yl)piperidin-3-yl][(2-methylpyridin-4-yl)methyl]amino}methyl)-1,4-dihydroquinolin-4-one; 7-[(3S)-3-(aminomethyl)pyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 7-{7-amino-5-azaspiro[2.4]heptan-5-yl}-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 3-({[(3S)-1-(6-aminopyridin-3-yl)piperidin-3-yl][(2-methylpyridin-4-yl)methyl]amino}methyl)-6,7-difluoro-1-(propan-2-yl)-1,4-dihydroquinolin-4-one; 7-(4-amino-3,3-difluoropiperidin-1-yl)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-[3-(hydroxymethyl)azetidin-1-yl]-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-[(3R)-3-hydroxypiperidin-1-yl]-3-({[(3S)-1-(6-methylpyridin-3-yl)piperidin-3-yl][(2-methylpyridin-4-yl)methyl]amino}methyl)-1,4-dihydroquinolin-4-one; 3-({[(3S)-1-(6-aminopyridin-3-yl)piperidin-3-yl][(2-methylpyridin-4-yl)methyl]amino}methyl)-7-bromo-1-methyl-1,4-dihydroquinolin-4-one; 7-[3-(aminomethyl)-3-fluoropyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-[(3S)-3-hydroxypiperidin-1-yl]-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-(4-hydroxypiperidin-1-yl)-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-[3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one; 3-({[(3S)-1-(6-aminopyridin-3-yl)piperidin-3-yl][(2-methylpyridin-4-yl)methyl]amino}methyl)-1-(propan-2-yl)-1,4-dihydroquinolin-4-one; 7-amino-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one; 1-cyclopropyl-6-fluoro-7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1,4-dihydro-1,8-naphthyridin-4-one; 1-cyclopropyl-6-fluoro-7-[(3S)-3-hydroxypyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one; 6-fluoro-7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one; 1-cyclopropyl-7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-(2-hydroxyethoxy)-3-({[(3S)-1-(6-methylpyridin-3-yl)piperidin-3-yl][(2-methylpyridin-4-yl)methyl]amino}methyl)-1,4-dihydroquinolin-4-one; 7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one; 1-cyclopropyl-6-fluoro-7-[(3R)-3-(methylamino)pyrrolidin-1-yl]-3-({[(3S)-1-(6-methylpyridin-3-yl)

piperidin-3-yl][(2-methylpyridin-4-yl)methyl] amino}methyl)-1,4-dihydroquinolin-4-one; 7-[(4R)-4-amino-3,3-difluoropiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 7-[(4 S)-4-amino-3,3-difluoropiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-[(3S)-3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-[1-(2-hydroxyethyl)-1H-pyrazol-4-yl]-3-({[(3S)-1-(6-methylpyridin-3-yl) piperidin-3-yl][(2-methylpyridin-4-yl)methyl] amino}methyl)-1,4-dihydroquinolin-4-one; 1-cyclopropyl-6-fluoro-7-[(3R)-3-hydroxypyrrolidin-1-yl]-3-({[(2-methoxypyridin-4-yl)methyl][(3S)-1-(pyridin-3-yl) piperidin-3-yl]amino}methyl)-1,4-dihydroquinolin-4-one; 1-cyclopropyl-6-fluoro-7-[2-(hydroxymethyl)morpholin-4-yl]-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-[(25)-2-(hydroxymethyl)morpholin-4-yl]-3-({[(3S)-1-(6-methylpyridin-3-yl)piperidin-3-yl][(2-methylpyridin-4-yl) methyl]amino}methyl)-1,4-dihydroquinolin-4-one; 1-cyclopropyl-6-fluoro-7-[(2R)-2-(hydroxymethyl)morpholin-4-yl]-3-({[(3S)-1-(6-methylpyridin-3-yl)piperidin-3-yl] [(2-methylpyridin-4-yl)methyl]amino}methyl)-1,4-dihydroquinolin-4-one; 1-cyclopropyl-6-fluoro-3-({[(3S,5S)-5-fluoro-1-(6-methylpyridin-3-yl)piperidin-3-yl][(2-methylpyridin-4-yl)methyl]amino}methyl)-7-(2-hydroxyethoxy)-1,4-dihydroquinolin-4-one; 1-cyclopropyl-6-fluoro-7-[(3R)-3-hydroxypyrrolidin-1-yl]-3-({[(2-methylpyridin-4-yl)methyl][(3S)-1-(pyridin-3-yl)piperidin-3-yl]amino}methyl)-1,4-dihydroquinolin-4-one; 1-cyclopropyl-6-fluoro-7-[3-(hydroxymethyl)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-[(3S)-3-hydroxypiperidin-1-yl]-3-({[(3S)-1-(5-methylpyrazin-2-yl) piperidin-3-yl][(2-methylpyridin-4-yl)methyl] amino}methyl)-1,4-dihydroquinolin-4-one; 1-cyclopropyl-6-fluoro-3-({[(3S,5S)-5-fluoro-1-(5-methylpyrazin-2-yl) piperidin-3-yl][(2-methylpyridin-4-yl)methyl] amino}methyl)-7-[(3S)-3-hydroxypiperidin-1-yl]-1,4-dihydroquinolin-4-one; 1-cyclopropyl-6-fluoro-7-(2-hydroxyethoxy)-3-({[(2-methylpyridin-4-yl)methyl][(3S)-1-(pyridin-3-yl)piperidin-3-yl]amino}methyl)-1,4-dihydroquinolin-4-one; 1-cyclopropyl-6-fluoro-7-(2-hydroxyethoxy)-3-({[(2-methylpyridin-4-yl)methyl][(3S)-1-(pyrazin-2-yl)piperidin-3-yl]amino}methyl)-1,4-dihydroquinolin-4-one; 1-cyclopropyl-6-fluoro-7-[(3S)-3-hydroxypiperidin-1-yl]-3-({[(2-methylpyridin-4-yl)methyl] [(3S)-1-(pyridin-3-yl)piperidin-3-yl]amino}methyl)-1,4-dihydroquinolin-4-one; 1-cyclopropyl-6-fluoro-7-[(3S)-3-(hydroxymethyl)pyrrolidin-1-yl]-3-({[(2-methylpyridin-4-yl)methyl][(3S)-1-(pyridin-3-yl)piperidin-3-yl] amino}methyl)-1,4-dihydroquinolin-4-one; 1-cyclopropyl-6-fluoro-7-[(3R)-3-(hydroxymethyl)pyrrolidin-1-yl]-3-({[(2-methylpyridin-4-yl)methyl][(3S)-1-(pyridin-3-yl)piperidin-3-yl]amino}methyl)-1,4-dihydroquinolin-4-one; 1-cyclopropyl-6-fluoro-3-({[(3S,5S)-5-fluoro-1-(pyridin-3-yl)piperidin-3-yl][(2-methylpyridin-4-yl)methyl] amino}methyl)-7-(2-hydroxyethoxy)-1,4-dihydroquinolin-4-one; 1-cyclopropyl-6-fluoro-7-[(3R)-3-(hydroxymethyl) pyrrolidin-1-yl]-3-({[(2-methylpyridin-4-yl)methyl][(3S)-1-(pyrazin-2-yl)piperidin-3-yl]amino}methyl)-1,4-dihydroquinolin-4-one; 1-cyclopropyl-6-fluoro-7-[(3S)-3-(hydroxymethyl)pyrrolidin-1-yl]-3-({[(2-methylpyridin-4-yl)methyl][(3S)-1-(pyrazin-2-yl)piperidin-3-yl] amino}methyl)-1,4-dihydroquinolin-4-one; 1-cyclopropyl-6-fluoro-3-({[(3S,5S)-5-fluoro-1-(pyrazin-2-yl)piperidin-3-yl][(2-methylpyridin-4-yl)methyl]amino}methyl)-7-(2-hydroxyethoxy)-1,4-dihydroquinolin-4-one; 1-cyclopropyl-6-fluoro-7-[(3S)-3-hydroxypiperidin-1-yl]-3-({[(2-methylpyridin-4-yl)methyl][(3S)-1-(pyrazin-2-yl)piperidin-3-yl]amino}methyl)-1,4-dihydroquinolin-4-one.

Further particularly preferred compound-linker constructs and conjugates according to the present invention comprise a compound of formula (I), which is selected from the group consisting of 3-({[(3S)-1-(6-aminopyridin-3-yl)piperidin-3-yl][(2-methylpyridin-4-yl)methyl]amino}methyl)-1-methyl-1,4-dihydroquinolin-4-one; 3-({[(3S)-1-(6-amino-pyridin-3-yl)piperidin-3-yl][(2-methoxypyridin-4-yl) methyl]amino}methyl)-1-cyclopropyl-6,7-difluoro-1,4-dihydroquinolin-4-one; 7-[(3R)-3-aminopyrrolidin-1-yl]-1-cyclopropyl-6-fluoro-3-({[(3S)-1-(6-methylpyridin-3-yl) piperidin-3-yl][(2-methylpyridin-4-yl)methyl] amino}methyl)-1,4-dihydroquinolin-4-one; 7-[(3S)-3-aminopyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 1-cyclopropyl-6-fluoro-7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one; 7-[(3R)-3-(aminomethyl)pyrrolidin-1-yl]-1-cyclopropyl-6-fluoro-3-({[(3S)-1-(6-methylpyridin-3-yl) piperidin-3-yl][(2-methylpyridin-4-yl)methyl] amino}methyl)-1,4-dihydroquinolin-4-one; 7-[(3S)-3-aminopiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one; 7-[(3R)-3-aminopiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one.

Preferred compound-linker constructs and conjugates according to the present invention comprise a compound of formula (I), which comprise a stereocenter at the $R^5$ substituent in S-configuration. The configuration of this stereocenter can be predefined in the preparation of the compounds when introducing the substituent $R^5$ by selecting a precursor with the respective configuration (see, e.g., Example 1).

In certain scenarios, a further stereocenter may be present at another position of the molecule.

In case the configuration of the further stereocenter can also be predefined by using a suitable precursor in the preparation of the compounds, the exact structure of the resulting molecule is predefined as well, meaning that a clear R/S-nomenclature can be provided for both stereocenters in the molecule.

However, if the further stereocenter is introduced based on a precursor in racemic form (i.e. not enantiomerically pure), two diastereoisomers will be formed, which can be separated afterwards.

In such scenarios, the nomenclature of the additional stereocenter is provided arbitrarily herein.

In other words, for example in case of the diastereoisomer pair 7-[(4R)-4-amino-3,3-difluoropiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one and 7-[(4S)-4-amino-3,3- difluoropiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (see Examples 56 and 57), it is clear that both compounds are obtained and separated, but it is not clear which compound has which structure as further experimental work (such as X-ray crystallography) would be needed to determine this. Thus, if it is referred herein to 7-[(4R)-4-amino-3,3-difluoropiperidin-1-yl]-1-cyclopropyl-6-fluoro-3-({[(3S)-1-(6-methylpyridin-3-yl)piperidin-3-yl][(2-methylpyridin-4-yl) methyl]amino}methyl)-1,4-dihydroquinolin-4-one this could also be 7-[(4S)-4-amino-3,3-difluoropiperidin-1-yl]-1-cyclopropyl-6-fluoro-3-({[(3S)-1-(6-methylpyridin-3-yl) piperidin-3-yl][(2-methylpyridin-4-yl)methyl] amino}methyl)-1,4-dihydroquinolin-4-one and vice versa.

In another embodiment, compound-linker constructs and conjugates according to the present invention comprise a compound of formula (I), (I)

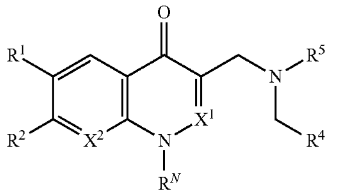

or a salt, stereoisomer, tautomer, or N-oxide thereof, wherein $X^1$ is CH or N;

$X^2$ is $CR^3$ or N;

$R^1$, $R^2$ and $R^3$ are independently H, OH, $NR^CR^D$, CN, halogen, $C_1$-$C_4$-alkyl, $NR^CR^D$—$C_1$-$C_4$-alkyl, $C_1$-$C_4$-alkoxy, aryloxy, benzyloxy, C(═O)$R^E$, $NR^F$C(═O)$R^E$, $NR^F$—($C_1$-$C_4$-alkylene) C(═O)$R^E$, $NR^F$—($C_1$-$C_4$-alkylene)-$NR^CR^D$, O—($C_1$-$C_4$-alkylene)-$NR^CR^D$, or 4- to 6-membered saturated, partially or fully unsaturated, or aromatic carbocyclyl, carbocyclyl-$C_1$-$C_2$-alkyl, heterocyclyl, heterocyclyloxy, or heterocyclyl-$C_1$-$C_2$alkyl, or 8- to 10-membered saturated, partially or fully unsaturated, or aromatic carbobicyclyl or heterobicyclyl, wherein the aforementioned heterocyclic or heterobicyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents $R^X$;

$R^5$ is a 5- or 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents $R^Y$;

and wherein $R^N$ is H, $C_1$-$C_4$-alkyl, HO(C═O)—$C_1$-$C_4$-alkyl, $NR^CR^D$—$C_1$-$C_4$-alkyl, $C_1$-$C_2$-alkoxy-$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, $C_1$-$C_2$-alkyl, or C(═O)$R^E$; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, $NR^CR^D$—$C_1$-$C_4$-alkyl, phenyl, benzyl, $OR^G$, or $NR^HR^I$; or a 5- or 6-membered saturated, partially or fully unsaturated heterocyclyl, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^F$;

$R^F$ is H, $C_1$-$C_2$-alkyl, $C_3$-$C_6$-cycloalkyl, phenyl, benzyl, or C(═O)$NR^HR^I$;

$R^G$ is H, $C_1$-$C_2$-alkyl, or 5- or 6-membered aromatic carbocyclyl, carbocyclyl-$C_1$-$C_2$alkyl, heterocyclyl, or heterocyclyl-$C_1$-$C_2$alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is OH, $NR^CR^D$, halogen, CN, $NO_2$, $C_1$-$C_2$-alkyl, cyclopropyl, $C_1$-$C_2$haloalkyl, $NR^CR^D$—$C_1$-$C_4$-alkyl, $R^CO$—$C_1$-$C_4$-alkyl, $C_1$-$C_2$alkoxy, $R^CO$—$C_1$-$C_4$-alkyloxy, C(═O)$R^E$, or two $R^X$ form ═O, or two $R^X$ together with the carbon atom to which they are bonded form a 3- to 5-membered saturated, partially or fully unsaturated, or aromatic carbocyclic ring;

$R^Y$ is halogen, CN, OH, $C_1$-$C_2$-alkyl, HO—$C_1$-$C_2$alkyl, $C_3$-$C_6$-cycloalkyl, $C_1$-$C_2$-alkoxy, $NR^CR^D$, S(=O)$_2$ $NR^CR^D$, C(=O)$R^E$, or 5- or 6-membered saturated, partially or fully unsaturated, or aromatic carbocyclyl, carbocyclyl-$C_1$-$C_2$alkyl, heterocyclyl, and heterocyclyl-$C_1$-$C_2$alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form =O; or two $R^Y$ attached to identical or neighboring carbon atoms may form a 3-membered carbocyclic ring;

with the proviso that either any one of $R^1$, $R^2$, or $R^3$ is $NR^CR^D$, $NR^CR^D$—$C_1$-$C_4$-alkyl, $NR^F$—($C_1$-$C_4$-alkylene)-$NR^CR^D$, O—($C_1$-$C_4$-alkylene)-$NR^CR^D$, or 8- to 10-membered saturated, partially or fully unsaturated, or aromatic carbobicyclyl or heterobicyclyl, wherein the aforementioned heterobicyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or any one of $R^1$, $R^2$, or $R^3$ is $NR^F$C(=O)$R^E$, wherein $R^E$ is $NR^CR^D$—$C_1$-$C_4$-alkyl;

or $R^N$ is $NR^CR^D$—$C_1$-$C_4$-alkyl, or $C_1$-$C_2$-alkoxy-$C_1$-$C_4$-alkyl;

or any one of the substituents $R^1$, $R^2$, $R^3$, $R^4$, $R^5$, $R^N$ carries a substituent $R^X$, wherein $R^X$ is OH, $NR^CR^D$, $NR^CR^D$—$C_1$-$C_4$-alkyl, $R^C$O—$C_1$-$C_4$-alkyl, or $R^C$O—$C_1$-$C_4$-alkyloxy.

As indicated above, the compound-linker constructs and conjugates according to the invention comprise the compound of formula (I) covalently bonded to the linker $L^1$ or $L^2$. In case of the conjugates of the invention the linker $L^2$ is further covalently bonded to the targeting moiety T. It is described hereinafter how the covalent bonds can be established and how the linkers $L^1$ and $L^2$ preferably look like.

In general, the covalent bonds are preferably obtained based on functional groups such as carbonate, carbamate, ester, amide, urea and/or lactam functional groups of the molecule forming the linker (Beck, A. et. al., Nat. Revs. Drug Disc., 2017, 16, 315-337 and J. D. Bargh et al., Chem. Soc. Rev., 2019, DOI: 10.1039/c8cs00676h). Said linkers will be known to those skilled in the art as either 'stable', i.e. non-cleavable, linkers which are resistant to degradation in cells and in the systemic circulation or 'conditionally labile', i.e. cleavable, linkers which are designed to degrade in cells and/or in the systemic circulation following a defined trigger event, which may be a change in pH or a metabolic process such as ester or amide hydrolysis. Specific hydrolysis processes have been described, such as the peptidase cleavage of a dipeptide e.g. the valine-citrulline dipeptide moiety contained in the clinically precedented ADC brentuximab vedotin or the hydrolysis of a labile hydrazone moiety in gemtuzumab ozogamicin. Non-cleavable linkers include that contained in the clinically precedented ADC trastuzumab emtansine.

In one embodiment of the compound-linker construct of the invention, the covalent bond between the compound of formula (I) and the linker $L^1$ is established by the reaction of a functional group of the compound of formula (I) with a functional group handle of the linker $L^1$; wherein preferably the functional group of the compound of formula (I) is attached to or part of the substituents $R^2$, $R^4$, $R^5$, or $R^N$ so that the linker $L^1$ will be covalently bonded to the compound of formula (I) according to any one of the following structures:

(I-$R^2$-$L^1$)

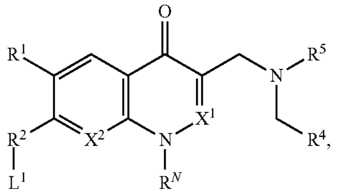

(I-$R^N$-$L^1$)

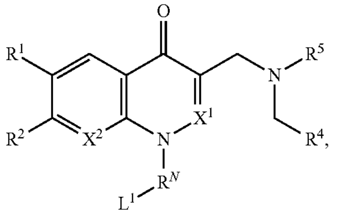

(I-$R^4$-$L^1$)

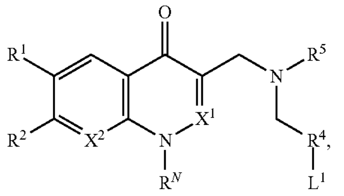

(I-$R^5$-$L^1$)

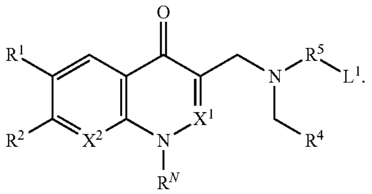

The functional group, which is attached to or part of the substituents $R^2$, $R^4$, $R^5$ or $R^N$ preferably comprises an amino or hydroxy group. This functional group establishes the covalent bond to the linker $L^1$ by reaction with a functional group, preferably a benzyl alcohol group, a carbonate group, a carbamate group, a carboxylic acid group, a carboxylic ester group, a carboxylic amide group, an urea group or a lactam group of a precursor of the linker $L^1$ under suitable conditions. Accordingly, the covalent bond is preferably a bond between an oxygen or nitrogen atom of the compound of formula (I) and a carbon atom of the linker $L^1$. In other words, a hydrogen atom at an amino of hydroxy group of the compound of formula (I) is replaced by a carbon atom of the linker $L^1$. As a result, the compound-linker construct of the formula (I)-$L^1$ is obtained, wherein a nitrogen or oxygen atom of the compound of formula (I) forms the connection to $L^1$. The linker $L^1$ preferably has the structure $H^{1A}$-$L^C$-$H^{1B}$, wherein $H^{1A}$ is a functional group handle, which is covalently bonded to the compound of formula (I), preferably a nitrogen or oxygen atom thereof, and wherein $H^{1B}$ is a functional group handle suitable for forming a covalent bond to a targeting moiety T. In this connection, "suitable for forming a covalent bond to a targeting moiety T" means that the functional moiety can be used as such or further derivatized in order to form a covalent bond to the targeting moiety T. This is explained in further detail below.

In one embodiment, the functional group of the compound of formula (I), which is attached to or part of the substituents $R^2$, $R^4$, $R^5$, or $R^N$, and which forms the covalent bond to the functional group handle $H^{1A}$ of the linker $L^1$, is selected from the following options:

either $R^2$ is $NHR^D$, $NHR^D$—$C_1$-$C_4$-alkyl, NH—($C_1$-$C_4$-alkylene)-$NR^CR^D$, $NR^F$—($C_1$-$C_4$-alkylene)-$NHR^D$, O—($C_1$-$C_4$-alkylene)-$NHR^D$, or 8- to 10-membered saturated heterobicyclyl, wherein the aforementioned heterobicyclic ring comprises at least one nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or $R^2$ is $NR^FC(=O)R^E$, wherein $R^E$ is $NHR^D$—$C_1$-$C_4$-alkyl;

or $R^N$ is $NHR^D$—$C_1$-$C_4$-alkyl;

or any one of the substituents $R^2$, $R^4$, $R^5$, $R^N$ carries a substituent $R^X$, wherein $R^X$ is OH, $NHR^D$, $NHR^D$—$C_1$-$C_4$-alkyl, or HO—$C_1$-$C_4$-alkyl;

and preferably either $R^2$ is $NH_2$, $NH_2$—$C_1$-$C_2$-alkyl, NH—($C_1$-$C_3$-alkylene)-$NH_2$, NH—($C_1$-$C_3$-alkylene)-$NHCH_3$, NH—($C_1$-$C_3$-alkylene)-$N(CH_3)_2$, O—($C_1$-$C_3$-alkylene)-$NH_2$, or O—($C_1$-$C_3$-alkylene)-$NHCH_3$;

or $R^2$ is $NHC(=O)R^E$, wherein $R^E$ is $NH_2$—$C_1$-$C_4$-alkyl;

or $R^N$ is $NH_2$—$C_1$-$C_3$-alkyl;

or any one of the substituents $R^2$, $R^4$, or $R^5$ carries a substituent $R^X$, wherein $R^X$ is OH, $NH_2$, $NHCH_3$, $NH_2$—$C_1$-$C_2$-alkyl, or HO—$C_1$-$C_2$-alkyl.

In one embodiment of the compound-linker construct of the invention, the linker $L^1$ comprises (i) a chain $L^C$ of 2 to 100 atoms selected from carbon, nitrogen, oxygen, and sulfur atoms, which may be interrupted by 5- to 10-membered aryl and heteroaryl groups and/or 3- to 8-membered saturated carbocyclyl or heterocyclyl groups, wherein the aforementioned heteroaryl and heterocyclic groups comprise one or more, same or different heteroatoms selected from O, N or S, wherein said N- and/or S-atoms are independently oxidized or non-oxidized, and wherein each substitutable carbon or heteroatom in the chain is independently unsubstituted or substituted with one or more same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

and preferably a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$haloalkoxy;

(ii) a functional group handle $H^{1A}$, which is covalently bonded to the compound of formula (I);

(iii) a functional group handle $H^{1B}$ suitable for forming a covalent bond to a targeting moiety T.

Preferred functional group handles $H^{1A}$ of the linker $L^1$ are based on a functional group selected from a benzyl alcohol group, a carbonate group, a carbamate group, a carboxylic acid group, a carboxylic ester group, a carboxylic amide group, an urea group and a lactam group, from which a covalent bond to the compound of formula (I) is established by reaction with a suitable functional group of the compound of formula (I), in particular a hydroxy or amino group of the compound of formula (I).

Preferred functional group handles $H^{1B}$ of the linker $L^1$ selected from lysine reactive groups including succinyl esters, pentafluorophenyl esters, β-lactam am-ides, isocyanates, and isothiocyanates; azide reactive groups including alkynes and strained alkynes; cysteine reactive groups including maleimide groups, α-haloacetamides, pyridyl disulfides and vinyl sulfoxides; and ketone reactive groups including hydroxylamines, hydrazines and acyl hydrazides. Particularly preferred functional group handles $H^{1B}$ include succinyl esters, pentafluorophenyl esters and maleimide groups. These groups may then react with the mentioned functional groups of a targeting moiety to give the conjugates as defined herein. Alternatively, the functional group handle may be an $NH_2$, OH, C(=O)OH, or $C(=O)NH_2$ group, which may optionally be further derivatized to give a functional group handle selected from lysine reactive groups including succinyl esters, pentafluorophenyl esters, β-lactam am-ides, isocyanates, and isothiocyanates; azide reactive groups including alkynes and strained alkynes; cysteine reactive groups including maleimide groups, α-haloacetamides, pyridyl disulfides and vinyl sulfoxides; and ketone reactive groups including hydroxylamines, hydrazines and acyl hydrazides. These groups may then react with the mentioned functional groups of a targeting moiety to give the conjugates as defined herein.

Preferred chains $L^C$ of the linker $L^1$ include:
(L^c-1)
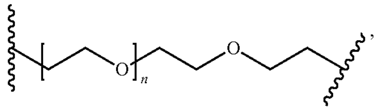
(L^c-2)
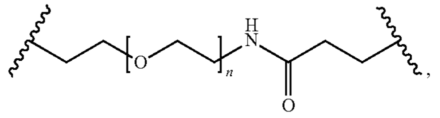
(L^c-3)
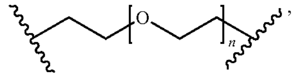
(L^c-4)
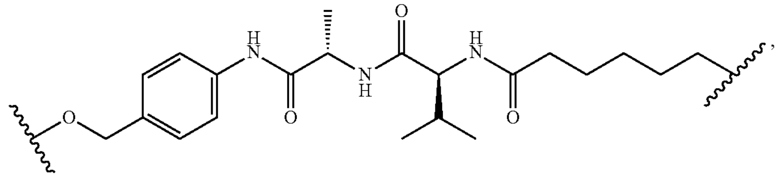
(L^c-5)
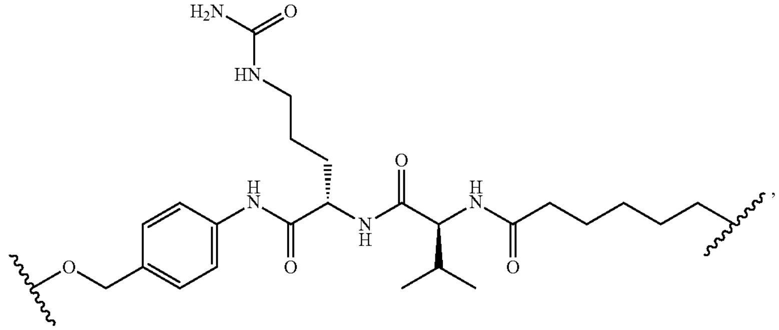
(L^c-6)
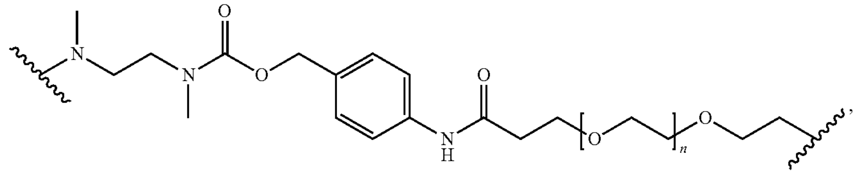
(L^c-7)
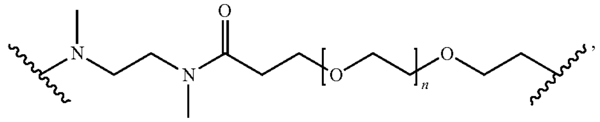
(L^c-8)
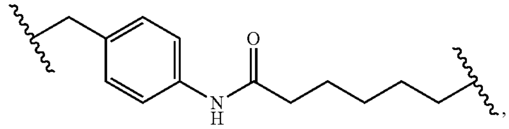
(L^c-9)
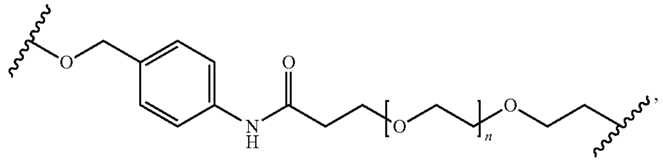

-continued (L$^c$-10)

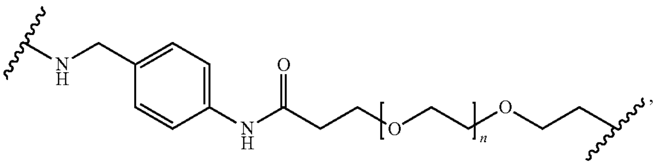

and (L$^c$-11)

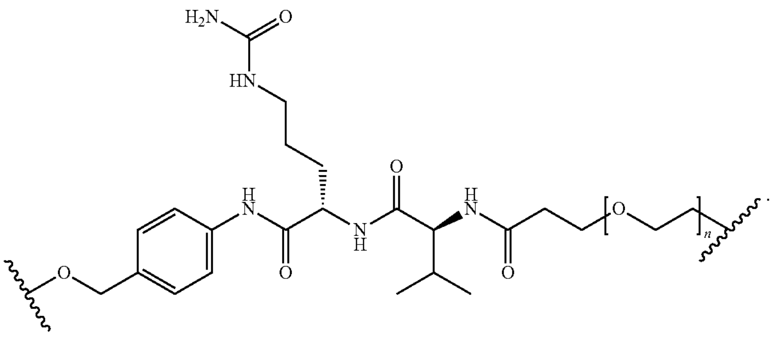

Preferably, n is 0, 1, 2, 3, 4, 5, 6, 7, or 8.

It is to be understood that the above definitions of $L^C$ with stereocenters preferably also cover stereoisomers, i.e. enantiomers and diastereoisomers of the depicted structures.

Preferably, the linker $L^1$ has a structure $H^{1A}$-$L^C$-$H^{1B}$, wherein $H^{1A}$, $L^C$, and $H^{1B}$ are as defined above, and wherein the definitions of $L^C$ preferably also cover possible stereoisomers.

Further preferred chains $L^C$ of the linker $L^1$ include:

(L$^c$-1)

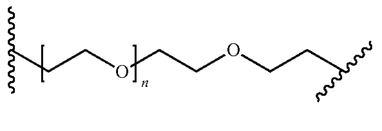

, (L$^c$-2)

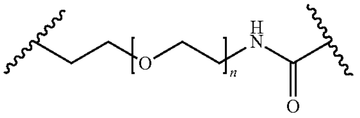

, (L$^c$-3)

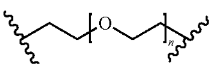

, (L$^c$-4)

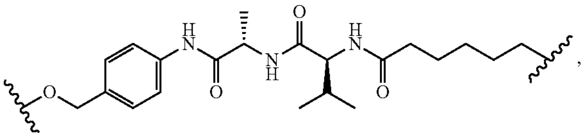

, (L$^c$-5)

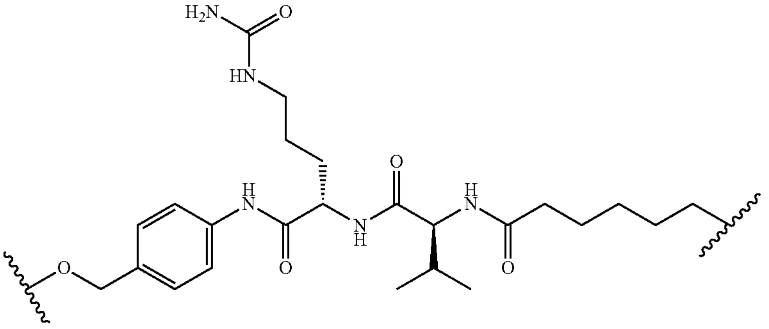

,

-continued (L^c-6)

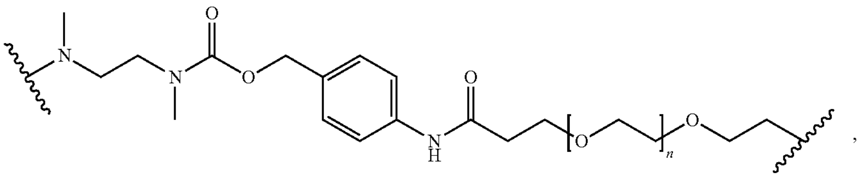

, (L^c-7)

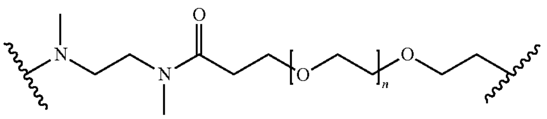

, (L^c-8)

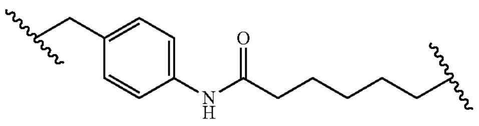

, and (L^c-9)

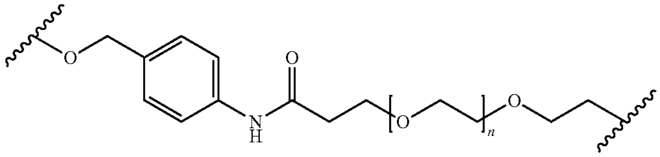

.

Preferably, n is 0, 1, 2, 3, 4, 5, 6, 7, or 8.

It is to be understood that the above definitions of $L^C$ with stereocenters preferably also cover stereoisomers, i.e. enantiomers and diastereoisomers of the depicted structures.

Preferably the linker L, has a structure $H^{1A}$-$L^C$-$H^{1B}$, wherein $H^{1A}$, $L^C$, and $H^{1B}$ are as defined above, and wherein the definitions of $L^C$ preferably also cover possible stereoisomers.

In one embodiment of the compound-linker construct, the linker L, has the structure $H^{1A}$-$L^C$-$H^{1B}$ and is selected from the group consisting of (L¹-1)

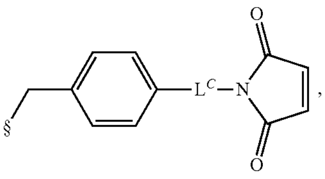

, (L¹-2)

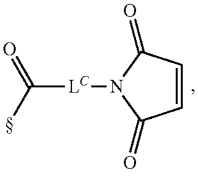

, (L¹-3)

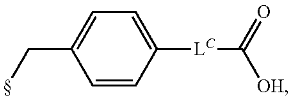

(L¹-4)

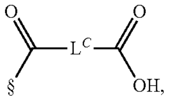

(L¹-5)

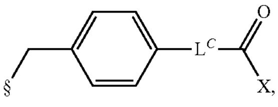

-continued (L¹-6)

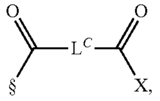

(L¹-7)

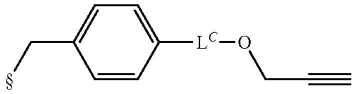

, (L¹-8)

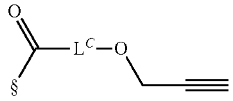

(L¹-9)

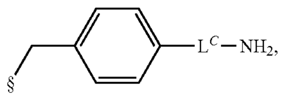

(L¹-10)

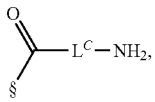

(L¹-11)

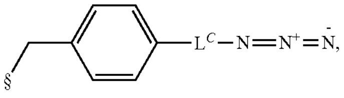

(L¹-12)

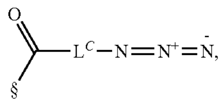

(L¹-13)

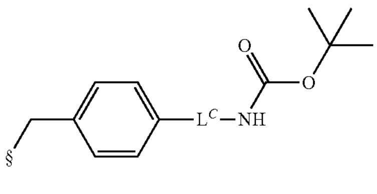

,

-continued (L¹-14)

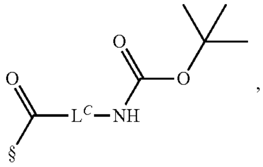

(L¹-15)

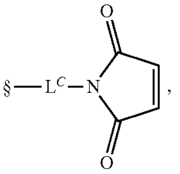

(L¹-16)

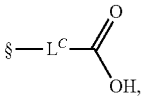

(L¹-17)

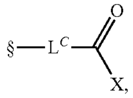

(L¹-18)

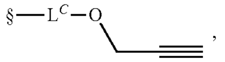

(L¹-19)

§—$L^C$—$NH_2$, (L¹-20)

§—$L^C$—N═$N^+$═$N^-$, and (L¹-21)

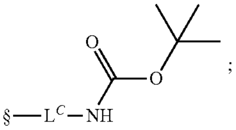

wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, ═O, $C_1$-$C_2$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$haloalkoxy; and § marks the connection to the compound of formula (I); and X represents a leaving group selected from (X-1)

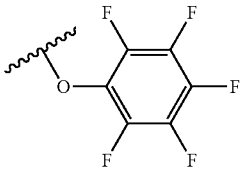

and (X-2)

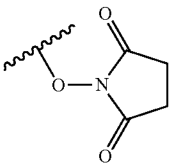

and wherein preferably $L^C$ is selected from the group consisting of ($L^C$-1)

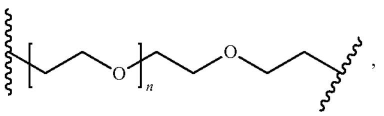

($L^C$-2)

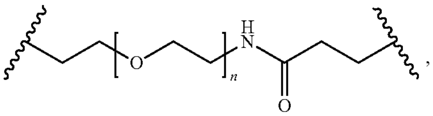

($L^C$-3)

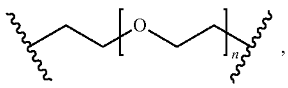

($L^C$-4)

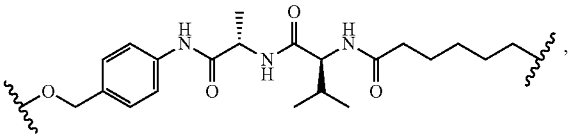

-continued (L^C-5)

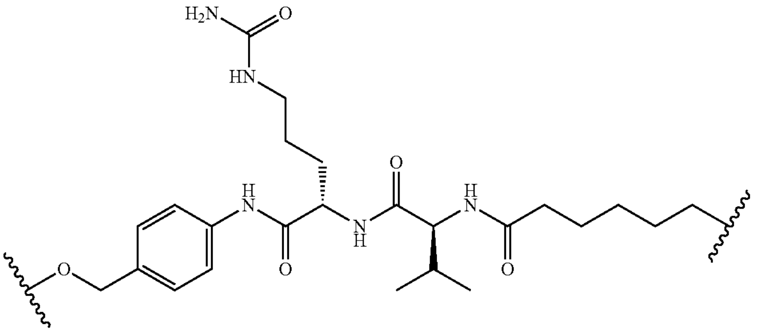
, (L^C-6)

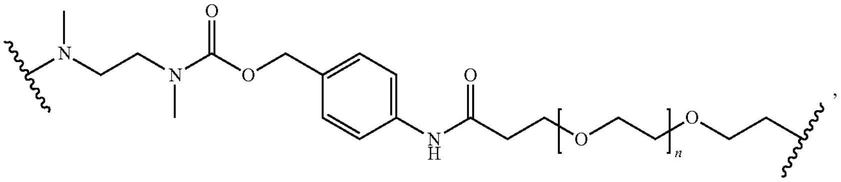
, (L^C-7)

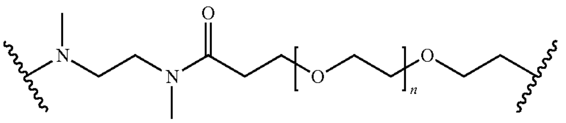
, (L^C-8)

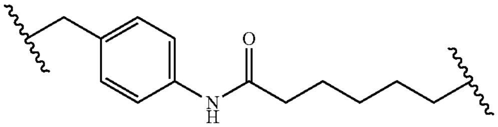
, (L^C-9)

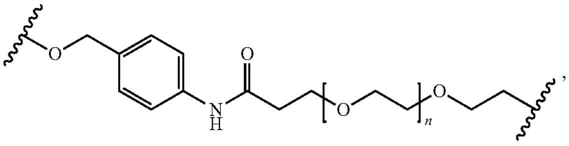
, (L^C-10)

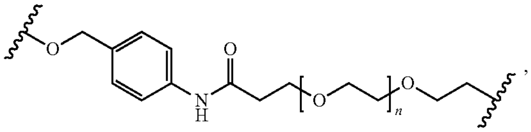
, and (L^C-11)

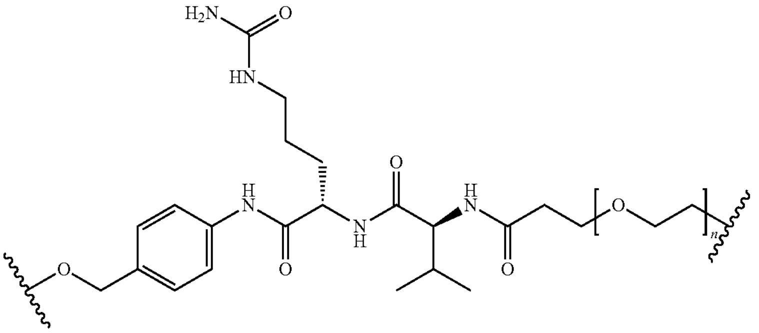
.

Preferably, n is 0, 1, 2, 3, 4, 5, 6, 7, or 8.

It is to be understood that the above definitions of $L^C$ with stereocenters preferably also cover stereoisomers, i.e. enantiomers and diastereoisomers of the depicted structures.

In one embodiment of the compound-linker construct, the linker $L^1$ has the structure $H^{1A}$-$L^C$-$H^{1B}$ and is selected from the group consisting of ($L^1$-1)

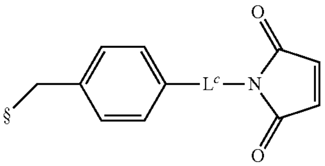
,

-continued (L1-2)

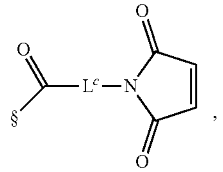

, (L1-3)

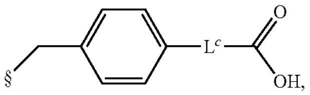

(L1-4)

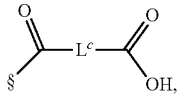

(L1-5)

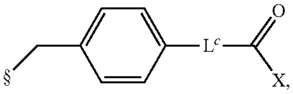

and (L1-6)

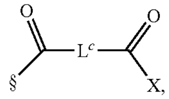

wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_2$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy; and § marks the connection to the compound of formula (I); and X represents a leaving group selected from (X-1)

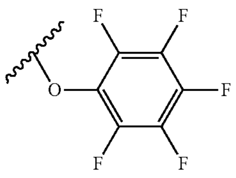

and (X-2)

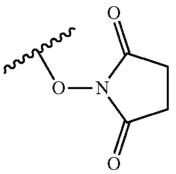

and wherein preferably $L^C$ is selected from the group consisting of (LC-1)

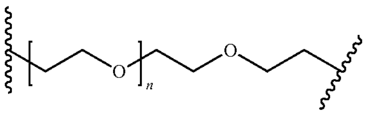

, (LC-2)

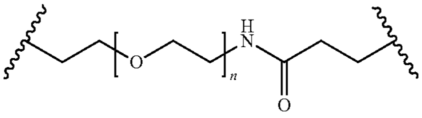

, (LC-3)

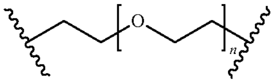

, (LC-4)

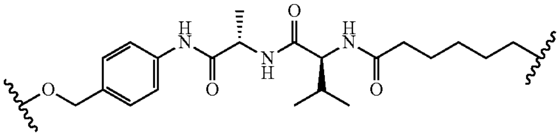

, (LC-5)

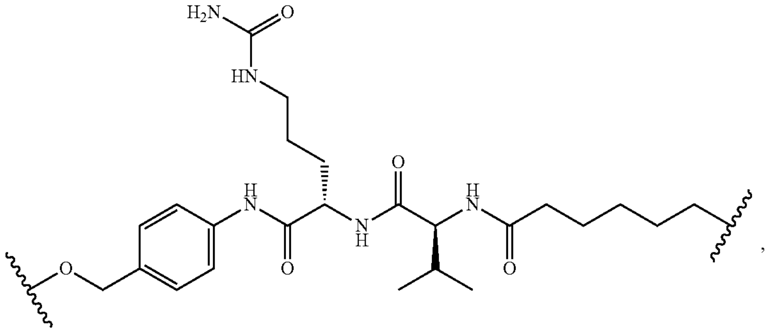

, (LC-6)

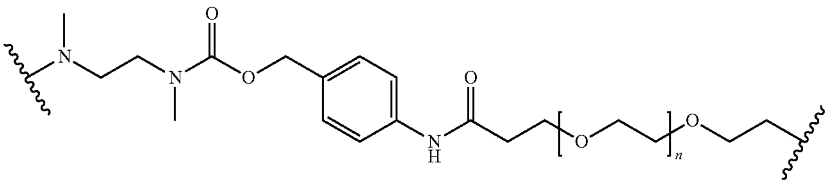

,

-continued ($L^C$-7)

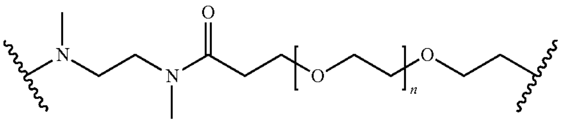

, ($L^C$-8)

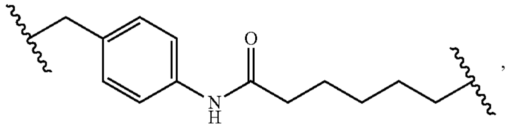

, and ($L^C$-9)

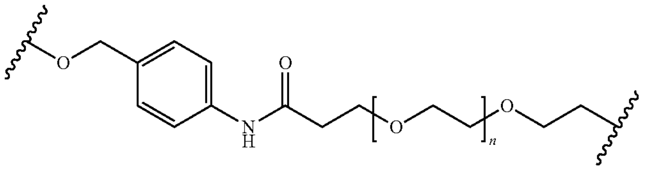

.

Preferably, n is 0, 1, 2, 3, 4, 5, 6, 7, or 8.

It is to be understood that the above definitions of $L^C$ with stereocenters preferably also cover stereoisomers, i.e. enantiomers and diastereoisomers of the depicted structures.

In a preferred embodiment of the compound-linker construct, the linker $L^1$ is selected from the group consisting of:

($L^1$-a)

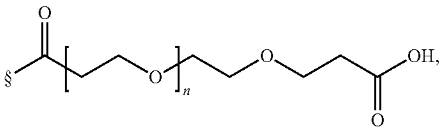

, ($L^1$-b)

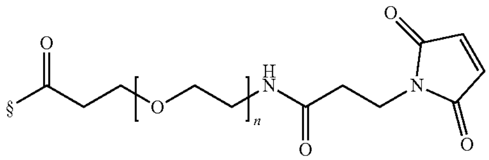

, ($L^1$-c)

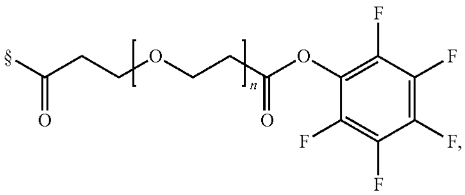

, ($L^1$-d)

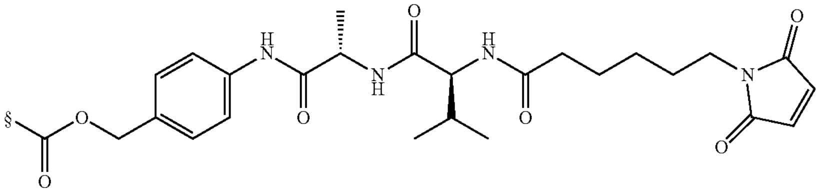

, ($L^1$-e)

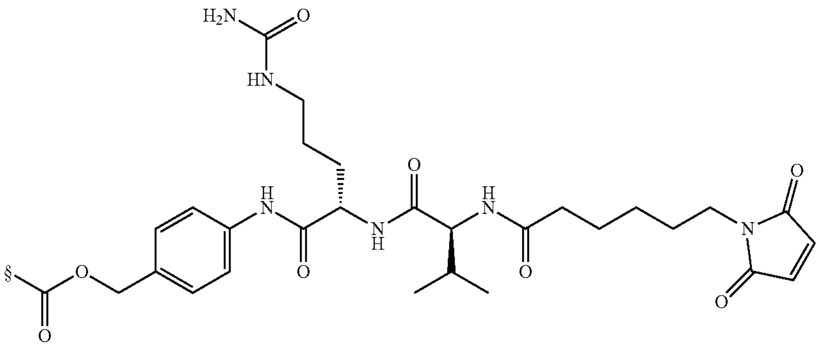

,

-continued ($L^1$-f)

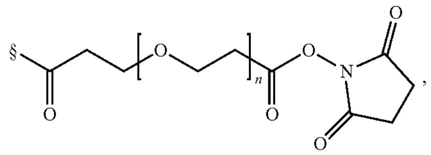

, ($L^1$-g)

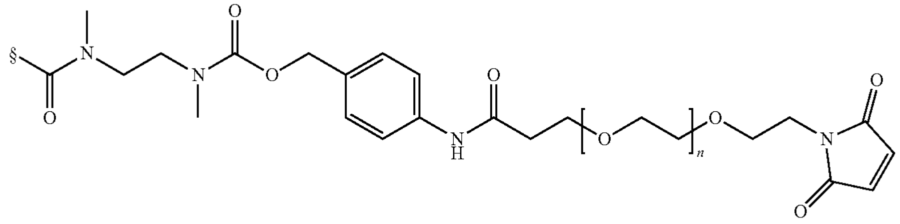

, ($L^1$-h)

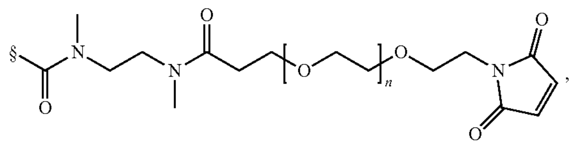

, ($L^1$-i)

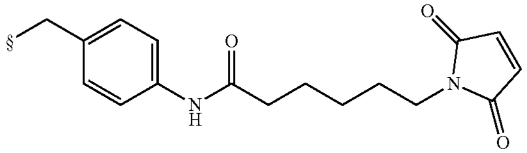

, ($L^1$-j)

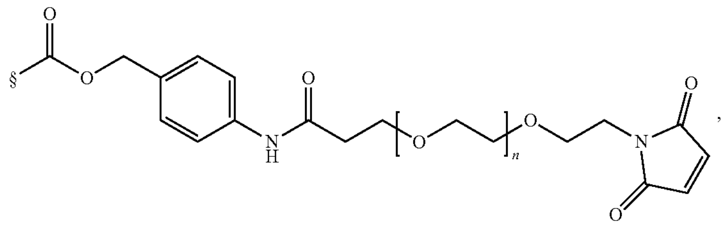

, and ($L^1$-k)

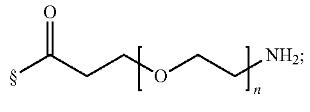

wherein

§ marks the connection to the compound of formula (I).

Preferably, n is 0, 1, 2, 3, 4, 5, 6, 7, or 8.

Preferably, the above definitions of L also cover stereoisomers, i.e. enantiomers and diastereoisomers of the depicted structures.

As explained above, the connection of the linker $L^1$ to the compound of formula (I) is preferably established via an oxygen or nitrogen atom of a former hydroxy or amino group of the compound of formula I, which is particularly preferably attached to or part of the substituents $R^2$, $R^4$, $R^5$, or $R^N$ of the compound of formula (I). The linker $L^1$ may be cleavable or non-cleavable. A cleavable linker can be sensitive to enzymes and may be cleaved by enzymes such as proteases.

In one embodiment of the conjugate of the invention, the covalent bond between the compound of formula (I) and the linker $L^2$ is established by the reaction of a functional group of the compound of formula (I) with a functional group handle of the linker $L^2$, and the covalent bond between the targeting moiety T and the linker $L^2$ is established by the reaction of a functional group of the targeting moiety T with a functional group handle of the linker $L^2$; and preferably the functional group of the compound of formula (I) is attached to or part of the substituents $R^2$, $R^4$, $R^5$, or $R^N$ so that the linker $L^2$, to which the targeting moiety is covalently bonded on one end, will on the other end be covalently bonded to the compound of formula (I) according to any one of the following structures:

(I-$R^2$-$L^2$-T)

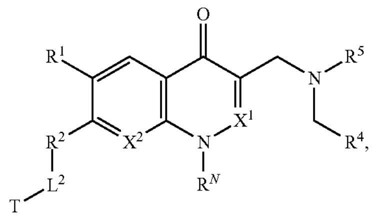

(I-$R^N$-$L^2$-T)

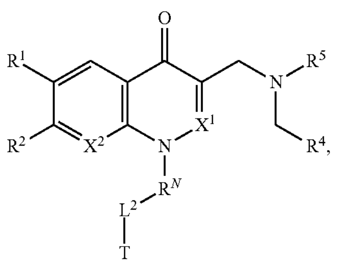

-continued (I-$R^4$-$L^2$-T)

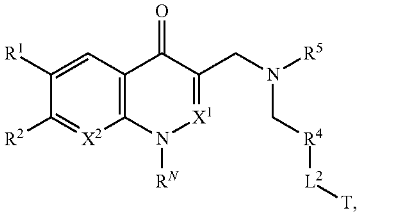

(I-$R^5$-$L^2$-T)

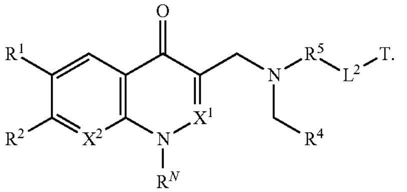

The functional group, which is attached to or part of the substituents $R^2$, $R^4$, $R^5$ or $R^N$ preferably comprises an amino or hydroxy group. This functional group establishes the covalent bond to the linker $L^2$ by reaction with a functional group, preferably a benzyl alcohol group, a carbonate group, a carbamate group, a carboxylic acid group, a carboxylic ester group, a carboxylic amide group, an urea group or a lactam group of a precursor of the linker $L^2$ under suitable conditions. Accordingly, the covalent bond is preferably a bond between an oxygen or nitrogen atom of the compound of formula (I) and a carbon atom of the linker $L^2$. In other words, a hydrogen atom at an amino of hydroxy group of the compound of formula (I) is replaced by a carbon atom of the linker $L^2$. The linker $L^2$ further establishes the connection to the targeting moiety T. A functional group of the targeting moiety T, preferably a lysine group, an azide group, a cysteine group, or a ketone group, establishes the covalent bond to the linker $L^2$ by reaction with a functional group, preferably a functional group selected from lysine reactive groups including succinyl esters, pentafluorophenyl esters, β-lactam amides, isocyanates, and isothiocyanates; azide reactive groups including alkynes and strained alkynes; cysteine reactive groups including maleimide groups, α-haloacetamides, pyridyl disulfides and vinyl sulfoxides; and ketone reactive groups including hydroxylamines, hydrazines and acyl hydrazides of a precursor of the linker $L^2$ under suitable conditions. Accordingly, the covalent bond between the linker $L^2$ and the targeting moiety T is preferably a bond between a nitrogen, sulfur or carbon atom of the targeting moiety T and a carbon atom of the linker $L^2$.

As a result, a conjugate of the formula (I)-$L^2$-T is obtained, and if several compounds of formula (I) are linked to the targeting moiety, a conjugate of the formula $[(I)\text{-}L^2]_a$-T, wherein a is an integer of from 1 to 30, and wherein a nitrogen or oxygen atom of the compound of formula (I) forms the connection to $L^2$, and wherein a nitrogen, sulfur or carbon atom of the targeting moiety T forms the connection to $L^2$, so that the linker $L^2$ forms a covalent connection between the compound(s) of formula (I) and the targeting moiety T. The linker $L^2$ preferably has the structure $H^{1A}$-$L^C$-$H^{2B}$, wherein $H^{1A}$ is a functional group handle, which is covalently bonded to the compound of formula (I), preferably a nitrogen or oxygen atom thereof, and wherein $H^{2B}$ is a functional group handle, which is covalently bonded to the targeting moiety T, preferably a nitrogen, sulfur or carbon atom thereof.

In one embodiment, the functional group of the compound of formula (I), which is attached to or part of the substituents $R^2$, $R^4$, $R^5$, or $R^N$, and which forms the covalent bond to the functional group handle $H^{1A}$ of the linker $L^2$, is selected from the following options:

either $R^2$ is $NHR^D$, $NHR^D$—$C_1$-$C_4$-alkyl, NH—($C_1$-$C_4$-alkylene)-$NR^CR^D$, $NR^F$—($C_1$-$C_4$-alkylene)-$NHR^D$, O—($C_1$-$C_4$-alkylene)-$NHR^D$, or 8- to 10-membered saturated heterobicyclyl, wherein the aforementioned heterobicyclic ring comprises at least one nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or $R^2$ is $NR^FC(=O)R^E$, wherein $R^E$ is $NHR^D$—$C_1$-$C_4$-alkyl;

or $R^N$ is $NHR^D$—$C_1$-$C_4$-alkyl;

or any one of the substituents $R^2$, $R^4$, $R^5$, $R^N$ carries a substituent $R^X$, wherein $R^X$ is OH, $NHR^D$, $NHR^D$—$C_1$-$C_4$-alkyl, or HO—$C_1$-$C_4$-alkyl;

and preferably either $R^2$ is $NH_2$, $NH_2$—$C_1$-$C_2$-alkyl, NH—($C_1$-$C_3$-alkylene)-$NH_2$, NH—($C_1$-$C_3$-alkylene)-$NHCH_3$, NH—($C_1$-$C_3$-alkylene)-$N(CH_3)_2$, O—($C_1$-$C_3$-alkylene)-$NH_2$, or O—($C_1$-$C_3$-alkylene)-$NHCH_3$;

or $R^2$ is $NHC(=O)R^E$, wherein $R^E$ is $NH_2$—$C_1$-$C_4$-alkyl;

or $R^N$ is $NH_2$—$C_1$-$C_3$-alkyl;

or any one of the substituents $R^2$, $R^4$, or $R^5$ carries a substituent $R^X$, wherein $R^X$ is OH, $NH_2$, $NHCH_3$, $NH_2$—$C_1$-$C_2$-alkyl, or HO—$C_1$-$C_2$-alkyl.

In one embodiment of the conjugate of the invention, the linker $L^2$ comprises (i) a chain $L^C$ of 2 to 100 atoms selected from carbon, nitrogen, oxygen, and sulfur atoms, which may be interrupted by 5- to 10-membered aryl and heteroaryl groups and/or 3- to 8-membered saturated carbocyclyl or heterocyclyl groups, wherein the aforementioned heteroaryl and heterocyclic groups comprise one or more, same or different heteroatoms selected from O, N or S, wherein said N- and/or S-atoms are independently oxidized or non-oxidized, and wherein each substitutable carbon or heteroatom in the chain is independently unsubstituted or substituted with one or more same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

and preferably a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$- alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$haloalkoxy;

(ii) a functional group handle $H^{1A}$, which is covalently bonded to the compound of formula (I);

(iii) a functional group handle $H^{2B}$, which is covalently bonded to the targeting moiety T.

Preferred functional group handles $H^{1A}$ of the linker $L^2$ are based on a functional group selected from a benzyl alcohol group, a carbonate group, a carbamate group, a carboxylic acid group, a carboxylic ester group, an carboxylic amide group, an urea group and a lactam group, from which a covalent bond to the compound of formula (I) is established by reaction with a suitable functional group of the compound of formula (I), in particular a hydroxy or amino group of the compound of formula (I).

Preferred functional group handles $H^{2B}$ of the linker $L^2$ are based on a functional group selected from lysine reactive groups including succinyl esters, pentafluorophenyl esters, β-lactam am-ides, isocyanates, and isothiocyanates; azide reactive groups including alkynes and strained alkynes; cysteine reactive groups including maleimide groups, α-haloacetamides, pyridyl disulfides and vinyl sulfoxides; and ketone reactive groups including hydroxylamines, hydrazines and acyl hydrazides, from which a covalent bond to the targeting moiety T is established by reaction with a suitable functional group of the targeting moiety T, in particular a lysine, an azide, a cysteine or a ketone group.

Preferred chains $L^C$ of the linker $L^2$ include:

($L^C$-1)

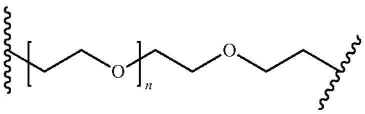

, ($L^C$-2)

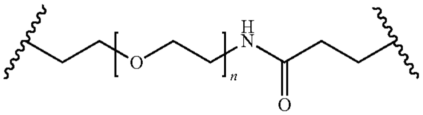

, ($L^C$-3)

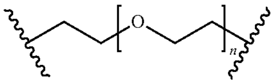

, ($L^C$-4)

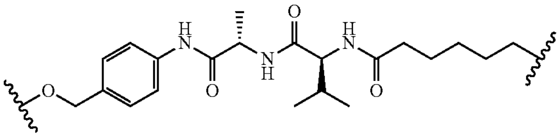

, ($L^C$-5)

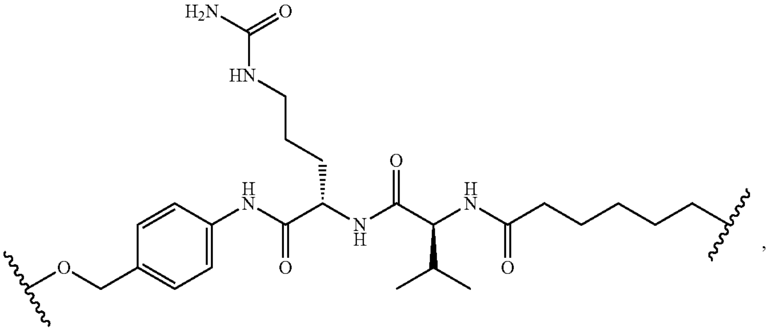

, ($L^C$-6)

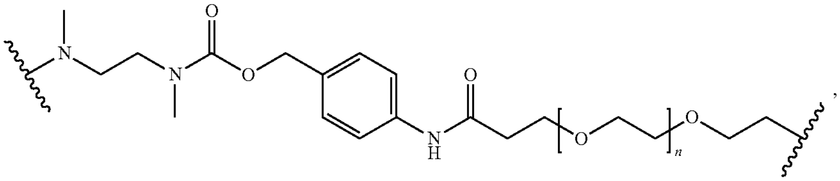

, ($L^C$-7)

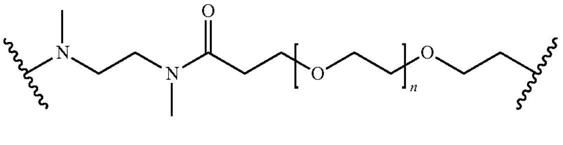

, ($L^C$-8)

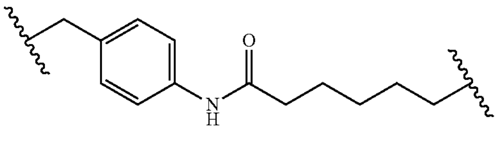

, ($L^C$-9)

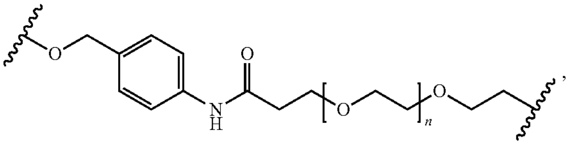

, ($L^C$-10)

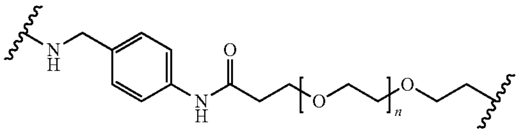

, and

-continued (L^C-11)

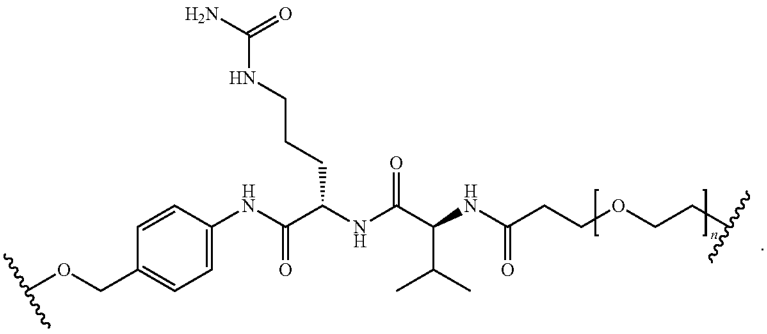

Preferably, n is 0, 1, 2, 3, 4, 5, 6, 7, or 8.

It is to be understood that the above definitions of $L^C$ with stereocenters preferably also cover stereoisomers, i.e. enantiomers and diastereoisomers of the depicted structures.

Preferably, the linker $L^2$ has a structure $H^{1A}$-$L^C$-$H^{2B}$, wherein $H^{1A}$, $L^C$, and $H^{2B}$ are as defined above, and wherein the definitions of $L^C$ preferably also cover possible stereoisomers.

Further referred chains $L^C$ of the linker $L^2$ include:

(L^C-1)

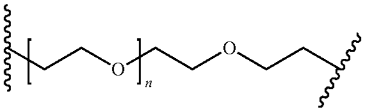

, (L^C-2)

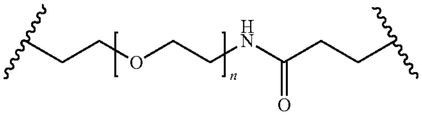

, (L^C-3)

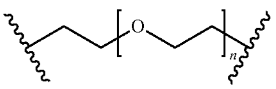

, (L^C-4)

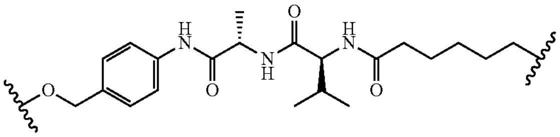

, (L^C-5)

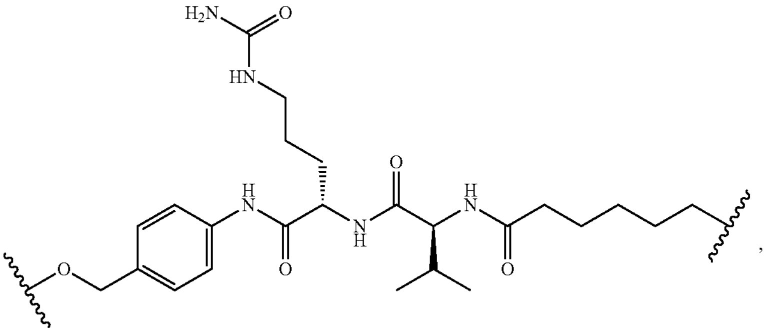

, (L^C-6)

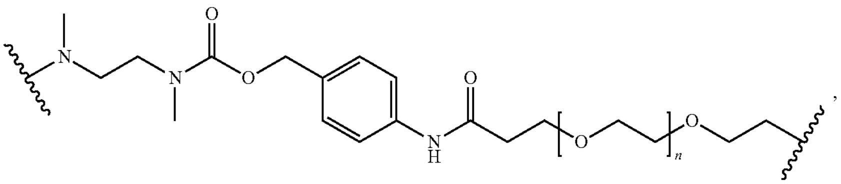

, (L^C-7)

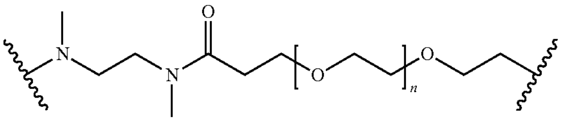

, (L^C-8)

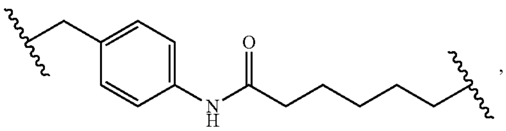

, and

-continued (L^C-9)

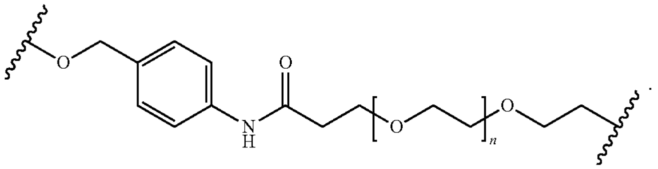

Preferably, n is 0, 1, 2, 3, 4, 5, 6, 7, or 8.

It is to be understood that the above definitions of $L^C$ with stereocenters preferably also cover stereoisomers, i.e. enantiomers and diastereoisomers of the depicted structures.

Preferably, the linker $L^2$ has a structure $H^{1A}$-$L^C$-$H^{2B}$, wherein $H^{1A}$, $L^C$, and $H^{2B}$ are as defined above, and wherein the definitions of $L^C$ preferably also cover possible stereoisomers.

In one embodiment of the conjugate, the linker $L^2$ has the structure $H^{1A}$-$L^C$-$H^{2B}$ and is selected from the group consisting of:

(L^2-1)

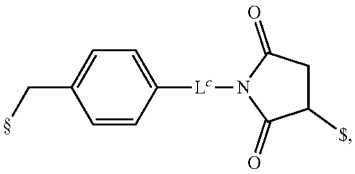

(L^2-2)

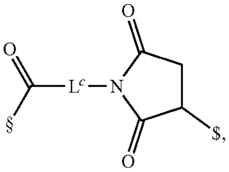

(L^2-3)

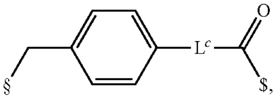

(L^2-4)

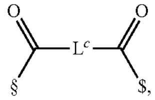

(L^2-5)

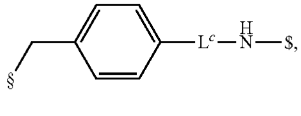

(L^2-6)

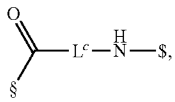

(L^2-7)

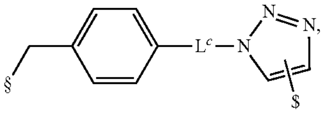

-continued (L^2-8)

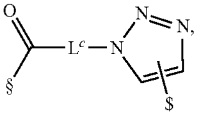

(L^2-9)

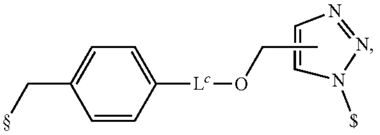

(L^2-10)

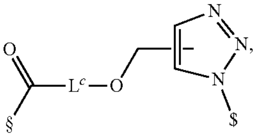

(L^2-11)

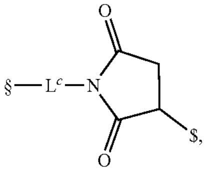

(L^2-12)

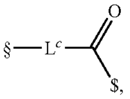

(L^2-13)

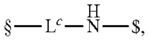

(L^2-14)

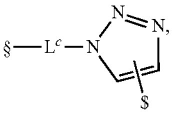

and (L^2-15)

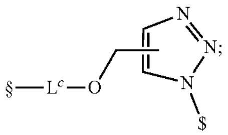

wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy; and § marks the connection to the compound of formula (I); and $ marks the connection to the targeting moiety T; and and wherein preferably $L^C$ is selected from the group consisting of ($L^C$-1)

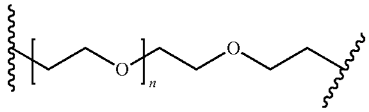, ($L^C$-2)

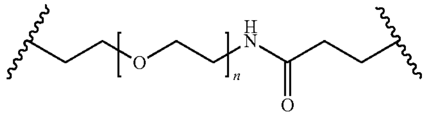, ($L^C$-3)

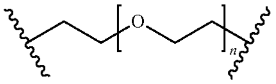, ($L^C$-4)

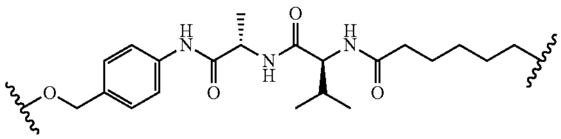, ($L^C$-5)

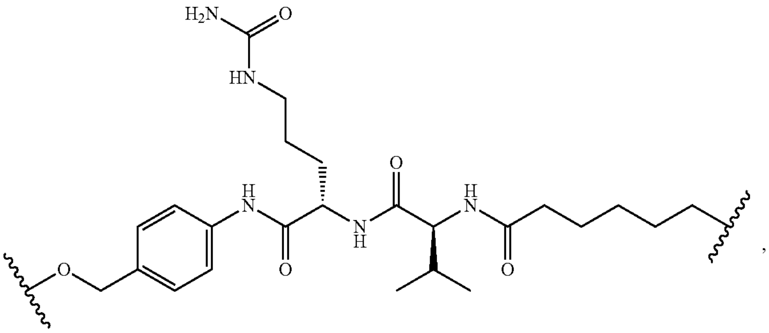, ($L^C$-6)

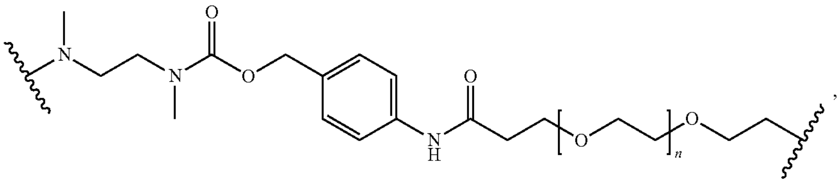, ($L^C$-7)

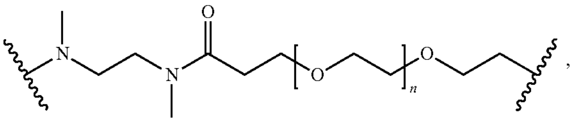, ($L^C$-8)

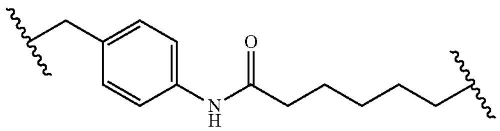, ($L^C$-9)

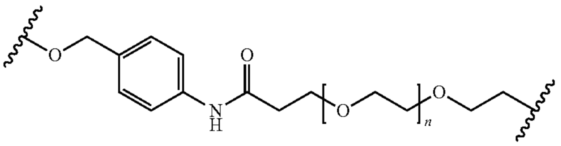, ($L^C$-10)

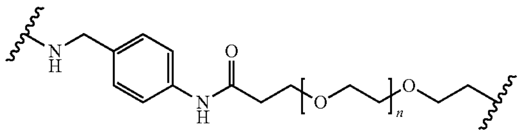, and

-continued (L$^C$-11)

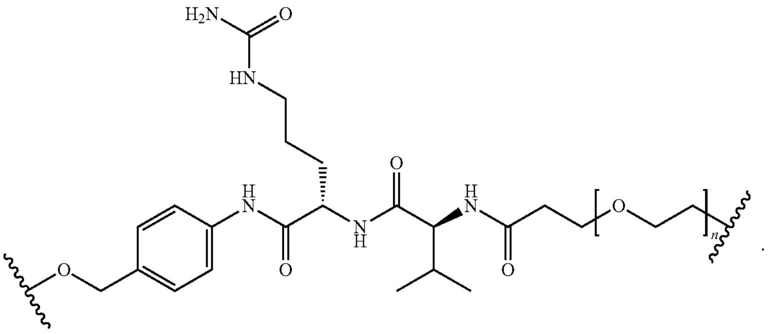

Preferably, n is 0, 1, 2, 3, 4, 5, 6, 7, or 8.

It is to be understood that the above definitions of $L^C$ with stereocenters preferably also cover stereoisomers, i.e. enantiomers and diastereoisomers of the depicted structures.

In one embodiment of the conjugate, the linker $L^2$ has the structure $H^{1A}$-$L^C$-$H^{2B}$ and is selected from the group consisting of:

(L$^2$-1)

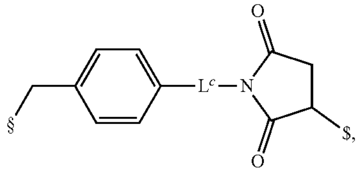

(L$^2$-2)

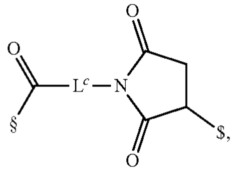

-continued (L$^2$-3)

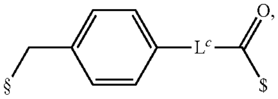

and (L$^2$-4)

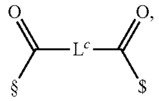

wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$haloalkoxy;

§ marks the connection to the compound of formula (I); and $ marks the connection to the targeting moiety T.

and wherein preferably $L^C$ is selected from the group consisting of (L$^C$-1)

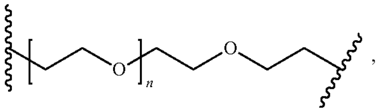

(L$^C$-2)

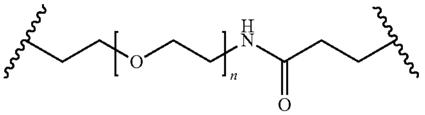

(L$^C$-3)

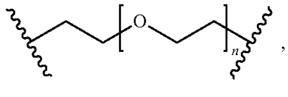

(L$^C$-4)

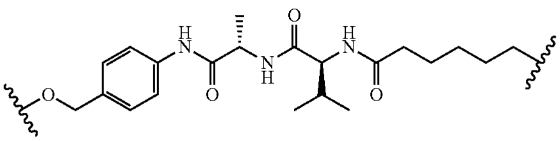

-continued $(L^C\text{-}5)$

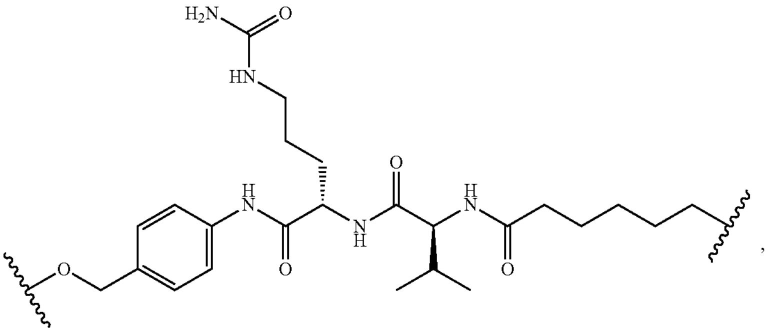, $(L^C\text{-}6)$

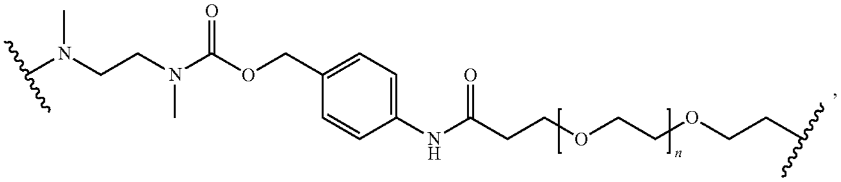, $(L^C\text{-}7)$

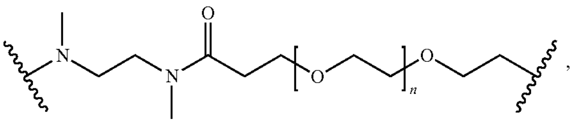, $(L^C\text{-}8)$

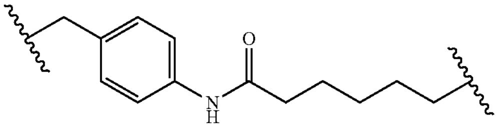, and $(L^C\text{-}9)$

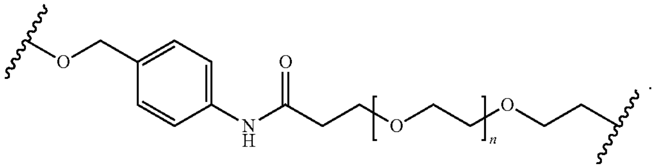.

Preferably, n is 0, 1, 2, 3, 4, 5, 6, 7, or 8.

Preferably, n is 0, 1, 2, 3, 4, 5, 6, 7, or 8.

It is to be understood that the above definitions of $L^C$ with stereocenters preferably also cover stereoisomers, i.e. enantiomers and diastereoisomers of the depicted structures.

As explained above, the connection of the linker $L^2$ to the compound of formula (I) is preferably established via an oxygen or nitrogen atom of a former hydroxy or amino group of the compound of formula I, which is particularly preferably attached to or part of the substituents $R^2$, $R^4$, $R^5$, or $R^N$ of the compound of formula (I). On the other hand, the connection of the linker $L^2$ to the targeting moiety T is preferably established via a nitrogen, sulfur or carbon atom of a former lysine, cysteine, azide or ketone group of the targeting moiety T. The linker $L^2$ may be cleavable or non-cleavable. A cleavable linker can be sensitive to enzymes and may be cleaved by enzymes such as proteases.

As indicated above, the conjugates of the invention inter alia comprise a targeting moiety T. Preferred embodiments in this regard are defined hereinafter.

In one embodiment of the conjugate of the invention, the targeting moiety T comprises an antibody, an antibody fragment, a nucleic acid based molecule, a carbohydrate, a peptide, or a modified peptide, in particular an antibody or an antigen-binding fragment, which is designed to target the Human Epidermal Growth Factor Receptor (EGFR), a plasminogen activator, a cytotoxic T-lymphocyte associated antigen (CTLA) such as CTLA-4, PD-1, PD-L1, KIR, TIM3, VISTA, TIGIT, LAG3, OX40, ROR1, ROR2, vascular endothelial growth factor (VEGF), fibroblast growth factor receptor (FGFR), platelet-derived growth factor (PDGF), transforming growth factor (TGF), neurotrophic factors, a nerve growth factor, platelet-derived growth factor (PDGF), interleukin receptors, transforming growth factor (TGF), estrogen receptor, progesterone receptor, c-Kit, cMET, ErbB2/Her2, ErbB3/Her3, ErbB4/Her4, CD3, CD20, CD22, CD30, CD33, CD40, CD47, CD79, CD123, CD133, CD166, CD137, the mesothelin protein, EpCAM, FLT3, PSMA, PSCA, STEAP, CEA, folate receptor, the CD39/CD73 receptors, adenosine receptors, SLC34A2 gene product, the EphA2 tyrosine kinase, the Mucl/Muc16 cell-surface antigens, ALK, AFP, bcr-Abl, PAP.

In another embodiment, the targeting moiety T comprises an antibody or an antigen-binding fragment thereof, which is monovalent, divalent, or polyvalent, or an antibody or an antigen-binding fragment thereof, which comprises a monoclonal or a polyclonal antibody, or an antigen-binding fragment thereof.

Monovalent antibodies are dimers (HL) comprising a heavy (H) chain associated by a disulfide bridge with a light chain (L). Divalent antibodies are tetramer (H2L2) comprising two dimers associated by at least one disulfide bridge. Polyvalent antibodies may also be produced, for example by linking multiple dimers. The basic structure of an antibody molecule consists of two identical light chains and two identical heavy chains which associate non-covalently and can be linked by disulfide bonds. Each heavy and light chain contains an amino-terminal variable region of about 110 amino acids, and constant sequences in the remainder of the chain. The variable region includes several hypervariable regions, or Complementarity Determining Regions (CDRs), that form the antigen-binding site of the antibody molecule and determine its specificity for the antigen or variant or fragment thereof (e.g. an epitope). On either side of the CDRs of the heavy and light chains is a framework region, a relatively conserved sequence of amino acids that anchors and orients the CDRs. Antibody fragments may include a bi-specific antibody (BsAb) or a chimeric antigen receptor (CAR).

The constant region consists of one of five heavy chain sequences (μ, γ, ζ, α, or ε) and one of two light chain sequences (K or A). The heavy chain constant region sequences determine the isotype of the antibody and the effector functions of the molecule.

Preferably, the antibody or antigen-binding fragment thereof is isolated or purified.

In one preferred embodiment, the antibody or antigen-binding fragment thereof comprises a polyclonal antibody, or an antigen-binding fragment thereof. The antibody or antigen-binding fragment thereof may be generated in a rabbit, mouse or rat.

In another preferred embodiment, the antibody or antigen-binding fragment thereof comprises a monoclonal antibody or an antigen-binding fragment thereof. Preferably, the antibody is a human antibody. As used herein, the term "human antibody" can mean an antibody, such as a monoclonal antibody, which comprises substantially the same heavy and light chain CDR amino acid sequences as found in a particular human antibody exhibiting immunospecificity. An amino acid sequence, which is substantially the same as a heavy or light chain CDR, exhibits a considerable amount of sequence identity when compared to a reference sequence. Such identity is definitively known or recognizable as representing the amino acid sequence of the particular human antibody. Substantially the same heavy and light chain CDR amino acid sequence can have, for example, minor modifications or conservative substitutions of amino acids.

The term "human monoclonal antibody" can include a monoclonal antibody with substantially or entirely human CDR amino acid sequences produced, for example by recombinant methods such as production by a phage library, by lymphocytes or by hybridoma cells.

The term "humanised antibody" can mean an antibody from a non-human species (e.g. mouse or rabbit) whose protein sequences have been modified to increase their similarity to antibodies produced naturally in humans.

The antibody may be a recombinant antibody. The term "recombinant human antibody" can include a human antibody produced using recombinant DNA technology.

The term "antigen-binding region" can mean a region of the antibody having specific binding affinity for its target antigen or a variant or fragment thereof. Preferably, the fragment is an epitope. The binding region may be a hypervariable CDR or a functional portion thereof. The term "functional portion" of a CDR can mean a sequence within the CDR which shows specific affinity for the target antigen. The functional portion of a CDR may comprise a ligand which specifically binds to the target antigen or a fragment thereof.

The term "CDR" can mean a hypervariable region in the heavy and light variable chains. There may be one, two, three or more CDRs in each of the heavy and light chains of the antibody. Normally, there are at least three CDRs on each chain which, when configured together, form the antigen-binding site, i.e. the three-dimensional combining site with which the antigen binds or specifically reacts. It has however been postulated that there may be four CDRs in the heavy chains of some antibodies.

The definition of CDR also includes overlapping or subsets of amino acid residues when compared against each other. The exact residue numbers which encompass a particular CDR or a functional portion thereof will vary depending on the sequence and size of the CDR. Those skilled in the art can routinely determine which residues comprise a particular CD R given the variable region amino acid sequence of the antibody.

The term "functional fragment" of an antibody can mean a portion of the antibody which retains a functional activity. A functional activity can be, for example antigen binding activity or specificity. A functional activity can also be, for example, an effector function provided by an antibody constant region. The term "functional fragment" is also intended to include, for example, fragments produced by protease digestion or reduction of a human monoclonal antibody and by recombinant DNA methods known to those skilled in the art. Human monoclonal antibody functional fragments include, for example individual heavy or light chains and fragments thereof, such as VL, VH and Fd; monovalent fragments, such as Fv, Fab, and Fab'; bivalent fragments such as F(ab')2; single chain Fv (scFv); and Fe fragments.

The term "VL fragment" can mean a fragment of the light chain of a human monoclonal antibody which includes all or part of the light chain variable region, including the CDRs. A VL fragment can further include light chain constant region sequences.

The term "VH fragment" can means a fragment of the heavy chain of a human monoclonal antibody which includes all or part of the heavy chain variable region, including the CDRs.

The term "Fd fragment" can mean the heavy chain variable region coupled to the first heavy chain constant region, i.e. VH and CH-1. The "Fd fragment" does not include the light chain, or the second and third constant regions of the heavy chain.

The term "Fv fragment" can mean a monovalent antigen-binding fragment of a human monoclonal antibody, including all or part of the variable regions of the heavy and light chains, and absent of the constant regions of the heavy and light chains. The variable regions of the heavy and light chains include, for example, the CDRs. For example, an Fv fragment includes all or part of the amino terminal variable region of about 110 amino acids of both the heavy and light chains.

The term "Fab fragment" can mean a monovalent antigen-binding fragment of a human monoclonal antibody that is larger than an Fv fragment. For example, a Fab fragment includes the variable regions, and all or part of the first constant domain of the heavy and light chains. Thus, a Fab fragment additionally includes, for example, amino acid residues from about 110 to about 220 of the heavy and light chains.

The term "Fab' fragment" can mean a monovalent antigen-binding fragment of a human monoclonal antibody that is larger than a Fab fragment. For example, a Fab' fragment includes all of the light chain, all of the variable region of the heavy chain, and all or part of the first and second constant domains of the heavy chain. For example, a Fab' fragment can additionally include some or all of amino acid residues 220 to 330 of the heavy chain.

The term "F(ab')2 fragment" can mean a bivalent antigen-binding fragment of a human monoclonal antibody. An F(ab')2 fragment includes, for example, all or part of the variable regions of two heavy chains- and two light chains, and can further include all or part of the first constant domains of two heavy chains and two light chains.

The term "single chain Fv (scFv)" can mean a fusion of the variable regions of the heavy (VH) and light chains (VL) connected with a short linker peptide.

The term "bispecific antibody (BsAb)" can mean a bispecific antibody comprising two scFv linked to each other by a shorter linked peptide.

One skilled in the art knows that the exact boundaries of a fragment of an antibody are not important, so long as the fragment maintains a functional activity. Using well-known recombinant methods, one skilled in the art can engineer a polynucleotide sequence to express a functional fragment with any endpoints desired for a particular application. A functional fragment of the antibody may comprise or consist of a fragment with substantially the same heavy and light chain variable regions as the human antibody.

The antigen-binding fragment thereof may comprise or consist of any of the fragments selected from a group consisting of VH, VL, Fd, Fv, Fab, Fab', scFv, F (ab')2 and Fc fragment.

The antigen-binding fragment thereof may comprise or consist of any one of the antigen binding region sequences of the VL, any one of the antigen binding region sequences of the VH, or a combination of VL and VH antigen binding regions of a human antibody. The appropriate number and combination of VH and VL antigen binding region sequences may be determined by those skilled in the art depending on the desired affinity and specificity and the intended use of the antigen-binding fragment Functional fragments or antigen-binding fragments of antibodies may be readily produced and isolated using methods well known to those skilled in the art. Such methods include, for example, proteolytic methods, recombinant methods and chemical synthesis. Proteolytic methods for the isolation of functional fragments comprise using human antibodies as a starting material. Enzymes suitable for proteolysis of human immunoglobulins may include, for example, papain, and pepsin. The appropriate enzyme may be readily chosen by one skilled in the art, depending on, for example, whether monovalent or bivalent fragments are required. For example, papain cleavage results in two monovalent Fab' fragments that bind antigen and an Fc fragment. Pepsin cleavage, for example, results in a bivalent F (ab') fragment. An F(ab')2 fragment of the invention may be further reduced using, for example, DTT or 2-mercaptoethanol to produce two monovalent Fab' fragments.

Functional or antigen-binding fragments of antibodies produced by proteolysis may be purified by affinity and column chromatographic procedures. For example, undigested antibodies and Fe fragments may be removed by binding to protein A. Additionally, functional fragments may be purified by virtue of their charge and size, using, for example, ion exchange and gel filtration chromatography. Such methods are well known to those skilled in the art.

The antibody or antigen-binding fragment thereof may be produced by recombinant methodology. Preferably, one initially isolates a polynucleotide encoding desired regions of the antibody heavy and light chains. Such regions may include, for example, all or part of the variable region of the heavy and light chains. Preferably, such regions can particularly include the antigen binding regions of the heavy and light chains, preferably the antigen binding sites, most preferably the CDRs.

As used herein, the term "immunospecificity" can mean the binding region is capable of immunoreacting with the target antigen, or a variant or fragment thereof, by specifically binding therewith. The antibody or antigen-binding fragment thereof can selectively interact with an antigen with an affinity constant of approximately $10^{-5}$ to $10^{-13}$ $M^{-1}$, preferably $10^{-6}$ to $10^{-9}$ $M^{-1}$, even more preferably, $10^{-10}$ to $10^{-12}$ $M^{-1}$.

The term "epitope" can mean any region of an antigen with the ability to elicit, and combine with, a binding region of the antibody or antigen-binding fragment thereof.

In a preferred embodiment, T is an antibody or a fragment thereof, preferably selected from antibodies that have already been applied in the field of immune oncology. Exemplary anti-PD1 antibodies include lambrolizumab (MK-3475, Merck), nivolumab (BMS-936558, Bristol-Myers Squibb), AMP-224 (Merck) and pidilizumab (CT-011, Curetech Ltd.). Known anti-PDL1 antibodies include further MDX-1105 (Medarex), MED14736 (Medimmune), MPDL4280A (Genentech) and BMS-936559 (Bristol-Myers Squibb). Exemplary anti-CTLA4 antibodies include ipilimumab (Yervoy, Bristol-Myers Squibb) and tremelimumab (Pfizer). Exemplary anti-ErbB2/Her2 antibodies include trastuzumab (Roche), pertuzumab (Genentech), margetuximab (Macrogenics) and HT-19 (Mersana Therapeutics). In a preferred embodiment, T is trastuzumab or a fragment or derivative thereof.

In one embodiment, T comprises a nucleic acid based molecule. The nucleic acid base molecule may be an aptamer. The nucleic acid based molecule may target the CD33/CD34 or PSMA tumor antigens, or any other tumor antigen known to those skilled in the art, for example as described in Orava, E., Biochem. Biophys. Acta, 2010, 1798, 2190-2200.

Aptamers are nucleic acid or peptide molecules that assume a specific, sequence-dependent shape and bind to specific target ligands based on a lock-and-key fit between the aptamer and ligand. Typically, aptamers may comprise either single or double-stranded DNA molecules (ssDNA or dsDNA) or single-stranded RNA molecules (ssRNA). Peptide aptamers consist of a short variable peptide domain, attached at both ends to a protein scaffold. Aptamers may be used to bind both nucleic acid and non-nucleic acid targets.

Suitable aptamers may be selected from random sequence pools, from which specific aptamers may be identified which bind to the selected antigen with high affinity. Methods for the production and selection of aptamers having desired specificity are well known to those skilled in the art, and include the SELEX (systematic evolution of ligands by exponential enrichment) process. Briefly, large libraries of oligonucleotides are produced, allowing the isolation of large amounts of functional nucleic acids by an iterative process of in vitro selection and subsequent amplification through polymerase chain reaction. Preferred methodologies for producing aptamers include those disclosed in WO 2004/042083.

In an alternative embodiment, the targeting moiety T comprises a peptide or a modified peptide. The peptide or modified peptide may comprise the RGD sequence motif, as described in Mousavizadeh, A., Colloids Surfaces B., 2017, 158, 507-517.

The compound-linker constructs and the conjugates of the invention can be obtained by applying standard synthetic protocols as outlined hereinafter.

The compound-linker constructs of the invention can be synthesized based on the formation of an amide bond and a subsequent derivatization reaction according to the following scheme:

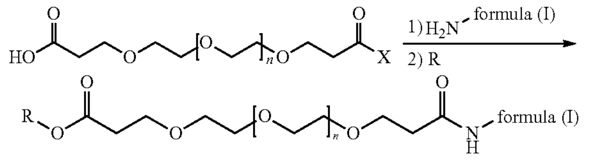

A PEGylated carboxylic acid, i.e. a carboxylic acid comprising a polyethylene glycol chain as depicted in the above scheme, that has been activated (as indicated by “X”, which may be a leaving group X-1 or X-2 as defined above) for amide bond formation can be reacted with an amino group of the compound of formula (I) to afford an intermediate amide. Formation of an activated ester (R) can be achieved by reaction of the intermediate amide-containing carboxylic acid using a reagent such as N-hydroxysuccinimide or pentafluorophenol in the presence of a coupling agent such as diisopropylcarbodiimide (DIC) to provide the compound-linker construct, which may then be further reacted with, e.g., with a lysine group, of a targeting moiety T to provide a conjugate according to the invention.

Alternatively, the compound-linker constructs of the invention can be synthesized based on the formation of an amide bond according to the following scheme:

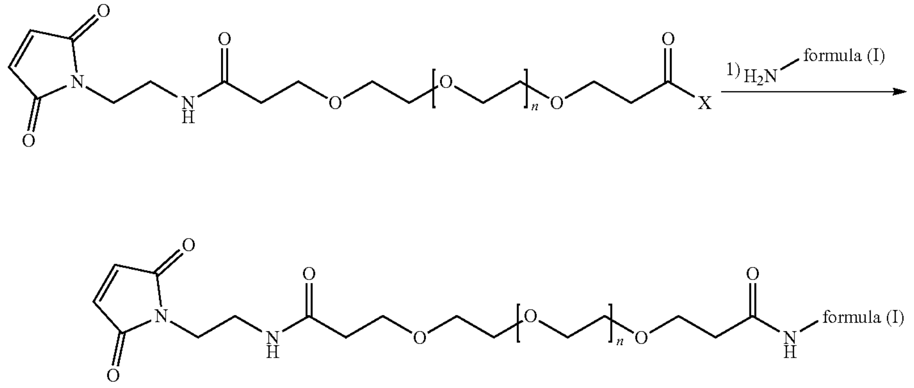

An activated carboxylic ester such as the one depicted in the above scheme can be reacted with an amino group of the compound of formula (I) to afford an amide as compound-linker construct. The maleimide group allows for a covalent bond to a targeting moiety T by reaction with a cysteine group of the targeting moiety T to thereby provide a conjugate according to the invention.

Alternatively, carboxylic acids can be coupled to an amino group of the compound of formula (I) in the presence of an amide bond forming agent such as dicyclohexycarbodiimde (DCC) to provide the compound-linker construct:

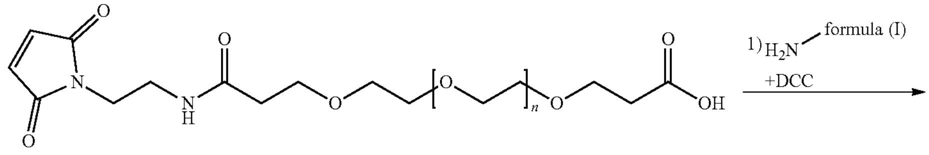

-continued

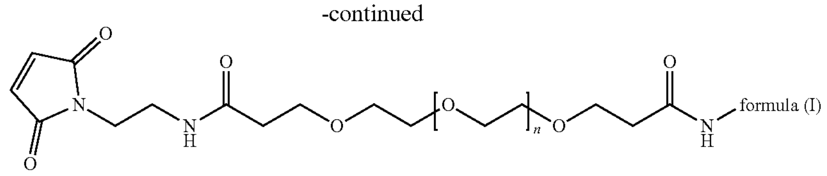

Again, the maleimide group allows for a covalent bond to a targeting moiety T by reaction with a cysteine group of the targeting moiety T to thereby provide a conjugate according to the invention.

Alternatively, the compound-linker constructs of the invention can be synthesized based on the formation of an amide bond according to the following scheme:

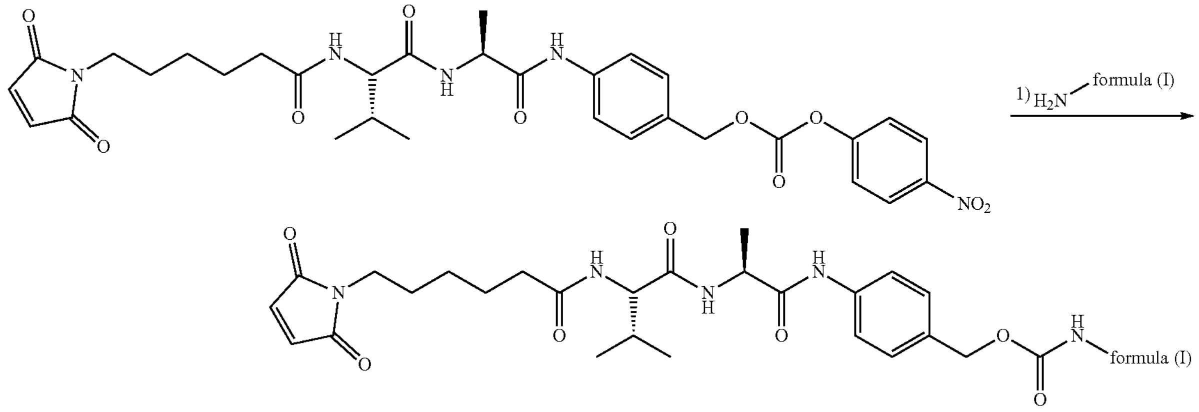

An activated carbonate such as the one depicted in the above scheme can react with an amino group of the compound of formula (I) to afford carbamates (ii) as the compound-linker construct. The maleimide group allows for a covalent bond to a targeting moiety T by reaction with a cysteine group of the targeting moiety T to thereby provide a conjugate according to the invention.

In general, the covalent bond between the linkers of the invention and the targeting moiety T may be formed, for example, by the reaction of the cysteine or lysine group of the targeting moiety with a maleimide or NHS ester derivative group from the linker, and the other covalent bond is the result of the reaction of a suitable functional group of the compound of formula (I) with a hydroxy group, an amino group, a carbonate group, a carbamate group, an ester group, an amide group, an urea group, or a lactam group from the linker.

One skilled in the art may be able to make various compound-linker constructs and conjugates by similar methods or by combining other methods known to one skilled in the art. It is also understood that one skilled in the art would be able to make compound-linker constructs and conjugates, in a similar manner as described herein, by using the appropriate starting materials and modifying the synthetic route as needed. Starting materials and reagents can be obtained from commercially available material or synthesized according to sources known to those skilled in the art.

Definitions

As used herein, the term "compound-linker construct" refers to a construct comprises a compound of formula (I) as defined herein and a linker $L^1$ as defined herein, which are covalently bonded to each other as explained in detail above.

As used herein, the term conjugate refers to a conjugate comprising a compound of formula (I), a linker $L^2$, and a targeting moiety T, wherein the linker $L^2$ links the compound of formula (I) to the targeting moiety T by covalent bonds. The targeting moiety may have from 1 to 30 compounds of formula (I) attached via a linker $L^2$, wherein the linker $L^2$ may in each case be identical, or different linkers $L^2$ may be present.

As used herein, the term "linker" can refer to a short, flexible, rigid, cleavable, non-cleavable, hydrophilic or hydrophobic chain covalently connecting the compound of formula (I) with the targeting moiety T. A cleavable linker can be cleaved by enzymes such as proteases. A cleavable linker can be a valine-citrulline linker or a valine-alanine linker.

As used herein, the term "targeting moiety" refers to moiety that has targeting capabilities such that it may specifically target a specific antigen, in particular a tumor antigen. Targeting in this context means that the moiety specifically binds to or is immunologically reactive toward the specific antigen. Preferred antigens include proteins, preferably proteins that can only be found in or on tumor cells. Suitable targeting moieties include antibodies, antibody fragments, nucleic acid based molecules, carbohydrates, peptides or modified peptides. A preferred targeting moiety according to the invention is an antibody or an antibody fragment Thus, preferred conjugates according to the invention are so-called antibody-drug conjugates (ADCs). The targeting moiety may direct the compound of formula (I) of the conjugates specifically to tumor cells, in order to deliver the compound of formula (I) in a cell-specific manner. The principle is described in Polakis, P., Pharmacol. Revs., 2016, 68, 3-19. If the linker between the targeting moiety and the compound of formula (I) is designed to be cleavable, the compound of formula (I) will diffuse into the cell and contact the STING protein.

As used herein, the term "antibody drug conjugate" ("ADC") refers to conjugate as defined herein, wherein the targeting moiety T is an antibody or antibody fragment.

As used herein, the term "antibody" can refer to an immunoglobulin molecule that specifically binds to, or is immunologically reactive toward, a specific antigen. Antibodies can include, for example, polyclonal, monoclonal, genetically engineered antibodies, and antigen binding fragments thereof. An antibody can be for example, murine, chimeric, humanized, heteroconjugate, bispecific, diabody, triabody, or tetrabody. The antigen binding fragment can include, for example, Fab', $F(ab')_2$, Fab, Fv, rIgG, and scFv.

As used herein, a "tumor antigen" can be an antigenic substance associated with a tumor or cancer call, and can trigger an immune response in a host.

An antigen can elicit an immune response. An antigen can be a protein, polysaccharide, lipid, or glycolipid, which can be recognized by an immune cell, such as a T cell or a B cell. Exposure of immune cells to one or more of these antigens can elicit a rapid cell division and differentiation response resulting in the formation of clones of the exposed T cells and B cells. B cells can differentiate into plasma cells which in turn can produce antibodies which selectively bind to the antigens.

In cancer, there are four general groups of tumor antigens: (i) viral tumor antigens which can be identical for any viral tumor of this type, (ii) carcinogenic tumor antigens which can be specific for patients and for the tumors, (iii) isoantigens of the transplantation type or tumorspecific transplantation antigens which can be different in all individual types of tumor but can be the same in different tumors caused by the same virus; and (iv) embryonic antigens.

As a result of the discovery of tumor antigens, tumor antigens have become important in the development of new cancer treatments that can specifically target the cancer. This has led to the development of antibodies directed against these tumor antigens.

In addition to the development of antibodies against tumor antigens for cancer treatment, antibodies that target immune cells to boost the immune response have also been developed. For example, an anti-CD40 antibody that is a CD40 agonist can be used to activate dendritic cells to enhance the immune response.

The term "compound(s) of formula (I)" also covers a salt, stereoisomer, tautomer or N-oxide thereof. The compounds of formula (I) are an essential part of the compound-linker constructs and conjugates according to the invention. In connection with the term ADC, the compounds of formula (I) represent the drug part of the antibody-drug conjugates.

The compounds of formula (I) may be amorphous or may exist in one or more different crystalline states (polymorphs), which may have different macroscopic properties such as stability or show different biological properties such as activities. The present invention covers amorphous and crystalline forms of compounds of formula (I), mixtures of different crystalline states of the compounds of formula (I), as well as amorphous or crystalline salts thereof.

Salts of the compounds of formula (I) are preferably pharmaceutically acceptable salts, such as those containing counterions present in drug products listed in the US FDA Orange Book database. They can be formed in a customary manner, e.g., by reacting the compound with an acid of the anion in question, if the compounds according to the invention have a basic functionality, or by reacting acidic compounds according to the invention with a suitable base.

Suitable cationic counterions are in particular the ions of the alkali metals, preferably lithium, sodium and potassium, of the alkaline earth metals, preferably calcium, magnesium and barium, and of the transition metals, preferably manganese, copper, silver, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore the cations of 1,4-piperazine, meglumine, benzathine and lysine.

Suitable anionic counterions are in particular chloride, bromide, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate, furthermore lactate, gluconate, and the anions of poly acids such as succinate, oxalate, maleate, fumarate, malate, tartrate and citrate, furthermore sulfonate anions such as besylate (benzenesulfonate), tosylate (p-toluenesulfonate), napsylate (naphthalene-2-sulfonate), mesylate (methanesulfonate), esylate (ethanesulfonate), and ethanedisulfonate. They can be formed by reacting compounds according to the invention that have a basic functionality with an acid of the corresponding anion.

Depending on the substitution pattern, the compounds of formula (I) may have one or more centers of chirality, including axial chirality. The invention provides both, pure enantiomers or pure diastereomers, of the compounds of formula (I), and their mixtures, including racemic mixtures. Suitable compounds of formula (I) also include all possible geometrical stereoisomers (cis/trans isomers or E/Z isomers) and mixtures thereof. E/Z-isomers may be present with respect to, e.g., an alkene, carbon-nitrogen double-bond or amide group.

Tautomers may be formed, if a substituent is present at the compound of formula (I), which allows for the formation of tautomers such as keto-enol tautomers, imine-enamine tautomers, amide-imidic acid tautomers or the like. Furthermore, the core structure comprising the 6-membered ring that contains the =O substituent principally allows for keto-enol-tautomerization.

The term "N-oxide" includes any compound of the present invention which has at least one tertiary nitrogen atom that is oxidized to a N-oxide moiety.

The term "substituted", as used herein, means that a hydrogen atom bonded to a designated atom is replaced with a specified substituent, provided that the substitution results in a stable or chemically feasible compound. Unless otherwise indicated, a substituted atom may have one or more substituents and each substituent is independently selected.

The term "substitutable", when used in reference to a designated atom, means that attached to the atom is a hydrogen, which can be replaced with a suitable substituent.

In connection with the above term "substitutable", in particular with regard to the expression "wherein each substitutable carbon or heteroatom is independently unsubstituted or substituted with one or more, same or different substituents" it is to be understood that this term covers all possible options wherein e.g. carbon and heteroatoms are independently unsubstituted or substituted or wherein e.g. only carbon or only heteroatoms are independently unsubstituted or substituted with one or more, same or different substituents.

When it is referred to certain atoms or moieties being substituted with "one or more" substituents, the term "one or more" is intended to cover at least one substituent, e.g. 1 to 10 substituents, preferably 1, 2, 3, 4, or 5 substituents, more preferably 1, 2, or 3 substituents, most preferably 1, or 2 substituents. When neither the term "unsubstituted" nor "substituted" is explicitly mentioned concerning a moiety, said moiety is to be considered as unsubstituted.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine, or bromine.

The term "alkyl" as used herein denotes in each case a straight-chain or branched alkyl group having usually from 1 to 6 carbon atoms, preferably 1 to 5 or 1 to 4 carbon atoms, more preferably 1 to 3 or 1 or 2 carbon atoms. Examples of an alkyl group are methyl, ethyl, n-propyl, isopropyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein denotes in each case a straight-chain or branched alkyl group having usually from 1 to 6 carbon atoms, frequently 1 to 5 or 1 to 4 carbon atoms, preferably 1 to 3 or 1 or 2 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_6$-haloalkyl or $C_1$-$C_2$haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkenyl" as used herein denotes in each case an unsaturated hydrocarbon group having usually 2 to 6, preferably 2 to 4 carbon atoms comprising at least one carbon-carbon double bond in any position, e.g. vinyl (ethenyl), allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like. If geometric isomers are possible with regard to the double bond, the present invention relates to both, the E- and Z-isomers. Preferred alkenyl groups according to the invention are terminal alkenyl groups. The bonding of vinyl is exemplified below:

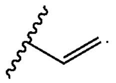

The term "haloalkenyl" as used herein refers to an alkenyl group as defined above, wherein the hydrogen atoms are partially or totally replaced with halogen atoms.

The term "alkynyl" as used herein denotes in each case an unsaturated hydrocarbon group having usually 2 to 6, preferably 2 to 5 or 2 to 4 carbon atoms, more preferably 2 to 3 carbon atoms, comprising at least one carbon-carbon triple bond in any position, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the hydrogen atoms are partially or totally replaced with halogen atoms.

The term "alkoxy" as used herein denotes in each case a straight-chain or branched alkyl group which is bonded via an oxygen atom and has usually from 1 to 6 carbon atoms, preferably 1 to 2 carbon atoms, more preferably 1 carbon atom. Examples of an alkoxy group are methoxy, ethoxy, n-propoxy, iso-propoxy, n-butyloxy, 2-butyloxy, iso-butyloxy, tert.-butyloxy, and the like.

The term "haloalkoxy" as used herein denotes in each case a straight-chain or branched alkoxy group having from 1 to 6 carbon atoms, preferably 1 to 2 carbon atoms, more preferably 1 carbon atom, wherein the hydrogen atoms of this group are partially or totally replaced with halogen atoms, in particular fluorine atoms. Preferred haloalkoxy moieties include $C_1$-haloalkoxy, in particular $C_1$-fluoroalkoxy, such as trifluoromethoxy and the like.

The term "alkoxyalkyl" as used herein refers to an alkoxy group, preferably a $C_1$-$C_4$-alkoxy group, more preferably a $C_1$-$C_2$alkoxy group which is bonded to the remainder of the molecule via an alkyl group preferably a $C_1$-$C_4$-alkyl group, more preferably a $C_1$-$C_2$-alkyl group. Preferred examples include methoxymethyl, ethoxymethyl, methoxyethyl, and ethoxyethyl.

The term "$R^C$O-alkyl" as used herein refers to a $R^C$O group, which is bonded to the remainder of the molecule via an alkyl group preferably a $C_1$-$C_4$-alkyl group, more preferably a $C_1$-$C_2$-alkyl group. Preferred examples include hydroxymethyl and hydroxyethyl if $R^C$ is H. Other examples include alkoxyalkyl groups as defined above.

The term "HO-alkyl" as used herein refers to a OH group, which is bonded to the remainder of the molecule via an alkyl group preferably a $C_1$-$C_4$-alkyl group, more preferably a $C_1$-$C_2$-alkyl group. Preferred examples include hydroxymethyl and hydroxyethyl.

The term "$NR^CR^D$-alkyl" as used herein refers to an aminoalkyl group, i.e. to an amino group $NR^CR^D$ which is bonded to the remainder of the molecule via an alkyl group, preferably a $C_1$-$C_4$-alkyl group, more preferably a $C_1$-$C_2$-alkyl group. Preferred examples include aminomethyl and aminoethyl if $R^C$ and $R^D$ are H.

The term "HO(C=O)—$C_1$-$C_4$-alkyl" as used herein refers to a carboxylalkyl group, i.e. to a carboxyl group C(=O)OH which is bonded to the remainder of the molecule via an alkyl group, preferably a $C_1$-$C_4$-alkyl group, more preferably a $C_1$-$C_2$-alkyl group. Preferred examples include carboxylmethyl and carboxylethyl.

The term "cycloalkyl" as used herein denotes in each case a monocyclic cycloaliphatic radical having usually from 3 to 10 or from 3 to 6 carbon atoms, such as cyclopropyl, cyclobutyl, cyclopentyl, cyclohexyl, cycloheptyl, cyclooctyl, cyclononyl and cyclodecyl or cyclopropyl, cyclobutyl, cyclopentyl and cyclohexyl.

The term "carbocyclic" or "carbocyclyl" includes, unless otherwise indicated, in general a 3- to 9-membered, preferably a 4- to 8-membered or a 3- to 6-membered or a 5- to 7-membered, more preferably a 5- or 6-membered monocyclic ring comprising 3 to 9, preferably 4 to 8 or 3 to 6 or 5 to 7, more preferably 5 or 6 carbon atoms. The carbocycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. The term "carbocylce" or "carbocyclyl", unless otherwise indicated, may therefore cover inter alia cycloalkyl, cycloalkenyl, as well as phenyl. Preferably, the term "carbocycle" covers cycloalkyl and cycloalkenyl groups, for example cyclopropane, cyclobutane, cyclopentane and cyclohexane rings.

The term "carbobicyclic" or "carbobicyclyl" includes in general 6 to 14-membered, preferably 7- to 12-membered or 8- to 10-membered, more preferably 9- or 10-membered bicyclic rings comprising 6 to 14, preferably 7 to 12 or 8 to 10, more preferably 9 or 10 carbon atoms. The carbobicycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. Preferably, the term "aromatic" in connection with the carbobicyclic ring means that both rings of the bicyclic moiety are aromatic, so that, e.g., 8 π electrons are present in case of a 10-membered aromatic carbobicyclic ring. The term "carbobicyclic" or "carbobicyclyl", unless otherwise indicated, may therefore cover inter alia bicycloalkyl, bicycloalkenyl, as well as bicyclic aromatic groups, for example bicyclohexane (decalin), bicycloheptane (such as norbornane), bicyclooctane (such as bicyclo[2.2.2]octane, bicyclo[3.2.1]octane or bicyclo[4.2.0]octane), bicyclononane (such as bicyclo[3.3.1]nonane or bicyclo[4.3.0]nonane), bicyclodecane (such as bicyclo[4.4.0]decane), bicycloundecane (such as bicyclo[3.3.3]undecane), norbornene, naphthalene and the like. Preferably, the carbobicycle is a fused carbobicycle, which is preferably aromatic, for example naphthalene.

The term "carbocyclyloxy" includes a carbocyclic ring or carbocyclyl which is bonded to the remainder of the molecule via an oxygen atom.

The term "heterocyclic" or "heterocyclyl" includes, unless otherwise indicated, in general a 3- to 9-membered, preferably a 4- to 8-membered or 5- to 7-membered, more preferably 5- or 6-membered, in particular 6-membered monocyclic ring. The heterocycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. The heterocycle typically comprises one or more, e.g. 1, 2, 3, or 4, preferably 1, 2, or 3 heteroatoms selected from N, O and S as ring members, where S-atoms as ring members may be present as S, SO or $SO_2$. The remaining ring members are carbon atoms. In a preferred embodiment, the heterocycle is an aromatic heterocycle, preferably a 5- or 6-membered aromatic heterocycle comprising one or more, e.g. 1, 2, 3, or 4, preferably 1, 2, or 3 heteroatoms selected from N, O and S as ring members, where S-atoms as ring members may be present as S, SO or $SO_2$. Examples of aromatic heterocycles are provided below in connection with the definition of "hetaryl". "Hetaryls" or "heteroaryls" are covered by the term "heterocycles". The saturated or partially or fully unsaturated heterocycles usually comprise 1, 2, 3, 4 or 5, preferably 1, 2 or 3 heteroatoms selected from N, O and S as ring members, where S-atoms as ring members may be present as S, SO or $SO_2$. The skilled person is aware that S, SO or $SO_2$ is to be understood as follows:

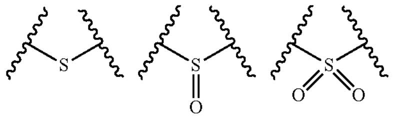

Further, a skilled person is aware that resonance structures of the oxidized forms may be possible. Saturated heterocycles include, unless otherwise indicated, in general 3- to 9-membered, preferably 4- to 8-membered or 5- to 7-membered, more preferably 5- or 6-membered monocyclic rings comprising 3 to 9, preferably 4 to 8 or 5 to 7, more preferably 5 or 6 atoms comprising at least one heteroatom, such as pyrrolidine, tetrahydrothiophene, tetrahydrofuran, piperidine, tetrahydropyran, dioxane, morpholine or piperazine.

The term "heterocyclyloxy" includes a heterocyclic ring or heterocyclyl which is bonded to the remainder of the molecule via an oxygen atom.

The term "heterobicyclic" or "heterobicyclyl" includes, unless otherwise indicated, in general 6 to 14-membered, preferably 7- to 12-membered or 8- to 10-membered, more preferably 9- or 10-membered bicyclic rings. The heterobicycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. In principal, for being "aromatic", it is sufficient if one of the two rings of the bicyclic moieties is aromatic, while the other is non-aromatic. However, it is preferred in connection with the term "aromatic" that both rings of the bicyclic moiety are aromatic, so that, e.g., 8 π electrons are present in case of a 9- or 10-membered aromatic heterobicyclic ring. The heterobicycle typically comprises one or more, e.g. 1, 2, 3, or 4, preferably 1, 2, or 3 heteroatoms selected from N, O and S as ring members, where S-atoms as ring members may be present as S, SO or $SO_2$. The remaining ring members are carbon atoms. Examples of heterobicycles include benzofuranyl, benzothienyl, indolyl, indazolyl, benzimidazolyl, benzoxathiazolyl, benzoxadiazolyl, benzothiadiazolyl, benzoxazinyl, quinolinyl, isoquinolinyl, purinyl, 1,8-naphthyridyl, pteridyl, pyrido[3,2-d]pyrimidyl, pyridoimidazolyl, triethylenediamine or quinuclidine and the like. Preferred heterobicycles according to the invention are aromatic heterobicycles such as benzodiazole, benzothiazole, quinoline, and iso-quinoline.

The term "hetaryl" or "heteroaryl" or "aromatic heterocycle" or "aromatic heterocyclic ring" includes monocyclic 5- or 6-membered aromatic heterocycles comprising as ring members 1, 2, 3 or 4 heteroatoms selected from N, O and S, where S-atoms as ring members may be present as S, SO or $SO_2$. Examples of 5- or 6-membered aromatic heterocycles include pyridyl (also referred to as pyridinyl), i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. Unless otherwise indicated, the term "hetaryl" further covers "aromatic heterobicycles" as defined above.

The term "aryl" or "aromatic carbocycle" preferably includes 6-membered aromatic carbocyclic rings based on carbon atoms as ring members. A preferred example is phenyl. Unless otherwise indicated, the term "aryl" further covers "aromatic carbobicycles" as defined above.

As used herein, the terms "carbocyclylalkyl" and "heterocyclylalkyl" as well as the terms "arylalkyl", "cycloalkylalkyl", "hetarylalkyl", and the like refer to the corresponding groups, which are bonded to the remainder of the molecule via an alkyl, preferably via a $C_1$-$C_2$-alkyl group. Preferred examples include benzyl (i.e. phenylmethyl), cyclohexylmethyl, pyridinylmethyl, and piperidinomethyl.

As used herein, the terms "aryloxy" and "benzyloxy" refer to the corresponding groups, which are bonded to the remainder of the molecule via an oxygen atom. Preferred examples include phenyloxy and phenylmethyloxy (i.e. benzyloxy).

As used herein, the term "alkylene" refers to a linking straight-chain or branched alkylene group having usually from 1 to 4 carbon atoms, e.g. 1, 2, 3, or 4 carbon atoms. The alkylene group bridges a certain group to the remainder of the molecule. Preferred alkylene groups include methylene ($CH_2$), ethylene ($CH_2CH_2$), propylene ($CH_2CH_2CH_2$) and the like. A skilled person understands that, if it is referred, e.g., to $CH_2$ that the carbon atom being tetravalent has two valences left for forming a bridge ($—CH_2—$). Similarly, when it is referred, e.g., to $CH_2CH_2$, each carbon atom has one valence left for forming a bridge ($—CH_2CH_2$-). Furthermore, when it is referred, e.g., to $CH_2CH_2CH_2$, each terminal carbon atom has one valence left for forming a bridge ($—CH_2CH_2CH_2$-).

If the term "alkylene" is used in connection with, e.g. $NR^F—(C_1$-$C_4$-alkylene)-$NR^CR^D$ or O—($C_1$-$C_4$-alkylene)-$NR^CR^D$, it is to be understood that the alkylene chain bridges the $NR^CR^D$ group to the $NR^F$ group or to the oxygen atom, which are bonded to the remainder of the molecule. Similarly, if the term "alkylene" is used in connection with, e.g. $NR^F—(C_1$-$C_4$-alkylene)-C(═O)$R^E$, it is to be understood that the alkylene chain bridges the C(═O)$R^E$ group to the $NR^F$ group, which is bonded to the remainder of the molecule The term "cyclic" moiety can refer to any cyclic groups, which are present in the compounds of formula (I), and which are defined above, e.g., cycloalkyl, cycloalkenyl, carbocycle.

As used in the specification and the claims, the singular forms of "a" and "an" also include the corresponding plurals unless the context clearly dictates otherwise. The same applies for plural forms used herein, which also include the singular forms unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group, which preferably consists of these embodiments only.

The term "pharmaceutically acceptable excipient" as used herein refers to compounds commonly comprised in pharmaceutical compositions, which are known to the skilled person. Examples of suitable excipients are exemplary listed below. Typically, a pharmaceutically acceptable excipient can be defined as being pharmaceutically inactive.

The term "treatment" is to be understood as also including the option of "prophylaxis". Thus, whenever reference is made herein to a "treatment" or "treating", this is to be understood as "treatment and/or prophylaxis" or "treating and/or preventing".

DESCRIPTION OF PHARMACEUTICAL COMPOSITIONS ACCORDING TO THE PRESENT INVENTION

A pharmaceutical composition according to the present invention may be formulated for oral, buccal, nasal, rectal, topical, transdermal or parenteral application. Preferred non-parenteral routes include mucosal (e.g., oral, vaginal, nasal, cervical, etc.) routes, of which the oral application may be preferred. Preferred parenteral routes include but, are not limited to, one or more of subcutaneous, intravenous, intramuscular, intraarterial, intradermal, intrathecal and epidural administrations. Preferably administration is by subcutaneous, intra-tumoral or peri-tumoral routes. Particularly preferred is intratumoral administration. The compound-linker constructs or conjugates according to the invention should be applied in pharmaceutically effective amounts, for example in the amounts as set out herein below.

A pharmaceutical composition of the present invention may also be designated as formulation or dosage form. The compound-linker constructs or conjugates according to the invention may also be designated in the following as (pharmaceutically) active agent or active compound.

Pharmaceutical compositions may be solid or liquid dosage forms or may have an intermediate, e.g. gel-like character depending inter alia on the route of administration.

In general, the inventive dosage forms can comprise various pharmaceutically acceptable excipients which will be selected depending on which functionality is to be achieved for the dosage form. A "pharmaceutically acceptable excipient" in the meaning of the present invention can be any substance used for the preparation of pharmaceutical dosage forms, including coating materials, film-forming materials, fillers, disintegrating agents, release-modifying materials, carrier materials, diluents, binding agents and other adjuvants. Typical pharmaceutically acceptable excipients include substances like sucrose, mannitol, sorbitol, starch and starch derivatives, lactose, and lubricating agents such as magnesium stearate, disintegrants and buffering agents.

The term "carrier" denotes pharmaceutically acceptable organic or inorganic carrier substances with which the active ingredient is combined to facilitate the application. Suitable pharmaceutically acceptable carriers include, for instance, water, aqueous salt solutions, alcohols, oils, preferably vegetable oils, propylene glycol, polyoxyethelene sorbitans, polyethylene-polypropylene block co-polymers such as poloxamer 188 or poloxamer 407, polyethylene glycols such as polyethylene glycol 200, 300, 400, 600, etc., gelatin, lactose, amylose, magnesium stearate, surfactants, perfume oil, fatty acid monoglycerides, diglycerides and triglycerides, polyoxyethylated medium or long chain fatty acids such as ricinoleic acid, and polyoxyethylated fatty acid mono-, di, and triglycerides such as capric or caprilic acids, petroethral fatty acid esters, hydroxymethyl celluloses such as hydroxymethyl, hydroxyethyl, hydroxypropyl, hydroxypropyl acetate succinate, polyvinylpyrrolidone, crosspovidone and the like. Preferably, the compound-linker constructs or conjugates according to the invention are administered in a pharmaceutical composition comprising of lipids, interbilayer crosslinked multilamellar vesicles, biodegradable poly(D,L-lactic-co-glycolic acid) [PLGA]-based or poly anhydride-based nanoparticles or microparticles, nanoporous particle-supported lipid bilayers and as a conjugate with an antibody.

The pharmaceutical compositions can be sterile and, if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the compound-linker constructs or conjugates according to the invention.

If liquid dosage forms are considered for the present invention, these can include pharmaceutically acceptable emulsions, solutions, suspensions and syrups containing inert diluents commonly used in the art such as water. These dosage forms may contain e.g. microcrystalline cellulose for imparting bulk, alginic acid or sodium alginate as a suspending agent, methylcellulose as a viscosity enhancer and sweeteners/flavoring agents.

For parenteral application, particularly suitable vehicles consist of solutions, preferably oily or aqueous solutions, as well as suspensions, emulsions, or implants. Pharmaceutical formulations for parenteral administration are particularly preferred and include aqueous solutions of the compound-linker constructs or conjugates according to the invention in water-soluble form. Additionally, suspensions of the compound-linker constructs or conjugates according to the invention may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran.

Particularly preferred dosage forms are injectable preparations of compound-linker constructs or conjugates according to the invention. Thus, sterile injectable aqueous or oleaginous suspensions can for example be formulated according to the known art using suitable dispersing agents, wetting agents and/or suspending agents. A sterile injectable preparation can also be a sterile injectable solution or suspension in a non-toxic parenterally acceptable diluent or solvent. Among the acceptable vehicles and solvents that can be used are water and isotonic sodium chloride solution. Sterile oils are also conventionally used as solvent or suspending medium. Preferred applications for injectable preparations comprising the compound-linker constructs or conjugates according to the invention are intravenous, intratumoral and peritumoral administration.

Compound-linker constructs or conjugates according to the invention may be injected repeatedly as boluses or given via a continuous infusion. Particularly preferred is continuous infusion.

Suppositories for rectal administration of a compound-linker construct or conjugate according to the invention can be prepared by e.g. mixing the compound-linker construct or conjugate with a suitable non-irritating excipient such as cocoa butter, synthetic triglycerides and polyethylene glycols which are solid at room temperature but liquid at rectal temperature such that they will melt in the rectum and release the compound-linker constructs or conjugates according to the invention from said suppositories.

For administration by inhalation, the compound-linker constructs or conjugates according to the invention may be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound-linker construct or conjugate and a suitable powder base such as lactose or starch.

Oral dosage forms may be liquid or solid and include e.g. tablets, troches, pills, capsules, powders, effervescent formulations, dragees and granules. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. The oral dosage forms may be formulated to ensure an immediate release of the compound-linker constructs or conjugates according to the invention or a sustained release of the compound-linker constructs or conjugates according to the invention.

A solid dosage form may comprise a film coating. For example, the inventive dosage form may be in the form of a so-called film tablet. A capsule of the invention may be a two-piece hard gelatin capsule, a two-piece hydroxypropylmethylcellulose capsule, a two-piece capsule made of vegetable or plant-based cellulose or a two-piece capsule made of polysaccharide.

The dosage form according to the invention may be formulated for topical application. Suitable pharmaceutical application forms for such an application may be a topical nasal spray, sublingual administration forms and controlled and/or sustained release skin patches. For buccal administration, the compositions may take the form of tablets or lozenges formulated in conventional manner.

The compositions may conveniently be presented in unit dosage forms and may be prepared by any of the methods well known in the art of pharmacy. The methods can include the step of bringing the compound-linker constructs or conjugates according to the invention into association with a carrier, which constitutes one or more accessory ingredients. In general, the compositions are prepared by unitrormly and intimately bringing the compound-linker construct or conjugate into association with a liquid carrier, a finely divided solid carrier, or both, and then, if necessary, shaping the product Liquid dose units are vials or ampoules. Solid dose units are tablets, capsules and suppositories.

As regards human patients, the compound-linker constructs or conjugates according to the invention may be administered to a patient in an amount of about 0.001 mg to about 5000 mg per day, preferably of about 0.01 mg to about 1000 mg per day, more preferably of about 0.05 mg to about 250 mg per day, which is the effective amount. The phrase “effective amount” means an amount of compound-linker construct or conjugate that, when administered to a mammal in need of such treatment, is sufficient to treat or prevent a particular disease or condition.

Indications, for which the compounds of the present invention may be used

The compound-linker constructs or conjugates according to the invention are suitable for use in medicine. In particular, the compound-linker constructs or conjugates according to the invention are suitable for use in the treatment of a disease selected from the group consisting of inflammatory diseases, allergic diseases, autoimmune diseases, infectious diseases, cancer, and pre-cancerous syndromes. Further, the compound-linker constructs or conjugates according to the invention are suitable for use in immunogenic compositions and as vaccine adjuvants.

In one embodiment, the compound-linker constructs or conjugates according to the invention are suitable for the treatment of diseases/disorders including, but not limited to, cancer, vaccine adjuvant, infectious diseases both bacterial and viral (e.g., HIV, HBV, HCV, HPV, filoviruses (for example Ebola or Marburg), flaviviruses (for example yellow fever virus, dengue fever virus, or Japanese encaphilitis virus), poxviruses, arenaviruses (for example Lassa fever virus, Lymphocytic choriomeningitis virus (LCMV), Mobala virus, Junin virus), paramyxoviruses (for example human respiratory syncythial virus, Sendai virus, mumps, Nipah), orthomyxoviruses (for example influenza virus), coronaviruses (for example SARS, SARS-COV2), rhabdoviruses (for example rabies virus, vesicular stomatitis virus), bunyaviruses (such as Bunyamwera virus, Hantaan virus, Crimean Congo virus, California encephalitis virus, Rift Valley fever virus, or sandfly fever virus).

In one embodiment, the compound-linker constructs or conjugates according to the invention or a pharmaceutical composition comprising the same is for use in the treatment of a disease selected from the group consisting of cancer, pre-cancerous syndromes, and infectious diseases; or for use in an immunogenic composition or as vaccine adjuvant.

In another embodiment, the compound-linker constructs or conjugates according to the invention or a pharmaceutical composition comprising the same is for use in the treatment of a disease selected from the group consisting of inflammatory diseases, allergic diseases, and autoimmune diseases.

In one preferred embodiment, the compound-linker constructs or conjugates according to the invention or a pharmaceutical composition comprising the same is for use in the treatment of a disease selected from the group consisting of cancer or pre-cancerous syndromes.

In another preferred embodiment, the compound-linker constructs or conjugates according to the invention or a pharmaceutical composition comprising the same is for use in the treatment of a disease selected from the group consisting of infectious diseases or for use in an immunogenic composition or as vaccine adjuvant.

In another embodiment, the compound-linker constructs or conjugates according to the invention or a pharmaceutical composition comprising the same is for use in the treatment of inflammatory diseases, allergic diseases, infectious diseases.

Of particular relevance in connection with the present invention is the treatment of cancer. Preferably, said cancer is selected from the group consisting of breast cancer, inflammatory breast cancer, ductal carcinoma, lobular carcinoma, colon cancer, pancreatic cancer, insulinomas, adenocarcinoma, ductal adenocarcinoma, adenosquamous carcinoma, acinar cell carcinoma, glucagonoma, skin cancer, melanoma, metastatic melanoma, lung cancer, small cell lung cancer, non-small cell lung cancer, squamous cell carcinoma, adenocarcinoma, large cell carcinoma, brain (gliomas), glioblastomas, astrocytomas, glioblastoma multiforme, Bannayan-Zonana syndrome, Cowden disease, Lhermitte-Duclos disease, Wilm’s tumor, Ewing’s sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocyte leukemia, promyelocytic leukemia, erythroleukemia, malignant lymphoma, hodgkins lymphoma, non-hodgkins lymphoma, lymphoblastic T cell lymphoma, Burkitt’s lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), neuroendocrine cancers and testicular cancer.

More preferably, said cancer is selected from prostate cancer, renal carcinoma, melanoma, pancreatic cancer, cervical cancer, ovarian cancer, colon cancer, head and neck cancer, lung cancer, fibrosarcoma and breast cancer.

Preferably, said autoimmune disease is selected from the group consisting of systemic lupus erythematosis, Addison’s disease, autoimmune polyglandular disease (also known as autoimmune polyglandular syndrome), glomerulonephritis, rheumatoid arthritis scleroderma, chronic thyroiditis, Graves’ disease, autoimmune gastritis, diabetes, autoimmune hemolytic anemia, glomerulonephritis, rheumatoid arthritis autoimmune neutropenia, thrombocytopenia, atopic dermatitis, chronic active hepatitis, myasthenia gravis, multiple sclerosis, inflammatory bowel disease, ulcerative colitis, Crohn’s disease, psoriasis, graft vs. host disease, asthma, bronchitis, acute pancreatitis, chronic pancreatitis and allergies of various types.

It is to be understood that in connection with the medical uses of the invention it can be preferred that the compound-linker constructs or conjugates according to the invention are administered in combination with antibodies, radiotherapy, surgical therapy, immunotherapy, chemotherapy, toxin therapy, gene therapy, or any other therapy known to those of ordinary skill in the art for treatment of a particular disease. This is particularly relevant in connection with the treatment of cancer. Preferably, the compound-linker constructs or conjugates according to the invention are administered in combination with antibodies. Preferred antibodies include anti-PD-1, anti-PD-L1, anti-CTLA-4, anti-IDO, anti-KIR, anti-TIM-3, anti-Vista, anti-TIGIT, anti-BTLA and anti-LAG3 antibody. Non-limiting examples are BMS-936559, MPDL3280A and MED14736 or avelumab (anti-PD-L1 antibodies), MK-3475, pembrolizumab or pidilizumab (anti-PD-1 antibodies) as well as ipilimumab (anti-CTLA-4 antibodies). Preferably, the compound-linker constructs or conjugates according to the invention are administered in a pharmaceutical composition comprising one or more of adjuvants, inactivated or attenuated bacteria (e.g., inactivated or attenuated Listeria monocytogenes), modulators of innate immune activation, preferably agonists of Toll-like Receptors (TLRs, preferably TLR7 or TLR9 agonists, e.g. SM360320, AZD8848), (NOD)-like receptors (NLRs, preferably NOD2 agonist), retinoic acid inducible gene-based (RIG)-I-like receptors (RLRs), C-type lectin receptors (CLRs), or pathogen-associated molecular patterns ("PAMPs"), cytokines (not limiting examples e.g. IL-2, IL-12, IL-6), interferons (including, but not limited to IFN alpha, IFN beta, IFN gamma, IFN lambda) or chemotherapeutic agents. The medical use may further compromise administering at least one H BV vaccine, a nucleoside HBV inhibitor or any combination thereof (e.g. RECOMBIVAX HB, ENGERIX-B, GENEVAC-B).

Combination therapy may be achieved by use of a single pharmaceutical composition that includes both agents, or by administering two distinct compositions at the same time, wherein one composition includes a compound-linker constructs or conjugates according to the invention, and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In some embodiments, the compound-linker constructs or conjugates according to the invention are administered prior to administration of the distinct cancer treatment. In other embodiments, the distinct cancer treatment is administered prior to administration of the compound-linker constructs or conjugates according to the invention.

The present invention is further illustrated by the following examples.

EXAMPLES

The following abbreviations are used herein:

| Abbreviation | Meaning |
|---|---|
| 4Å MS | 4Å molecular sieves |
| ACN | Acetonitrile |
| $Ac_2O$ | Acetic anhydride |
| anh. | Anhydrous |
| aq. | Aqueous |
| BBBPY | 4,4'-di-tert-butyl-2,2'-bipyridine |
| BINAP | 2,2'-Bis(diphenylphosphino)-1,1'-binaphthalene |
| BrettPhos | 2-(Dicyclohexylphosphino)-3,6-dimethoxy-2',4',6'-triisopropyl-1,1'-biphenyl |
| BTFFH | Fluoro-N,N,N',N'-bis(tetramethylene)formamidinium hexafluorophosphate |
| t-BuXPhos | 2-Di-tert-butylphosphino-2',4',6'-triisopropylbiphenyl |
| $CH_3I$ | Iodomethane |
| $Cs_2CO_3$ | Cesium carbonate |
| $CuCl_2$ | Copper(II) chloride |
| $CuSO_4*5H_2O$ | Cooper sulfate pentahydrate |
| CyPF-t-Bu | (R)-1-[(SP)-2-(Dicyclohexylphosphino)ferrocenyl]ethyldi-tert-butylphosphine |
| DBU | 1,8-Diazabicyclo(5.4.0)undec-7-en |
| DCC | N,N'-dicyclohexylmethanediimine |
| DCE | 1,2-Dichloroethane |
| DCM | Dichloromethane |
| DIBAL-H | Diisobutylaluminum hydride |
| DIPEA | N,N-Diisopropylethylamine |
| DMAP | 4-(Dimethylamino)pyridine |
| DMF | N,N-Dimethylformamide |
| DMSO-$d_6$ | Deuterated dimethylsulfoxide |
| $D_2O$ | Deuterium Oxide |
| EDC | N-(3-Dimethylaminopropyl)-N-ethylcarbodiimide |
| eq. | Equivalent |
| ESI-MS | Electrospray Ionisation-Mass spectrometry |
| $Et_2O$ | Diethyl ether |
| EtOAc | Ethyl acetate |
| EtOH | Ethanol |
| FA | Formic acid |
| FB | Free base form of a compound |
| fAb | Fragment of antibody |
| FCC | Flash column chromatography |
| $H_2$ | Molecular hydrogen |
| HATU | 1-[Bis(dimethylamino)methylene]-1H-1,2,3-triazolo[4,5-b]pyridinium 3-oxide hexafluorophosphate |
| HCl | Hydrochloric acid |
| HCOOH | Formic acid |
| Hex | Hexane |
| $H_2O$ | Water |
| HMT | 1,3,5,7-tetraazatricyclo[3.3.1.13,7]decane |

-continued

| Abbreviation | Meaning |
|---|---|
| HOBt | Hydroxybenzotriazole |
| HPLC | High-performance liquid chromatography |
| HRMS | High Resolution Mass Spectometry |
| iPrOH | Isopropyl alcohol |
| $K_2CO_3$ | Potassium carbonate |
| LC-MS | Liquid chromatography-mass spectrometry |
| LDA | Lithium diisopropylamide solution |
| LiOH × $H_2O$/ LiOH * $H_2O$ | Lithium hydroxide monohydrate |
| MeTHF | 2-Methyltetrahydrofuran |
| Me4tButylXphos | 2-Di-tert-butylphosphino-3,4,5,6-tetramethyl-2',4',6'-triisopropyl-1,1'-biphenyl |
| mAb | Monoclonal antibody |
| MeCN | Acetonitrile |
| MeOD-$d_4$ | Deuterated methanol |
| MeOH | Methanol |
| MeONa | Sodium methoxide |
| $MgSO_4$ | Magnesium sulfate |
| $MnO_2$ | Manganese(IV) oxide |
| MPA | Mercaptophenylaminobut-2-enoate ester |
| MW | Microwave irradiation, microwave heating |
| N/M | Molar concentration [mol/$dm^3$] |
| $NaBH_4$ | Sodium borohydride |
| $NaBH(OAc)_3$, STAB | Sodium triacetoxyborohydride |
| NaH | Sodium hydride |
| $NaHCO_3$ | Sodium bicarbonate |
| NaHMDC | Sodium bis(trimethylsilyl)amide |
| NaI | Sodium iodide |
| NaO t-Bu | Sodium tert-butoxide |
| NaOAc | Sodium acetate |
| NaOH | Sodium hydroxide |
| $Na_2SO_4$ | Sodium sulfate |
| $NH_3$ | Ammonia |
| $NH_2$ column | PF-NH2, Normal Phase, Bonded Silica, NH2 |
| $NH_4OH$ | Ammonium hydroxide |
| $NH_4Cl$ | Ammonium chloride |
| NMR | Nuclear magnetic resonance |
| o/n | overnight |
| o/w | over weekend |
| Pd/C | Palladium(0) on carbon |
| $Pd(dba)_2$ | bis((1E,4E)-1,5-diphenylpenta-1,4-dien-3-one) palladium |
| $Pd_2(dba)_3$ | Tris(dibenzylideneacetone)dipalladium(0) |
| $Pd(dppf)Cl_2$*DCM | [1,1'-Bis(diphenylphosphino)ferrocene]dichloropalladium(II), complex with dichloromethane |
| $Pd(OAc)_2$ | Palladium II acetate |
| $Pd[P(o\text{-}Tol)_3]_2$ | Bis[tris(2-methylphenyl)phosphine]palladium |
| PF-50DIOL | Puriflash DIOL 50 μM flash column |
| $POCl_3$ | Phosphorus (V) oxychloride |
| PTSA | p-Toluenesulfonic acid |
| prep-HPLC | Preparative HPLC purification |
| rac | Racemate/racemic |
| rac-BI-NAP/ BINAP | (±)-2,2'-Bis(diphenylphosphino)-1,1'-binaphthalene |
| RP-FCC | Reversed-phase flash column chromatography |
| RM | Reaction mixture |
| RT | Room temperature, i.e. 20-25° C. |
| RuPhos PdG3 | (2-Dicyclohexylphosphino-2',6'-diisopropoxy-1,1'-biphenyl)[2-(2'-amino-1,1'-biphenyl)]palladium(II) methanesulfonate |
| SEM | 2-(Trimethylsilyl)ethoxymethyl |
| SPhos | 2-Dicyclohexylphosphino-2',6'-dimethoxybiphenyl |
| SiHP | Silica PuriFlash Columns High Performance |
| C18HP | C18 PuriFlash Columns High Performance |
| ALN | Alumina Neutral PuriFlash Columns |
| TBDMS | tert-Butyldimethylsilyl |
| TBDMSCl | tert-Butyldimethylsilyl chloride |
| tBuBrettPhos | di-tert-butyl[3,6-dimethoxy-2',4',6'-tris(propan-2-yl)-[1,1'-biphenyl]-2-yl]phosphane |
| tBuXPhosPd-G3 | [(2-Di-tert-butylphosphino-2',4',6'-triisopropyl-1,1'-biphenyl)-2-(2'amino-1,1-biphenyl)] palladium(II) methanesulfonate |
| TEA | Triethylamine |
| TFA | Trifluoroacetic acid |
| THF | Tetrahydrofurane |
| UPLC | Ultra performance liquid chromatography |
| UPLC-MS | Ultra performance liquid chromatography-mass spectometry |
| Xantphos | (9,9-Dimethyl-9H-xanthene-4,5-diyl)bis(diphenylphosphine) |

The compounds of formula (I) were prepared according to the procedures of the following Schemes and Examples, using appropriate materials and are further exemplified by the following specific examples. The compounds of formula (I) can then be used as starting materials for the preparation of the compound-linker constructs and conjugates of the invention.

Unless otherwise specified, all starting materials are obtained from commercial suppliers and used without further purifications. Unless otherwise specified, all temperatures are expressed in ° C. and all reactions are conducted at RT.

Methods and Analytical Data:

General:

Microwave heating (MW) was done using Anton Paar Monowave 450 or Biotage Emrys Initiator microwave reactor. Column chromatography was carried out using the Isco Rf200d or the Interchim PuriFlash 450. Solvent removal was carried out using either a Büchi rotary evaporator or a Genevac centrifugal evaporator. Analytical LC-MS was conducted using a Waters I Class SQD2, column X Bridge 1.7 um 2.1×50 mm under acidic conditions. Preparative HPLC was conducted using Waters auto-purification system or Shimadzu Preparative H PLC system, column 19×150 mm XSelect 5 micron C18 column under basic mobile phase conditions or Phenomenex Gemini NX 21, 2×250 mm C18 column under acidic conditions. NMR spectra were recorded using a Bruker 300 MHz or 400 MHz spectrometer. Chemical shifts (6) are reported in ppm relative to the residual solvent signal (measurement range-6.4 kHz). $^1$H NMR data are reported as follows: chemical shift (multiplicity, coupling constants and number of hydrogens). Multiplicity is abbreviated as follows: s (singlet), d (doublet), t (triplet), q (quartet), m (multiplet), dd (doublet of doublets), dt (doublet of triplets), ddd (doublet of doublet of doublets). ESI-MS: Desolvatation Gas Flow 993 l/h; Desolvatation temperature 500° C.; cone gas: 50 l/min; 500-1000 m/z; polarity: positive and/or negative.

Preparative HPLC Conditions for the Purification of Target Compounds:

Chromatography Conditions 1:

- Prep HPLC Instrument: Shimadzu or Auto-purification System Waters
- Column: Gemini-NX 5 μm C18 110 Å, 21.2*250 mm
- Detector SPD −20 A/20 AV UV-VIS
- Flow Rate: 20 mL/min Representative Mobile Phase:

(1)

- Mobile Phase: A: 0.1% formic acid (FA) or trifluoroacetic acid (TFA) in water
- Mobile Phase: B: 0.1% FA or TFA in MeCN (2)

- Mobile Phase: A: 0.1% $NH_4OH$ in water
- Mobile Phase: B: 0.1% $NH_4OH$ in MeCN Chromatography Conditions 2:

- Prep HPLC Instrument: Shimadzu or Auto-purification System Waters
- Column: Chiralpak AD-H, 5 μm, 20*250 mm or IF, 5 μm, 20*200 mm
- Detector. SPD −20 A/20 AV UV-VIS
- Flow Rate: 20 mL/min Representative Mobile Phase:

- Mobile Phase: A: EtOH
- Mobile Phase: B: hexane
- UPLC, HPLC and MS data provided in the examples described below were registered on:

LC-MS Analyses on Waters:

- Method name: Ic-ms1-2-ba

Equipment:

- Waters I Class SQD2
- UPLC with DAD detector
- column: Waters Acquity UPLC X Bridge C18, 50 mm×2.1 mm×1.7 μm Eluents:

- (A) 0.1% formic acid in water
- (B) 0.1% formic acid in MeCN

Analytical Method:

- Autosampler injection volume: 1 μL
- Pump:

| Time [min] | Flow [mL/min] | % B |
|---|---|---|
| 0.00 | 0.5 | 1 |
| 0.10 | 0.5 | 1 |
| 1.10 | 0.5 | 100 |
| 2.00 | 0.5 | 100 |
| 2.50 | 0.5 | 1 |
| 3.00 | 0.5 | 1 |

- Column compartment: column temperature: 40'C; time of analysis: 3 min
- Detector wave length: 254, 214, 280 nm LC-MS Analyses on Bruker Amazon SL

- Method name: Ic-ms1-2-ba

Equipment:

- MS Bruker Amazon SL
- LC Dionex Ultimate 3000
- HPLC with UV-Vis or DAD detector
- column: Waters Acquity UPLC HSS C18, 50 mm×2.1 mm×1.8 μm Eluents:

- (A) 0.1% formic acid in MeCN
- (B) 0.1% formic acid in water

Analytical Method:

- Auto sampler injection volume: 1 μL
- Pump:

| Time [min] | Flow [mL/min] | % B |
|---|---|---|
| 0.00 | 0.5 | 95 |
| 0.00 | 0.5 | 95 |
| 4.00 | 0.5 | 5 |
| 5.00 | 0.5 | 5 |
| 5.20 | 0.5 | 95 |
| 6.00 | 0.5 | 95 |

- Column compartment column temperature: 5'; time of analysis: 6 min
- Detector: wave length: 254, 230, 270, 280 nm LC-MS Analyses on Bruker Amazon SL

- Method name: BCM-30

Equipment:

- MS Bruker Amazon SL
- LC Dionex Ultimate 3000
- HPLC with UV-Vis or DAD detector
- column: Waters Symmetry C18 3.9×150 mm 5 μm Eluents:

- (A) 0.1% formic acid in water
- (B) 0.1% formic acid in MeCN

Analytical Method:

- Autosampler: injection volume: 3 μL
- Pump:
- flow: 1.2 mL/min

| Time [min] | [%] B |
|---|---|
| 0.0 | 20 |
| 20.0 | 80 |
| 22.0 | 80 |
| 22.5 | 95 |
| 25.0 | 95 |
| 25.3 | 20 |
| 30.0 | 20 |

Column compartment column temperature: 25° C.; time of analysis: 30 min

Detector: wave length: 254 nm

LC-MS Analyses on Corona Ultra:

Method name: BCM-30

Equipment:

Corona ultra

LC Dionex Ultimate 3000 column: Waters Symmetry C18 3.9×150 mm 5 μm

Eluents:

(A) 0.1% formic acid in water (B) 0.1% formic acid in MeCN

Analytical Method:

Autosampler: injection volume: 3 μL

Pump:

flow: 1.2 mL/min

| Time [min] | [%] B |
|---|---|
| 0.0 | 20 |
| 20.0 | 80 |
| 22.0 | 80 |
| 22.5 | 95 |
| 25.0 | 95 |
| 25.3 | 20 |
| 30.0 | 20 |

Synthetic Procedures for the Preparation of Compounds of Formula (I):

The following compounds are commercially available and/or can be prepared in a number of ways well known to one skilled in the art of organic synthesis. More specifically, disclosed compounds can be prepared using the reactions and techniques described herein. In the description of the synthetic methods described below, it is to be understood that all proposed reaction conditions, including choice of solvent, reaction atmosphere, reaction temperature, duration of the experiment, and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

PREPARATION OF EXAMPLES

Preparation of Compounds of Formula (I)

Example 1. 3-({[(3S)-1-(3-Aminophenyl)piperidin-3-yl][(2-methylpyridin-4-yl)methyl]amino}methyl)-1-methyl-1,4-dihydroquinolin-4-one hydrochloride

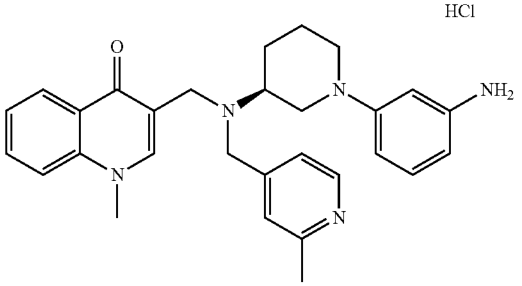 [SMILES: Cl ; Cc1cc(CN(Cc2cn(C)c3ccccc3c2=O)[C@H]2CCCN(c3cccc(N)c3)C2)ccn1]

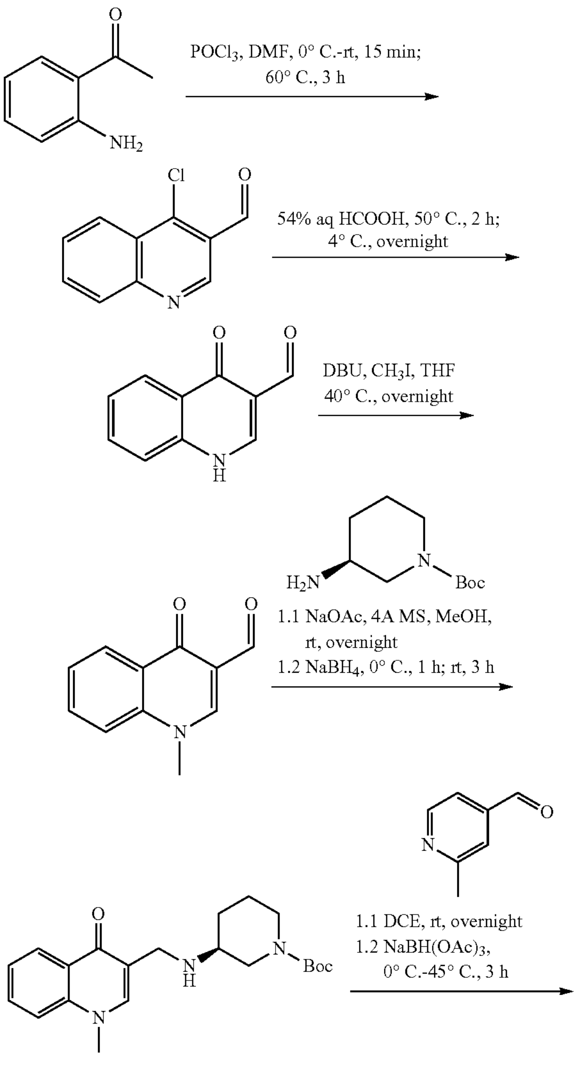

-continued

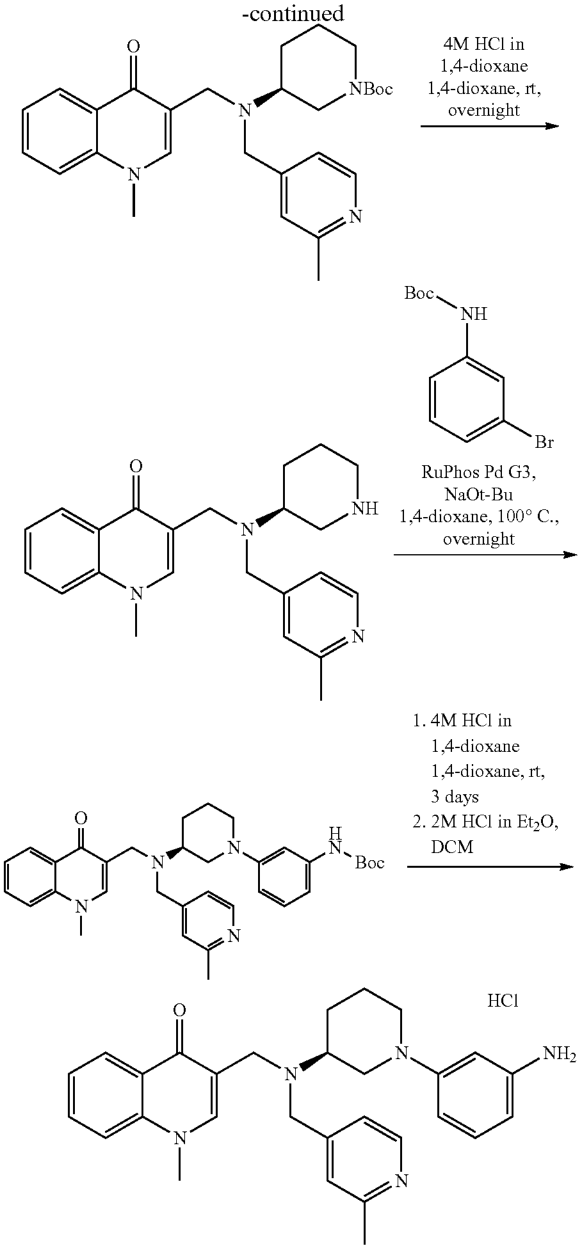

Preparation of 4-oxo-1,4-dihydroquinoline-3-carbaldehyde (Intermediate 1)

To anh. DMF (5.0 mL), $POCl_3$ (3.10 mL, 6.0 eq.) was added dropwise at 0° C. and the mixture was stirred at RT for 15 min. Then 1-(2-aminophenyl)ethan-1-one (0.75 g, 1.0 eq.) in anh. DMF (3.0 mL) was added dropwise and the reaction was heated at 60° C. for 3 h. Afterwards, the reaction was cooled down and quenched with water. Then the mixture was neutralized with aq. solution of $NaHCO_3$ and extracted with DCM. The organic layer was dried over anh. $MgSO_4$ and the solvent was removed in vacuo to give a crude brown solid (0.33 g). 0.15 g of the crude residue was suspended in 54% aq. solution of HCOOH (1.83 mL) and the reaction was stirred at 50° C. for 2 h and subsequently kept at 4° C. overnight. A precipitate formed, which was filtered off, washed with water, and triturated with diethyl ether to give the product (0.135 g) as an orange solid. ESI-MS: 174.0 $[M+H]^+$.

Preparation of 1-methyl-4-oxo-1,4-dihydroquinoline-3-carbaldehyde

4-Oxo-1,4-dihydroquinoline-3-carbaldehyde (Intermediate 1) (0.50 g, 1.0 eq.) was suspended in THF (13.0 mL). DBU (1.1 g, 2.5 eq.) was added followed by methyl iodide (4.1 g, 10.0 eq.) and the reaction was stirred at 40° C. overnight. Additional portions of DBU and methyl iodide were added and the reaction was continued overnight. Afterwards, the reaction was quenched with water and extracted with DCM. Organic layer was dried over anh. $Na_2SO_4$ and solvent was removed in vacuo. The residue was purified by FCC (SiHP; DCM:MeOH) to provide the product (0.350 g, yield 63%) as a yellow solid. ESI-MS: 188.1 $[M+H]^+$.

Preparation of tert-butyl (3S)-3-{[(1-methyl-4-oxo-1,4-dihydroquinolin-3-yl)methyl]amino}piperidine-1-carboxylate A mixture of (5)-1-tert-butoxycarbonyl-3-aminopiperidine (4.17 g, 1.3 eq.), 1-methyl-4-oxo-1,4-dihydroquinoline-3-carbaldehyde (3.0 g, 1.0 eq.), NaOAc (1.32 g, 1.0 eq.) and 4 Å MS (0.7 g) in anh. MeOH (100.0 mL) was stirred under inert atmosphere at RT overnight. After that the mixture was cooled to 0° C. and $NaBH_4$ (0.67 g, 1.1 eq.) was added portionwise over 1 h. The reaction was continued at RT for 3 h. The mixture was filtered through a pad of Celite, the filter cake was washed with methanol and the filtrate was concentrated in vacuo. The residue was diluted with DCM and washed with 10% aq. solution of NaOH, brine, dried over anh. $MgSO_4$ and concentrated in vacuo. The residue was purified by FCC (ALN; DCM:MeOH) to afford the product (5.60 g, yield 94%) as a yellow solid. ESI-MS: 372.2 $[M+H]^+$.

Preparation of tert-butyl (3S)-3-{[(1-methyl-4-oxo-1,4-dihydroquinolin-3-yl)methyl][(2-methylpyridin-4-yl)methyl]amino}piperidine-1-carboxylate A mixture of tert-butyl (3S)-3-{[(1-methyl-4-oxo-1,4-dihydroquinolin-3-yl)methyl]amino}piperidine-1-carboxylate (0.550 g, 1.0 eq.), 2-methyl-4-pyridinecarboxaldehyde (0.18 g, 1.0 eq.) and 4 Å MS in a mixture of anh. DCE and DMF (20.0 mL, 1:1) was stirred at RT overnight, then cooled to 0° C. and $NaBH(OAc)_3$ (0.47 g, 1.5 eq.) was added portionwise. The mixture was stirred at 45° C. for 3 h, then filtered through a pad of Celite pad, washed with DCM and concentrated in vacuo. The residue was diluted with DCM and washed with 10% aq. solution of NaOH, brine, dried over anh. $MgSO_4$ and concentrated in vacuo. The residue was purified by FCC (SiHP; DCM:MeOH) to afford the product (0.61 g, yield 86%) as a pale yellow solid. ESI-MS: 477.2 $[M+H]^+$.

Preparation of 1-methyl-3-({[(2-methylpyridin-4-yl)methyl][(3S)-piperidin-3-yl]amino}methyl)-1,4-dihydroquinolin-4-one (Intermediate 5)

To a solution of tert-butyl (3S)-3-{[(1-methyl-4-oxo-1,4-dihydroquinolin-3-yl)methyl][(2-methylpyridin-4-yl)methyl]amino}piperidine-1-carboxylate (0.60 g, 1.0 eq.) in 1,4-dioxane (10 mL) 4M HCl in 1,4-dioxane (1.57 mL, 5.0 eq.) was added. The resulting mixture was stirred at RT overnight and subsequently poured into water and basified with 1M aq. solution of NaOH. The mixture was extracted with DCM, combined organic layers were washed with brine and dried over anh. $Na_2SO_4$. The solvent was removed under reduced pressure to afford the product (0.375 g, yield 79%) as a white solid. ESI-MS: 377.5 [M+H].

Preparation of tert-butyl N-{3-[(3S)-3-{[(1-methyl-4-oxo-1,4-dihydroquinolin-3-yl)methyl][(2-methylpyridin-4-yl)methyl]amino}piperidin-1-yl]phenyl}carbamate 1-Methyl-3-({[(2-methylpyridin-4-yl)methyl][(3S)-piperidin-3-yl]amino}methyl)-1,4-dihydroquinolin-4-one (Intermediate 5) (0.150 g, 1.0 eq.), tert-butyl N-(3-bromophenyl)carbamate (0.108 g, 1.0 eq.) and NaO t-Bu (0.077 g, 2.0 eq.) were suspended in anh. 1,4-dioxane and argon was bubbled through the mixture. Under an inert atmosphere RuPhos Pd G3 (0.033 g, 0.1 eq.) was added. The reaction was carried out at 100° C. overnight. Subsequently, the mixture was cooled to ambient temperature and filtered through a pad of Celite. The filter cake was washed with AcOEt and the filtrate was concentrated under reduced pressure. The residue was purified by FCC (SiHP; DCM: MeOH) to afford the product (0.162 g, yield 72%) as a yellow oil. ESI-MS: 568.7 $[M+H]^+$.

Preparation of 3-({[(3S)-1-(3-aminophenyl)piperidin-3-yl][(2-methylpyridin-4-yl)methyl]amino}methyl)-1-methyl-1,4-dihydroquinolin-4-one To a solution of tert-butyl N-{3-[(3S)-3-{[(1-methyl-4-oxo-1,4-dihydroquinolin-3-yl)methyl][(2-methylpyridin-4-yl)methyl]amino}piperidin-1-yl]phenyl}carbamate (0.162 g, 1.0 eq.) in 1,4-dioxane (3.0 mL) 4M HCl in 1,4-dioxane was added (0.438 mL, 5.0 eq.). The mixture was stirred at RT for 3 days and subsequently concentrated in vacuo. The residue was diluted with DCM and washed with 15% aq. solution of NaOH. The organic layer was washed with brine, dried over anh. $Na_2SO_4$ and concentrated in vacuo. The mixture was separated by prep-HPLC ($MeOH:H_2O$; FA). Obtained solid was partitioned between DCM and saturated aq. solution of $NaHCO_3$. Organic layer was dried over anh. $Na_2SO_4$, filtered and evaporated. The residue was repurified by prep-HPLC ($MeOH:H_2O$; $NH_3$). The compound was converted to HCl salt using 2M HCl in $Et_2O$ (0.045 mL, 3.0 eq.) and DCM as a solvent (3.0 mL) to provide the product (0.017 g, yield 15%) as a yellow solid. ESI-MS: 468.3 $[M+H]^+$. $^1H$ NMR (400 MHz, Deuterium Oxide) δ 8.16 (d, J=6.2 Hz, 1H), 8.11 (s, 1H), 8.05 (dd, J=8.3, 1.5 Hz, 1H), 7.84 (ddd, J=8.7, 7.1, 1.6 Hz, 1H), 7.68 (d, J=8.7 Hz, 1H), 7.62 (d, J=6.3 Hz, 1H), 7.58 (s, 1H), 7.52 (t, J=7.6 Hz, 1H), 7.35 (t, J=8.2 Hz, 1H), 7.07 (dd, J=8.5, 1.8 Hz, 2H), 7.01-6.98 (m, 1H), 6.93 (dd, J=7.9, 2.0 Hz, 1H), 4.62-4.53 (m, 3H), 4.31 (d, J=13.5 Hz, 1H), 3.88 (s, 3H), 3.85-3.79 (m, 1H), 3.71-3.65 (m, 1H), 3.63-3.56 (m, 1H), 3.39-3.26 (m, 2H), 2.32 (s, 3H), 2.25-2.10 (m, 3H), 1.87 (s, 1H).

Example 2. 3-({[(3S)-1-(6-Aminopyridin-3-yl)piperidin-3-yl][(2-methylpyridin-4-yl)methyl]amino}methyl)-1-methyl-1,4-dihydroquinolin-4-one

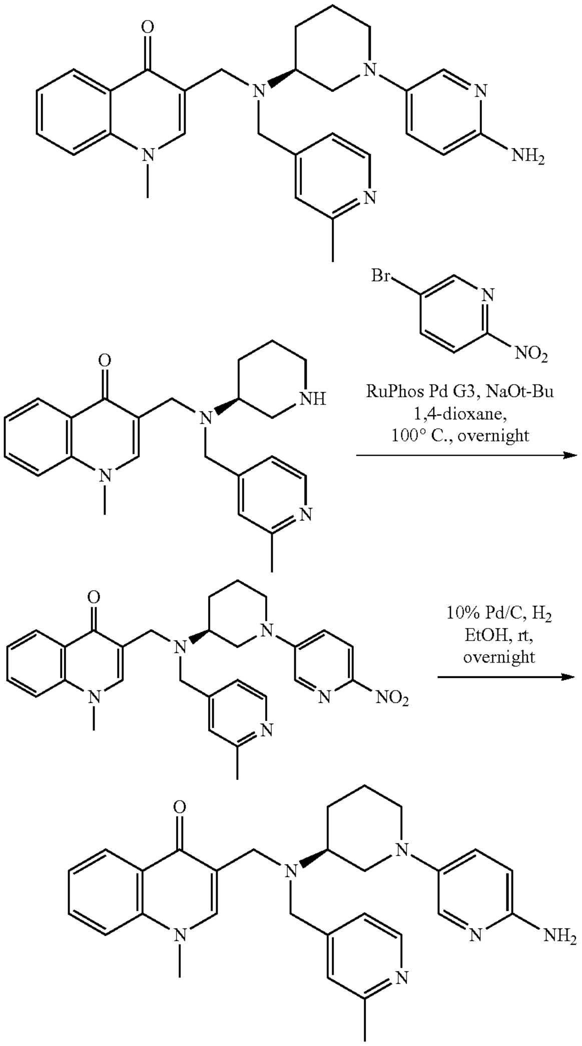

Preparation of 1-methyl-3-({[(2-methylpyridin-4-yl)methyl][(3S)-1-(6-nitropyridin-3-yl)piperidin-3-yl]amino}methyl)-1,4-dihydroquinolin-4-one Reaction vessel was charged with 1-methyl-3-({[(2-methylpyridin-4-yl)methyl][(3S)-piperidin-3-yl]amino}methyl)-1,4-dihydroquinolin-4-one (Intermediate 5) (0.10 g, 1.0 eq.), 5-bromo-2-nitropyridine (0.108 g, 2.0 eq.), NaO t-Bu (0.051 g, 2.0 eq.) and RuPhos Pd G3 (0.022 g, 0.1 eq.). Air was removed and the vessel was backfilled with argon. Anh. 1,4-dioxane (5.0 mL) was added and the mixture was heated at 100° C. overnight. After that the solvent was removed in vacuo and the residue was separated by FCC (SiHP; DCM: MeOH) and re-purified by RP-FCC (C18HP; $H_2O$:MeCN) to afford the product (0.08 g, yield 60%) as a yellow solid. ESI-MS: 499.2 $[M+H]^+$. $^1H$ NMR (300 MHz, DMSO-$d_6$) δ 8.33-8.27 (m, 1H), 8.25 (d, J=3.0 Hz, 1H), 8.19 (dd, J=8.1, 1.6 Hz, 1H), 8.08 (d, J=9.2 Hz, 1H), 8.03 (s, 1H), 7.71 (ddd, J=8.5, 6.8, 1.6 Hz, 1H), 7.62 (d, J=8.5 Hz, 1H), 7.44 (dd, J=9.4, 3.1 Hz, 1H), 7.37 (ddd, J=8.0, 6.8, 1.1 Hz, 1H), 7.30-7.19 (m, 2H), 4.37-4.19 (m, 1H), 4.11-3.95 (m, 1H), 3.86 (s, 3H), 3.83-3.71 (m, 2H), 3.71-3.56 (m, 2H), 3.24-3.12 (m, 1H), 3.05-2.90 (m, 1H), 2.70-2.57 (m, 1H), 2.38 (s, 3H), 2.07-1.93 (m, 1H), 1.90-1.61 (m, 2H), 1.53-1.28 (m, 1H).

Preparation of 3-({[(3S)-1-(6-aminopyridin-3-yl) piperidin-3-yl][(2-methylpyridin-4-yl)methyl] amino}methyl)-1-methyl-1,4-dihydroquinolin-4-one To a solution of 1-methyl-3-({[(2-methylpyridin-4-yl) methyl][(3S)-1-(6-nitropyridin-3-yl)piperidin-3-yl] amino}methyl)-1,4-dihydroquinolin-4-one (0.025 g, 0.050 mmol, 1.0 eq.) in ethanol (5.0 mL), Pd/C (10 wt. %, 0.001 g, 0.1 eq.) was added. The mixture was stirred overnight under hydrogen atmosphere. After filtration and solvent evaporation, the residue was purified using RP-FCC (C18HP; $H_2O$:MeCN) to afford the product (0.014 g, yield 85%) as a yellow solid. ESI-MS: 469.3 $[M+H]^+$. $^1H$ NMR (300 MHz, DMSO-$d_6$) δ 8.33-8.24 (m, 1H), 8.19 (dd, J=8.1, 1.6 Hz, 1H), 7.99 (s, 1H), 7.72 (ddd, J=8.6, 6.8, 1.6 Hz, 1H), 7.66-7.55 (m, 2H), 7.37 (ddd, J=8.0, 6.8, 1.1 Hz, 1H), 7.28-7.18 (m, 2H), 7.14 (dd, J=8.9, 2.9 Hz, 1H), 6.37 (d, J=8.8 Hz, 1H), 5.37 (s, 2H), 3.84 (s, 3H), 3.78-3.54 (m, 4H), 3.54-3.46 (m, 1H), 3.28-3.17 (m, 1H), 2.83-2.73 (m, 1H), 2.63-2.54 (m, 1H), 2.43 (d, J=12.6 Hz, 1H), 2.36 (s, 3H), 2.05-1.90 (m, 1H), 1.82-1.69 (m, 1H), 1.58-1.32 (m, 2H).

Example 3. 3-({[(3S)-1-[6-(Aminomethyl)pyridin-3-yl]piperidin-3-yl][(2-methylpyridin-4-yl)methyl] amino}methyl)-1-methyl-1,4-dihydroquinolin-4-one hydrochloride

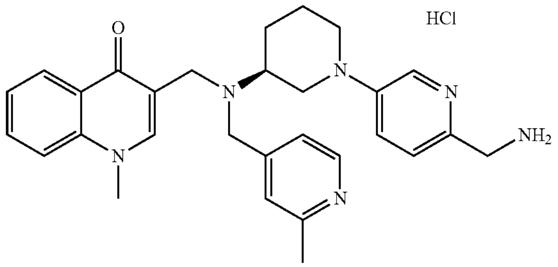

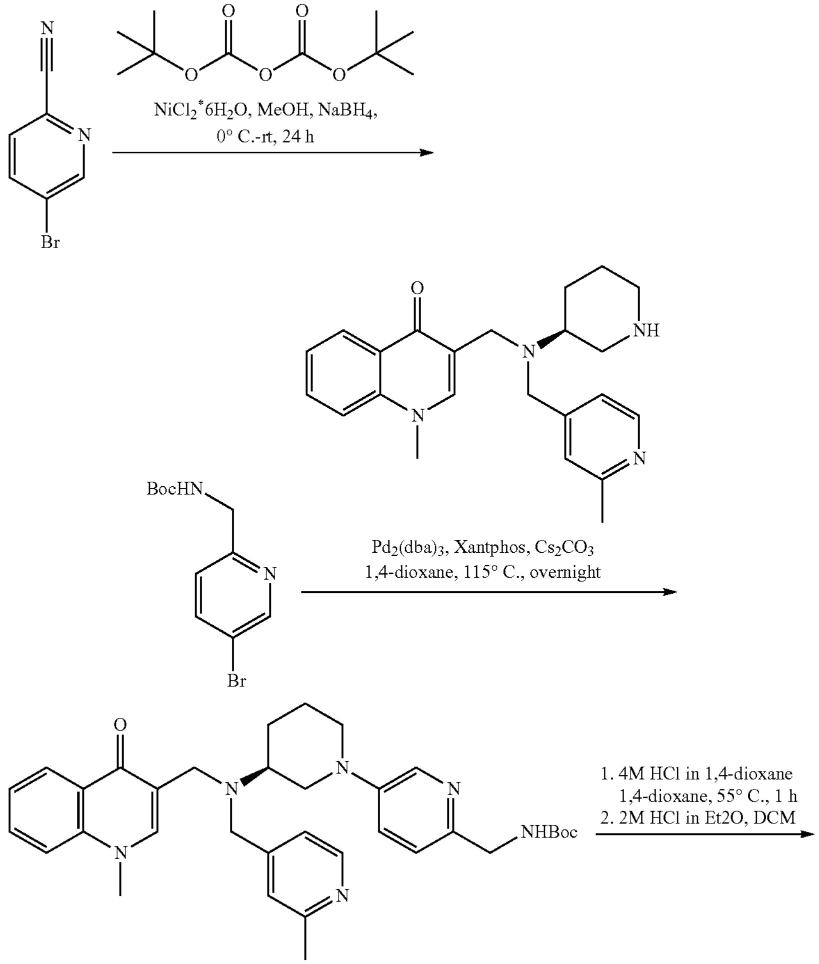

-continued

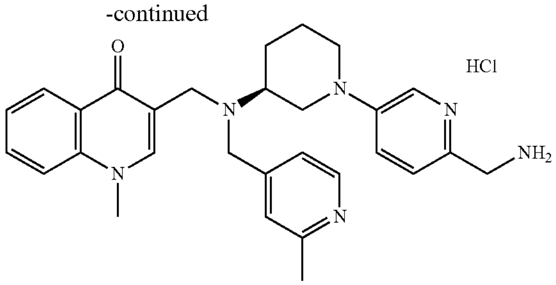

Preparation of tert-butyl N-(5-bromopyridin-2-yl)methyl)carbamate

To a solution of 5-bromopyridine-2-carbonitrile (1.0 g, 1.0 eq.) in methanol (10.0 mL) $NiCl_2.6H_2O$ (0.13 g, 0.1 eq.) and di-tert-butyl dicarbonate (2.39 g, 2.0 eq.) were added. The mixture was coaled to 0° C. and $NaBH_4$ (0.41 g, 2.0 eq) was added. The resulting reaction mixture was stirred at RT for 24 h. Subsequently, solvent was evaporated in vacuo and the residue was diluted with water and extracted with AcOEt. The organic layer was dried over anh. $Na_2SO_4$ and solvent was evaporated in vacuo. The residue was purified by FCC (SIH P; Hex:AcOEt) and repurified by RP-FCC (C18HP; $MeOH:H_2O$) to provide the product (0.19 g, yield 12%) as a yellow oil. ESI-MS: 287.1 $[M+H]^+$ Preparation of tert-butyl N-({5-[(3S)-3-{[(1-methyl-4-oxo-1,4-dihydroquinolin-3-yl)methyl][(2-methylpyridin-4-yl)methyl]amino}piperidin-1-yl]pyridin-2-yl}methyl)carbamate 1-Methyl-3-({[(2-methylpyridin-4-yl)methyl][(3S)-piperidin-3-yl]amino}methyl)-1,4-dihydroquinolin-4-one (Intermediate 5) (0.16 g, 1.0 eq.), tert-butyl N-(5-bromopyridin-2-yl)methyl)arbamate (0.134 g, 1.1 eq.) and $Cs_2CO_3$ (0.28 g, 2.0 eq.) were suspended in anh. 1,4-dioxane and argon was bubbled through the reaction mixture for 5 minutes. Under inert atmosphere $Pd_2(dba)_3$ (0.078 g, 0.2 eq.) and Xantphos (0.074 g, 0.3 eq.) were added and the reaction was stirred at 115° C. overnight. Subsequently, the mixture was cooled to ambient temperature, filtered through a pad of Celite and concentrated under reduced pressure. The residue was combined with a parallel reaction performed in the same manner starting from 1-methyl-3-({[(2-methylpyridin-4-yl)methyl][(3S)-piperidin-3-yl]amino}methyl)-1,4-dihydroquinolin-4-one (Intermediate 5) (0.05 g), tart-butyl N-(5-bromopyridin-2-yl)methyl)arbamate (0.05 g, 1.3 eq.), $Cs_2CO_3$ (0.087 g, 2.0 eq.), $Pd_2(dba)_3$ (0.024 g, 0.2 eq.) and Xantphos (0.023 g, 0.3 eq.). The combined residues were purified by FCC (SiHP; DCM:MeOH) to afford the product (0.158 g, combined yield 64%) as a yellow solid. ESI-MS: 583.8 $[M+H]^+$.

Preparation of 3-({[(3S)-1-[6-(aminomethyl)pyridin-3-yl]piperidin-3-yl][(2-methylpyridin-4-yl)methyl]amino}methyl)-1-methyl-1,4-dihydroquinolin-4-one To a solution of tert-butyl N-({5-[(3S)-3-{[(1-methyl-4-oxo-1,4-dihydroquinolin-3-yl)methyl][(2-methylpyridin-4-yl)methyl]amino}piperidin-1-yl]pyridin-2-yl}methyl)carbamate (0.158 g, 1.0 eq.) in 1,4-dioxane (4.2 mL) 4M HCl in 1,4-dioxane (5.0 mL) was added. The mixture was stirred at 55° C. for 1 h and subsequently concentrated in vacuo. The residue was diluted with DCM and washed with aq. solution of NaOH. The organic layer was dried over $Na_2SO_4$ and concentrated in vacuo. The residue was purified by prep-HPLC ($MeOH:H_2O$; $NH_3$). The compound was converted to HCl salt using 2M HCl in $Et_2O$ (0.08 mL, 2.0 eq.) and DCM as a solvent (5.0 mL) to provide the product (0.046 g, yield 31%) as a yellow solid. ESI-MS: 483.2 $[M+H]^+$. $^1H$ NMR (400 MHz, $D_2O$) δ 8.27 (d, J=6.1 Hz, 1H), 8.25 (d, J=2.9 Hz, 1H), 8.12 (s, 1H), 8.05 (dd, J=8.3, 1.5 Hz, 1H), 7.86 (ddd, J=8.6, 7.1, 1.6 Hz, 1H), 7.80-7.74 (m, 2H), 7.74-7.66 (m, 2H), 7.57-7.50 (m, 2H), 4.79-4.64 (m, $2H+H_2O$), 4.62 (d, J=13.7 Hz, 1H), 4.45 (d, J=13.8 Hz, 1H), 4.24 (d, J=3.2 Hz, 2H), 4.00 (d, J=12.8 Hz, 1H), 3.88 (s, 4H), 3.61 (dd, J=12.8, 8.4 Hz, 1H), 3.58-3.50 (m, 1H), 3.29-3.18 (m, 1H), 2.39 (s, 3H), 2.35-2.27 (m, 1H), 2.26-2.16 (m, 1H), 2.14-2.05 (m, 1H), 1.88-1.77 (m, 1H).

Example 4. 3-({[(3S)-1-(6-Aminopyridin-3-yl)piperidin-3-yl][(2-methoxypyridin-4-yl)methyl]amino}methyl)-1-cyclopropyl-6,7-difluoro-1,4-dihydroquinolin-4-one hydrochloride

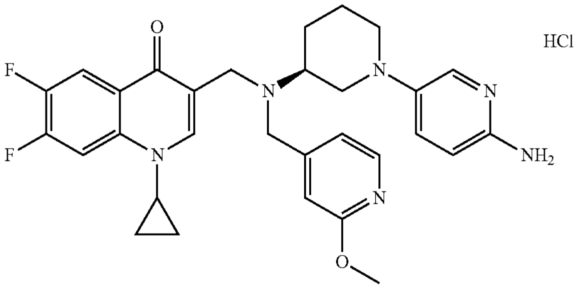

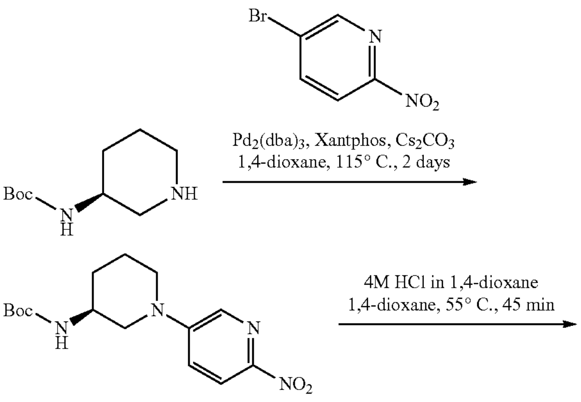

-continued

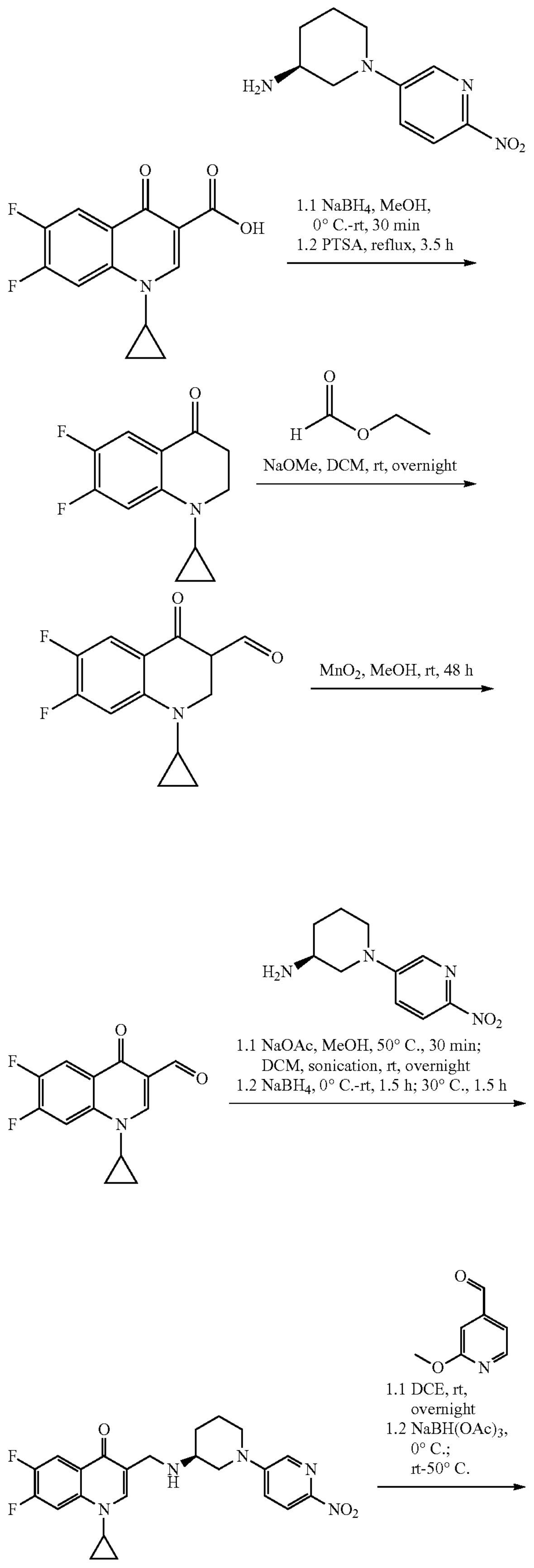

-continued

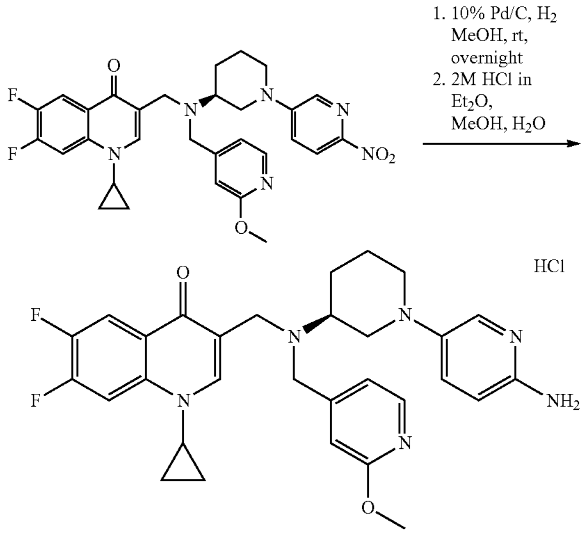

Preparation of tert-butyl N-[(3S)-1-(6-nitropyridin-3-yl)piperidin-3-yl]carbamate To a solution of 5-bromo-2-nitropyridine (2.25 mL, 1.0 eq.) in anh. 1,4-dioxane (96.0 mL) tert-butyl N-[(3S)-piperidin-3-yl]carbamate (4.62 g, 1.3 eq.) and $Cs_2CO_3$ (7.8 g, 1.35 eq.) were added and argon was bubbled through the mixture for 5 minutes. Then $Pd_2(dba)_3$ (0.81 g, 0.05 eq.) and Xantphos (0.62 g, 0.06 eq.) were added and the resulting mixture was heated at 115° C. under an inert atmosphere for 2 days. Subsequently, the mixture was cooled to ambient temperature, filtered through a pad of Celite and concentrated under reduced pressure. The residue was re-dissolved in DCM, stirred overnight with MPA metal scavenger and purified by FCC (SIHP; Hex:EtOAc) to give the product (3.6 g, yield 63%) as a pale yellow oil. ESI-MS: 323.1 $[M+H]^+$. $^1H$ NMR (300 MHz, DMSO-$d_6$) δ 8.21 (d, J=3.0 Hz, 1H), 8.14 (d, J=9.3 Hz, 1H), 7.42 (dd, J=9.3, 3.1 Hz, 1H), 7.03 (d, J=7.1 Hz, 1H), 3.99-3.76 (m, 2H), 3.48-3.37 (m, 1H), 3.21-2.97 (m, 2H), 1.94-1.70 (m, 2H), 1.56-1.46 (m, 2H), 1.41 (s, 9H).

Preparation of (3S)-1-(6-nitropyridin-3-yl)piperidin-3-amine

To a stirred solution of tert-butyl N-[(3S)-1-(6-nitropyridin-3-yl)piperidin-3-yl]carbamate (3.50 g, 1.0 eq.) in 1,4-dioxane (25.0 mL) 4M HCl in 1,4-dioxane (23.0 mL, 30.0 eq.) was added. The resulting mixture was stirred at 55° C. for 45 minutes and subsequently concentrated in vacuo. The residue was diluted with DCM, washed with 10% aq. solution of NaOH and brine, dried over anh. $Na_2SO_4$ and filtered. Solvents were removed under reduced pressure to provide the product (2.40 g, yield 99%) as a yellow solid which was taken to the next step without an additional purification. ESI-MS: 223.3 $[M+H]^+$. $^1H$ NMR (300 MHz, DMSO-$d_6$) δ 8.22 (d, J=3.1 Hz, 1H), 8.12 (d, J=9.3 Hz, 1H), 7.42 (dd, J=9.3, 3.1 Hz, 1H), 4.00-3.80 (m, 2H), 3.02 (ddd, J=13.7, 11.0, 3.1 Hz, 1H), 2.86-2.64 (m, 2H), 1.95-1.82 (m, 1H), 1.82-1.70 (m, 1H), 1.69-1.52 (m, 2H), 1.52-1.40 (m, 1H), 1.35-1.20 (m, 1H).

Preparation of 1-cyclopropyl-6,7-difluoro-1,2,3,4-tetrahydroquinolin-4-one

To a solution of 1-cyclopropyl-6,7-difluoro-4-oxo-1,4-dihydroquinoline-3-carboxylic acid (9.0 g, 1.0 eq.) in anh.

MeOH (150.0 mL) under inert atmosphere $NaBH_4$ (5.4 g, 4.5 eq.) was added portionwise over 30 minutes. The mixture was allowed to reach RT, p-toluenesulfonic acid monohydrate (0.61 g, 0.10 eq.) was added and the reaction mixture was heated at reflux for 3.5 h. Subsequently, the mixture was allowed to reach RT and the solvent was removed in vacuo. The residue was purified by FCC (SiHP; Hex:EtOAc) to provide the product (5.73 g, yield 80%) as a yellow solid. ESI-MS: 224.1 $[M+H]^+$. 1H NMR (400 MHz, DMSO-$d_6$) δ 7.60 (dd, J=10.8, 9.3 Hz, 1H), 7.21 (dd, J=13.6, 6.7 Hz, 1H), 3.52 (dd, J=7.5, 6.4 Hz, 2H), 2.59 (dd, J=7.5, 6.3 Hz, 2H), 2.45-2.38 (m, 1H), 0.95-0.89 (m, 2H), 0.71-0.66 (m, 2H).

Preparation of 1-cyclopropyl-6,7-difluoro-4-oxo-1,4-dihydroquinoline-3-carbaldehyde (Intermediate 4)

To a mixture of NaOMe (5.41 g, 3.9 eq.) and ethyl formate (8.14 mL, 3.9 eq.) in anh. DCM (150.0 mL) the solution of 1-cyclopropyl-6,7-difluoro-1,2,3,4-tetrahydroquinolin-4-one (5.73 g, 1.0 eq.) in anh. DCM (5.0 mL) was added under inert atmosphere and the mixture was stirred at RT overnight Subsequently, the reaction was quenched with ice-cold water. The organic layer was washed with 3M aq. solution of NaOH. Combined aq. phases were acidified to pH=6 and extracted with DCM. Organic layers were combined, dried over anh. $MgSO_4$ and concentrated under reduced pressure. The residue was diluted with anh. MeOH (150.0 mL) and $MnO_2$ (8.44 g, 5.0 eq.) was added. After stirring at RT for 48 h, the mixture was filtered through a pad of Celite and the filter cake was washed with a mixture of DCM and MeOH (1:1). The filtrate was concentrated in vacuo and the residue was purified by FCC (SiHP; DCM:MeOH). Solvents were evaporated and the residue was re-dissolved in a small volume of DCM and hexane was added. The precipitate was filtered and dried to provide the product (3.95 g, yield 62%) as a white solid. ESI-MS: 250.2 $[M+H]^+$. $^1H$ NMR (400 MHz, DMSO-$d_6$) δ 10.11 (s, 1H), 8.41 (s, 1H), 8.22 (dd, J=12.1, 6.7 Hz, 1H), 8.14 (dd, J=10.5, 8.8 Hz, 1H), 3.73-3.64 (m, 1H), 1.32-1.24 (m, 2H), 1.18-1.12 (m, 2H).

Preparation of 1-cyclopropyl-6,7-difluoro-3-({[(3S)-1-(6-nitropyridin-3-yl)piperidin-3-yl]amino}methyl)-1,4-dihydroquinolin-4-one A mixture of 1-cyclopropyl-6,7-difluoro-4-oxo-1,4-dihydroquinoline-3-carbaldehyde (Intermediate 4) (0.40 g, 1.0 eq), (3S)-1-(6-nitropyridin-3-yl)piperidin-3-amine (0.39 g, 1.1 eq.), and NaOAc (0.145 g, 1.1 eq.) in anh. MeOH (50.0 mL) was stirred under inert atmosphere at 50° C. for 30 minutes. DCM (9.0 mL) was added, the mixture was sonicated until clear and stirred at RT overnight. Then, the mixture was cooled to 0° C. and sodium borohydride (0.067 g, 1.1 eq.) was added portionwise. The mixture was allowed to reach RT and stirred for 1.5 h followed by stirring at 30° C. for 1.5 h. Subsequently, the mixture was concentrated in vacuo. The residue was partitioned between DCM and 2M aq. solution of NaOH. Organic layer was washed with brine, dried over anh. $Na_2SO_4$ and filtered. Solvents were removed under reduced pressure and the residue was purified by FCC (SiHP, DCM:MeOH) to provide the product (0.62 g, yield 85%) as a yellow solid. ESI-MS: 456.2 $[M+H]^+$. $^1H$ NMR (400 MHz, DMSO-$d_6$) δ 8.23 (d, J=3.1 Hz, 1H), 8.09 (d, J=9.3 Hz, 1H), 8.05-7.99 (m, 3H), 7.44 (dd, J=9.4, 3.1 Hz, 1H), 3.99 (dd, J=13.3, 3.5 Hz, 1H), 3.85-3.78 (m, 1H), 3.70-3.59 (m, 2H), 3.51 (tt, J=7.2, 3.9 Hz, 1H), 3.23-3.14 (m, 1H), 3.02 (dd, J=13.2, 8.6 Hz, 1H), 2.63-2.56 (m, 1H), 2.15 (s, 1H), 1.93-1.85 (m, 1H), 1.82-1.73 (m, 1H), 1.54-1.35 (m, 2H), 1.27-1.19 (m, 2H), 1.06-0.96 (m, 2H).

Preparation of 1-cyclopropyl-6,7-difluoro-3-({[(2-methoxypyridin-4-yl)methyl][(3S)-1-(6-nitropyridin-3-yl)piperidin-3-yl]amino}methyl)-1,4-dihydroquinolin-4-one A mixture of 1-cyclopropyl-6,7-difluoro-3-({[(3S)-1-(6-nitropyridin-3-yl)piperidin-3-yl]amino}methyl)-1,4-dihydroquinolin-4-one (0.62 g, 1.0 eq.) and 2-methoxypyridine-4-carbaldehyde (0.16 mL, 1.0 eq.) in anh. DCE (20.0 mL) was stirred under inert atmosphere at RT overnight. Then, the mixture was cooled to 0° C. and $NaBH(OAc)_3$ (0.433 g, 1.5 eq.) was added portionwise. The reaction was stirred at 40° C. for 3 h. Additional portions of 2-methoxypyridine-4-carbaldehyde and $NaBH(OAc)_3$ was added to the reaction mixture and stirring at 50° C. was continued until no further progress of reaction was observed. Subsequently DCM and 2 M aq. solution of NaOH were added. Organic layer was washed with brine, dried over anh. $Na_2SO_4$ and concentrated in vacuo. The residue was purified by FCC (SiHP; DCM:MeOH) and re-purified by RP-FCC (C18HP; $H_2O$:MeCN) to afford the title compound (0.545 g, yield 69%) as a yellow solid. ESI-MS: 577.5 $[M+H]^+$. $^1H$ NMR (400 MHz, DMSO-$d_6$) δ 8.23 (d, J=3.0 Hz, 1H), 8.08 (d, J=9.3 Hz, 1H), 8.04-7.95 (m, 3H), 7.91 (s, 1H), 7.44 (dd, J=9.3, 3.1 Hz, 1H), 6.96 (dd, J=5.3, 1.3 Hz, 1H), 6.78 (s, 1H), 4.24-4.18 (m, 1H), 4.06-3.99 (m, 1H), 3.78 (s, 2H), 3.76 (s, 3H), 3.65 (s, 2H), 3.51-3.45 (m, 1H), 3.20-3.13 (m, 1H), 3.01-2.92 (m, 1H), 2.73-2.65 (m, 1H), 2.00-1.93 (m, 1H), 1.84-1.75 (m, 1H), 1.74-1.65 (m, 1H), 1.52-1.39 (m, 1H), 1.26-1.18 (m, 2H), 0.96-0.85 (m, 2H).

Preparation of 3-({[(3S)-1-(6-aminopyridin-3-yl)piperidin-3-yl][(2-methoxypyridin-4-yl)methyl]amino}methyl)-1-cyclopropyl-6,7-difluoro-1,4-dihydroquinolin-4-one hydrochloride To a solution of 1-cyclopropyl-6,7-difluoro-3-({[(2-methoxypyridin-4-yl)methyl][(3S)-1-(6-nitropyridin-3-yl)piperidin-3-yl]amino}methyl)-1,4-dihydroquinolin-4-one (0.50 g, 1.0 eq) in MeOH (50.0 mL), Pd/C (10 wt. %, 0.04 g, 0.45 eq.) was added and the mixture was stirred overnight under hydrogen atmosphere. Subsequently, the reaction mixture was filtered through a pad of Celite, and the filtrate was stirred with MPA scavenger for 30 minutes. After filtration and solvent evaporation, the residue was purified using FCC (SiHP; DCM:MeOH) and re-purified by FCC (ALN; DCM:MeOH), RP-FCC (C18HP; $H_2O$:MeCN), and FCC (SiHP; DCM:MeOH). The compound was converted to HCl salt using 2M HCl in $Et_2O$ (0.064 mL, 1.0 eq.) and a mixture of MeOH (5.0 mL) and $H_2O$ (1.0 mL) as a solvent to provide the product (0.078 g, yield 15%) as a yellow solid. ESI-MS: 547.3 $[M+H]^+$. $^1H$ NMR (400 MHz, Methanol-$d_4$) δ 8.06 (dd, J=10.9, 8.8 Hz, 1H), 7.99 (s, 1H), 7.95 (dd, J=12.1, 6.7 Hz, 1H), 7.86 (d, J=5.3 Hz, 1H), 7.76 (dd, J=9.5, 2.8 Hz, 1H), 7.38 (d, J=2.8 Hz, 1H), 6.90 (dd, J=5.4, 1.4 Hz, 1H), 6.84 (d, J=9.4 Hz, 1H), 6.74 (s, 1H), 3.86-3.71 (m, 7H), 3.70-3.64 (m, 1H), 3.51-3.44 (m, 1H), 3.40-3.35 (m, 1H), 3.02-2.92 (m, 1H), 2.78-2.70 (m, 1H), 2.63-2.54 (m, 1H), 2.14-2.06 (m, 1H), 1.96-1.89 (m, 1H), 1.75-1.55 (m, 2H), 1.33-1.26 (m, 2H), 0.99-0.93 (m, 2H).

Example 5. 3-({[(2-Aminopyridin-4-yl)methyl][(3S)-1-(6-methylpyridin-3-yl)piperidin-3-yl]amino}methyl)-1-cyclopropyl-6,7-difluoro-1,4-dihydroquinolin-4-one hydrochloride
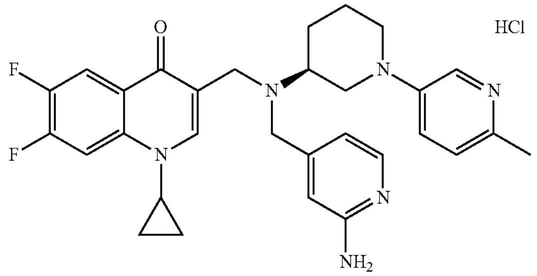
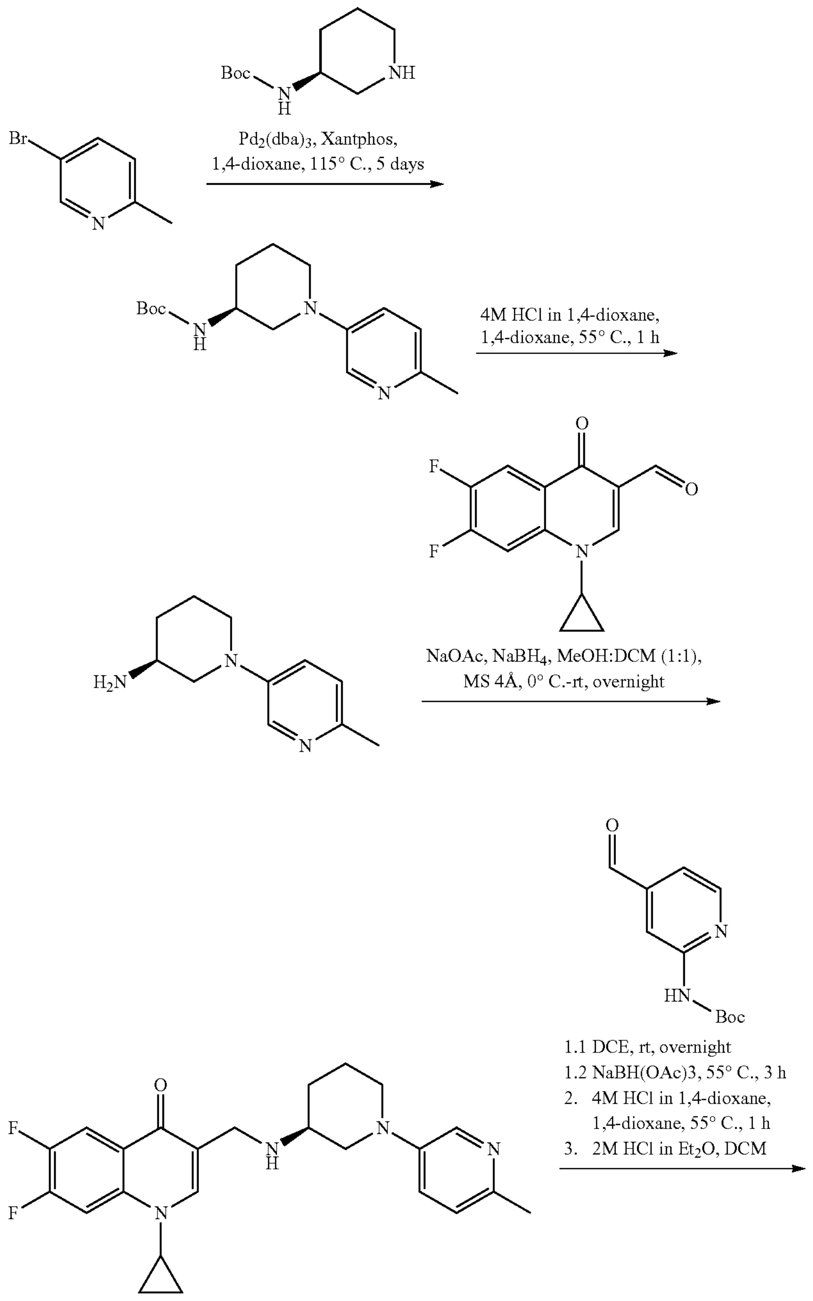

-continued

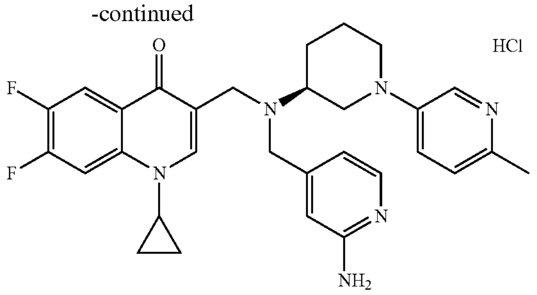

HCl

Preparation of tert-butyl N-[(3S)-1-(6-methylpyridin-3-yl)piperidin-3-yl]carbamate Through a mixture of 5-bromo-2-methylpyridine (3.0 g, 1.0 eq.) in anh. 1,4-dioxane (80.0 mL) tert-butyl N-[(3S)-piperidin-3-yl]carbamate (4.54 g, 1.3 eq.) and $Cs_2CO_3$ (7.7 g, 1.4 eq.) argon was bubbled for 5 minutes. Then $Pd_2(dba)_3$ (0.80 g, 0.05 eq.), and Xantphos (0.60 g, 0.06 eq.) were added and the resulting mixture was heated at 115° C. under inert atmosphere for 5 days. Subsequently, the mixture was cooled to ambient temperature, filtered through a pad of Celite and concentrated under reduced pressure. The residue was purified by FCC (SiHP; Hex:EtOAc) to give the product (3.90 g, yield 77%) as a pale yellow oil. ESI-MS: 292.1 $[M+H]^+$.

Preparation of (3S)-1-(6-methylpyridin-3-yl)piperidin-3-amine (Intermediate 6)

To a stirred solution of tert-butyl N-[(3S)-1-(6-methylpyridin-3-yl)piperidin-3-yl]carbamate (0.53 g, 1.0 eq.) in 1,4-dioxane (3.0 mL) 4M HCl in 1,4-dioxane (2.73 mL, 30.0 eq.) was added and the reaction mixture was stirred at 55° C. for 1 h. After concentration under reduced pressure, the residue was diluted with DCM and washed with 10% aq. solution of NaOH. Organic layer was dried over anh. $Na_2SO_4$, filtered and solvents were removed under reduced pressure to provide the product (0.34 g, yield 98%) as a yellow oil which was taken to the next step without additional purification. ESI-MS: 192.3 $[M+H]^+$.

Preparation of 1-cyclopropyl-6,7-difluoro-3-({[(3S)-1-(6-methylpyridin-3-yl)piperidin-3-yl]amino}methyl)-1,4-dihydroquinolin-4-one A mixture of 1-cyclopropyl-6,7-difluoro-4-oxo-1,4-dihydroquinoline-3-carbaldehyde (Intermediate 4) (0.20 g, 1.0 eq.), (3S)-1-(6-methylpyridin-3-yl)piperidin-3-amine (Intermediate 6) (0.16 g, 1.05 eq.), NaOAc (0.066 g, 1.0 eq.) and MS 4 Å (0.3 g) in a mixture of anh. MeOH and DCM (1:1, 7.0 mL) was stirred under inert atmosphere at RT overnight. Then, the mixture was cooled to 0° C., sodium borohydride (0.033 g, 1.1 eq.) was added portionwise and the mixture was stirred at RT for 1 h. Subsequently, the mixture was filtered through a pad of Celite, washed with MeOH and concentrated in vacuo. The residue was partitioned between DCM and 10% aq. solution of NaOH. Aqueous layer was washed with DCM and the combined organic phases were washed with brine and dried over anh. $Na_2SO_4$. Solvents were removed under reduced pressure to provide the crude product (0.315 g, yield 93%) as a yellow oil which was taken to the next step without additional purification 425.5 $[M+H]^+$.

Preparation of 3-({[(2-aminopyridin-4-yl)methyl][(3S)-1-(6-methylpyridin-3-yl)piperidin-3-yl]amino}methyl)-1-cyclopropyl-6,7-difluoro-1,4-dihydroquinolin-4-one A mixture of 1-cyclopropyl-6,7-difluoro-3-({[(3S)-1-(6-methylpyridin-3-yl)piperidin-3-yl]amino}methyl)-1,4-dihydroquinolin-4-one (0.315 g, 1.0 eq.) and tert-butyl N-(4-formylpyridin-2-yl)carbamate (0.215 g, 1.3 eq.) in anh. DCE (7.0 mL) was stirred at RT overnight in presence of $MgSO_4$. Then $NaBH(OAc)_3$ (0.236 g, 1.5 eq.) was added and the reaction was stirred at 55° C. for 3 h and subsequently concentrated in vacuo. The residue was purified by FCC (SiHP; DCM:MeOH) and the product was then dissolved in 1,4-dioxane (3.0 mL) and 4M HCl in 1,4-dioxane (0.6 mL) was added. The mixture was stirred at 55° C. for 1 h and then concentrated in vacuo. The residue was diluted with DCM and washed with 5% aq. solution of NaOH. Organic phase was dried over anh. $Na_2SO_4$, filtered, concentrated in vacuo and purified by prep-HPLC ($H_2O$:MeCN; $NH_3$). The compound was converted to HCl salt using 2M HCl in $Et_2O$ (0.04 mL, 2.0 eq.) and DCM as a solvent (5.0 mL) to provide the product (0.023 g, yield 5%) as a yellow solid. ESI-MS: 531.2 $[M+H]^+$. $^1H$ NMR (400 MHz, Deuterium Oxide) δ 8.17 (s, 1H), 8.09-8.01 (m, 2H), 7.99-7.91 (m, 2H), 7.56 (d, J=9.1 Hz, 1H), 7.44 (d, J=6.7 Hz, 1H), 6.87 (s, 1H), 6.75 (dd, J=6.7, 1.7 Hz, 1H), 4.46-4.26 (m, 4H), 4.05-3.97 (m, 1H), 3.70-3.62 (m, 1H), 3.60-3.53 (m, 1H), 3.53-3.46 (m, 1H), 3.46-3.38 (m, 1H), 3.12-3.03 (m, 1H), 2.54 (s, 3H), 2.31-2.22 (m, 1H), 2.09-1.98 (m, 2H), 1.82-1.71 (m, 1H), 1.31-1.25 (m, 2H), 0.99-0.92 (m, 2H).

Example 6. 7-(4-Aminopiperidin-1-yl)-1-methyl-3-({[(3S)-1-(6-methylpyridin-3-yl)piperidin-3-yl][(2-methylpyridin-4-yl)methyl]amino}methyl)-1,4-dihydroquinolin-4-one hydrochloride
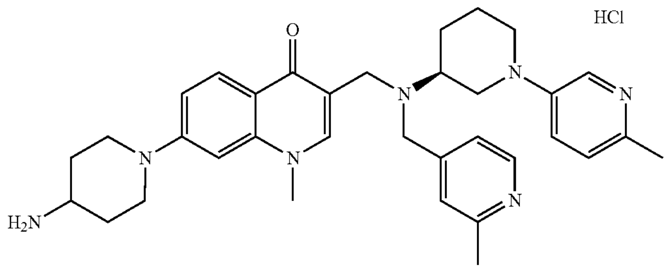
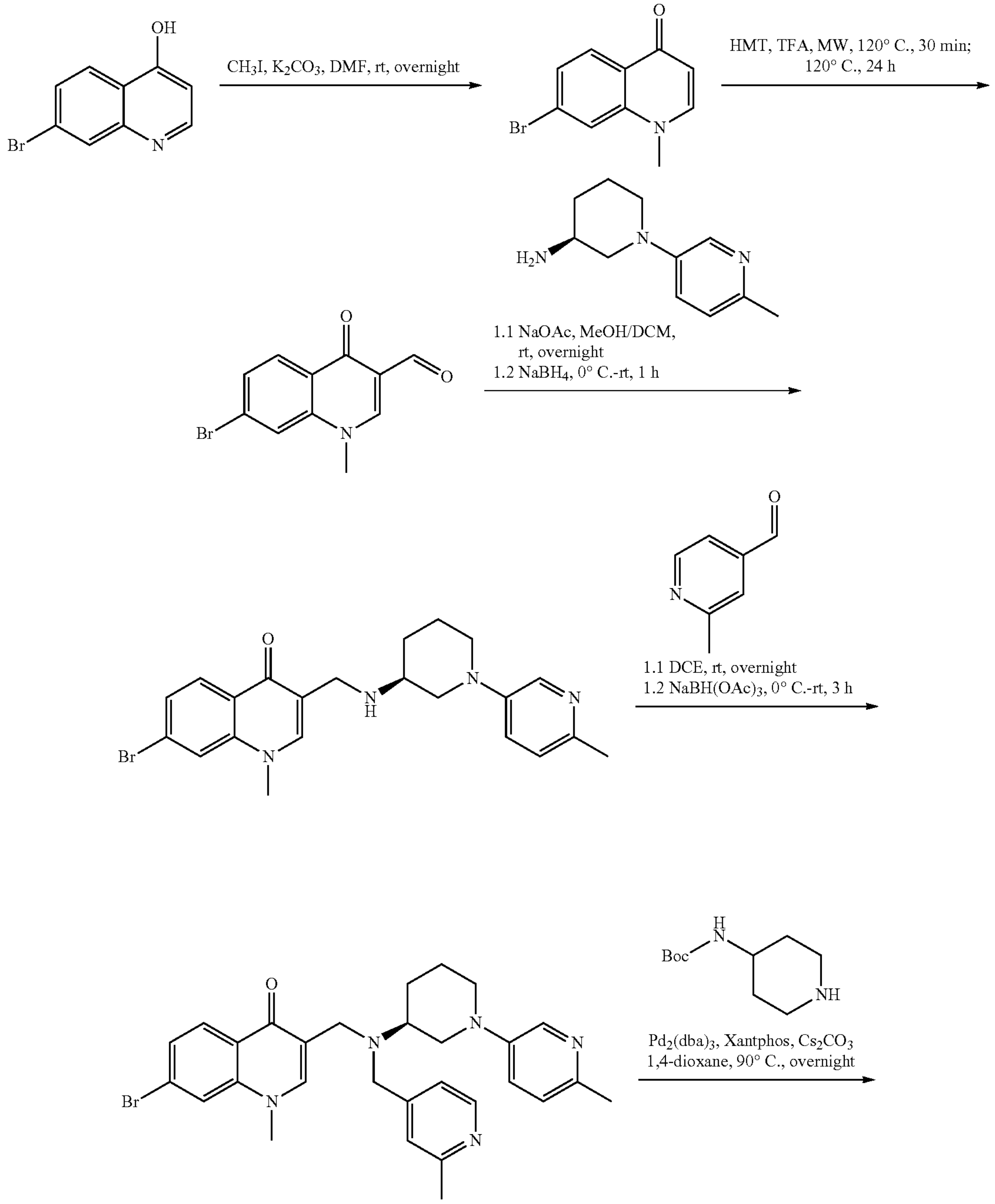

-continued

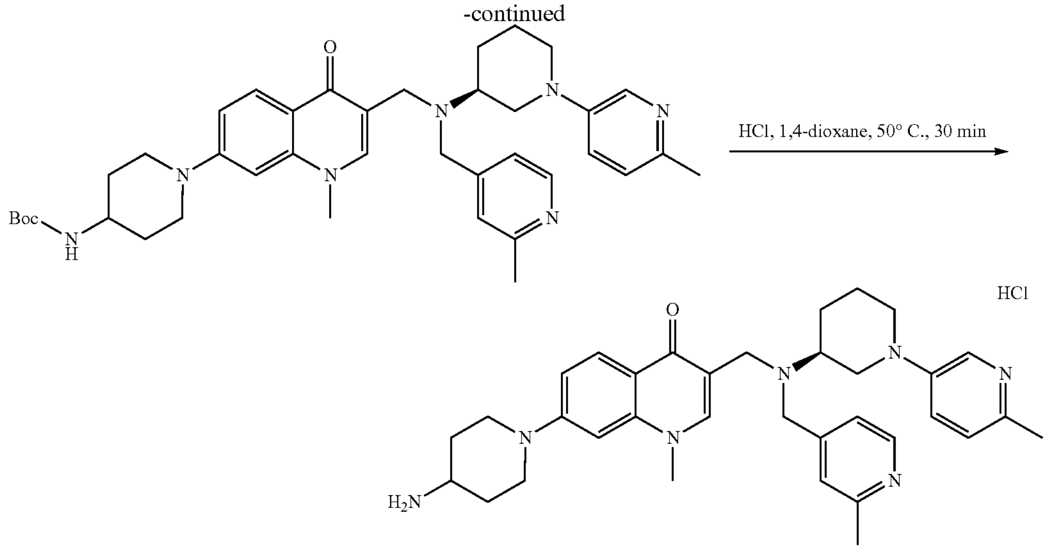

Preparation of 7-bromo-1-methyl-1,4-dihydroquinolin-4-one

7-Bromo-4-quinolinol (3.0 g, 1.0 eq.) was dissolved in anh. DMF (6.0 mL), $K_2CO_3$ was added (4.45 g, 2.0 eq.). The mixture was stirred at RT for 0.5 h, then methyl iodide (1.25 mL, 1.5 eq.) was added and the mixture was stirred at RT overnight. The reaction mixture was diluted with DCM, washed with water, brine and dried over anh. $Na_2SO_4$. Subsequently solvents were removed under reduced pressure to afford the product (2.57 g, yield 79%) as a yellow solid used in the next step without further purification. ESI-MS: 237.9 $[M+H]^+$.

Preparation of 7-bromo-1-methyl-4-oxo-1,4-dihydroquinoline-3-carbaldehyde

7-Bromo-1-methyl-1,4-dihydroquinolin-4-one (2.50 g, 1.0 eq.), HMT (2.94 g, 2.0 eq.) and TFA (10.0 mL) were irradiated in microwave at 120° C. for 0.5 h. After that the mixture was heated in a conventional manner at 120° C. overnight. The mixture was diluted with water and stirred for 10 min at RT, then neutralized with saturated aq. solution of $Na_2CO_3$ and extracted with DCM. The organic phase was washed with brine, dried over anh. $Na_2SO_4$ and concentrated in vacuo. The residue was triturated with EtOAc and dried to afford the product as a white solid (2.02 g, yield 72%). ESI-MS: 265.9 $[M+H]^+$. $^1H$ NMR (300 MHz, DMSO-$d_6$) δ 10.15 (s, 1H), 8.61 (s, 1H), 8.22-8.15 (m, 1H), 8.06-8.00 (m, 1H), 7.75-7.68 (m, 1H), 3.96 (s, 3H).

Preparation of 7-bromo-1-methyl-3-({[(3S)-1-(6-me)ylpyridin-3-yl)piperidin-3-yl]amino}methyl)-1,4-dihydroquinolin-4-one A mixture of (3S)-1-(6-methylpyridin-3-yl)piperidin-3-amine (Intermediate 6) (0.44 g, 1.1 eq.), 7-bromo-1-methyl-4-oxo-1,4-dihydroquinoline-3-carbaldehyde (0.56 g, 21.0 eq.), NaOAc (0.173 g, 1.0 eq.) and 4 Å MS in a mixture of anh. MeOH and anh. DCM (1:1; 50.0 mL) was stirred under inert atmosphere at RT overnight. Then, the mixture was cooled to 0° C. and sodium borohydride (0.088 g, 1.1 eq.) was added portionwise. The mixture was allowed to reach RT over 1 h. Subsequently, the mixture was filtered through a pad of Celite, washed with MeOH and the solvent was removed in vacuo. The residue was partitioned between DCM and 10% aq. solution of NaOH, aq. layer was extracted with DCM and the combined organic layers were dried over anh. $MgSO_4$. Solvents were removed under reduced pressure to provide the product (0.90 g, yield 97%) as a yellow oil which was taken to the next step without additional purification.

Preparation of 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one A mixture of 7-bromo-1-methyl-3-({[(3S)-1-(6-methylpyridin-3-yl)piperidin-3-yl]amino}methyl)-1,4-dihydroquinolin-4-one (0.90 g, 1.0 eq.), 2-methylpyridine-4-carbaldehyde (0.32 g, 1.3 eq.) and anh. $Na_2SO_4$ (3.0 g) in anh. DCE (20.0 mL) was stirred under inert atmosphere at RT overnight. Then, the mixture was cooled to 0° C. and $NaBH(OAc)_3$ (0.65 g, 1.5 eq.) was added portionwise. The reaction was stirred at RT over 3 h. The mixture was filtered through a pad of Celite pad which was then rinsed with DCM. The filtrate was washed with water, and organic layer was dried over anh. $MgSO_4$ and concentrated in vacuo. The residue was purified by FCC (SiHP; DCM:MeOH; $NH_3$) an re-purified by two RP-FCCs (C18HP; $H_2O$:MeCN) to afford the title compound (0.450 g, yield 40%) as a yellow solid. ESI-MS: 546.3 $[M+H]^+$.

Preparation of tert-buty N-{1-[1-methyl-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-4-yl}carbamate Reaction vessel was charged with 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one (0.20 g, 1.0 eq.), tert-butyl N-(piperidin-4-yl) carbamate (0.11 g, 1.5 eq.), $Cs_2CO_3$ (0.24 g, 2.0 eq.), $Pd_2(dba)_3$ (0.034 g, 0.1 eq.) and Xantphos (0.042 g, 0.2 eq.). Air was removed and the vessel was backfilled with argon. anh. 1,4-dioxane (5.0 mL) was added and the mixture was stirred at 90° C. overnight Subsequently, the mixture was cooled to ambient temperature, filtered through a pad of Celite and concentrated under reduced pressure. The residue was purified by FCC (SiHP; DCM:MeOH), dissolved in DCM, stirred with MPA scavenger, filtered and evaporated to afford the product (0.16 g, yield 62%) as a yellow oil. ESI-MS: 666.4 $[M+H]^+$.

Preparation of 7-(4-aminopiperidin-1-yl)-1-methyl-3-({[(3S)-1-(6-methylpyridin-3-yl)piperidin-3-yl][(2-methylpyridin-4-yl)methyl]amino}methyl)-1,4-dihydroquinolin-4-one A stirred solution of tert-butyl N-{1-[1-methyl-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-4-yl}carbamate (0.16 g, 1.0 eq.) in 1,4-dioxane (5.0 mL) was treated with 4M HCl in 1,4-dioxane (2.0 mL, 33.3 eq.). The reaction was carried out at 50° C. for 0.5 h, then the mixture was concentrated in vacuo, basified using 2M aq. solution of NaOH and separated by RP-FCC (C18HP; $H_2O$: MeCN). The isolated product was re-purified by prep-HPLC ($H_2O$:MeCN; $NH_3$). The compound was converted to HCl salt using 2M HCl in $Et_2O$ (0.062 mL, 1.0 eq.) and DCM as a solvent (5.0 mL) to provide the title compound (0.071 g, yield 43%) as a yellow solid. ESI-MS: 566.5 $[M+H]^+$. $^1H$ NMR (300 MHz, Deuterium Oxide) δ 8.03-7.97 (m, 1H), 7.93-7.82 (m, 2H), 7.46 (s, 1H), 7.37-7.28 (m, 1H), 7.15-7.02 (m, 2H), 6.93 (d, J=5.4 Hz, 1H), 6.82 (s, 1H), 6.50 (s, 1H), 4.00-3.86 (m, 2H), 3.71-3.52 (m, 5H), 3.50 (s, 3H), 3.49-3.32 (m, 2H), 3.03-2.81 (m, 3H), 2.68-2.43 (m, 2H), 2.35 (s, 3H), 2.16-1.80 (m, 7H), 1.78-1.38 (m, 4H).

Example 7. 7-Amino-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one

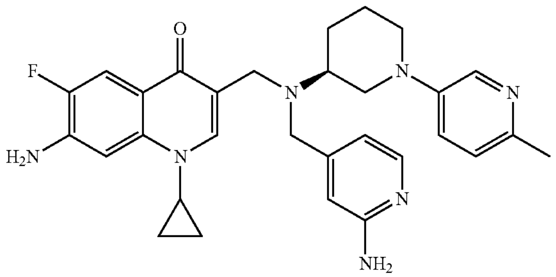

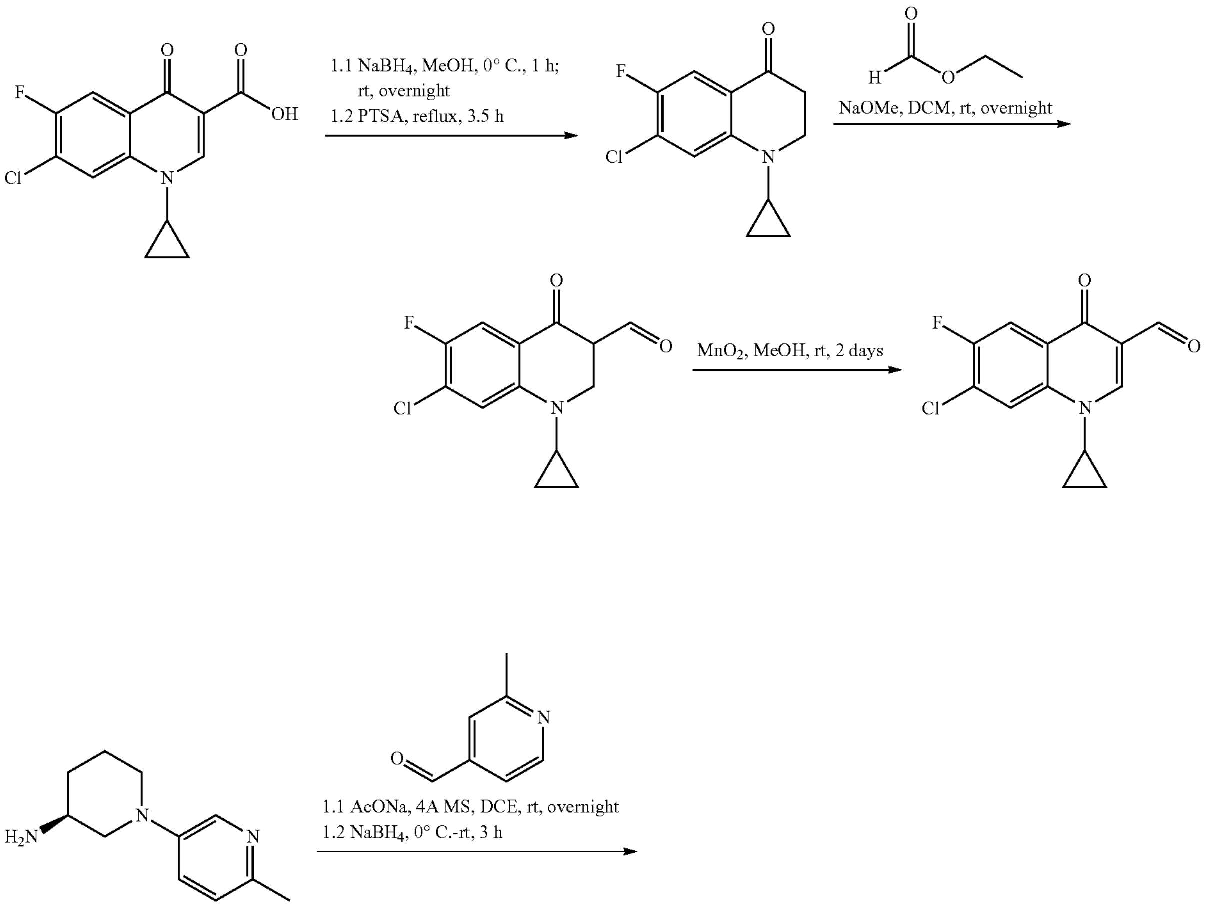

-continued

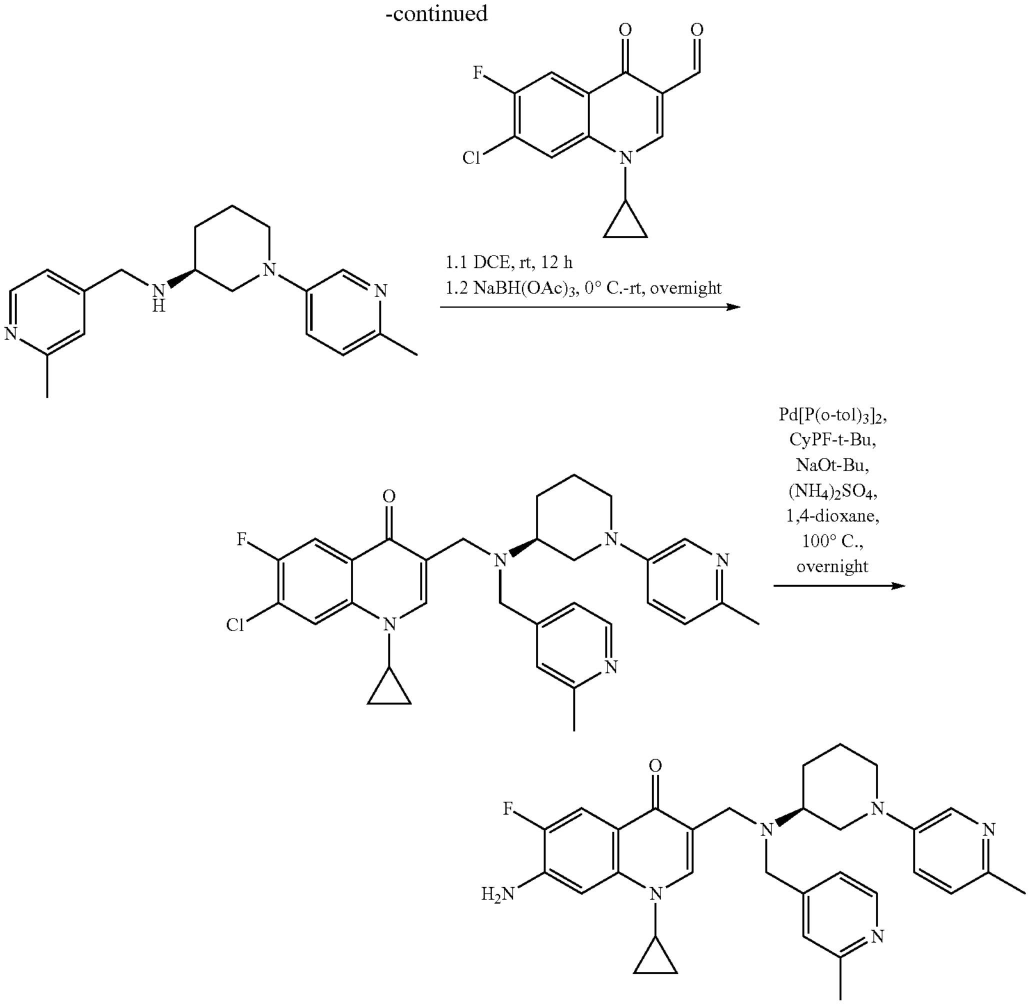

Preparation of 7-chloro-1-cyclopropyl-6-fluoro-1,2,3,4-tetrahydroquinolin-4-one To a cooled solution of 7-chloro-1-cyclopropyl-6-fluoro-4-oxo-1,4-dihydroquinoline-3-carboxylic acid (10.0 g, 1.0 eq.) in anh. MeOH (150.0 mL) $NaBH_4$ (6.0 g, 4.5 eq.) was added portionwise over 1 h. The mixture was allowed to reach RT and was stirred overnight. Afterwards p-toluenesulfonic acid monohydrate (0.67 g, 0.10 eq.) was added and the reaction mixture was heated at reflux for 3.5 h. Subsequently, the mixture was allowed to reach RT and the solvent was removed in vacuo. The residue was diluted with water and extracted with DCM. Combined organic layers was dried over anh. $MgSO_4$ and concentrated under reduced pressure. FCC (SiHP; Hex:EtOAc) afforded the product (6.98 g, yield 82%) as a yellow solid. ESI-MS: 240 $[M+H]^+$. $^1H$ NMR (400 MHz, DMSO-$d_6$) δ 7.55 (d, J=9.3 Hz, 1H), 7.39 (d, J=6.2 Hz, 1H), 3.52 (dd, J=7.5, 6.3 Hz, 2H), 2.61 (dd, J=7.5, 6.3 Hz, 2H), 2.47-2.41 (m, 1H), 0.96-0.86 (m, 2H), 0.76-0.66 (m, 2H).

Preparation of 7-chloro-1-cyclopropyl-6-fluoro-4-oxo-1,4-dihydroquinoline-3-carbaldehyde To a mixture of NaOMe (5.67 g, 3.9 eq.) and ethyl formate (8.53 mL, 3.9 eq.) in anh. DCM (140.0 mL) the solution of 7-chloro-1-cyclopropyl-6-fluoro-1,2,3,4-tetrahydroquinolin-4-one (6.45 g, 1.0 eq.) was added and the mixture was stirred under inert atmosphere at RT overnight. Subsequently, the reaction mixture was poured into ice-cold water. The organic layer was washed with 3M aq. solution of NaOH. Combined aq. phases were acidified to pH=6 with concentrated HCl and extracted with DCM. Organic layers were combined, dried over anh. $MgSO_4$ and concentrated under reduced pressure. The residue was diluted with anh. MeOH (150.0 mL) and $MnO_2$ (10.6 g, 5.0 eq.) was added. After stirring at RT for 2 days, the mixture was filtered through a pad of Celite and the filter cake was washed with a mixture of DCM and MeOH (1:1). The filtrate was concentrated in vacuo and the residue was purified by FCC (SiHP; DCM:MeOH). Solvents were evaporated and the residue was redissolved in a small volume of DCM and hexane was added. The precipitate was filtered and dried to provide the product as an off white solid (3.86 g, yield 54%). ESI-MS: 266.8 $[M+H]^+$. $^1H$ NMR (400 MHz, DMSO-$d_6$) δ 10.11 (s, 1H), 8.41 (s, 1H), 8.36 (d, J=6.1 Hz, 1H), 8.09 (d, J=9.1 Hz, 1H), 3.78-3.70 (m, 1H), 1.32-1.24 (m, 2H), 1.22-1.12 (m, 2H).

Preparation of (3S)-1-(6-methylpyridin-3-yl)-N-[(2-methylpyridin-4-yl)methyl]piperidin-3-amine (Intermediate 2)

To a mixture of (3S)-1-(6-methylpyridin-3-yl)piperidin-3-amine (Intermediate 6) (2.73 g, 1.0 eq.) in anh. DCE (25.0 mL), NaOAc (2.34 g, 2.0 eq.) and 4 Å MS 2-methylpyridine-4-carbaldehyde (1.73, 1.0 eq.) were added. The mixture was stirred at RT overnight. After that the mixture was cooled to 0° C. and sodium borohydride (1.09 g, 2.0 eq.) was added portionwise. The mixture was stirred at RT for 3 h, then concentrated in vacuo. The residue was diluted with DCM and washed with aq. solution of 10% NaOH, brine, dried over anh. $MgSO_4$ and concentrated in vacuo. The residue was separated by FCC (SiHP; DCM:MeOH). The isolated product was repurified by RP-FCC (C18HP; $H_2O$: MeCN) to obtain the title compound (3.05 g, yield 34%) as a yellow oil. ESI-MS: 297.1 $[M+H]^+$. $^1H$ NMR (400 MHz, DMSO-$d_6$) δ 8.34 (dd, J=5.1, 0.7 Hz, 1H), 8.11 (d, J=2.9 Hz, 1H), 7.25-7.22 (m, 1H), 7.20 (dd, J=8.5, 3.1 Hz, 1H), 7.17 (dd, J=5.1, 1.4 Hz, 1H), 7.04 (d, J=8.5 Hz, 1H), 3.78 (s, 2H), 3.73-3.61 (m, 1H), 3.52-3.44 (m, 1H), 2.71-2.63 (m, 1H), 2.61-2.52 (m, 2H), 2.48-2.42 (m, 4H), 2.36-2.32 (m, 3H), 1.96-1.88 (m, 1H), 1.78-1.68 (m, 1H), 1.57-1.43 (m, 1H), 1.28-1.14 (m, 1H).

Preparation of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3)

To a solution of (3S)-1-(6-methylpyridin-3-yl)-N-[(2-methylpyridin-4-yl)methyl]piperidin-3-amine (Intermediate 2) (2.22 g, 1.0 eq.) in anh. DCE (20.0 mL), 7-chloro-1-cyclopropyl-6-fluoro-4-oxo-1,4-dihydroquinoline-3-carbaldehyde (1.99 g, 1.0 eq.) was added. The mixture was stirred at RT for 12 h, then cooled to 0° C. $NaBH(OAc)_3$ (2.22 g, 1.4 eq.) was added portionwise and the reaction was stirred at RT overnight. The mixture was diluted with DCM and washed with $H_2O$, saturated aq. solution of $NaHCO_3$, brine, dried over anh. $Na_2SO_4$ and concentrated in vacuo. The residue was purified by FCC (SiHP; DCM:MeOH) and re-purified by RP-FCC (C18HP; $H_2O$: MeCN) to obtain the product (3.20 g, yield 75%) as a yellow solid. ESI-MS: 546.8 $[M+H]^+$. $^1H$ NMR (400 MHz, DMSO-$d_6$) δ 8.31-8.24 (m, 1H), 8.16 (d, J=6.2 Hz, 1H), 8.13 (d, J=2.9 Hz, 1H), 7.97 (d, J=9.5 Hz, 1H), 7.91 (s, 1H), 7.26-7.18 (m, 2H), 7.17-7.13 (m, 1H), 7.02 (d, J=8.5 Hz, 1H), 3.82-3.70 (m, 3H), 3.66-3.50 (m, 4H), 2.83-2.69 (m, 2H), 2.65-2.54 (m, 1H), 2.36 (s, 3H), 2.33 (s, 3H), 2.08-1.92 (m, 1H), 1.80-1.72 (m, 1H), 1.62-1.41 (m, 2H), 1.27-1.18 (m, 2H), 1.00-0.82 (m, 2H).

Preparation of 7-amino-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one To a mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.05 g, 1.0 eq.), ammonium sulfate (0.024 g, 2.0 eq.) and NaO t-Bu (0.04 g, 4.5 eq.) in anh. 1,4-dioxane (2.0 mL), a solution of $Pd[P(o\text{-}tol)_3]_2$ (0.003 g, 0.05 eq.) and CyPF-t-Bu (0.003 g, 0.05 eq.) in anh. 1,4-dioxane (1.0 mL) was added. The reaction was stirred under inert atmosphere at 100° C. overnight. Next the mixture was diluted with EtOAc, filtered through a pad of Celite and concentrated in vacuo. Separation by FCC (SiHP; DCM: MeOH) and subsequent repurification by RP-FCC (C18HP; $H_2O$:MeCN) provided the product (0.031 g, yield 63%) as a white solid. ESI-MS: 527.2 $[M+H]^+$. $^1H$ NMR (400 MHz, MeOD-$d_4$) δ 8.16 (d, J=5.1 Hz, 1H), 8.08 (d, J=2.9 Hz, 1H), 7.79 (s, 1H), 7.75 (d, J=11.9 Hz, 1H), 7.35 (dd, J=8.6, 3.0 Hz, 1H), 7.26-7.19 (m, 3H), 7.11 (d, J=8.6 Hz, 1H), 3.91-3.81 (m, 3H), 3.77 (s, 2H), 3.64-3.57 (m, 1H), 3.40-3.26 (m, overlap with MeOH), 3.02-2.93 (m, 1H), 2.89-2.80 (m, 1H), 2.75-2.63 (m, 1H), 2.41 (s, 3H), 2.34 (s, 3H), 2.17-2.09 (m, 1H), 1.97-1.88 (m, 1H), 1.75-1.58 (m, 2H), 1.28-1.21 (m, 2H), 0.92-0.85 (m, 2H).

Example 8. 7-[(2-Aminoethyl)amino]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one

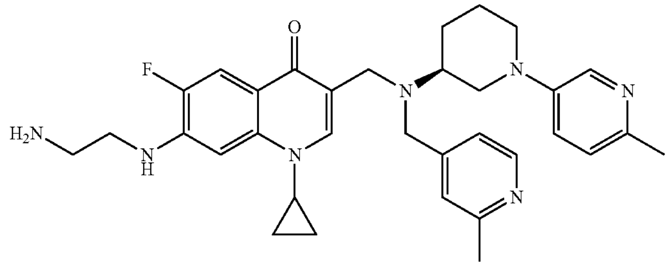

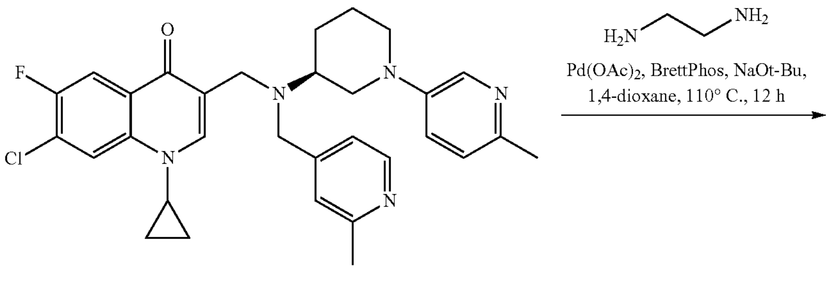

-continued

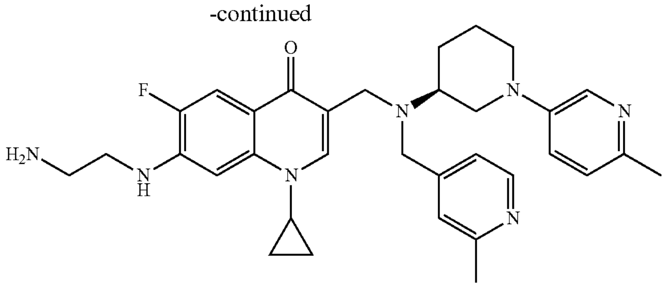

Preparation of 7-[(2-aminoethyl)amino]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.10 g, 1.0 eq.), ethylenediamine (0.017 mL, 1.4 eq.) and NaO t-Bu (0.025 g, 1.4 eq.) were dissolved in anh. 1,4-dioxane (3.0 mL). Air was removed, the vessel was backfilled with argon, $Pd(OAc)_2$ (0.004 g, 0.1 eq.) and BrettPhos (0.02 g, 0.2 eq.) were added and the reaction mixture was stirred under an inert atmosphere at 110° C. for 12 h. Next the mixture was diluted with EtOAc, filtered through Celite pad and concentrated in vacuo. The separation by FCC (SiHP; DCM:MeOH) afforded the product (0.07 g, yield 66%) as a beige solid. ESI-MS: 570.5 $[M+H]^+$. $^1H$ NMR (400 MHz, DMSO-$d_6$) δ 8.29 (d, J=5.0 Hz, 1H), 8.13 (d, J=2.9 Hz, 1H), 7.71 (s, 1H), 7.61 (d, J=12.3 Hz, 1H), 7.27-7.19 (m, 2H), 7.19-7.16 (m, 1H), 7.02 (d, J=8.5 Hz, 1H), 6.92 (d, J=7.5 Hz, 1H), 6.38-6.31 (m, 1H), 3.83-3.70 (m, 3H), 3.63-3.56 (m, 3H), 3.45-3.40 (m, 1H), 3.23-3.18 (m, 2H), 2.83 (t, J=6.3 Hz, 2H), 2.80-2.70 (m, 2H), 2.63-2.54 (m, 1H), 2.39 (s, 3H), 2.33 (s, 3H), 2.01-1.93 (m, 1H), 1.80-1.70 (m, 1H), 1.57-1.42 (m, 2H), 1.24-1.17 (m, 2H), 0.95-0.79 (m, 2H).

Example 9. 1-Cyclopropyl-7-{[2-(dimethylamino)ethyl]amino}-6-fluoro-3-({[(3S)-1-(6-methylpyridin-3-yl)piperidin-3-yl][(2-methylpyridin-4-yl)methyl]amino}methyl)-1,4-dihydroquinolin-4-one

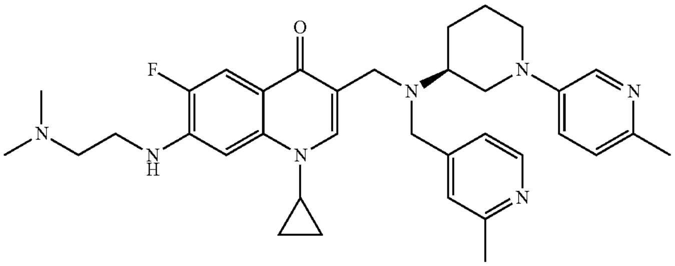

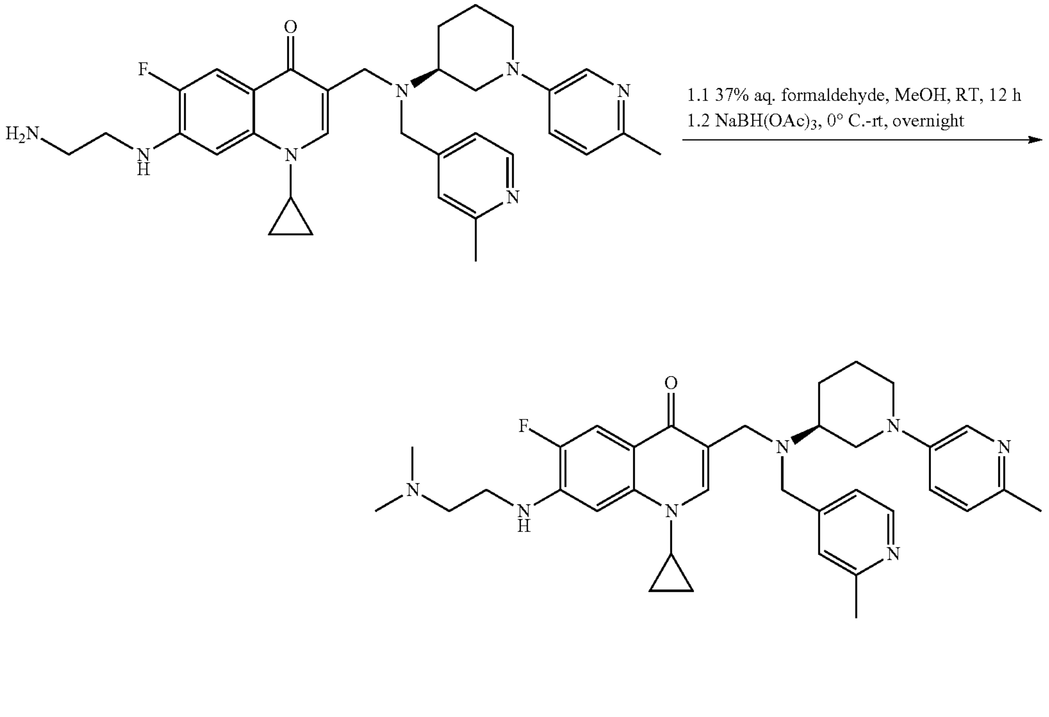

Preparation of 1-Cyclopropyl-7-{[2-(dimethylamino)ethyl]amino}-6-fluoro-3-({[(3S)-1-(6-methylpyridin-3-yl)piperidin-3-yl][(2-methylpyridin-4-yl)methyl]amino}methyl)-1,4-dihydroquinolin-4-one To a solution of 7-[(2-aminoethyl)amino]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Example 8) (0.048 g, 1.0 eq.) in anh. MeOH (5.0 mL) 37% aq. solution of formaldehyde (0.01 mL) was added. The mixture was stirred at RT for 12 h, then cooled to 0° C. $NaBH(OAc)_3$ (0.021 g, 1.2 eq.) was added and the reaction was continued overnight at RT. After that the mixture was concentrated under reduced pressure. Then saturated aqueous sodium bicarbonate solution was added and the product was extracted to ethyl acetate. The organic layer was washed with brine, dried over anh. $Na_2SO_4$ and concentrated under reduced pressure. The residue was purified by FCC (SiHP; DCM:MeOH:$NH_3$) to afford the product (0.015 g, yield 29%) as a pale yellow powder ESI-MS: 598.3 $[M+H]^+$. $^1H$ NMR (400 MHz, DMSO-$d_6$) δ 68.30 (d, J=5.1 Hz, 1H), 8.13 (d, J=3.0 Hz, 1H), 7.72 (s, 1H), 7.62 (d, 0.1=12.3 Hz, 1H), 7.23-7.19 (m, 2H), 7.19-7.15 (m, 1H), 7.04-7.00 (m, 1H), 6.94 (d, 0.1=7.4 Hz, 1H), 6.21-6.08 (m, 1H), 3.82-3.71 (m, 3H), 3.62-3.55 (m, 3H), 3.46-3.41 (m, 1H), 3.39-3.26 (m, 2H+HDO), 2.80-2.71 (m, 2H), 2.64-2.57 (m, 1H), 2.57-2.45 (m, 2H+DMSO), 2.39 (s, 3H), 2.33 (s, 3H), 2.22 (s, 6H), 2.02-1.93 (m, 1H), 1.79-1.72 (m, 1H), 1.58-1.44 (m, 2H), 1.25-1.13 (m, 2H), 0.92-0.82 (m, 2H).

Example 10. 7-(2-Aminoethoxy)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one

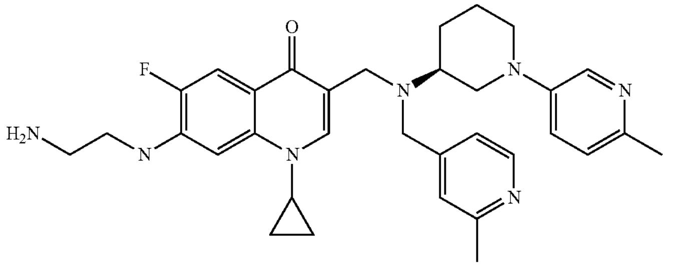

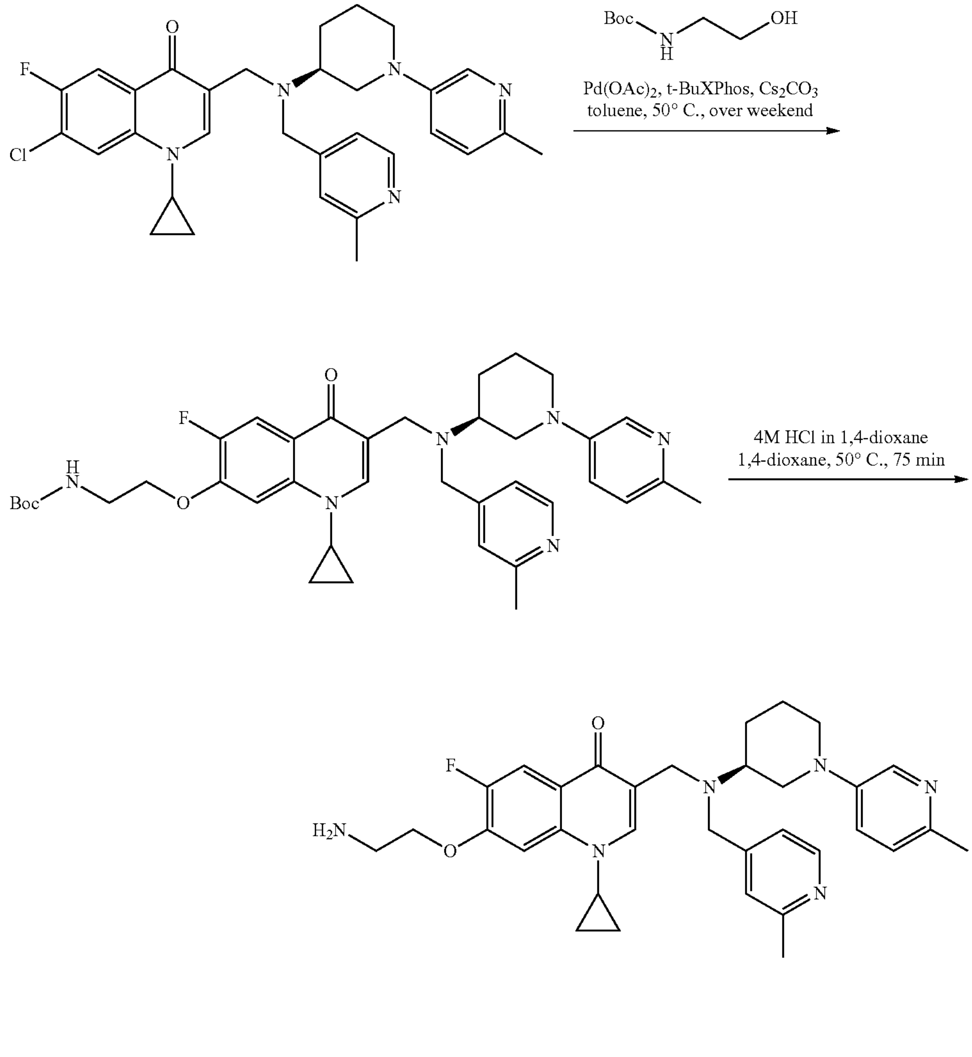

Preparation of tert-butyl N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl) carbamate Through a suspension of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.15 g, 1.0 eq.), tert-butyl N-(2-hydroxyethyl)carbamate (0.044 g, 1.0 eq.) and $Cs_2CO_3$ (0.134 g, 1.5 eq.) in anh. toluene (2.5 mL) argon was bubbled for 5 min. After that $Pd(OAc)_2$ (0.019 g, 0.3 eq.) and t-BuXPhos (0.07 g, 0.6 eq.) were added and the reaction was stirred under an inert atmosphere at 50° C. over weekend. Subsequently the mixture was filtered through Celite pad and concentrated in vacuo. The residue was partitioned between water and DCM. Organic layer was washed with brine, dried over anh. $Na_2SO_4$, filtered and solvents were evaporated. The residue was purified by FCC (SiHP; DCM: MeOH) to afford the product (0.097 g, yield 53%) as a pale yellow solid. ESI-MS: 671.8 $[M+H]^+$.

Preparation of 7-(2-aminoethoxy)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one To a solution of tert-butyl N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)carbamate (0.097 g, 1.0 eq.) in 1,4-dioxane (10.0 mL) was added 4M HCl in 1,4-dioxane (2.02 mL, 56.0 eq.) and the mixture was stirred at 50° C. for 75 min. Subsequently the reaction was poured into water and basified with 2N NaOH and extracted with DCM. Organic layer was dried over anh. $Na_2SO_4$, filtered and evaporated. The residue was purified by FCC (SiHP; DCM:MeOH). The compound was converted into HCl salt using 2M HCl in $Et_2O$ (0.058 mL, 1.0 eq.) and a mixture of MeOH (5.0 mL) and $H_2O$ (1.0 mL) as a solvent to provide the product (0.065 g, yield 76%) as a yellow solid. ESI-MS: 571.2 $[M+H]^+$. $^1H$ NMR (400 MHz, DMSO-$d_6$) δ 8.28 (d, J=5.0 Hz, 1H), 8.20-8.11 (m, 3H), 7.89-7.81 (m, 2H), 7.52 (d, J=7.2 Hz, 1H), 7.27-7.20 (m, 2H), 7.18-7.15 (m, 1H), 7.04 (d, J=8.5 Hz, 1H), 4.45 (t, J=5.0 Hz, 2H), 3.84-3.70 (m, 3H), 3.65-3.57 (m, 3H), 3.56-3.48 (m, 1H), 3.39-3.28 (m, 2H+HDO), 2.81-2.72 (m, 2H), 2.65-2.55 (m, 1H), 2.37 (s, 3H), 2.33 (s, 3H), 2.01-1.94 (m, 1H), 1.82-1.74 (m, 1H), 1.58-1.45 (m, 2H), 1.29-1.22 (m, 2H), 0.94-0.85 (m, 2H).

Example 11. 1-Cyclopropyl-6-fluoro-7-[2-(methylamino)ethoxy]-3-({[(3S)-1-(6-methylpyridin-3-yl)piperidin-3-yl][(2-methylpyridin-4-yl)methyl]amino}methyl)-1,4-dihydroquinolin-4-one hydrochloride

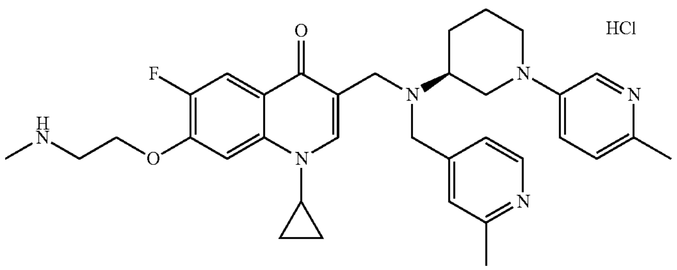

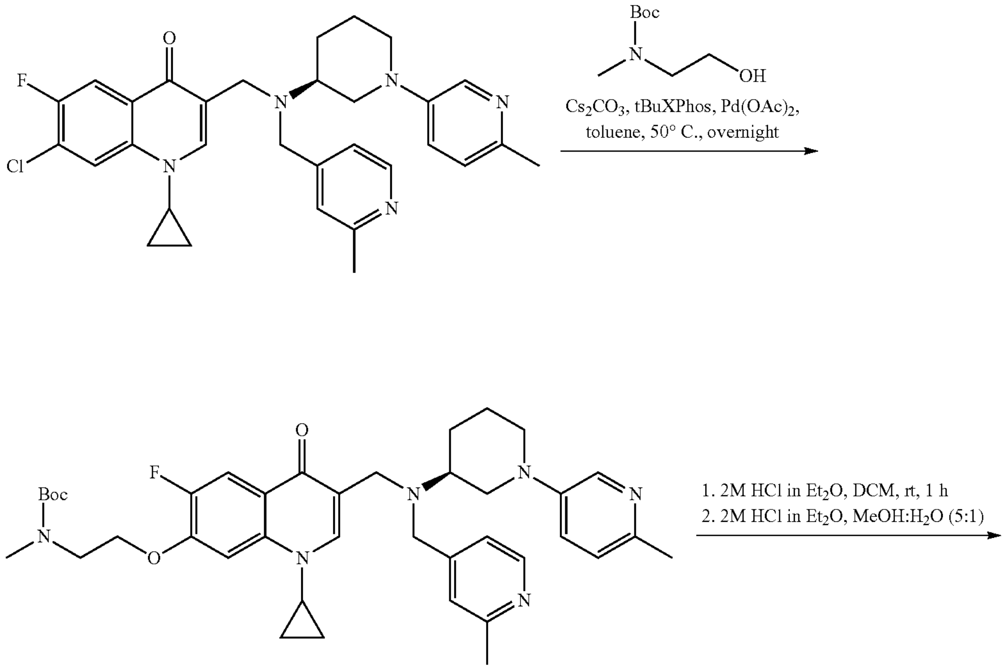

-continued

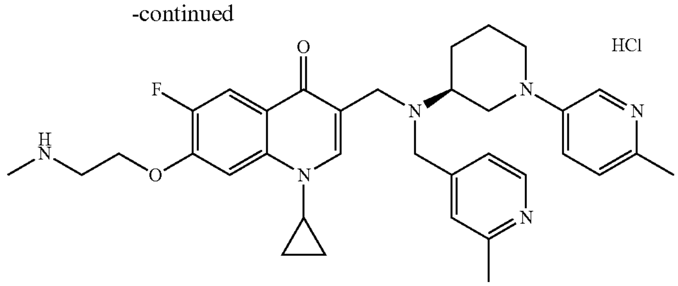

Preparation of tert-butyl N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)-N-methylcarbamate Through a suspension of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.12 g, 1.0 eq.), tert-butyl N-(2-hydroxyethyl)-N-methylcarbamate (0.039 g, 1.0 eq.) and $Cs_2CO_3$ (0.107 g, 1.5 eq.) in anh. toluene (2.0 mL) argon was bubbled for 5 min. After that tBuXPhos (0.056 g, 0.6 eq.) and $Pd(OAc)_2$ (0.015 g, 0.3 eq.) were added and the reaction mixture was stirred at 50° C. overnight. Subsequently the mixture was filtered through a pad of Celite. The filtrate was concentrated in vacuo and partitioned between water and DCM. The organic layer was washed with brine and dried over anh. $Na_2SO_4$, filtered and evaporated. The residue was purified by FCC (SiHP; DCM:MeOH) and re-purified by RP-FCC (C18HP; $H_2O$: MeCN) to provide the product (0.042 g, yield 28%) as a pale brown solid. ESI-MS: 685.9 $[M+H]^+$. $^1H$ NMR (300 MHz, DMSO-4) δ 8.28 (d, J=5.1 Hz, 1H), 8.12 (d, J=3.0 Hz, 1H), 7.85 (s, 1H), 7.79 (d, J=11.6 Hz, 1H), 7.62-7.41 (m, 1H), 7.30-7.07 (m, 3H), 7.02 (d, J=8.5 Hz, 1H), 4.45-4.25 (m, 2H), 3.91-3.71 (m, 3H), 3.71-3.47 (m, 6H), 2.99-2.83 (m, 3H), 2.78-2.68 (m, 2H), 2.66-2.54 (m, 2H), 2.37 (s, 3H), 2.32 (s, 3H), 2.04-1.87 (m, 1H), 1.85-1.68 (m, 1H), 1.62-1.43 (m, 2H), 1.43-1.18 (m, 10H), 1.02-0.76 (m, 2H).

Preparation of 1-cyclopropyl-6-fluoro-7-[2-(methylamino)ethoxy]-3-({[(3S)-1-(6-methylpyridin-3-yl)piperidin-3-yl][(2-methylpyridin-4-yl)methyl]amino}methyl)-1,4-dihydroquinolin-4-one Tert-butyl N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)-N-methylcarbamate (0.042 g, 1.0 eq.) was dissolved in DCM (4.0 mL) and 2M HCl in $Et_2O$ was added dropwise (1.07 mL, 35.0 eq.) and the mixture was stirred at RT for 1 h. Subsequently the reaction was poured into water and basified with 2N NaOH. The product was extracted to DCM. Organic layer was dried over $Na_2SO_4$, filtered and concentrated in vacuo. The residue was purified by FCC (SiHP; DCM:MeOH:$NH_3$). The compound was converted to HCl salt using 2M HCl in $Et_2O$ (0.027 mL, 1.0 eq.) and a mixture of MeOH (5.0 mL) and $H_2O$ (1.0 mL) as a solvent to provide the product (0.031 g, 0.050 mmol, yield 84%) as a yellow solid. ESI-MS: 585.2 $[M+H]^+$. $^1H$ NMR (400 MHz, DMSO-$d_6$) δ 8.28 (br m, 3H), 8.14 (d, J=2.9 Hz, 1H), 7.88-7.82 (m, 2H), 7.52 (d, J=7.2 Hz, 1H), 7.25-7.20 (m, 2H), 7.17 (d, J=5.3 Hz, 1H), 7.03 (d, J=8.5 Hz, 1H), 4.48 (t, J=5.0 Hz, 2H), 3.83-3.74 (m, 3H), 3.65-3.57 (m, 3H), 3.57-3.49 (m, 1H), 3.38 (t, J=5.0 Hz, 2H), 2.81-2.72 (m, 2H), 2.63 (s, 3H), 2.61-2.55 (m, 1H), 2.38 (s, 3H), 2.33 (s, 3H), 2.02-1.94 (m, 1H), 1.81-1.73 (m, 1H), 1.58-1.45 (m, 2H), 1.30-1.20 (m, 2H), 0.96-0.84 (m, 2H).

Example 12. 7-[(3R)-3-Aminopyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one hydrochloride

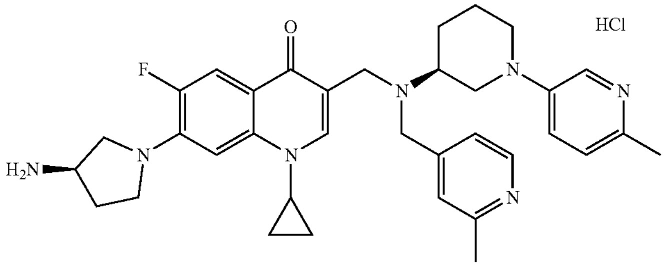

-continued

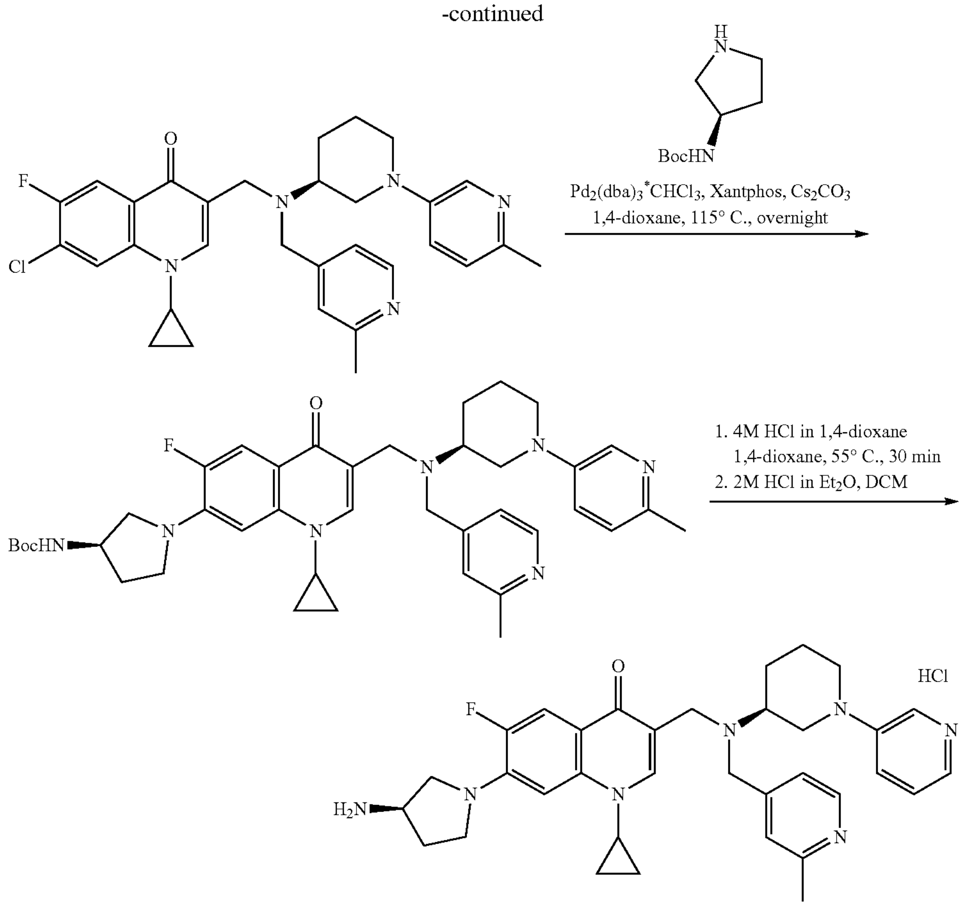

Preparation of tert-butyl N-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]carbamate Through a suspension of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.10 g, 1.0 eq.), tert-butyl N-[(3R)-pyrrolidin-3-yl]carbamate (0.051 g, 1.5 eq.) and $Cs_2CO_3$ (0.119 g, 2.0 eq.) in anh. 1,4-dioxane (2.7 mL) argon was bubbled for 5 min. After that $Pd_2(dba)_3$*$CHCl_3$ (0.038 g, 0.2 eq.) and Xantphos (0.032 g, 0.3 eq.) were added and the reaction mixture was stirred at 115° C. overnight. The reaction mixture was filtered through a pad of Celite, evaporated and purified by FCC (SiHP deactivated with $NH_3$:DCM; DCM:MeOH) to provide the product (0.13 g) as a yellow solid which was used in the next step without further purification. ESI-MS: 696.7 $[M+H]^+$.

Preparation of 7-[(3R)-3-aminopyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one hydrochloride To a solution of tert-butyl N-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]carbamate (0.13 g, 1.0 eq.) in 1,4-dioxane (3.5 mL) was added 4M HCl in 1,4-dioxane (3.0 mL) and the mixture was stirred at 55° C. for 30 min. Then the solvents were evaporated and the residue was partitioned between DCM and aq. solution of $NaHCO_3$. The aqueous layer was additionally extracted with DCM. The combined organic layers were dried over anh. $MgSO_4$, filtered and evaporated. The residue was purified by prep-HPLC ($H_2O$:MeCN:$NH_3$). The compound was converted to HCl salt using 2M HCl in $Et_2O$ (0.09 mL, 2.0 eq.) and DCM as a solvent (5.0 mL) to provide the product (0.06 g, yield 48%) as a pale yellow solid. ESI-MS: 596.3 $[M+H]^+$. $^1H$ NMR (400 MHz, Deuterium Oxide) δ 8.50-8.41 (m, 1H), 8.20-8.06 (m, 2H), 7.97 (dd, J=9.1, 3.0 Hz, 1H), 7.92-7.83 (m, 2H), 7.70-7.54 (m, 2H), 7.00 (d, J=7.5 Hz, 1H), 4.90-4.68 (m, 2H+$H_2O$), 4.65-4.44 (m, 2H), 4.23-4.11 (m, 1H), 4.06-3.80 (m, 5H), 3.79-3.70 (m, 1H), 3.69-3.60 (m, 1H), 3.60-3.46 (m, 2H), 3.33-3.21 (m, 1H), 2.57 (s, 3H), 2.55 (s, 3H), 2.54-2.45 (m, 1H), 2.44-2.32 (m, 1H), 2.32-2.19 (m, 2H), 2.18-2.06 (m, 1H), 1.96-1.79 (m, 1H), 1.43-1.25 (m, 2H), 1.12-0.88 (m, 2H).

Example 13. 7-[(3S)-3-Aminopyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one hydrochloride

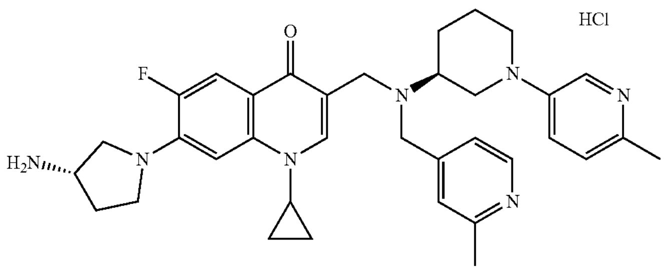

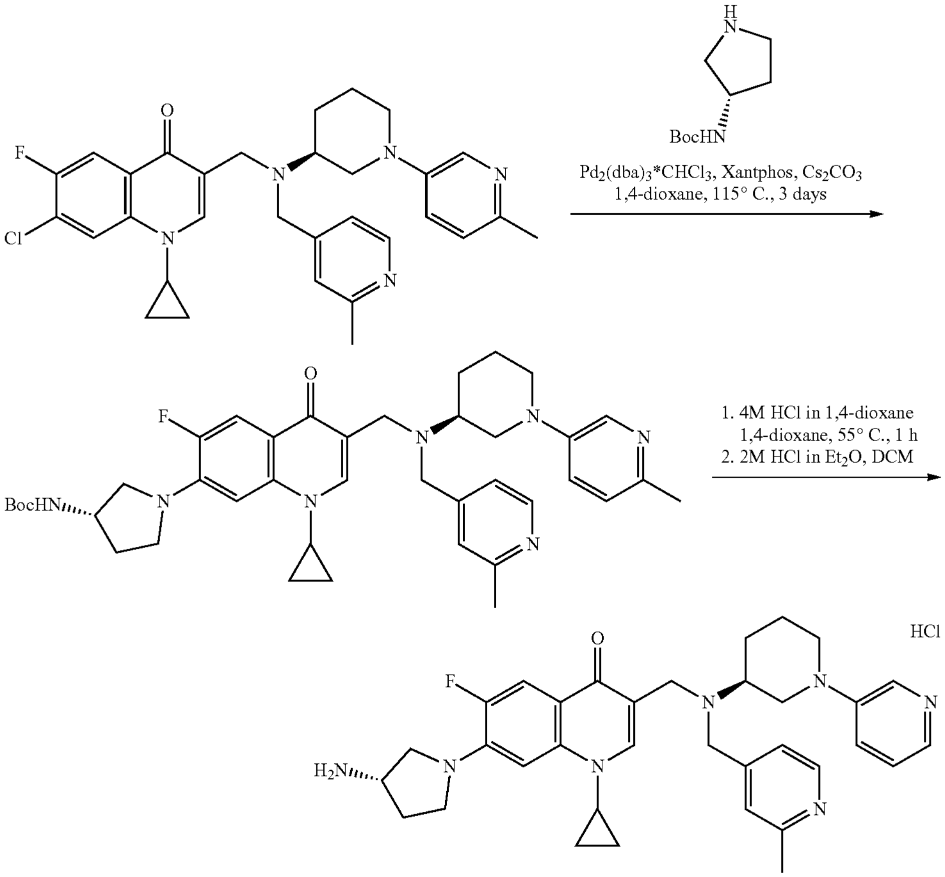

Preparation of tert-butyl N-[(3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]carbamate Through a suspension of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.10 g, 1.0 eq.), tert-butyl N-[(3S)-pyrrolidin-3-yl]carbamate (0.051 g, 1.5 eq.) and $Cs_2CO_3$ (0.119 g, 2.0 eq.) in anh. 1,4-dioxane (2.7 mL) argon was bubbled for 5 min. After that $Pd_2(dba)_3$ (0.034 g, 0.2 eq.) and Xantphos (0.032 g, 0.3 eq.) were added and the reaction mixture was stirred at 115° C. for 3 days. The reaction mixture was filtered through a pad of Celite, evaporated and purified by FCC (SiHP deactivated with $NH_3$: DCM; DCM:MeOH) to provide the product (0.10 g, yield 78%) as a yellow solid which was used in the next step without further purification. ESI-MS: 696.7 $[M+H]^+$.

Preparation of 7-[(3S)-3-aminopyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one hydrochloride To a solution of tert-butyl N-[(3S)-1-[1-cyclopropyl-6-fluoro-3-({[(3S)-1-(6-methylpyridin-3-yl)piperidin-3-yl]

[(2-methylpyridin-4-yl)methyl]amino}methyl)-4-oxo-1,4-dihydroquinolin-7-yl]pyrrolidin-3-yl]carbamate (0.10 g, 1.0 eq.) in 1,4-dioxane (2.7 mL) was added 4M HCl in 1,4-dioxane (3.0 mL) and the mixture was stirred at 55° C. for 1 h. Then the solvents were evaporated and the residue was partitioned between DCM and aq. solution of NaOH. The combined organic layers were dried over anh. $MgSO_4$, filtered and evaporated. The residue was purified by prep-HPLC ($H_2O$:MeCN:$NH_3$). The compound was converted to HCl salt using 2M HCl in $Et_2O$ (0.04 mL, 2.0 eq.) and DCM as a solvent (5.0 mL) to provide the product (0.024 g, yield 25%) as a pale yellow solid. ESI-MS: 596.3 $[M+H]^+$. $^1H$ NMR (400 MHz, $D_2O$) δ 8.39-8.33 (m, 1H), 8.05-8.00 (m, 2H), 7.87 (dd, J=9.1, 2.9 Hz, 1H), 7.81-7.77 (m, 2H), 7.54

(d, J=14.2 Hz, 1H), 7.50 (d, J=9.1 Hz, 1H), 6.91 (d, J=7.5 Hz, 1H), 4.79-4.61 (m, 2H+$H_2O$), 4.55-4.34 (m, 2H), 4.12-4.04 (m, 1H), 4.01-3.92 (m, 1H), 3.92-3.73 (m, 4H), 3.66-3.52 (m, 2H), 3.50-3.36 (m, 2H), 3.24-3.15 (m, 1H), 2.48 (s, 3H), 2.47 (s, 3H), 2.45-2.37 (m, 1H), 2.29-2.12 (m, 3H), 2.10-1.96 (m, 1H), 1.88-1.73 (m, 1H), 1.29-1.21 (m, 2H), 0.98-0.83 (m, 2H).

Example 14. 1-Cyclopropyl-6-fluoro-7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride

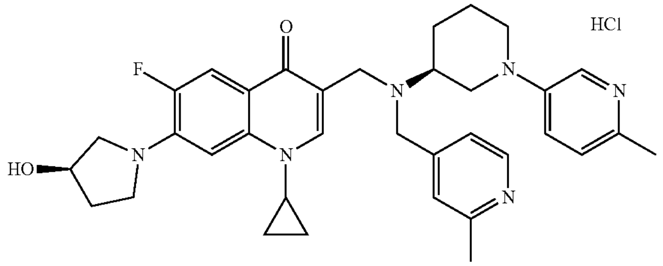

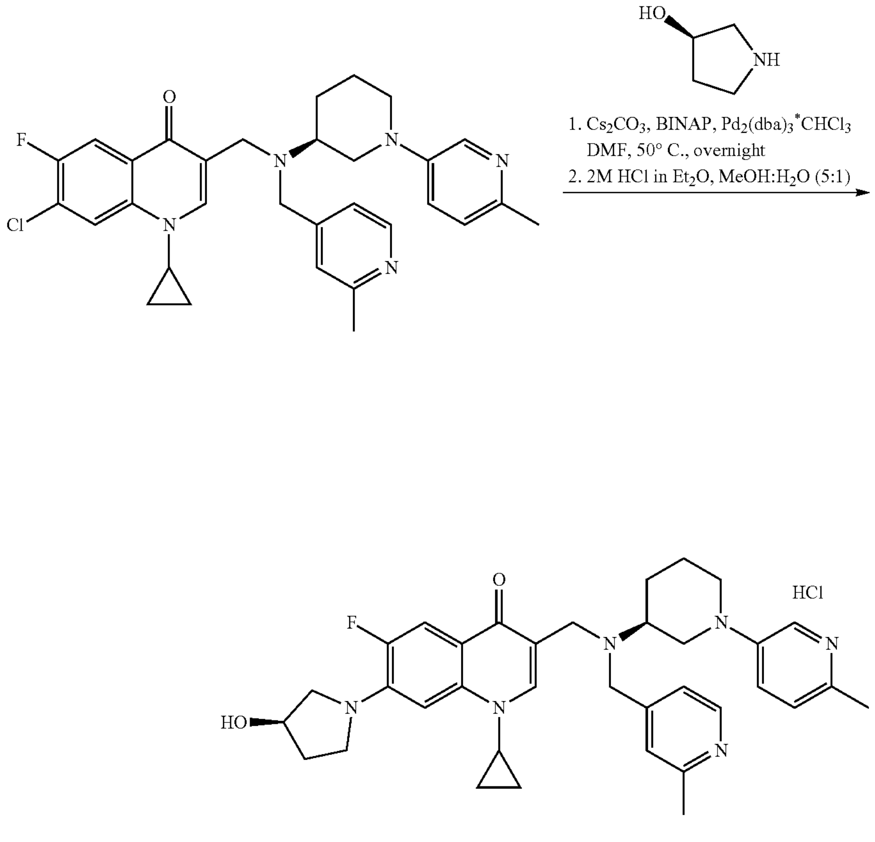

Preparation of 1-Cyclopropyl-6-fluoro-7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride Through a suspension of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.054 g, 1.0 eq.), (3R)-pyrrolidin-3-ol (0.026 g, 3.0 eq.), and $Cs_2CO_3$ (0.068 g, 2.1 eq.) in anh. DMF (3.0 mL) argon was bubbled for 5 min. After that $Pd_2(dba)_3$*$CHCl_3$ (0.020 g, 0.2 eq.) and BINAP (0.018 g, 0.3 eq.) were added and the reaction mixture was stirred at 115° C. overnight Subsequently the reaction mixture was combined with a mixture from a parallel reaction performed following the same protocol and starting from 0.030 g of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) and using corresponding equivalents of remaining reagents. The combined mixtures were filtered through a pad of Celite the pad was washed with DCM. The filtrate was concentrated in vacuo and the residue was purified by FCC (SiHP; DCM: MeOH), re-dissolved in DCM and stirred with MPA scavenger for 10 min. Subsequently the mixture was filtered, concentrated in vacuo and purified by prep-HPLC ($H_2O$:MeCN:$NH_3$). The compound was converted to HCl salt using 2M HCl in $Et_2O$ (0.044 mL, 1.05 eq.) and a mixture of MeOH (5.0 mL) and $H_2O$ (1.0 mL) as a solvent to provide the product (0.053 g, yield 56%) as a yellow solid. ESI-MS: 597.3 $[M+H]^+$. $^1H$ NMR (400 MHz, Pyridine-$d_5$) δ 8.63-8.59 (m, 1H), 8.57 (d, J=3.0 Hz, 1H), 8.42 (d, J=14.6 Hz, 1H), 7.94 (s, 1H), 7.42-7.36 (m, 2H), 7.33 (dd, J=8.5, 3.0 Hz, 1H), 7.06 (d, J=8.5 Hz, 1H), 6.83 (d, J=7.7 Hz, 1H), 4.75-4.70 (m, 1H), 4.20-4.12 (m, 1H), 4.08 (s, 2H), 3.94-3.75 (m, 5H), 3.57-3.46 (m, 2H), 3.28-3.20 (m, 1H), 3.19-3.11 (m, 1H), 2.93-2.83 (m, 1H), 2.59-2.47 (m, 7H), 2.23-2.03 (m, 3H), 1.73-1.64 (m, 1H), 1.60-1.48 (m, 2H), 1.13-1.03 (m, 2H), 0.97-0.89 (m, 2H).

Example 15. 7-[(3R)-3-(Aminomethyl)pyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one hydrochloride

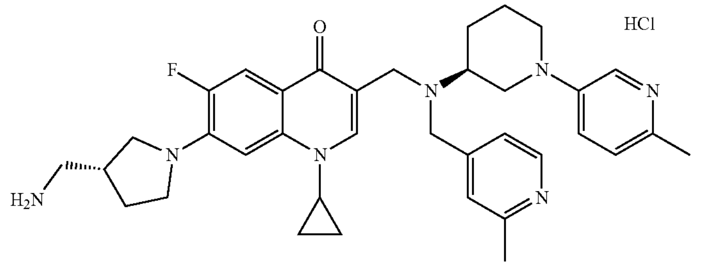

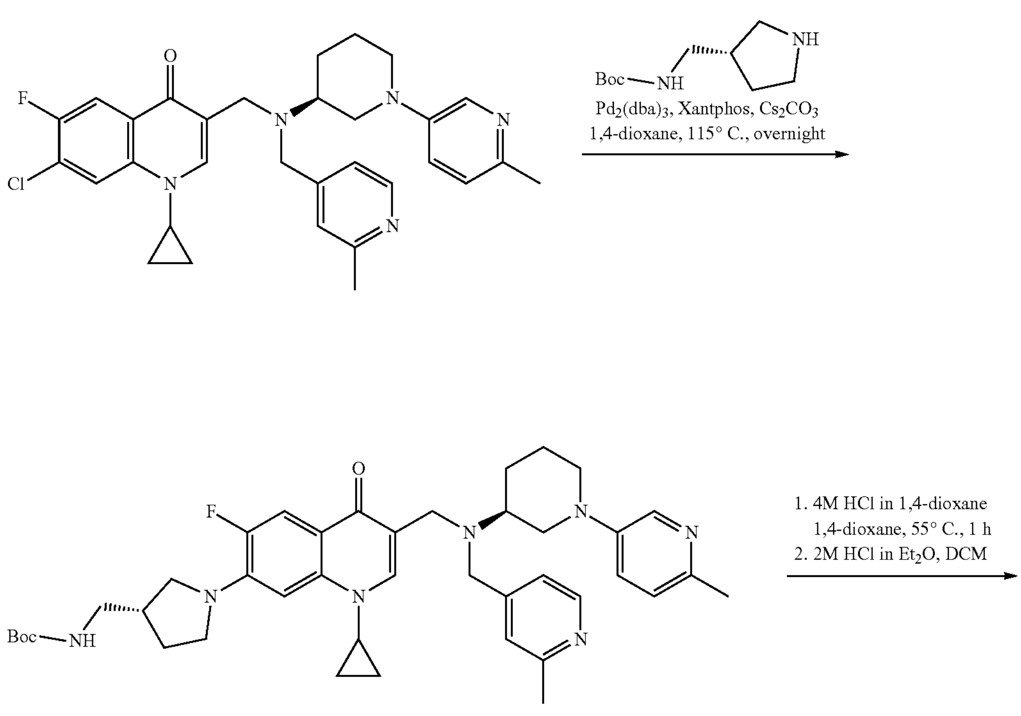

-continued

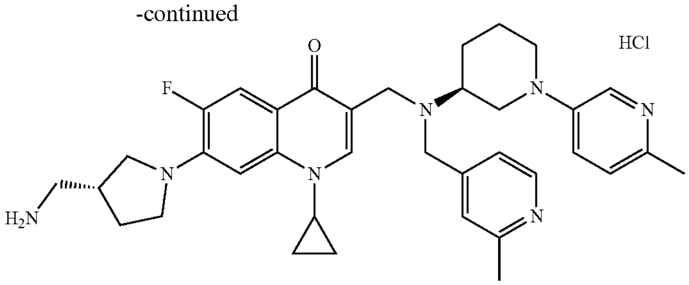

Preparation of tert-butyl N-{[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]methyl}carbamate Through a suspension of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.10 g, 1.0 eq.), tert-butyl N-{[(3S)-pyrrolidin-3-yl]methyl}carbamate (0.055 g, 1.5 eq.) and $Cs_2CO_3$ (0.119 g, 2.0 eq.) in anh. 1,4-dioxane (2.7 mL) argon was bubbled for 5 minutes. After that $Pd_2(dba)_3$ (0.034 g, 0.2 eq.) and Xantphos (0.032 g, 0.3 eq.) were added and the reaction mixture was stirred at 115° C. overnight. The mixture was filtered through a pad of Celite and purified by FCC (SiHP deactivated with $NH_3$:DCM; DCM:MeOH), triturated with $Et_2O$ and dried to provide the product (0.08 g, yield 61%) as a pale yellow solid. ESI-MS: 710.4 $[M+H]^+$. $^1$H NMR (400 MHz, DMSO-$d_6$) δ 68.28 (d, J=5.1 Hz, 1H), 8.12 (d, J=3.0 Hz, 1H), 7.72 (s, 1H), 7.62 (d, J=14.6 Hz, 1H), 7.25-7.17 (m, 2H), 7.20-7.13 (m, 1H), 7.08-6.98 (m, 2H), 6.84 (d, J=7.7 Hz, 1H), 3.84-3.69 (m, 3H), 3.62-3.45 (m, 6H), 3.45-3.35 (m, 1H), 3.29-3.20 (m, 1H), 3.08-2.98 (m, 2H), 2.79-2.68 (m, 2H), 2.63-2.53 (m, 1H), 2.38 (s, 4H), 2.32 (s, 3H), 2.10-1.90 (m, 2H), 1.81-1.64 (m, 2H), 1.58-1.43 (m, 2H), 1.38 (s, 9H), 1.21-1.15 (m, 2H), 0.92-0.78 (m, 2H).

Preparation of 7-[(3R)-3-(aminomethyl)pyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one hydrochloride To a solution of tert-butyl N-{[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]methyl}carbamate (0.057 g, 1.0 eq.) in 1,4-dioxane (1.5 mL) was added 4M HCl in 1,4-dioxane (1.0 mL) and the mixture was stirred at 55° C. for 1 h. Then 7N $NH_3$ in MeOH was added and the solvents were evaporated. The residue was purified by prep-HPLC ($H_2O$:MeCN $NH_3$). The compound was converted to HCl salt using 2M HCl in $Et_2O$ (0.07 mL, 2.0 eq.) and DCM as a solvent (5.0 mL) to provide the product (0.045 g, yield 81%) as a pale yellow solid. ESI-MS: 610.3 $[M+H]^+$. $^1$H NMR (400 MHz, Deuterium Oxide) δ 8.41-8.37 (m, 1H), 8.02-7.98 (m, 2H), 7.85 (dd, J=9.1, 2.9 Hz, 1H), 7.83-7.79 (m, 2H), 7.48 (dd, J=11.6, 2.6 Hz, 2H), 6.85-6.77 (m, 1H), 4.83-4.62 (m, 43H), 4.56-4.35 (m, 2H), 3.91-3.77 (m, 3H), 3.74-3.65 (m, 1H), 3.65-3.56 (m, 2H), 3.48-3.33 (m, 3H), 3.31-3.19 (m, 1H), 3.17-3.03 (m, 2H), 2.71-2.57 (m, 1H), 2.49 (s, 3H), 2.47 (s, 3H), 2.30-2.18 (m, 3H), 2.09-1.97 (m, 1H), 1.88-1.73 (m, 2H), 1.28-1.20 (m, 2H), 0.98-0.83 (m, 2H).

Example 16. 7-[(3S)-3-Aminopiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one

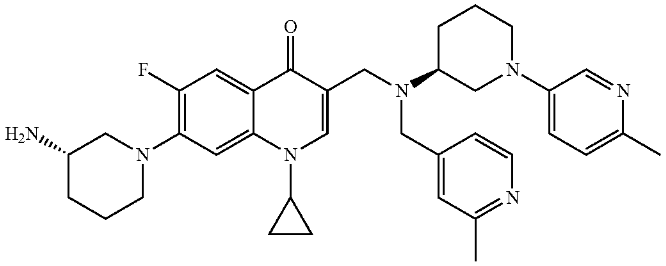

-continued

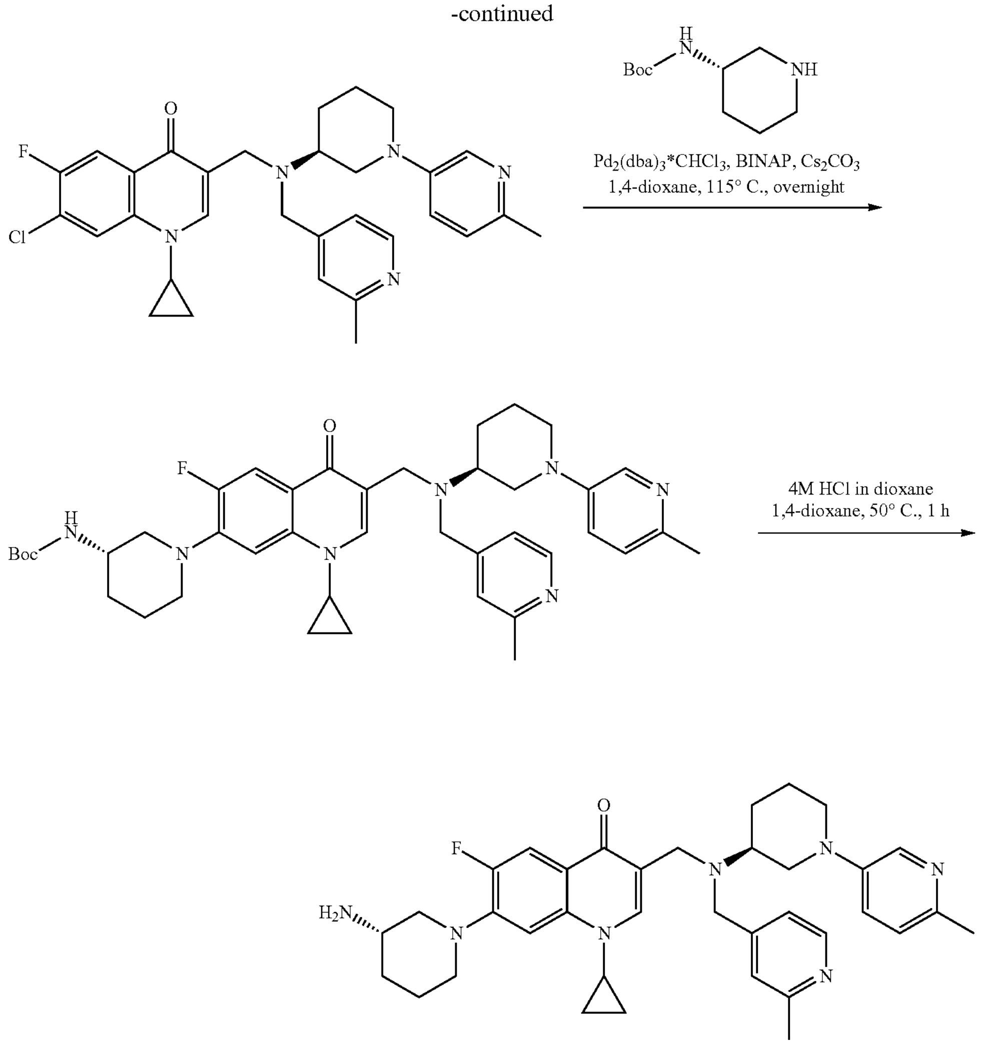

Preparation of tert-butyl N-[(3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl]carbamate A reaction vessel was charged with 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.050 g, 1.0 eq.), tert-butyl N-[(3S)-piperidin-3-yl]carbamate (0.037 g, 2.0 eq.), $Cs_2CO_3$ (0.063 g, 2.1 eq.), $Pd_2(dba)_3$*$CHCl_3$ (0.019 g, 0.2 eq.) and BINAP (0.017 g, 0.3 eq.). Next the vessel was capped, air was removed and the vessel was filled with argon. Then anh. DMF (2.0 mL) was added and the reaction mixture was stirred at 115° C. overnight. The mixture was filtered through a pad of Celite and purified by FCC (SiHP; DCM:MeOH) and repurified by prep-HPLC ($H_2O$:MeCN: $NH_3$) to afford the product (0.041 g, yield 59%) as a white solid. ESI-MS: 710.6 $[M+H]^+$.

Preparation of 7-[(3S)-3-aminopiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one To a solution of tert-butyl N-[(3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl]carbamate (0.041 g, 1.0 eq.) in 1,4-dioxane (3.0 mL) was added 4M HCl in 1,4-dioxane (2.0 mL) and the mixture was stirred at 50° C. for 1 h. Then the solvents were evaporated. The residue was suspended in water, basified with 2M aq. solution of NaOH, evaporated, purified by prep-HPLC ($H_2O$:MeCN:$NH_3$) and re-purified by FCC (C18HP; $H_2O$:MeCN) to provide the product (0.010 g, yield 28%) as a light yellow solid. ESI-MS: 610.3 $[M+H]^+$. $^1H$ NMR (400 MHz, MeOD-$d_4$) δ 8.17 (d, J=5.1 Hz, 1H), 8.10 (d, J=3.0 Hz, 1H), 7.93 (s, 1H), 7.84 (d, J=13.4 Hz, 1H), 7.43 (d, J=7.4 Hz, 1H), 7.36 (dd, J=8.6, 3.0 Hz, 1H), 7.27-7.20 (m, 2H), 7.13 (d, J=8.6 Hz, 1H), 3.92-3.84 (m, 3H), 3.82-3.78 (m, 2H), 3.65-3.55 (m, 2H), 3.51-3.42 (m, 2H), 3.21-3.11 (m, 1H), 3.08-2.93 (m, 2H), 2.93-2.81 (m, 2H), 2.75-2.66 (m, 1H), 2.42 (s, 3H), 2.35 (s, 3H), 2.20-2.10 (m, 1H), 2.08-2.00 (m, 1H), 2.00-1.87 (m, 2H), 1.87-1.75 (m, 1H), 1.75-1.59 (m, 2H), 1.56-1.43 (m, 1H), 1.35-1.25 (m, 2H), 0.99-0.88 (m, 2H).

Example 17. 7-[(3R)-3-Aminopiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one

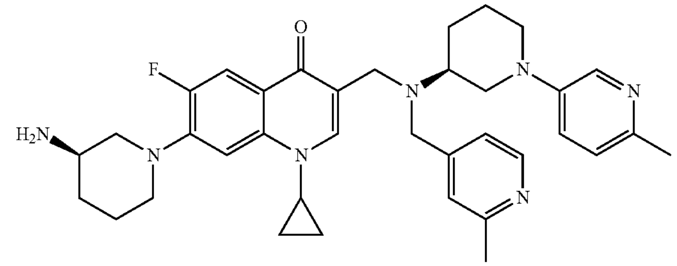

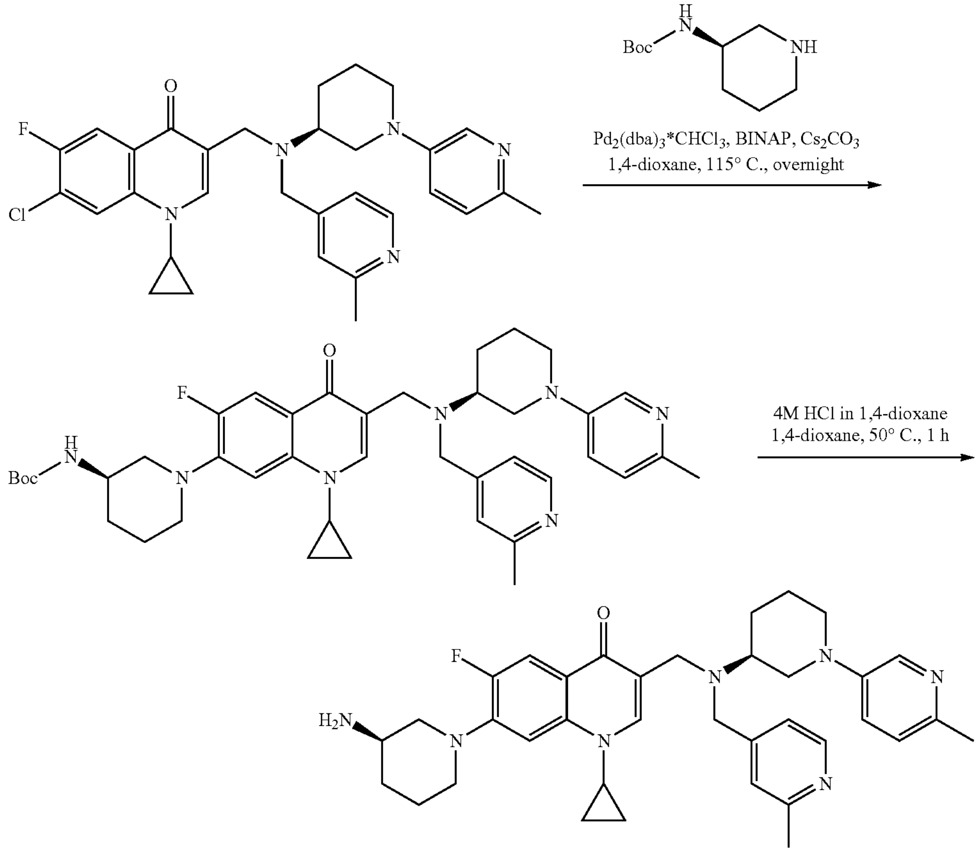

Preparation of tert-butyl N-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl]carbamate A reaction vessel was charged with 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.10 g, 1.0 eq.), tert-butyl N-[(3R)-piperidin-3-yl]carbamate (0.073 g, 2.0 eq.), $Cs_2CO_3$ (0.125 g, 2.1 eq.), $Pd_2(dba)_3$*$CHCl_3$ (0.038 g, 0.2 eq.) and BINAP (0.034 g, 0.3 eq.). Next the vessel was capped, air was removed and the vessel was filled with argon. Then anh. DMF (3.0 mL) was added and the reaction mixture was stirred at 115° C. overnight. The mixture was filtered through a pad of Celite and the pad was washed with DCM. The filtrate was evaporated and the residue was purified by FCC (SiHP; DCM:MeOH) and re-purified by prep-HPLC ($H_2O$:MeCN:$NH_3$) to afford the product (0.052 g, yield 38%) as a white powder. ESI-MS: 710.6 $[M+H]^+$.

Preparation of 7-[(3R)-3-aminopiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one To a solution of tert-butyl N-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl]carbamate (0.052 g, 1.0 eq.) in 1,4-dioxane (3.0 mL) was added 4M HCl in 1,4- dioxane (2.0 mL) and the mixture was stirred at 50° C. for 1 h. Then the solvents were evaporated. The residue was suspended in water, basified with 2M aq. solution of NaOH, evaporated, purified by prep-HPLC ($H_2O$:MeCN:$NH_3$) and re-purified by RP-FCC (C18HP; $H_2O$:MeCN) to provide the product (0.01 g, yield 22%) as a white solid. ESI-MS: 610.3 $[M+H]^+$. $^1H$ NMR (400 MHz, Methanol-$d_4$) δ 8.17 (d, J=5.1 Hz, 1H), 8.10 (d, J=3.0 Hz, 1H), 7.93 (s, 1H), 7.85 (d, J=13.4 Hz, 1H), 7.44 (d, J=7.4 Hz, 1H), 7.37 (dd, J=8.6, 3.0 Hz, 1H), 7.26-7.21 (m, 2H), 7.13 (d, J=8.6 Hz, 1H), 3.93-3.82 (m, 3H), 3.81 (s, 2H), 3.65-3.54 (m, 2H), 3.52-3.38 (m, 2H), 3.30-3.22 (m, 1H), 3.13-3.05 (m, 1H), 3.03-2.94 (m, 2H), 2.86 (t, J=11.1 Hz, 1H), 2.75-2.67 (m, 1H), 2.42 (s, 3H), 2.34 (s, 3H), 2.19-2.10 (m, 1H), 2.10-1.92 (m, 3H), 1.91-1.76 (m, 1H), 1.75-1.53 (m, 3H), 1.35-1.27 (m, 2H), 0.98-0.88 (m, 2H).

Example 18. 1-(2-Aminoethyl)-3-({[(3S)-1-(6-methylpyridin-3-yl)piperidin-3-yl][(2-methylpyridin-4-yl)methyl]amino}methyl)-1,4-dihydroquinolin-4-one

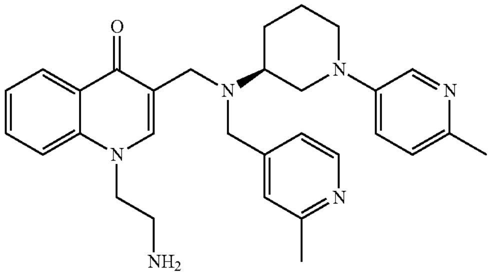

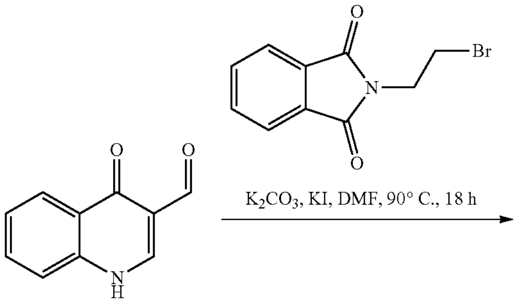

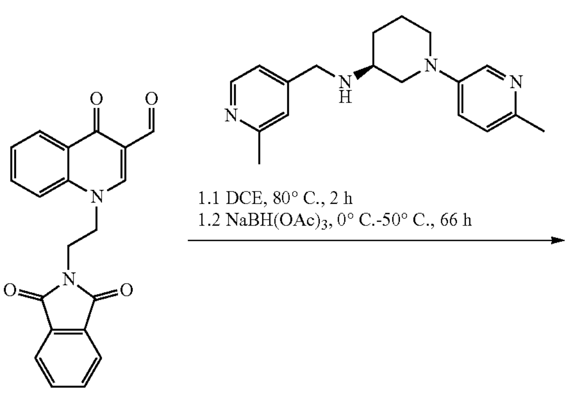

-continued

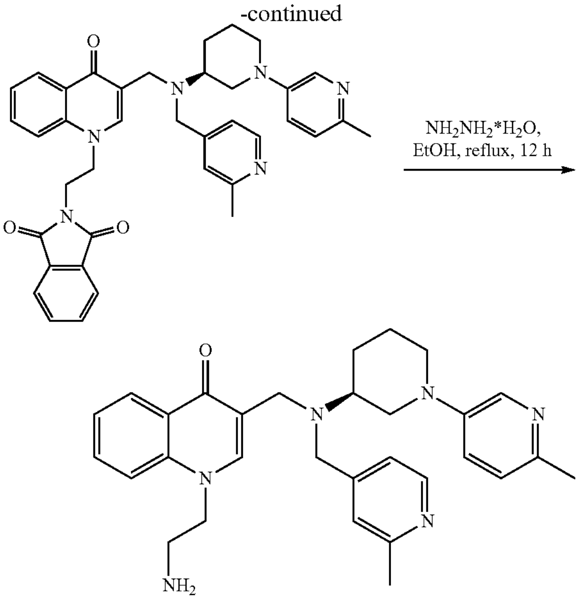

Preparation of 1-[2-(1,3-dioxo-2,3-dihydro-1H-isoindol-2-yl)ethyl]-4-oxo-1,4-dihydroquinoline-3-carbaldehyde To a mixture of 4-oxo-1,4-dihydroquinoline-3-carbaldehyde (Intermediate 1) (0.050 g, 1.0 eq.), $K_2CO_3$ (0.112 g, 2.8 eq.) and DMF (3.0 mL) under nitrogen atmosphere were added 2-(2-bromoethyl)-2,3-dihydro-1H-isoindole-1,3-dione (0.205 g, 2.8 eq.) and KI (0.134 g, 2.8 eq.). The reaction mixture was heated at 90° C. for 18 h. Then the reaction was quenched with addition of $H_2O$ and aq. solution of sodium bicarbonate and the mixture with DCM. The combined organic layers were washed with brine, dried over anh. $Na_2SO_4$ and concentrated in vacuo. The residue was purified by FCC (SiHP; DCM:MeOH) to afford the product (0.050 g, yield 17%) as a white powder. ESI-MS: 347.5 $[M+H]^+$. $^1H$ NMR (400 MHz, DMSO-$d_6$) δ 10.07 (s, 1H), 8.54 (s, 1H), 8.31 (dd, J=8.0, 1.6 Hz, 1H), 7.96 (d, J=8.5 Hz, 1H), 7.86-7.81 (m, 5H), 7.54 (ddd, J=8.0, 7.0, 0.9 Hz, 1H), 4.74-4.67 (m, 2H), 4.03-3.98 (m, 2H).

Preparation of 2-{2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]ethyl}-2,3-dihydro-1H-isoindole-1,3-dione A dry reactor vessel was charged with 1-[2-(1,3-dioxo-2,3-dihydro-1H-isoindol-2-yl)ethyl]-4-oxo-1,4-dihydroquinoline-3-carbaldehyde (0.045 g, 1.0 eq.), (3S)-1-(6-methylpyridin-3-yl)-N-[(2-methylpyridin-4-yl)methyl]piperidin-3-amine (Intermediate 2) (0.039 g, 1.0 eq.) and anh. DCE (6.0 mL). The reaction was carried out at 80° C. for 2 h, then cooled to 0° C. and then $NaBH(OAc)_3$ (0.039 g, 1.4 eq.) was added. The reaction was continued for 48 h at RT. Additional portion of $NaBH(OAc)_3$ (0.028 g, 1.0 eq.) was added and the reaction was stirred for 6 h at RT, and then at 50° C. for 12 h. Subsequently the reaction was quenched with addition of $H_2O$ and aq. solution of sodium bicarbonate and the mixture was extracted with DCM. The combined organic layers were washed with brine, dried over anh. $Na_2SO_4$ and concentrated in vacuo. The residue was purified by FCC (SiHP; DCM:

MeOH) to afford the product (0.035 g, yield 42%) as a yellow solid. ESI-MS: 627.7 [M+H]. $^1H$ NMR (400 MHz, DMSO-$d_6$) δ 8.25 (d, J=5.0 Hz, 1H), 8.20 (dd, J=8.1, 1.6 Hz, 1H), 8.09 (d, J=2.9 Hz, 1H), 7.86 (s, 1H), 7.81 (d, J=8.7 Hz, 1H), 7.75-7.67 (m, 5H), 7.38-7.33 (m, 1H), 7.15 (dd, J=8.6, 3.0 Hz, 1H), 7.11 (s, 1H), 7.10-7.07 (m, 1H), 7.00 (d, J=8.5 Hz, 1H), 4.66-4.51 (m, 2H), 4.00-3.92 (m, 2H), 3.76-3.65 (m, 1H), 3.59-3.43 (m, 5H), 2.63-2.53 (m, 2H), 2.42 (s, 3H), 2.32 (s, 3H), 1.73-1.57 (m, 2H), 1.38-1.25 (m, 3H).

Preparation of 1-(2-aminoethyl)-3-({[(3S)-1-(6-methylpyridin-3-yl)piperidin-3-yl][(2-methylpyridin-4-yl)methyl]amino}methyl)-1,4-dihydroquinolin-4-one To a solution of 2-{2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]ethyl}-2,3-dihydro-1H-isoindole-1,3-dione (0.03 g, 1.0 eq.) in absolute EtOH (5.0 mL) was added hydrazine monohydrate (0.005 g, 2.0 eq.) and the mixture was stirred at reflux for 12 h under argon atmosphere. The mixture was concentrated in vacuo and the residue was purified by RP-FCC (C18HP; $H_2O$: MeCN) to afford the product (0.018 g, yield 74%) as a yellow powder. ESI-MS: 497.5 $[M+H]^+$. $^1H$ NMR (400 MHz, DMSO-$d_6$) δ 8.29 (d, J=5.0 Hz, 1H), 8.20 (dd, J=8.1, 1.6 Hz, 1H), 8.14 (d, J=3.0 Hz, 1H), 8.05 (s, 1H), 7.74 (d, J=8.6 Hz, 1H), 7.68 (ddd, J=8.6, 6.8, 1.7 Hz, 1H), 7.34 (ddd, J=7.9, 6.8, 1.0 Hz, 1H), 7.27-7.19 (m, 3H), 7.01 (d, J=8.5 Hz, 1H), 4.29-4.18 (m, 2H), 3.90-3.72 (m, 3H), 3.66-3.56 (m, 3H), 2.91-2.83 (m, 2H), 2.81-2.71 (m, 2H), 2.62-2.53 (m, 2H), 2.39 (s, 3H), 2.32 (s, 3H), 2.04-1.97 (m, 1H), 1.81-1.40 (m, 4H).

Example 19. 1-cyclopropyl-6-fluoro-7-[4-(methylamino)piperidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride

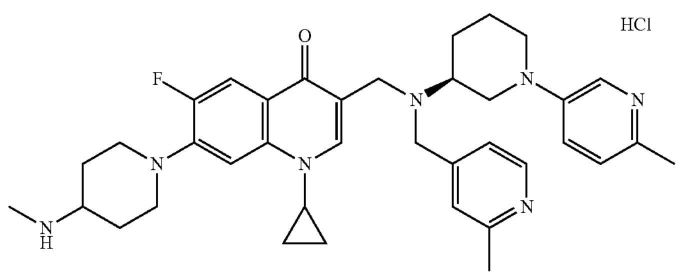

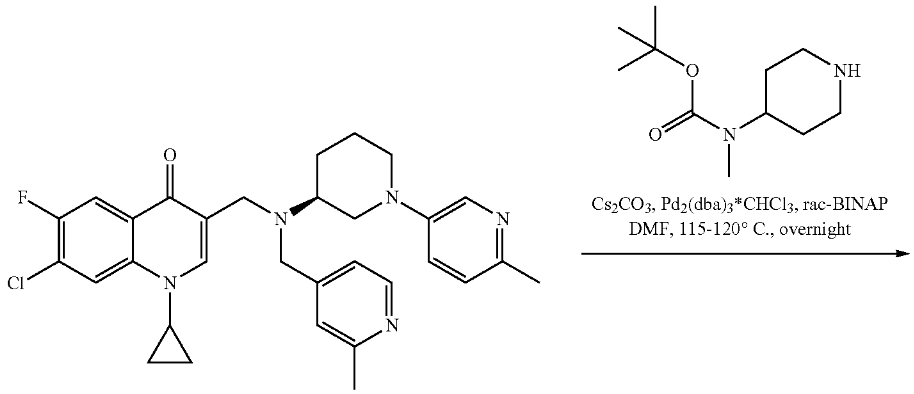

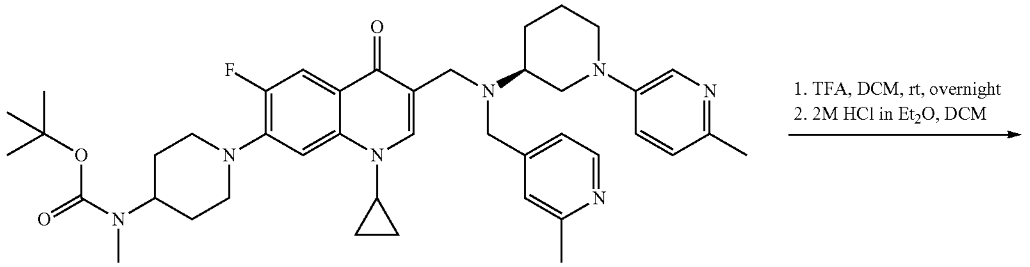

-continued

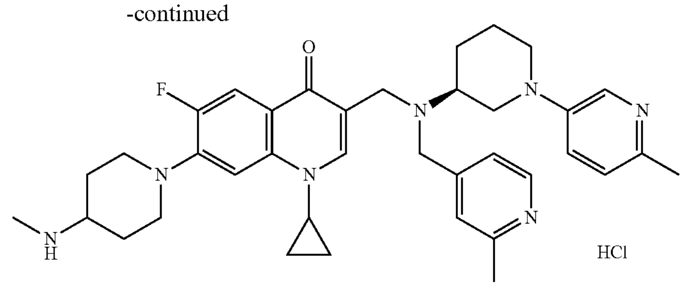

Preparation of tert-butyl N-{1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-4-yl}-N-methylcarbamate A pressure vessel was charged with 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.12 g, 1.0 eq.), tert-butyl N-methyl-N-(piperidin-4-yl)carbamate (0.094 g, 2.0 eq.), $Cs_2CO_3$ (0.15 g, 2.1 eq.) and DMF (2.0 mL). The resulting mixture was purged with argon for 5 min. Then, BINAP (0.041 g, 0.3 eq.) and $Pd_2(dba)_3$*$CHCl_3$ (0.023 g, 0.1 eq.) were added and the reaction mixture was stirred overnight at 120° C. The mixture was then filtered through a pad of Celite and concentrated in vacuo. The residue was purified by FCC (SiHP, DCM:MeOH) to give the product (0.14 g, 83% yield) as a yellow oil. ESI-MS: 724.8 $[M+H]^+$.

Preparation of 1-cyclopropyl-6-fluoro-7-[4-(methylamino)piperidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride Tert-butyl N-{1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-4-yl}-N-methyl-carbamate (0.14 g, 1.0 eq.) was dissolved in DCM (5.0 mL) and TFA (1.0 mL) was added. The reaction mixture was stirred overnight at RT. Then, the mixture was concentrated in vacuo. To the residue, water was added followed by saturated aq. solution of $NaHCO_3$ and the resulting mixture was washed with DCM. The organic layer was dried over anh. $Na_2SO_4$, filtered and concentrated in vacuo. The residue was purified by prep-HPLC ($H_2O$:MeCN:$NH_3$) and re-purified by prep-HPLC ($H_2O$:MeCN:TFA). The obtained sample was dissolved in DCM, washed with saturated aq. solution of $NaHCO_3$, dried over anh. $Na_2SO_4$, filtered and concentrated in vacuo. The compound was converted to the HCl salt using 2 M HCl in $Et_2O$ (0.3 mL, 1.0 eq. to FB) and DCM as a solvent (5.0 mL) to give the product (0.038 g, 29% yield) as a yellow solid. ESI-MS: 624.4 $[M+H]^+$. $^1H$ NMR (400 MHz, DMSO-$d_6$) δ 8.28 (d, J=4.9 Hz, 1H), 8.12 (d, J=2.9 Hz, 1H), 7.82 (s, 1H), 7.71 (d, J=13.4 Hz, 1H), 7.34 (d, J=7.5 Hz, 1H), 7.23-7.19 (m, 2H), 7.18-7.15 (m, 1H), 7.02 (d, J=8.6 Hz, 1H), 3.82-3.69 (m, 3H), 3.66-3.55 (m, 5H), 3.51-3.45 (m, 1H), 3.07-2.96 (m, 1H), 2.91-2.81 (m, 2H), 2.79-2.69 (m, 2H), 2.62-2.55 (m, 1H), 2.52 (s, 3H), 2.37 (s, 3H), 2.32 (s, 3H), 2.12-2.07 (m, 2H), 1.99-1.92 (m, 1H), 1.79-1.73 (m, 1H), 1.70-1.60 (m, 2H), 1.55-1.44 (m, 2H), 1.24-1.16 (m, 2H), 0.95-0.83 (m, 2H).

Example 20. 7-[(3S)-3-(aminomethyl)pyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one hydrochloride

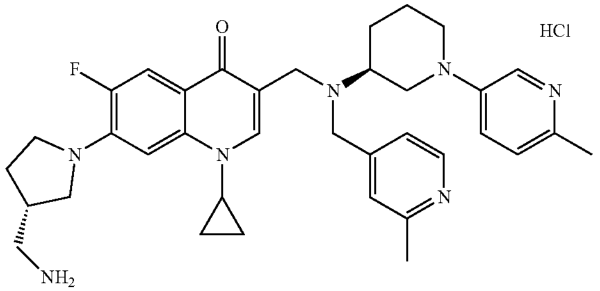

-continued

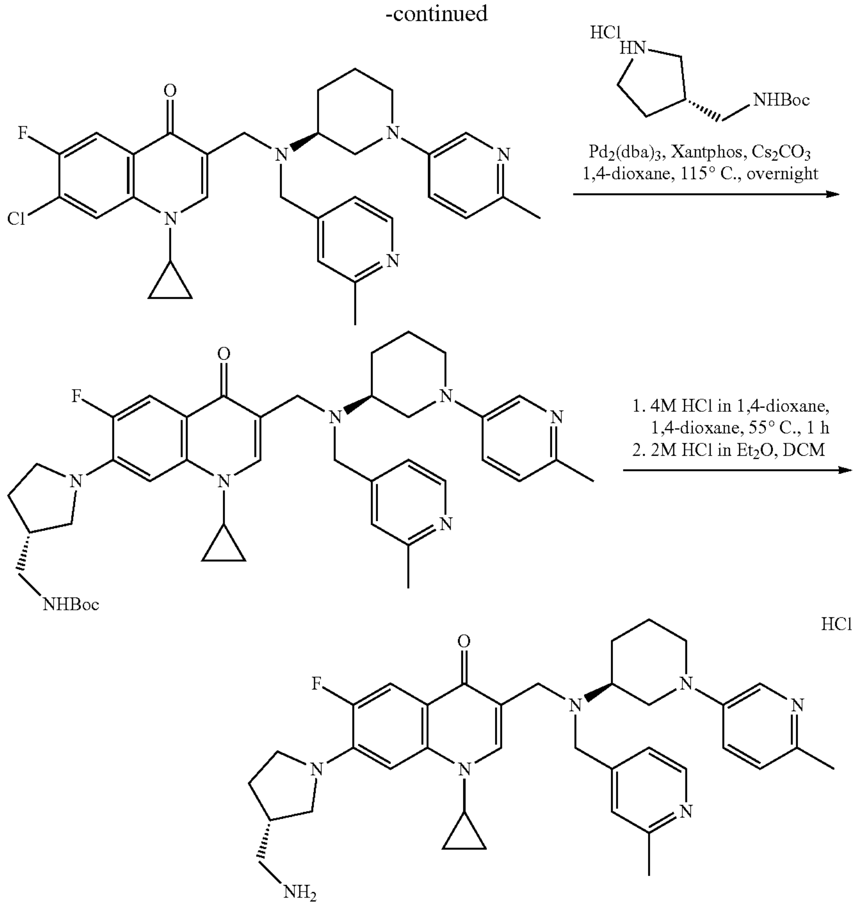

Preparation of tert-butyl N-{[(3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]methyl}carbamate 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.13 g, 1.0 eq.), tert-butyl N-{[(3R)-pyrrolidin-3-yl]methyl}carbamate hydrochloride (0.085 g, 1.5 eq.) and $Cs_2CO_3$ (0.248 g, 3.2 eq.) were suspended in anh. 1,4-dioxane (3.5 mL) and the mixture was purged with argon. Under inert atmosphere, $Pd_2(dba)_3$ (0.044 g, 0.2 eq.) and Xantphos (0.041 g, 0.3 eq.) were added and the reaction mixture was stirred overnight at 115° C. Subsequently, the mixture was cooled to ambient temperature and filtered through a pad of celite. The filtrate was concentrated in vacuo and the residue was purified by FCC (SiHP; DCM:MeOH) and re-purified by RP-FCC (C18HP; MeCN:$H_2O$) to afford (0.1 g, 59% yield) as a white solid. ESI-MS: 710.4 $[M+H]^+$. $^1H$ NMR (400 MHz, DMSO-$d_6$) δ 8.28 (d, J=5.0 Hz, 1H), 8.12 (d, J=3.0 Hz, 1H), 7.72 (s, 1H), 7.62 (d, J=14.6 Hz, 1H), 7.25-7.13 (m, 3H), 7.07-6.97 (m, 2H), 6.84 (d, J=7.8 Hz, 1H), 3.83-3.67 (m, 3H), 3.63-3.44 (m, 6H), 3.43-3.35 (m, 1H), 3.28-3.21 (m, 1H), 3.11-2.96 (m, 2H), 2.81-2.68 (m, 2H), 2.63-2.53 (m, 1H), 2.44-2.35 (m, 4H), 2.32 (s, 3H), 2.06-1.91 (m, 2H), 1.80-1.65 (m, 2H), 1.58-1.42 (m, 2H), 1.38 (s, 9H), 1.21-1.13 (m, 2H), 0.92-0.76 (m, 2H).

Preparation of 7-[(3S)-3-(aminomethyl)pyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one hydrochloride 4M HCl in 1,4-dioxane solution (1.5 mL) was added to a solution of tert-butyl N-{[(3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]methyl}carbamate (0.078 g, 1.0 eq.) in 1,4-dioxane (2.0 mL). The mixture was stirred at 55° C. for 1 h and subsequently concentrated in vacuo. The residue was partitioned between DCM and aq. solution of NaOH. The organic layer was dried over anh. $Na_2SO_4$, filtered and concentrated in vacuo. The residue was purified by FCC (SiHP deactivated with $NH_3$; DCM:MeOH). The obtained sample was converted to HCl salt using 2M HCl in $Et_2O$ solution and DCM as solvent but due to insufficient purity it was re-purified by prep-HPLC ($H_2O$:MeCN:$NH_3$) and converted once again to the HCl salt using 2 M HCl in $Et_2O$ solution (0.02 mL) and DCM (5.0 mL) as a solvent to provide the product (0.013 g, 17% yield) as a pale yellow solid. ESI-MS: 610.3 $[M+H]^+$. $^1H$ NMR (400 MHz, Deuterium Oxide) δ 8.14-7.98 (m, 2H), 7.81 (s, 1H), 7.75-7.63 (m, 1H), 7.56 (d, J=14.4 Hz, 1H), 7.43-7.32 (m, 1H), 7.31-7.24 (m, 1H), 7.26-7.15 (m, 1H), 6.86-6.77 (m, 1H), 4.29-3.88 (m, 4H), 3.88-3.76 (m, 2H), 3.72-3.56 (m, 2H), 3.56-3.46 (m, 1H), 3.45-3.27 (m, 3H), 3.26-3.09 (m, 3H), 3.08-2.93 (m, 1H), 2.79-2.61 (m, 1H), 2.49 (s, 3H), 2.38-

2.14 (m, 5H), 2.10-1.91 (m, 2H), 1.90-1.80 (m, 1H), 1.80-1.70 (m, 1H), 1.33-1.21 (m, 2H), 0.91-0.78 (m, 2H).

Example 21. 3-({[(3S)-1-(6-aminopyridin-3-yl)piperidin-3-yl][(2-methylpyridin-4-yl)methyl]amino}methyl)-1-(2-methoxyethyl)-1,4-dihydroquinolin-4-one hydrochloride

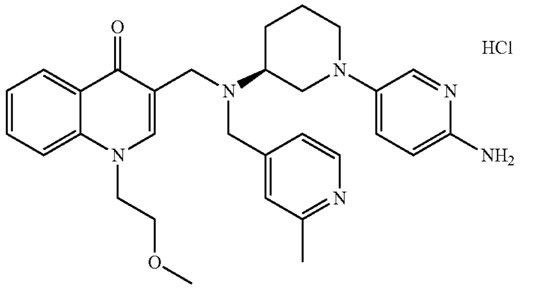

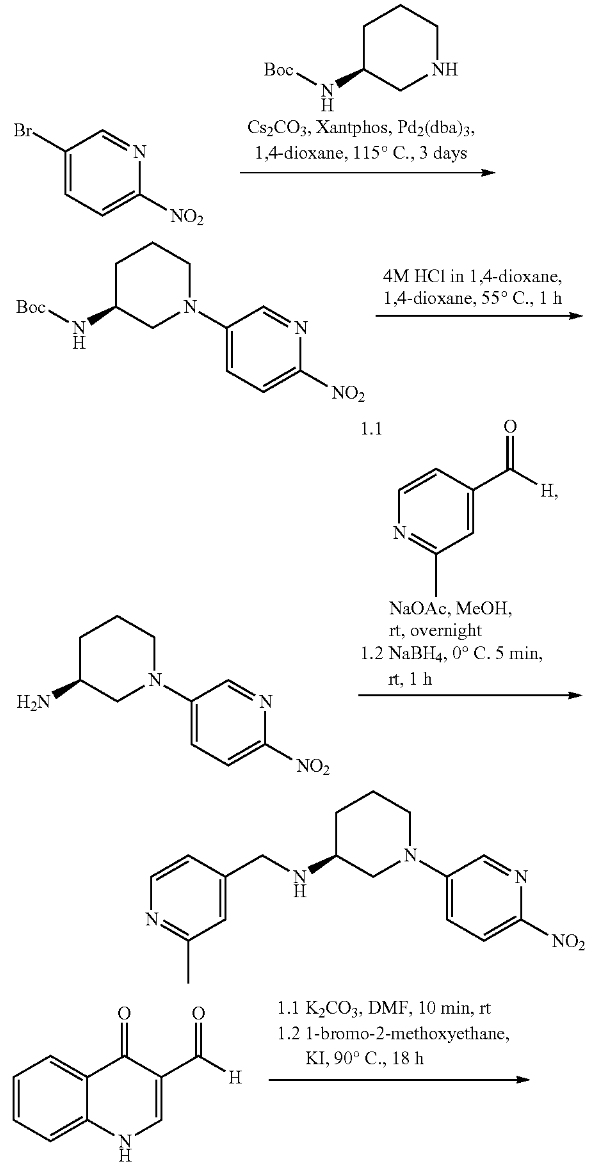

-continued

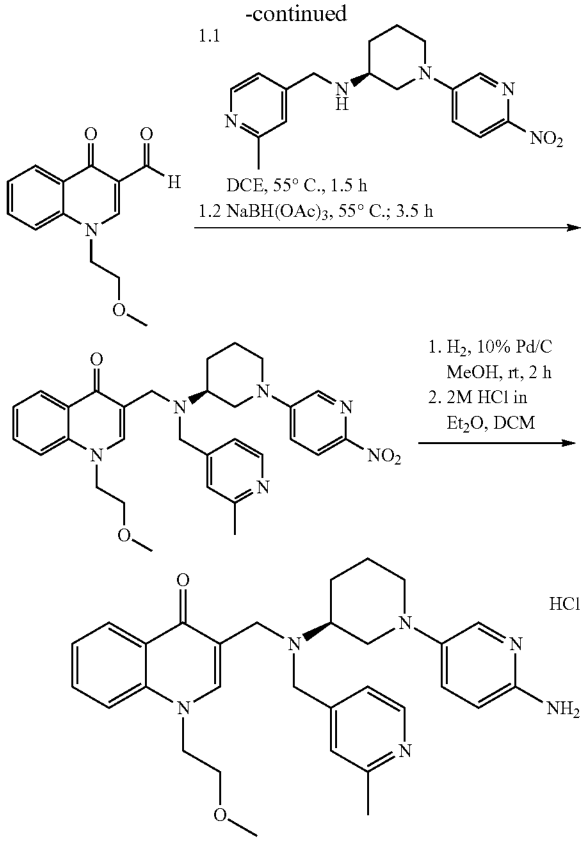

Preparation of tert-butyl N-[(3S)-1-(6-nitropyridin-3-yl)piperidin-3-yl]carbamate A mixture of 5-bromo-2-nitropyridine (3.6 g, 1.0 eq.), tert-butyl N-[(3S)-piperidin-3-yl]carbamate (4.62 g, 1.3 eq.), $Cs_2CO_3$ (7.8 g, 1.35 eq.) and 1,4-dioxane (96.0 mL) was purged with argon for 5 min. Then, Xantphos (0.616 g, 0.06 eq.) and $Pd_2(dba)_3$ (0.812 g, 0.05 eq.) were added and the reaction mixture was stirred at 115° C. for 3 days. Afterwards, the reaction mixture was cooled to ambient temperature, filtered through a pad of celite and concentrated in vacuo. The residue was dissolved in DCM and stirred overnight with scavenger QuadraPure MPA (3.0 g). The mixture was filtered and concentrated in vacuo. The residue was purified by two subsequent FCCs (SiHP; Hex:EtOAc) to give the product (3.7 g, 65% yield) as a yellow solid. ESI-MS: 323.4 $[M+H]^+$.

Preparation of (3S)-1-(6-nitropyridin-3-yl)piperidin-3-amine (Intermediate 12)

4M HCl solution in 1,4-dioxane (23.0 mL, 8.0 eq.) to a solution of tert-butyl N-[(3S)-1-(6-nitropyridin-3-yl)piperidin-3-yl]carbamate (3.7 g, 1.0 eq.) in 1,4-dioxane (25.0 mL) was added. The resulting slurry was stirred at 55° C. for 1 h. Then, the reaction mixture was concentrated in vacuo and the residue was partitioned between DCM and 10% NaOH aq. solution. The combined organic layers were dried over anh. $Na_2SO_4$, filtered and concentrated in vacuo to give the product (2.5 g, 62% yield) as a yellow solid which was used directly in the next step. ESI-MS: 223.2 $[M+H]^+$.

Preparation of (3S)—N-[(2-methylpyridin-4-yl) methyl]-1-(6-nitropyridin-3-yl)piperidin-3-amine (Intermediate 11)

A solution of 2-methylpyridine-4-carbaldehyde (0.24 mL, 1.0 eq.), (3S)-1-(6-nitropyridin-3-yl)piperidin-3-amine (Intermediate 12) (0.50 g, 1.5 eq.) and NaOAc (0.176 g, 1.0 eq.) in anh. MeOH (7.0 mL) was stirred overnight at RT under an inert atmosphere. Then, the solution was cooled to 0° C. and $NaBH_4$ (0.09 g, 1.1 eq.) was added in in portions over 5 minutes. The resulting mixture was left stirring for 1 h at RT. Afterwards, the reaction mixture was filtered through a pad of celite, the pad was washed with MeOH and the filtrate was concentrated in vacuo. The residue was partitioned between DCM and aq. solution of NaOH. The organic layer was washed with brine, dried over anh. $Na_2SO_4$ and filtered. Solvents were removed under reduced pressure and the residue was purified by FCC (SiHP deactivated with $NH_3$; DCM:MeOH) to give the product (0.65 g, 78% yield) as a yellow solid. ESI-MS: 328.5 $[M+H]^+$.

Preparation of 1-(2-methoxyethyl)-4-oxo-1,4-dihydroquinoline-3-carbaldehyde

A suspension of 4-oxo-1,4-dihydroquinoline-3-carbaldehyde (Intermediate 1) (0.7 g, 1.0 eq.) and $K_2CO_3$ (1.56 g, 2.8 eq.) in anh. DMF (20.0 mL) was stirred for 10 min at RT under inert atmosphere. Then, KI (1.88 g, 2.8 eq.) and 1-bromo-2-methoxyethane (1.1 mL, 2.8 eq.) were added and the resulting mixture was stirred for 18 h at 90° C. Afterwards, the reaction mixture was filtered through a pad of celite and concentrated in vacuo. The residue was purified by FCC (SiHP; DCM:MeOH) to give the product (0.7 g, 75% yield) as a beige solid. ESI-MS: 232.6 $[M+H]^+$. $^1$H NMR (300 MHz, Chloroform-d) δ 10.45 (s, 1H), 8.63-8.53 (m, 1H), 8.38 (s, 1H), 7.82-7.71 (m, 1H), 7.58-7.48 (m, 2H), 4.42 (t, J=5.1 Hz, 2H), 3.80 (t, J=5.1 Hz, 2H), 3.34 (s, 3H).

Preparation of 1-(2-methoxyethyl)-3-({[(2-methylpyridin-4-yl)methyl][(3S)-1-(6-nitropyridin-3-yl) piperidin-3-yl]amino}methyl)-1,4-dihydroquinolin-4-one A mixture of (3S)—N-[(2-methylpyridin-4-yl)methyl]-1-(6-nitropyridin-3-yl)piperidin-3-amine (Intermediate 11) (0.13 g, 1.0 eq.) and 1-(2-methoxyethyl)-4-oxo-1,4-dihydroquinoline-3-carbaldehyde (0.10 g, 1.1 eq.) in DCE (3.0 mL) was stirred for 1.5 h at 55° C. Then, $NaBH(OAc)_3$ (0.21 g, 2.5 eq.) was added in portions and the resulting mixture was stirred for another 3.5 h at 55° C. Afterwards, the mixture was diluted with DCM and NaOH aq. solution and the product was extracted to DCM. Organic layer was dried over anh. $Na_2SO_4$, filtered and concentrated in vacuo. The residue was purified by FCC (SiHP; DCM:MeOH) and re-purified by RP-FCC (C18HP; $H_2O$:MeCN) to give the product (0.083 g, 39% yield) as a yellow solid. ESI-MS: 543.8 $[M+H]^+$.

Preparation of 3-({[(3S)-1-(6-aminopyridin-3-yl) piperidin-3-yl][(2-methylpyridin-4-yl)methyl] amino}methyl)-1-(2-methoxyethyl)-1,4-dihydroquinolin-4-one hydrochloride A solution of 1-(2-methoxyethyl)-3-({[(2-methylpyridin-4-yl)methyl][(3S)-1-(6-nitropyridin-3-yl)piperidin-3-yl] amino}methyl)-1,4-dihydroquinolin-4-one (0.08 g, 1.0 eq.) in MeOH (3.0 mL) was purged with argon and Pd/C (10 wt. %, 0.008 g) was added. The mixture was stirred for 2 h under hydrogen atmosphere at RT. Then, the reaction mixture was filtered through a pad of celite, concentrated in vacuo and the residue was purified by RP-FCC (C18HP; $H_2O$:MeCN). The obtained sample was converted into HCl salt using 2 M HCl solution in $Et_2O$ (0.059 mL, 1.0 eq. to FB) and DCM (3.0 mL) as a solvent to give the product (0.045 g, 56% yield) as a pale yellow solid. ESI-MS: 513.4 $[M+H]^+$. $^1$H NMR (400 MHz, Deuterium Oxide) δ 8.01 (dd, J=8.2, 1.5 Hz, 1H), 7.90 (d, J=5.5 Hz, 1H), 7.81 (s, 1H), 7.67 (ddd, J=8.6, 7.0, 1.6 Hz, 1H), 7.54 (d, J=8.8 Hz, 1H), 7.46 (dd, J=9.2, 2.9 Hz, 1H), 7.43-7.40 (m, 1H), 7.40-7.34 (m, 1H), 7.13-7.02 (m, 2H), 6.66 (d, J=9.2 Hz, 1H), 4.30 (t, J=5.1 Hz, 2H), 3.94-3.70 (m, 4H), 3.66 (t, J=5.0 Hz, 2H), 3.50-3.40 (m, 1H), 3.14 (s, 5H), 2.81-2.66 (m, 1H), 2.64-2.51 (m, 1H), 2.08 (s, 3H), 2.05-1.95 (m, 1H), 1.94-1.82 (m, 1H), 1.70-1.49 (m, 2H).

Example 22. 7-{7-amino-5-azaspiro[2.4]heptan-5-yl}-1-cyclopropyl-6-fluoro-3-({[(3S)-1-(6-methylpyridin-3-yl)piperidin-3-yl][(2-methylpyridin-4-yl) methyl]amino}methyl)-1,4-dihydroquinolin-4-one hydrochloride

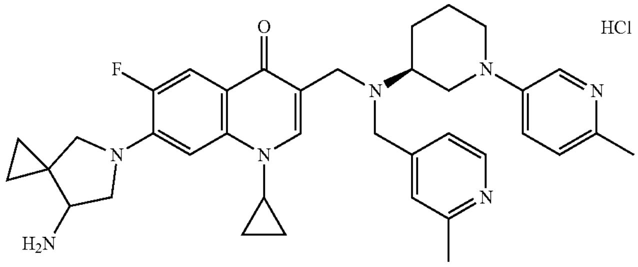

-continued

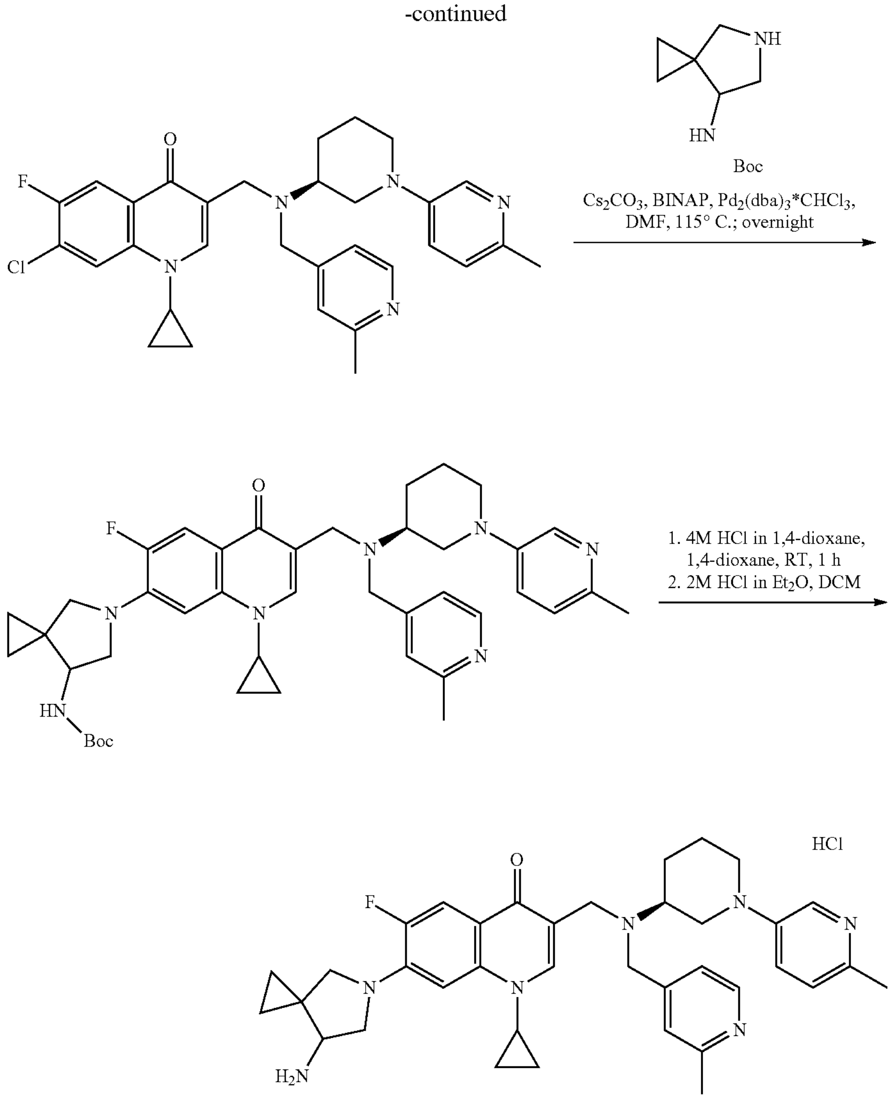

Preparation of tert-butyl N-{5-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-5-azaspiro[2.4]heptan-7-yl}carbamate Argon was bubbled for 5 min through a suspension of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.114 g, 1.0 eq.), tert-butyl N-{5-azaspiro[2.4]heptan-7-yl}carbamate (0.088 g, 2.0 eq.) and $Cs_2CO_3$ (0.143 g, 2.1.0 eq.) in DMF (3.0 mL). Then BINAP (0.039 g, 0.3 eq.) and $Pd_2(dba)_3$*$CHCl_3$ (0.043 g, 0.2 eq.). The resulting mixture was stirred overnight at 115° C. Afterwards the mixture was filtered through a pad of celite and then rinsed with DCM. The filtrate was concentrated in vacuo and the residue was purified by FCC (SiHP, DCM:MeOH). The isolated sample was dissolved in DCM and stirred with for 20 min with scavenger QuadraPure MPA. The scavenger was filtered off and the filtrate was concentrated to give the product (0.105 g, 70% yield) as a yellow oil. AP-MS: 722.7 $[M+H]^+$.

Preparation of 7-(7-amino-5-azaspiro[2.4]heptan-5-yl)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one hydrochloride 4 M HCl in 1,4-dioxane (1.1 mL) was added to a solution of tert-butyl N-{5-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-5-azaspiro[2.4]heptan-7-yl}carbamate (0.105 g, 1.0 eq.) in 1,4-dioxane (6.0 mL) and the mixture was stirred for 1 h at RT. Then, the reaction mixture was poured into water. The pH of the resulting mixture was adjusted to ~11 with 2 M aq. solution of NaOH and washed with DCM. The organic layer was dried over anh. $Na_2SO_4$, filtered and concentrated under reduced pressure. The compound was converted to the HCl salt using 2 M HCl in $Et_2O$ (0.062 mL, 2.0 eq. to FB) and DCM as a solvent (2.4 mL) to provide the desired product (0.039 g, 41% yield) as a white solid. ESI-MS: 622.3 $[M+H]^+$. $^1H$ NMR (400 MHz, Deuterium Oxide) δ 8.05-7.95 (m, 1H), 7.93-7.83 (m, 1H), 7.69-7.58 (m, 1H), 7.58-7.47 (m, 1H), 7.41-7.29 (m, 1H), 7.14-7.03 (m, 1H), 6.98-6.89 (m, 1H), 6.89-6.80 (m, 1H), 6.77-6.67 (m, 1H), 4.10-3.95 (m, 1H), 3.95-3.80 (m, 2H), 3.79-3.53 (m, 4H), 3.50-3.45 (m, 1H), 3.44-3.33 (m, 1H), 3.23-3.10 (m, 2H), 3.06-2.84 (m, 1H), 2.84-2.52 (m, 2H), 2.31 (s, 3H), 2.07-1.92 (m, 4H), 1.91-1.80 (m, 1H), 1.70-1.40 (m, 2H), 1.25-1.05 (m, 3H), 1.05-0.93 (m, 1H), 0.95-0.83 (m, 2H), 0.83-0.72 (m, 1H), 0.72-0.59 (m, 2H).

Example 23. 7-[(3R)-3-hydroxypyrrolidin-1-yl]-1-methyl-3-({[(3S)-1-(6-methylpyridin-3-yl)piperidin-3-yl][(2-methylpyridin-4-yl)methyl]amino}methyl)-1,4-dihydroquinolin-4-one

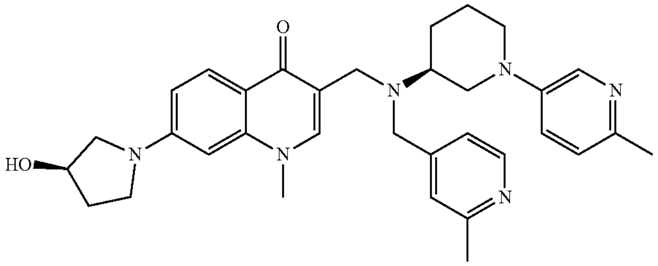

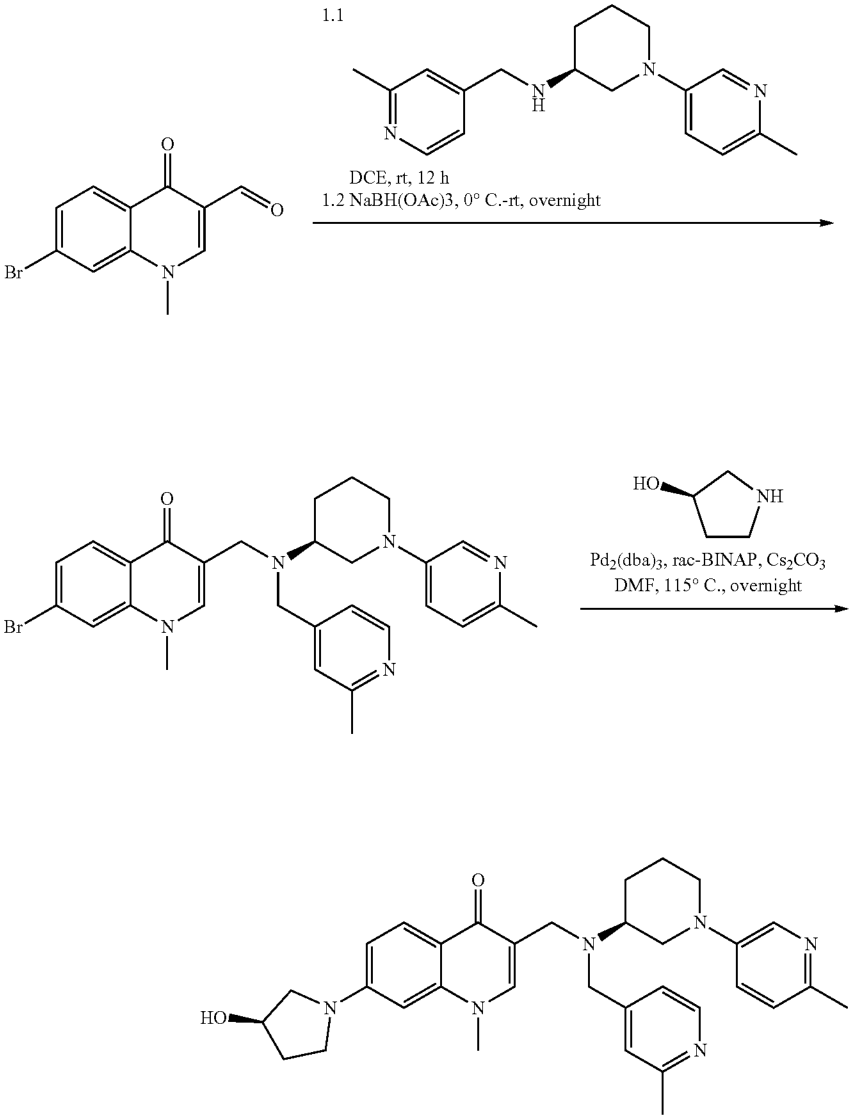

Preparation of 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one (Intermediate 13)

7-bromo-1-methyl-4-oxo-1,4-dihydroquinoline-3-carbaldehyde (Intermediate 8) (0.5 g, 1.0 eq.) and (3S)-1-(6-methylpyridin-3-yl)-N-[(2-methylpyridin-4-yl)methyl]piperidin-3-amine (Intermediate 2) (0.56 g, 1.0 eq.) were suspended in anh. DCE (15.0 mL) and the reaction mixture was stirred overnight at RT. Then, $NaBH(OAc)_3$ (0.56 g, 1.4 eq.) was added and the stirring was continued for an additional 24 h. Afterwards, the reaction mixture was diluted with DCM, washed with sat. aq. sodium bicarbonate, water, brine, dried over anh. $Na_2SO_4$, filtered and concentrated in vacuo. The residue was purified by FCC (SiHP, DCM:MeOH) to give the product (0.495 g, 46% yield) as a yellow solid. ESI-MS: 546.3, 548.2 $[M+H]^+$.

Preparation of 7-[(3R)-3-hydroxypyrrolidin-1-yl]-1-methyl-3-({[(3S)-1-(6-methylpyridin-3-yl)piperidin-3-yl][(2-methylpyridin-4-yl)methyl]amino}methyl)-1,4-dihydroquinolin-4-one A pressure vessel was charged with 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one (Intermediate 13) (0.08 g, 1.0 eq.), (3R)-pyrrolidin-3-ol (0.035 mL, 3.0 eq.), $Cs_2CO_3$ (0.1 g, 2.1 eq.) in DMF (3.0 mL). The mixture was purged with argon for 5 min and then, BINAP (0.027 g, 0.3 eq.) and $Pd_2(dba)_3$ (0.03 g, 0.2 eq.) were added and the reaction mixture was stirred at 115° C. for 6 h. Subsequently, the mixture was filtered through a pad of celite, washed with DCM and the filtrate was concentrated in vacuo. The residue was purified by RP-FCC (C18HP; $H_2O$:MeCN) to afford the product (0.025 g, 22% yield) as a yellow solid. ESI-MS: 553.3 $[M+H]^+$. $^1H$ NMR (400 MHz, DMSO-$d_6$) δ 8.29 (d, J=5.0 Hz, 1H), 8.13 (d, J=3.0 Hz, 1H), 7.95 (d, J=8.9 Hz, 1H), 7.79 (s, 1H), 7.29-7.17 (m, 3H), 7.01 (d, J=8.5 Hz, 1H), 6.73-6.61 (m, 1H), 6.27-6.13 (m, 1H), 5.03 (d, J=3.7 Hz, 1H), 4.49-4.37 (m, 1H), 3.89-3.65 (m, 6H), 3.62-3.36 (m, 6H), 3.26-3.18 (m, 1H), 2.81-2.64 (m, 2H), 2.63-2.54 (m, 1H), 2.40 (s, 3H), 2.32 (s, 3H), 2.13-2.01 (m, 1H), 2.00-1.89 (m, 2H), 1.80-1.69 (m, 1H), 1.56-1.37 (m, 2H).

Example 24. 3-({[(3)-1-(6-aminopyridin-3-yl)piperidin-3-yl][(2-methylpyridin-4-yl)methyl]amino}methyl)-6,7-difluoro-1-(propan-2-yl)-1,4-dihydroquinolin-4-one hydrochloride

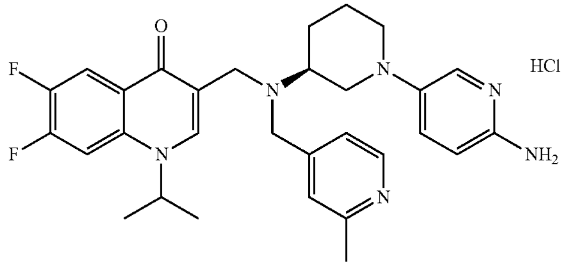

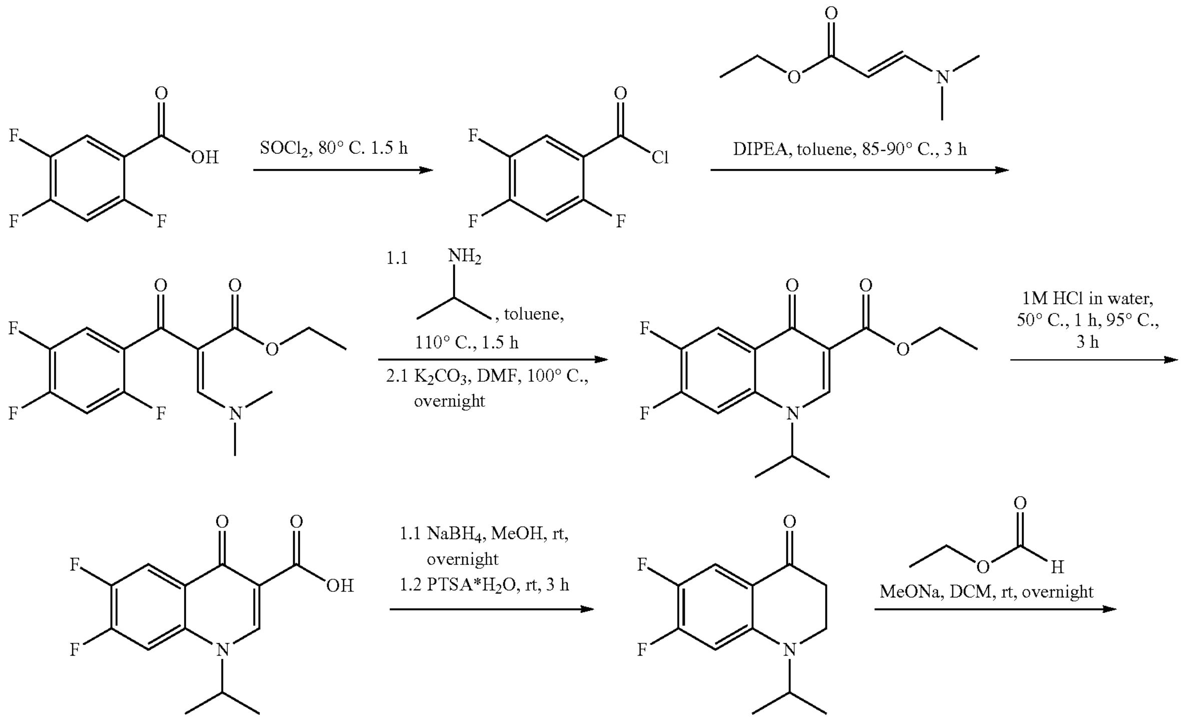

-continued

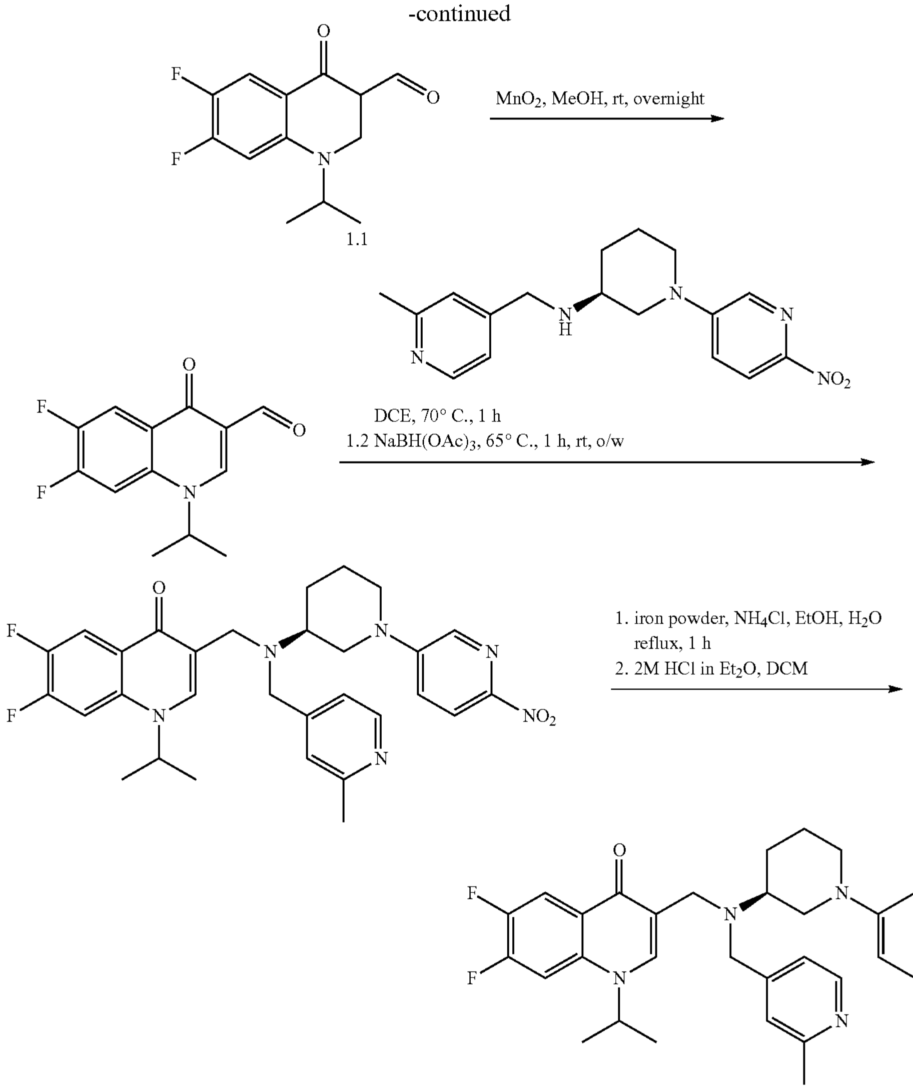

Preparation of 2,4,5-trifluorobenzoyl chloride 2,4,5-Trifluorobenzoic acid (0.5 g, 1.0 eq.) was suspended in $SOCl_2$ (1.15 mL, 5.6 eq.) and the resulting mixture was stirred for 1.5 h at 80° C. Afterwards, the reaction mixture was concentrated with DCM in vacuo and the isolated product (0.55 g, 98.5% yield) was used directly in the next step without further purification.

Preparation of ethyl 3-(dimethylamino)-2-(2,4,5-trifluorobenzoyl)prop-2-enoate

A solution of 2,4,5-trifluorobenzoyl chloride (0.55 g, 1.0 eq.) in toluene (5.0 mL) was added to a stirring at RT mixture of ethyl 3-(dimethylamino)prop-2-enoate (0.41 mL, 1.0 eq.) and DIPEA (1.0 mL, 2.1 eq.) over 5 min. The resulting mixture was stirred for 3 h at 90° C. Then, the mixture was partitioned between DCM and water. The organic layer was dried over anh. $Na_2SO_4$, filtered and concentrated under reduced pressure. The residue was purified by FCC (SiHP; EtOAc) to give the product (0.21 g, 24% yield) as a yellow oil. ESI-MS: 302.1 $[M+H]^+$.

Preparation of ethyl 6,7-difluoro-4-oxo-1-(propan-2-yl)-1,4-dihydroquinoline-3-carboxylate A mixture of ethyl 3-(dimethylamino)-2-(2,4,5-trifluorobenzoyl)prop-2-enoate (0.65 g, 1.0 eq.), isopropylamine (0.22 mL, 1.3 eq.) and toluene (5.0 mL) was heated for 1.5 h at 110° C. Afterwards, the reaction mixture was concentrated in vacuo and DMF (5.0 mL) was added to the residue followed by $K_2CO_3$ (0.74 g, 2.5 eq.). The resulting mixture was heated overnight at 100° C. Then, the mixture was cooled to RT and partitioned between DCM and water. The organic layer was washed with brine, dried over anh. $Na_2SO_4$, filtered and concentrated in vacuo. The residue was purified by FCC (SiHP; Hex:EtOAc) to give the product (0.311 g, 47% yield) as a yellow solid. ESI-MS: 296.4 $[M+H]^+$. $^1H$ NMR (300 MHz, DMSO-$d_6$) δ 8.60 (s, 1H), 8.21 (dd, J=13.1, 6.6 Hz, 1H), 8.11 (dd, J=10.8, 9.1 Hz, 1H), 5.01 (hept, J=6.4 Hz, 1H), 4.24 (q, J=7.1 Hz, 2H), 1.49 (d, J=6.5 Hz, 6H), 1.28 (t, J=7.1 Hz, 3H).

Preparation of 6,7-difluoro-4-oxo-1-(propan-2-yl)-1,4-dihydroquinoline-3-carboxylic acid Ethyl 6,7-difluoro-4-oxo-1-(propan-2-yl)-1,4-dihydroquinoline-3-carboxylate (0.29 g, 1.0 eq.) was suspended in a 1 M HCl aq. solution (6.0 mL, 6.1 eq.). The resulting mixture was stirred at 50° C. for 1 h and additionally for 3 h at 95° C. ESI-MS: 268.3 $[M+H]^+$. Subsequently, the reaction mixture was concentrated under reduced pressure to give the product (0.24 g, 87% yield) as a yellow solid. $^1H$ NMR (300 MHz, DMSO-$d_6$) δ 14.89 (br, 1H), 8.89 (s, 1H), 8.47 (dd, J=13.0, 6.7 Hz, 1H), 8.30 (dd, J=10.5, 8.8 Hz, 1H), 5.19 (hept, J=6.6 Hz, 1H), 1.56 (d, J=6.5 Hz, 6H).

Preparation of 6,7-difluoro-1-(propan-2-yl)-1,2,3,4-tetrahydroquinolin-4-one 6,7-difluoro-4-oxo-1-(propan-2-yl)-1,4-dihydroquinoline-3-carboxylic acid (0.24 g, 1.0 eq.) was dissolved in MeOH (4.0 mL) and the mixture was cooled in an ice-bath. Then, $NaBH_4$ (0.15 g, 4.5 eq.) was added in portions and the reaction mixture was left stirring overnight at RT. Subsequently, PTSA monohydrate (0.017 g, 0.1 eq.) was added and stirring was continued for 3 h. Then, the reaction mixture was concentrated in vacuo and the residue was partitioned between DCM and water. The organic layer was washed with brine, dried over anh. $Na_2SO_4$, filtered and concentrated in vacuo. The residue was purified by FCC (SiHP; Hex:EtOAc) to give the product (0.20 g, 96% yield) as a bright yellow solid. ESI-MS: 226.2 [M+H]. $^1H$ NMR (300 MHz, DMSO-$d_6$) δ 7.58 (dd, J=11.0, 9.6 Hz, 1H), 7.13 (dd, J=14.6, 6.6 Hz, 1H), 4.16 (h, J=6.6 Hz, 1H), 3.43-3.35 (m, 2H), 2.62-2.50 (m, 2H), 1.16 (d, J=6.6 Hz, 6H).

Preparation of 6,7-difluoro-4-oxo-1-(propan-2-yl)-1,2,3,4-tetrahydroquinoline-3-carbaldehyde A solution of 6,7-difluoro-1-(propan-2-yl)-1,2,3,4-tetrahydroquinolin-4-one (0.1 g, 1.0 eq.) in anh. DCM (5.0 mL) was added to a mixture of MeONa (0.094 g, 3.9 eq.) and ethyl formate (0.14 mL, 3.94 eq.) at RT and the resulting mixture was stirred overnight. Subsequently, the reaction mixture was washed with 2 M NaOH aq. solution. The aqueous layer was acidified using 1 M HCl (aq. Solution) and washed with DCM. The organic layers were dried over anh. $Na_2SO_4$, filtered and concentrated in vacuo to give the product (0.1 g, 64% yield) as a yellow solid that was used directly in the next step without further purification. ESI-MS: 254.1 $[M+H]^+$.

Preparation of 6,7-difluoro-4-oxo-1-(propan-2-yl)-1,4-dihydroquinoline-3-carbaldehyde 6,7-Difluoro-4-oxo-1-(propan-2-yl)-1,2,3,4-tetrahydroquinoline-3-carbaldehyde (0.1 g, 1.0 eq.) was dissolved in anh. MeOH (5.0 mL) and $MnO_2$ (0.17 g, 5.0 eq.) was added. The resulting mixture was stirred overnight at RT. Then, the reaction mixture was filtered through a pad of celite and the pad was washed carefully with MeOH. The filtrate was concentrated in vacuo to give the product (0.077 g, 74% yield) as a yellow solid. ESI-MS: 252.3 $[M+H]^+$.

Preparation of 6,7-difluoro-3-({[(2-methylpyridin-4-yl)methyl][(3S)-1-(6-nitropyridin-3-yl)piperidin-3-yl]amino}methyl)-1-(propan-2-yl)-1,4-dihydroquinolin-4-one A dry pressure vessel was charged with 6,7-difluoro-4-oxo-1-(propan-2-yl)-1,4-dihydroquinoline-3-carbaldehyde (0.077 g, 1.0 eq.), (3S)—N-[(2-methylpyridin-4-yl)methyl]-1-(6-nitropyridin-3-yl)piperidin-3-amine (Intermediate 11) (0.1 g, 1.0 eq.) and anh. DCE (3.0 mL). The resulting mixture was stirred for 1 h at 70° C. Then, the mixture was cooled to RT and $NaBH(OAc)_3$ (0.182 g, 2.8 eq.) was added in portions. Heating was continued at 65° C. for 1 h and then, the mixture was left stirring over the weekend at RT. Afterwards, the reaction mixture was partitioned between DCM and $NaHCO_3$ aq. solution. The organic layer was dried over anh. $Na_2SO_4$, filtered and concentrated in vacuo. The residue was purified by FCC (SiHP; DCM:MeOH) to give the product (0.1 g, 35% yield) as a yellow solid. ESI-MS: 563.8 $[M+H]^+$.

Preparation of 3-({[(3S)-1-(6-aminopyridin-3-yl)piperidin-3-yl][(2-methylpyridin-4-yl)methyl]amino}methyl)-6,7-difluoro-1-(propan-2-yl)-1,4-dihydroquinolin-4-one hydrochloride A mixture of 6,7-difluoro-3-({[(2-methylpyridin-4-yl)methyl][(3S)-1-(6-nitropyridin-3-yl)piperidin-3-yl]amino}methyl)-1-(propan-2-yl)-1,4-dihydroquinolin-4-one (0.1 g, 1.0 eq.), iron powder (0.03 g, 3 eq.), $NH_4Cl$ (0.05 g, 5.0 eq.) in EtOH (6.0 mL) and $H_2O$ (0.5 mL) was stirred at reflux for 1 h. Then, the reaction mixture was cooled to RT, diluted with MeOH, filtered through a pad of celite and concentrated in vacuo. The residue was purified by RP-FCC (C18HP, $H_2O$:MeCN). The compound obtained was converted into its HCl salt using 2 M HCl in $Et_2O$ (0.014 mL, 1.0 eq. to FB) and DCM (2.0 mL) to provide the product (0.015 g, 14% yield) as a yellow solid. ESI-MS: 533.3 $[M+H]^+$. $^1H$ NMR (300 MHz, Methanol-$d_4$) δ 8.18-8.07 (m, 3H), 7.88 (dd, J=12.9, 6.6 Hz, 1H), 7.74 (dd, J=9.5, 2.8 Hz, 1H), 7.37 (d, J=2.8 Hz, 1H), 7.27 (s, 1H), 7.25-7.20 (m, 1H), 6.82 (d, J=9.4 Hz, 1H), 4.98-4.90 (m, 1H), 3.89-3.73 (m, 4H), 3.70-3.63 (m, 1H), 3.40-3.33 (m, 1H), 3.01-2.91 (m, 1H), 2.78-2.69 (m, 1H), 2.61-2.52 (m, 1H), 2.37 (s, 31H), 2.14-2.06 (m, 1H), 1.95-1.88 (m, 1H), 1.70-1.56 (m, 2H), 1.46 (d, J=6.5 Hz, 61H).

Example 25. 2-amino-N-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]acetamide

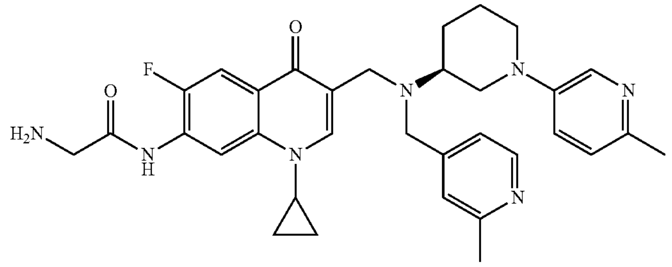

-continued

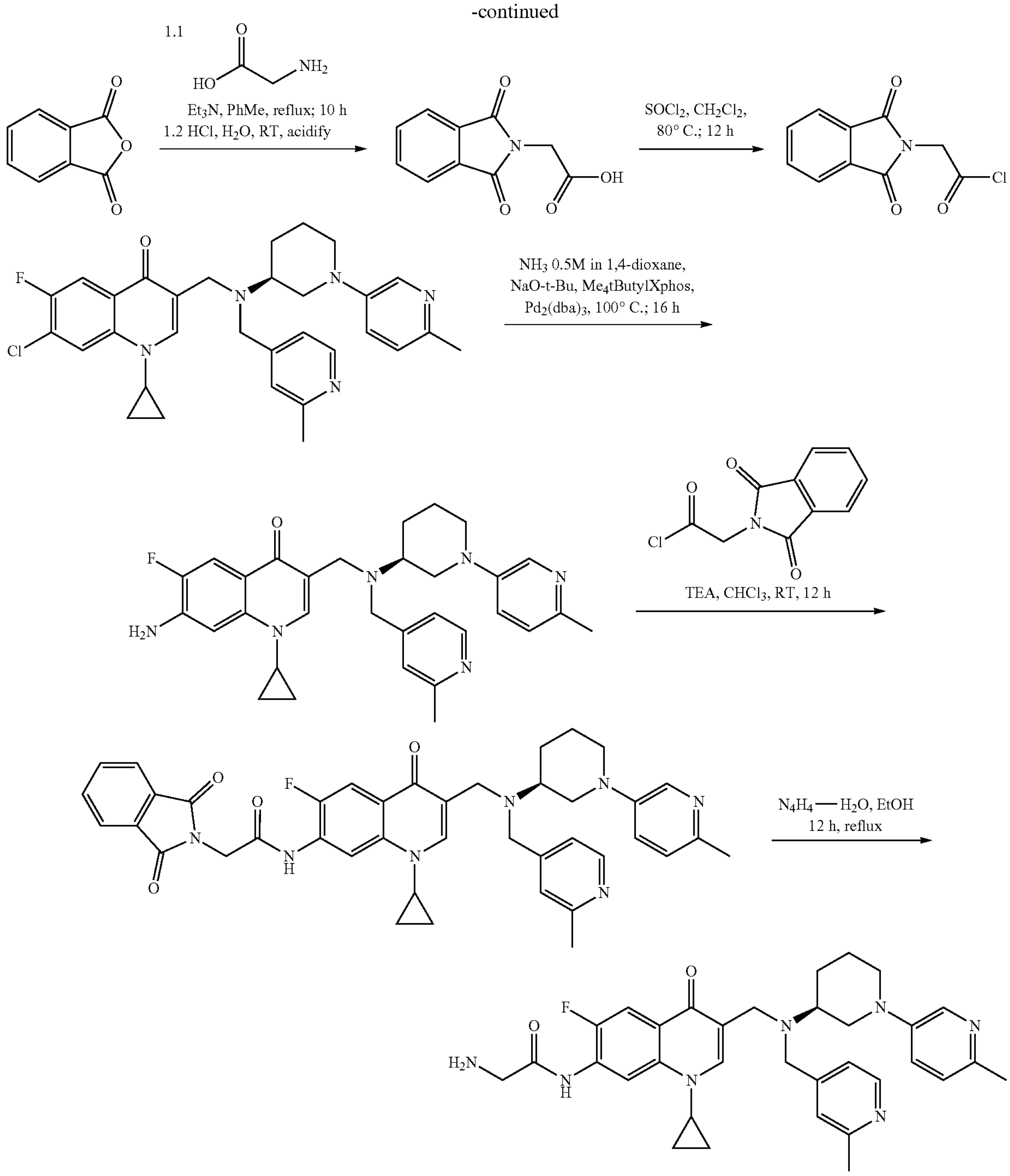

Preparation of 7-amino-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 14)

$Pd_2(dba)_3$ (0.042 g, 0.1 eq.) and $Me_4$ tButylXphos (0.022 g, 0.1 eq.) were added to a mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.25 g, 1.0 eq.) and NaO-t-Bu (0.062 g, 1.4 eq.) in ammonia solution 0.5 M in 1,4-dioxane (13.7 mL). The reaction mixture was stirred at 100° C. for 16 h. Subsequently, the mixture was cooled to ambient temperature, filtered through a pad of celite and washed with an aq. solution of NaOH. The organic layer was dried over anh. $Na_2SO_4$ and solvent was evaporated in vacuo. The residue was purified by FCC (SiHP; DCM: MeOH) to afford the product (0.137 g, 56% yield) as a yellow powder. ESI-MS: 527.8 $[M+H]^+$.

Preparation of 2-(1,3-dioxo-2,3-dihydro-1H-isoindol-2-yl)acetic acid

The reaction vessel was charged with glycine (0.30 g, 1.0 eq.), phthalic anhydride (0.89 g, 1.5 eq.), triethylamine (0.607 g, 1.5 eq.), toluene (5.0 mL) and 4 Å MS. The mixture was heated to reflux, stirred for 10 h and then concentrated in vacuo. The resulting white solid was taken up in water (50.0 mL) and the mixture was acidified with conc. HCl (3.0 mL). The product was collected by filtration, washed with water (2×30.0 mL) and freeze-dried to provide the product (0.65 g, 28% yield) as a white powder. ESI-MS: 203.9 $[M-H]^-$. $^1H$ NMR (400 MHz, DMSO-$d_6$) δ 13.28 (s, 1H), 7.97-7.87 (m, 4H), 4.32 (s, 2H).

Preparation of 2-(1,3-dioxo-2,3-dihydro-1H-isoindol-2-yl)acetyl chloride

In an oven dried reactor, 2-(1,3-dioxo-2,3-dihydro-1H-isoindol-2-yl)acetic acid (0.25 g, 1.0 eq.) and anh. DCE (6.0 mL) were introduced. Thionyl chloride (0.13 mL, 1.5 eq.) was then added, and the mixture refluxed at 80° C. for 12 h. Subsequently, the mixture was concentrated in vacuo and product was used immediately after this workup as the reactant for the next step.

Preparation of N-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-2-(1,3-dioxo-2,3-dihydro-1H-isoindol-2-yl)acetamide Triethylamine (0.032 mL, 2.5 eq.) and 2-(1,3-dioxo-2,3-dihydro-1H-isoindol-2-yl)acetyl chloride (0.26 g, 10.0 eq.) were sequentially added to a mixture of 7-amino-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 14) (0.06 g, 1.0 eq.) in $CHCl_3$ (3.0 mL). and the reaction mixture was stirred at RT for 12 h. Afterwards, the reaction was quenched with water and the mixture washed with DCM. The organic layer was dried over anh. $Na_2SO_4$ and solvent was removed in vacuo. The residue was purified by FCC (SiHP; DCM:MeOH) to provide the product (0.037 g, 34% yield) as a beige powder. ESI-MS: 714.6 $[M+H]^+$.

Preparation of 2-amino-N-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]acetamide Hydrazine monohydrate (0.004 g, 2.0 eq.) was added to a solution of N-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-2-(1,3-dioxo-2,3-dihydro-1H-isoindol-2-yl)acetamide (0.025 g, 1.0 eq.) in EtOH (5.0 mL). The mixture was stirred at reflux for 12 h and subsequently concentrated in vacuo. The residue was purified by FCC (C18HP; $H_2O$:MeCN) to provide the product (0.009 g, 41% yield) as a yellow powder. ESI-MS: 584.4 $[M+H]^+$. 1H NMR (400 MHz, DMSO-d6) δ 9.07 (d, J=6.7 Hz, 1H), 8.28 (d, J=5.1 Hz, 1H), 8.15-8.12 (m, 1H), 7.89-7.84 (m, 2H), 7.25-7.20 (m, 2H), 7.18-7.15 (m, 1H), 7.03 (d, J=8.5 Hz, 1H), 5.44-4.96 (m, 2H), 3.84-3.74 (m, 3H), 3.65-3.62 (m, 2H), 3.62-3.57 (m, 1H), 3.51-3.44 (m, 1H), 3.39-3.39 (m, 2H), 2.79-2.73 (m, 2H), 2.64-2.57 (m, 1H), 2.37 (s, 3H), 2.33 (s, 3H), 2.02-1.95 (m, 1H), 1.81-1.74 (m, 1H), 1.59-1.45 (m, 2H), 1.26-1.15 (m, 2H), 0.95-0.84 (m, 2H).

Example 26. 7-(4-amino-3,3-difluoropiperidin-1-yl)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one

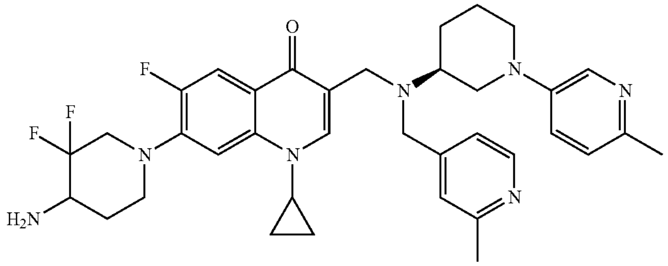

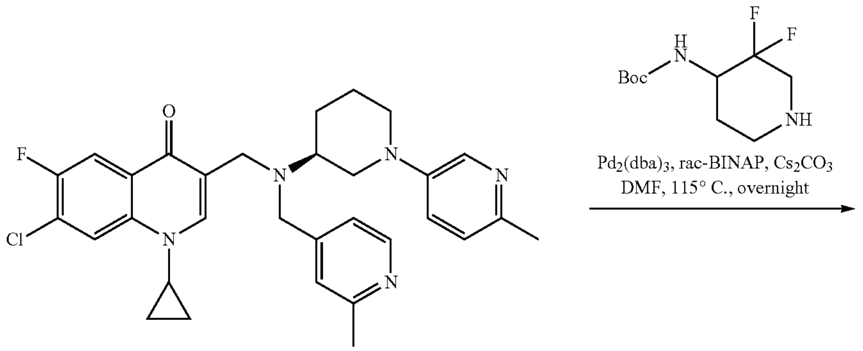

-continued

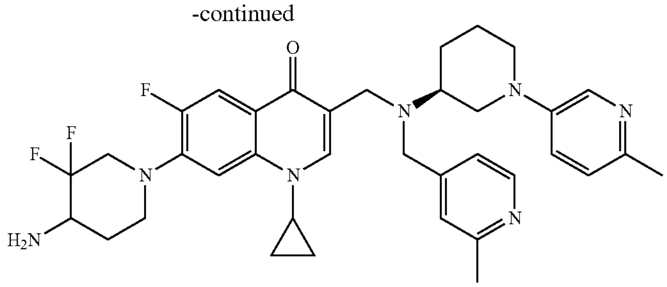

Preparation of 7-(4-amino-3,3-difluoropiperidin-1-yl)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one A pressure vessel was charged with 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.29 g, 1.0 eq.), tert-butyl N-(3,3-difluoropiperidin-4-yl)carbamate (0.25 g, 2.0 eq.), $Cs_2CO_3$ (0.36 g, 2.1 eq.) and DMF (3.0 mL). The mixture was purged with argon for 5 min. Then, BINAP (0.099 g, 0.3 eq.) and $Pd_2(dba)_3$ (0.055 g, 0.1 eq.) were added and the resulting mixture was stirred overnight at 115° C. Afterwards, the reaction mixture was filtered through a pad of celite and concentrated in vacuo. The residue was purified by two consecutive RP-FCCs (C18HP, $H_2O$:MeCN) and re-purified by prep-HPLC ($H_2O$:MeCN:$NH_3$) to give the product (0.026 g, 7% yield) as a white solid. ESI-MS: 646.3 $[M+H]^+$. $^1H$ NMR (400 MHz, DMSO-$d_6$) δ 8.28 (d, J=5.0 Hz, 1H), 8.12 (d, J=3.0 Hz, 1H), 7.82 (s, 1H), 7.72 (d, J=13.4 Hz, 1H), 7.37 (d, J=7.6 Hz, 1H), 7.25-7.18 (m, 2H), 7.18-7.12 (m, 1H), 7.01 (d, J=8.5 Hz, 1H), 3.87-3.67 (m, 4H), 3.65-3.46 (m, 5H), 3.39-3.26 (m, 1H, overlapping with water peak), 3.20-3.05 (m, 2H), 2.82-2.63 (m, 2H), 2.63-2.54 (m, 1H), 2.37 (s, 3H), 2.32 (s, 3H), 2.02-1.89 (m, 2H), 1.85-1.60 (m, 4H), 1.59-1.39 (m, 2H), 1.30-1.15 (m, 2H), 0.97-0.81 (m, 2H).

Example 27. 1-cyclopropyl-6-fluoro-7-[3-(hydroxymethyl)azetidin-1-yl]-3-({[(3S)-1-(6-methylpyridin-3-yl)piperidin-3-yl][(2-methylpyridin-4-yl)methyl]amino}methyl)-1,4-dihydroquinolin-4-one

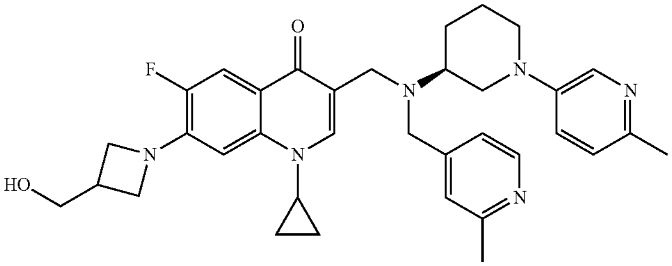

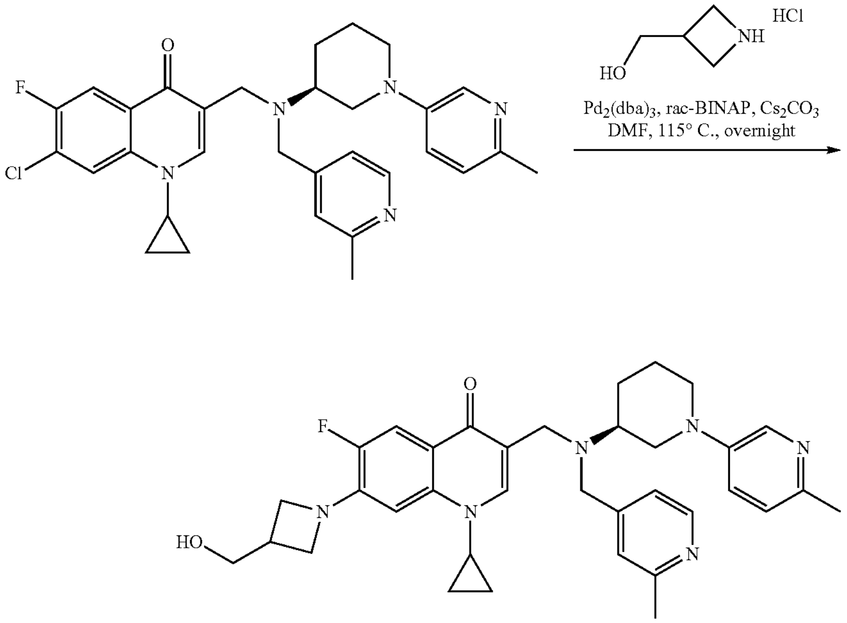

Preparation of 1-cyclopropyl-6-fluoro-7-[3-(hydroxymethyl)azetidin-1-yl]-3-({[(3S)-1-(6-methylpyridin-3-yl)piperidin-3-yl][(2-methylpyridin-4-yl)methyl]amino}methyl)-1,4-dihydroquinolin-4-one A pressure vessel was charged with 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.15 g, 1.0 eq.), (azetidin-3-yl)methanol hydrochloride (0.068 g, 2.0 eq.), $Cs_2CO_3$ (0.188 g, 2.1 eq.) and DMF (5.0 mL) and the mixture was purged with argon for 5 min. Then, BINAP (0.051 g, 0.3 eq.) and $Pd_2(dba)_3$ (0.028 g, 0.1 eq.) were added and the resulting mixture was stirred overnight at 115° C. Afterwards, the reaction mixture was filtered through a pad of celite and concentrated in vacuo. The residue was dissolved in DCM, the scavenger QuadraPure MPA was added and the mixture was stirred for 10 min at RT. Subsequently, it was filtered, concentrated in vacuo and the residue purified by prep-HPLC ($H_2O$:MeCN:$NH_3$) to give the product (0.07 g, 42% yield) as a yellow solid. ESI-MS: 597.3 $[M+H]^+$. $^1H$ NMR (400 MHz, DMSO-$d_6$) δ 8.29 (d, J=5.1 Hz, 1H), 8.13 (d, J=2.9 Hz, 1H), 7.73 (s, 1H), 7.62 (d, J=13.2 Hz, 1H), 7.24-7.15 (m, 3H), 7.02 (d, J=8.5 Hz, 1H), 6.68 (d, J=7.9 Hz, 1H), 4.83 (t, J=5.3 Hz, 1H), 4.14-4.08 (m, 2H), 3.87-3.82 (m, 2H), 3.81-3.69 (m, 3H), 3.64-3.56 (m, 5H), 3.44-3.38 (m, 1H), 2.89-2.81 (m, 1H), 2.79-2.70 (m, 2H), 2.62-2.55 (m, 1H), 2.39 (s, 3H), 2.33 (s, 3H), 1.99-1.93 (m, 1H), 1.79-1.72 (m, 1H), 1.56-1.43 (m, 2H), 1.21-1.16 (m, 2H), 0.90-0.80 (m, 2H).

Example 28. 1-cyclopropyl-6-fluoro-7-[(3R)-3-hydroxypiperidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride

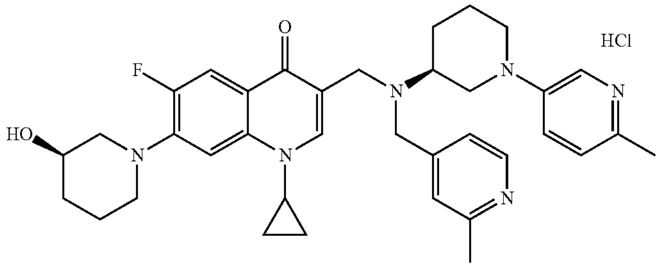

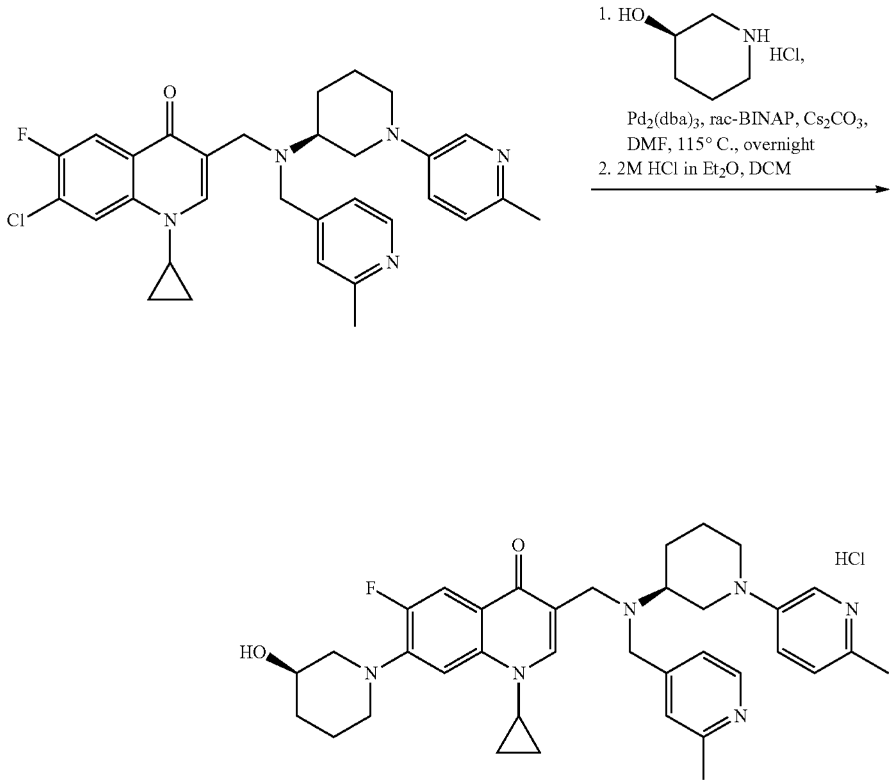

Preparation of 1-cyclopropyl-6-fluoro-7-[(3R)-3-hydroxypiperidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride A pressure vessel was charged with 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.15 g, 1.0 eq.), (3R)-piperidin-3-ol hydrochloride (0.056 g, 2.0 eq.), $Cs_2CO_3$ (0.188 g, 2.1 eq.) and DMF (5.0 mL) and the mixture was purged with argon. Then, BINAP (0.051 g, 0.3 eq.) and $Pd_2(dba)_3$ (0.028 g, 0.1 eq.) were added and the reaction mixture was stirred overnight at 115° C. Afterwards, the reaction mixture was filtered through a pad of celite and concentrated in vacuo. The residue was dissolved in DCM, the scavenger QuadraPure MPA added and the resulting mixture was stirred for 10 min at RT. Subsequently the mixture was filtered and the filtrate was concentrated in vacuo. The residue was purified by prep-HPLC ($H_2O$:MeCN:$NH_3$). The isolated sample was converted to HCl salt using 2 M HCl in $Et_2O$ solution (0.033 mL, 1.0 eq. to FB) and DCM (2.0 mL) as a solvent to give the product (0.037 g, 20% yield) as a yellow solid. ESI-MS: 611.4 $[M+H]^+$. $^1H$ NMR (400 MHz, Methanol-$d_4$) δ 8.20 (d, J=5.4 Hz, 1H), 8.15 (d, J=3.0 Hz, 1H), 7.89 (s, 1H), 7.81 (d, J=13.5 Hz, 1H), 7.78-7.71 (m, 1H), 7.50-7.29 (m, 4H), 4.09-3.77 (m, 6H), 3.76-3.60 (m, 2H), 3.53-3.40 (m, 2H), 3.11-2.90 (m, 3H), 2.90-2.74 (m, 2H), 2.52 (s, 3H), 2.37 (s, 3H), 2.21-2.11 (m, 1H), 2.10-2.02 (m, 1H), 2.00-1.89 (m, 2H), 1.81-1.60 (m, 3H), 1.54-1.43 (m, 1H), 1.35-1.24 (m, 2H), 1.01-0.88 (m, 2H).

Example 29. 3-({[(3S)-1-(6-aminopyridin-3-yl)piperidin-3-yl][(2-methylpyridin-4-yl)methyl]amino}methyl)-7-bromo-1-methyl-1,4-dihydroquinolin-4-one hydrochloride

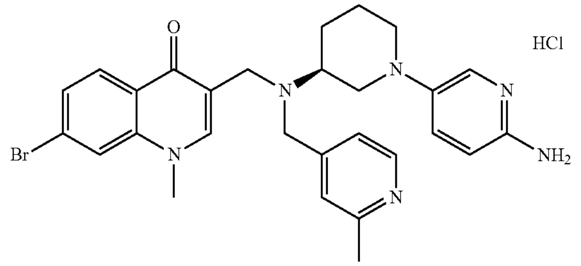

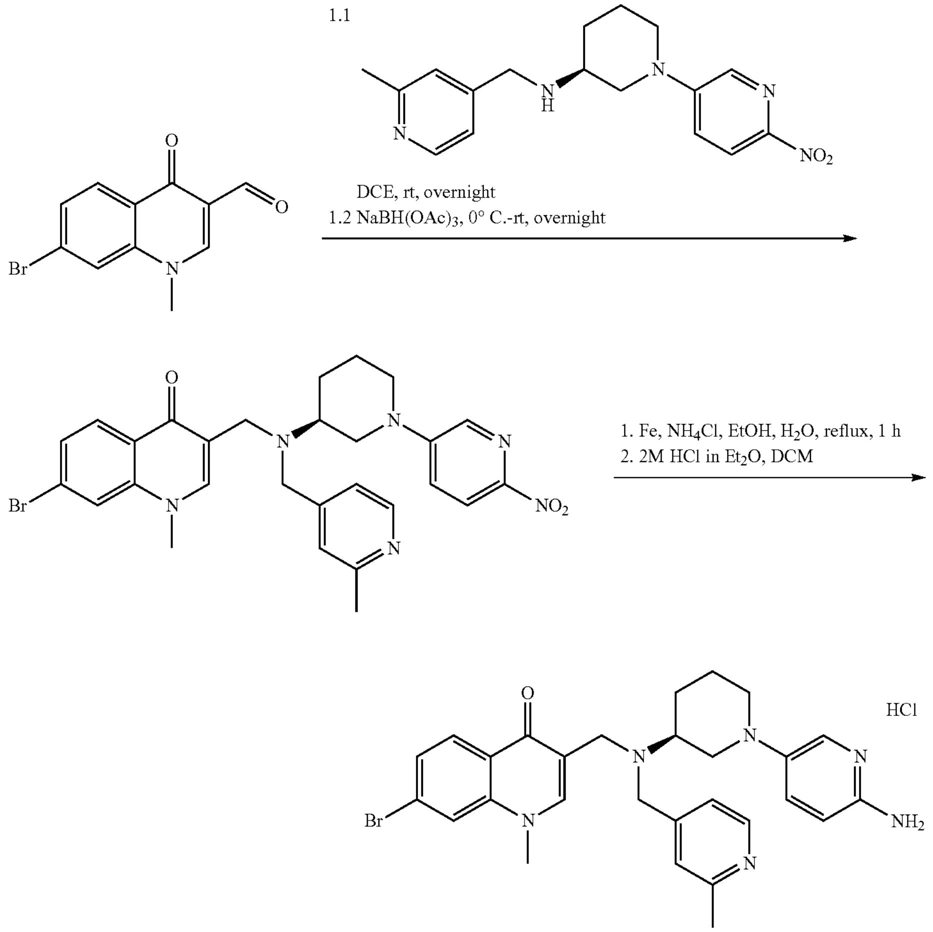

Preparation of 7-bromo-1-methyl-({[(2-methylpyridin-4-yl)methyl][(3S)-1-(6-nitropyridin-3-yl)piperidin-3-yl]amino}methyl)-1,4-dihydroquinolin-4-one $NaBH(OAc)_3$ (0.29 g, 1.5 eq.) was added in portions to a mixture of (3S)—N-[(2-methylpyridin-4-yl)methyl]-1-(6-nitropyridin-3-yl)piperidin-3-amine (Intermediate 11) (0.3 g, 1.0 eq.) and 7-bromo-1-methyl-4-oxo-1,4-dihydroquinoline-3-carbaldehyde (Intermediate 8) (0.245 g, 1.0 eq.) in DCE (6.0 mL). The reaction mixture was stirred overnight at RT. Then, an additional portion of $NaBH(OAc)_3$ (0.20 g, 1.0 eq.) was added and stirring was continued for 3 h. The reaction mixture was diluted with DCM, washed with water, brine, dried over anh. $Na_2SO_4$, filtered and concentrated in vacuo. The residue was purified by FCC (SiHP, DCM: MeOH) to afford the product (0.28 g, 47% yield) as a yellow solid. ESI-MS: 577.3, 578.6 $[M+H]^+$.

Preparation of 3-({[(3S)-1-(6-aminopyridin-3-yl)piperidin-3-yl][(2-methylpyridin-4-yl)methyl]amino}methyl)-7-bromo-1-methyl-1,4-dihydroquinolin-4-one hydrochloride A mixture of 7-bromo-1-methyl-3-({[(2-methylpyridin-4-yl)methyl][(3S)-1-(6-nitropyridin-3-yl)piperidin-3-yl]

amino}methyl)-1,4-dihydroquinolin-4-one (0.28 g, 1.0 eq.), iron powder (0.081 g, 3.0 eq.), $NH_4Cl$ (0.13 g, 5.0 eq.), EtOH (6.0 mL) and $H_2O$ (0.5 mL) was stirred at reflux for 1 h. The reaction mixture was cooled to RT, diluted with DCM and filtered through a pad of celite. The pad was washed with DCM and the filtrate was concentrated in vacuo. The residue was purified by FCC (SiHP; DCM: MeOH) and re-purified twice by RP-FCC (C18HP, MeCN: $H_2O$). The obtained compound was converted to the HCl salt using 2 M HCl in $Et_2O$ (0.094 mL, 1.0 eq. to FB) with DCM as the solvent (5.0 mL) to give the product (0.108 g, 38% yield) as a yellow solid. ESI-MS: 547.1, 549.3 $[M+H]^+$. $^1H$ NMR (400 MHz, DMSO-$d_6$) δ 8.28 (d, J=5.1 Hz, 1H), 8.08 (d, J=8.6 Hz, 1H), 7.96 (s, 1H), 7.85 (d, J=1.7 Hz, 1H), 7.56-7.47 (m, 3H), 7.25-7.17 (m, 2H), 6.65-6.58 (m, 1H), 6.40 (brs, 2H) 3.82 (s, 3H), 3.76-3.71 (m, 2H), 3.62-3.53 (m, 3H), 3.29-3.26 (m, 1H), 2.80-2.70 (m, 1H), 2.65-2.59 (m, 1H), 2.47-2.40 (m, 1H), 2.36 (s, 3H), 2.02-1.93 (m, 1H), 1.80-1.71 (m, 1H), 1.54-1.37 (m, 2H).

Example 30. 7-[3-(aminomethyl)-3-fluoropyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one

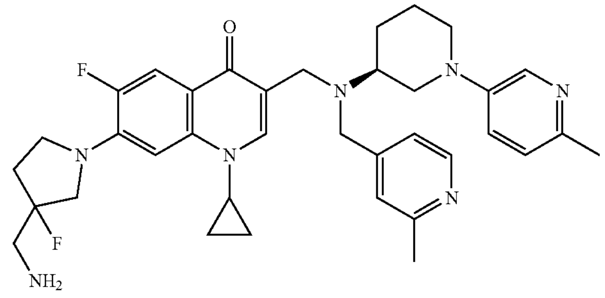

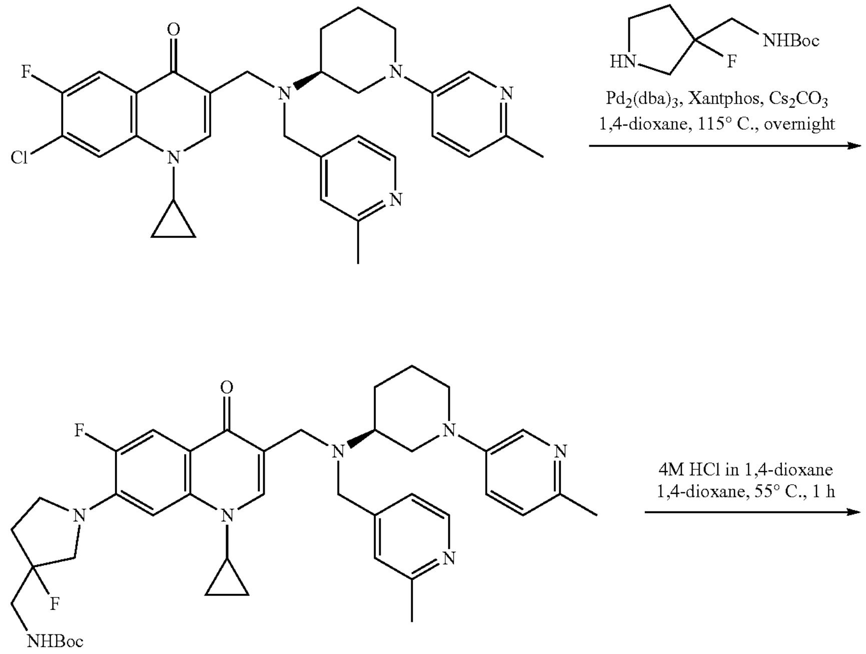

-continued

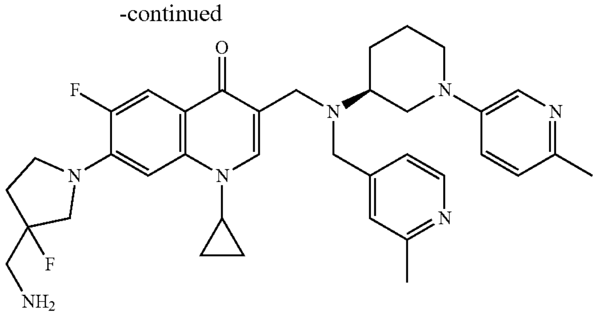

Preparation of tert-butyl N-({1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-3-fluoropyrrolidin-3-yl}methyl)carbamate A mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.24 g, 1.0 eq.), tert-butyl N-[(3-fluoropyrrolidin-3-yl)methyl]carbamate (0.144 g, 1.5 eq.), $Cs_2CO_3$ (0.46 g, 3.2 eq.) in anh. 1,4-dioxane (6.4 mL) was purged with argon for 5 min. Then, $Pd_2(dba)_3$ (0.08 g, 0.2 eq.) and Xantphos (0.076 g, 0.3 eq.) were added under inert atmosphere. The resulting mixture was purged with argon for additional 5 min and then heated overnight at 115° C. Subsequently, the mixture was cooled to ambient temperature, filtered through a pad of celite and concentrated in vacuo. The residue was purified by FCC (SiHP; DCM:MeOH). The obtained sample was dissolved in DCM, the scavenger QuadraPure MPA (0.35 g) was added and the mixture was left stirring overnight at RT. Then, the mixture was filtered and concentrated in vacuo to give the product (0.21 g, 66% yield) as a yellow solid. ESI-MS: 728.4 $[M+H]^+$.

Preparation of 7-[3-(aminomethyl)-3-fluoropyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one 4 M HCl in 1,4-dioxane solution (2.2 mL, 30.0 eq.) was added to a solution of tert-butyl N-({1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-3-fluoropyrrolidin-3-yl}methyl)carbamate (0.209 g, 1.0 eq.) in 1,4-dioxane (5.6 mL). The resulting mixture was stirred at 55° C. for 1 h and subsequently concentrated in vacuo. The residue was partitioned between DCM and NaOH aq. solution. The organic layer was dried over anh. $Na_2SO_4$, filtered and concentrated in vacuo. The residue was purified by prep-HPLC ($H_2O$:MeCN:$NH_3$) to give the product (0.13 g, 72% yield) as a white solid. ESI-MS: 628.3 $[M+H]^+$. $^1H$ NMR (400 MHz, DMSO-$d_6$) δ 8.28 (d, J=5.0 Hz, 1H), 8.12 (d, J=2.9 Hz, 1H), 7.74 (s, 1H), 7.65 (d, J=14.6 Hz, 1H), 7.25-7.18 (m, 2H), 7.18-7.14 (m, 1H), 7.02 (d, J=8.5 Hz, 1H), 6.90 (d, J=7.8 Hz, 1H), 3.89-3.53 (m, 10H), 3.48-3.38 (m, 1H), 3.03-2.85 (m, 2H), 2.81-2.68 (m, 2H), 2.62-2.52 (m, 1H), 2.38 (s, 3H), 2.32 (s, 3H), 2.25-2.10 (m, 2H), 2.05-1.92 (m, 1H), 1.94-1.59 (m, 3H), 1.60-1.38 (m, 2H), 1.29-1.15 (m, 2H), 0.92-0.75 (m, 2H).

Example 31. 1-cyclopropyl-6-fluoro-7-[(3S)-3-hydroxypiperidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride

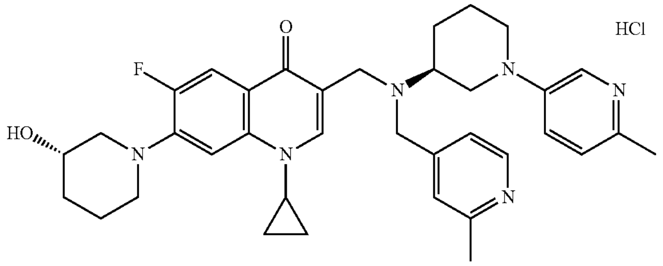

-continued

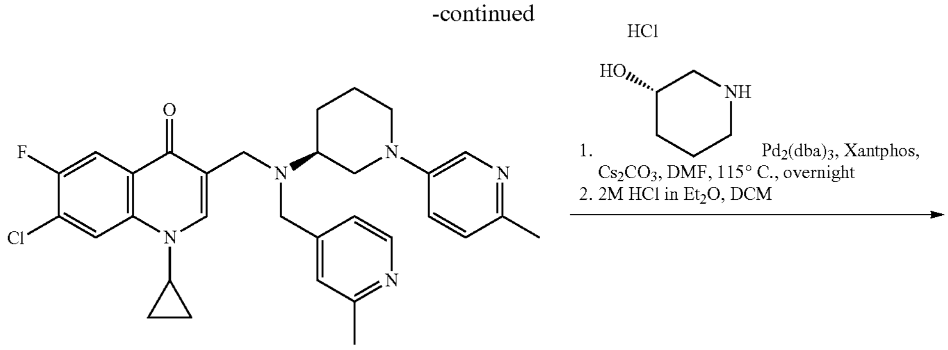

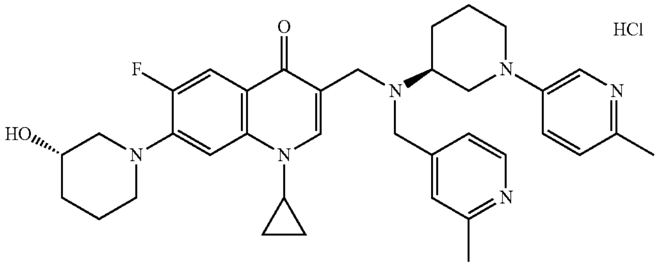

Preparation of 1-cyclopropyl-6-fluoro-7-[(3S)-3-hydroxypiperidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride A mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.15 g, 1.0 eq.), (3S)-piperidin-3-ol hydrochloride (0.113 g, 3.0 eq.), $Cs_2CO_3$ (0.2 g, 2.1 eq.) and anh. DMF (4.0 mL) was purged with argon for 5 min. Then, $Pd_2(dba)_3$ (0.05 g, 0.2 eq.) and BINAP (0.051 g, 0.3 eq.) were added. The resulting mixture was additionally purged with argon and left stirring overnight at 115° C. Subsequently, it was cooled to ambient temperature, filtered through a pad of celite and the filtrate concentrated in vacuo. The residue was dissolved in DCM and scavenger QuadraPure MPA was added. The resulting mixture was stirred overnight at RT, filtered and concentrated in vacuo. The residue was purified by FCC (SiHP; DCM:MeOH) and re-purified by prep-HPLC ($H_2O$:MeCN:$NH_3$). The obtained sample was converted into HCl salt using 2 M HCl in $Et_2O$ (0.024 mL, 1.0 eq. to FB) and DCM (5.0 mL) as a solvent to give the product (0.029 g, 16% yield) as a pale yellow solid. ESI-MS: 611.4 $[M+H]^+$. $^1H$ NMR (400 MHz, Methanol-$d_4$) δ 8.20 (d, J=5.4 Hz, 1H), 8.15 (d, J=2.9 Hz, 1H), 7.88 (s, 1H), 7.81 (d, J=13.5 Hz, 1H), 7.74-7.69 (m, 1H), 7.43-7.34 (m, 3H), 7.34-7.30 (m, 1H), 4.07-3.76 (m, 6H), 3.74-3.62 (m, 2H), 3.53-3.41 (m, 2H), 3.10-2.89 (m, 3H), 2.88-2.76 (m, 2H), 2.51 (s, 3H), 2.36 (s, 3H), 2.22-2.13 (m, 1H), 2.11-2.01 (m, 1H), 2.00-1.90 (m, 2H), 1.82-1.63 (m, 3H), 1.56-1.43 (m, 1H), 1.33-1.25 (m, 2H), 0.97-0.90 (m, 2H).

Example 32. 1-cyclopropyl-6-fluoro-7-(4-hydroxypiperidin-1-yl)-3-({[(3S)-1-(6-methylpyridin-3-yl)piperidin-3-yl][(2-methylpyridin-4-yl)methyl]amino}methyl)-1,4-dihydroquinolin-4-one hydrochloride

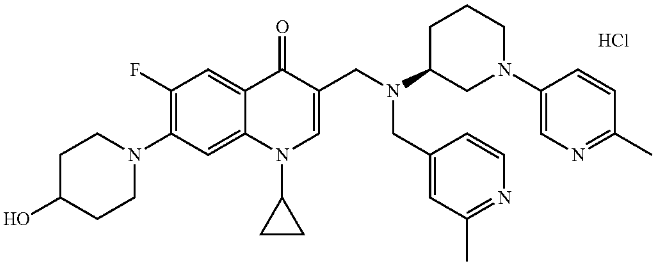

-continued

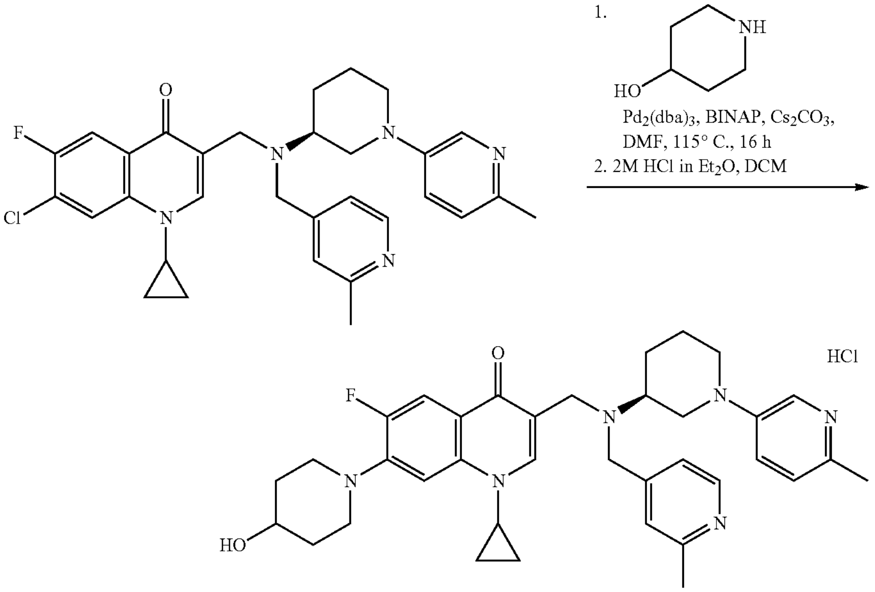

Preparation of 1-cyclopropyl-6-fluoro-7-(4-hydroxypiperidin-1-yl)-3-({[(3S)-1-(6-methylpyridin-3-yl)piperidin-3-yl][(2-methylpyridin-4-yl)methyl]amino}methyl)-1,4-dihydroquinolin-4-one hydrochloride A mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.15 g, 1.0 eq.), 4-hydroxypiperidine (0.083 g, 3.0 eq.), $Cs_2CO_3$ (0.18 g, 2.0 eq.) and BINAP (0.051 g, 0.3 eq.) was dried on a rotary evaporator under reduced pressure for 15 min. Then anh. DMF (3.0 mL) was added and the resulting mixture was stirred for 16 h at 115° C. under inert atmosphere. Afterwards, the reaction mixture was diluted with EtOAc and filtered through a pad of celite. The filtrate was concentrated in vacuo and partitioned between water and EtOAc. The organic layer was dried over anh. $Na_2SO_4$, filtered and concentrated in vacuo. The residue was purified by FCC (SiHP, DCM:MeOH). The isolated sample was dissolved in DCM and stirred for 15 min with scavenger QuadraPure MPA. The scavenger was filtered off and the filtrate was concentrated in vacuo and the residue was additionally purified by prep-HPLC ($H_2O$:MeCN:$NH_3$). The compound was converted to the HCl salt using 2 M HCl in $Et_2O$ (0.032 mL, 1.0 eq. to FB) and DCM as a solvent (10.0 mL) to provide the product (0.040 g, 93% yield) as a yellow powder. ESI-MS: 611.3 $[M+H]^+$. $^1H$ NMR (400 MHz, Methanol-$d_4$) δ 8.23-8.20 (m, 1H), 8.19-8.15 (m, 1H), 7.92-7.88 (m, 1H), 7.86-7.80 (m, 1H), 7.78-7.73 (m, 1H), 7.45-7.33 (m, 4H), 4.08-3.78 (m, 6H), 3.76-3.68 (m, 1H), 3.66-3.57 (m, 2H), 3.51-3.43 (m, 1H), 3.12-2.99 (m, 4H), 2.91-2.81 (m, 1H), 2.57-2.50 (m, 3H), 2.42-2.35 (m, 3H), 2.23-2.15 (m, 1H), 2.10-1.93 (m, 3H), 1.82-1.64 (m, 4H), 1.36-1.27 (m, 2H), 0.99-0.92 (m, 2H).

Example 33. 1-cyclopropyl-6-fluoro-7-[3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one

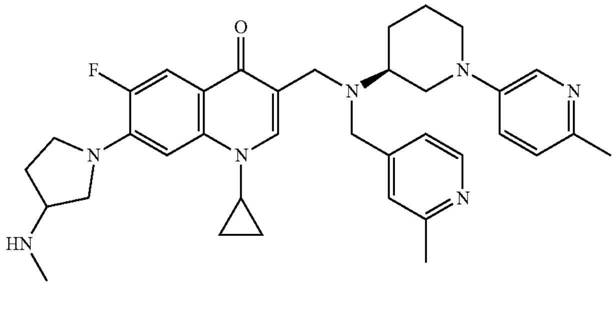

-continued

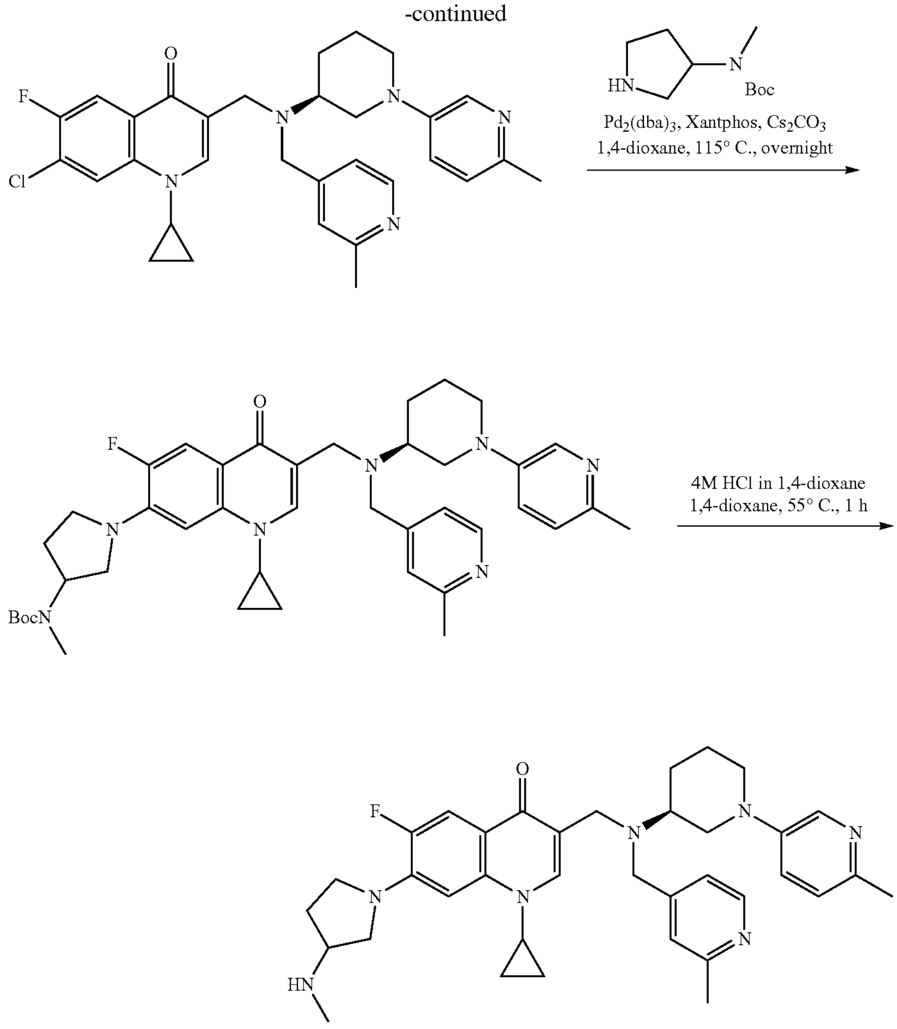

Preparation of tert-butyl N-{1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl}-N-methylcarbamate A mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.22 g, 1.0 eq.), tert-butyl N-methyl-N-(pyrrolidin-3-yl)carbamate (0.12 g, 1.5 eq.), $Cs_2CO_3$ (0.42 g, 3.2 eq.) and anh. 1,4-dioxane (5.9 mL) was purged with argon for 5 min. Then, $Pd_2(dba)_3$ (0.074 g, 0.2 eq.) and Xantphos (0.07 g, 0.3 eq.) were added. The resulting mixture was again purged with argon for a few minutes and left stirring overnight at 115° C. Subsequently, the mixture was cooled to ambient temperature, filtered through a pad of celite, the pad was washed with DCM and the filtrate was concentrated in vacuo. The residue was dissolved in DCM, scavenger QuadraPure MPA was added and the mixture was left stirring overnight at RT. Then, the mixture was filtered and concentrated in vacuo. The residue was purified by FCC (SiHP deactivated with $NH_3$; DCM:MeOH) and re-purified by RP-FCC (C18HP; $H_2O$:MeCN) to give the product (0.21 g, 73% yield) as a white solid. ESI-MS: 710.3 $[M+H]^+$.

Preparation of 1-cyclopropyl-6-fluoro-7-[3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one 4 M HCl solution in 1,4-dioxane (3.0 mL, 44.0 eq.) was added to a solution of tert-butyl N-{1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl}-N-methylcarbamate (0.194 g, 1.0 eq.) in 1,4-dioxane (5.2 mL) and the resulting mixture was stirred for 1 h at 55° C. Then, the reaction mixture was concentrated in vacuo and the residue was basified to pH ~11 with 7 M $NH_3$ solution in MeOH and purified by prep-HPLC ($H_2O$:MeCN:$NH_3$) to give the product (0.09 g, 54% yield) as a yellowish solid. ESI-MS: 610.3 $[M+H]^+$. $^1H$ NMR (400 MHz, Methanol-$d_4$) δ 8.15 (d, J=5.2 Hz, 1H), 8.08 (d, J=2.9 Hz, 1H), 7.81 (s, 1H), 7.75 (d, J=14.8 Hz, 1H), 7.34 (dd, J=8.6, 3.0 Hz, 1H), 7.24 (s, 1H), 7.23-7.17 (m, 1H), 7.10 (d, J=8.6 Hz, 1H), 6.91 (d, J=7.6 Hz, 1H), 3.89-3.68 (m, 7H), 3.64-3.54 (m, 2H), 3.47-3.34 (m, 3H), 3.00-2.89 (m, 1H), 2.89-2.78 (m, 1H), 2.71-2.62 (m, 1H), 2.44 (s, 3H), 2.40 (s, 3H), 2.35 (s, 3H), 2.30-2.20 (m, 1H), 2.18-2.09 (m, 1H), 1.98-1.85 (m, 2H), 1.74-1.57 (m, 2H), 1.30-1.20 (m, 2H), 0.96-0.81 (m, 2H).

Example 34. 3-({[(3S)-1-(6-aminopyridin-3-yl)piperidin-3-yl][(2-methylpyridinyl-4-yl)methyl]amino}methyl)-1-(propan-2-yl)-1,4-dihydroquinolin-4-one hydrochloride
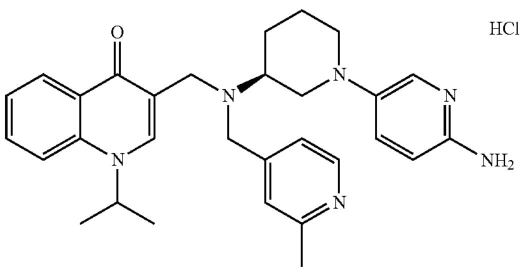
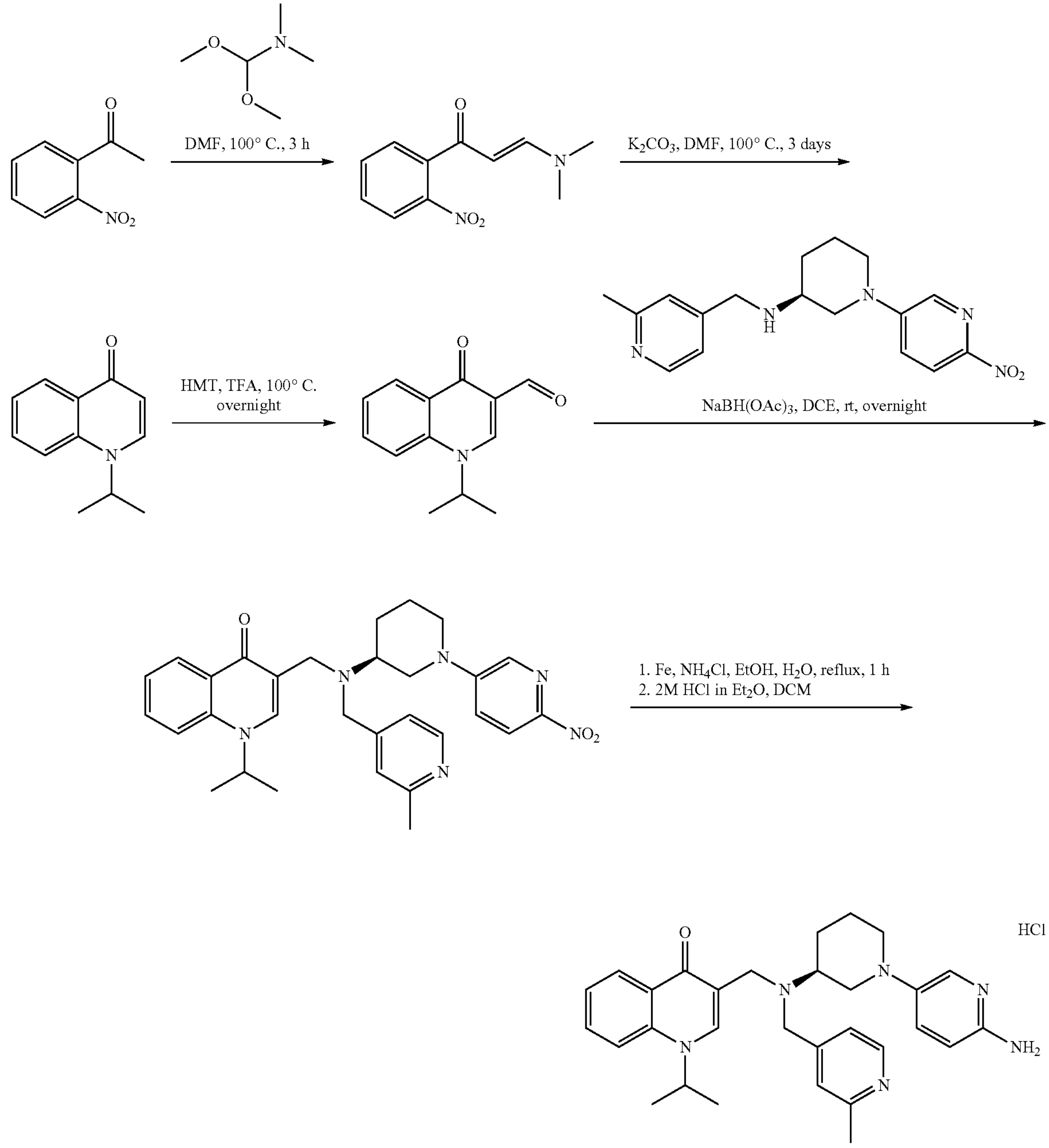

Preparation of 3-(dimethylamino)-1-(2-nitrophenyl) prop-2-en-1-one

A solution of 1-(2-nitrophenyl)ethan-1-one (0.81 mL, 1.0 eq.) and (dimethoxymethyl)dimethylamine (0.77 mL, 0.95 eq.) in DMF (5.0 mL) was heated for 3 h at 100° C. Then, the reaction mixture was concentrated under reduced pressure, and the solid formed was washed with $Et_2O$ and collected by filtration to give the product (1.14 g, 80% yield) as a yellow solid. ESI-MS: 221.3 $[M+H]^+$.

Preparation of 1-(propan-2-yl)-1,4-dihydroquinolin-4-one

A mixture of 3-(dimethylamino)-1-(2-nitrophenyl)prop-2-en-1-one (0.8 g, 1.0 eq.), $K_2CO_3$ (1.4 g, 3.0 eq.) in DMF (6.0 mL) was heated for 2 h at 100° C., and then heating was continued for 3 days at the same temperature. Afterwards, the reaction mixture was coaled to RT and partitioned between EtOAc and water. The organic layer was dried over anh. $Na_2SO_4$, filtered and concentrated in vacuo. The residue was purified by FCC (SiHP; Hex:EtOAc) to give the product (0.43 g, 65% yield) as a yellow solid. ESI-MS: 188.1 $[M+H]^+$.

Preparation of 4-oxo-1-(propan-2-yl)-1,4-dihydroquinoline-3-carbaldehyde

A mixture of 1-(propan-2-yl)-1,4-dihydroquinolin-4-one (0.43 g, 1.0 eq.), HMT (0.64 g, 2.0 eq.) and TFA (6.0 mL) was heated overnight at 100° C. Then, the reaction mixture was cooled to RT and ice-cold water was added. The resulting mixture was stirred for 10 min, then basified with sat $Na_2CO_3$ eq. solution and washed with DCM. The organic layers was dried over anh. $Na_2SO_4$, filtered and concentrated in vacuo. The residue was purified by FCC (SiHP; DCM: MeOH) give the product (0.28 g, 57% yield) as a white solid. ESI-MS: 216.3 $[M+H]^+$.

Preparation of 3-({[(2-methylpyridin-4-yl)methyl] [(3S)-1-(6-nitropyridin-3-yl)piperidin-3-yl] amino}methyl)-1-(propan-2-yl)-1,4-dihydroquinolin-4-one A pressure vessel charged with (3S)—N-[(2-methylpyridin-4-yl)methyl]-1-(6-nitropyridin-3-yl)piperidin-3-amine (Intermediate 11) (0.15 g, 1.0 eq.), 4-oxo-1-(propan-2-yl)-1,4-dihydroquinoline-3-carbaldehyde (0.099 g, 1.0 eq.) and DCE (3.0 mL) was treated with $NaBH(OAc)_3$ (0.27 g, 2.8 eq.) in portions. The resulting mixture was stirred overnight at RT and then partitioned between water and DCM. The organic layer was washed with $NaHCO_3$, brine, dried over anh. $Na_2SO_4$, filtered and concentrated in vacuo. The residue was purified by FCC (SiHP; DCM:MeOH) to give the product (0.18 g, 61% yield) as a yellow solid. ESI-MS: 527.7 $[M+H]^+$.

Preparation of 3-({[(3S)-1-(6-aminopyridin-3-yl) piperidin-3-yl][(2-methylpyridin-4-yl)methyl] amino}methyl)-1-(propan-2-yl)-1,4-dihydroquinolin-4-one hydrochloride A mixture of 3-({[(2-methylpyridin-4-yl)methyl][(3S)-1-(6-nitropyridin-3-yl)piperidin-3-yl]amino}methyl)-1-(propan-2-yl)-1,4-dihydroquinolin-4-one (0.18 g, 1.0 eq.), iron powder (0.06 g, 3.0 eq.), $NH_4Cl$ (0.09 g, 5.0 eq.), EtOH (6.0 mL) and $H_2O$ (0.5 mL) was stirred at reflux for 1 h. Then, the reaction mixture was cooled to RT, diluted with MeOH, filtered through a pad of celite and concentrated in vacuo. The residue was purified by RP-FCC (C18HP; $H_2O$:MeCN). The obtained sample was converted into the HCl salt using 2 M HCl in $Et_2O$ (0.102 mL, 1.0 eq. to FB) and DCM (2.0 mL) as a solvent to give the product (0.094 g, 51% yield) as a brownish solid. ESI-MS: 497.3 $[M+H]^+$. $^1H$ NMR (400 MHz, Methanol-$d_4$) δ 8.37 (dd, J=8.2, 1.6 Hz, 1H), 8.24-8.15 (m, 1H), 8.11 (s, 1H), 7.91-7.82 (m, 2H), 7.76 (ddd, J=8.7, 6.9, 1.7 Hz, 1H), 7.45 (ddd, J=8.0, 6.9, 0.9 Hz, 1H), 7.40-7.26 (m, 3H), 6.90 (d, J=9.5 Hz, 1H), 5.09 (hept, J=6.6 Hz, 1H), 4.06-3.78 (m, 4H), 3.78-3.67 (m, 1H), 3.43-3.35 (m, 1H), 3.11-2.93 (m, 1H), 2.86-2.72 (m, 1H), 2.70-2.52 (m, 1H), 2.36 (s, 3H), 2.18-2.06 (m, 1H), 2.01-1.87 (m, 1H), 1.77-1.56 (m, 2H), 1.50 (d, J=6.6 Hz, 6H).

Example 35. 3-({[(3S)-1-(6-aminopyridin-3-yl)piperidin-3-yl][(2-methylpyridin-4-yl)methyl] amino}methyl)-1-(oxetan-3-yl)-1,4-dihydroquinolin-4-one

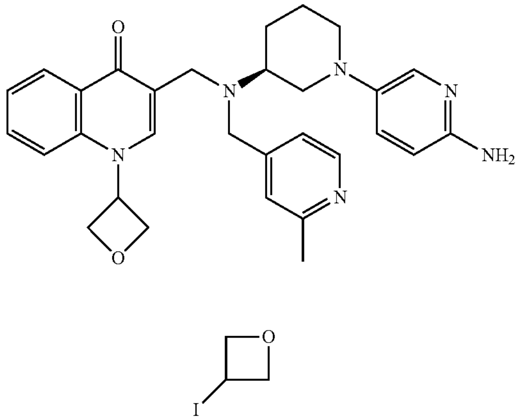

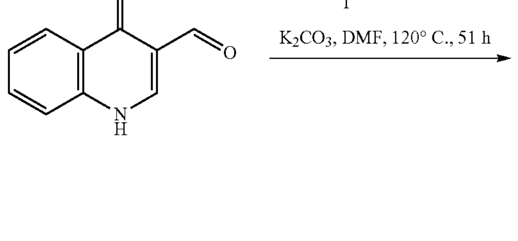

-continued

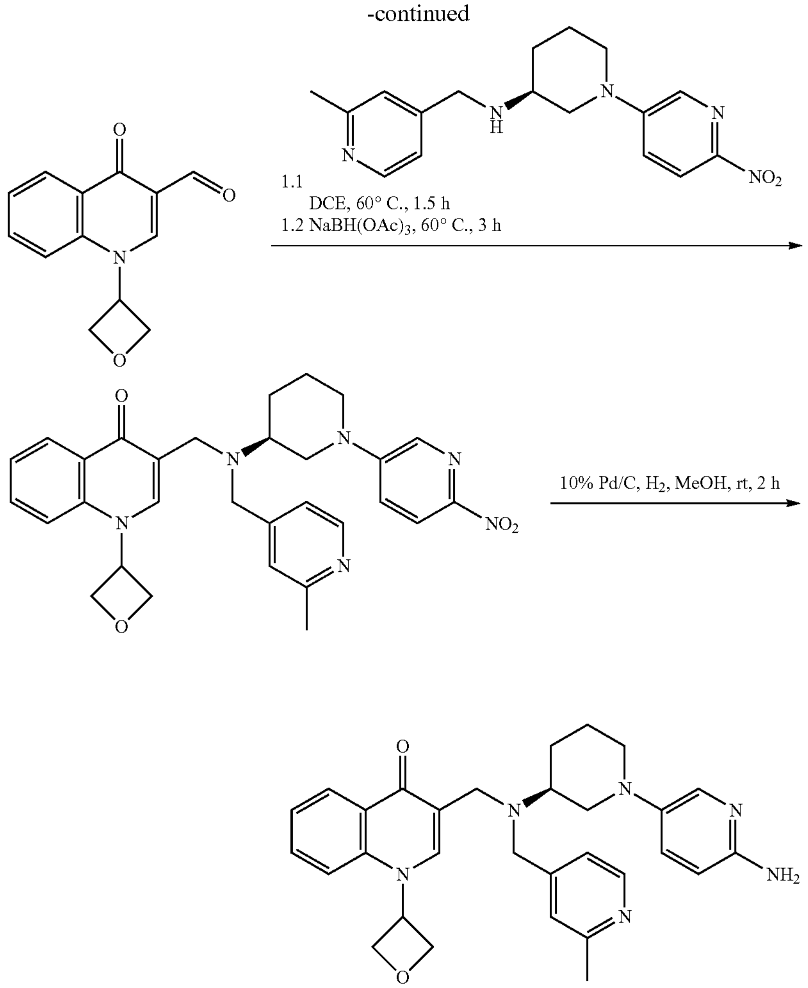

Preparation of 1-(oxetan-3-yl)-4-oxo-1,4-dihydroquinoline-3-carbaldehyde 4-oxo-1,4-dihydroquinoline-3-carbaldehyde (Intermediate 1) (0.5 g, 1.0 eq.) was added to a mixture of 3-iodooxetane (0.73 g, 1.4 eq.) and $K_2CO_3$ (1.6 g, 4.0 eq.) in DMF (13.3 mL) was added. The resulting mixture was stirred for 24 h at 120° C., then an additional portion of 3-iodooxetane (0.5 g, 0.94 eq.) was added and heating was continued for an additional 27 h at 120° C. Afterwards, the reaction mixture was filtered through a pad of celite and concentrated in vacuo. The residue was purified by FCC (SiHP; DCM:MeOH) and re-purified by RP-FCC (C18HP; $H_2O$:MeCN) to give the product (0.139 g, 21% yield) as a beige solid. ESI-MS: 230.1 $[M+H]^+$. $^1H$ NMR (400 MHz, DMSO-$d_6$) δ 10.20 (s, 1H), 8.47 (s, 1H), 8.34 (dd, J=8.0, 1.6 Hz, 1H), 7.83 (ddd, J=8.7, 7.1, 1.7 Hz, 1H), 7.60-7.55 (m, 1H), 7.51 (d, J=8.5 Hz, 1H), 5.82 (quint, J=6.9 Hz, 1H), 5.13-5.06 (m, 2H), 5.00-4.94 (m, 2H).

Preparation of 3-({[(2-methylpyridin-4-yl)methyl](3S)-1-(6-nitropyridin-3-yl)piperidin-3-yl]amino}methyl)-1-(oxetan-3-yl)-1,4-dihydroquinolin-4-one A mixture of (3S)—N-[(2-methylpyridin-4-yl)methyl]-1-(6-nitropyridin-3-yl)piperidin-3-amine (Intermediate 11) (0.095 g, 1.0 eq.), 1-(oxetan-3-yl)-4-oxo-1,4-dihydroquinoline-3-carbaldehyde (0.073 g, 1.1 eq.) and anh. DCE (3.0 mL) was stirred for 1.5 h at 60° C. Then, NaBH(OAc)$_3$ (0.154 g, 2.5 eq.) was added in portions and the resulting mixture was stirred for 3 h at 60° C. Subsequently, the reaction mixture was partitioned between NaOH aq. solution and DCM. The organic layer was dried over anh. $Na_2SO_4$, filtered and concentrated in vacuo. The residue was purified by FCC (SiHP; DCM:MeOH) to obtain the product (0.12 g, 76% yield) as a yellow solid. ESI-MS: 541.6 $[M+H]^+$.

Preparation of 3-({[(3S)-1-(6-aminopyridin-3-yl)piperidin-3-yl][(2-methylpyridin-4-yl)methyl]amino}methyl)-1-(oxetan-3-yl)-1,4-dihydroquinolin-4-one A solution of 3-({[(2-methylpyridin-4-yl)methyl][(3S)-1-(6-nitropyridin-3-yl)piperidin-3-yl]amino}methyl)-1-(oxetan-3-yl)-1,4-dihydroquinolin-4-one (0.12 g, 1.0 eq.) in MeOH (3.0 mL) was degassed in vacuo and purged with argon (3 times). Then, Pd/C (10 wt. %, 0.012 g) was added in one portion and the resulting mixture was purged again with argon (twice). Then, hydrogen was introduced and the mixture was left stirring for 2 h under the hydrogen atmosphere at RT. Then, the reaction mixture was filtered through a pad of celite and concentrated in vacuo. The residue was purified by prep-HPLC ($H_2O$:MeCN:$NH_3$) to give the product (0.037 g, 33% yield) as a white solid. ESI-MS: 511.4 $[M+H]^+$. $^1H$ NMR (400 MHz, Methanol-$d_4$) δ 8.40-8.35 (m, 1H), 8.22 (s, 1H), 8.21-8.18 (m, 1H), 7.74 (ddd, J=8.7, 7.0, 1.6 Hz, 1H), 7.67-7.64 (m, 1H), 7.46 (ddd, J=8.1, 7.0, 0.9 Hz, 1H), 7.40 (d, J=8.7 Hz, 1H), 7.35 (dd, J=8.9, 2.9 Hz, 1H), 7.32-7.24 (m, 2H), 6.58 (dd, J=8.9, 0.7 Hz, 1H), 5.82-5.73 (m, 1H), 5.25-5.17 (m, 2H), 4.88-4.83 (m, 2H), 3.92-3.86 (m, 4H), 3.68-3.58 (m, 1H), 3.32-3.26 (m, 1H), 3.09-2.96 (m, 1H), 2.76 (t, J=10.8 Hz, 1H), 2.63-2.53 (m, 1H), 2.35 (s, 3H), 2.22-2.11 (m, 1H), 1.98-1.88 (m, 1H), 1.78-1.54 (m, 2H).
Example 36. 7-amino-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one
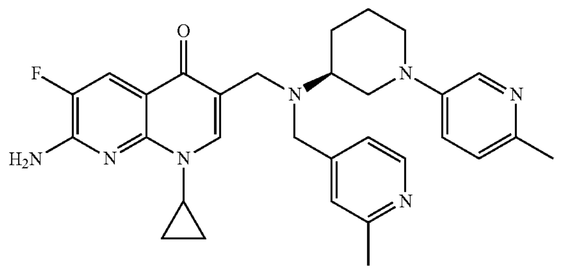 [SMILES: Cc1ccc(N2CCC[C@H](N(Cc3ccnc(C)c3)Cc3cn(C4CC4)c4cc(N)c(F)cc4c3=O)C2)cn1]
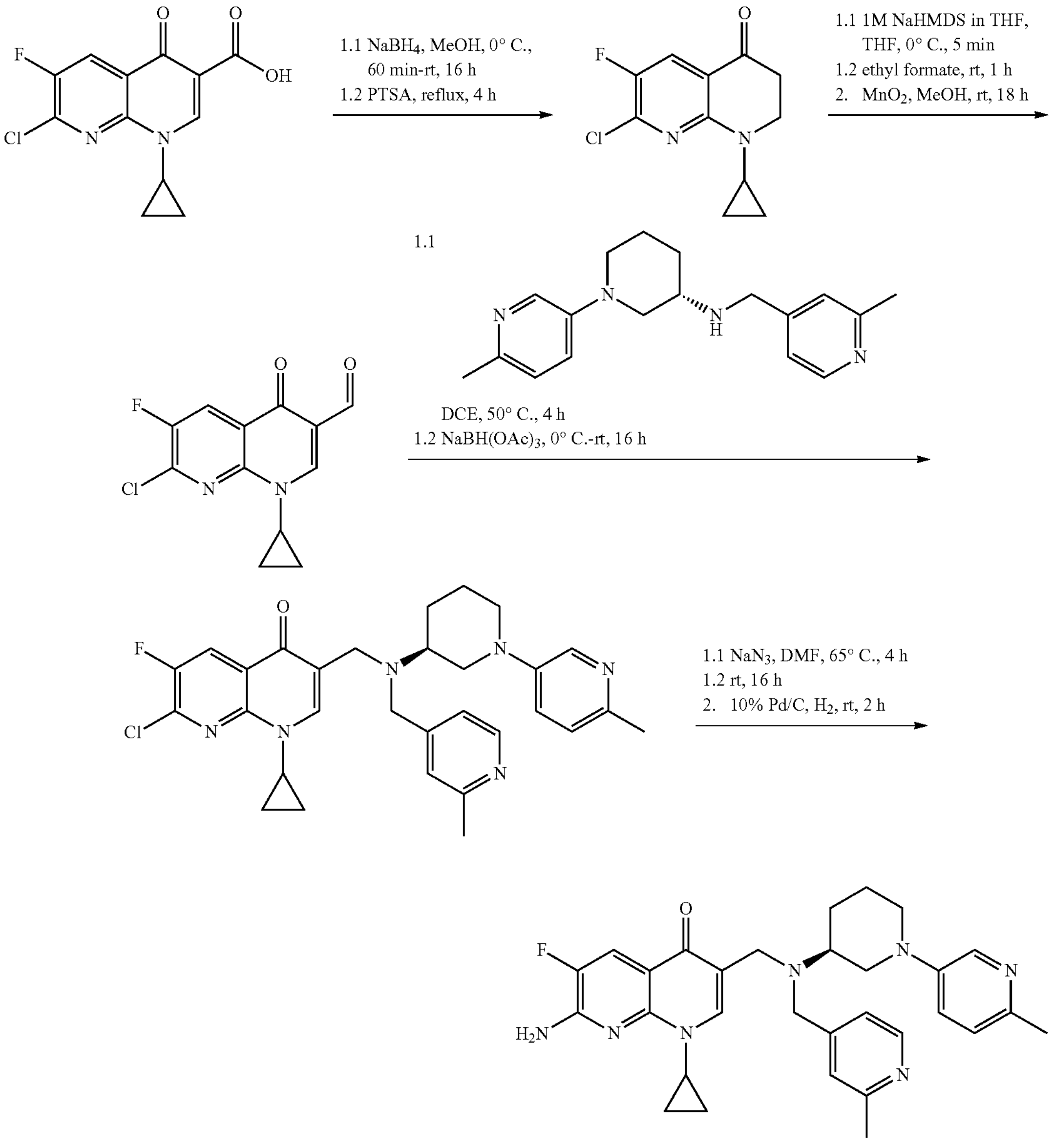

Preparation of 7-chloro-1-cyclopropyl-6-fluoro-1,2,3,4-tetrahydro-1,8-naphthyridin-4-one $NaBH_4$ (6.0 g, 4.5 eq.) was added slowly to a solution of 7-chloro-1-cyclopropyl-6-fluoro-4-oxo-1,4-dihydro-1,8-naphthyridine-3-carboxylic acid (10.0 g, 1.0 eq.) in MeOH (150.0 mL) kept under inert atmosphere in an ice cooling bath. The mixture was allowed to warm to RT and was left stirring for 16 h. Then, PTSA monohydrate (0.67 g, 0.1 eq.) was added and the resulting mixture was heated at reflux for 4 h. Afterwards, the mixture was allowed to cool to RT and the solvent was removed in vacuo. The residue was partitioned between water and DCM. The combined organic layers were dried over anh. $MgSO_4$ and concentrated in vacuo. The residue was purified by FCC (SiHP; Hex:EtOAc) to give the product (5.97 g, 70% yield) as a yellow solid. ESI-MS: 241.1 $[M+H]^+$. 1H NMR (400 MHz, DMSO-$d_6$) δ 7.90 (d, J=7.9 Hz, 1H), 3.62-3.56 (m, 2H), 2.68-2.61 (m, 3H), 0.88-0.82 (m, 2H), 0.72-0.67 (m, 2H).

Preparation of 7-chloro-1-cyclopropyl-6-fluoro-4-oxo-1,4-dihydro-1,8-naphthyridine-3-carbaldehyde A solution of 7-chloro-1-cyclopropyl-6-fluoro-1,2,3,4-tetrahydro-1,8-naphthyridin-4-one (0.59 g, 1.0 eq.) in THF (5.0 mL) was added to a solution of 1 M NaHMDS in THF (0.54 g, 1.2 eq.) in THF (5.0 mL) at 0° C. The reaction mixture was stirred for 5 min at 0° C. and then, ethyl formate (0.26 mL, 1.3 eq.) was added, stirring was continued for 1 h. The reaction was quenched by addition of saturated aq. $NH_4Cl$ solution (to pH neutral). The product was extracted into EtOAc. The combined organic layers were dried over anh. $Na_2SO_4$, filtered and concentrated in vacuo. Additionally, the aq. layer was also concentrated in vacuo and the residue was rinsed with ethyl acetate. Both the crude residues were combined and dissolved in anh. MeOH (20.0 mL) and $MnO_2$ (1.073 g, 5.0 eq.) was added. After stirring this mixture at RT for 18 h, it was filtered through celite. The filter cake was flushed with DCM-methanol mixture (1:1) and the filtrate was concentrated in vacuo. The residue was purified by FCC (SiHP; Hex:EtOAc) and re-purified by two subsequent rounds of FCC (SiHP; DCM:MeOH) and (SIHP: 15 μm; Hex:EtOAc with 2% of DCM) to give the product (0.181 g, 28% yield) as an orange solid. ESI-MS: 268.1 $[M+H]^+$.

Preparation of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one (Intermediate 15)

A dry reactor vessel was charged with (3S)-1-(6-methylpyridin-3-yl)-N-[(2-methylpyridin-4-yl)methyl]piperidin-3-amine (Intermediate 2) (0.31 g, 1.0 eq.), 7-chloro-1-cyclopropyl-6-fluoro-4-oxo-1,4-dihydro-1,8-naphthyridine-3-carbaldehyde (0.28 g, 1.0 eq.) and DCE (15.0 mL) and the resulting mixture was heated at 50° C. for 4 h. Then, the mixture was cooled to 0° C. and $NaBH(OAc)_3$ (0.45 g, 2.0 eq.) was added. The reaction was continued for 16 h at RT. Afterwards, water and sat aq. solution of $NaHCO_3$ were added and the mixture was extracted with DCM. The combined organic layers were washed with brine, dried over $Na_2SO_4$, filtered and concentrated in vacuo. The residue was purified by FCC (SiHP; DCM:MeOH) to give the product (0.46 g, 75% yield) as a yellow solid. ESI-MS: 547.5 $[M+H]^+$.

Preparation of 7-amino-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one A solution of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one (Intermediate 15) (0.1 g, 1.0 eq.) and $NaN_3$ (0.036 g, 3.0 eq.) in DMF (5.0 mL) was heated at 65° C. for 4 h. Then, the reaction mixture was allowed to cool to RT and was left stirring for 16 h. Afterwards, the reaction mixture was poured into 50.0 mL of cold water and the resulting mixture was washed with EtOAc. The organic layer was dried over anh. $MgSO_4$, filtered, concentrated in vacuo and dried. The residue was dissolved in EtOH (10.0 mL) and 10% Pd/C (0.011 g, 0.05 eq.) was added. The resulting mixture was stirred for 2 h under $H_2$ atmosphere. Then, the mixture was filtered through a pad of celite. The pad was washed with MeOH and the filtrate was concentrated in vacuo. The residue was purified by FCC (SiHP; DCM:MeOH with $NH_3$) and re-purified by RP-FCC (C18HP; $H_2O$:MeCN) to give the product (0.039 g, 40% yield) as a white solid. ESI-MS: 528.3 $[M+H]^+$. $^1H$ NMR (400 MHz, Methanol-$d_4$) δ 8.17 (d, J=5.2 Hz, 1H), 8.08 (d, J=2.9 Hz, 1H), 7.87 (d, J=10.8 Hz, 1H), 7.79 (s, 1H), 7.34 (dd, J=8.6, 3.0 Hz, 1H), 7.25 (s, 1H), 7.24-7.18 (m, 1H), 7.11 (d, J=8.6 Hz, 1H), 3.90-3.82 (m, 3H), 3.76 (s, 2H), 3.64-3.56 (m, 1H), 3.53-3.45 (m, 1H), 3.00-2.91 (m, 1H), 2.90-2.80 (m, 1H), 2.75-2.65 (m, 1H), 2.41 (s, 3H), 2.38 (s, 3H), 2.16-2.09 (m, 1H), 1.96-1.88 (m, 1H), 1.75-1.58 (m, 2H), 1.20-1.11 (m, 2H), 0.86-0.79 (m, 2H).

Example 37. 1-cyclopropyl-6-fluoro-7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1,4-dihydro-1,8-naphthyridin-4-one hydrochloride

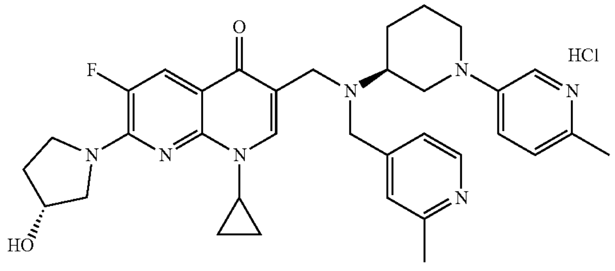

-continued

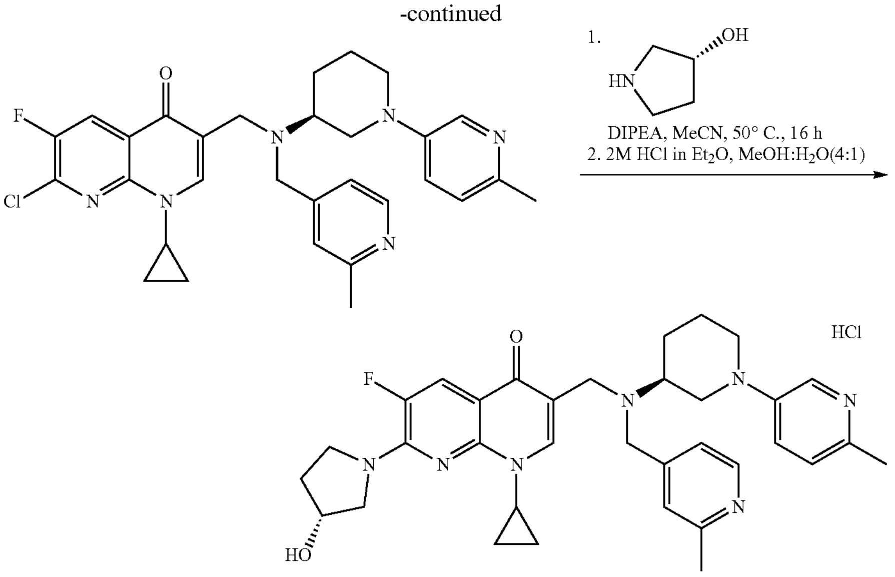

Preparation of 1-cyclopropyl-6-fluoro-7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1,4-dihydro-1,8-naphthyridin-4-one hydrochloride DIPEA (0.157 mL, 2.0 eq.) was added to a mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one (Intermediate 15) (0.247 g, 1.0 eq.) and (3R)-pyrrolidin-3-ol (0.047 mL, 1.3 eq.) in MeCN (5.0 mL) at 25° C. The resulting mixture was heated for 16 h at 50° C. and subsequently partitioned between water and DCM. The organic layer was dried over anh. $Na_2SO_4$, filtered and concentrated in vacuo. The residue was purified by FCC (SiHP; DCM:MeOH) and re-purified by RP-FCC (C18HP; $H_2O$:MeCN). The compound was converted to the HCl salt using 2 M HCl in $Et_2O$ (0.175 mL, 1.05 eq.) and a mixture of MeOH (21.0 mL) and $H_2O$ (5.0 mL) as a solvent to provide the product (0.21 g, 99% yield) as a yellow solid. ESI-MS: 598.3 $[M+H]^+$. $^1H$ NMR (400 MHz, Methanol-$d_4$) δ 8.20 (d, J=5.2 Hz, 1H), 8.12 (d, J=2.9 Hz, 1H), 7.87 (d, J=13.2 Hz, 1H), 7.81 (s, 1H), 7.56-7.48 (m, 1H), 7.34-7.30 (m, 1H), 7.29-7.22 (m, 2H), 4.59-4.51 (m, 1H), 4.02-3.75 (m, 9H), 3.71-3.62 (m, 1H), 3.53-3.44 (m, 1H), 3.05-2.88 (m, 2H), 2.84-2.70 (m, 1H), 2.47 (s, 3H), 2.41 (s, 3H), 2.22-2.02 (m, 3H), 2.02-1.88 (m, 1H), 1.80-1.62 (m, 2H), 1.24-1.15 (m, 2H), 0.91-0.80 (m, 2H).

Example 38. 3-({[(3S)-1-(6-aminopyridin-3-yl)piperidin-3-yl][(2-methylpyridin-4-yl)methyl]amino}methyl)-1,4-dihydroquinolin-4-one

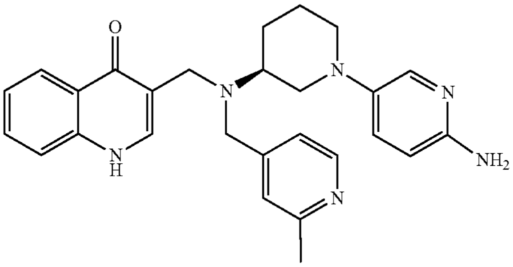

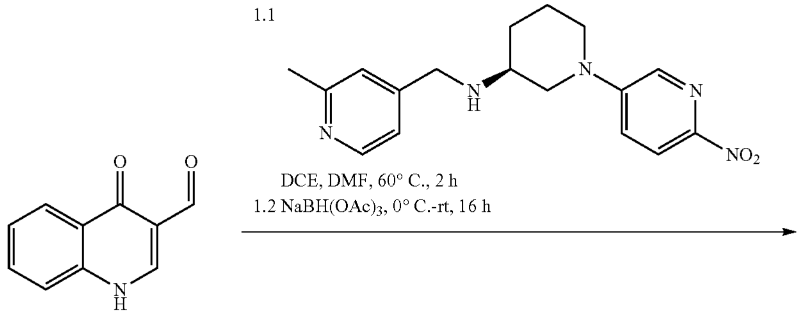

-continued

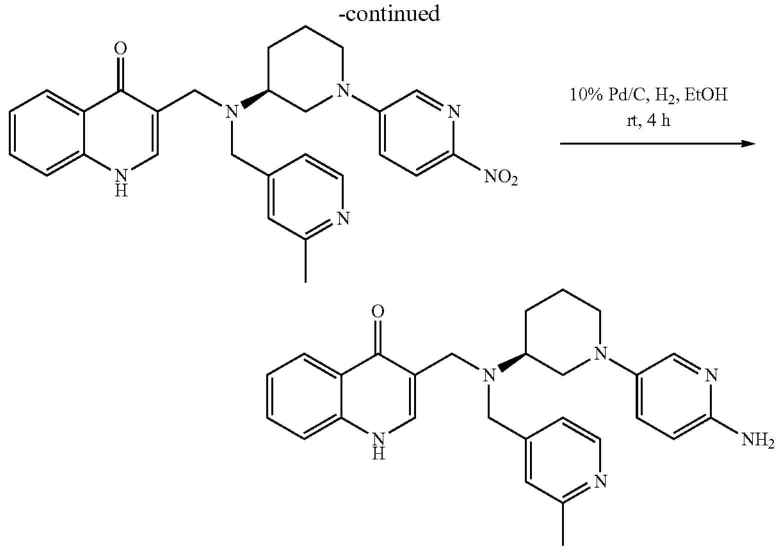

Preparation of 3-({[(2-methylpyridin-4-yl)methyl][(3S-1-(nitropyridin-3-yl)piperidin-3-yl]amino}methyl)-1,4-dihydroquinolin-4-one A dry reactor vessel was charged with (3S)-[(2-methylpyridin-4-yl)methyl]-1-(6-nitropyridin-3-yl)piperidin-3-amine (Intermediate 11) (0.38 g, 1.0 eq.), 4-oxo-1,4-dihydroquinoline-3-carbaldehyde (Intermediate 1) (0.2 g, 1.0 eq.) and a mixture of DCE and DMF (19.0 mL, v/v, 15/4). The reaction mixture was stirred for 2 h at 60° C. Then, the mixture was cooled to 0° C. and $NaBH(OAc)_3$ (0.49 g, 2.0 eq.) was added and the reaction was continued for 16 h at RT. Afterwards, water and sat. $NaHCO_3$ aq. solution were added and the resulting mixture was washed with DCM. The combined organic layers were washed with brine, dried over anh. $Na_2SO_4$, filtered and concentrated in vacuo. The residue was purified by FCC (SIHP; DCM:MeOH) and repurified by prep-HPLC ($H_2O$:MeCN:$NH_3$) to give the product (0.35 g, 60% yield) as a yellow solid. ESI-MS: 485.2 $[M+H]^+$. $^1H$ NMR (300 MHz, Methanol-$d_4$) δ 8.29-8.20 (m, 1H), 8.18 (d, J=5.4 Hz, 1H), 8.14-8.06 (m, 2H), 7.99 (s, 1H), 7.65 (ddd, J=8.4, 7.0, 1.5 Hz, 1H), 7.52-7.46 (m, 1H), 7.44-7.34 (m, 2H), 7.27 (d, J=8.5 Hz, 2H), 4.31-4.19 (m, 1H), 4.11-3.95 (m, 1H), 3.91-3.74 (m, 4H), 3.25-3.14 (m, 1H), 3.11-2.96 (m, 1H), 2.97-2.79 (m, 1H), 2.37 (s, 3H), 2.23-2.10 (m, 1H), 1.99-1.73 (m, 2H), 1.71-1.50 (m, 1H).

Preparation of 3-({[(3S)-1-(6-aminopyridin-3-yl)piperidin-3-yl][(2-methylpyridin-4-yl)methyl]amino}methyl)-1,4-dihydroquinolin-4-one 10% Pd/C (0.03 g, 0.1 eq.) was added to a solution of the 3-({[(2-methylpyridin-4-yl)methyl][(3S)-1-(6-nitropyridin-3-yl)piperidin-3-yl]amino}methyl)-1,4-dihydroquinolin-4-one (0.13 g, 1.0 eq.) in EtOH (10.0 mL). The resulting mixture was stirred under $H_2$ atmosphere for 4 h. Then, the reaction mixture was filtered through a pad of celite. The pad was washed with MeOH and the filtrate was concentrated in vacuo. The residue was purified by prep-H PLC ($H_2O$:MeCN:TFA). The sample was basified with saturated aq. solution of $NaHCO_3$ and re-purified by RP-FCC (C18HP; $H_2O$:MeCN) to give the product (0.06 g, 48% yield) as a white solid. ESI-MS: 455.7 $[M+H]^+$. $^1H$ NMR (400 MHz, Methanol-$d_4$) δ 8.26 (ddd, J=8.3, 1.5, 0.6 Hz, 1H), 8.19 (dd, J=5.1, 0.8 Hz, 1H), 8.02 (s, 1H), 7.69-7.63 (m, 2H), 7.53-7.49 (m, 1H), 7.39 (ddd, J=8.1, 6.9, 1.1 Hz, 1H), 7.34 (dd, J=8.9, 2.9 Hz, 1H), 7.29-7.25 (m, 2H), 6.59-6.56 (m, 1H), 3.88-3.78 (m, 4H), 3.63-3.56 (m, 1H), 3.29-3.26 (m, 1H), 3.02-2.92 (m, 1H), 2.77-2.69 (m, 1H), 2.59-2.50 (m, 1H), 2.39 (s, 3H), 2.16-2.08 (m, 1H), 1.94-1.86 (m, 1H), 1.73-1.52 (m, 2H).

Example 39. 1-cyclopropyl-6-fluoro-7-[(3S)-3-hydroxypyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride

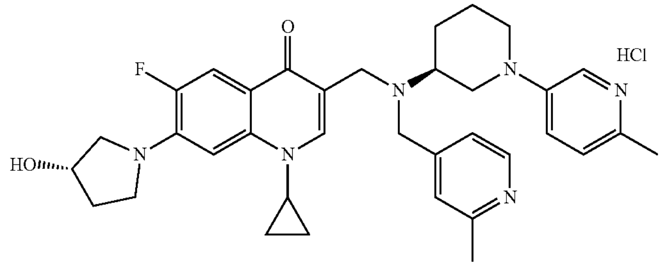

-continued

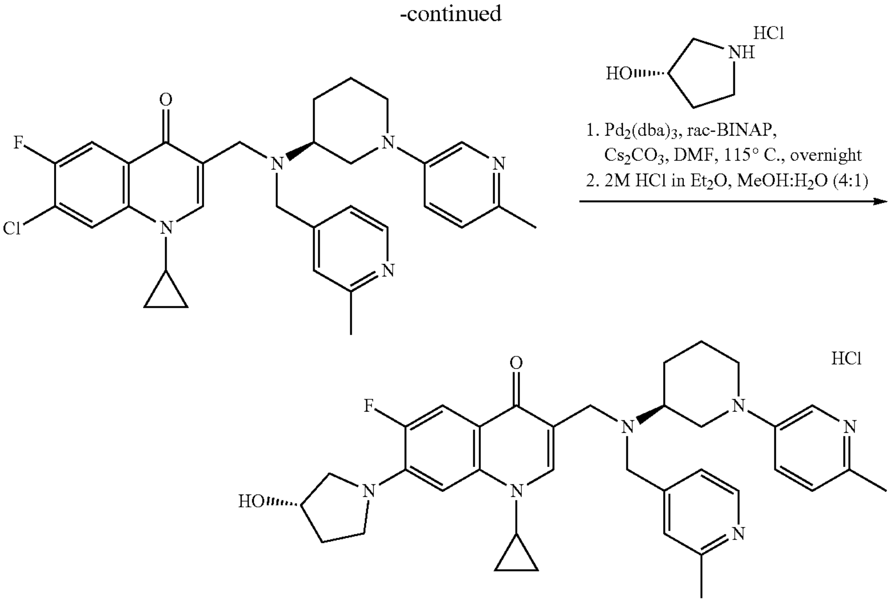

Preparation of 1-cyclopropyl-6-fluoro-7-[(3S)-3-hydroxypyrrolidin-1-yl]-3-({[(3S)-1-(6-methylpyridin-3-yl)piperidin-3-yl][(2-methylpyridin-4-yl) methyl]amino}methyl)-1,4-dihydroquinolin-4-one hydrochloride A pressure vessel was charged with 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.3 g, 1.0 eq.), (3S)-pyrrolidin-3-ol hydrochloride (0.136 g, 2.0 eq.), $Cs_2CO_3$ (0.38 g, 2.1 eq.) and DMF (3.0 mL). The resulting mixture was purged with argon for 5 min. Subsequently, BINAP (0.034 g, 0.1 eq.) and $Pd_2(dba)_3$ (0.028 g, 0.05 eq.) were added, the vessel was closed and the resulting mixture was stirred overnight at 115° C. Then, the reaction mixture was filtered through a pad of celite and concentrated in vacuo. The residue was purified by two consecutive FCCs (SiHP; DCM:MeOH) and (SiHP, 15 μm; DCM:MeOH) followed by RP-FCC ($H_2O$:MeCN) and re-purified by prep-HPLC ($H_2O$:MeCN:$NH_3$). After trituration with $Et_2O$ the precipitate was filtered off and dried in vacuo. The isolated sample was converted into the HCl salt using 2 M HCl in $Et_2O$ (0.042 mL, 1.0 eq. to FB) and a mixture of MeOH (20.0 mL) and $H_2O$ (5.0 mL) as the solvent to give the product (0.053 g, 15% yield) as a yellow solid. ESI-MS: 597.3 $[M+H]^+$. $^1H$ NMR (400 MHz, Methanol-$d_4$) δ 8.31 (d, J=5.8 Hz, 1H), 8.26 (d, J=3.0 Hz, 1H), 8.07-8.02 (m, 1H), 7.88 (s, 1H), 7.75 (d, J=14.6 Hz, 1H), 7.70-7.59 (m, 3H), 6.94 (d, J=7.7 Hz, 1H), 4.60-4.54 (m, 1H), 4.24-4.12 (m, 3H), 4.07-3.74 (m, 51H), 3.69-3.61 (m, 1H), 3.58-3.53 (m, 1H), 3.48-3.40 (m, 1H), 3.23-3.08 (m, 2H), 2.98-2.88 (m, 1H), 2.62 (s, 3H), 2.50 (s, 3H), 2.29-1.96 (m, 4H), 1.89-1.66 (m, 2H), 1.37-1.27 (m, 2H), 1.02-0.94 (m, 2H).

Example 40. 3-({[(3S)-1-[6-(hydroxymethyl)pyridin-3-yl]piperidin-3-yl][(2-methylpyridin-4-yl) methyl]amino}methyl)-1-methyl-1,4-dihydroquinolin-4-one

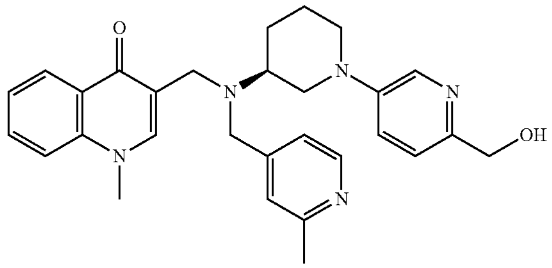

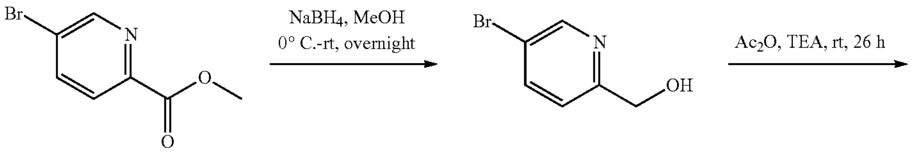

-continued

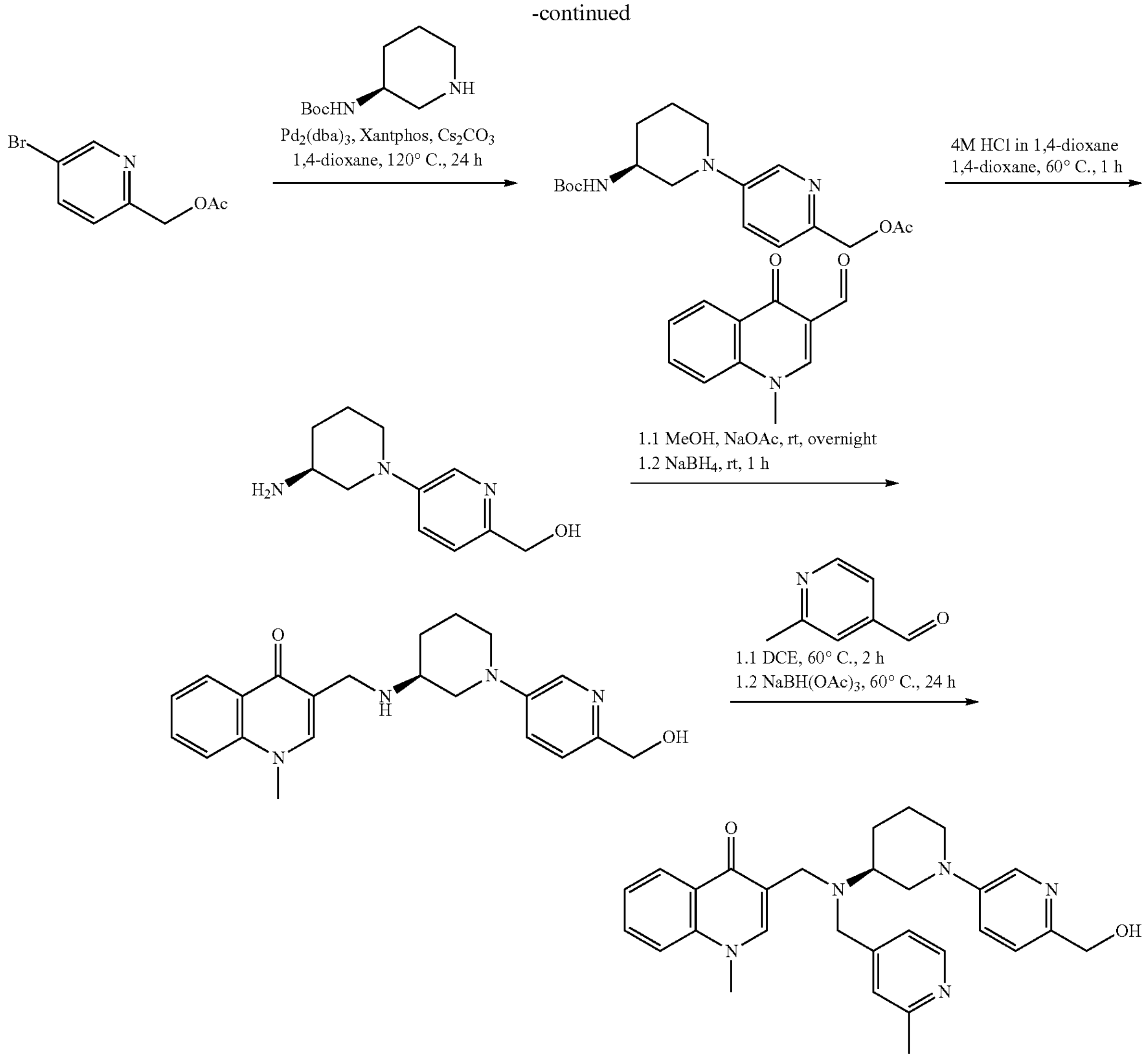

Preparation of (5-bromopyridin-2-yl)methanol

NaBH$_4$ (0.82 g, 2.5 eq.) was added in portions to a solution of methyl 5-bromopyridine-2-carboxylate (1.87 g, 1.0 eq.) in anh. MeOH (20.0 mL) coaled to 0° C. The resulting mixture was stirred overnight at RT under argon atmosphere. Then, the reaction mixture was concentrated in vacuo and the residue was partitioned between NaOH aq. solution and DCM. The combined organic layers were dried over anh. Na$_2$SO$_4$, filtered and concentrated in vacuo to give the product (1.6 g, 98% yield) as a colorless oil. ESI-MS: 188.0 [M+H]$^+$.

Preparation of (5-bromopyridin-2-yl)methyl acetate

Ac$_2$O (2.0 mL, 2.5 eq.) was added to a solution of (5-bromopyridin-2-yl)methanol (1.6 g, 1.0 eq.) and TEA (4.74 mL, 4.0 eq.) in anh. DCM (20.0 mL). The resulting mixture was stirred for 26 h at RT under argon atmosphere. Then, the reaction mixture was partitioned between NaOH aq. solution and DCM. The combined organic layers were dried over anh. Na$_2$SO$_4$, filtered and concentrated in vacuo. The residue was purified by two consecutive FCCs (SiHP; Hex:EtOAc) to give the product (1.5 g, 77% yield) as a yellow solid. ESI-MS: 230.1 [M+H]$^+$.

Preparation of {5-[(3S)-3-{[(tert-butoxy)carbonyl]amino}piperidin-1-yl]pyridin-2-yl}methyl acetate A mixture of tert-butyl N-[(3S)-piperidin-3-yl]carbamate (1.12 g, 1.3 eq.), (5-bromopyridin-2-yl)methyl acetate (1.0 g, 1.0 eq.), Cs$_2$CO$_3$ (2.8 g, 2 eq.) and anh. 1,4-dioxane (20.0 mL) was purged with argon for 10 min. Then, Pd$_2$(dba)$_3$ (0.197 g, 0.05 eq.) and Xantphos (0.149 g, 0.06 eq.) were added under inert atmosphere and the resulting mixture was again purged with argon for another 10 min. Then, the mixture was stirred for 24 h at 120° C. Subsequently, the reaction mixture was cooled to ambient temperature, filtered through a pad of celite and concentrated under reduced pressure. The residue was purified by FCC (SiHP; Hex: EtOAc) to give the product (0.98 g, 61% yield) as a dark brown oil. ESI-MS: 350.3 [M+H]$^+$.

Preparation of (5-[(3S)-3-aminopiperidin-1-yl]pyridin-2-ylmethanol

To a solution of {5-[(3S)-3-{[(tert-butoxy)carbonyl]amino}piperidin-1-yl]pyridin-2-yl}methyl acetate (0.98 g, 1.0 eq.) in 1,4-dioxane (7.0 mL) was added 4M HCl in 1,4-dioxane solution (3.3 g, 5.0 eq.). The resulting mixture was stirred for 1 h at 60° C. Then, the reaction mixture was concentrated in vacuo. The residue was partitioned between NaOH aq. solution and a mixture of $CHCl_3$ and iPrOH (4/1). The combined organic layers were dried over anh. $Na_2SO_4$, filtered and concentrated in vacuo to give product (0.46 g, 74% yield) as a dark brown oil. ESI-MS: 208.1 $[M+H]^+$.

Preparation of 3-({[(3S)-1-[6-(hydroxymethyl)pyridin-3-yl]piperidin-3-yl]amino}methyl)-1-methyl 1,4-dihydroquinolin-4-one A solution of 1-methyl-4-oxo-1,4-dihydroquinoline-3-carbaldehyde (Intermediate 7) (0.33 g, 1.0 eq.), NaOAc (0.14 g, 1.0 eq.) and {5-[(3S)-3-aminopiperidin-1-yl]pyridin-2-yl}methanol (0.46 g, 1.1 eq.) in anh. MeOH (10.0 mL) was stirred overnight at RT. Then, $NaBH_4$ (0.09 g, 1.3 eq.) was added and the resulting mixture was stirred for 1 h at RT. Afterwards, the reaction mixture was concentrated in vacuo and the residue was partitioned between NaOH aq. solution and DCM. The organic layer was dried over anh. $Na_2SO_4$, filtered and concentrated in vacuo. The residue was purified by RP-FCC (C18HP; $H_2O$:MeCN) to give the product (0.34 g, 51% yield) as a white solid. ESI-MS: 379.6 $[M+H]^+$.

Preparation of 3-({[(3S)-1-[6-(hydroxymethyl)pyridin-3-yl]piperidin-3-yl][(2-methylpyridin-4-yl)methyl]amino}methyl)-1-methyl-1,4-dihydroquinolin-4-one A mixture of 2-methylpyridine-4-carbaldehyde (0.07 g, 1.2 eq.) and 3-({[(3S)-1-[6-(hydroxymethyl)pyridin-3-yl]piperidin-3-yl]amino}methyl)-1-methyl-1,4-dihydroquinolin-4-one (0.2 g, 1.0 eq.) in DCE (5.0 mL) was stirred for 2 h at 60° C. Then, $NaBH(OAc)_3$ (0.28 g, 2.5 eq.) was added and the resulting mixture was stirred for an additional 24 h at 60° C. Subsequently, the reaction mixture was partitioned between NaOH aq. solution and DCM. The organic layer was dried over anh. $Na_2SO_4$, filtered and concentrated in vacuo. The residue was purified by RP-FCC (C18HP; $H_2O$: MeCN) to give the product (0.088 g, 34% yield) as a white solid. ESI-MS: 484.9 $[M+H]^+$. $^1H$ NMR (400 MHz, DMSO-$d_6$) δ 8.31-8.27 (m, 1H), 8.22-8.17 (m, 2H), 8.04 (s, 1H), 7.72 (ddd, J=8.6, 6.9, 1.7 Hz, 1H), 7.63 (d, J=8.4 Hz, 1H), 7.38 (ddd, J=8.0, 6.9, 1.0 Hz, 1H), 7.32 (dd, J=8.7, 2.9 Hz, 1H), 7.27-7.20 (m, 3H), 5.15 (t, J=5.8 Hz, 1H), 4.43 (d, J=5.8 Hz, 2H), 3.96-3.88 (m, 1H), 3.86 (s, 3H), 3.82-3.55 (m, 5H), 2.83 (t, J=11.3 Hz, 1H), 2.78-2.58 (m, 2H), 2.38 (s, 3H), 2.07-1.95 (m, 1H), 1.82-1.71 (m, 1H), 1.63-1.39 (m, 2H).

Example 41. 1-(2-hydroxyethyl)-3-({[(3S)-1-(6-methylpyridin-3-yl)piperidin-3-yl][(2-methylpyridin-4-yl)methyl]amino}methyl)-1,4-dihydroquinolin-4-one

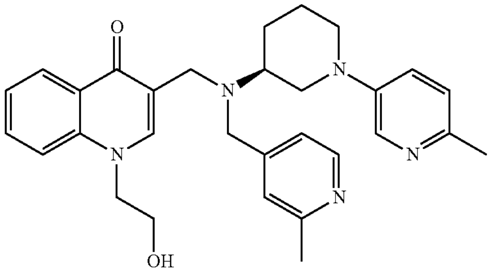

-continued

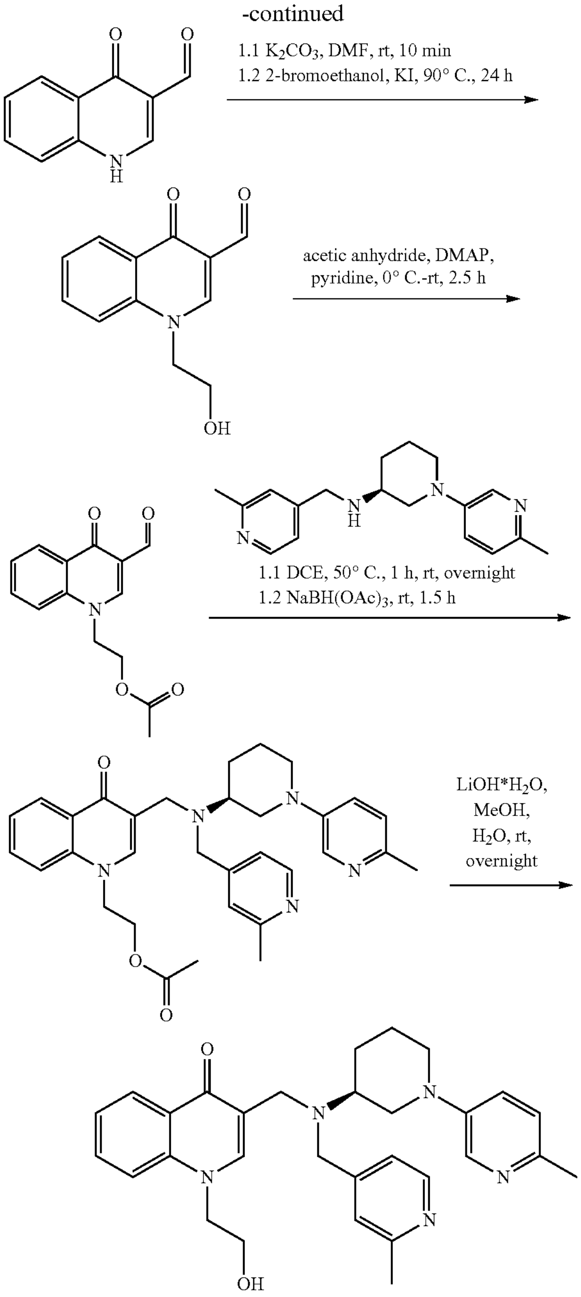

Preparation of 1-(2-hydroxyethyl)-4-oxo-1,4-dihydroquinoline-3-carbaldehyde 4-oxo-1,4-dihydroquinoline-3-carbaldehyde (Intermediate 1) (0.5 g, 1.0 eq.) was suspended in anh. DMF (20.0 mL) and $K_2CO_3$ (1.12 g, 2.8 eq.) was added. The resulting mixture was stirred for 10 min at RT and then KI (1.3 g, 2.8 eq.) and 2-bromoethanol (0.57 mL, 2.8 eq.) were added sequentially. The reaction mixture was stirred at 90° C. for 24 h. Subsequently the mixture was filtered through a funnel and the residue was washed with DCM. The filtrate was concentrated in vacuo and the residue was purified by FCC (SiHP; DCM:MeOH) and re-purified by FCC (SiHP; DCM: EtOAc) to give the product (0.16 g, 25% yield) as a beige solid. ESI-MS: 218.2 $[M+H]^+$.

Preparation of 2-(3-formyl-4-oxo-1,4-dihydroquinolin-1-yl)ethyl acetate

Acetic anhydride (0.1 mL, 2.3 eq.) was added to a mixture of 1-(2-hydroxyethyl)-4-oxo-1,4-dihydroquinoline-3-carbaldehyde (0.1 g, 1.0 eq.), DMAP (0.003 g, 0.05 eq.) and pyridine (2.0 mL) placed in a cooling bath and the mixture was stirred at RT for 2.5 h. The mixture was diluted with sat. $NaHCO_3$ aq. solution and the product was extracted into ethyl acetate. The organic layer was washed with brine, dried over anh. $Na_2SO_4$, filtered and concentrated in vacuo. The residue was purified by FCC (SiHP; Hex:EtOAc) to give the product (0.082 g, 69% yield) as a white solid. ESI-MS: 260.3 $[M+H]^+$.

Preparation of 2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]ethyl acetate A mixture of 2-(3-formyl-4-oxo-1,4-dihydroquinolin-1-yl)ethyl acetate (0.082 g, 1.0 eq.), (3S)-1-(6-methylpyridin-3-yl)-N-[(2-methylpyridin-4-yl)methyl]piperidin-3-amine (Intermediate 2) (0.11 g, 1.1 eq.) and DCE (5.0 mL) was heated at 50° C. for 1 h and then left stirring overnight at RT. Subsequently, $NaBH(OAc)_3$ (0.15 g, 2.2 eq.) was added and the resulting mixture was stirred for 1.5 h at RT. Then, the mixture was partitioned between water and DCM. The organic layer was washed with water, brine, dried over anh. $Na_2SO_4$, filtered and concentrated in vacuo. The residue was purified by FFC (SiHP; DCM:MeOH) to give the product (0.103 g, 61% yield) as a yellow solid. ESI-MS: 540.1 $[M+H]^+$. $^1$H NMR (400 MHz, DMSO-$d_6$) δ 8.29 (d, J=5.1 Hz, 1H), 8.20 (dd, J=8.1, 1.6 Hz, 1H), 8.13 (d, J=2.9 Hz, 1H), 8.02 (s, 1H), 7.77 (d, J=8.6 Hz, 1H), 7.70 (ddd, J=8.6, 6.8, 1.7 Hz, 1H), 7.36 (ddd, J=7.9, 6.8, 1.0 Hz, 1H), 7.30-7.23 (m, 2H), 7.20 (dd, J=8.5, 3.0 Hz, 1H), 7.01 (d, J=8.5 Hz, 1H), 4.58 (t, J=5.2 Hz, 2H), 4.33 (t, J=5.2 Hz, 2H), 3.89-3.52 (m, 6H), 2.81-2.69 (m, 2H), 2.61-2.53 (m, 1H), 2.39 (s, 3H), 2.32 (s, 3H), 2.04-1.94 (m, 1H), 1.77 (s, 3H), 1.76-1.71 (m, 1H), 1.59-1.36 (m, 2H).

Preparation of 1-(2-hydroxyethyl)-3-({[(3S)-1-(6-methylpyridin-3-yl)piperidin-3-yl][(2-methylpyridin-4-yl)methyl]amino}methyl)-1,4-dihydroquinolin-4-one A mixture of 2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]ethyl acetate (0.097 g, 1.0 eq.), LiOH*$H_2O$ (0.038 g, 5.0 eq.), methanol (5.0 mL) and $H_2O$ (1.0 mL) was stirred overnight at RT. Then, the mixture was diluted with water and sat. $NaHCO_3$ aq. solution and the product was extracted into DCM. The organic layer was dried over anh. $Na_2SO_4$, filtered and concentrated in vacuo. The residue was purified by prep-HPLC ($H_2O$:MeCN:$NH_3$) to give the product (0.047 g, 52% yield) as a light yellow solid. ESI-MS: 498.5 $[M+H]^+$. $^1$H NMR (400 MHz, DMSO-$d_6$) δ 8.29 (d, J=5.0 Hz, 1H), 8.20 (dd, J=8.1, 1.6 Hz, 1H), 8.13 (d, J=3.0 Hz, 1H), 8.03 (s, 1H), 7.73 (d, J=8.6 Hz, 1H), 7.67 (ddd, J=8.6, 6.7, 1.7 Hz, 1H), 7.34 (ddd, J=8.0, 6.8, 1.0 Hz, 1H), 7.27 (s, 1H), 7.24 (d, J=5.0 Hz, 1H), 7.20 (dd, J=8.5, 3.0 Hz, 1H), 7.00 (d, J=8.5 Hz, 1H), 4.99 (t, J=5.3 Hz, 1H), 4.43-4.26 (m, 2H), 3.88-3.69 (m, 5H), 3.66-3.54 (m, 3H), 2.80-2.67 (m, 2H), 2.62-2.53 (m, 1H), 2.39 (s, 3H), 2.31 (s, 3H), 2.05-1.91 (m, 1H), 1.81-1.67 (m, 1H), 1.59-1.38 (m, 2H).

Example 42. 6-fluoro-7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one

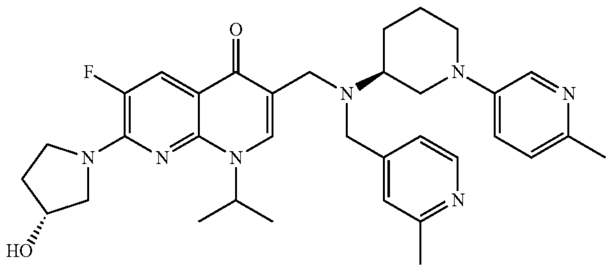

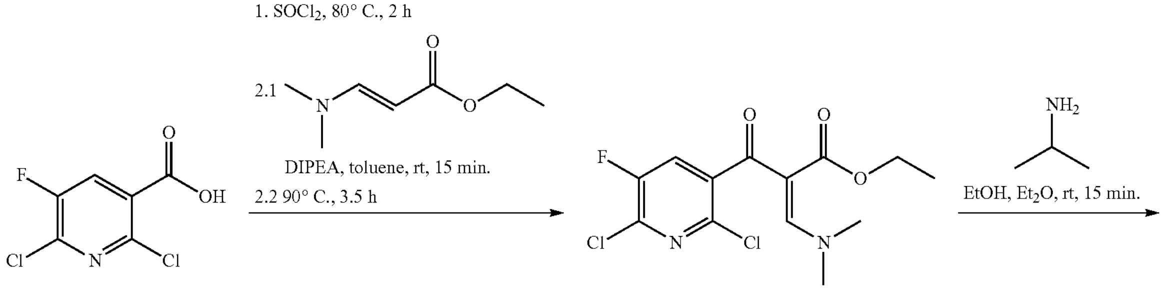

-continued

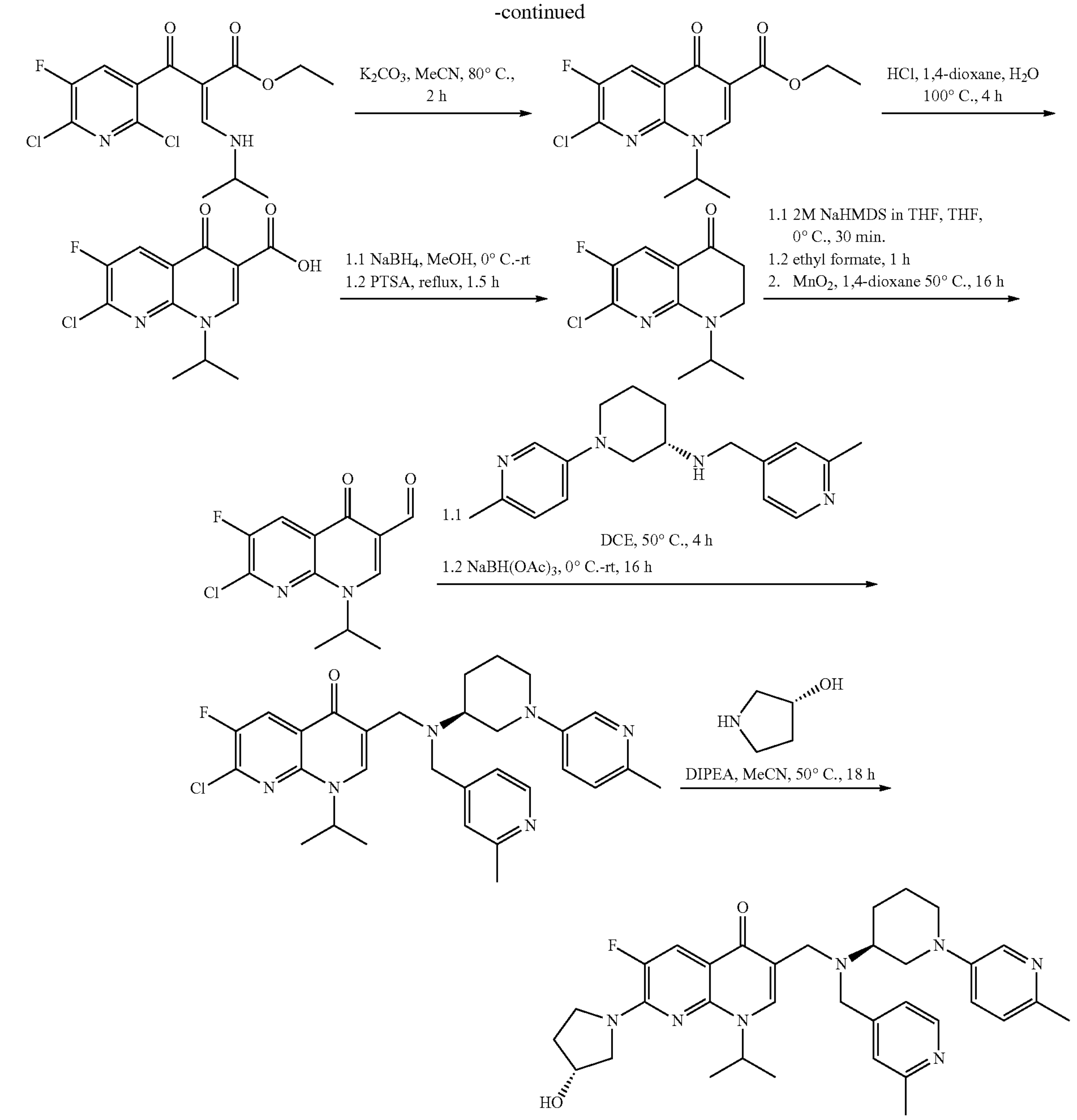

Preparation of ethyl 2-(2,6-dichloro-5-fluoropyridine-3-carbonyl)-3-(dimethylamino)prop-2-enoate 2,6-dichloro-5-fluoropyridine-3-carboxylic acid (5.4 g, 1.0 eq.) was suspended in $SOCl_2$ (9.4 mL, 5.0 eq.) and the resulting mixture was stirred at 80° C. for 2 h. During that time the solution became clear. Then, the mixture was concentrated with the co-solvent DCM to dryness. The residue was dissolved in toluene (20.0 mL) and the resulting solution was added over 5 min to a stirring mixture of ethyl 3-(N,N-dimethylamino)acrylate (3.7 mL, 1.0 eq.) and DIPEA (9.45 mL, 2.1 eq.) at RT. The reaction mixture was stirred at RT for 15 min and then heated at 90° C. for 3.5 h. Afterwards, the mixture was partitioned between DCM and water. The organic layer was dried over anh. $Na_2SO_4$, filtered and concentrated in vacuo. The residue was purified by FCC (SIHP; Hex:EtOAc) to give the product (2.8 g, 32% yield) as an orange oil. ESI-MS: 335.0 $[M+H]^+$. $^1H$ NMR (400 MHz, DMSO-$d_6$) δ 8.04 (d, J=7.9 Hz, 1H), 7.95 (s, 1H), 3.91 (q, J=7.1 Hz, 2H), 3.39 (s, 3H), 2.93 (s, 3H), 0.94 (t, J=7.1 Hz, 3H).

Preparation of ethyl 2-(2,6-dichloro-5-fluoropyridine-3-carbonyl)-3-(propan-2-yl)aminoprop-2-enoate Isopropylamine (0.3 mL, 1.1 eq.) was added to a solution of ethyl 2-(2,6-dichloro-5-fluoropyridine-3-carbonyl)-3-(dimethylamino)prop-2-enoate (1.05 g, 1.0 eq.) in EtOH:$Et_2O$ mixture (8:3) (22.0 mL). The reaction mixture was stirred at RT for 15 min. Then, solvents were evaporated in vacuo affording the product (1.18 g, 99% yield) as an orange oil which was used in the next step without further purification. ESI-MS: 349.0 [M+H]+

Preparation of ethyl 7-chloro-6-fluoro-4-oxo-1-(propan-2-yl)-1,4-dihydro-1,8-naphthyridine-3-carboxylate A solution of ethyl 2-(2,6-dichloro-5-fluoropyridine-3-carbonyl)-3-[(propan-2-yl)amino]prop-2-enoate (0.85 g, 1.0 eq.) in MeCN (8.0 mL) was treated with $K_2CO_3$ (0.53 g, 1.6 eq.) and the resulting mixture was stirred for 2 h at 80° C. Afterwards, the reaction was quenched by the addition of water. Then, the reaction mixture was mixed with three other crude mixtures of trial reactions set up using different solvents (MeCN, NMP and DMAc) using identical conditions but starting from a smaller amount of ethyl 2-(2,6-dichloro-5-fluoropyridine-3-carbonyl)-3-[(propan-2-yl) amino]prop-2-enoate (0.1 g, 0.3 mmol). The resulting mixture was washed with DCM and the combined organic layers were dried over anh. $MgSO_4$, filtered and concentrated in vacuo. The residue was dissolved in 5.0 mL of DCM and heptane was added. The precipitate was filtered off and dried in vacuo affording ethyl 7-chloro-6-fluoro-4-oxo-1-(propan-2-yl)-1,4-dihydro-1,8-naphthyridine-3-carboxylate (0.81 g, 85% yield) as an off-white solid. ESI-MS: 313.9 $[M+H]^+$. $^1H$ NMR (400 MHz, DMSO-$d_6$) δ 8.71 (s, 1H), 8.48 (d, J=7.9 Hz, 1H), 5.53-5.43 (m, 1H), 4.26 (q, J=7.1 Hz, 2H), 1.50 (s, 3H), 1.49 (s, 3H), 1.29 (t, J=7.1 Hz, 3H).

Preparation of 7-chloro-6-fluoro-4-oxo-1-(propan-2-yl)-1,4-dihydro-1,8-naphthyridine-3-carboxylic acid A mixture of ethyl 7-chloro-6-fluoro-4-oxo-1-(propan-2-yl)-1,4-dihydro-1,8-naphthyridine-3-carboxylate (0.81 g, 1.0 eq.), conc. HCl (2.0 mL), $H_2O$ (6.0 mL) and 1,4-dioxane (12.0 mL) was stirred for 4 h at 100° C. Subsequently, the reaction mixture was cooled to RT, the precipitate was filtered off and dried to give the product (0.67 g, 90% yield) as an off-white solid which was used in the next step without further purification. ESI-MS: 285.0 $[M+H]^+$. $^1H$ NMR (400 MHz, DMSO-$d_6$) δ 14.40 (s, 1H), 9.01 (s, 1H), 8.73 (d, J=7.6 Hz, 1H), 5.61 (hept, J=6.4 Hz, 1H), 1.56 (d, J=6.7 Hz, 6H).

Preparation of 7-chloro-6-fluoro-1-(propan-2-yl)-1,2,3,4-tetrahydro-1,8-naphthyridin-4-one $NaBH_4$ (0.40 g, 4.5 eq.) was added slowly to a solution of 7-chloro-6-fluoro-4-oxo-1-(propan-2-yl)-1,4-dihydro-1,8-naphthyridine-3-carboxylic acid (0.67 g, 1.0 eq.) in anh. MeOH (10.0 mL) stirring under inert atmosphere. Afterwards, the mixture was allowed to warm to RT and PTSA monohydrate (0.045 g, 0.1 eq.) was added. After heating at reflux for 1.5 h, the mixture was allowed to cool to RT and the solvent was removed in vacuo. The residue was purified by FCC (SiHP; Hex:EtOAc) to give the product (0.46 g, 81% yield) as a yellow solid. ESI-MS: 243.1 $[M+H]^+$. $^1H$ NMR (400 MHz, DMSO-$d_6$) δ 7.88 (d, J=8.0 Hz, 1H), 4.88 (hept, J=6.7 Hz, 1H), 3.52-3.44 (m, 2H), 2.67-2.59 (m, 2H), 1.17 (d, J=6.8 Hz, 6H).

Preparation of 7-chloro-6-fluoro-4-oxo-1-(propen-2-yl)-1,4-dihydro-1,8-naphthyridine-3-carbaldehyde 7-Chloro-6-fluoro-1-(propan-2-yl)-1,2,3,4-tetrahydro-1,8-naphthyridin-4-one (0.46 g, 1.0 eq.) dissolved in anh. THF (2.0 mL) was added to a solution of NaHMDS (2 M in THF, 1.14 mL, 1.2 eq.) in anh. THF (2.0 mL) at 0° C. The reaction mixture was stirred for 30 min at the same temperature and subsequently a solution of ethyl formate (0.2 mL, 1.3 eq.) in THF (2.0 mL) was added. The mixture was stirred for 1 h, then the reaction was quenched by addition of sat $NH_4Cl$ aq. solution and the mixture was washed with EtOAc. The aqueous layer was washed further with EtOAc (×3). The combined organic layers were dried over anh. $Na_2SO_4$, filtered, concentrated and dried in vacuo. The residue was dissolved in anh. 1,4-dioxane (10.0 mL) and $MnO_2$ (0.82 g, 4.2 eq.) was added. The resulting mixture was heated at 50° C. for 16 h. Afterwards, the reaction mixture was cooled to RT, filtered through a pad of celite and the pad was washed with a mixture of DCM:MeOH (v/v, 7/3). The filtrate was concentrated in vacuo and the residue was purified by FCC (SiHP; DCM:EtOAc) to give the product (0.291 g, 57% yield) as a yellow solid. APMS: 269.0 $[M+H]^+$. $^1H$ NMR (400 MHz, DMSO-$d_6$) δ 10.14 (s, 1H), 8.68 (s, 1H), 8.58 (d, J=7.7 Hz, 1H), 5.51 (hept, J=6.7 Hz, 1H), 1.52 (d, J=6.8 Hz, 6H).

Preparation of 7-chloro-6-fluoro-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one A dry reactor vessel was charged with (3S)-1-(6-methylpyridin-3-yl)-N-[(2-methylpyridin-4-yl)methyl]piperidin-3-amine (Intermediate 2) (0.31 g, 1.02 eq.), 7-chloro-6-fluoro-4-oxo-1-(propan-2-yl)-1,4-dihydro-1,8-naphthyridine-3-carbaldehyde (0.29 g, 1.0 eq.) and DCE (10.0 mL). The mixture was heated for 4 h at 50° C. and then cooled to 0° C. Then, $NaBH(OAc)_3$ (0.43 g, 2.0 eq.) was added and the resulting mixture was left stirring for 16 h at RT. Subsequently, water and sat $NaHCO_3$ aq. solution were added and the mixture was washed with DCM. The combined organic layers were washed with brine, dried over anh. $Na_2SO_4$, filtered and concentrated in vacuo. The residue was purified by FCC (SiHP; DCM:MeOH). The isolated material was additionally re-purified by FCC (SiHP; DCM:MeOH with $NH_3$) and RP-FCC (C18HP; $H_2O$:MeCN) to give the product (0.40 g, 70% yield) as a white solid. ESI-MS: 549.4 $[M+H]^+$. $^1H$ NMR (400 MHz, Methanol-$d_4$) δ 8.42-8.34 (m, 1H), 8.24-8.15 (m, 2H), 8.06 (d, J=3.0 Hz, 1H), 7.34 (dd, J=8.6, 3.0 Hz, 1H), 7.30 (s, 1H), 7.27-7.22 (m, 1H), 7.11 (d, J=8.6 Hz, 1H), 5.75-5.59 (m, 1H), 3.96-3.76 (m, 5H), 3.64-3.53 (m, 1H), 3.02-2.92 (m, 1H), 2.90-2.82 (m, 1H), 2.77-2.64 (m, 1H), 2.48-2.35 (m, 6H), 2.22-2.07 (m, 1H), 2.00-1.85 (m, 1H), 1.77-1.57 (m, 2H), 1.53-1.36 (m, 6H).

Preparation of 6-fluoro-7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one A mixture of 7-chloro-6-fluoro-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one (0.15 g, 1.0 eq.) and (3R)-pyrrolidin-3-ol (0.028 mL, 1.3 eq.) in MeCN (5.0 mL) at 25° C. was treated with DIPEA (0.093 mL, 2.0 eq.). The reaction mixture was heated for 18 h at 50° C. Then, water was added and the resulting mixture was washed with DCM. The organic layer was dried over anh. $Na_2SO_4$, filtered and concentrated in vacuo. The residue was purified by FCC (C18HP; $H_2O$:MeCN) to give the product (0.16 g, 95% yield) as a yellow solid. ESI-MS: 600.8 $[M+H]^+$. 1 H NMR (400 MHz, Methanol-$d_4$) δ 8.19 (d, J=5.3 Hz, 1H), 8.07 (d, J=2.9 Hz, 1H), 7.94 (s, 1H), 7.89 (d, J=13.2 Hz, 1H), 7.37-7.28 (m, 2H), 7.27-7.22 (m, 1H), 7.10 (d, J=8.6 Hz, 1H), 5.72-5.57 (m, 1H), 4.56-4.46 (m, 1H), 3.99-3.73 (m, 9H), 3.65-3.54 (m, 1H), 3.01-2.89 (m, 1H), 2.90-2.78 (m, 1H), 2.73-2.62 (m, 1H), 2.41 (s, 3H), 2.40 (s, 3H), 2.18-1.99 (m, 3H), 1.96-1.85 (m, 1H), 1.76-1.59 (m, 2H), 1.43 (d, J=6.8 Hz, 6H).

Example 43. 3-({[(3S)-1-[6-(2-hydroxyethyl)pyridin-3-yl]piperidin-3-yl][(2-methylpyridin-4-yl)methyl]amino}methyl)-1-methyl-1,4-dihydroquinolin-4-one

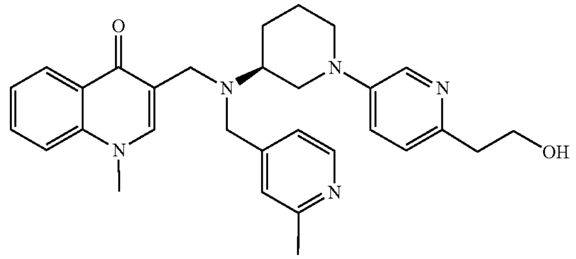

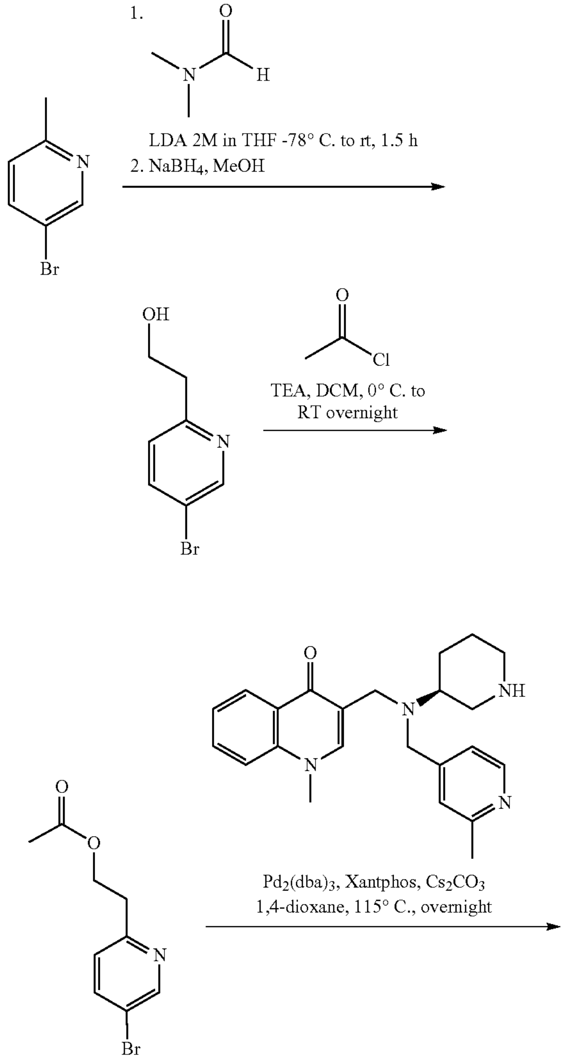

-continued

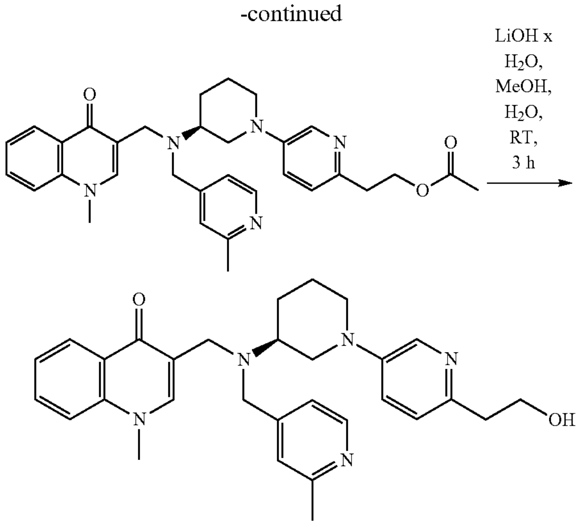

Preparation of 2-(5-bromopyridin-2-yl)ethan-1-ol

A two-necked round-bottomed flask equipped with thermometer was charged with anh. THF (2.0 mL) and cooled to −78° C. Then, LDA (2 M in THF/heptane/ethylbenzene, 1.74 mL, 1.5 eq.) was added dropwise at −78° C. The resulting mixture was stirred for is min and then solution of 5-bromo-2-methylpyridine (0.4 g, 1.0 eq.) in anh. THF (4.0 mL) was dropped in slowly at −78° C. and the reaction mixture was stirred for 1.5 h at −78° C. Afterwards, DMF (1.8 mL, 10.0 eq.) was added dropwise and stirring was continued for 1 h at −78° C. Subsequently, the mixture was allowed to warm to RT and MeOH (4.5 mL) was added followed by $NaBH_4$ (0.089 g, 1.0 eq.). During $NaBH_4$ addition generation of heat was observed, temperature increased to 30° C. The reaction was continued for 30 min at RT and then quenched with saturated $NH_4Cl$ aq. solution. The resulting mixture was extracted with EtOAc (3×). The combined organic layers were washed with brine, dried over anh. $Na_2SO_4$, filtered and concentrated in vacuo. The residue was purified by two consecutive FCC (SiHP; DCM:MeOH) and (SiHP; hexane:EtOAc) to give the product (0.204 g, 35% yield) as a yellowish oil. ESI-MS: 202.0 $[M+H]^+$.

Preparation of 2-(5-bromopyridin-2-yl)ethyl acetate 2-(5-bromopyridin-2-yl)ethan-1-ol (0.17 g, 1.0 eq.) was placed into an oven-dried flask flushed with argon, and anh. DCM (4.0 mL) and TEA (0.19 mL, 2.0 eq.) were sequentially added. The reaction mixture was cooled in an ice-water bath and stirred for 15 min, and then acetyl chloride (0.07 mL, 1.5 eq.) was added dropwise. The reaction mixture was stirred overnight at RT and quenched with sat. $NaHCO_3$ solution and extracted with DCM (3×). The combined organic layers were washed with water and brine, then dried over anh. $Na_2SO_4$ and concentrated in vacuo. The residue was purified by FCC (SiHP, Hex:EtOAc) to give the desired product (0.19 g, quantitative yield) as a yellow liquid. ESI-MS: 244.1, 245.8 $[M+H]^+$.

Preparation of 2-{5-[(3S)-3-{[(1-methyl-4-oxo-1,4-dihydroquinolin-3-yl)methyl][(2-methylpyridin-4-yl)methyl]amino}piperidin-1-yl]pyridin-2-yl}ethyl acetate 1-methyl-3-({[(2-methylpyridin-4-yl)methyl][(3S)-piperidin-3-yl]amino}methyl)-1,4-dihydroquinolin-4-one (Intermediate 5) (0.12 g, 1.0 eq.), 2-(5-bromopyridin-2-yl)ethyl acetate (0.09 g, 1.1 eq.), $Cs_2CO_3$ (0.14 g, 1.4 eq.) and anh. 1,4-dioxane (3.0 mL) were placed into a pressure vessel. The resulting mixture was purged with argon for 5 min, $Pd_2(dba)_3$ (0.014 g, 0.05 eq.) and Xantphos (0.018 g, 0.1 eq.) were then added and the reaction mixture was stirred at 115° C. overnight. After cooling to room temperature, the reaction mixture was filtered through a pad of celite and concentrated in vacuo. The residue was purified by FCC (SiHP, DCM:MeOH) to give a product (0.049 g, 28% yield) as a yellow solid. ESI-MS: 540.4 $[M+H]^+$. $^1H$ NMR (300 MHz, DMSO-$d_6$) δ 8.28 (d, J=5.1 Hz, 1H), 8.23-8.15 (m, 2H), 8.03 (s, 1H), 7.76-7.67 (m, 1H), 7.65-7.58 (m, 1H), 7.41-7.33 (m, 1H), 7.28-7.21 (m, 3H), 7.07 (d, J=8.6 Hz, 1H), 4.28 (t, J=6.9 Hz, 2H), 3.94-3.83 (m, 4H), 3.82-3.71 (m, 2H), 3.70-3.54 (m, 3H), 2.88 (t, J=6.7 Hz, 2H), 2.83-2.55 (m, 3H), 2.37 (s, 2H), 2.05-1.91 (m, 4H), 1.81-1.69 (m, 1H), 1.64-1.38 (m, 2H), 1.36-1.20 (m, 1H).

Preparation of 3-({[(3S)-1-[6-(2-hydroxyethyl)pyridin-3-yl]piperidin-3-yl][(2-methylpyridin-4-yl)methyl]amino}methyl)-1-methyl-1,4-dihydroquinolin-4-one 2-{5-[(3S)-3-{[(1-methyl-4-oxo-1,4-dihydroquinolin-3-yl)methyl][(2-methylpyridin-4-yl)methyl]amino}piperidin-1-yl]pyridin-2-yl}ethyl acetate (0.05 g, 1.0 eq.) was dissolved in MeOH (2.5 mL), then $H_2O$ (1.0 mL) was added followed by the addition of LiOH $xH_2O$ (0.018 g, 4.9 eq.). The reaction mixture was stirred for 3 h at RT, then concentrated to dryness and partitioned between $H_2O$ and DCM. The aqueous phase was basified with 15 M NaOH top H≈12 and extracted with DCM (3×). The combined organic layers were dried over anh. $Na_2SO_4$ and concentrated in vacuo. The residue was purified by prep-HPLC ($H_2O$:MeCN:$NH_3$) to give the product (0.025 g, 57% yield) as a white solid. ESI-MS: 498.5 $[M+H]^+$. $^1H$ NMR (400 MHz, DMSO-$d_6$) δ 8.28 (d, J=5.0 Hz, 1H), 8.21-8.17 (m, 2H), 8.02 (s, 1H), 7.74-7.69 (m, 1H), 7.62 (d, J=8.6 Hz, 1H), 7.40-7.34 (m, 1H), 7.26-7.20 (m, 3H), 7.04 (d, J=8.5 Hz, 1H), 4.57 (t, J=5.3 Hz, 1H), 3.90-3.83 (m, 4H), 3.73 (q, 2H), 3.68-3.55 (m, 5H), 2.79 (t, J=11.1 Hz, 1H), 2.76-2.69 (m, 3H), 2.64-2.55 (m, 1H), 2.37 (s, 3H), 2.03-1.96 (m, 1H), 1.79-1.72 (m, 1H), 1.59-1.39 (m, 21H).

Example 44. 3-({[(3S)-1-[5-(hydroxymethyl)pyridin-3-yl]piperidin-3-yl][(2-methylpyridin-4-yl)methyl]amino}methyl)-1,4-dihydroquinolin-4-one

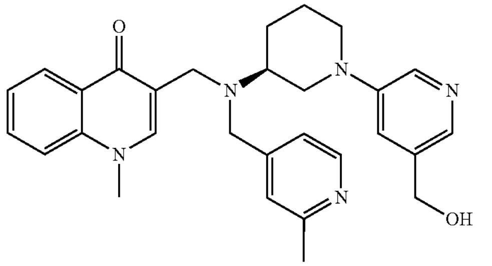

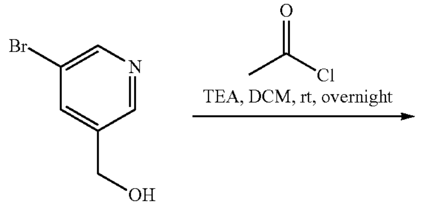

-continued

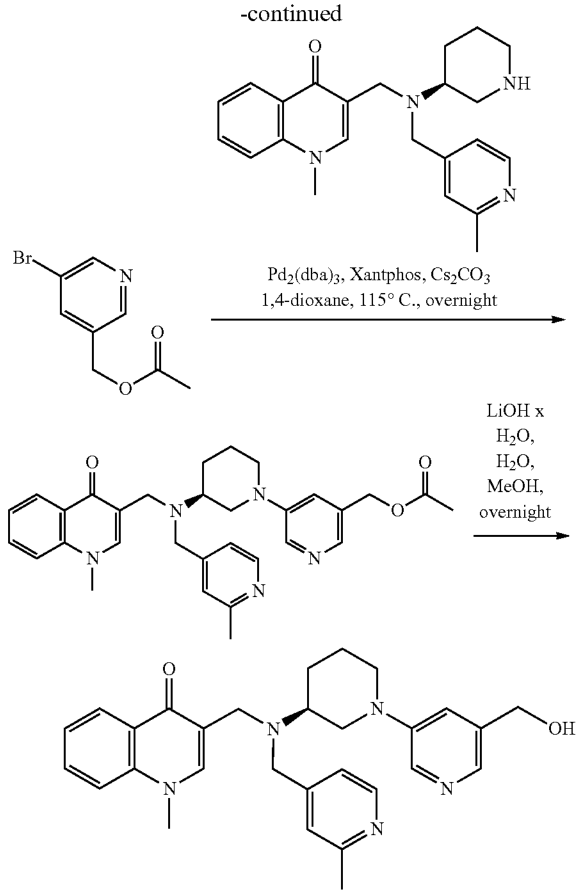

Preparation of (5-bromopyridin-3-yl)methyl acetate 5-bromo-3-pyridinemethanol (0.50 g, 1.0 eq.) was suspended in DCM (3.0 mL) and trimethylamine (0.74 mL, 2.0 eq.) was added followed by the addition of acetyl chloride (0.47 g, 1.5 eq.). The reaction mixture was stirred at RT overnight After that, the reaction mixture was diluted with DCM and washed with aq. sol. $NaHCO_3$, brine and dried over anh. $Na_2SO_4$. Crude product was purified by FCC (SIHP, Hex:EtOAc) provide to product (0.56 g, 82% yield) as a colorless liquid. ESI-MS: 231.1 $[M+2]^+$.

Preparation of {5-[(3S)-3-{[(1-methyl-4-oxo-1,4-dihydroquinolin-3-yl)methyl][(2-methylpyridin-4-yl)methyl]amino}piperidin-1-yl]pyridin-3-yl}methyl acetate 1-methyl-3-({[(2-methylpyridin-4-yl)methyl][(3S)-piperidin-3-yl]amino}methyl)-1,4-dihydroquinolin-4-one (Intermediate 5) (0.15 g, 1.0 eq.), (5-bromopyridin-3-yl)methyl acetate (0.10 g, 1.1 eq.), cesium carbonate (0.18 g, 1.4 eq.) and 1,4-dioxane (3.0 mL) were placed in a pressure vessel. The resulting mixture was purged with argon for 5 min, then $Pd_2(dba)_3$ (0.018 g, 0.1 eq.) and Xantphos (0.023 g, 0.1 eq.) were added. The reaction mixture was stirred at 115° C. overnight, filtered through a pad of celite and concentrated under reduced pressure. The crude mixture was purified by FCC (SiHP, DCM:MeOH) give of product (0.133 g, 57% yield) as a yellow solid. ESI-MS: 526.5 $[M+H]^+$.

Preparation of 3-({[(3S)-1-[5-(hydroxymethyl)pyridin-3-yl]piperidin-3-yl][(2-methylpyridin-4-yl)methyl]amino}methyl)-1-methyl-1,4-dihydroquinolin-4-one {5-[(3S)-3-{[(1-methyl-4-oxo-1,4-dihydroquinolin-3-yl)methyl][(2-methylpyridin-4-yl)methyl]amino}piperidin-1-yl]pyridin-3-yl}methyl acetate (0.13 g, 1.0 eq.) was suspended in water (1.0 mL) and methanol (5.0 mL). Then lithium hydroxide monohydrate (0.03 g, 5.0 eq.) was added and the reaction mixture was stirred at RT overnight. The reaction mixture was concentrated under reduced pressure and the residue was partitioned between DCM and 15 M NaOH aq. solution. Separated organic layer was dried over anh. $Na_2SO_4$ and concentrated. The residue was purified by RP-FCC (C18HP, $H_2O$:MeCN) and re-purified by prep-HPLC ($H_2O$:MeCN:$NH_3$) give a product (0.043 g, 40% yield) as white powder. ESI-MS: 484.4 $[M+H]^+$. $^1H$ NMR (400 MHz, Methanol-$d_4$) 8.35 (dd, J=8.3, 1.5 Hz, 1H), 8.19-8.15 (m, 2H), 8.02 (s, 1H), 7.93-7.90 (m, 1H), 7.81-7.75 (m, 1H), 7.67 (d, J=8.6 Hz, 1H), 7.50-7.44 (m, 1H), 7.42-7.37 (m, 1H), 7.29-7.24 (m, 2H), 4.60 (s, 2H), 4.07-3.97 (m, 1H), 3.93-3.81 (m, 7H), 3.77-3.71 (m, 1H), 3.01-2.92 (m, 2H), 2.82-2.74 (m, 1H), 2.33 (s, 3H), 2.22-2.15 (m, 1H), 1.96-1.90 (m, 1H), 1.69 (d, J=7.5 Hz, 2H).

Example 45. 1-cyclopropyl-7-[(3R)-3-hydroxypyrrolidin-1-yl]-3-({[(3S)-1-(6-methylpyridin-3-yl)piperidin-3-yl][(2-methylpyridin-4-yl)methyl]amino}ethyl)-1,4-dihydroquinolin-4-one

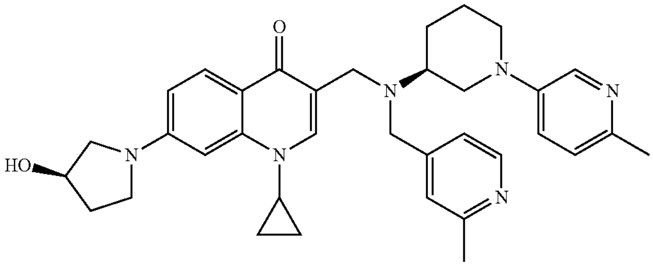

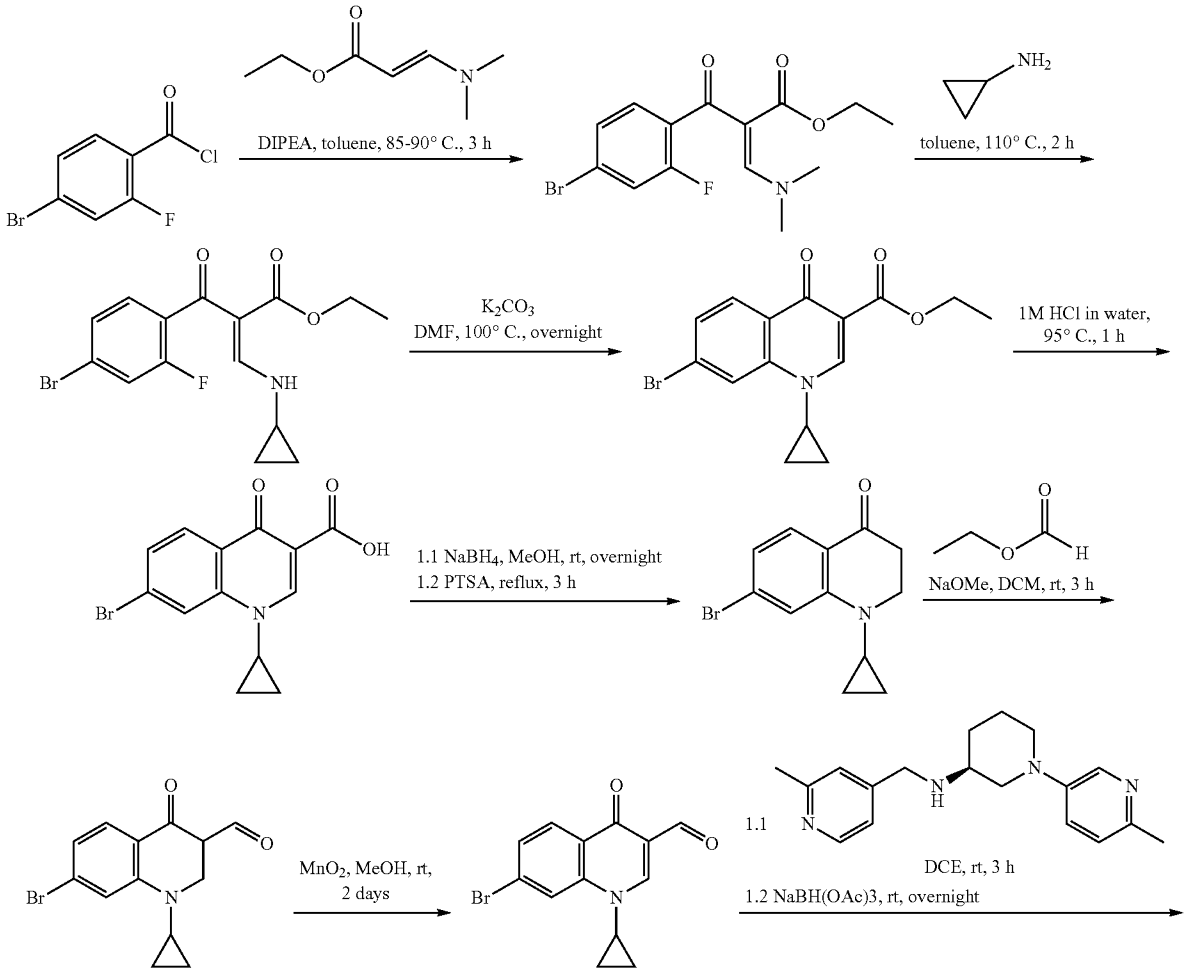

-continued

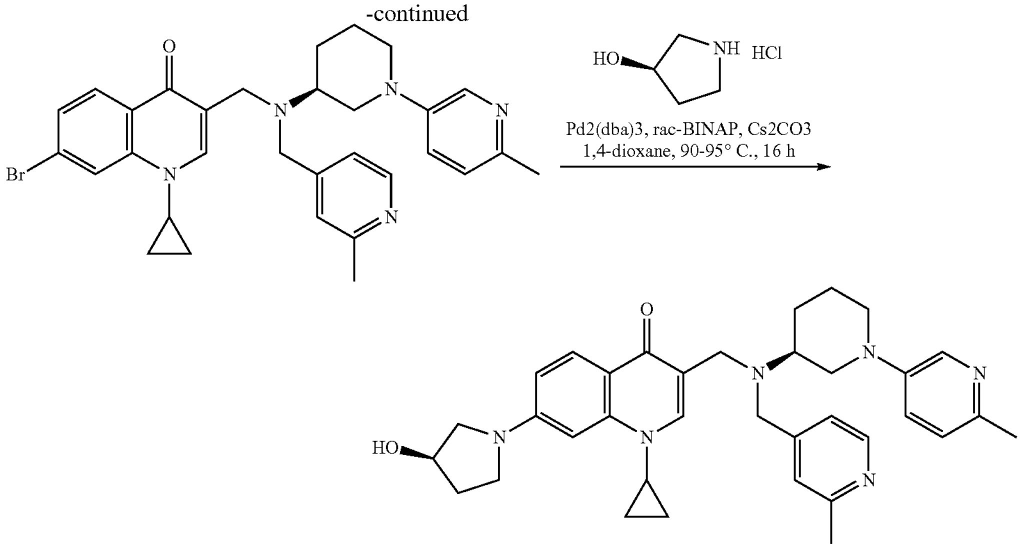

Preparation of ethyl (2Z)-2-[(Z)-4-bromo-2-fluorobenzoyl]-3-(dimethylamino)prop-2-enoate A mixture of ethyl (2E)-3-(dimethylamino)prop-2-enoate (0.60 g, 1.0 eq.) and N,N-diisopropylethylamine (1.1 g, 2.1 eq.) was stirred at RT and the solution of 4-bromo-2-fluorobenzoyl chloride (1.0 g, 1.0 eq.) in toluene (5.0 mL) was added over 5 min. The yellow solution that formed was heated in an oil bath at 90° C. After 3 h, the mixture was diluted with DCM/water. The separated organic layer was dried over anh. $Na_2SO_4$ and concentrated in vacuo. The residue was purified by FCC (SiHP, EtOAc) to give the product (1.24 g, 81% yield) as a yellow oil. ESI-MS: 344.0 $[M+H]^+$.

Preparation of ethyl 7-bromo-1-cyclopropyl-4-oxo-1,4-dihydroquinoline-3-carboxylate Ethyl (22)-2-[(2)-4-bromo-2-fluorobenzoyl]-3-(dimethylamino)prop-2-enoate (1.24 g, 1.0 eq.) and cyclopropylamine (0.27 g, 1.3 eq.) were heated in toluene (10.0 mL) at 110° C. for 2 h. The reaction mixture was concentrated and the residue was diluted in DMF (8.0 mL). Then $K_2CO_3$ (1.25 g, 2.5 eq.) was added and the reaction mixture was heated at 100° C. overnight. After cooling, the reaction mixture was diluted with DCM, washed with water, brine, dried over anh. $Na_2SO_4$, filtered and concentrated in vacuo. The residue was purified by FCC (SiHP, Hex:EtOAc) give the product (0.97 g, 88% yield) as a yellow solid. ESI-MS: 337.2 $[M+2]^+$.

Preparation of 7-bromo-1-cyclopropyl-4-oxo-1,4-dihydroquinoline-3-carboxylic acid Ethyl 7-bromo-1-cyclopropyl-4-oxo-1,4-dihydroquinoline-3-carboxylate was suspended (0.95 g, 1.0 eq.) in 1 M aq. HCl (8.0 mL) and the mixture was stirred at 95° C. overnight. The reaction mixture was concentrated in vacuo. Then, the residue was further dissolved in toluene and traces of moisture were removed as an azeotropic mixture to give the product (0.80 g, 92% yield) as a white solid. ESI-MS: 309.9 $[M+2]^+$.

Preparation of 7-bromo-1-cyclopropyl-1,2,3,4-tetrahydroquinolin-4-one 7-bromo-1-cyclopropyl-4-oxo-1,4-dihydroquinoline-3-carboxylic acid (0.80 g, 1.0 eq.) was dissolved in MeOH (10.0 mL) and the mixture was cooled in an ice-bath. Then sodium borohydride (0.51 g, 4.5 eq.) was added in portions and the reaction mixture was stirred at RT overnight. Then, PTSA monohydrate (0.06 g, 0.1 eq.) was added and stirring was continued at reflux for 3 h. The reaction mixture was concentrated in vacuo, then diluted with DCM, washed with water, brine, dried over anh. $Na_2SO_4$ and concentrated in vacuo. The crude product mixture was purified by FCC (SiHP, Hex:EtOAc) to give the product (0.52 g, 66% yield) as a yellow solid. ESI-MS: 266.0 [M+H], 267.9 $[M+2+H]^+$.

Preparation of 7-bromo-1-cyclopropyl-4-oxo-1,2,3,4-tetrahydroquinoline-3-carbaldehyde A solution of 7-bromo-1-cyclopropyl-1,2,3,4-tetrahydroquinolin-4-one (0.40 g, 1.0 eq.) in DCM (10.0 mL) was added dropwise to a viscous mixture of ethyl formate (0.48 mL, 4.0 eq.) and sodium methoxide (0.32 g, 4.0 eq.). The reaction mixture was stirred at RT for 3 hours and subsequently quenched with ice-water. After separation, the organic layer was washed with 2 M NaOH. The aqueous layer was acidified to pH=6 with conc. hydrochloric acid and then washed with DCM. The organic extract was dried over anh. $Na_2SO_4$, filtered and concentrated in vacuo to give the product (0.44 g, 91% yield) as an orange solid. ESI-MS: 293.9 $[M+H]^+$.

Preparation of 7-bromo-1-cyclopropyl-4-oxo-1,4-dihydroquinoline-3-carbaldehyde (Intermediate 16)

A mixture of 7-bromo-1-cyclopropyl-4-oxo-1,2,3,4-tetrahydroquinoline-3-carbaldehyde (0.44 g, 1.0 eq.) and manganese (IV) oxide (0.59 g, 5.0 eq.) in MeOH (10.0 mL) was stirred at RT for 2 days. The reaction mixture was filtered through a pad of celite. The pad was washed with DCM:MeOH (4:1) and the filtrate was concentrated in vacuo. The residue was purified by FCC (SiHP, DCM:MeOH). The purified product was triturated by MeOH to give product (0.17 g, 41% yield) as a yellow solid. ESI-MS: 293.2 $[M+2]^+$.

Preparation of 7-bromo-1-cyclopropyl-3-({[(3S)-1-(6-methylpyridin-3-yl)piperidin-3-yl][(2-methylpyridin-4-yl)methyl]amino}methyl)-1,4-dihydroquinolin-4-one 7-bromo-1-cyclopropyl-4-oxo-1,4-dihydroquinoline-3-carbaldehyde (Intermediate 16) (0.13 g, 1.0 eq.) and (3S)-1-(6-methylpyridin-3-yl)-N-[(2-methylpyridin-4-yl)methyl]piperidin-3-amine (Intermediate 2) (0.14 g, 1.0 eq.) were suspended in anh. DCE (5.0 mL). The resulting mixture was stirred at RT for 30 min, then sodium triacethoxyborohydride (0.26 g, 2.8 eq.) was added and stirring was continued overnight. The reaction mixture was poured into ice-cold water, then $NaHCO_3$ was added. to the mixture was then washed with DCM (3×). The combined organic layers were dried over anh. $Na_2SO_4$ and concentrated in vacuo. The residue was purified by RP-FCC (C18HP, $H_2O$:MeCN) give the product (0.18 g, 68% yield) as white solid. ESI-MS: 574.1 $[M+2+H]^+$.

Preparation of 1-cyclopropyl-7-[(3R-3-hydroxypyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one A mixture of 7-bromo-1-cyclopropyl-3-({[(3S)-1-(6-methylpyridin-3-yl)piperidin-3-yl][(2-methylpyridin-4-yl)methyl]amino}methyl)-1,4-dihydroquinolin-4-one (0.1 g, 1.0 eq.), (R)-Pyrrolidin-3-ol hydrochloride (0.022 g, 1.5 eq.), cesium carbonate (0.098 g, 1.8 eq.) and 1,4-dioxane (2.0 mL) was taken in a pressure vessel. The resulting mixture was purged with argon for 5 min, then BINAP (0.021 g, 0.2 eq.) and $Pd_2(dba)_3$ (0.015 g, 0.1 eq.) were added and the reaction mixture was stirred at 95° C. for 16 h. The reaction was cooled and filtered through a short pad of celite and concentrated in vacuo. The residue was suspended in DCM, washed with water, brine and dried over anh. $Na_2SO_4$. The crude product mixture was purified by FCC (SiHP, MeOH:DCM), then repurified by prep-HPLC ($H_2O$:MeCN:$NH_3$) and RP-FCC (C18HP; $H_2O$:MeCN) to provide the product (0.017 g, 17% yield) as a yellow solid. ESI-MS: 579.6 $[M+H]^+$. $^1$H NMR (400 MHz, Methanol-$d_4$) δ 8.17 (d, J=5.2 Hz, 1H), 8.13 (d, J=9.1 Hz, 1H), 8.10 (d, J=2.9 Hz, 1H), 7.81 (s, 1H), 7.36 (dd, J=8.6, 3.0 Hz, 1H), 7.26 (s, 1H), 7.24-7.22 (m, 1H), 7.12 (d, J=8.6 Hz, 1H), 6.83 (dd, J=9.1, 2.2 Hz, 1H), 6.77 (d, J=2.2 Hz, 1H), 4.63-4.56 (m, 1H), 3.92-3.77 (m, 5H), 3.66-3.57 (m, 3H), 3.56-3.49 (m, 1H), 3.41-3.35 (m, 2H), 3.03-2.94 (m, 1H), 2.86 (t, J=11.1 Hz, 1H), 2.76-2.64 (m, 1H), 2.42 (s, 3H), 2.35 (s, 3H), 2.28-2.08 (m, 3H), 1.99-1.86 (m, 1H), 1.76-1.60 (m, 2H), 1.34-1.21 (m, 3H), 0.95-0.84 (m, 2H).

Example 46. 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylic acid

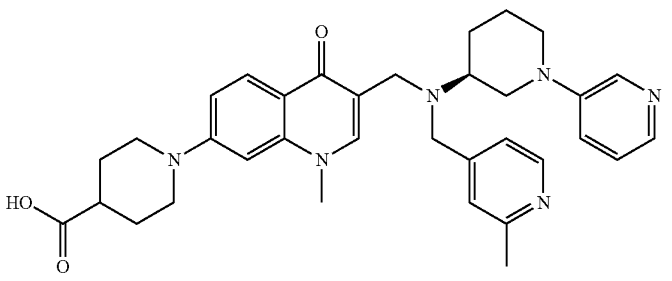

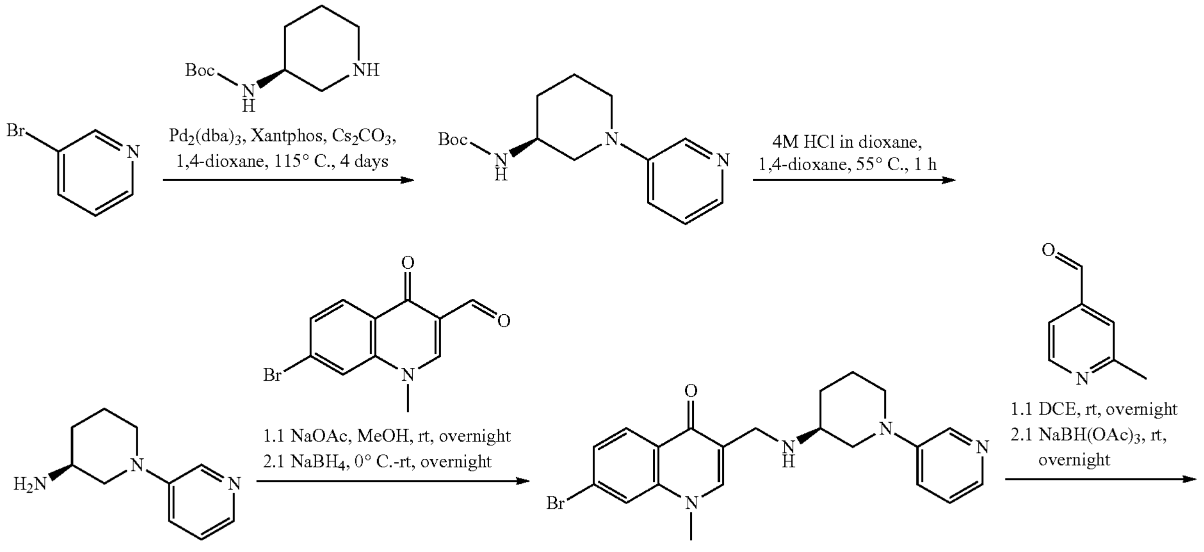

-continued

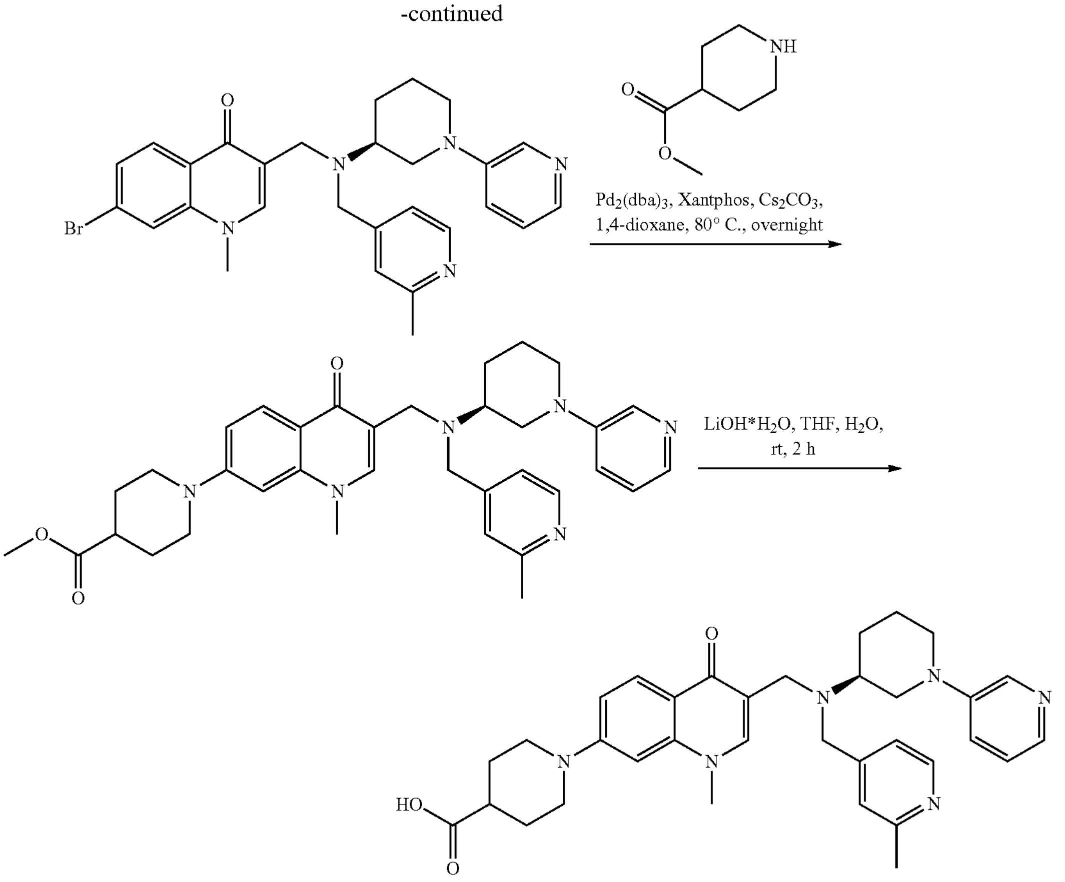

Preparation of tert-butyl N-[(3S)-1-(pyridin-3-yl) piperidin-3-yl]carbamate

A pressure vessel was charged with 3-bromopyridine (3.0 g, 1.0 eq.), tert-butyl N-[(3S)-piperidin-3-yl]carbamate (4.9 g, 1.3 eq.), $Cs_2CO_3$ (8.35 g, 1.4 eq.) and 1,4-dioxane (80.0 mL). The resulting mixture was purged with argon for 15 min. Then, $Pd_2(dba)_3$ (0.87 g, 0.05 eq.) and Xantphos (0.66 g, 0.06 eq.) were added, the vessel was sealed and the reaction mixture was stirred for 4 days at 115° C. Subsequently, the mixture was filtered through a pad of celite, the pad was washed with DCM and the filtrate was concentrated in vacuo. The residue was purified by FCC (SiHP; DCM: EtOAc) to give the product (3.8 g, 69% yield) as a yellow oil. ESI-MS: 278.4 $[M+H]^+$.

Preparation of (3S)-1-(pyridin-3-yl)piperidin-3-amine (Intermediate 17)

4 M HCl in 1,4-dioxane (20.0 mL) was added to a suspension of tert-butyl N-[(3S)-1-(pyridin-3-yl)piperidin-3-yl]carbamate (3.76 g, 1.0 eq.) in 1,4-dioxane (20.0 mL) and the resulting mixture was stirred for 1 h at 55° C. Then, the reaction mixture was concentrated in vacuo and the residue was partitioned between 15% NaOH aq. solution and DCM. The organic layer was dried over anh. $Na_2SO_4$, filtered and concentrated in vacuo to give the crude product (2.3 g, 92% yield) as a dark yellow oil which was used in the next step without further purification. ESI-MS: 178.1 $[M+H]^+$. $^1H$ NMR (300 MHz, DMSO-$d_6$) δ 8.26 (d, J=3.0 Hz, 1H), 7.92 (dd, J=4.5, 1.4 Hz, 1H), 7.26 (ddd, J=8.5, 3.0, 1.4 Hz, 1H), 7.17 (ddd, J=8.5, 4.5, 0.7 Hz, 1H), 3.69-3.51 (m, 2H), 2.80-2.58 (m, 2H), 2.46-2.33 (m, 1H), 1.92-1.33 (m, 5H), 1.24-1.02 (m, 1H).

Preparation of 7-bromo-1-methyl-3-({[(3S)-1-(pyridin-3-yl)piperidin-3-yl]amino}methyl)-1,4-dihydroquinolin-4-one A mixture of 7-bromo-1-methyl-4-oxo-1,4-dihydroquinoline-3-carbaldehyde (Intermediate 8) (0.5 g, 1.0 eq.), (3S)-1-(pyridin-3-yl)piperidin-3-amine (Intermediate 17) (0.33 g, 1.0 eq.), NaOAc (0.15 g, 1.0 eq.) in MeOH (4.0 mL) was stirred overnight at RT under argon atmosphere. Then, the reaction mixture was cooled to 0° C., $NaBH_4$ (0.073 g, 1.02 eq.) was added in portions and the mixture was left stirring overnight at RT. Subsequently, the mixture was partitioned between DCM and $NaHCO_3$ saturated aq. solution. The organic layer was washed with brine, dried over anh. $Na_2SO_4$, filtered and concentrated in vacuo to give the crude product (0.63 g, 67% yield) as a yellow solid which was used in the next step without further purification. ESI-MS: 427.1 $[M+H]^+$.

Preparation of 7-bromo-1-methyl-3-({[(2-methylpyridin-4-yl)methyl][(3S)-1-(pyridin-3-yl)piperidin-3-yl]amino}methyl)-1,4-dihydroquinolin-4-one A suspension of 7-bromo-1-methyl-3-({[(3S)-1-(pyridin-3-yl)piperidin-3-yl]amino}methyl)-1,4-dihydroquinolin-4-one (0.47 g, 1.0 eq.) and 2-methylpyridine-4-carbaldehyde (0.13 g, 1.0 eq.) in DCE (8.0 mL) was stirred overnight at RT. Then, $NaBH(OAc)_3$ (0.33 g, 1.4 eq.) was added and the resulting mixture was left stirring overnight at RT. Subsequently, the mixture was partitioned between DCM and sat. $NaHCO_3$ aq. solution. The organic layer was washed with water, brine, dried over anh. $Na_2SO_4$, filtered and concentrated in vacuo. The residue was purified by FCC (SiHP; DCM:MeOH) to give the product (0.38 g, 62% yield) as a yellow solid. ESI-MS: 532.1 $[M+H]^+$.

Preparation of methyl 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylate A pressure vessel was charged with 7-bromo-1-methyl-3-({[(2-methylpyridin-4-yl)methyl][(3S)-1-(pyridin-3-yl)piperidin-3-yl]amino}methyl)-1,4-dihydroquinolin-4-one (0.1 g, 1.0 eq.), methyl piperidine-4-carboxylate (0.05 mL, 2.0 eq.), $Cs_2CO_3$ (0.122 g, 2.0 eq.), Xantphos (0.022 g, 0.2 eq.) and $Pd_2(dba)_3$ (0.017 g, 0.1 eq.). Then, the vessel was capped, the evacuated of air and filled with argon. Subsequently, 1,4-dioxane (1.0 mL) was added via a syringe and the resulting mixture was left stirring overnight at 80° C. Then, the reaction mixture was cooled to RT, filtered through a pad of celite and the pad was washed with DCM and EtOAc. The filtrate was concentrated in vacuo and the residue was purified by FCC (SiHP; DCM:MeOH) and re-purified by prep-HPLC ($H_2O$:MeCN:$NH_3$) to give the product (0.026 g, 23% yield) as a white powder. ESI-MS: 595.5 $[M+H]^+$.

Preparation of 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylic acid $LiOH·H_2O$ (0.004 g, 3.0 eq.) was added to a solution of 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylate (0.02 g, 1.0 eq.) in a mixture of THF (1.0 mL) and $H_2O$ (1.0 mL) and the resulting mixture was stirred for 2 h at RT. Then, the reaction mixture was concentrated in vacuo and the residue was diluted with water, acidified using 1 M HCl aq. solution and concentrated in vacuo. The residue was purified by RP-FCC (C18HP; $H_2O$:MeCN). The isolated sample was freeze-dried (x2) to give the product (0.014 g, 71% yield) as a yellow solid. ESI-MS: 581.4 $[M+H]^+$. $^1H$ NMR (300 MHz, DMSO-$d_6$) δ 14. (brs, 1H), 8.38-8.19 (m, 2H), 7.96 (d, J=9.1 Hz, 1H), 7.91 (dd, J=4.5, 1.3 Hz, 1H), 7.85 (s, 1H), 7.32-7.19 (m, 3H), 7.14 (dd, J=8.5, 4.5 Hz, 1H), 7.06 (dd, J=9.1, 2.1 Hz, 1H), 6.67 (d, J=2.1 Hz, 1H), 4.01-3.83 (m, 3H), 3.81-3.48 (m, 9H), 3.01-2.90 (m, 2H), 2.88-2.76 (m, 1H), 2.71-2.56 (m, 2H), 2.39 (s, 3H), 2.04-1.84 (m, 3H), 1.81-1.35 (m, 5H).

Example 47. 1-Cyclopropyl-6-fluoro-7-(2-hydroxyethoxy)-3-({[(3S)-1-(6-methylpyridin-3-yl)piperidin-3-yl][(2-methylpyridin-4-yl)methyl]amino}methyl)-1,4-dihydroquinolin-4-one

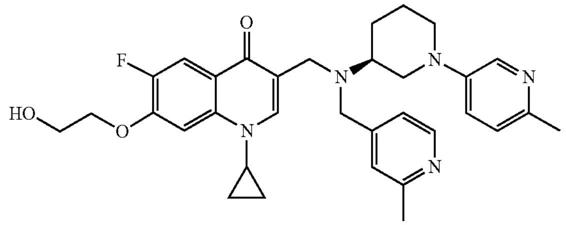

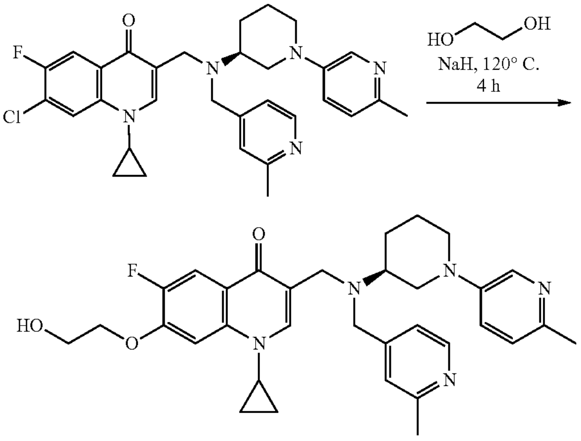

Preparation of 1-cyclopropyl-6-fluoro-7-(2-hydroxyethoxy)-3-({[(3S)-1-(6-methylpyridin-3-yl)piperidin-3-yl][(2-methylpyridin-4-yl)methyl]amino}methyl)-1,4-dihydroquinolin-4-one NaH (0.02 g, 1.5 eq.) was added in two portions to a mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.2 g, 1.0 eq.) and ethylene glycol (3.0 mL). The resulting mixture was heated for 4 h at 120° C. Then, MeOH (2.0 mL) was added followed by $H_2O$ (5.0 mL) and the mixture was washed with DCM (x4). The combined organic layers were washed with water, brine, dried over anh. $MgSO_4$, filtered and concentrated in vacuo. The residue was purified by FCC (SiHP; DCM:MeOH) and re-purified by prep-HPLC ($H_2O$:MeCN:$NH_3$) to give the product (0.032 g, 16% yield) as a beige solid. ESI-MS: 572.6 $[M+H]^+$. $^1H$ NMR (400 MHz, DMSO-$d_6$) δ 8.30-8.24 (m, 1H), 8.15-8.10 (m, 1H), 7.84 (s, 1H), 7.79 (d, J=11.7 Hz, 1H), 7.51 (d, J=7.3 Hz, 1H), 7.25-7.18 (m, 2H), 7.18-7.13 (m, 1H), 7.02 (d, J=8.5 Hz, 1H), 5.12-4.93 (m, 1H), 4.30-4.18 (m, 2H), 3.88-3.69 (m, 5H), 3.65-3.55 (m, 3H), 3.55-3.47 (m, 1H), 2.81-2.69 (m, 2H), 2.61-2.55 (m, 1H), 2.37 (s, 3H), 2.32 (s, 3H), 2.01-1.88 (m, 1H), 1.83-1.71 (m, 1H), 1.64-1.39 (m, 2H), 1.30-1.17 (m, 2H), 0.97-0.77 (m, 2H).

Example 48. 1-cyclopropyl-6-fluoro-7-[(3R)-3-hydroxypyrrolidin-1-yl]-3-({[(3S)-1-(5-methyl-1,2,4-oxadiazol-3-yl)piperidin-3-yl][(2-methylpyridin-4-yl)methyl]amino}methyl)-1,4-dihydroquinolin-4-one hydrochloride

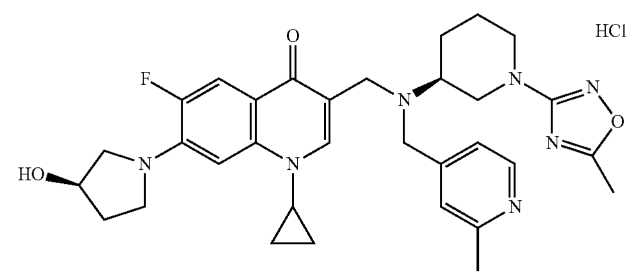

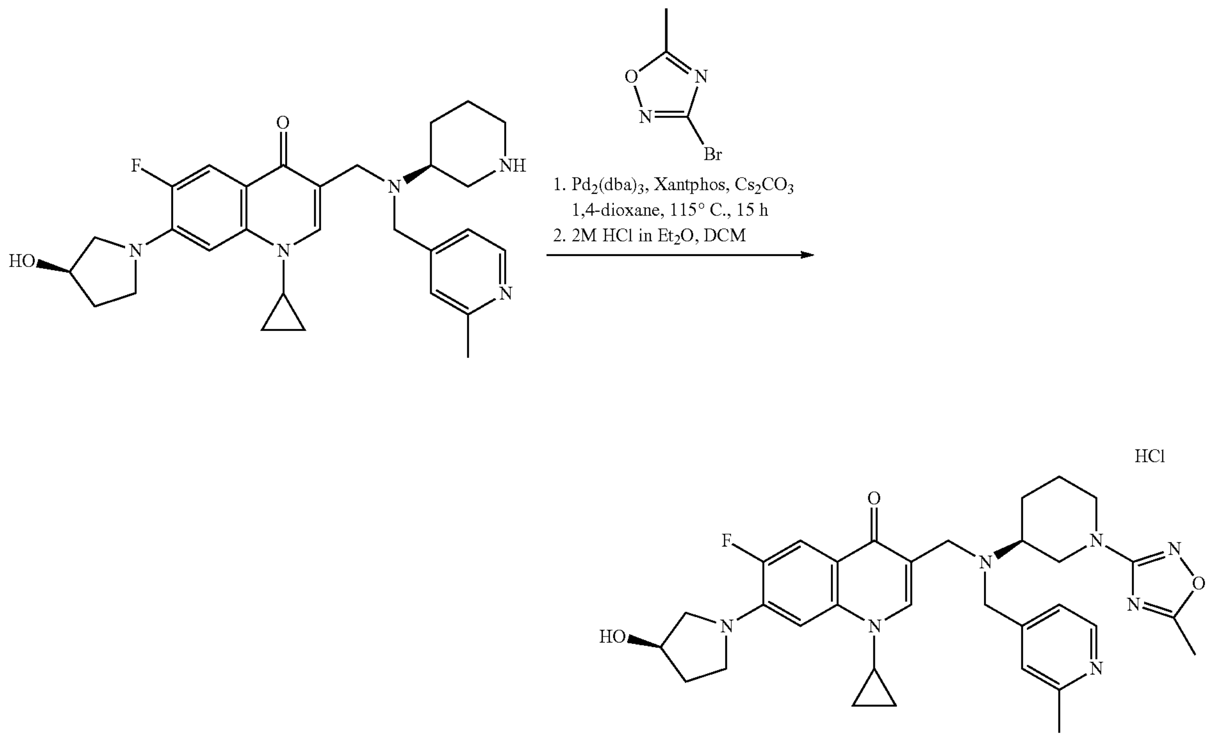

Preparation of 1-cyclopropyl-6-fluoro-7-[(3R-3-hydroxypyrrolidin-1-yl]-3-({[(3S)-1-(5-methyl 1,2,4-oxadiazol-3-yl)piperidin-3-yl][(2-methylpyridin-4-yl)methyl]amino}methyl)-1,4-dihydroquinolin-4-one A suspension of 1-cyclopropyl-6-fluoro-7-[(3R)-3-hydroxypyrrolidin-1-yl]-3-({[(2-methylpyridin-4-yl)methyl][(3S)-piperidin-3-yl]amino}methyl)-1,4-dihydroquinolin-4-one (Intermediate 28) (0.107 g, 1.0 eq.), 3-bromo-5-methyl-1,2,4-oxadiazole (0.043 g, 1.3 eq.) and $Cs_2CO_3$ (0.10 g, 1.5 eq.) in anh. 1,4-dioxane (3.0 mL) was purged with argon for 10 min. Subsequently, Xantphos (0.014 g, 0.12 eq.) and $Pd_2(dba)_3$ (0.011 g, 0.06 eq.) were added. After stirring at 115° C. for 15 h, the mixture was filtered through celite, concentrated in vacuo and purified by FCC (SiHP; DCM: MeOH). The obtained product was dissolved in DCM and scavenger QuadraPure MPA (0.2 g) was added. After stirring for 1 h, the scavenger was filtrated off and filtrate was concentrated under reduced pressure and re-purified by FCC (C18HP; $H_2O$:MeCN). The product was converted to the HCl salt using 2 M HCl in $Et_2O$ (0.028 mL, 1.0 eq.) and DCM as a solvent (2.0 mL) to provide the product (0.035 g, 28% yield) as an orange solid. ESI-MS: 588.7 $[M+H]^+$. $^1H$ NMR (300 MHz, Methanol-$d_4$) δ 8.68 (d, J=6.2 Hz, 1H), 8.37 (s, 1H), 8.13 (s, 1H), 8.10-7.93 (m, 1H), 7.79 (d, J=14.4 Hz, 1H), 7.08 (d, J=7.6 Hz, 1H), 4.74-4.67 (m, 1H), 4.62-4.54 (m, 1H), 4.49 (s, 2H), 4.36-4.10 (m, 1H), 3.97-3.59 (m, 7H), 3.56-3.44 (m, 2H), 3.22-2.97 (m, 1H), 2.76 (s, 3H), 2.45 (s, 3H), 2.39-2.28 (m, 1H), 2.27-2.08 (m, 2H), 2.03-1.91 (m, 1H), 1.80-1.55 (m, 2H), 1.50-1.39 (m, 2H), 1.24-1.08 (m, 2H).

Example 49. 7-[(3R)-3-hydroxypyrrolidin-1-yl]-3-({[(2-methylpyridin-4-yl)methyl][(3S)-1-(pyridazin-4-yl)piperidin-3-yl]amino}methyl)-1-(propan-2-yl)-1,4-dihydroquinolin-4-one
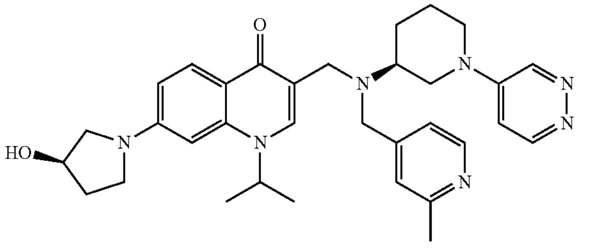
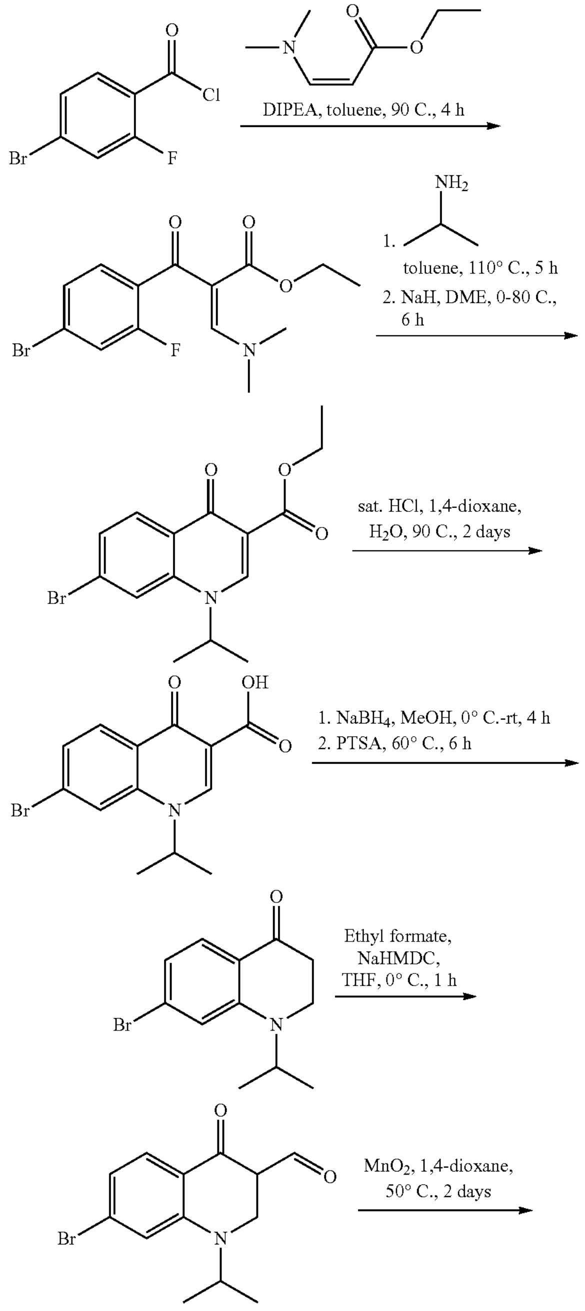
-continued
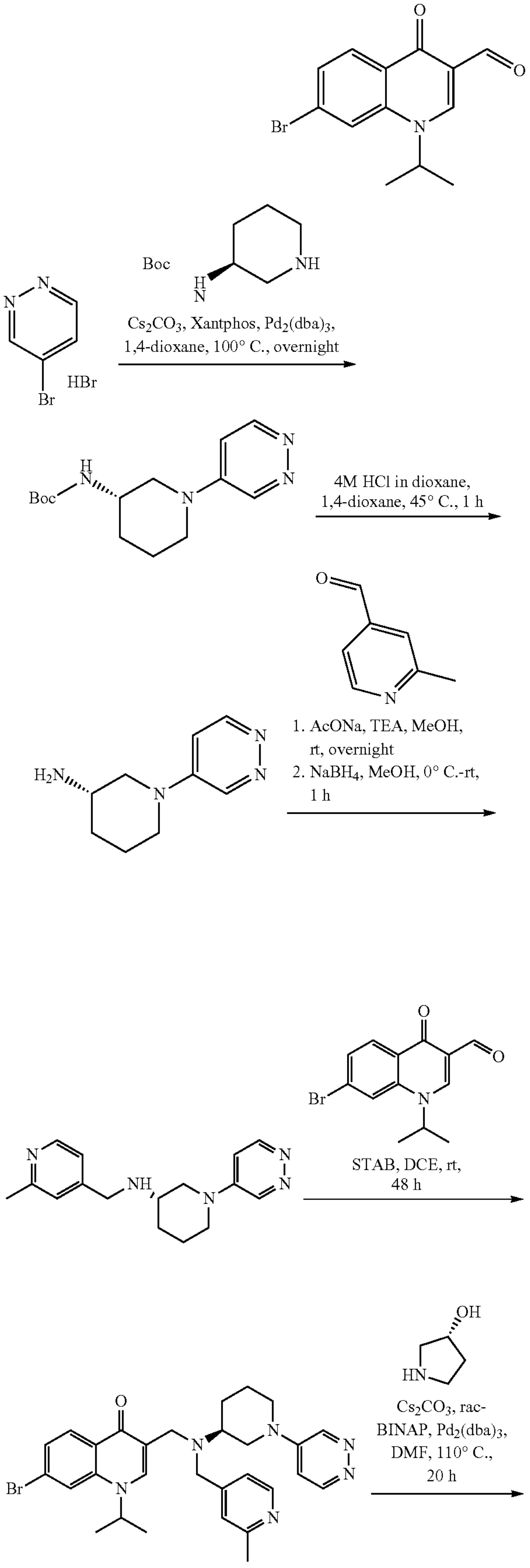

-continued

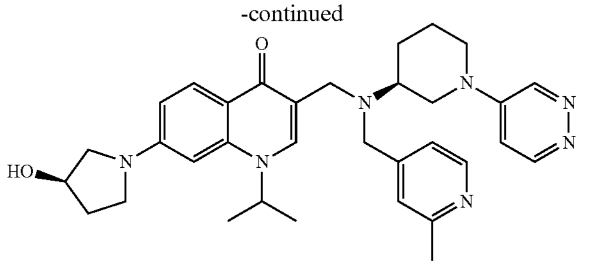

Preparation of ethyl (2Z)-2-[(Z)-4-bromo-2-fluorobenzoyl]-3-(dimethylamino)prop-2-enoate The reaction was divided into two identical batches and the same procedure was used for each reactor. A mixture of ethyl 3-(dimethylamino)prop-2-enoate (7.58 mL, 1.0 eq.) and anh. N,N-Diisopropylethylamine, (19.3 mL, 2.1 eq.) was stirred for 10 minutes, after which time a solution of 4-bromo-2-fluorobenzoyl chloride (12.5 g, 1.0 eq.) in anh. toluene (100.0 mL) was added dropwise to the reaction mixture and then heated at 90° C. for 4 h. A colorless precipitate formed. The precipitate was filtered off on a sintered funnel and the solvents of the filtrate were evaporated under reduced pressure. The resulting oily product was then dry-deposited on silica gel and purified via FCC (SIHP; Hex:EtOAc) to give desired product (26.5 g, 64% yield) as a dark orange oil. ESI-MS: 345.9 $[M+2+H]^+$.

Preparation of ethyl 7-bromo-4-oxo-1-(propan-2-yl)-1,4-dihydroquinoline-3-carboxylate A mixture of ethyl (22)-2-[(Z)-4-bromo-2-fluorobenzoyl]-3-(dimethylamino)prop-2-enoate (26.5 g, 1.0 eq.) and propan-2-amine (6.0 mL, 1.1 eq.) in anh. toluene (200.0 mL) was heated at 110° C. for 5 hours. Solvent was evaporated and the resulting crude material was dissolved in DME (200.0 mL) and cooled to 0° C., after which sodium hydride (60% dispersion in mineral oil, 5.4 g, 2.0 eq.) was added slowly. The resulting reaction mixture was then heated to 80° C. for another 6 h after which it was cooled to RT. The mixture was diluted with EtOAc, saturated ammonium chloride solution was added and the mixture was washed with additional portions of ethyl acetate. The organic phase was washed with brine, dried over $Na_2SO_4$ and the solvent removed under reduced pressure. Some product remained in the form of solid residue and some dissolved in the aqueous layer. The solid residues were filtered off and the desired product in the aqueous layer was extracted into DCM. The fraction contained in the ethyl acetate was purified via FCC (SiHP; Hex:EtOAc). was All fractions were combined to yield the product (13.7 g, 56% yield) to be used in the next step without further purification. ESI-MS: 338.9 [M+2]+.

Preparation of 7-bromo-4-oxo-1-(propan-2-yl)-1,4-dihydroquinoline-3-carboxylic acid Saturated hydrochloric acid (20.0 mL) was added to a cooled in ice-water bath suspension of ethyl 7-bromo-4-oxo-1-(propan-2-yl)-1,4-dihydroquinoline-3-carboxylate (13.7 g, 1.0 eq.) in 1,4-dioxane (60.0 mL) and water (50.0 mL) was added and the resulting mixture was then heated at 90° C. for 2 days. The reaction mixture was cooled to RT and the resulting precipitate filtered off using a sintered funnel. It was washed with additional portions of water and dried. The resulting solid with residual water was dissolved in DCM. This solution was washed with brine, dried over $Na_2SO_4$ and the solvent removed under reduced pressure to give the product (12.4 g, 98% yield) that was then used in the next step without further purification. ESI-MS: 311.1 $[M+H]^+$.

Preparation of 7-bromo-1-(propan-2-yl)-1,2,3,4-tetrahydroquinolin-4-one

Sodium borohydride (6.2 g, 4.5 eq.) was added to a cooled in ice-water bath solution of 7-bromo-4-oxo-1-(propan-2-yl)-1,4-dihydroquinoline-3-carboxylic acid (12.4 g, 1.0 eq.) in methanol (400.0 mL), kept under argon, slowly over 5 min. The mixture was warmed to RT and was stirred for 4 h. p-Toluene sulfonic acid (0.69 g, 0.1 eq.) was then added and the reaction mixture was heated at 60° C. for 6 h. Silica gel (40 g) was added to the reaction mixture and the solvent removed under reduced pressure. The crude product, now adsorbed on silica, was purified by FCC (SiHP; Hex:EtOAc) to give product (8.03 g, 81% yield). ESI-MS: 269.0 $[M+H]^+$.

Preparation of 7-bromo-4-oxo-1-(propan-2-yl)-1,2,3,4-tetrahydroquinoline-3-carbaldehyde 7-bromo-1-(propan-2-yl)-1,2,3,4-tetrahydroquinolin-4-one (8.0 g, 1.0 eq.) dissolved in THF (20 mL) was added at 0° C. to a solution of sodium bis(trimethylsilyl)amide solution (17.7 mL, 1.2 eq.) in THF (50 mL). The reaction mixture was stirred for 30 min at 0° C. and then, ethyl formate (2.9 mL, 1.2 eq.) dissolved in THF (10 mL) was added. After 1 h the reaction was quenched by addition of saturated $NH_4Cl$, which was followed by washing the product mixture with ethyl acetate (×3). The combined organic layers were washed with brine, dried over $Na_2SO_4$, and the solvent removed under reduced pressure. The resulting product (9.02 g, 69% yield) was used directly in next step without further purification. ESI-MS: 296.0, 297.9 [M+H].

Preparation of 7-bromo-4-oxo-1-(propan-2-yl)-1,4-dihydroquinoline-3-carbaldehyde (Intermediate 19)

7-Bromo-4-oxo-1-(propan-2-yl)-1,2,3,4-tetrahydroquinoline-3-carbaldehyde (9.02 g, 1.0 eq.) was dissolved in anh. 1,4-dioxane (200.0 mL). $MnO_2$ (8.87 g, 5.0 eq.) was added and the reaction was heated at 50° C. for 2 days. The reaction mixture was cooled to RT and filtered through celite. The pad of celite was washed with the mixture of DCM:MeOH (7:3). The filtrate was concentrated under reduced pressure and the residue was redissolved in 200.0 mL of DCM. The yellow solids that precipitated were filtered on a sintered funnel and washed with additional portions of DCM to give product (3.95 g, 64% yield). The crude product mixture was purified by FCC (SiHP; DCM:MeOH) to give the product (0.375 g, 6% yield). ESI-MS: 295.9 $[M+2+H]^+$.

Preparation of tert-butyl N-[(3S)-1-(pyridazin-4-yl)piperidin-3-yl]carbamate

In a sealed tube, tert-Butyl N-[(3S)-piperidin-3-yl]carbamate (0.22 g, 1.3 eq.), 4-bromopyridazine hydrobromide (0.2 g, 1.0 eq.) and cesium carbonate (0.543 g, 2.0 eq.) were suspended in dry 1,4-dioxane. The reaction mixture was purged with argon for 10 min and Xantphos (0.029 g, 0.06 eq.) and $Pd_2(dba)_3$ (0.038 g, 0.05 eq.) were added. The reaction mixture was purged one more time with argon for 5 min, the tube was closed and reaction was heated at 100° C. overnight Dichloromethane and water were added to the mixture and the compound was partitioned between the two layers. The organic layer was dried over anh. $MgSO_4$, filtered and concentrated. The crude mixture was purified by FCC (SiHP, DCM:MeOH) to give the product (0.125 g, 49% yield). ESI-MS: 279.4 $[M+H]^+$.

Preparation of (3S)-1-(pyridazin-4-yl)piperidin-3-amine 4.0 M HCl in 1,4-dioxane (0.66 mL, 5.0 eq.) was added to a solution of tert-butyl N-[(3S)-1-(pyridazin-4-yl)piperidin-3-yl]carbamate (0.152 g, 1.0 eq.) in 1,4-dioxane. The reaction mixture was stirred for 1 h at 60° C. The crude mixture was concentrated and partitioned between with DCM and NaOH aq. The organic layers were combined, dried over $Na_2SO_4$, filtered and concentrated under reduced pressure. The aqueous phase was freeze-dried since some product was detected in it and the combined residues were purified by FCC (PF—$NH_2$; DCM:MeOH) to give the product (0.065 g, 70% yield). ESI-MS: 179.0 $[M+H]^+$.

Preparation of (3S)—N-[(2-methylpyridin-4-yl)methyl]-1-(pyridazin-4-yl)piperidin-3-amine (3S)-1-(Pyridazin-4-yl)piperidin-3-amine (0.065 g, 1.0 eq.), 2-methylpyridine-4-carbaldehyde (0.039 mL, 1.0 eq.) and sodium acetate (0.029 g, 1.0 eq.) were dissolved in methanol (3.0 mL) and the reaction mixture was stirred at RT overnight. Then the mixture was cooled to 0° C. and sodium borohydride (0.015 g, 1.1 eq.) was added in portions and the reaction mixture was stirred at RT for 1 h. Methanol was evaporated and The product was purified by FCC (SiHP, DCM:MeOH) to give the product (0.079 g, 73% yield) as a yellowish oil. ESI-MS: 284.1 $[M+H]^+$. $^1$H NMR (300 MHz, Methanol-$d_4$) δ 8.84 (dd, J=3.4, 0.8 Hz, 1H), 8.53 (dd, J=6.6, 0.8 Hz, 1H), 8.33 (d, J=5.5 Hz, 1H), 7.32 (d, J=1.5 Hz, 1H), 7.26 (d, J=5.4 Hz, 1H), 6.98 (dd, J=6.7, 3.4 Hz, 1H), 4.02 (dd, J=13.3, 3.6 Hz, 1H), 3.90 (s, 1H), 3.85 (s, 1H), 3.23-3.12 (m, 1H), 3.04 (dd, J=13.2, 9.1 Hz, 1H), 2.72 (td, J=9.1, 4.3 Hz, 1H), 2.52 (s, 3H), 2.15-2.04 (m, 1H), 1.97 (s, 2H), 1.92-1.85 (m, 1H), 1.64-1.49 (m, 2H).

Preparation of 7-bromo-3-({[(2-methylpyridin-4-yl)methyl][(3S)-1-(pyridazin-4-yl)piperidin-3-yl]amino}methyl)-1-(propan-2-yl)-1,4-dihydroquinolin-4-one 7-bromo-4-oxo-1-(propan-2-yl)-1,4-dihydroquinoline-3-carbaldehyde (Intermediate 19) (0.078 g, 1.0 eq.) and (3S)—N-[(2-methylpyridin-4-yl)methyl]-1-(pyridazin-4-yl)piperidin-3-amine (0.079 g, 1.0 eq.) were dissolved in DCE. The resulting mixture was stirred at RT overnight. Then sodium triacethoxyborohydride (0.15 g, 2.8 eq.) was added and mixture was stirred for another 24 h at RT. The reaction mixture was diluted with DCM, washed with sat. aq. sodium bicarbonate, water, brine, dried over anh. $MgSO_4$ and concentrated under reduced pressure. The residue was purified by FCC (SiHP; DCM:MeOH) to give the product (0.066 g, 45% yield) as an off-white foam. ESI-MS: 561.3, 563.1 $[M+H]^+$.

Preparation of 7-[(3R)-3-hydroxypyrrolidin-1-yl]-3-({[(2-methylpyridin-4-yl)methyl][(3S)-1-(pyridazin-4-yl)piperidin-3-yl]amino}methyl)-1-(propan-2-yl)-1,4-dihydroquinolin-4-one A solution of 7-bromo-3-({[(2-methylpyridin-4-yl)methyl][(3S)-1-(pyridazin-4-yl)piperidin-3-yl]amino}methyl)-1-(propan-2-yl)-1,4-dihydroquinolin-4-one (0.066 g, 1.0 eq.), (3R)-pyrrolidin-3-ol (0.015 g, 1.5 eq.) and cesium carbonate (0.067 g, 1.8 eq.) in anh. DMF (1.5 mL) taken in a sealed tube was purged with argon for 15 min. Then BINAP (0.014 g, 0.2 eq.) and $Pd_2(dba)_3$ (0.011 g, 0.1 eq.) were added. The reaction mixture was purged with argon for another 2 min and the tube was sealed. The resulting mixture was heated to 110° C. for 20 h and the mixture was filtered through a pad of celite. The filtrate was sonicated with scavenger, filtered on a pad of cotton and concentrated. The crude mixture was purified by FCC (SiHP; DCM:MeOH) to give the product (0.053 g, 80% yield) as a beige solid. ESI-MS: 568.5 $[M+H]^+$. $^1$H NMR (400 MHz, DMSO-$d_6$) δ 8.95 (d, J=3.2 Hz, 1H), 8.54 (d, J=6.4 Hz, 1H), 8.30 (d, J=5.0 Hz, 1H), 7.99 (d, J=8.9 Hz, 1H), 7.80 (s, 1H), 7.29 (s, 1H), 7.21 (d, J=5.2 Hz, 1H), 6.93 (dd, J=6.5, 3.3 Hz, 1H), 6.65 (dd, J=9.0, 1.9 Hz, 1H), 6.41 (d, J=2.0 Hz, 1H), 5.01 (d, J=3.7 Hz, 1H), 4.96-4.89 (m, 1H), 4.46-4.38 (m, 1H) J, 4.18 (d, J=12.9 Hz, 1H), 3.98 (d, J=13.1 Hz, 1H), 3.78 (s, 2H), 3.63 (s, 2H), 3.51 (dd, J=10.6, 4.8 Hz, 1H), 3.48-3.39 (m, 2H), 3.21 (d, J=10.2 Hz, 1H), 3.06 (t, J=11.8 Hz, 1H), 2.84 (t, J=12.6 Hz, 1H), 2.62 (s, 1H), 2.40 (s, 3H), 2.10-2.01 (m, 1H), 1.95 (s, 2H), 1.77 (d, J=13.7 Hz, 1H), 1.67 (dd, J=14.0, 10.4 Hz, 1H), 1.38 (t, J=7.0 Hz, 6H).

Example 50 and Example 51. Diastereomer s A and B of 7-(4-amino-3,3-difluoropiperidin-1-yl)-1-methyl-3-({[(3S)-1-(6-methylpyridin-3-yl)piperidin-3-yl][(2-methylpyridin-4-yl)methyl]amino}methyl)-1,4-dihydroquinolin-4-one. Example 50. 7-[(4R)-4-Amino-3,3-difluoropiperidin-1-yl]-1-methyl-3-({[(3S)-1-(6-methylpyridin-3-yl)piperidin-3-yl][(2-methylpyridin-4-yl)methyl]amino}methyl)-1,4-dihydroquinolin-4-one (A); Example 51. 7-[(4S)-4-Amino-3,3-difluoropiperidin-1-yl]-1-methyl-3-({[(3S)-1-(6-methylpyridin-3-yl)piperidin-3-yl][(2-methylpyridin-4-yl)methyl]amino}methyl)-1,4-dihydroquinolin-4-one (B)

A

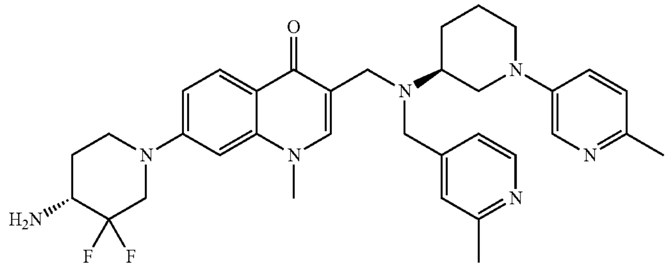

and

-continued

B

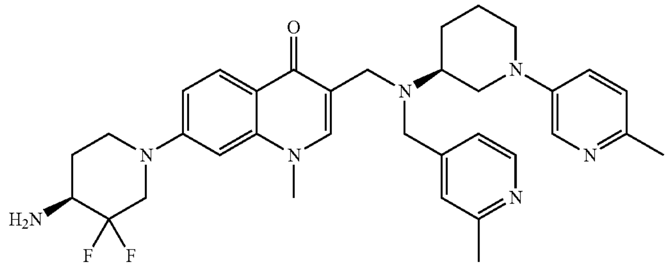

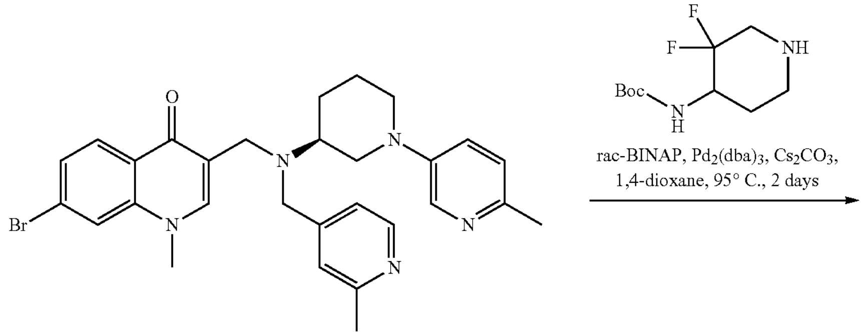

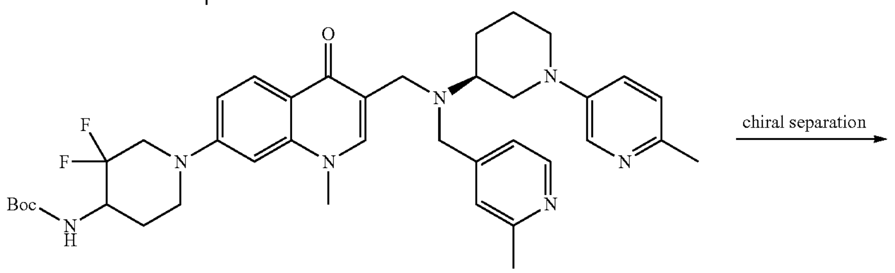

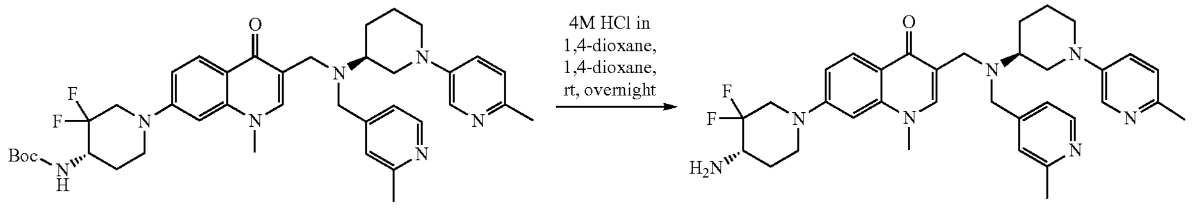

and

A

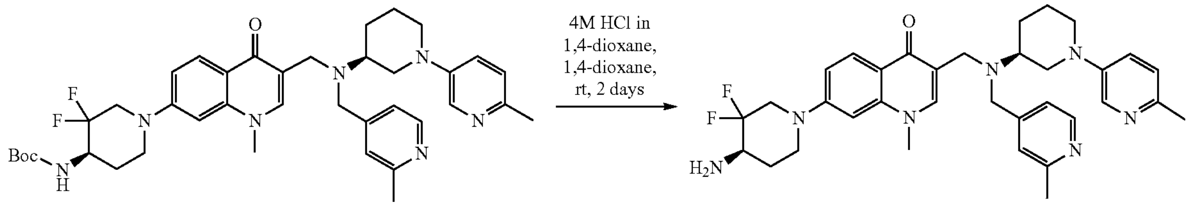

B

Preparation of tert-butyl N-{3,3-difluoro-1-[1-methyl-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-4-yl}carbamate A solution of 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one (Intermediate 13) (0.30 g, 1.0 eq.), tert-butyl N-(3,3-difluoropiperidin-4-yl)carbamate (0.26 g, 2.0 eq.) and cesium carbonate (0.372 g, 2.1 eq.) in anh. 1,4-dioxane taken in a sealed tube was purged with argon for 15 min. Then BINAP (0.102 g, 0.3 eq.) and $Pd_2(dba)_3$ (0.050 g, 0.1 eq.) were added. The reaction mixture was purged with argon for another 2 min and the tube was sealed. The resulting mixture was heated to 95° C. for 2 days and it was filtered on a pad of celite. Scavenger QuadraPure MPA was added to the filtrate and mixture was sonicated. Then the scavenger was filtered off and solvent was concentrated. The crude mixture was purified by FCC (SiHP, DCM:MeOH) to product (0.27 g, 67% yield). ESI-MS: 702.6 $[M+H]^+$. Chiral separation of this racemate was performed (IF; Hex:EtOH 35% isocratic) to provide Boc-protected diastereomers A (0.085 g, 32% yield) and B (0.114 g, 43% yield). ESI-MS: 702.6 $[M+H]^+$. Stereochemistry was assigned arbitrary.

Preparation of 7-[(4R)-4-Amino-3,3-difluoropiperidin-1-yl]-1-methyl-3-({[(3S)-1-(6-methylpyridin-3-yl)piperidin-3-yl][(2-methylpyridin-4-yl)methyl]amino}methyl)-1,4-dihydroquinolin-4-one—Diastereomer A 4 M hydrogen chloride solution in 1,4-dioxane (0.143 mL, 5.0 eq.) was added to a solution of Boc-protected diastereomer A (0.085 g, 1.0 eq.) in 1,4-dioxane. The reaction mixture was stirred overnight at RT. However, the reaction did not go to completion and an additional portion of 4 M hydrogen chloride solution in 1,4-dioxane (0.143 mL, 5.0 eq.) was added and reaction time was prolonged to 2 days. Solvents was concentrated, extracted with DCM and NaOH aq. Organic layers were combined, dried over anh. $MgSO_4$, filtrated and concentrated. Crude was purified by FCC (PF-diol, DCM:MeOH) to give a product (0.020 g, 29% yield). ESI-MS: 602.5 $[M+H]^+$.

Preparation of 7-[(4S)-4-Amino-3,3-difluoropiperidin-1-yl]-1-methyl-3-({[(3S)-1-(6-methylpyridin-3-yl)piperidin-3-yl][(2-methylpyridin-4-yl)methyl]amino}methyl)-1,4-dihydroquinolin-4-one—Diastereomer B 4 M hydrogen chloride solution in 1,4-dioxane (0.2 mL, 5.0 eq.) was added to a solution of Boc-protected diastereomer B (0.114 g, 1.0 eq.) in 1,4-dioxane. The reaction mixture was stirred overnight at RT and the mixture was concentrated and partitioned between DCM and aq. NaOH. The organic layer was combined, dried over $MgSO_4$, filtered and concentrated under reduced pressure. The crude mixture was purified by FCC (PF-diol, DCM:MeOH) to give product (0.021 g, 22% yield). ESI-MS: 602.4 $[M+H]^+$. 1H NMR (400 MHz, Methanol-$d_4$) δ 8.16 (s, 1H), 8.15 (d, J=3.4 Hz, 1H), 8.08 (d, J=2.9 Hz, 1H), 7.83 (s, 1H), 7.34 (dd, J=8.6, 3.0 Hz, 1H), 7.25-7.21 (m, 2H), 7.17 (dd, J=9.3, 2.2 Hz, 1H), 7.10 (d, J=8.6 Hz, 1H), 6.76 (d, J=2.2 Hz, 1H), 4.25-4.16 (m, 1H), 3.99 (d, J=13.7 Hz, 1H), 3.88 (d, J=10.9 Hz, 1H), 3.83 (d, J=4.0 Hz, 2H), 3.78 (s, 5H), 3.60 (d, J=12.2 Hz, 1H), 3.22-3.12 (m, 2H), 2.98-2.90 (m, 1H), 2.84 (t, J=11.1 Hz, 1H), 2.68 (t, J=11.1 Hz, 1H), 2.40 (s, 3H), 2.32 (s, 3H), 2.15 (s, 1H), 2.09-2.01 (m, 1H), 1.94-1.88 (m, 1H), 1.76 (q, J=11.7 Hz, 1H), 1.65 (q, J=8.8 Hz, 2H).

Example 52. 7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one

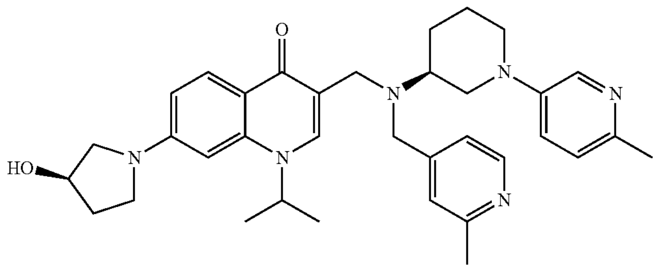

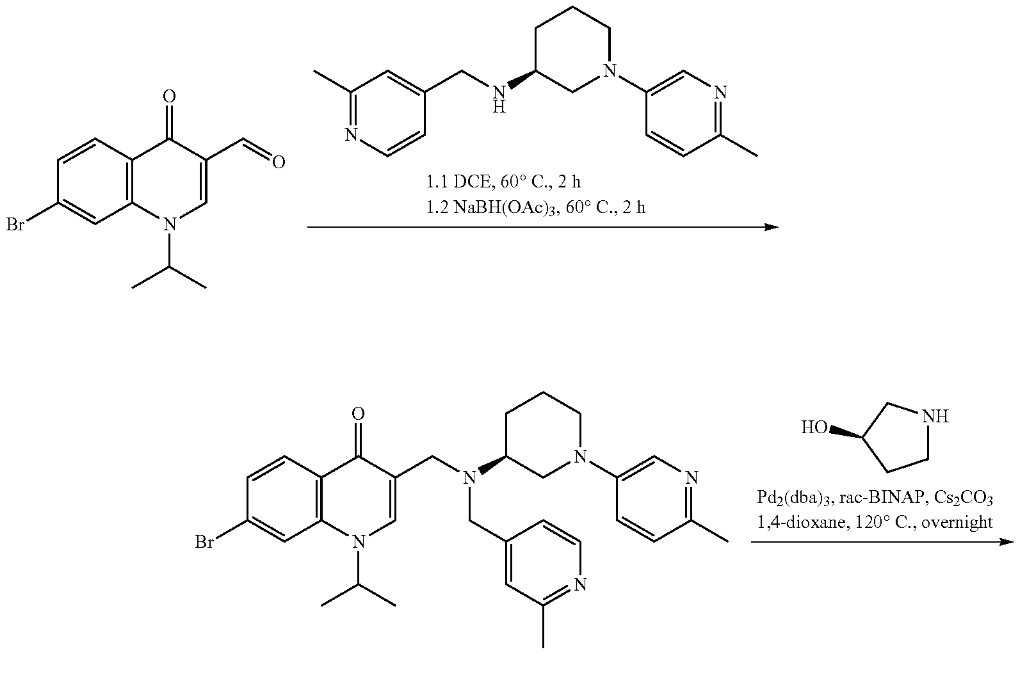

-continued

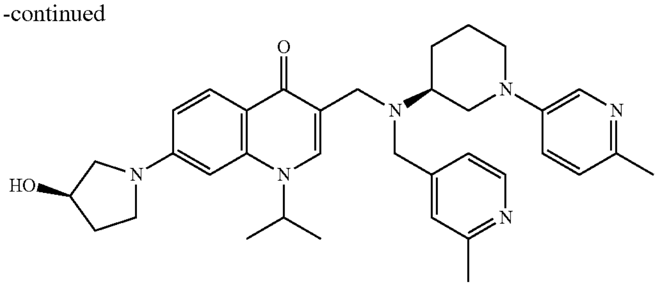

Preparation of 7-bromo-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one (Intermediate 20)

A solution of (3S)-1-(6-methylpyridin-3-yl)-N-[(2-methylpyridin-4-yl)methyl]piperidin-3-amine (Intermediate 2) (0.57 g, 1.1 eq.) and 7-bromo-4-oxo-1-(propan-2-yl)-1,4-dihydroquinoline-3-carbaldehyde (Intermediate 19) (0.5 g, 1.0 eq.) in anh. DCE (10.0 mL) was stirred in 60° C. over 2 h. Then $NaBH(OAc)_3$ (0.98 g, 2.8 eq.) was added and the reaction mixture was stirred for an additional 2 h at 60° C. The mixture was diluted with DCM and washed with aq. solution of NaOH, dried over anh. $Na_2SO_4$, concentrated in vacuo and purified by FCC (SiHP; DCM:MeOH) to give product (0.64 g, 65% yield) as a yellow solid. ESI-MS: 576.1 $[M+2+H]^+$.

Preparation of 7-[(3R)-3-hydroxypyrrolidin-1-yl]-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one In a sealed tube, (3R)-pyrrolidin-3-ol (0.066 g, 1.5 eq.), $Cs_2CO_3$ (0.294 g, 1.8 eq.) and 7-bromo-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one (Intermediate 20) (0.3 g, 1.0 eq.) were suspended in anh. 1,4-dioxane (5.0 mL). The suspension was purged with argon for 5 min and then BINAP (0.062 g, 0.2 eq.) and $Pd_2(dba)_3$ (0.046 g, 0.1 eq.) were added. The reaction mixture was purged with argon one more time, the tube was closed and stirred at 120° C. overnight. The residue was filtered through celite, the solvent was concentrated in vacuo and purified by FCC (SiHP; DCM:MeOH) and repurified by RP FCC (C18HP; $H_2O$:MeCN) to afford (0.178 g, 61% yield) as a white solid. ESI-MS: 581.2 $[M+H]^+$. $^1$H NMR (400 MHz, DMSO-$d_6$) 8.30 (d, J=5.0 Hz, 1H), 8.12 (d, J=2.9 Hz, 1H), 7.99 (d, J=9.0 Hz, 1H), 7.82 (s, 1H), 7.27 (s, 1H), 7.24-7.17 (m, 2H), 7.00 (d, J=8.5 Hz, 1H), 6.65 (dd, J=8.9, 2.0 Hz, 1H), 6.41 (d, J=2.0 Hz, 1H), 5.01 (d, J=3.6 Hz, 1H), 4.98-4.89 (m, 1H), 4.43 (s, 1H), 3.86-3.70 (m, 3H), 3.63-3.55 (m, 3H), 3.54-3.36 (m, 3H), 3.26-3.16 (m, 1H), 2.79-2.69 (m, 2H), 2.52 (s, 1H), 2.40 (s, 3H), 2.32 (s, 3H), 2.12-2.00 (m, 1H), 1.99-1.88 (m, 2H), 1.76 (d, J=10.7 Hz, 1H), 1.60-1.44 (m, 2H), 1.43-1.32 (m, 6H).

Example 53. 7-[4-(2-Hydroxyethyl)piperazin-1-yl]-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one

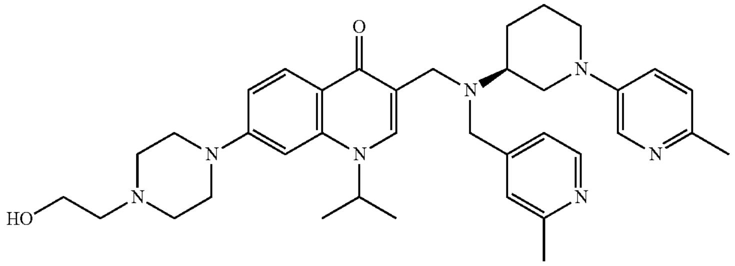

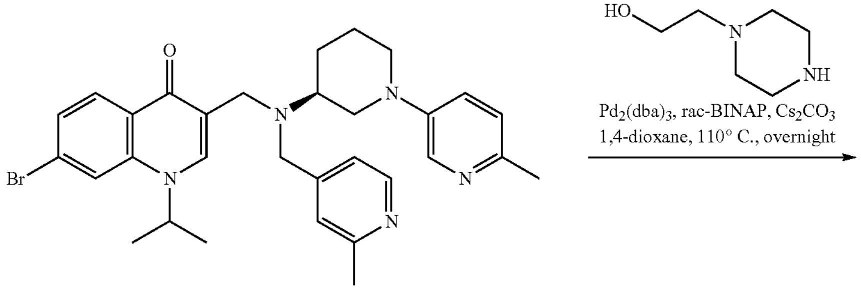

-continued

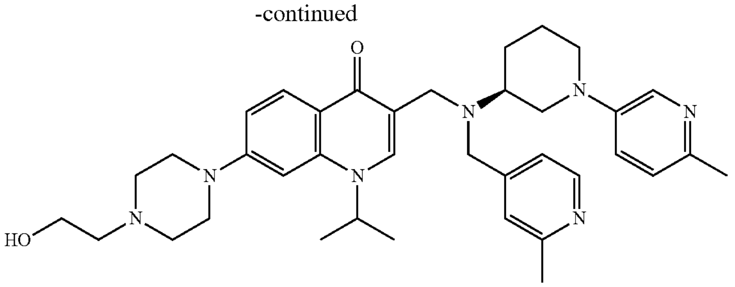

Preparation of 7-[4-(2-hydroxyethyl)piperazin-1-yl]-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one 7-Bromo-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one (Intermediate 20) (0.043 g, 1.0 eq.), 2-(piperazin-1-yl)ethan-1-01 (0.019 g, 2.0 eq.) and cesium carbonate (0.043 g, 1.8 eq.) were dissolved in anh. 1,4-dioxane (2.0 mL). The solution was purged by argon for 5 min and then BINAP (0.009 g, 0.2 eq.) and $Pd_2(dba)_3$ (0.007 g, 0.1 eq.) were added. The tube was closed and stirred at 110° C. overnight. The reaction mixture was filtered through celite, water was added and the mixture was washed with DCM (×3). The combined organic layers were washed with brine, dried over $MgSO_4$, filtered and concentrated in vacuo. The residue was purified by RP-FCC (C18HP; $H_2O$:MeCN). The obtained product was dissolved in methanol and stirred with scavenger QuadraPure MPA (0.2 g) for 1 h. The scavenger was filtered off and the filtrate was concentrated to give the product (0.039 g, 85% yield) as an off-white powder. ESI-MS: 624.5 $[M+H]^+$. $^1H$ NMR (300 MHz, DMSO-$d_6$) δ 8.30 (d, J=5.0 Hz, 1H), 8.12 (d, J=2.9 Hz, 1H), 8.01 (d, J=9.0 Hz, 1H), 7.88 (s, 1H), 7.30-7.16 (m, 3H), 7.10-6.95 (m, 2H), 6.89 (s, 1H), 5.01 (quint, J=6.6 Hz, 1H), 4.45 (t, J=5.3 Hz, 1H), 3.84-3.69 (m, 3H) 1), 3.61 (s, 2H), 3.54 (q, J=5.8 Hz, 3H), 2.83-2.66 (m, 3H), 2.64-2.54 (m, 6H) J, 2.44 (t, J=6.2 Hz, 3H), 2.39 (s, 3H), 2.32 (s, 3H), 1.95 (s, 1H), 1.76 (d, J=10.3 Hz, 1H), 1.50 (q, J=11.9 Hz, 2H), 1.38 (dd, J=6.4, 2.6 Hz, 6H).

Example 54. 7-[(3R,4S)-3,4-dihydroxypyrrolidin-1-yl]-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one

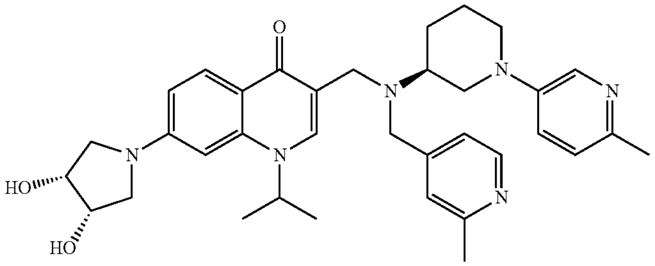

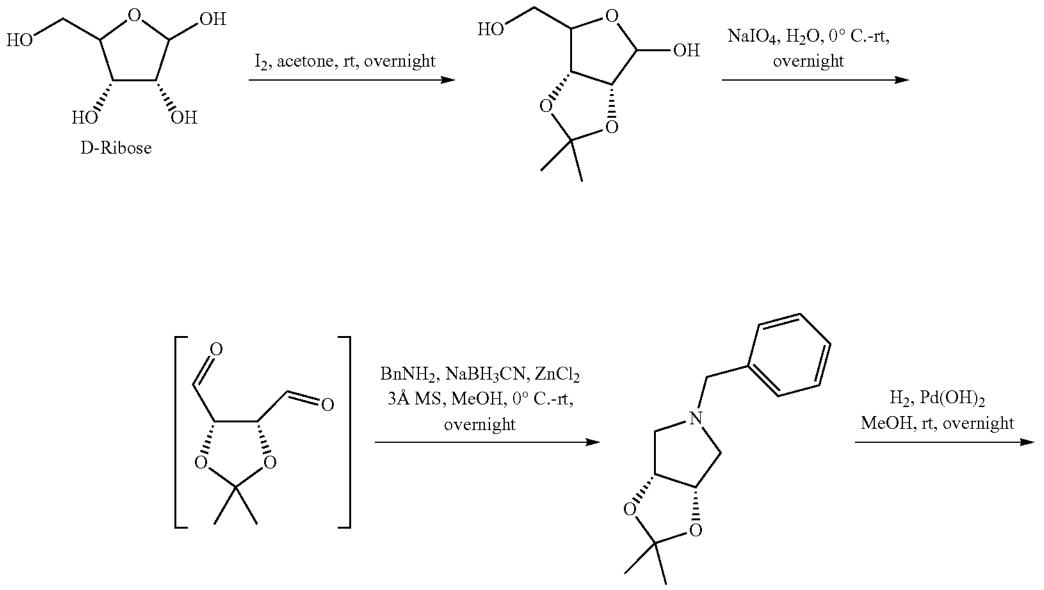

-continued

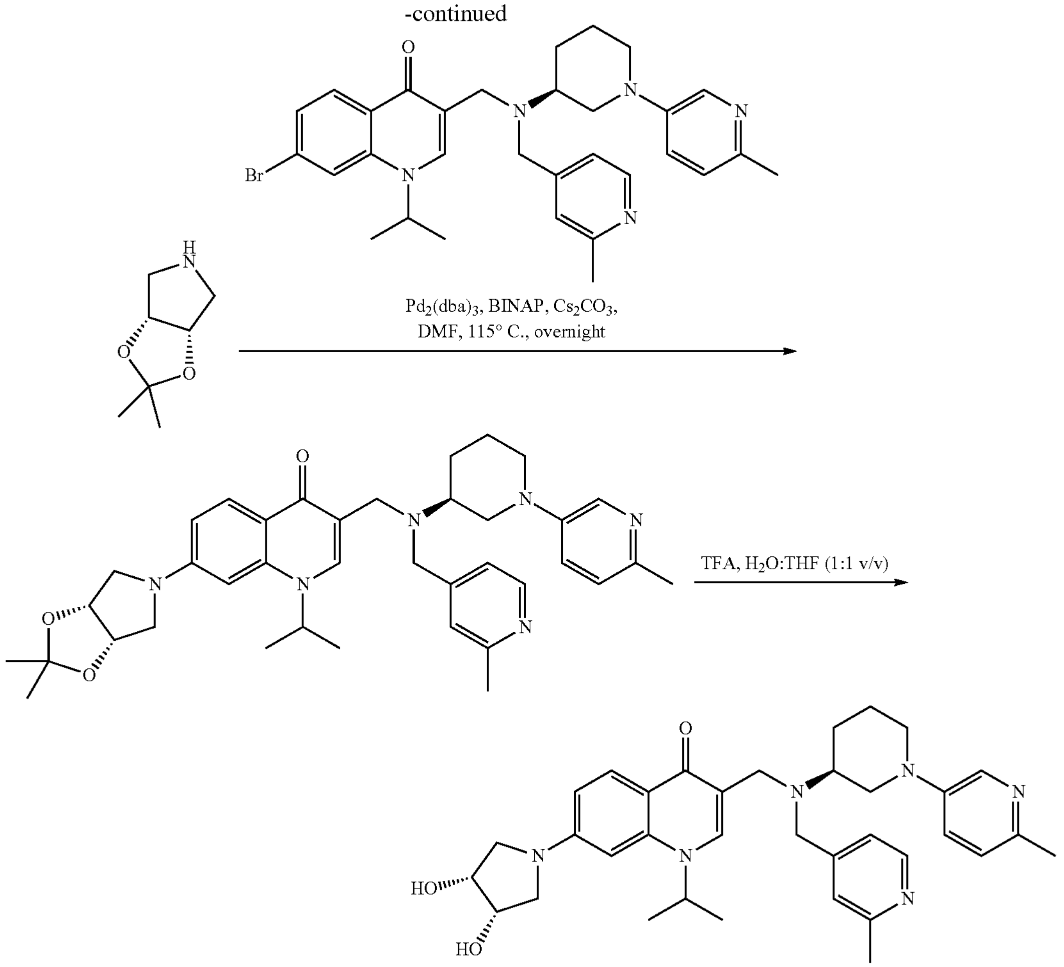

Preparation of (3aR,6aR)-6-(hydroxymethyl)-2,2-dimethyl-tetrahydro-2H-furo[3,4-d][1,3]dioxol-4-ol Iodine (0.01 g, 0.003 eq.) was added to a solution of D-ribose (2.0 g, 1.0 eq.) in acetone (HPLC Grade 99.5+%, 10.0 mL) and the resulting yellow solution was stirred at RT overnight. The reaction mixture was concentrated to dryness. The residue was dissolved in satd. aq. solution of sodium thiosulphate (50.0 mL), stirred for 10 min. and washed with EtOAc (200 mL×4). The combined organic layers were dried over $MgSO_4$, filtered and concentrated in vacuo to give product (2.46 g, 97% yield) as a colorless oil, that was used directly in the next step.

Preparation of (4R,5S)-2,2-dimethyl-1,3-dioxolane-4,5-dicarbaldehyde

A solution of (3aR,6aR)-6-(hydroxymethyl)-2,2-dimethyl-tetrahydro-2H-furo[3,4-d][1,3]dioxol-4-ol (1.58 g, 1.0 eq.) in water (15.0 mL) was added dropwise to a solution of $NalO_4$ (3.55 g, 2.0 eq.) in water (LC-MS Grade, 80.0 mL) at 0° C. The reaction mixture was stirred at 0° C. for 30 min, warmed to RT and stirred at this temperature overnight. After the disappearance of the starting material as detected by TLC (petroleum ether/EtOAc=1:2), the reaction mixture was concentrated under reduced pressure. The residue was diluted with EtOAc (100.0 mL) and then filtered through a pad of celite. The filtrate was concentrated under vacuum to give product (1.50 g) as a colorless oil, which was used immediately in the next step.

Preparation of (3aR,6aS)-5-benzyl-2,2-dimethyl-hexahydro-[1,3]dioxolo[4,5-c]pyrrole A solution of (4R,5S)-2,2-dimethyl-1,3-dioxolane-4,5-dicarbaldehyde (1.3 g, 1.0 eq.) in anh. MeOH (10.0 mL) was added dropwise to a suspension of activated 3 Å molecular sieves, $NaBH_3CN$ (1.12 g, 2.6 eq.) and zinc chloride (3.85 mL, 1.9 M in 2-MeTHFm 1.0 eq.) in 70.0 mL of anh. MeOH at 0° C. and was followed by the addition of benzylamine (ReagentPlus 99%, 1.0 mL, 1.2 eq.). The reaction mixture was stirred at 0° C. for 30 min, brought to RT and stirred at this temperature overnight After the disappearance of the starting material as detected by TLC (petroleum ether/EtOAc=2:1), the reaction mixture was filtered through a pad of celite, and then the solvent was evaporated under reduced pressure. The residue was diluted with 100.0 mL of water, and then washed with EtOAc (50 mL×4). The combined organic layers were washed with brine, dried over $MgSO_4$ and concentrated under reduced pressure. The residue was purified by FCC (SiHP; Hex:EtOAc) to give a product (1.34 g, 75% yield) as a colorless oil. ESI-MS: 234.4 $[M+H]^+$; $^1H$ NMR (300 MHz, $CDCl_3$) δ 7.37-7.19 (m, 5H), 4.70-4.60 (m, 2H), 3.63 (s, 2H), 3.04 (d, J=12.0 Hz, 2H), 2.28-2.05 (m, 2H), 1.57 (s, 3H), 1.32 (s, 3H).

Preparation of (3aR,6aS)-2,2-dimethyl-hexahydro-[1,3]dioxolo[4,5-c]pyrrole

In a parr shaker vessel (3aR,6aS)-5-benzyl-2,2-dimethyl-hexahydro-[1,3]dioxolo[4,5-c]pyrrole (1.18 g, 1.0 eq.) was dissolved in anh. MeOH (100.0 mL) and the solution was purged with argon for 10 min. Palladium hydroxide on carbon (0.48 g, 0.7 eq.) was added and argon was bubbled for another 20 min. The vessel was placed in the parr shaker apparatus under 40 bar $H_2$ and the reaction was carried out overnight. The solution was filtered through a pad of celite, washed with methanol and the filtrate was concentrated in vacuo to give product (0.652 g, 95% yield) as a colorless oil J J.

Preparation of 7-[(3aR,6aS)-2,2-dimethyl-hexahydro-[1,3]dioxolo[4,5-c]pyrrol-5-yl]-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one A suspension of (3aR,6aS)-2,2-dimethyl-hexahydro-[1,3]dioxolo[4,5-c]pyrrole (0.1 g, 2.3 eq.), $Cs_2CO_3$ (0.207 g, 2.1 eq.), 7-bromo-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one (Intermediate 20) (0.174 g, 1.0 eq.) in anh. DMF (5.0 mL) was purged with argon for 10 min. BINAP (0.06 g, 0.3 eq.) and $Pd_2(dba)_3$ (0.06 g, 0.2 eq.) were then added. The reaction mixture was sonicated and purged with argon for 5 min. The mixture was then stirred at 115° C. overnight. The mixture was cooled and filtered through a pad of celite. The filtrate was concentrated in vacuo and the residue was purified by FCC (SiHP; DCM:MeOH), redissolved in DCM and stirred with scavenger QuadraPure MPA overnight Subsequently, the mixture was filtered, concentrated in vacuo to give the product (0.17 g, 85% yield) as a brown semisolid. ESI-MS: 637.5 $[M+H]^+$.

Preparation of 7-[(3R,4S)-3,4-dihydroxypyrrolidin-1-yl]-3-({[(3S)-1-(6-methylpyridin-3-yl)piperidin-3-yl][(2-methylpyridin-4-yl)methyl]amino}methyl)-1-(propen-2-yl)-1,4-dihydroquinolin-4-one 7-[(3aR,6aS)-2,2-dimethyl-hexahydro-[1,3]dioxolo[4,5-c]pyrrol-5-yl]-3-({[(3S)-1-(6-methylpyridin-3-yl)piperidin-3-yl][(2-methylpyridin-4-yl)methyl]amino}methyl)-1-(propan-2-yl)-1,4-dihydroquinolin-4-one (0.148 g, 1.0 eq.) was dissolved in a mixture of water (LC-MS Grade) and THF (2.0 mL, 1/1 v/v) then trifluoroacetic acid (0.05 mL, 3.0 eq.) was added. The resulting reaction mixture was stirred at RT overnight. The reaction mixture was basified to pH 12 using 2 M NaOH aq. solution and washed with DCM (4×50.0 mL). The combined organic layers were washed with water (10.0 mL) followed by brine (20.0 mL). The organic layer was dried over $MgSO_4$, filtered and concentrated in vacuo to give a brown residue. The crude material was purified by prep-HPLC ($H_2O$:MeCN:$NH_3$). The pure fractions were lyophilized and dried under high vacuum to give the product (0.033 g, 23% yield) as a yellow solid. ESI-MS: 597.6 $[M+H]^+$; $^1H$ NMR (400 MHz, DMSO-$d_6$) δ 8.35 (s, 2H), 8.30 (d, J=5.1 Hz, 1H), 8.12 (d, J=3.0 Hz, 1H), 7.98 (d, J=9.0 Hz, 1H), 7.82 (s, 1H), 7.27 (s, 1H), 7.23-7.16 (m, 2H), 7.00 (d, J=9.0 Hz, 1H), 6.62 (dd, J=9.0, 1.9 Hz, 1H), 6.38 (s, 1H), 4.94 (quint, J=6.5 Hz, 1H), 4.17 (t, J=4.3 Hz, 2H), 3.85-3.70 (m, 3H), 3.63-3.46 (m, 5H), 3.23 (dd, J=10.1, 4.1 Hz, 2H), 2.80-2.68 (m, 2H), 2.39 (s, 3H), 2.32 (s, 3H), 2.02-1.90 (m, 1H), 1.83-1.70 (m, 1H), 1.60-1.42 (m, 3H), 1.38 (dd, J=6.5, 4.2 Hz, 6H).

Example 55. 1-Cyclopropyl-6-fluoro-7-[(3R)-3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride

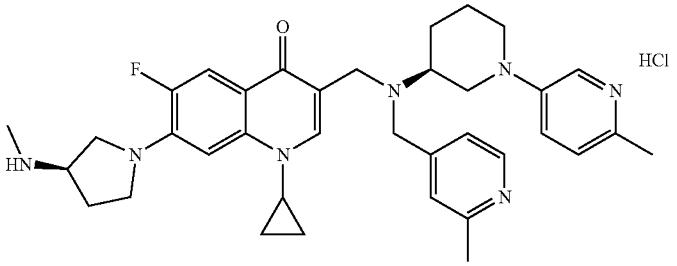

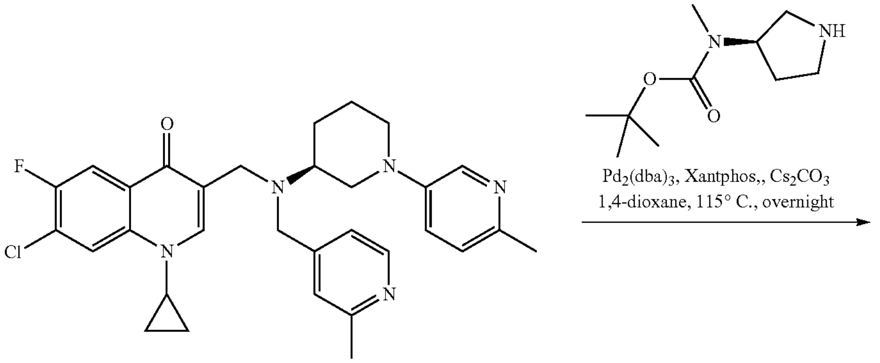

-continued

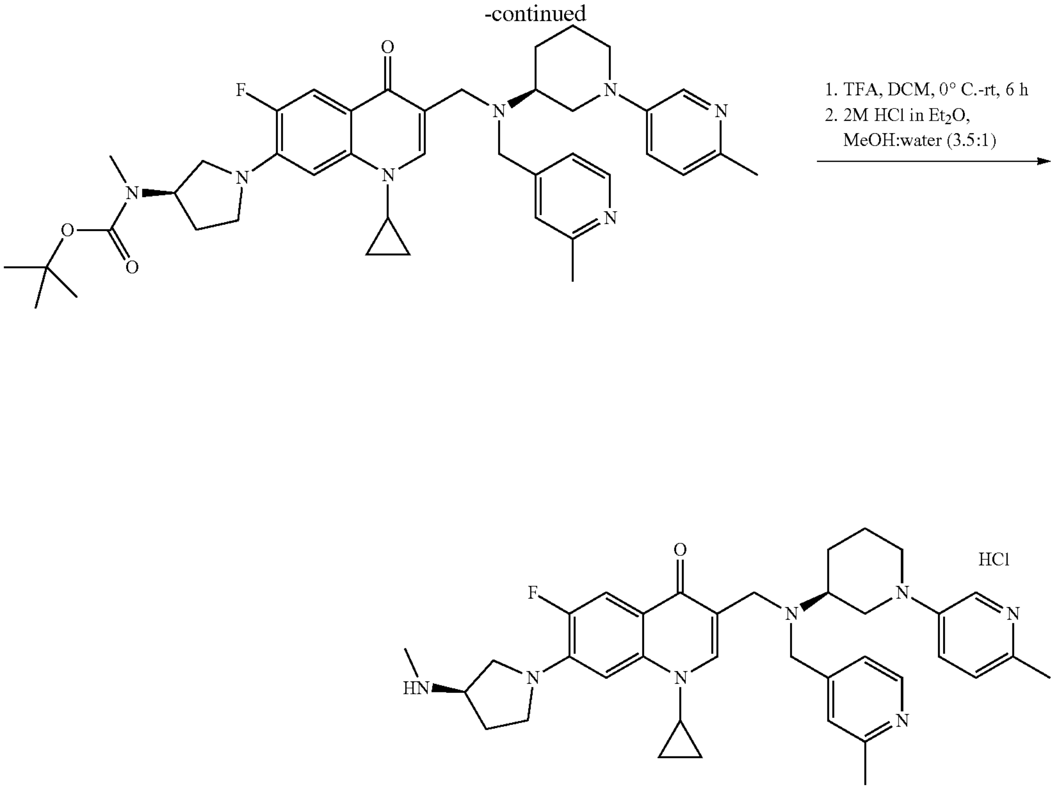

Preparation of tert-butyl N-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]-N-methylcarbamate A mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (1.0 g, 1.0 eq.), (R)-3-(N-Boc-N-methylamino)pyrrolidine (0.51 g, 1.5 eq.) and cesium carbonate (1.78 g, 3.2 eq.) in 1,4-dioxane (30 mL) was sparged with argon for 10 min, after which $Pd_2(dba)_3$ (0.31 g, 0.2 eq.) and Xantphos (0.30 g, 0.3 eq.) were added. The mixture was once again sparged with argon for 5 min, after which the reaction vessel was sealed and heated at 115° C. overnight. The mixture was passed through a pad of celite and washed with additional portions of EtOAc. The filtrate was then concentrated under reduced pressure and purified by FCC (SiHP deactivated with DCM:$NH_3$; DCM:MeOH) followed by RP-FCC (C18HP; $H_2O$:MeCN) yield the product (0.75 g, yield 61% yield) as a beige solid. ESI-MS: 710.7 [M+H].

Preparation of 1-cyclopropyl-6-fluoro-7-[(3R)-3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride tert-Butyl N-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]-N-methylcarbamate (0.728 g, 1.0 eq.) was dissolved in anh. DCM (20 mL) and trifluoroacetic acid (10 mL) was added slowly. The reaction mixture was stirred for 6 h at RT and then concentrated in vacuo. The residue was dissolved in DCM, water was added and the mixture was basified to pH 9 using 1 M eq. solution of NaOH and extracted by DCM. The organic layers were then washed with brine, dried over $Na_2SO_4$ and concentrated. The residue was purified by RP-FCC (C18HP; $H_2O$:MeCN), the resulting compound was dissolved in DCM and stirred for 4 h after the addition of the scavenger QuadraPure MPA (0.9 g). The scavenger was filtered off and filtrate was concentrated in vacuo. The resulting compound was converted into hydrochloride salt using 2 M HCl in $Et_2O$ (0.34 mL, 1.0 eq.) and MeOH (14.0 mL) and water (4.0 mL) as solvents to provide the product ((0.420 g, 74% yield). ESI-MS: 610.6 $[M+H]^+$. $^1H$ NMR (300 MHz, Methano-$d_4$) δ 8.17 (d, J=5.3 Hz, 1H), 8.13 (d, J=2.9 Hz, 1H), 7.88 (s, 1H), 7.82 (d, J=14.5 Hz, 1H), 7.56 (dd, J=8.7, 3.0 Hz, 1H), 7.34-7.22 (m, 3H), 7.07 (d, J=7.5 Hz, 1H), 4.06-3.88 (m, 6H), 3.88-3.76 (m, 3H), 3.72-3.56 (m, 2H), 3.51-3.37 (m, 1H), 3.09-2.87 (m, 2H), 2.84 (s, 3H), 2.81-2.70 (m, 1H), 2.64-2.51 (m, 1H), 2.48 (s, 3H), 2.36 (s, 3H), 2.34-2.21 (m, 1H), 2.21-2.12 (m, 1H), 2.00-1.88 (m, 1H), 1.80-1.61 (m, 2H), 1.39-1.25 (m, 2H), 0.93 (p, J=4.3 Hz, 2H).

Example 56. and Example 57. Diastereomer s A and B of 7-(4-amino-3,3-difluoropiperidin-1-yl)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one Example 56. (7-[(4R)-4-amino-3,3-difluoropiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one hydrochloride (A) and Example 57. 7-[(4S)-4-amino-3,3-difluoropiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one) hydrochloride (B)

A

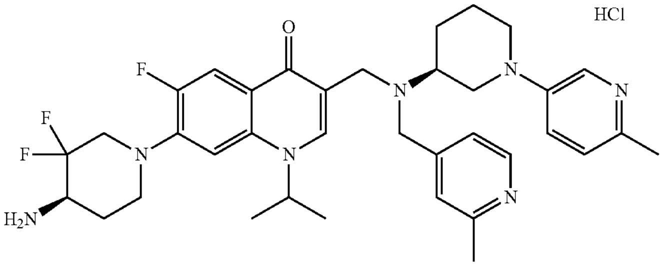

and

B

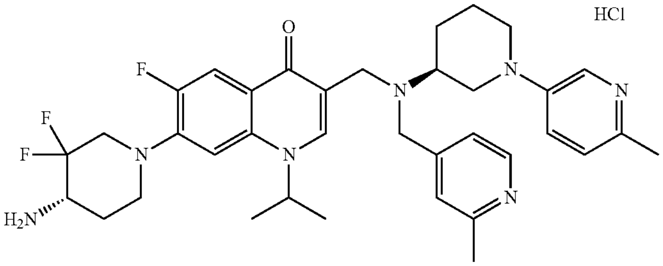

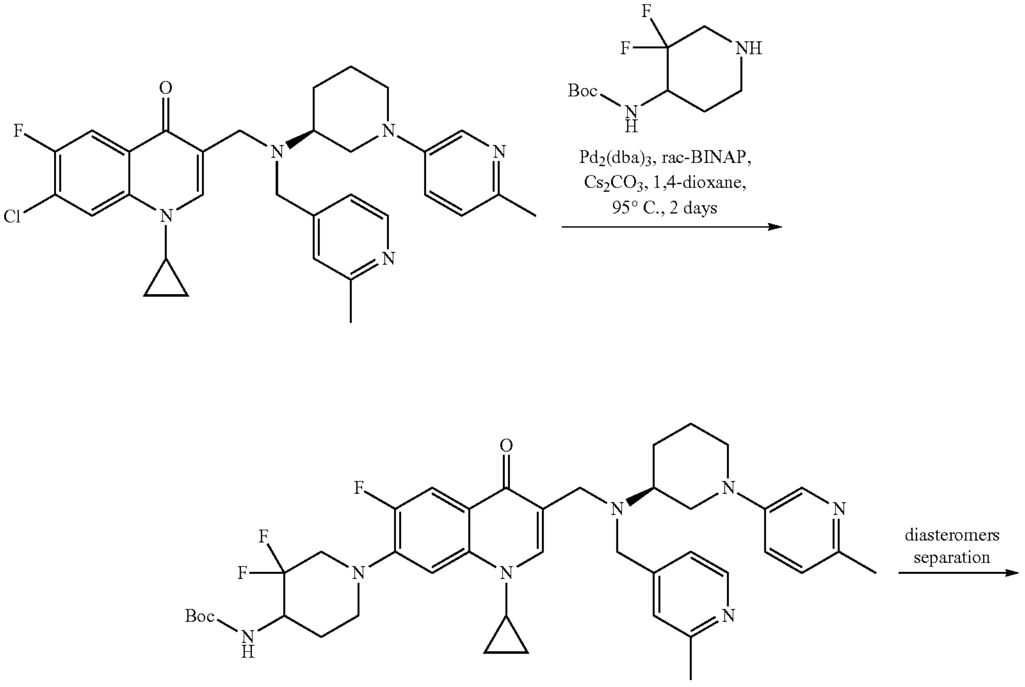

-continued

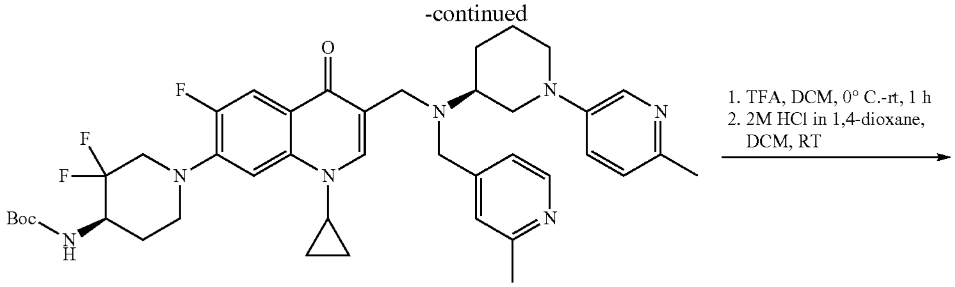

and

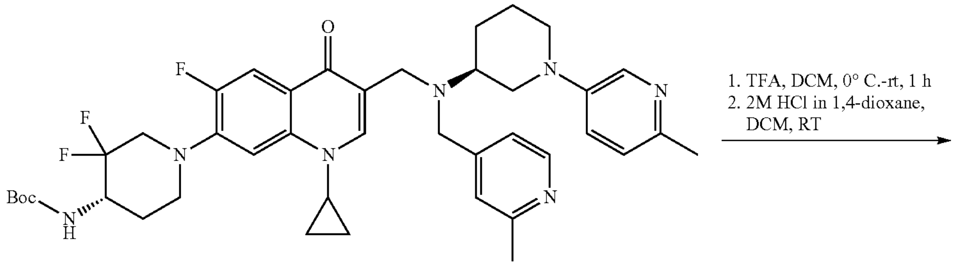

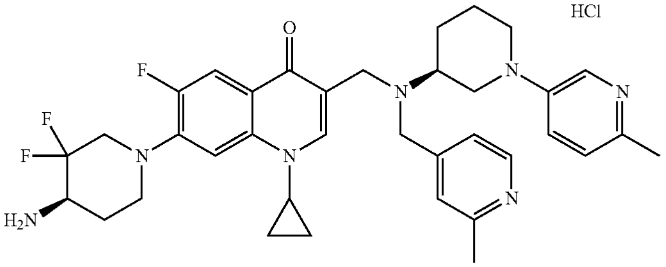

A

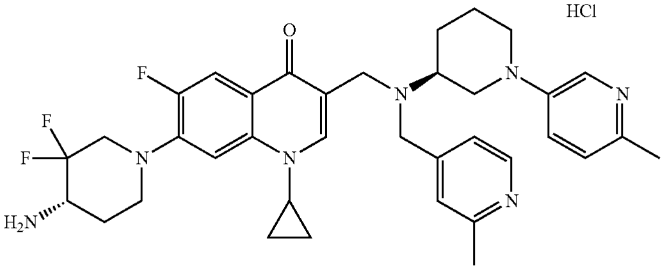

B

Preparation of Boc-protected diasteromers tert-butyl N-[(4R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-3,3-difluoropiperidin-4-yl]carbamate (A) and tert-butyl N-[(4S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-3,3-difluoropiperidin-4-yl] carbamate) (B)

A mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (1.85 g, 1.0 eq.), tert-butyl N-(3,3-difluoropiperidin-4-yl)carbamate (1.0 g, 1.3 eq.), $Cs_2CO_3$ (2.2 g, 2.1 eq.) in anh. 1,4-dioxane (70.0 mL) was purged with argon for 30 min. Then, BINAP (0.61 g, 0.3 eq.) and $Pd_2(dba)_3$ (0.30 g, 0.1 eq.) were added and the resulting mixture was purged with argon for another 15 min. The tube was sealed and the reaction mixture was heated for 2 days at 95° C. Subsequently, the mixture was filtered through a pad of celite and the pad was washed with MeOH. The filtrate was concentrated in vacuo and the residue was partitioned between DCM and water. The organic layer was washed with brine, dried over anh. $MgSO_4$, filtered and concentrated in vacuo. The residue was purified by FCC (SiHP; DCM:MeOH). The isolated sample was dissolved in DCM, scavenger QuadraPure MPA (1.3 g) was added and the resulting suspension was left stirring overnight at RT. Then, the scavenger was filtered off and the filtrate was concentrated in vacuo to give the mixture of Boc-protected diastereomers A and B (2.24 g, 86% yield) as a yellow solid. ESI-MS: 746.8 [M+H]r. The mixture was separated by chiral HPLC (ADH; Hex:EtOH 15% isocrat) to give Boc-protected diastereomer A (0.685 g, $t_R$ 43.6 min) ESI-MS: 746.8 $[M+H]^+$ and Boc-protected diastereomer B (0.656 g, $t_R$ 61.2 min). ESI-MS: 746.8 $[M+H]^+$, both as a yellow foams. The actual configurations of the diastereomers were not determined.

Preparation of (7-[(4R)-4-amino-3,3-difluoropiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one hydrochloride—Diastereomer A TFA (3.0 mL, 92.0 eq.) was added to a solution of Boc-protected Diastereomer A (0.325 g, 1.0 eq.) in DCM (6.5 mL) kept at 0° C. The resulting mixture was warmed to RT and stirred for 1 h. Then, the mixture was concentrated in vacuo, the residue was triturated with DCM and concentrated in vacuo (3 cycles). The obtained solid was partitioned between DCM and water after the aqueous layer was basified using 1 M NaOH aq. solution. The organic layer was dried over anh. $MgSO_4$, filtered and concentrated in vacuo. The residue was purified by RP-FCC (C18HP; $H_2O$:MeCN). The isolated sample was converted into the HCl salt using 2 M HCl solution in 1,4-dioxane (0.152 mL, 1.0 eq. to FB) and DCM (8.0 mL) as a solvent to give the product (0.205 g, 70% yield) as a yellow solid. ESI-MS: 646.6 $[M+H]^+$. 1H NMR (400 MHz, Methanol-$d_4$) δ 8.15 (d, J=5.2 Hz, 1H), 8.10 (d, J=2.9 Hz, 1H), 7.91 (s, 1H), 7.87 (d, J=13.3 Hz, 1H), 7.49 (dd, J=8.7, 3.0 Hz, 1H), 7.45 (d, J=7.4 Hz, 1H), 7.28-7.18 (m, 3H), 4.14-4.01 (m, 1H), 3.98-3.58 (m, 8H), 3.48-3.33 (m, 2H), 3.22-3.12 (m, 1H), 3.06-2.85 (m, 2H), 2.82-2.67 (m, 1H), 2.44 (s, 3H), 2.33 (s, 3H), 2.29-2.17 (m, 1H), 2.19-2.10 (m, 1H), 2.11-1.98 (m, 1H), 1.98-1.82 (m, 1H), 1.76-1.57 (m, 2H), 1.39-1.23 (m, 2H), 1.00-0.85 (m, 2H).

Preparation of 7-[(4S)-4-amino-3,3-difluoropiperidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one) hydrochloride—Diastereomer B TFA (3.0 mL, 93.0 eq.) was added to a solution of Boc-protected Diastereomer B (0.338 g, 1.0 eq.) in DCM (6.5 mL) kept at 0° C. The resulting mixture was stirred for 1 h at RT. Then, the mixture was concentrated in vacuo, the residue was triturated with DCM and concentrated in vacuo (3 cycles). The obtained solid was partitioned between DCM and water after the aqueous layer was basified using 1 M NaOH aq. solution. The combined organic layers were dried over anh. $MgSO_4$, filtered and concentrated in vacuo. The residue was purified by RP-FCC (C18HP; $H_2O$:MeCN). The isolated sample was converted into the HCl salt using 2 M HCl solution in 1,4-dioxane (0.153 mL, 1.0 eq. to FB) and DCM (8.0 mL) as a solvent to give the product (0.208 g, 71% yield) as a yellow solid. ESI-MS: 646.7 $[M+H]^+$. $^1H$ NMR (400 MHz, Methanol-$d_4$) δ 8.15 (d, J=5.2 Hz, 1H), 8.10 (d, J=2.9 Hz, 1H), 7.90 (s, 1H), 7.86 (d, J=13.4 Hz, 1H), 7.49-7.40 (m, 2H), 7.28-7.14 (m, 3H), 4.10-3.97 (m, 1H), 3.95-3.74 (m, 6H), 3.69-3.55 (m, 2H), 3.50-3.35 (m, 2H), 3.24-3.08 (m, 1H), 3.03-2.81 (m, 2H), 2.80-2.67 (m, 1H), 2.43 (s, 3H), 2.32 (s, 3H), 2.25-2.09 (m, 2H), 2.08-1.86 (m, 2H), 1.79-1.58 (m, 2H), 1.41-1.20 (m, 2H), 1.05-0.82 (m, 2H).

Example 58. 1-Cyclopropyl-6-fluoro-7-[(3S)-3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride

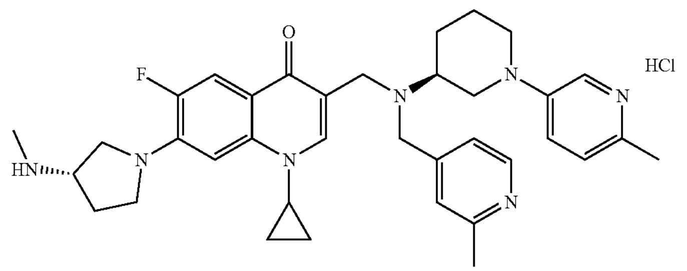

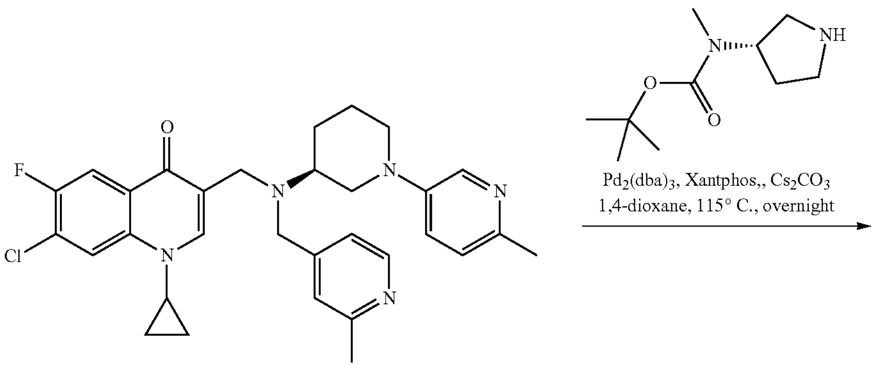

-continued

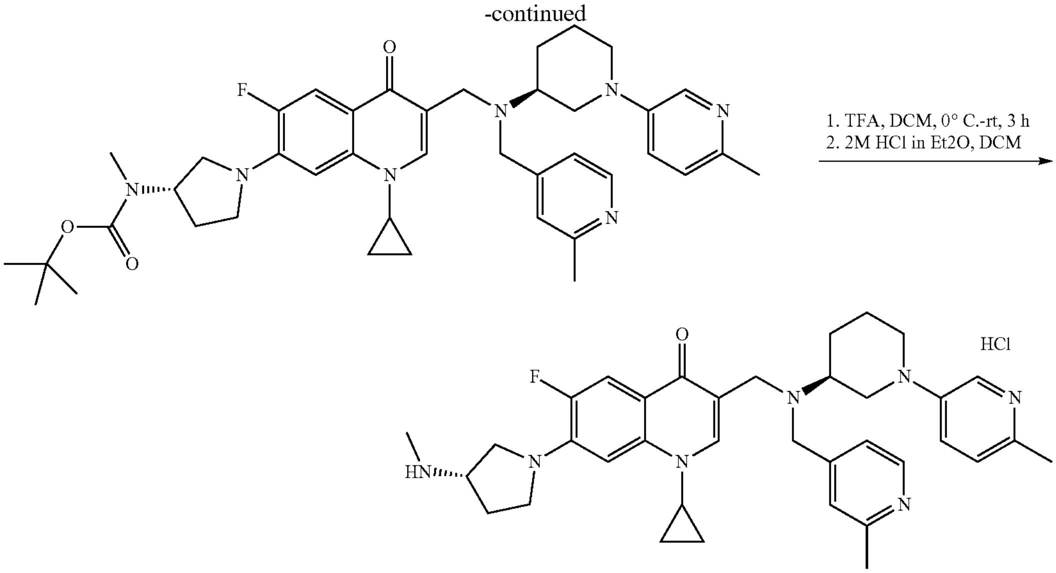

Preparation of tert-butyl N-[(3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]N-methylcarbamate A mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (1.0 g, 1.0 eq.), (S)-3-(N-Boc-N-methylamino)pyrrolidine (0.51 g, 1.5 eq.) and $Cs_2CO_3$ (1.78 g, 3.2 eq.) in anh. 1,4-dioxane (20.0 mL) was sparged with argon for 10 minutes, after which $Pd_2(dba)_3$ (0.31 g, 0.2 eq.) and Xantphos (0.30 g, 0.3 eq.) were added. The mixture was once again sparged with argon for 5 min, after which the reaction vessel was sealed and heated at 115° C. overnight. The mixture was passed through a pad of celite and washed with additional portions of EtOAc. The filtrate was then concentrated on a rotary evaporator. The crude material was purified by FCC (SIHP, DCM:MeOH) and repurified by RP-FCC (C18HP, $H_2O$:MeCN) to give product (0.799 g, 64% yield) as a beige solid. ESI-MS: 710.9 $[M+H]^+$.

Preparation of 1-cyclopropyl-6-fluoro-7-[(3S)-3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride tert-Butyl N-[(3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]-N-methylcarbamate (0.799 g, 1.0 eq.) was dissolved in anh. DCM (5.0 mL) and placed in an ice bath. Then, TFA (2.5 mL, 30.0 eq.) was added in slowly, stirring continued for 5 min and ice bath was removed. The reaction mixture was stirred for 3 h at RT, then concentrated under reduced pressure and diluted with water. This aqueous solution was basified with 2 M NaOH to pH value ~10 and washed with DCM. The organic layer was dried over anh. $Na_2SO_4$ and concentrated in vacuo. The residue was purified by RP-FCC (C18HP, $H_2O$:MeCN). The product was redissolved in DCM (10.0 mL) and stirred for 4 h with the scavenger QuadraPure MPA (0.9 g). The mixture was filtered through a Buchner funnel and washed with DCM (×2). The filtrate was concentrated and repurified using FCC (PF-50DIOL, DCM:MeOH). The compound was converted to the HCl salt using 2 M HCl in $Et_2O$ (0.22 mL, 1.1 eq.) and DCM as a solvent (6.0 mL) to give product (0.272 g, yield 39% yield over 2 steps) as a yellow solid. ESI-MS: 610.6 $[M+H]^+$. $^1H$ NMR (300 MHz, Methanol-$d_4$) δ 8.20-8.12 (m, 2H), 7.86 (s, 1H), 7.82 (d, J=14.5 Hz, 1H), 7.68 (dd, J=9.0, 3.0 Hz, 1H), 7.39-7.31 (m, 2H), 7.29 (d, J=5.6 Hz, 1H), 7.06 (d, J=7.6 Hz, 1H), 4.07-3.93 (m, 4H), 3.92-3.76 (m, 5H), 3.74-3.53 (m, 2H), 3.47-3.38 (m, 1H), 3.10-2.93 (m, 2H), 2.88-2.74 (m, 4H), 2.61-2.52 (m, 1H), 2.50 (s, 3H), 2.35 (s, 3H), 2.34-2.21 (m, 1H), 2.21-2.12 (m, 1H), 2.01-1.88 (m, 1H), 1.84-1.60 (m, 2H), 1.35-1.25 (m, 2H), 0.98-0.86 (m, 2H).

Example 59. 7-[(3R)-3-Hydroxypyrrolidin-1-yl]-3-({[(2-methylpyridin-4-yl)methyl][(3S)-1-(pyrimidin-5-yl)piperidin-3-yl]amino}methyl)-1-(propan-2-yl)-1,4-dihydroquinolin-4-one

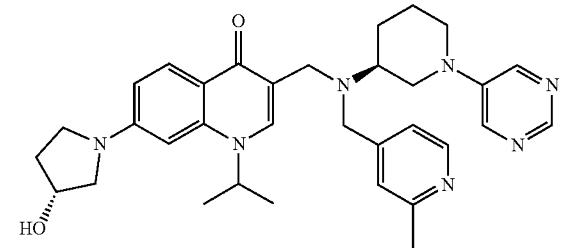

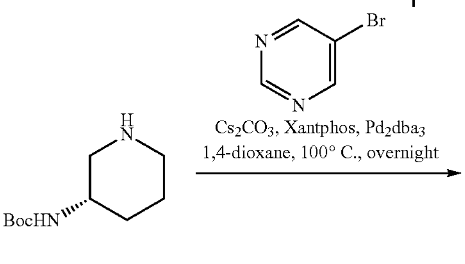

-continued

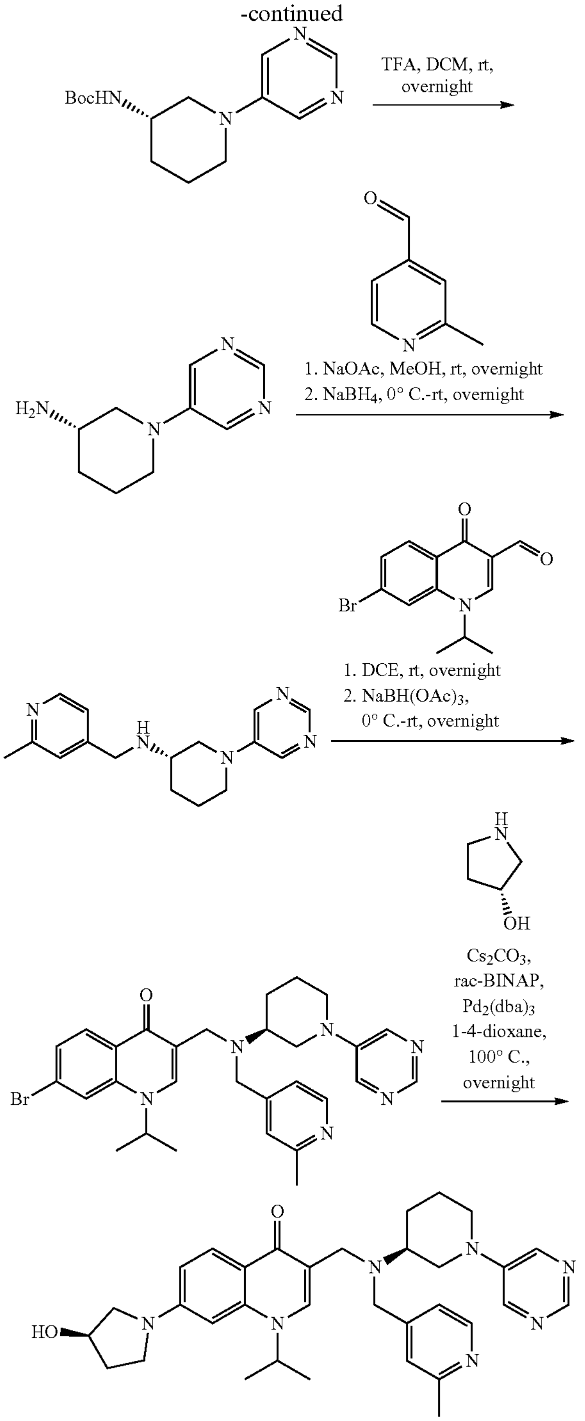

Preparation of tert-butyl N-[(3S)-1-(pyrimidin-5-yl)piperidin-3-yl]carbamate

In a sealed tube, 5-bromopyrimidine (0.2 g, 1.0 eq.), tert-butyl N-[(3S)-piperidin-3-yl]carbamate (0.33 g, 1.3 eq.) and cesium carbonate (0.82 g, 2.0 eq.) were suspended in anh. 1,4-dioxane (5.0 mL). The reaction mixture was purged with argon for 10 min, then Xantphos (0.044 g, 0.06 eq.) and $Pd_2(dba)_3$ (0.058 g, 0.05 eq.) were added. The reaction mixture was purged one more time with argon for 5 min, then reaction tube was closed and reaction was heated at 100° C. overnight. The reaction mixture was diluted with water and extracted with DCM (×3). The combined organic layers were washed with brine, dried over $MgSO_4$, filtered and concentrated. The crude material was loaded on a column and purified by FCC (SiHP; DCM:MeOH) to give the product (0.301 g, 82% yield) as a yellow solid. ESI-MS: 279.1 $[M+H]^+$.

Preparation of (3S)-1-(pyrimidin-5-yl)piperidin-3-amine tert-Butyl N-[(3S)-1-(pyrimidin-5-yl)piperidin-3-yl]carbamate (0.30 g, 1.0 eq.) was dissolved in anh. DCM (5.0 mL) and trifluoroacetic acid (0.79 mL, 10.0 eq.) was added and the reaction mixture was stirred at RT overnight. The solvent was evaporated and the crude product was further diluted with MeOH and traces of moisture were azeotropically removed (×3) to give product as a trifluoroacetate salt (0.3 g, 97% yield) which is a yellow oil. ESI-MS: 179.1 $[M+H]^+$.

Preparation of (3S)—N-[(2-methylpyridin-4-yl)methyl]-1-(pyrimidin-5-yl)piperidin-3-amine (3S)-1-(Pyrimidin-5-yl)piperidin-3-amine trifluoroacetate salt (0.30 g, 1.0 eq.), 2-methylpyridine-4-carbaldehyde (0.11 mL, 1.0 eq.) and sodium acetate (0.083 g, 1.0 eq.) were dissolved in anh. methanol (8.0 mL) and the reaction mixture was stirred at RT overnight. Then the mixture was cooled to 0° C., sodium borohydride (0.042 g, 1.1 eq.) was added and the reaction mixture was stirred at RT overnight Methanol was evaporated and the residue was dissolved in DCM, water was added and pH was adjusted to 11 by adding 2M aq. NaOH. The product mixture was washed with DCM (×3). The combined organic layers were washed with brine, dried over $MgSO_4$, filtered and concentrated in vacuo. The crude mixture was purified by FCC (SiHP; DCM:MeOH) to give the product (0.160 g, 54% yield) as a yellow oil. ESI-MS: 284.2 $[M+H]^+$.

Preparation of 7-bromo-3-({[(2-methylpyridin-4-yl)methyl][(3S)-1-(pyrimidin-5-yl)piperidin-3-yl]amino}methyl)-1-(propan-2-yl)-1,4-dihydroquinolin-4-one 7-Bromo-4-oxo-1-(propan-2-yl)-1,4-dihydroquinoline-3-carbaldehyde (Intermediate 19) (0.166 g, 0.55 mmol, 1.0 eq.) and (3S)—N-[(2-methylpyridin-4-yl)methyl]-1-(pyrimidin-5-yl)piperidin-3-amine (0.160 g, 1.0 eq.) were dissolved in anh. DCE (3.0 mL) and the mixture was stirred at RT overnight. Then the solution was cooled to 0° C., $NaBH(OAc)_3$ (0.348 g, 3.0 eq.) was added and the reaction mixture was stirred at RT overnight. Water was added, pH was adjusted to 11 by addition of 1 M aq. solution of NaOH and the product was extracted by DCM (×3). The combined organic layers were dried over $MgSO_4$, filtered and concentrated in vacuo. Crude was purified by FCC (SiHP; DCM:MeOH) to give the product (0.187 g, 60% yield) as a white solid. ESI-MS: 561.3 [M+H], 563.2 $[M+2+H]^+$. $^1H$ NMR (400 MHz, DMSO-$d_6$) δ 8.52 (s, 1H), 8.49 (s, 2H), 8.28 (d, J=5.1 Hz, 1H), 8.14-8.10 (m, 2H), 8.02 (s, 1H), 7.50 (dd, J=8.6, 1.6 Hz, 1H), 7.27 (s, 1H), 7.23-7.17 (m, 1H), 5.05 (hept, J=6.2 Hz, 1H), 4.06-3.98 (m, 1H), 3.83-3.72 (m, 3H), 3.72-3.63 (m, 2H), 2.91 (t, J=11.6 Hz, 1H), 2.76-2.66 (m, 2H), 2.38 (s, 3H), 2.00 (d, J=11.8 Hz, 1H), 1.79 (d, J=13.3 Hz, 1H), 1.66-1.45 (m, 2H), 1.39 (t, J=6.8 Hz, 6H).

Preparation of 7-[(3R-3-hydroxypyrrolidin-1-yl]-3-({[(2-methylpyridin-4-yl)methyl][(3S)-1-(pyrimidin-5-yl)piperidin-3-yl]amino}methyl)-1-(propan-2-yl)-1,4-dihydroquinolin-4-one 7-Bromo-3-({[(2-methylpyridin-4-yl)methyl][(3S)-1-(pyrimidin-5-yl)piperidin-3-yl]amino}methyl)-1-(propan-2-yl)-1,4-dihydroquinolin-4-one (0.12 g, 1.0 eq.), (3R)-pyrrolidin-3-ol (0.028 g, 1.5 eq.) and cesium carbonate (0.13 g, 1.8 eq.) were dissolved in anh. 1,4-dioxane (4.0 mL) and the resulting suspension was purged with argon for 10 min, then BINAP (0.027 g, 0.2 eq.) and $Pd_2(dba)_3$ (0.02 g, 0.1 eq.) were added. The vessel was closed and stirred at 100° C. overnight. The reaction mixture was filtered through a pad of celite, water was added and the mixture was extracted with DCM three times. The combined organic layers were washed with brine, dried over $MgSO_4$, filtered and concentrated in vacuo. Purification by FCC (SiHP; DCM:MeOH) afforded the product (0.078 g, 63% yield) as a yellow solid. ESI-MS: 568.5 $[M+H]^+$. $^1H$ NMR (400 MHz, DMSO-$d_6$) δ 8.51 (s, 1H), 8.48 (s, 2H), 8.30 (d, J=5.0 Hz, 1H), 7.99 (d, J=8.9 Hz, 1H), 7.83 (s, 1H), 7.30 (s, 1H), 7.22 (d, J=4.8 Hz, 1H), 6.66 (dd, J=9.0, 1.9 Hz, 1H), 6.42 (d, J=2.1 Hz, 1H), 5.02 (d, J=3.7 Hz, 1H), 4.94 (hept, J=5.5 Hz, 1H), 4.47-4.40 (m, 1H), 4.01 (d, J=11.3 Hz, 1H), 3.84-3.71 (m, 3H), 3.67-3.57 (m, 2H), 3.51 (dd, J=10.6, 4.8 Hz, 1H), 3.47-3.39 (m, 2H), 3.22 (d, J=10.9 Hz, 1H), 2.89 (t, J=11.6 Hz, 1H), 2.77-2.64 (m, 2H), 2.41 (s, 3H), 2.13-2.00 (m, 1H), 2.02-1.89 (m, 2H), 1.83-1.75 (m, 1H), 1.65-1.43 (m, 2H), 1.39 (t, J=7.0 Hz, 6H).

Example 60. 1-[1-Cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-1H-1,2,3-triazole-4-carboxamide

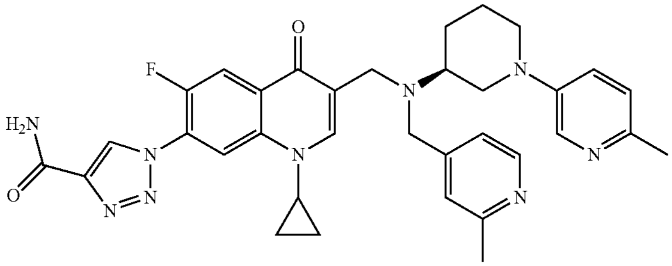

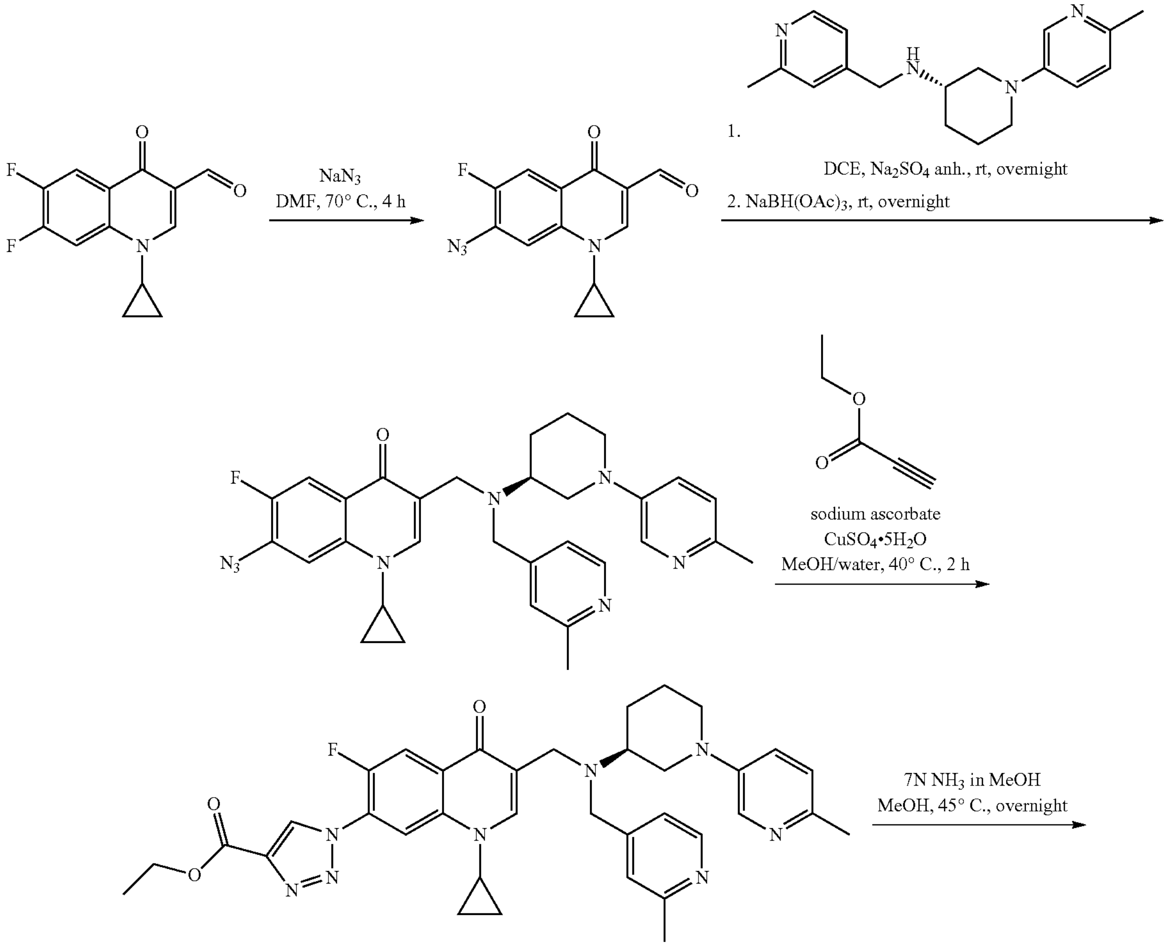

-continued

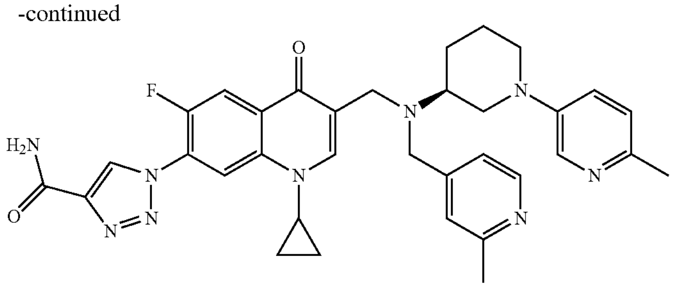

Preparation of 7-azido-1-cyclopropyl-6-fluoro-4-oxo-1,4-dihydroquinoline-3-carbaldehyde (Intermediate 21)

A suspension of 1-cyclopropyl-6,7-difluoro-4-oxo-1,4-dihydroquinoline-3-carbaldehyde (Intermediate 4) (0.700 g, 1.0 eq.) and sodium azide (0.27 g, 1.5 eq.) in anh. DMF (14.0 mL) was heated at 70° C. for 4 h. The reaction mixture was allowed to cool to RT and then poured into cold water (150.0 mL). The mixture was washed with EtOAc. The organic layer was washed with aqueous saturated solution of $NaHCO_3$ and brine, dried over anh. $Na_2SO_4$, filtered and concentrated. The product was used directly in the next step without further purification (0.820 g, 105% yield). ESI-MS: 273.0 $[M+H]^+$.

Preparation of 7-azido-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 21)

A suspension of 7-azido-1-cyclopropyl-6-fluoro-4-oxo-1,4-dihydroquinoline-3-carbaldehyde (0.82 g, 1.0 eq.), (3S)-1-(6-methylpyridin-3-yl)-N-[(2-methylpyridin-4-yl)methyl]piperidin-3-amine (Intermediate 2) (0.90 g, 1.05 eq.) and anh. sodium sulfate (0.41 g, 1.0 eq.) in anh. DCE (14.0 mL) was stirred in RT overnight, then sodium triacethoxyborohydride (1.7 g, 2.8 eq.) was slowly added in portions and the resulting reaction mixture was stirred overnight at RT. The reaction mixture was then washed using DCM and 1 M aqueous solution of NaOH. The organic layer was combined, washed with brine, dried over $Na_2SO_4$, filtered and concentrated. The residue was purified by FCC (SiHP; DCM:MeOH) to afford the product (0.88 g, 54% yield) as a beige solid. ESI-MS: 553.6 $[M+H]^+$.

Preparation of ethyl 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-1H-1,2,3-triazole-4-carboxylate Ethyl prop-2-ynoate (0.029 mL, 1.1 eq.), sodium ascorbate (0.006 g, 0.1 eq.) and copper(II) sulfate pentahydrate (0.003 g, 0.05 eq.) were sequentially added to a solution of 7-azido-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 21) (0.150 g, 1.0 eq.) in methanol (6.0 mL) and water (2.0 mL) and the reaction mixture was stirred at 40° C. for 2 h. Methanol was evaporated and the residue was diluted with DCM and water. The organic phase was separated and aqueous layer was washed with DCM. The combined organic layers were dried over $MgSO_4$, filtered and concentrated. The residue was purified by FCC (SiHP; DCM:MeOH) to afford the product (0.143 g, 79% yield) as a yellow solid. ESI-MS: 651.7 $[M+H]^+$. $^1H$ NMR (400 MHz, DMSO-$d_6$) δ 9.39 (d, J=1.7 Hz, 1H), 8.47 (d, J=6.1 Hz, 1H), 8.29 (br s, 1H), 8.18-8.10 (m, 2H), 8.01 (s, 1H), 7.27-7.20 (m, 2H), 7.18 (d, J=5.0 Hz, 1H), 7.04 (d, J=8.4 Hz, 1H), 4.40 (q, J=7.1 Hz, 2H), 3.85-3.76 (m, 3H), 3.68 (s, 2H), 3.65-3.55 (m, 2H), 2.84-2.74 (m, 2H), 2.61 (t, J=11.3 Hz, 1H), 2.38 (s, 3H), 2.33 (s, 3H), 2.00 (d, J=10.4 Hz, 1H), 1.79 (d, J=11.0 Hz, 1H), 1.61-1.45 (m, 2H), 1.35 (t, J=7.1 Hz, 3H), 1.27-1.21 (m, 2H), 1.00-0.89 (m, 2H).

Preparation of 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-1H-1,2,3-triazole-4-carboxamide Ethyl 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-1H-1,2,3-triazole-4-carboxylate (0.11 g, 1.0 eq.) was dissolved in anh. MeOH (1.0 mL) and 7 N ammonia in methanol (0.23 mL, 10.0 eq.) was added and the reaction mixture was stirred at 45° C. overnight. Then the solvent was evaporated and the residue was purified by RP-FCC (C18HP; $H_2O$:MeCN) to give the product (0.073 g, 73% yield) as a yellow solid. ESI-MS: 622.5 $[M+H]^+$. $^1H$ NMR (400 MHz, DMSO-$d_6$) δ 9.15 (d, J=1.8 Hz, 1H), 8.46 (d, J=6.1 Hz, 1H), 8.29 (d, J=5.0 Hz, 1H), 8.16-8.09 (m, 3H), 8.01 (s, 1H), 7.70 (s, 1H), 7.26-7.21 (m, 2H), 7.18 (d, J=5.1 Hz, 1H), 7.04 (d, J=8.5 Hz, 1H), 3.85-3.77 (m, 3H), 3.68 (s, 2H), 3.66-3.56 (m, 2H), 2.85-2.72 (m, 2H), 2.61 (t, J=11.5 Hz, 1H), 2.39 (s, 3H), 2.33 (s, 3H), 2.00 (d, J=10.3 Hz, 1H), 1.79 (d, J=11.1 Hz, 1H), 1.65-1.43 (m, 2H), 1.24 (d, J=7.1 Hz, 2H), 1.02-0.88 (m, 2H).

Example 61. 1-Cyclopropyl-6-fluoro-7-[4-(hydroxymethyl)-1H-1,2,3-triazol-1-yl]-3-({[(3S)-1-(6-methylpyridin-3-yl)piperidin-3-yl][(2-methylpyridin-4-yl)methyl]amino}methyl)-1,4-dihydroquinolin-4-one

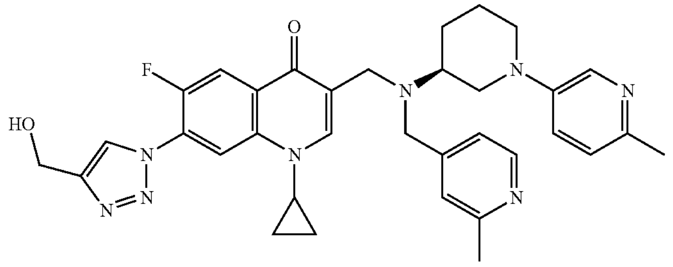

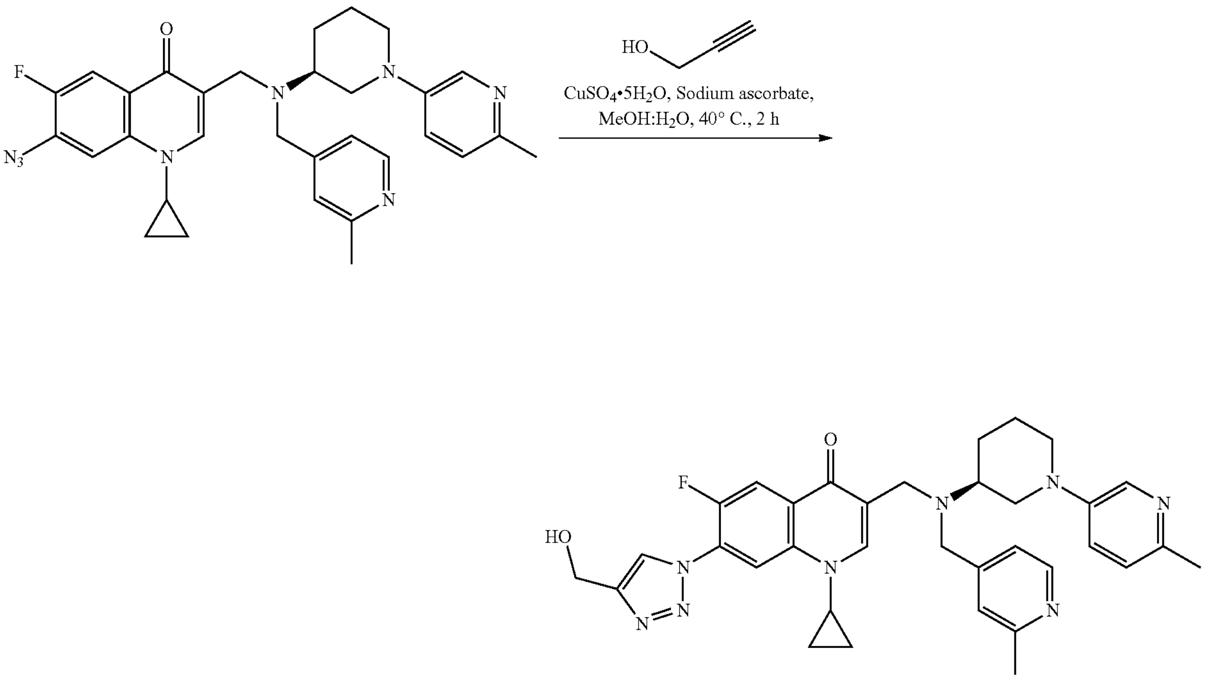

Preparation of 1-cyclopropyl-6-fluoro-7-[4-(hydroxymethyl)-1H-1,2,3-triazol-1-yl]-3-({[(3S)-1-(6-methylpyridin-3-yl)piperidin-3-yl][(2-methylpyridin-4-yl)methyl]amino}methyl)-1,4-dihydroquinolin-4-one Prop-2-yn-1-ol (0.011 mL, 1.1 eq.), sodium ascorbate (0.004 g, 0.1 eq.) and copper(II) sulfate pentahydrate (0.002 g, 0.05 eq.) were sequentially added to a solution of 7-azido-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 21)(0.10 g, 1.0 eq.) in a 3:1 mixture of methanol and water (6 mL). The resulting reaction mixture was stirred at 40° C. for 2 h. Then MeOH was evaporated and DCM was added. The organic phase was separated and the aqueous layer was washed with DCM again. The combined organic layers were dried over $MgSO_4$, filtered and concentrated. The residue was purified by FCC (SIHP; DCM:MeOH) to yield the product (0.068 mg, 62% yield) as an off-white solid. ESI-MS: 609.7 $[M+H]^+$. $^1H$ NMR (300 MHz, DMSO-$d_6$) δ 8.59 (d, J=2.5 Hz, 1H), 8.41 (d, J=6.2 Hz, 1H), 8.29 (d, J=5.0 Hz, 1H), 8.18-8.06 (m, 2H), 8.00 (s, 1H), 7.29-7.14 (m, 3H), 7.03 (d, J=8.5 Hz, 1H), 5.42 (t, J=5.7 Hz, 1H), 4.67 (d, J=5.5 Hz, 2H), 3.87-3.72 (m, 3H), 3.67 (s, 2H), 3.65-3.55 (m, 2H), 2.87-2.73 (m, 2H), 2.67-2.55 (m, 1H), 2.38 (s, 3H), 2.33 (s, 3H), 2.04-1.95 (m, 1H), 1.84-1.73 (m, 1H), 1.63-1.45 (m, 2H), 1.31-1.17 (m, 21H), 1.01-0.88 (m, 21H).

Example 62. 1-Cyclopropyl-6-fluoro-7-[1-(2-hydroxyethyl)-1H-pyrazol 4-yl]-3-({[(3S)-1-(6-methylpyridin-3-yl)piperidin-3-yl][(2-methylpyridin-4-yl)methyl]amino}methyl)-1,4-dihydroquinolin-4-one

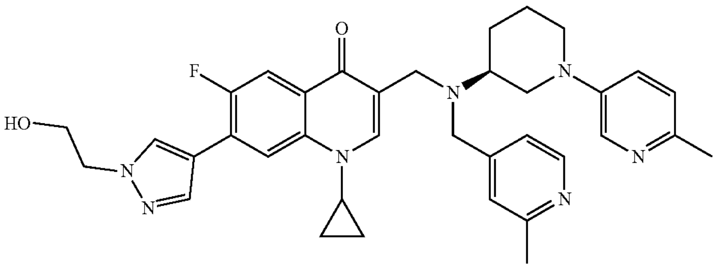

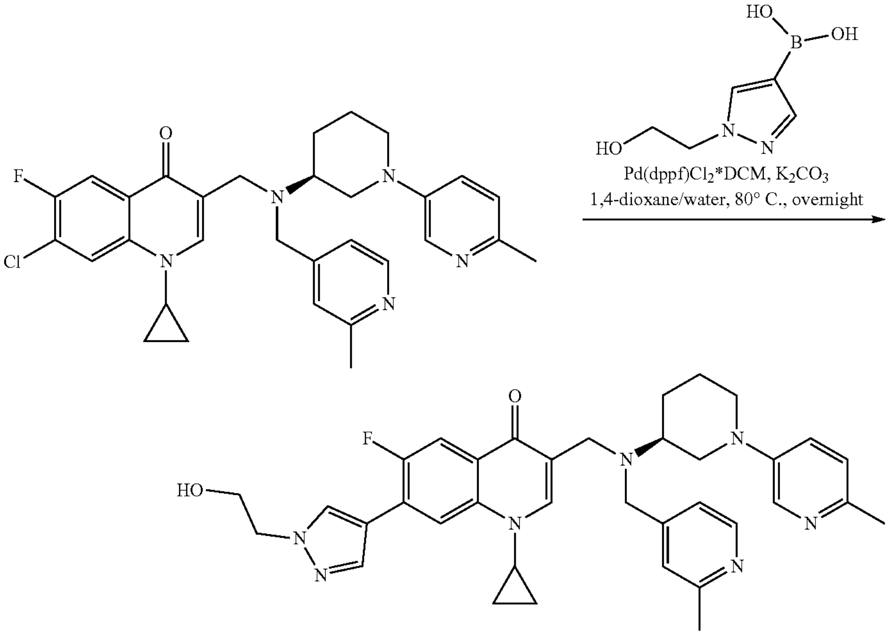

Preparation of 1-cyclopropyl-6-fluoro-7-[1-(2-hydroxyethyl)-1H-pyrazol-4-yl]-3-({[(3S)-1-(6-methylpyridin-3-yl)piperidin-3-yl][(2-methylpyridin-4-yl)methyl]amino}methyl)-1,4-dihydroquinolin-4-one A suspension of [1-(2-hydroxyethyl)-1H-pyrazol-4-yl]boronic acid (0.03 g, 1.0 eq.), 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.113 g, 1.0 eq.) and $K_2CO_3$ (0.04 g, 1.5 eq.) in a mixture of water (1.0 mL) and 1,4-dioxane (4.0 mL) was purged with argon for 10 min. Then, Pd(dppf)$Cl_2$*DCM (0.006 g, 0.05 eq.) was added and the resulting mixture was left stirring overnight at 80° C. Subsequently, the it was cooled to RT, water was added and the resulting mixture was extracted with DCM (3×). The combined organic layers were washed with brine, dried over anh. $MgSO_4$, filtered and concentrated in vacuo. The residue was purified by FCC (SiHP; DCM:MeOH) to give the product (0.02 g, 17% yield) as a beige solid. ESI-MS: 622.6 $[M+H]^+$. $^1H$ NMR (400 MHz, DMSO-$d_6$) δ 8.33 (d, J=2.5 Hz, 1H), 8.28 (d, J=5.1 Hz, 1H), 8.19 (d, J=6.4 Hz, 1H), 8.14 (d, J=2.9 Hz, 1H), 8.11-8.08 (m, 1H), 7.89 (s, 1H), 7.85 (d, J=11.5 Hz, 1H), 7.25-7.20 (m, 2H), 7.19-7.15 (m, 1H), 7.03 (d, J=8.5 Hz, 1H), 4.96 (t, J=5.3 Hz, 1H), 4.24 (t, J=5.5 Hz, 2H), 3.86-3.74 (m, 5H), 3.64 (s, 2H), 3.63-3.56 (m, 2H), 2.82-2.73 (m, 2H), 2.64-2.56 (m, 1H), 2.37 (s, 3H), 2.33 (s, 3H), 2.02-1.95 (m, 1H), 1.81-1.74 (m, 1H), 1.60-1.45 (m, 2H), 1.33-1.25 (m, 2H), 0.96-0.86 (m, 2H).

Example 63. 8-(2-hydroxyethoxy)-1-methyl-3-({[(3S)-1-(6-methylpyridin-3-yl)piperidin-3-yl][(2-methylpyridin-4-yl)methyl]amino}methyl)-1,4-dihydroquinolin-4-one

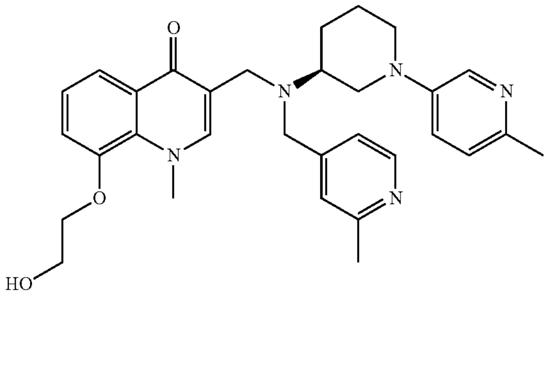

-continued

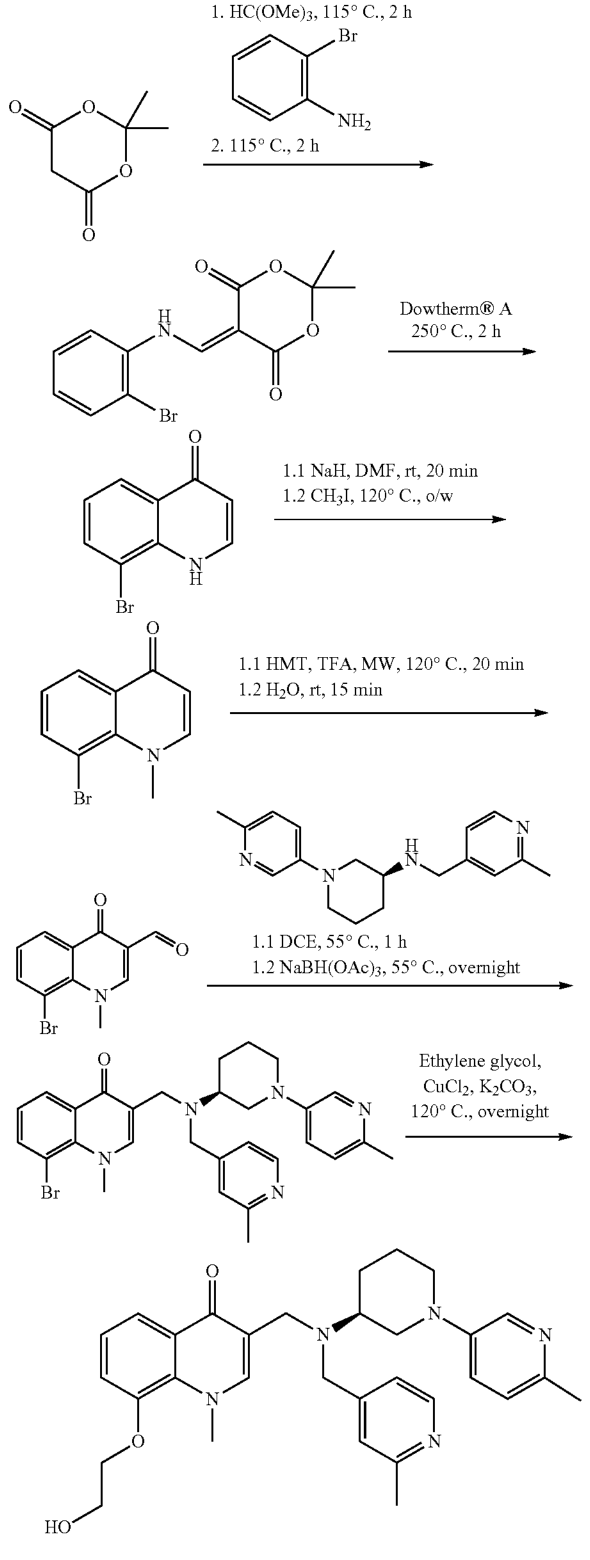

Preparation of 5-{[(2-bromophenyl)amino]methylidene}-2,2-dimethyl-1,3-dioxane-4,6-dione A solution of 2,2-dimethyl-1,3-dioxane-4,6-dione (4.4 g, 1.5 eq.) in trimethoxymethane (50.0 mL, 24.8 eq.) was refluxed for 2 h at 115° C. under argon atmosphere. Then, the reaction mixture was cooled to RT. Subsequently, 2-bromoaniline (3.5 g, 1.0 eq.) was added and the resulting mixture was stirred at 115° C. for another 2 h. Then, the reaction mixture was concentrated in vacuo to give the crude product (4.16 g, 61% yield) as white crystals which were used in the next step without further purification. ESI-MS: 324.0 $[M-H]^-$.

Preparation of 8-bromo-1,4-dihydroquinolin-4-one

A mixture of 5-{[(2-bromophenyl)amino]methylidene}-2,2-dimethyl-1,3-dioxane-4,6-dione (4.2 g, 1.0 eq.), and Dowtherm® A (40.0 mL) was heated for 2 h at 250° C. Then, the reaction mixture was cooled to RT and Hexanes (100.0 mL) was added. The mixture was filtered through a pad of silica gel and the pad was washed with Hexanes (3×150.0 mL). The filtrate was purified by FCC (SiHP; Hex:EtOAc: MeOH) to give the product (2.18 g, 75% yield) as a brown solid. ESI-MS: 225.1[M+2]

Preparation of 8-bromo-1-methyl-1,4-dihydroquinolin-4-one 8-bromo-1,4-dihydroquinolin-4-one (1.01 g, 1.0 eq.) was dissolved in anh. DMF (4.0 mL) under argon atmosphere. Then, NaH (60% dispersion in mineral oil; 0.32 g, 2.0 eq.) was added in portions with stirring and the reaction mixture was left stirring for 20 min at RT. Then, $CH_3I$ (1.0 mL, 4.0 eq.) was added dropwise and the mixture was heated at 120° C. over the weekend at the same temperature. Afterwards, MeOH (2.0 mL) was added and the mixture was concentrated in vacuo. The residue was purified by FCC (SiHP; Hex:EtOAc) to give the product (0.89 g, 82% yield) as a beige solid. ESI-MS: 239.1 [M+2]+.

Preparation of 8-bromo-1-methyl-4-oxo-1,4-dihydroquinoline-3-carbaldehyde

A microwave reaction vial was charged with a mixture of 8-bromo-1-methyl-1,4-dihydroquinolin-4-one (0.8 g, 1.0 eq.), HMT (0.84 g, 2.0 eq.) and TFA (4.5 mL, 20.0 eq.). The resulting mixture was irradiated for 15 min at 120° C. using a microwave oven. Then, additional HMT (0.42 g, 1.0 eq.) was added and microwave irradiation was continued for another 5 min at 120° C. Subsequently, the reaction mixture was transferred to a flask followed by addition of $H_2O$ (30.0 mL) and the resulting mixture was stirred for 15 min at RT. Subsequently, the mixture was concentrated in vacuo. The residue was suspended in water and extracted with EtOAc (4×100.0 mL). The combined organic layers were dried over anh. $MgSO_4$, filtered and concentrated in vacuo. The residue was purified by FCC (SiHP; Hex:EtOAc) to give the product (0.48 g, 57% yield) as a white solid. ESI-MS: 265.9 $[M+H]^+$. $^1H$ NMR (300 MHz, Chloroform-d) δ 10.38 (s, 1H), 8.55 (dd, J=7.9, 1.7 Hz, 1H), 8.24 (s, 1H), 8.01 (dd, J=7.7, 1.7 Hz, 1H), 7.32 (t, J=7.8 Hz, 1H), 4.34 (s, 3H).

Preparation of 8-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one A mixture of (3S)-1-(6-methylpyridin-3-yl)-N-[(2-methylpyridin-4-yl)methyl]piperidin-3-amine (Intermediate 2) (0.48 g, 1.05 eq.) and 8-bromo-1-methyl-4-oxo-1,4-dihydroquinoline-3-carbaldehyde (0.41 g, 1.0 eq.) in anh. DCE (10.0 mL) was stirred for 1 h at 55° C. Then, the reaction mixture was cooled to RT and $NaBH(OAc)_3$ (0.87 g, 2.8 eq.) was added. The resulting mixture was stirred overnight at 55° C. Afterwards, the reaction mixture was filtered through a pad of celite and the pad was washed with DCM. The filtrate was concentrated in vacuo. The residue was suspended in $NaHCO_3$ aq. solution and the resulting mixture was washed with DCM. The combined organic layers were dried over anh. $MgSO_4$, filtered and concentrated in vacuo. The residue was purified by FCC (SiHP; DCM:MeOH) to give the product (0.52 g, 55% yield) as a yellow oil. ESI-MS: 546.3 $[M+H]^+$.

Preparation of 8-(2-hydroxyethoxy)-1-methyl-3-({[(3S)-1-(6-methylpyridin-3-yl)piperidin-3-yl][(2-methylpyridin-4-yl)methyl]amino}methyl)-1,4-dihydroquinolin-4-one $CuCl_2$ (0.004 g, 0.1 eq.) was added to a mixture of 8-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one (0.2 g, 1.0 eq.), $K_2CO_3$ (0.13 g, 3.0 eq.) and ethylene glycol (5.0 mL) and the resulting mixture was heated at 120° C. overnight at the same temperature. Then, water (5 mL) was added and the resulting mixture was washed with EtOAc (4×50.0 mL). The combined organic layers were washed with water (2.0 mL), brine (5.0 mL), dried over anh. $MgSO_4$, filtered and concentrated in vacuo. The residue was purified by FCC (SiHP; DCM:MeOH) and re-purified by RP-FCC (C18HP; $H_2O$:MeCN) to give the product (0.038 g, 23% yield) as a yellow solid. ESI-MS: 528.7 $[M+H]^+$. $^1H$ NMR (400 MHz, DMSO-$d_6$) δ 8.28 (d, J=5.0 Hz, 1H), 8.14 (d, J=3.0 Hz, 1H), 7.85 (s, 1H), 7.79 (dd, J=7.0, 2.5 Hz, 1H), 7.30-7.17 (m, 5H), 7.01 (d, J=8.5 Hz, 1H), 4.94 (t, J=5.4 Hz, 1H), 4.15-4.08 (m, 5H), 3.87-3.68 (m, 5H), 3.67-3.53 (m, 3H), 2.82-2.69 (m, 2H), 2.63-2.53 (m, 1H), 2.38 (s, 3H), 2.32 (s, 3H), 2.02-1.94 (m, 1H), 1.79-1.71 (m, 1H), 1.59-1.41 (m, 2H).

Example 64. 1-[1-Cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-1H-imidazole-4-carboxamide

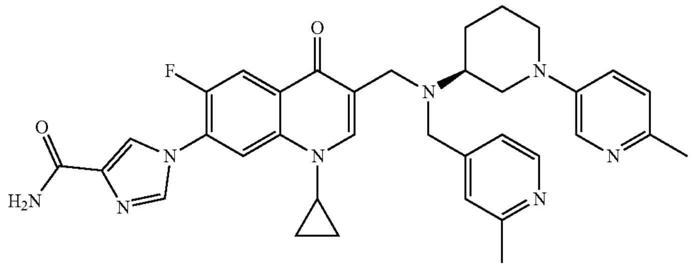

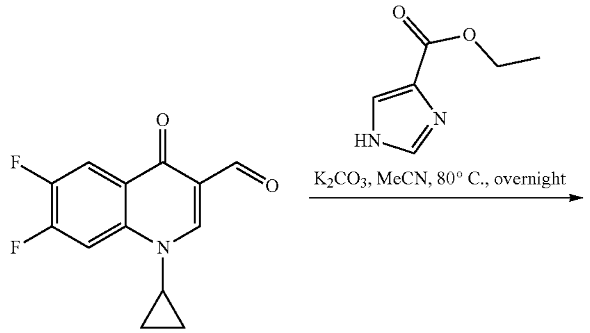

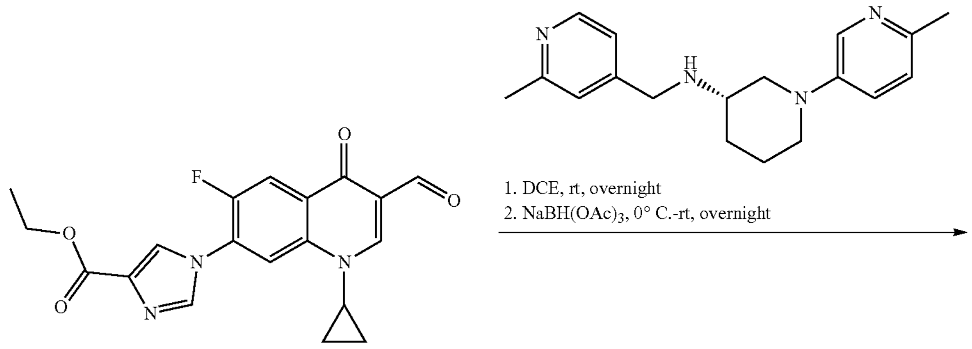

-continued

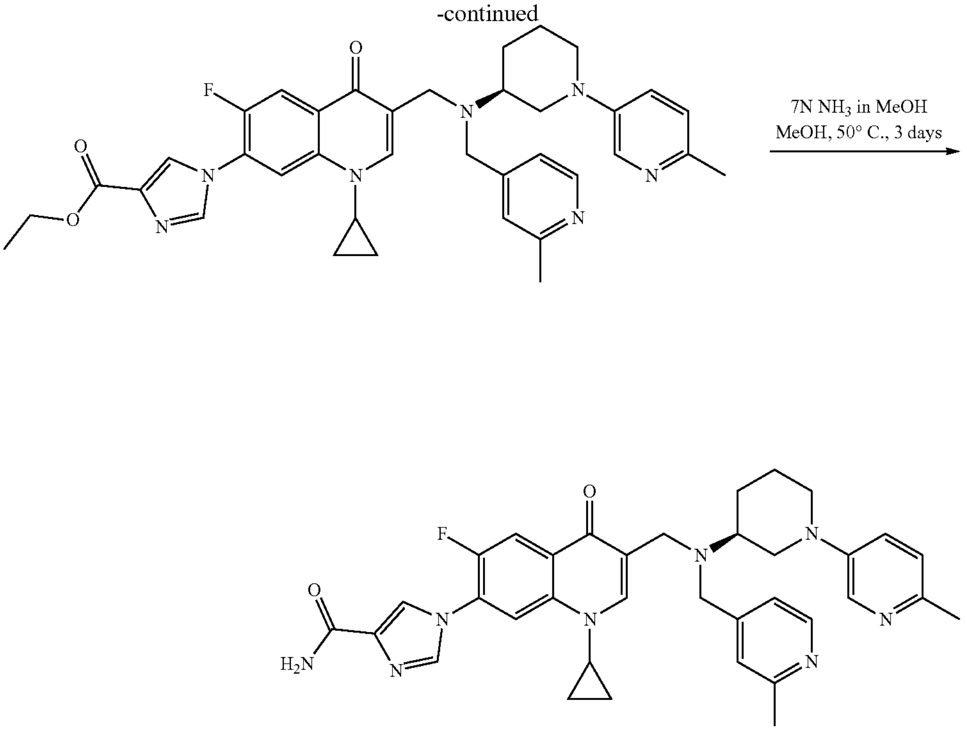

Preparation of ethyl 1-(1-cyclopropyl-6-fluoro-3-formyl-4-oxo-1,4-dihydroquinolin-7-yl)-1H-imidazole-4-carboxylate 1-Cyclopropyl-6,7-difluoro-4-oxo-1,4-dihydroquinoline-3-carbaldehyde (Intermediate 4)(0.050 g, 1.0 eq.), ethyl 1H-imidazole-5-carboxylate (0.027 g, 1.0 eq.) and potassium carbonate (0.054 g, 2.0 eq.) were suspended in anh. MeCN (3.0 mL) and the reaction mixture was stirred at 80° C. overnight. Then water was added and the mixture was extracted with DCM (×3). The combined organic layers were washed with brine, dried over $MgSO_4$, filtrated and concentrated. Crude was purified by FCC (SiHP; DCM:MeOH) to afford the product (0.064 g, 85% yield) as a white solid. ESI-MS: 370.1 $[M+H]^+$.

Preparation of ethyl 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-1H-imidazole-4-carboxylate A solution of ethyl 1-(1-cyclopropyl-6-fluoro-3-formyl-4-oxo-1,4-dihydroquinolin-7-yl)-1H-imidazole-4-carboxylate (0.064 g, 1.0 eq.) and (3S)-1-(6-methylpyridin-3-yl)-N-[(2-methylpyridin-4-yl)methyl]piperidin-3-amine (Intermediate 2) (0.053 g, 1.05 eq.) in anh. DCE (2.0 mL) was stirred at RT overnight. Then the mixture was cooled to 0° C., sodium triacethoxyborohydride (0.099 g, 2.8 eq.) was added and the reaction mixture was stirred at RT overnight. The reaction was quenched by water and basified to pH 11 by the addition of 1 M aq. solution of NaOH. The mixture was washed with DCM (×3). The combined organic layers were dried over $MgSO_4$, filtered and concentrated. The residue was purified by FCC (SiHP; DCM:MeOH) to afford the product (0.050 g, 40% yield) as a white solid. ESI-MS: 650.5 $[M+H]^+$. $^1H$ NMR (400 MHz, DMSO-$d_6$) δ 8.43 (t, J=1.5 Hz, 1H), 8.33-8.27 (m, 2H), 8.25 (d, J=6.4 Hz, 1H), 8.14 (d, J=2.9 Hz, 1H), 8.07 (d, J=10.9 Hz, 1H), 7.99 (s, 1H), 7.26-7.21 (m, 2H), 7.20-7.16 (m, 1H), 7.04 (d, J=8.5 Hz, 1H), 4.30 (q, J=7.1 Hz, 2H), 3.86-3.75 (m, 3H), 3.67 (s, 2H), 3.63-3.55 (m, 2H), 2.85-2.72 (m, 2H), 2.65-2.55 (m, 1H), 2.39 (s, 3H), 2.33 (s, 3H), 1.99 (d, J=10.2 Hz, 1H), 1.78 (d, J=11.2 Hz, 1H), 1.59-1.45 (m, 2H), 1.31 (t, J=7.1 Hz, 3H), 1.29-1.22 (m, 2H), 1.00-0.89 (m, 2H).

Preparation of 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-1H-imidazole-4-carboxamide Ethyl 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-1H-imidazole-4-carboxylate (0.043 g, 1.0 eq.) was dissolved in anh. MeOH (1.0 mL), then 7 N ammonia solution in methanol (0.08 mL, 10.0 eq.) was added and the reaction mixture was stirred at 50° C. for 3 days. The solvent was evaporated and the residue was purified by prep-HPLC ($H_2O$:MeOH:$NH_3$) to afford the product (0.014 g, 41% yield) as a white solid. ESI-MS: 621.6 $[M+H]^+$. $^1H$ NMR (300 MHz, DMSO-$d_6$) δ 8.29 (d, J=5.1 Hz, 1H), 8.26-8.18 (m, 3H), 8.13 (d, J=3.0 Hz, 1H), 8.06 (d, J=11.0 Hz, 1H), 7.98 (s, 1H), 7.54 (s, 1H), 7.31 (s, 1H), 7.26-7.20 (m, 2H), 7.20-7.16 (m, 1H), 7.03 (d, J=8.5 Hz, 1H), 3.85-3.74 (m, 3H), 3.66 (s, 2H), 3.63-3.55 (m, 2H), 2.83-2.71 (m, 2H), 2.66-2.56 (m, 1H), 2.39 (s, 3H), 2.32 (s, 3H), 1.98 (d, J=8.1 Hz, 1H), 1.78 (d, J=10.4 Hz, 1H), 1.62-1.43 (m, 2H), 1.29-1.20 (m, 2H), 1.00-0.89 (m, 2H).

Example 65. 1-cyclopropyl-6-fluoro-7-[(3R)-3-hydroxypyrrolidin-1-yl]-3-({[(2-methoxypyridin-4-yl)methyl][(3S)-1-(pyridin-3-yl)piperidin-3-yl]amino}methyl)-1,4-dihydroquinolin-4-one hydrochloride
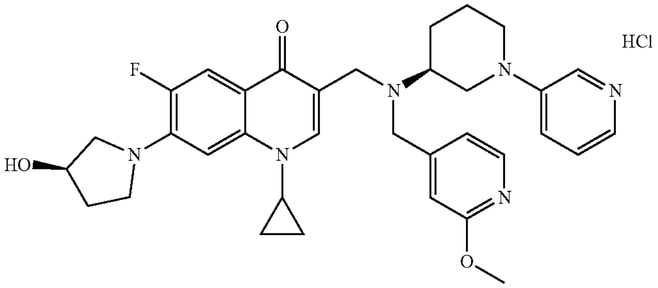
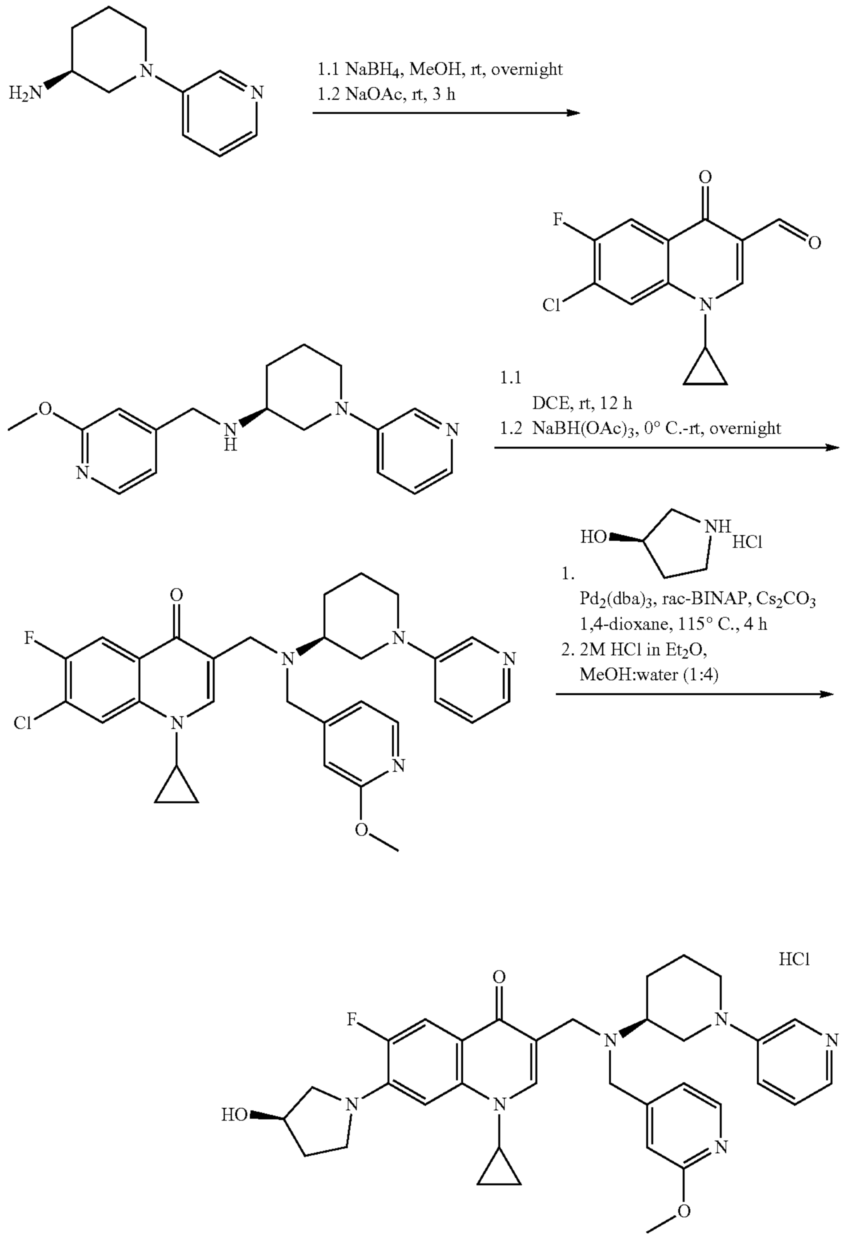

Preparation of (3S)—N-[(3-methoxyphenyl)methyl]-1-(pyridin-3-yl)piperidin-3-amine (Intermediate 16)

A mixture of (3S)-1-(pyridin-3-yl)piperidin-3-amine (Intermediate 17) (6.07 g, 1.1 eq.), 2-methoxypyridine-4-carbaldehyde (4.27 g, 1.0 eq.), sodium acetate (3.83 g, 1.5 eq.) and anh. MeOH (60.0 mL) was stirred at RT under argon overnight. The mixture was cooled to 0° C. and sodium borohydride (1.30 g, 1.1 eq.) was added in portions over 15 minutes. The mixture was stirred at RT for 3 hours. Solvents were evaporated and the residue was partitioned between DCM and NaOH aq. The combined organic layers were combined, dried over anh. $MgSO_4$, filtrated and concentrated in vacuo. The crude material was purified on FCC (SiHP (deactivated by $NH_3$/DCM) DCM:MeOH) to give product (4.95 g, 99% yield) as a yellow oil. ESI-MS: 299.4 $[M+H]^+$. $^1H$ NMR (300 MHz, DMSO-$d_6$) δ 8.25 (d, J=2.9 Hz, 1H), 8.06 (dd, J=5.2, 0.6 Hz, 1H), 7.92 (dd, J=4.5, 1.4 Hz, 1H), 7.26 (ddd, J=8.5, 3.0, 1.4 Hz, 1H), 7.16 (ddd, J=8.5, 4.5, 0.7 Hz, 1H), 6.98 (dd, J=5.3, 1.3 Hz, 1H), 6.81 (t, J=1.1 Hz, 1H), 3.82 (s, 3H), 3.80-3.71 (m, 3H), 3.57 (dt, J=12.9, 4.1 Hz, 1H), 2.72 (ddd, J=12.3, 11.1, 3.0 Hz, 1H), 2.54 (d, J=3.8 Hz, 2H), 2.33 (s, 1H), 1.98-1.82 (m, 1H), 1.79-1.64 (m, 1H), 1.58-1.38 (m, 1H), 1.32-1.12 (m, 1H).

Preparation of 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one 7-chloro-1-cyclopropyl-6-fluoro-4-oxo-1,4-dihydroquinoline-3-carbaldehyde (Intermediate 9)(0.3 g, 1.0 eq.) and (3S)—N-[(2-methoxypyridin-4-yl)methyl]-1-(pyridin-3-yl)piperidin-3-amine (0.115 g, 0.3 eq.) were suspended in anh. DCE (8.0 mL). The resulting mixture was stirred at RT for 30 min. Then sodium triacethoxyborohydride (0.206 g, 0.9 eq.) was added and stirring was continued overnight. The reaction mixture was poured into ice cold water and sat. aq. $NaHCO_3$ was added. Product was extracted with DCM. The combined organic layers were dried over anh. $Na_2SO_4$ and concentrated. The residue was purified by RP-FCC (C18HP, $H_2O$:MeCN) to give product (0.496 g, 71% yield) as a yellow solid. ESI-MS: 548.8 $[M+H]^+$.

Preparation of 1-cyclopropyl-fluoro-7-[(3R)-3-hydroxypyrrolidin-1-yl]-3-({[(2-methoxypyridin-4-yl)methyl][(3S)-1-(pyridin-3-yl)piperidin-3-yl]amino}methyl)-1,4-dihydroquinolin-4-one hydrochloride A pressure vessel was charged with 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one (0.1 g, 1.0 eq.), (3R)-Pyrrolidin-3-ol (0.022 g, 1.5 eq.), cesium carbonate (0.098 g, 1.8 eq.) and 1,4-dioxane (2.0 mL). The resulting mixture was purged with argon over 5 min, then BINAP (0.021 g, 0.2 eq.) and $Pd_2(dba)_3$ (0.015 g, 0.1 eq.) were added. The vessel was closed and the reaction mixture was stirred at 115° C. for 4 h. The reaction was concentrated in vacuo. The residue was dissolved in DCM and washed with water and brine. The organic layer was dried over anh. $Na_2SO_4$ and concentrated in vacuo. The residue was purified by FCC (SiHP, DCM:MeOH) and repurified by prep-HPLC ($H_2O$:MeOH:$NH_3$) to give the product (0.252 g, 56% yield). The compound was converted into the HCl salt using 2 M HCl in $Et_2O$ (0.139 mL, 1.0 eq to the FB), MeOH (5.0 mL) and water (20.0 mL) to provide the product (0.038 g, 96% yield) as a yellow solid. ESI-MS: 599.6 $[M+H]^+$. $^1H$ NMR (400 MHz, Methanol-$d_4$) δ 8.35 (d, J=2.9 Hz, 1H), 8.02 (d, J=4.9 Hz, 1H), 7.92 (d, J=5.3 Hz, 1H), 7.88 (s, 1H), 7.78-7.69 (m, 2H), 7.52-7.46 (m, 1H), 6.98-6.94 (m, 2H), 6.81 (s, 1H), 4.59-4.53 (m, 1H), 4.27-4.00 (m, 5H), 3.89-3.71 (m, 6H), 3.70-3.60 (m, 1H), 3.62-3.51 (m, 1H), 3.48-3.42 (m, 1H), 3.30-3.20 (m, 2H), 3.03-2.91 (m, 1H), 2.30-2.02 (m, 4H), 2.01-1.87 (m, 1H), 1.84-1.68 (m, 1H), 1.35-1.28 (m, 2H), 1.04-0.98 (m, 2H).

Example 66. 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidine-3-carboxylic acid

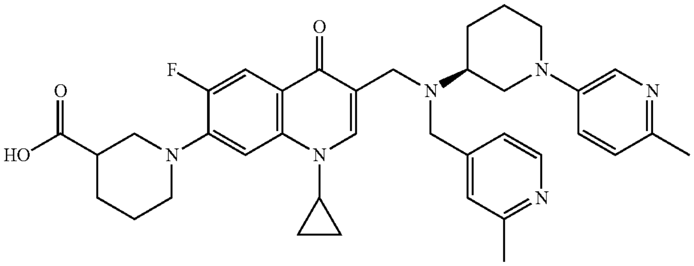

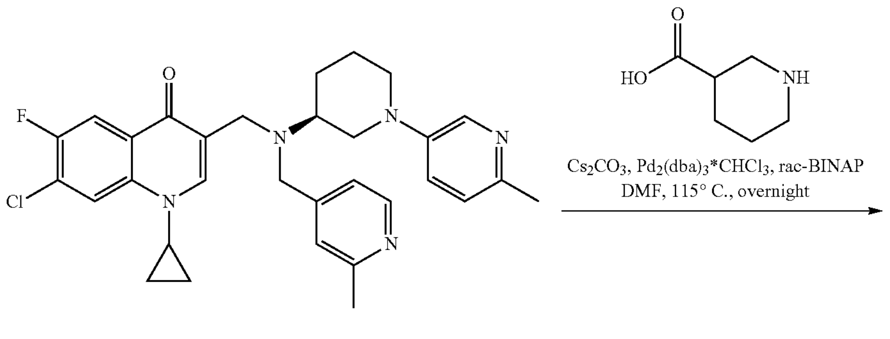

-continued

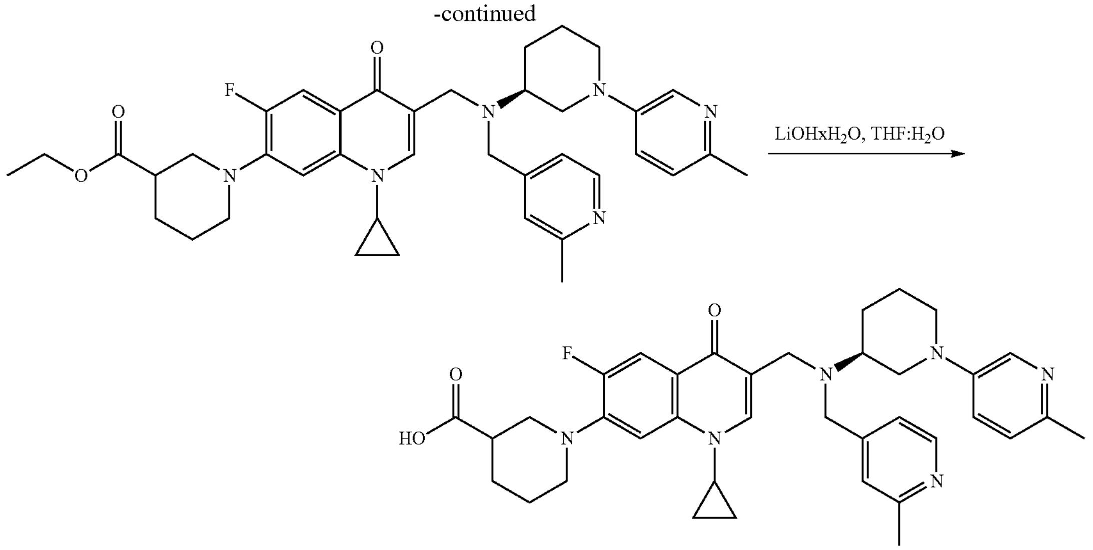

Preparation of ethyl 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidine-3-carboxylate A pressure vessel was charged with 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.20 g, 1.0 eq.), ethyl nipecotate (0.12 g, 2.0 eq.), $Cs_2CO_3$ (0.25 g, 2.1 eq.) and DMF (2.0 mL). The mixture was purged with argon for 5 min, followed by the addition of BINAP (0.068 g, 0.3 eq.) and $Pd_2(dba)_3$*$CHCl_3$ (0.038 g, 0.1 eq.) and stirred at 115° C. overnight. The reaction mixture was filtered through a pad of celite and concentrated in vacuo and the residue was purified by FCC (SiHP, DCM:MeOH) to give the product (0.10 g, 38% yield) as a yellow solid. ESI-MS: 667.7 $[M+H]^+$.

Preparation of 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidine-3-carboxylic acid Ethyl 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidine-3-carboxylate was dissolved in a mixture of THF and $H_2O$ (2:1, 5.0 mL). Subsequently, lithium hydroxide (0.013 g, 5.0 eq.) was added and the reaction mixture was stirred at RT overnight. The reaction mixture was concentrated, diluted with water and neutralized using 2 M HCl solution. The mixture was concentrated and the residue was purified by RP-FCC (C18HP, $H_2O$:MeCN) to give product (0.025 g, 95% yield) as a yellow solid. ESI-MS: 637.3 $[M-H]^-$. $^1H$ NMR (400 MHz, DMSO-$d_6$) δ 8.29 (d, J=5.1 Hz, 1H), 8.13 (d, J=3.0 Hz, 1H), 7.82 (s, 1H), 7.70 (d, J=13.4 Hz, 1H), 7.37 (d, J=7.5 Hz, 1H), 7.24-7.19 (m, 2H), 7.17 (d, J=5.2 Hz, 1H), 7.02 (d, J=8.5 Hz, 1H), 3.83-3.75 (m, 1H), 3.78-3.72 (m, 1H), 3.73-3.55 (m, 4H), 3.54-3.48 (m, 1H), 3.46-3.40 (m, 1H), 3.07-2.96 (m, 2H), 2.97-2.86 (m, 1H), 2.80-2.71 (m, 2H), 2.65-2.56 (m, 2H), 2.38 (s, 3H), 2.35-2.30 (m, 3H), 2.03-1.92 (m, 2H), 1.88-1.73 (m, 2H), 1.71-1.44 (m, 4H), 1.22-1.18 (m, 2H), 0.89 (td, J=9.9, 3.3 Hz, 2H).

Example 67. 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidine-4-carboxylic acid

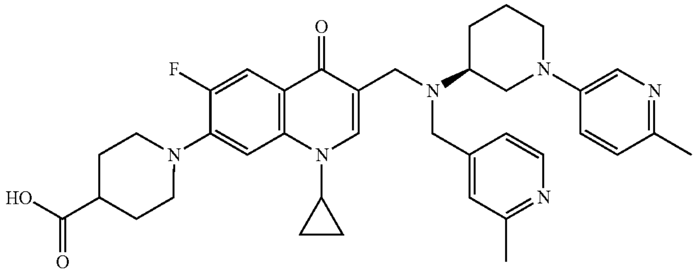

-continued

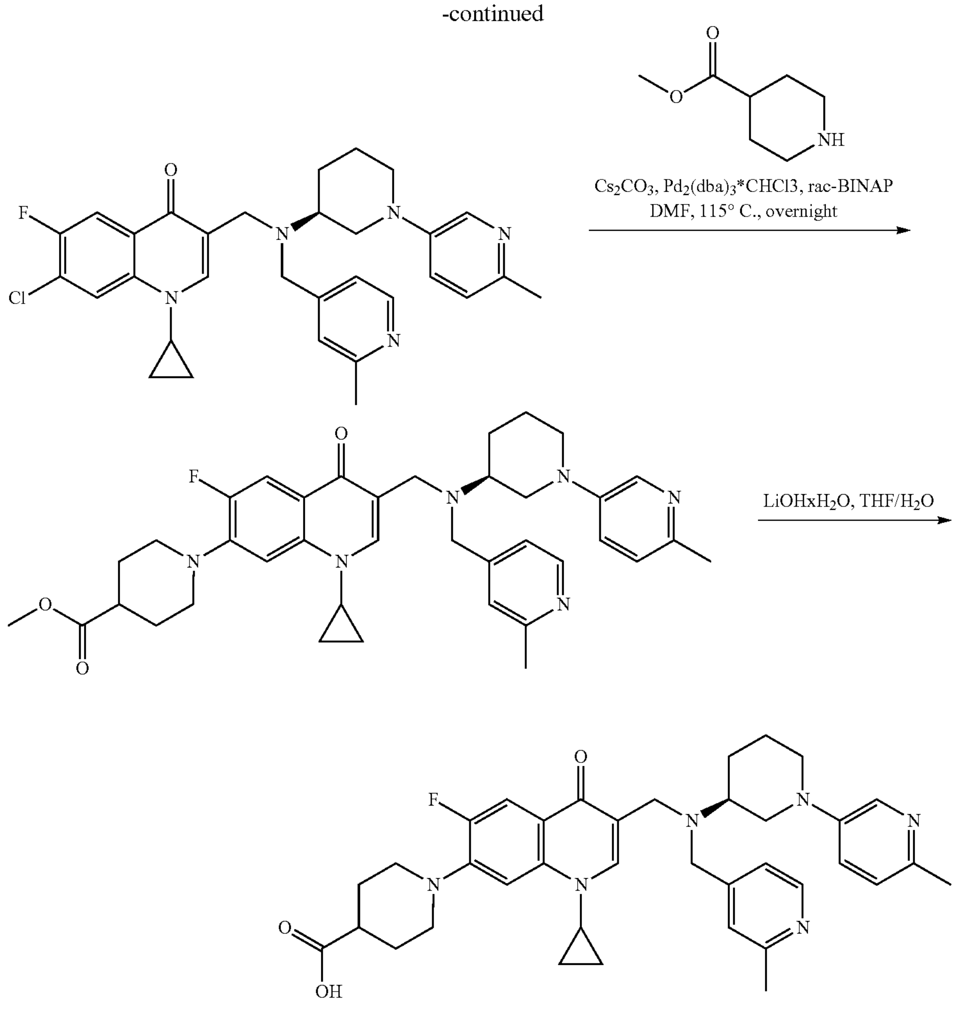

Preparation of methyl 1-[1-cyclopropyl-6-fluoro-3-({[(3S)-1-(6 methylpyridin-3-yl)piperidin-3-yl][(2-methylpyridin-4-yl)methyl]amino}methyl)-4-oxo-1,4-dihydroquinolin-7-yl]piperidine-4-carboxylate A pressure vessel was charged with 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.10 g, 1.0 eq.), methyl isonipecotate (0.052 g, 2.0 eq.), $Cs_2CO_3$ (0.125 g, 2.1 eq.) and DMF (5.0 mL). The mixture was purged with argon for 5 min, followed by the addition of BINAP (0.034 g, 0.3 eq.) and $Pd_2(dba)_3 \cdot CHCl_3$ (0.019 g, 0.1 eq.) and stirred at 115° C. overnight. The reaction mixture was filtered through a pad of celite and the filtrate was concentrated in vacuo. The residue was purified by FCC (SIHP, DCM:MeOH) to give the product (0.082 g, 58% yield) as a yellow oil. ESI-MS: 653.7 $[M+H]^+$.

Preparation of 1-[1-cyclopropyl-6-fluoro-3-({[(3S)-1-(6 methylpyridin-3-yl)piperidin-3-yl][(2-methylpyridin-4-yl)methyl]amino}methyl)-4-oxo-1,4-dihydroquinolin-7-yl]piperidine-4-carboxylic acid Methyl 1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidine-4-carboxylate (0.025 g, 1.0 eq.) was dissolved in a mixture of THF and $H_2O$ (2:1). Subsequently, lithium hydroxide (0.008 mg, 5.0 eq.) was added and the reaction mixture was stirred at RT overnight. The reaction mixture was concentrated, diluted with water and neutralized using 2 M HCl solution. DCM was added and layers were separated. Organic layer was concentrated and the residue was purified by RP-FCC (C18HP, $H_2O$:MeCN) to give product (0.012 g, 48% yield) as a yellow solid. ESI-MS: 639.3 $[M+H]^+$. $^1H$ NMR (400 MHz, DMSO-$d_6$) δ 8.28 (d, J=5.1 Hz, 1H), 8.12 (d, J=3.0 Hz, 1H), 7.81 (s, 1H), 7.69 (d, J=13.5 Hz, 1H), 7.33 (d, J=7.5 Hz, 1H), 7.23-7.19 (m, 2H), 7.17 (d, J=5.1 Hz, 1H), 7.01 (d, J=8.5 Hz, 1H), 3.81-3.69 (m, 31H), 3.61-3.56 (m, 31H), 3.54-3.46 (m, 3H), 2.93-2.84 (m, 2H), 2.80-2.70 (m, 2H), 2.62-2.54 (m, 1H), 2.43-2.36 (m, 4H), 2.32 (s, 3H), 1.99-1.92 (m, 3H), 1.80-1.68 (m, 3H), 1.57-1.45 (m, 2H), 1.24-1.17 (m, 2H), 0.92-0.83 (m, 2H).

Example 68. 1-cyclopropyl-6-fluoro-3-({[(3S)-1-(6-methylpyridin-3-yl)piperidin-3-yl][(2-methylpyridin-4-yl)methyl]amino}methyl)-7-{octahydro-1H-pyrrolo[3,2-c]pyridin-5-yl}-1,4-dihydroquinolin-4-one

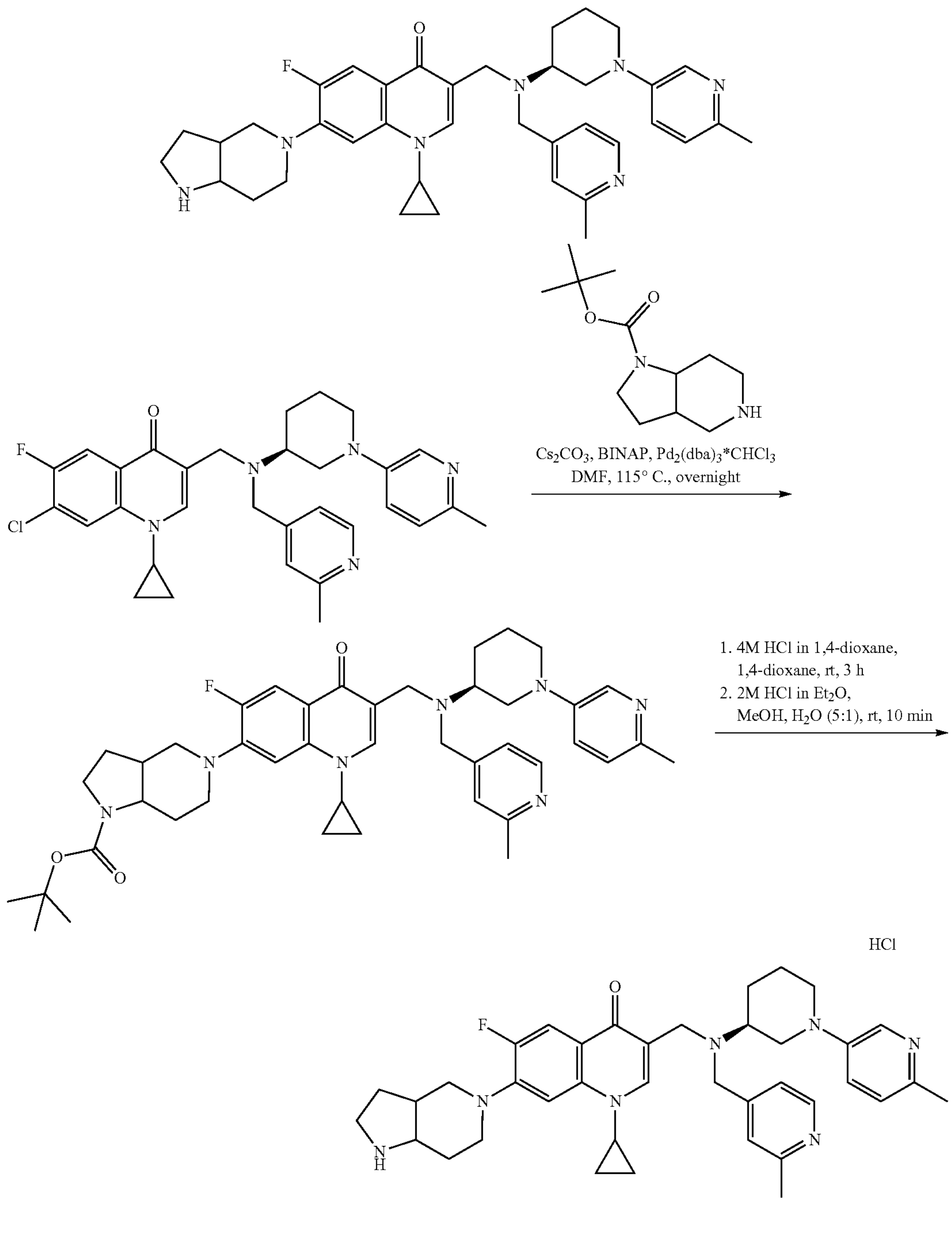

Preparation of tert-butyl 5-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-octahydro-1H-pyrrolo[3,2-c]pyridine-1-carboxylate 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.10 g, 1.0 eq), tert-butyl octahydro-1H-pyrrolo[3,2-c]pyridine-1-carboxylate (0.083 g, 2.0 eq) and cesium carbonate (0.125 g, 2.1 eq) were dissolved in DMF (3.0 mL) argon was bubbled through the mixture for 5 min. Then, BINAP (0.034 g, 0.3 eq) and $Pd_2(dba)_3$*$CHCl_3$ (0.038 g, 0.2 eq) were added and the reaction mixture was stirred at 115° C. overnight. The reactor was cooled to room temperature and the reaction mixture was filtered through a pad of celite. The pad was washed with DCM, filtrate concentrated in vacuo and the crude product purified by FCC (SiHP; DCM:MeOH). The product was redissolved in DCM and stirred with scavenger QuadraPure MPA for 20 min. The scavenger was filtered off, filtrate was concentrated and repurified by prep-HPLC ($H_2O$:MeOH:$NH_3$) to give product (0.063 mg; yield 44% yield) as a light yellow solid. ESI-MS: 737.3 [M+H].

Preparation of 1-cyclopropyl-6-fluoro-3-({[(3S)-1-(6-methylpyridin-3-yl)piperidin-3-yl][(2-methylpyridin-4-yl)methyl]amino}methyl)-7-{octahydro-1H-pyrrolo[3,2-c]pyridin-5-yl}-1,4-dihydroquinolin-4-one hydrochloride 4 M HCl in 1,4-dioxane (1.16 mL, 56.0 eq) was added to a solution of tert-butyl 5-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-octahydro-1H-pyrrolo[3,2-c]pyridine-1-carboxylate (0.061 g, 1.0 eq) in 1,4-dioxane (8.0 mL). The reaction mixture was stirred at RT for 3 h and then poured into water and further basified with 15% NaOH aq. solution. The product mixture was washed first with DCM, then $CHCl_3$:iPrOH (3:1). The combined organic layers were dried over anh. $Na_2SO_4$, filtered and concentrated. The product mixture was purified by FCC (SiHP; DCM:MeOH) to afford product (0.04 g; yield 76% yield) as a light yellow solid. The compound was converted to the HCl salt using 2 M HCl in $Et_2O$ (0.3 mL, 1.0 eq. to FB) and a mixture of MeOH and $H_2O$ (5:1) as a solvent to give the product (0.036 g, 90% yield) as a light yellow solid. ESI-MS: 636.3 $[M+H]^+$. $^1$H NMR (400 MHz, DMSO-$d_6$) δ 8.49 (br s, 1H), 8.28 (d, J=5.0 Hz, 1H), 8.12 (d, J=3.0 Hz, 1H), 7.81 (s, 1H), 7.71 (d, J=13.4 Hz, 1H), 7.33 (d, J=7.5 Hz, 1H), 7.23-7.19 (m, 2H), 7.16 (d, J=5.2 Hz, 1H), 7.02 (d, J=8.5 Hz, 1H), 3.81-3.77 (m, 1H), 3.74 (d, J=2.7 Hz, 2H), 3.71-3.64 (m, 1H), 3.62-3.55 (m, 3H), 3.51-3.46 (m, 1H), 3.45-3.38 (m, 1H), 3.28-3.24 (m, 2H), 3.22-3.14 (m, 1H), 3.12-3.04 (m, 1H), 2.80-2.70 (m, 2H), 2.62-2.54 (m, 1H), 2.37 (s, 3H), 2.32 (s, 3H), 2.07-1.92 (m, 4H), 1.91-1.83 (m, 1H), 1.79-1.72 (m, 1H), 1.58-1.43 (m, 2H), 1.25-1.18 (m, 2H), 0.93-0.84 (m, 2H).

Example 69. 7-[(3R)-3-hydroxypyrrolidin-1-yl]-3-({[(2-methylpyridin-4-yl)methyl][(3S)-1-(1H-pyrazol-4-yl)piperidin-3-yl]amino}methyl)-1-(propan-2-yl)-1,4-dihydroquinolin-4-one

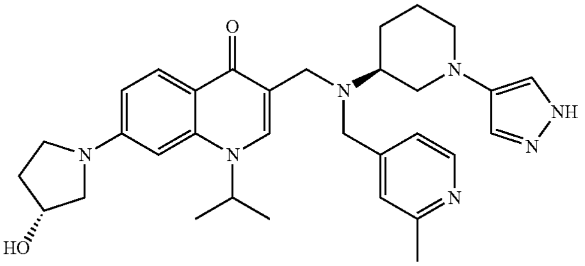

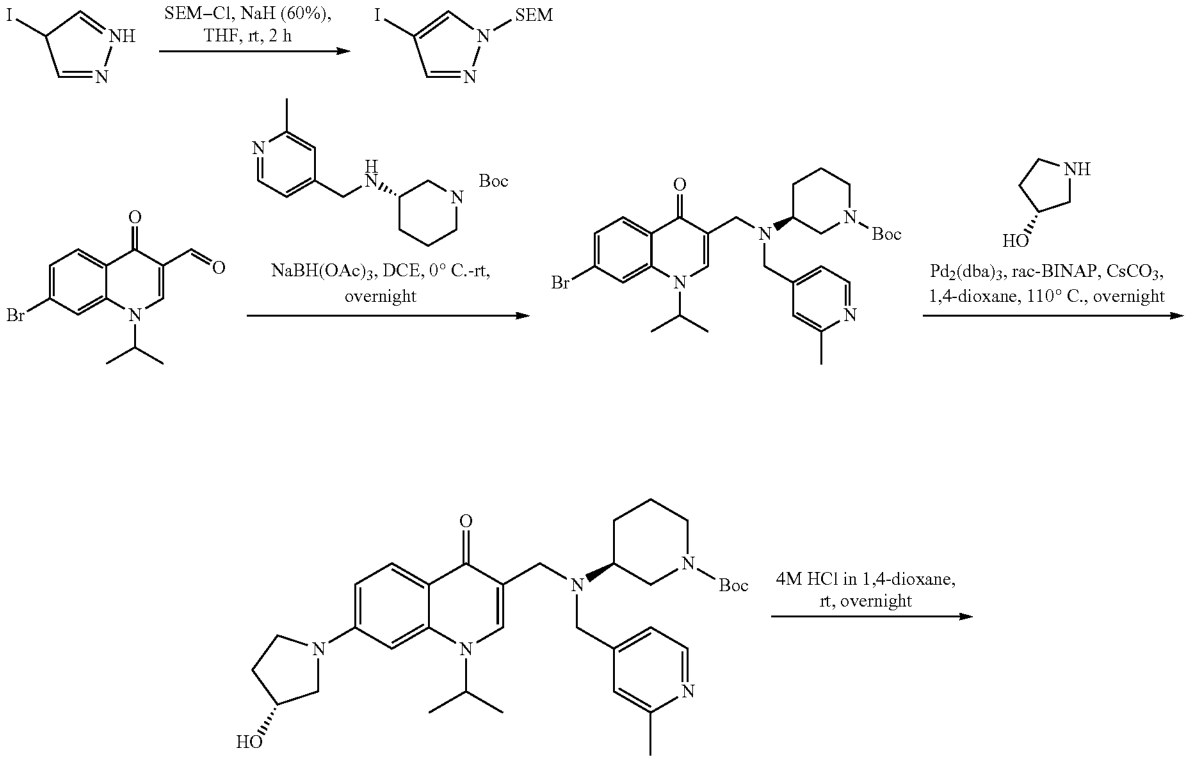

-continued

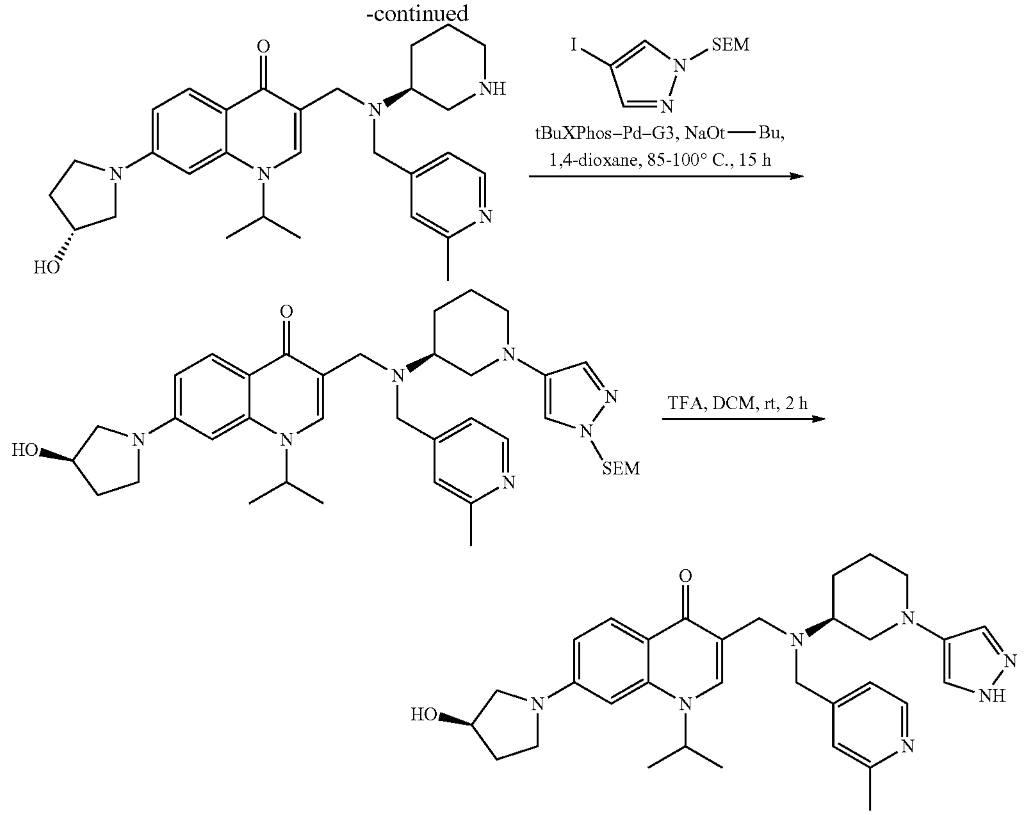

Preparation of tert-butyl (3S)-3-({[7-bromo-4-oxo-1-(propan-2-yl)-1,4-dihydroquinolin-3-yl]methyl}[(2-methylpyridin-4-yl)methyl]amino)piperidine-1-carboxylate 7-bromo-4-oxo-1-(propan-2-yl)-1,4-dihydroquinoline-3-carbaldehyde (Intermediate 19) (1.20 g, 1.0 eq.) and tert-butyl (3S)-3-{[(2-methylpyridin-4-yl)methyl]amino}piperidine-1-carboxylate (Intermediate 18) (1.25 g, 1.0 eq.) were dissolved in anh. 1,2-dichloroethane (20.0 mL) and stirred overnight at RT. The solution was cooled to 0° C. and then $NaBH(OAc)_3$ (2.52 g, 3.0 eq.) was added in portions. The reaction mixture was warmed to RT and stirred overnight. Then, the reaction mixture was quenched with water, basified to pH 11 with 1 M NaOH and extracted with DCM (3×150.0 mL). The combined organic layers were washed with brine, dried over anh. $MgSO_4$, filtered and concentrated in vacuo. The crude product was purified by FCC (SiHP; DCM:MeOH) to yield the title compound (1.74 g, 55% yield). ESI-MS: 583.3 [M+H].

Preparation of tert-buty (3S)-3-[({7-[(3R)-3-hydroxypyrrolidin-1-yl]-4-oxo-1-(propen-2-yl)-1,4-dihydroquinolin-3-yl}methyl)[(2-methylpyridin-4-yl)methyl]amino]piperidine-1-carboxylate $Cs_2CO_3$ (1.25 g, 1.8 eq.) was added to a solution of tert-butyl (3S)-3-({[7-bromo-4-oxo-1-(propan-2-yl)-1,4-dihydroquinolin-3-yl]methyl}[(2-methylpyridin-4-yl)methyl]amino)piperidine-1-carboxylate (1.70 g, 1.0 eq.) and (R)-pyrrolidin-3-ol (0.28 g, 1.5 eq.) in anh. 1,4-dioxane (40.0 mL). The solution was purged with argon for 15 min and BINAP (0.26 g, 0.2 eq.) and $Pd_2(dba)_3$ (0.2 g, 0.1 eq.) were added. The reaction mixture was stirred overnight at 110° C., then after cooling to RT, the reaction mixture was filtered through a pad of celite, diluted with water and extracted with DCM (3×100.0 mL). The combined organic layers were washed with brine, dried over anh. $MgSO_4$, filtered and concentrated in vacuo. The residue was purified by FCC (SiHP; DCM:MeOH) affording the title compound (1.30 g, 98% yield) as a yellow foam. ESI-MS: 590.7 $[M+H]^+$.

Preparation of 7-[(3R)-3-hydroxypyrrolidin-1-yl]-3-({[(2-methylpyridin-4-yl)methyl][(3S)-piperidin-3-yl]amino}methyl)-1-(propen-2-yl)-1,4-dihydroquinolin-4-one 4 M HCl in 1,4-dioxane (5.0 mL) was added to a solution of tert-butyl (3S)-3-[({7-[(3R)-3-hydroxypyrrolidin-1-yl]-4-oxo-1-(propan-2-yl)-1,4-dihydroquinolin-3-yl}methyl)[(2-methylpyridin-4-yl)methyl]amino]piperidine-1-carboxylate (1.30 g, 1.0 eq.) in 1,4-dioxane (30.0 mL). After stirring overnight at RT, the reaction mixture was cooled to 0° C. and basified to pH 11 with 1 M NaOH aq. solution. The resulting mixture was extracted with DCM (3×100.0 mL). The combined organic layers were washed with brine, dried over anh. $Na_2SO_4$ and concentrated in vacuo. The crude product was purified by FCC (SiHP $NH_2$-functionalized; DCM:MeOH) to yield the title compound (0.73 g, 63% yield). ESI-MS: 490.5 $[M+H]^+$.

Preparation of 4-iodo-1-{[2-(trimethylsilyl)ethoxy]methyl}-1H-pyrazole

NaH (60% suspension in mineral oil; 0.037 g, 1.2 eq.) was added in portions to a solution of 4-iodo-1H-pyrazole (0.15 g, 1.0 eq.) in dry THF (6.0 mL) in portions at 0° C. The resulting white suspension was stirred at 0° C. for 30 min and then [2-(chloromethoxy)ethyl]trimethylsilane (0.164 mL, 1.2 eq.) was added dropwise. The suspension was warmed to RT and was stirred for 2 h. The reaction mixture was diluted with water (1.0 mL) and concentrated in vacuo. The crude product was purified by FCC (SiHP; Hex:EtOAc) to give the title compound (0.157 g, 63% yield) as a colorless liquid. $^1$H NMR (300 MHz, DMSO-$d_6$) δ 8.09 (d, J=0.7 Hz, 1H), 7.61 (d, J=0.6 Hz, 1H), 5.39 (s, 2H), 3.63-3.41 (m, 2H), 1.14-0.68 (m, 2H), −0.05 (s, 9H).

Preparation of 7-[(3R)-3-hydroxypyrrolidin-1-yl]-3-({[(2-methylpyridin-4-yl)methyl][(3S)-1-(1-{[2-(trimethylsilyl)ethoxy]methyl}-1H-pyrazol-4-yl)piperidin-3-yl]amino}methyl)-1-(propan-2-yl)-1,4-dihydroquinolin-4-one 4-iodo-1-{[2-(trimethylsilyl)ethoxy]methyl}-1H-pyrazole (0.026 g, 1.1 eq.) and sodium tert-butoxide (0.01 g, 1.4 eq) were added to a solution of 7-[(3R)-3-hydroxypyrrolidin-1-yl]-3-({[(2-methylpyridin-4-yl)methyl][(3S)-piperidin-3-yl]amino}methyl)-1-(propan-2-yl)-1,4-dihydroquinolin-4-one (0.04 g, 1.0 eq.) in anh. 1,4-dioxane (3.0 mL). After flushing the reaction mixture with argon for 10 minutes, tBuXPhos Pd G3 (0.002 g, 0.035 eq.) was added. After stirring for 18 h at 85° C. and 3 h at 100° C., the mixture was cooled to RT and then concentrated in vacuo. The crude product was purified by FCC (SiHP; DCM:MeOH) to give the title compound (0.01 g, 14% yield) as a yellow solid. ESI-MS: 686.6 [M+H]$^+$.

Preparation of 7-[(3R)-3-hydroxypyrrolidin-1-yl]-3-({[(2-methylpyridin-4-yl)methyl][(3S)-1-(1H-pyrazol-4-yl)piperidin-3-yl]amino}methyl)-1-(propan-2-yl)-1,4-dihydroquinolin-4-one Trifluoroacetic acid (2.0 mL) was added to a solution of 7-[(3R)-3-hydroxypyrrolidin-1-yl]-3-({[(2-methylpyridin-4-yl)methyl][(3S)-1-(1-{[2-(trimethylsilyl)ethoxy]methyl}-1H-pyrazol-4-yl)piperidin-3-yl]amino}methyl)-1-(propan-2-yl)-1,4-dihydroquinolin-4-one (0.017 g, 1.0 eq.) in anh. DCM (6.0 mL) at 0° C. The reaction mixture was warmed to RT. After stirring for 2 h, the mixture was concentrated in vacuo. The crude compound was dissolved in MeOH (1.0 mL) and converted to free base using aqueous $NH_3$ (0.5 mL). The mixture was concentrated under reduced pressure and purified by prep-HPLC ($H_2O$:MeOH:$NH_3$) to give the title compound (0.004 g, 34% yield) as a white solid. ESI-MS: 556.6 [M+H]$^+$. $^1$H NMR (300 MHz, Methanol-$d_4$) δ 8.30-8.10 (m, 2H), 7.99 (s, 1H), 7.34 (s, 2H), 7.30 (s, 1H), 7.26 (d, J=5.5 Hz, 1H), 6.82 (dd, J=9.3, 1.9 Hz, 1H), 6.47 (s, 1H), 4.97 (quint, J=6.8 Hz, 1H), 4.58 (m, 1H), 3.85 (s, 2H), 3.79 (s, 2H), 3.69-3.46 (m, 4H), 3.39-3.34 (m, 1H), 3.29-3.24 (m, 1H), 3.10-2.85 (m, 1H), 2.65 (t, J=11.0 Hz, 1H), 2.54-2.42 (m, 1H), 2.39 (s, 3H), 2.26-2.04 (m, 3H), 1.97-1.83 (m, 1H), 1.80-1.53 (m, 2H), 1.49 (d, J=6.5 Hz, 6H).

Example 70. 1-cyclopropyl-6-fluoro-7-[4-(2-hydroxyethyl)piperazin-1-yl]-3-({[(3S)-1-(6-methylpyridin-3-yl)piperidin-3-yl][(2-methylpyridin-4-yl)methyl]amino}methyl)-1,4-dihydroquinolin-4-one

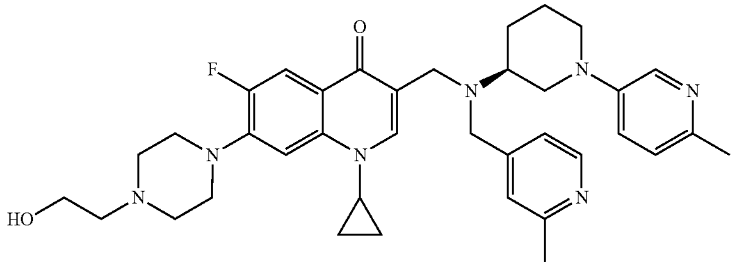

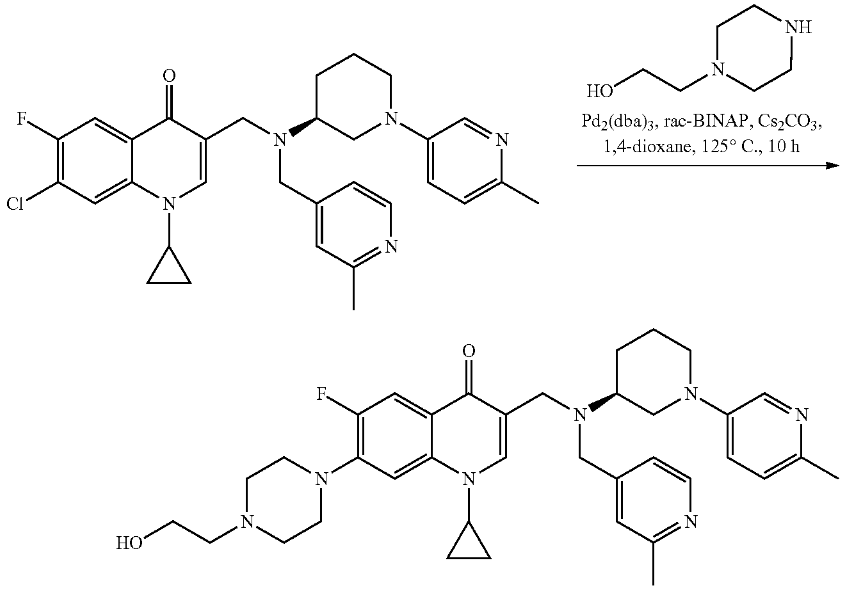

Preparation of 1-cyclopropyl-6-fluoro-7-[4-(2-hydroxyethyl)piperazin-1-yl]-3-({[(3S)-1-(6-methylpyridin-3-yl)piperidin-3-yl][(2-methylpyridin-4-yl)methyl]amino}methyl)-1,4-dihydroquinolin-4-one A suspension of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.1 g, 1.0 eq.), 2-(piperazin-1-yl)ethan-1-ol (0.044 g, 2.0 eq.) and $Cs_2CO_3$ (0.1 g, 1.8 eq.) in anh. 1,4-dioxane (3.0 mL) was purged with argon for 15 min. Subsequently, BINAP (0.021 g, 0.2 eq.) and $Pd_2(dba)_3$ (0.016 g, 0.1 eq.) were added. After stirring at 125° C. for 10 h, the mixture was diluted with DCM and washed with $H_2O$ and brine. The organic layer was dried over anh. $Na_2SO_4$, filtered and concentrated in vacuo. The residue was purified by FCC (SiHP; DCM:MeOH). The obtained sample was dissolved in MeOH and scavenger QuadraPure MPA (0.5 g) was added. After stirring at RT for 1 h, the scavenger was filtered off, the filtrate was concentrated in vacuo and the residue was re-purified by RP-FCC (C18HP; $H_2O$:MeCN) to give the product (0.01 g, 9% yield) as a white solid. ESI-MS: 640.6 $[M+H]^+$. $^1H$ NMR (400 MHz, DMSO-$d_6$) δ 8.29 (d, J=5.0 Hz, 1H), 8.13 (d, J=3.0 Hz, 1H), 7.82 (s, 1H), 7.71 (d, J=13.5 Hz, 1H), 7.34 (d, J=7.5 Hz, 1H), 7.24-7.19 (m, 2H), 7.19-7.15 (m, 1H), 7.02 (d, J=8.5 Hz, 1H), 4.45 (t, J=5.3 Hz, 1H), 3.89-3.69 (m, 3H), 3.61 (s, 2H), 3.58-3.46 (m, 4H), 3.22-3.18 (m, 4H), 2.82-2.71 (m, 2H), 2.69-2.55 (m, 5H), 2.47 (t, J=6.3 Hz, 2H), 2.38 (s, 3H), 2.33 (s, 3H), 2.03-1.91 (m, 1H), 1.82-1.71 (m, 1H), 1.61-1.35 (m, 2H), 1.29-1.12 (m, 2H), 0.95-0.80 (m, 2H).

Example 71. 1-cyclopropyl-6-fluoro-7-[2-(hydroxymethyl)morpholin-4-yl]-3-({[(3S)-1-(6-methylpyridin-3-yl)piperidin-3-yl][(2-methylpyridin-4-yl)methyl]amino}methyl)-1,4-dihydroquinolin-4-one

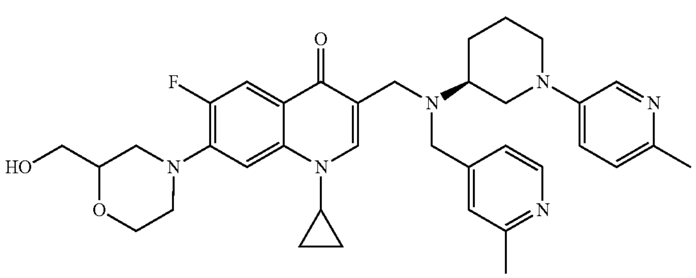

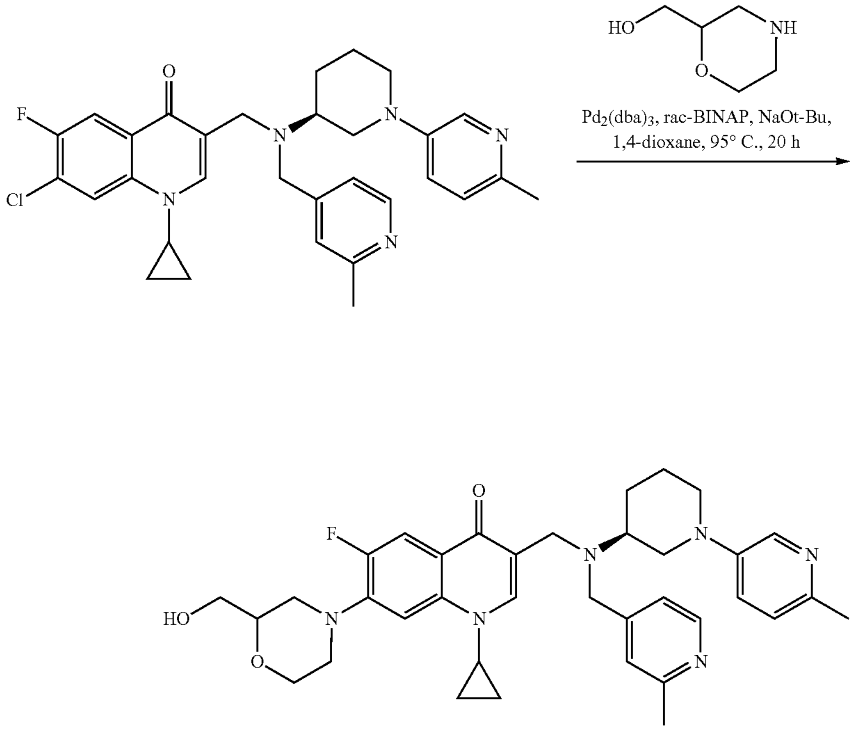

Preparation of 1-cyclopropyl-6-fluoro-7-[2-(hydroxymethyl)morpholin-4-yl]-3-({[(3S)-1-(6-methylpyridin-3-yl)piperidin-3-yl][(2-methylpyridin-4-yl)methyl]amino}methyl)-1,4-dihydroquinolin-4-one Sodium tert-butoxide (0.06 g, 1.5 eq.) was added to a solution of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.23 g, 1.0 eq.) and (morpholin-2-yl)methanol (0.048 g, 1.0 eq.) in anh. 1,4-dioxane (4.0 mL). After purging with nitrogen for 15 min, BINAP (0.077 g, 0.3 eq.) and $Pd_2(dba)_3$ (0.038 g, 0.1 eq.) were added to the reaction mixture. After stirring for 20 h at 95° C., the mixture was diluted with EtOAc, washed with water and brine. The organic layer was dried over anh. $Na_2SO_4$, filtered and concentrated in vacuo. The crude product was purified by FCC (SiHP; DCM:MeOH). The obtained product was dissolved in MeOH and scavenger QuadraPure MPA (0.2 g) was added. After stirring for 2 h, the scavenger was filtered off and the filtrate was concentrated in vacuo affording the title compound (0.094 g, 35% yield) as a beige solid. ESI-MS: 627.5 $[M+H]^+$. $^1H$ NMR (400 MHz, Methanol-$d_4$) δ 8.17 (d, J=5.2 Hz, 1H), 8.10 (d, J=2.9 Hz, 1H), 7.93 (s, 1H), 7.86 (d, J=13.6 Hz, 1H), 7.41 (d, J=7.3 Hz, 1H), 7.36 (dd, J=8.6, 3.0 Hz, 1H), 7.27-7.20 (m, 2H), 7.13 (d, J=8.6 Hz, 1H), 4.17-3.99 (m, 1H), 3.94-3.76 (m, 7H), 3.72-3.58 (m, 4H), 3.57-3.43 (m, 2H), 3.07-2.93 (m, 2H), 2.94-2.51 (m, 3H), 2.42 (s, 3H), 2.35 (s, 3H), 2.29-2.05 (m, 1H), 1.99-1.85 (m, 1H), 1.77-1.57 (m, 2H), 1.42-1.25 (m, 2H), 1.00-0.87 (m, 2H).

Example 72. and Example 73. Diastereomer s A and B of 1-cyclopropyl-6-fluoro-7-[2-(hydroxymethyl)morpholin-4-yl]-3-({[(3S)-1-(6-methylpyridin-3-yl)piperidin-3-yl][(2-methylpyridin-4-yl)methyl]amino}methyl)-1,4-dihydroquinolin-4-one: Example 72. 1-cyclopropyl-6-fluoro-7-[(2S)-2-(hydroxymethyl)morpholin-4-yl]-3-({[(3S)-1-(6-methylpyridin-3-yl)piperidin-3-yl][(2-methylpyridin-4-yl)methyl]amino}methyl)-1,4-dihydroquinolin-4-one (A) and Example 73. 1-cyclopropyl-6-fluoro-7-[(2R)-2-(hydroxymethyl)morpholin-4-yl]-3-({[(3S)-1-(6-methylpyridin-3-yl)piperidin-3-yl][(2-methylpyridin-4-yl)methyl]amino}methyl)-1,4-dihydroquinolin-4-one (B)

A

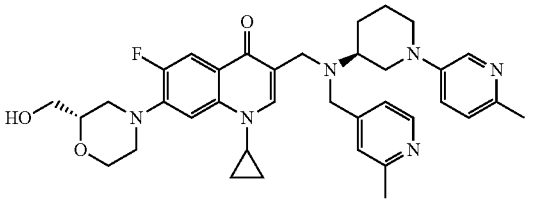

and

-continued

B

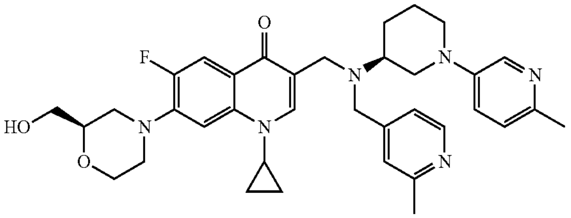

Preparation of 1-cyclopropyl-6-fluoro-7-[(2S)-2-(hydroxymethyl)morpholin-4-yl]-3-({[(3S)-1-(6-methylpyridin-3-yl)piperidin-3-yl][(2-methylpyridin-4-yl)methyl]amino}methyl)-1,4-dihydroquinolin-4-one (Example 72) and 1-cyclopropyl-6-fluoro-7-[(2R)-2-(hydroxymethyl)morpholin-4-yl]-3-({[(3S)-1-(6-methylpyridin-3-yl)piperidin-3-yl][(2-methylpyridin-4-yl)methyl]amino}methyl)-1,4-dihydroquinolin-4-one (Example 73)

1-cyclopropyl-6-fluoro-7-[2-(hydroxymethyl)morpholin-4-yl]-3-({[(3S)-1-(6-methylpyridin-3-yl)piperidin-3-yl][(2-methylpyridin-4-yl)methyl]amino}methyl)-1,4-dihydroquinolin-4-one (0.082 g, 1.0 eq.) was separated by chiral HPLC (IF; Hex:EtOH 25% isocratic) and obtained fractions were re-purified by FCC (SiHP; DCM:MeOH) each to give Example 72. (0.01 g, 12% yield) and Example 73. (0.009 g, 11% yield) as white solids. The configuration at the carbon within morpholine moiety was assigned randomly. Example 72: ESI-MS: 627.5 $[M+H]^+$ 0.1H NMR (400 MHz, Methanol-$d_4$) δ 8.19 (d, J=5.3 Hz, 1H), 8.13 (d, J=2.9 Hz, 1H), 7.92 (s, 1H), 7.86 (d, J=13.6 Hz, 1H), 7.54 (dd, J=8.7, 2.9 Hz, 1H), 7.41 (d, J=7.3 Hz, 1H), 7.30-7.21 (m, 3H), 4.10-4.02 (m, 1H), 3.98-3.75 (m, 7H), 3.73-3.59 (m, 4H), 3.56-3.42 (m, 2H), 3.09-2.90 (m, 3H), 2.87-2.69 (m, 2H), 2.47 (s, 3H), 2.36 (s, 3H), 2.20-2.09 (m, 1H), 2.03-1.91 (m, 1H), 1.77-1.63 (m, 2H), 1.35-1.29 (m, 2H), 1.00-0.87 (m, 2H). Example 73: ESI-MS: 627.8 $[M+H]^+$. 1H NMR (400 MHz, Methanol-$d_4$) δ 8.17 (d, J=5.2 Hz, 1H), 8.10 (d, J=2.9 Hz, 1H), 7.93 (s, 1H), 7.86 (d, J=13.6 Hz, 1H), 7.41 (d, J=7.4 Hz, 1H), 7.36 (dd, J=8.6, 3.0 Hz, 1H), 7.27-7.20 (m, 2H), 7.13 (d, J=8.6 Hz, 1H), 4.14-4.01 (m, 1H), 3.95-3.84 (m, 4H), 3.84-3.75 (m, 3H), 3.73-3.58 (m, 4H), 3.57-3.42 (m, 2H), 3.10-2.93 (m, 2H), 2.86 (t, J=11.1 Hz, 1H), 2.84-2.74 (m, 1H), 2.74-2.66 (m, 1H), 2.42 (s, 3H), 2.35 (s, 3H), 2.19-2.05 (m, 1H), 2.02-1.88 (m, 1H), 1.79-1.59 (m, 2H), 1.39-1.25 (m, 2H), 1.02-0.89 (m, 2H).

Example 74. 7-chloro-1-cyclopropyl-6-fluoro-3-({[(3S)-1-[4-(hydroxymethyl)pyridin-3-yl]piperidin-3-yl][(2-methylpyridin-4-yl)methyl]amino}methyl)-1,4-dihydroquinolin-4-one
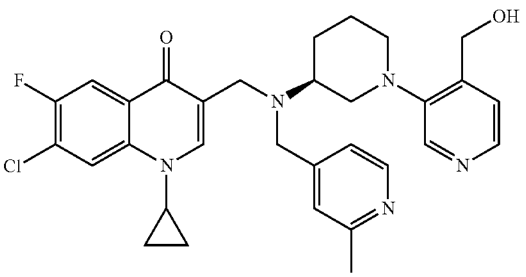
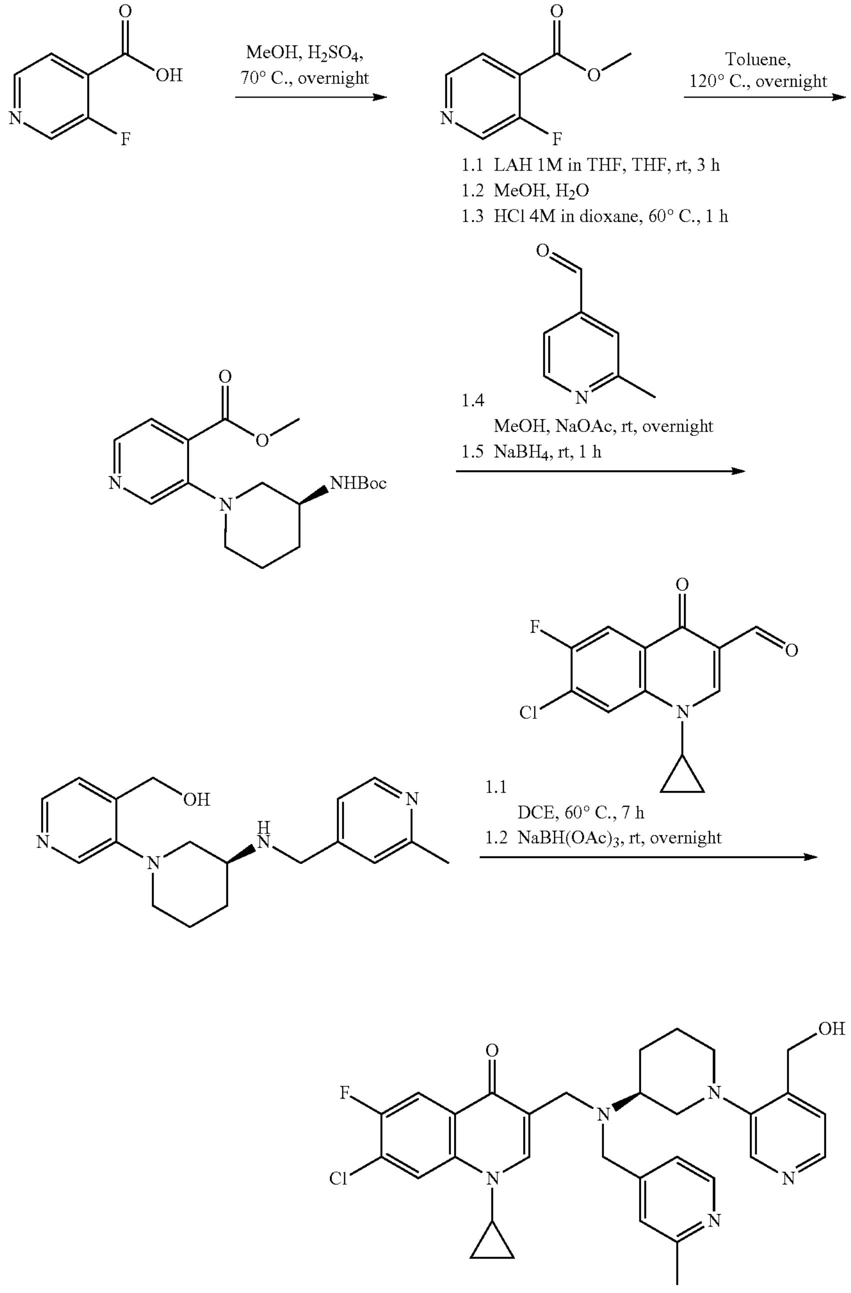

Preparation of Methyl 3-fluoropyridine-4-carboxylate

A solution of 3-fluoropyridine-4-carboxylic acid (1.0 g, 1.0 eq.) and sulfuric acid (4.2 mL, 11.0 eq.) in methanol (10.0 mL) was stirred overnight in 70° C. The residue was cooled, basified to pH 9 with sat. aq. $Na_2CO_3$ and washed with EtOAc. The organic layer was dried over anh. $Na_2SO_4$, filtered and concentrated in vacuo to give product (0.866 g, 76% yield) as a colorless oil. ESI-MS: 156.4 $[M+H]^+$.

Preparation of methyl 3-[(3S)-3-{[(tert-butoxy)carbonyl]amino}piperidin-1-yl]pyridine-4-carboxylate A solution of methyl 3-fluoropyridine-4-carboxylate (0.5 g, 1.0 eq.) and (S)-3-Boc-aminopiperidine (0.94 g, 1.5 eq.) in anh. toluene (7.0 mL) was heated at 120° C. for 24 h. The solvent was evaporated in vacuo. The crude product was purified by FCC (SiHP; Hex:EtOAc) to give product (0.72 g, 66% yield) as a yellow oil. ESI-MS: 336.4 $[M+H]^+$.

Preparation of {3-[(3S)-3-{[(2-methylpyridin-4-yl)methyl]amino}piperidin-1-yl]pyridin-4-yl}methanol A solution of methyl 3-[(3S)-3-{[(tert-butoxy)carbonyl]amino}piperidin-1-yl]pyridine-4-carboxylate (0.58 g, 1.0 eq.) in anh. THF (10.0 mL) was cooled in an ice bath to 0° C. and 1 M LAH in THF (2.16 mL, 1.3 eq.) was slowly added. The reaction mixture was stirred at RT for 3 h and quenched by adding MeOH and $H_2O$. Then 4 M HCl in 1,4-dioxane (4.2 mL) was added and the reaction mixture was stirred at 60° C. for 1 h. The solvent was evaporated, crude material was dissolved in DCM and TEA was added. The precipitated inorganic solid was filtered off, solvent was removed in vacuo and anh. MeOH (20.0 mL), NaOAc (0.272 g, 2.0 eq.) and 2-methylpyridine-4-carbaldehyde (0.24 mL, 1.3 eq.) were added. This reaction was stirred overnight and then $NaBH_4$ (0.094 g, 1.5 eq.) was added. Reaction was stirred 1 h at RT, then MeOH was evaporated and crude mixture was purified on RP-FCC (C18HP; $H_2O$:MeCN) to give product (0.186 g, 35% yield) as colorless oil. ESI-MS: 313.4 $[M+H]^+$.

Preparation of 7-chloro-1-cyclopropyl-6-fluoro-3-({[(3S)-1-[4-(hydroxymethyl)pyridin-3-yl]piperidin-3-yl][(2-methylpyridin-4-yl)methyl]amino}methyl)-1,4-dihydroquinolin-4-one A solution of {3-[(3S)-3-{[(2-methylpyridin-4-yl)methyl]amino}piperidin-1-yl]pyridin-4-yl}methanol (0.186 g, 1.0 eq.) and 7-chloro-1-cyclopropyl-6-fluoro-4-oxo-1,4-dihydroquinoline-3-carbaldehyde (Intermediate 9) (0.187 g, 1.1 eq.) in anh. DCE (10.0 mL) was stirred at 60° C. for 7 h. Then the reaction was cooled to 0° C., STAB (0.35 g, 2.8 eq.) was added and the reaction mixture was stirred overnight at RT. The crude mixture was washed with DCM and NaOH aq., the organic layer was dried over anh. $Na_2SO_4$, filtered and concentrated. The crude material was purified on RP-FCC (C18HP; $H_2O$:MeCN) to give product (0.22 g, 65% yield) as white solid. ESI-MS: 562.7 $[M+H]^+$. $^1H$ NMR (400 MHz, DMSO-$d_6$) 8.29-8.22 (m, 3H), 8.15 (d, J=6.2 Hz, 1H), 7.96 (d, J=9.4 Hz, 1H), 7.89 (s, 1H), 7.43 (d, J=4.9 Hz, 1H), 7.18 (s, 1H), 7.12 (dd, J=5.4, 1.4 Hz, 1H), 5.30 (t, J=5.7 Hz, 1H), 4.55-4.41 (m, 2H), 3.80-3.68 (m, 2H), 3.68-3.56 (m, 2H), 3.55-3.47 (m, 1H), 3.29-3.18 (m, 1H), 2.95 (d, J=11.4 Hz, 1H), 2.87-2.74 (m, 2H), 2.73-2.62 (m, 1H), 2.35 (s, 3H), 2.07-1.94 (m, 1H), 1.86-1.71 (m, 1H), 1.62-1.43 (m, 2H), 1.27-1.14 (m, 2H), 0.97-0.79 (m, 2H).

Example 75. 1-cyclopropyl-6-fluoro-3-({[(3S,5S)-5-fluoro-1-(6-methylpyridin-3-yl)piperidin-3-yl][(2-methylpyridin-4-yl)methy]amino}methyl)-7-(2-hydroxyethoxy)-1,4-dihydroquinolin-4-one

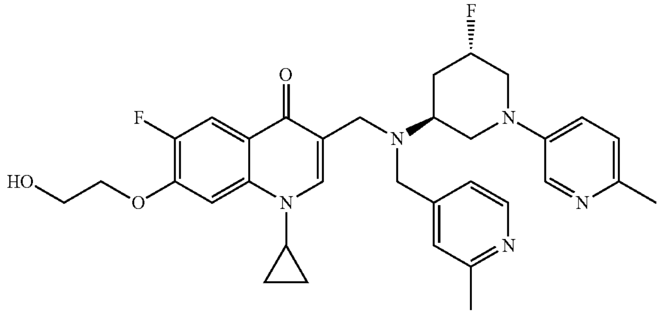 [SMILES: Cc1ccc(N2C[C@@H](F)C[C@H](N(Cc3ccnc(C)c3)Cc3cn(C4CC4)c4cc(OCCO)c(F)cc4c3=O)C2)cn1]

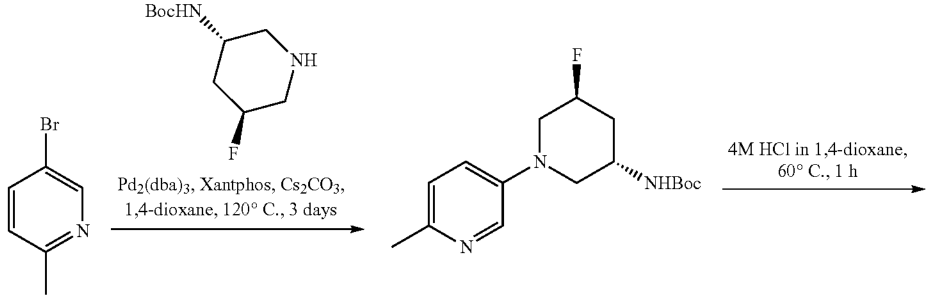

-continued

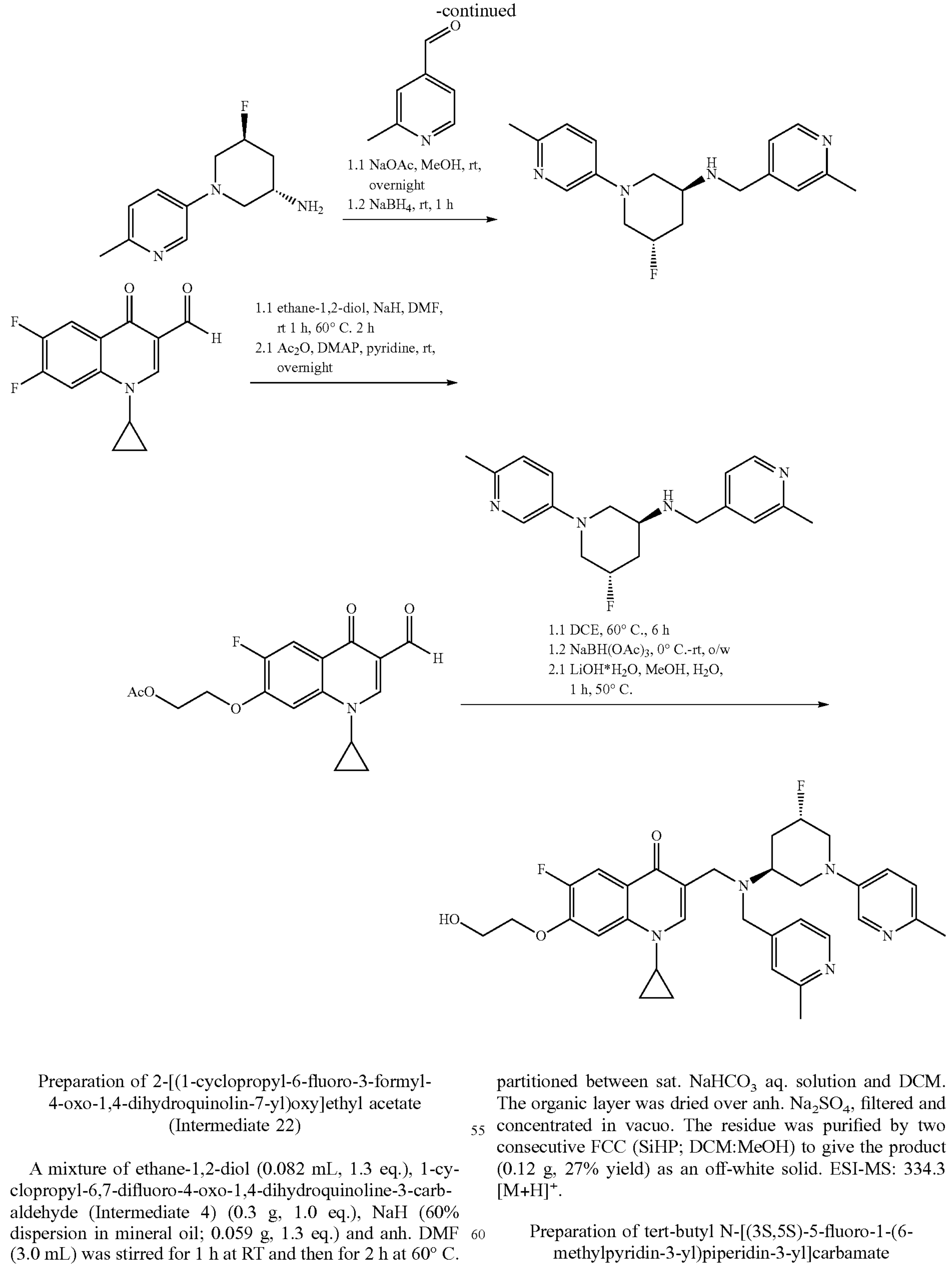

Preparation of 2-[(1-cyclopropyl-6-fluoro-3-formyl-4-oxo-1,4-dihydroquinolin-7-yl)oxy]ethyl acetate (Intermediate 22)

A mixture of ethane-1,2-diol (0.082 mL, 1.3 eq.), 1-cyclopropyl-6,7-difluoro-4-oxo-1,4-dihydroquinoline-3-carbaldehyde (Intermediate 4) (0.3 g, 1.0 eq.), NaH (60% dispersion in mineral oil; 0.059 g, 1.3 eq.) and anh. DMF (3.0 mL) was stirred for 1 h at RT and then for 2 h at 60° C. Subsequently, the reaction mixture was concentrated in vacuo and the residue was suspended in anh. pyridine (10.0 mL). $Ac_2O$ (0.21 mL, 2.0 eq.) was added to the above suspension followed by DMAP (0.007 g, 0.05 eq.) and the resulting mixture was stirred overnight at RT. Then, the mixture was concentrated in vacuo and the residue was partitioned between sat. $NaHCO_3$ aq. solution and DCM. The organic layer was dried over anh. $Na_2SO_4$, filtered and concentrated in vacuo. The residue was purified by two consecutive FCC (SiHP; DCM:MeOH) to give the product (0.12 g, 27% yield) as an off-white solid. ESI-MS: 334.3 $[M+H]^+$.

Preparation of tert-butyl N-[(3S,5S)-5-fluoro-1-(6-methylpyridin-3-yl)piperidin-3-yl]carbamate A suspension of tert-butyl N-[(3S,5S)-5-fluoropiperidin-3-yl]carbamate (0.99 g, 1.3 eq.), 5-bromo-2-methylpyridine (0.6 g, 1.0 eq.) and $Cs_2CO_3$ (1.5 g, 1.4 eq.) in anh. 1,4-dioxane (20.0 mL) was purged with argon for 10 min. Then, Xantphos (0.12 g, 0.06 eq.) and $Pd_2(dba)_3$ (0.16 g, 0.05 eq.)

were added and the resulting mixture was purged with argon for an additional 10 min. The vessel was sealed and the reaction mixture was stirred for 3 days at 120° C. Subsequently, the mixture was filtered through a pad of celite and concentrated in vacuo. The residue was purified by FCC (SiHP; Hex:EtOAc) and fractions containing the product were combined and concentrated in vacuo. To the residue dissolved in DCM was added scavenger QuadraPure MPA (0.3 g) and the resulting mixture was stirred overnight at RT. Then, the scavenger was filtered off, washed with DCM and the filtrate was concentrated in vacuo to give the product (0.38 g, 33% yield) as a yellow solid. ESI-MS: 310.6 [M+H]r.

Preparation of (3S,5S)-5-fluoro-1-(6-methylpyridin-3-yl)piperidin-3-amine

4 M HCl solution in 1,4-dioxane (1.42 mL, 5.0 eq.) was added to a solution of tert-butyl N-[(3S,5S)-5-fluoro-1-(6-methylpyridin-3-yl)piperidin-3-yl]carbamate (0.38 g, 1.0 eq.) in 1,4-dioxane (7.0 mL) and the resulting mixture was stirred for 1 h at 60° C. Then, the reaction mixture was concentrated in vacuo and the residue was partitioned between NaOH aq. solution and DCM. The combined organic layers were dried over anh. $Na_2SO_4$, filtered and concentrated in vacuo to give the crude product (0.23 g, 84% yield) as a brown oil which was used in the next step without further purification. ESI-MS: 210.3 $[M+H]^+$.

Preparation of (3S,5S)-5-fluoro-1-(6-methylpyridin-3-yl)-N-[(2-methylpyridin-4-yl)methyl]piperidin-3-amine A mixture of (3S,5S)-5-fluoro-1-(6-methylpyridin-3-yl) piperidin-3-amine (0.23 g, 1.0 eq.), NaOAc (0.078 g, 1.0 eq.), 2-methylpyridine-4-carbaldehyde (0.12 mL, 1.1 eq.) in anh. MeOH (7.0 mL) was stirred overnight at RT. Then, $NaBH_4$ (0.047 g, 1.3 eq.) was added and the resulting mixture was left stirring for 1 h at RT. Subsequently, the reaction mixture was concentrated in vacuo and the residue was partitioned between NaOH aq. solution and DCM. The organic layer was dried over anh. $Na_2SO_4$, filtered and concentrated in vacuo. The residue was purified by RP-FCC (C18HP; $H_2O$:MeCN) to give the product (0.26 g, 85% yield) as a pale yellow oil. ESI-MS: 315.4 $[M+H]^+$.

Preparation of 1-cyclopropyl-6-fluoro-3-({[(3S,5S)-5-fluoro-1-(6-methylpyridin-3-yl)piperidin-3-yl][(2-methylpyridin-4-yl)methyl]amino}methyl)-7-(2-hydroxyethoxy)-1,4-dihydroquinolin-4-one A mixture of (3S,5S)-5-fluoro-1-(6-methylpyridin-3-yl)-N-[(2-methylpyridin-4-yl)methyl]piperidin-3-amine (0.09 g, 1.0 eq.), 2-[(1-cyclopropyl-6-fluoro-3-formyl-4-oxo-1,4-dihydroquinolin-7-yl)oxy]ethyl acetate (Intermediate 22) (0.11 g, 1.0 eq.) and DCE (8.0 mL) was stirred for 6 h at 60° C. Then, the mixture was cooled to 0° C., $NaBH(OAc)_3$ (0.17 g, 2.8 eq.) was added and the resulting mixture was stirred over the weekend at RT. Subsequently, the reaction mixture was partitioned between NaOH aq. solution and DCM. The organic layer was dried over anh. $Na_2SO_4$, filtered and concentrated in vacuo. The residue was dissolved in a mixture of $H_2O$ and MeOH (10.0 mL, 1:2) and $LiOH*H_2O$ (0.048 g, 4.0 eq.) was added. The resulting mixture was stirred for 1 h at 50° C. Then, the reaction mixture was concentrated in vacuo and the residue was purified by RP-FCC (C18HP; $H_2O$:MeCN) and re-purified by prep-HPLC ($H_2O$:MeCN:$NH_3$) to give the product (0.054 g, 32% yield) as a white solid. ESI-MS: 590.5 $[M+H]^+$. $^1H$ NMR (400 MHz, DMSO-$d_6$) δ 8.29 (d, J=5.0 Hz, 1H), 8.14 (d, J=3.0 Hz, 1H), 7.85 (s, 1H), 7.80 (d, J=11.7 Hz, 1H), 7.51 (d, J=7.3 Hz, 1H), 7.26-7.20 (m, 2H), 7.20-7.14 (m, 1H), 7.02 (d, J=8.5 Hz, 1H), 5.14-4.93 (m, 2H), 4.28-4.18 (m, 2H), 3.93-3.70 (m, 6H), 3.70-3.56 (m, 2H), 3.56-3.46 (m, 1H), 3.16-3.02 (m, 1H), 3.00-2.78 (m, 2H), 2.38 (s, 3H), 2.32 (s, 3H), 2.29-2.13 (m, 1H), 2.01-1.78 (m, 1H), 1.36-1.15 (m, 2H), 1.00-0.78 (m, 2H).

Example 76. 1-cyclopropyl-7-[(4R)-4-hydroxypyrrolidin-2-yl]-3-({[(3S)-1-(6-methylpyridin-3-yl)piperidin-3-yl][(2-methylpyridin-4-yl)methyl]amino}methyl)-1,4-dihydroquinolin-4-one

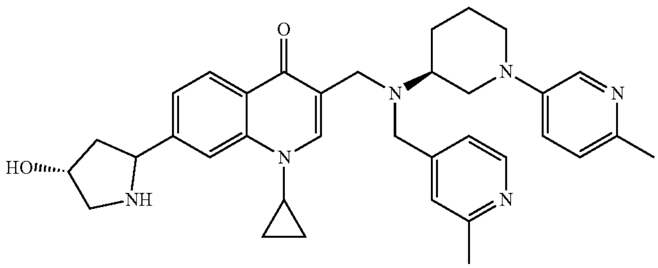

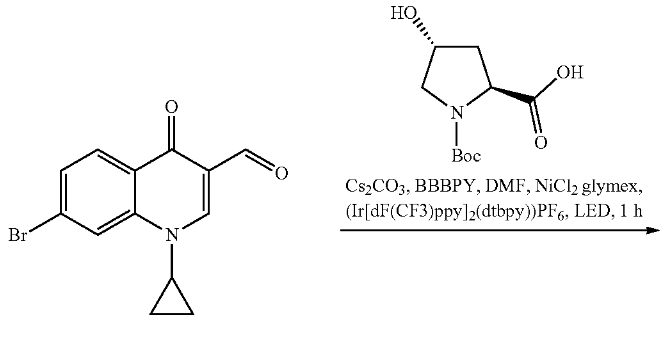

-continued

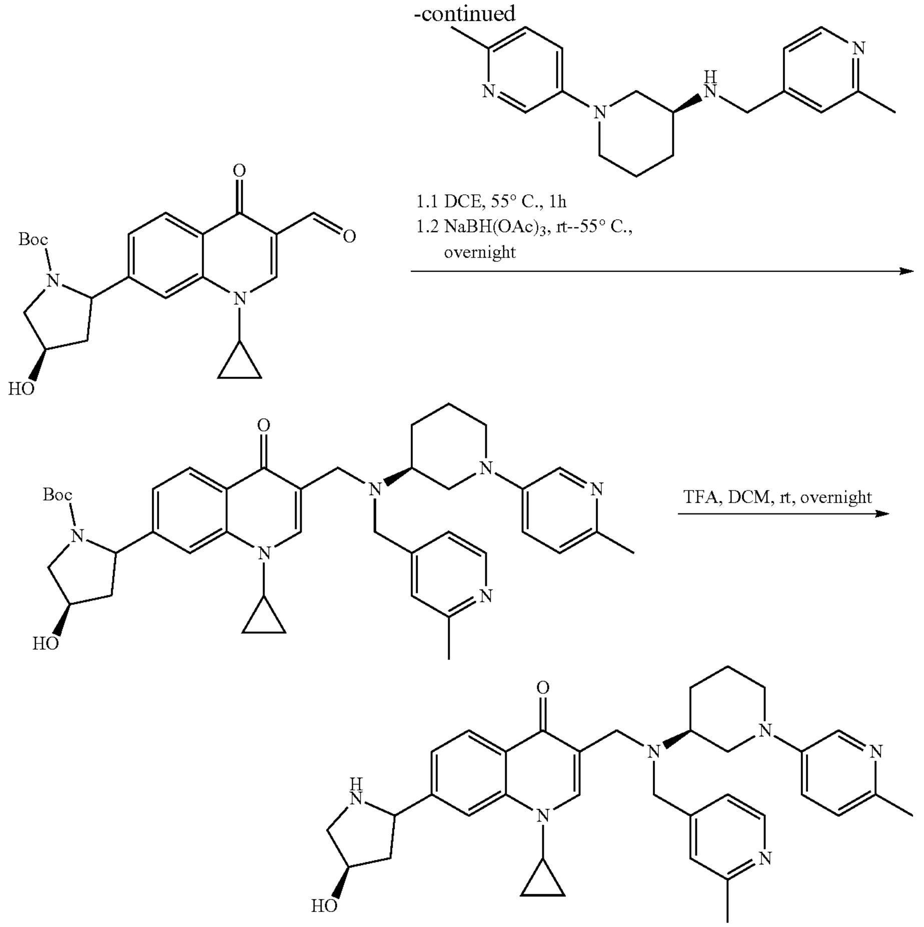

Preparation of tert-buty (4R)-2-(1-cyclopropyl-3-formyl-4-oxo-1,4-dihydroquinolin-7-yl)-4-hydroxy-pyrrolidine-1-carboxylate 7-Bromo-1-cyclopropyl-4-oxo-1,4-dihydroquinoline-3-carbaldehyde (Intermediate 16) (0.3 g, 1.0 eq.), trans-N-(tert-Butoxycarbonyl)-4-hydroxy-L-proline (0.59 g, 2.5 eq.), powdered cesium carbonate (0.67 g, 2.0 eq.) and 4,4'-di-tert-butyl-2,2'-bipyridine (0.041 g, 0.15 eq.) were dissolved in anh. DMF (7.0 mL)., Nickel (II) chloride ethylene glycol dimethyl ether complex (0.045 g, 0.2 eq.) and [4,4'-Bis(1,1-dimethylethyl)-2,2'-bipyridine-N1,N1']bis [3,5-difluoro-2-[5-(trifluoromethyl)-2-pyridinyl-N]phenyl-C]Iridium(III) hexafluorophosphate (0.01 g, 0.01 eq.) were added to the resulting suspension and the green reaction mixture was put in a photoreactor with the following parameters—stirring speed=650 rpm, LED %=70% —for 1 h. After the reaction completed, the solvents were evaporated in vacuo and the residue was purified by FCC (SiHP Hex:EtOAc:MeOH) to give product (0.287 g, 67% yield) as a white solid. ESI-MS: 399.6 [M+H].

Preparation of tert-butyl (4R)-2-[1-cyclopropyl-3-({[(3S)-1-(6-methylpyridin-3-yl)piperidin-3-yl)][(2-methylpyridin-4-yl)methyl]amino}methyl)-4-oxo-1,4-dihydroquinolin-7-yl]-4-hydroxypyrrolidine-1-carboxylate A solution of tert-butyl (4R)-2-(1-cyclopropyl-3-formyl-4-oxo-1,4-dihydroquinolin-7-yl)-4-hydroxypyrrolidine-1-carboxylate (0.25 g, 1.0 eq.) and (3S)-1-(6-methylpyridin-3-yl)-N-[(2-methylpyridin-4-yl)methyl]piperidin-3-amine (Intermediate 2) (0.19 g, 1.0 eq.) in anh. DCE (8.0 mL) was stirred at 55° C. for 3 h. The reaction mixture was cooled to RT and STAB (0.36 g, 2.8 eq.) was added. The resulting suspension was stirred overnight at RT. The reaction mixture was filtered through a pad of celite, washed with DCM (50.0 mL) and MeOH (50.0 mL). The filtrate was concentrated in vacuo. The crude was purified using FCC (SiHP; DCM: MeOH) to give product (0.20 g, 48% yield) as a white solid. ESI-MS: 679.8 $[M+H]^+$.

Preparation of 1-cyclopropyl-7-[(4R)-4-hydroxypyrrolidin-2-yl]-3-({[(3S)-1-(6-methylpyridin-3-yl)piperidin-3-yl][(2-methylpyridin-4-yl)methyl]amino}methyl)-1,4-dihydroquinolin-4-one tert-Butyl (4R)-2-[1-cyclopropyl-3-({[(3S)-1-(6-methylpyridin-3-yl)piperidin-3-yl][(2-methylpyridin-4-yl)methyl]amino}methyl)-4-oxo-1,4-dihydroquinolin-7-yl]-4-hydroxypyrrolidine-1-carboxylate (0.18 g, 1.0 eq.) was dissolved in DCM (5.0 mL) and trifluoroacetic acid (0.40 mL, 21.0 eq.) was added dropwise. The resulting mixture was stirred overnight at RT. Solvents were evaporated in vacuo. The residue was dissolved in water and pH of the solution was adjusted to 8 by adding 1 N NaOH aq. solution. The aqueous layer was extracted with DCM (70.0 mL×4). The combined organic layers were washed with water and brine, dried over anh. $MgSO_4$ and concentrated in vacuo.

The residue was purified by FCC (C18HP $H_2O$:MeCN) to give the product as a mixture of diastereomers (82:15). (0.082 g, 54% yield) as white solid. ESI-MS: 579.3 $[M+H]^+$. $^1H$ NMR (400 MHz, Methanol-$d_4$) δ 8.27 (dd, J=8.4, 2.8 Hz, 1H), 8.20-8.13 (m, 1H) J, 8.08 (d, J=2.9 Hz, 1H), 8.06-7.95 (m, 2H), 7.45 (dd, J=8.4, 1.6 Hz, 1H), 7.34 (dd, J=8.6, 3.0 Hz, 1H), 7.27-7.19 (m, 2H), 7.10 (d, J=8.6 Hz, 1H), 4.61-4.48 (m, 2H), 3.89 (s, 1H), 3.85 (s, 2H), 3.81 (s, 2H), 3.60 (d, J=12.2 Hz, 1H), 3.53-3.44 (m, 1H), 3.40 (dd, J=11.9, 5.2 Hz, 1H), 3.01-2.92 (m, 2H), 2.85 (t, J=11.1 Hz, 1H), 2.76-2.63 (m, 1H), 2.40 (s, 3H), 2.32 (s, 3H), 2.30-2.22 (m, 1H), 2.19-2.09 (m, 1H), 2.01-1.87 (m, 2H), 1.73-1.60 (m, 2H), 1.36-1.24 (m, 2H), 0.99-0.84 (m, 2H).

Example 77. 2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]acetamide

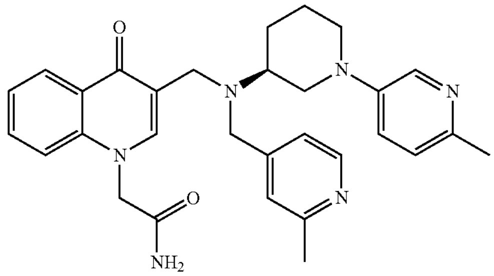

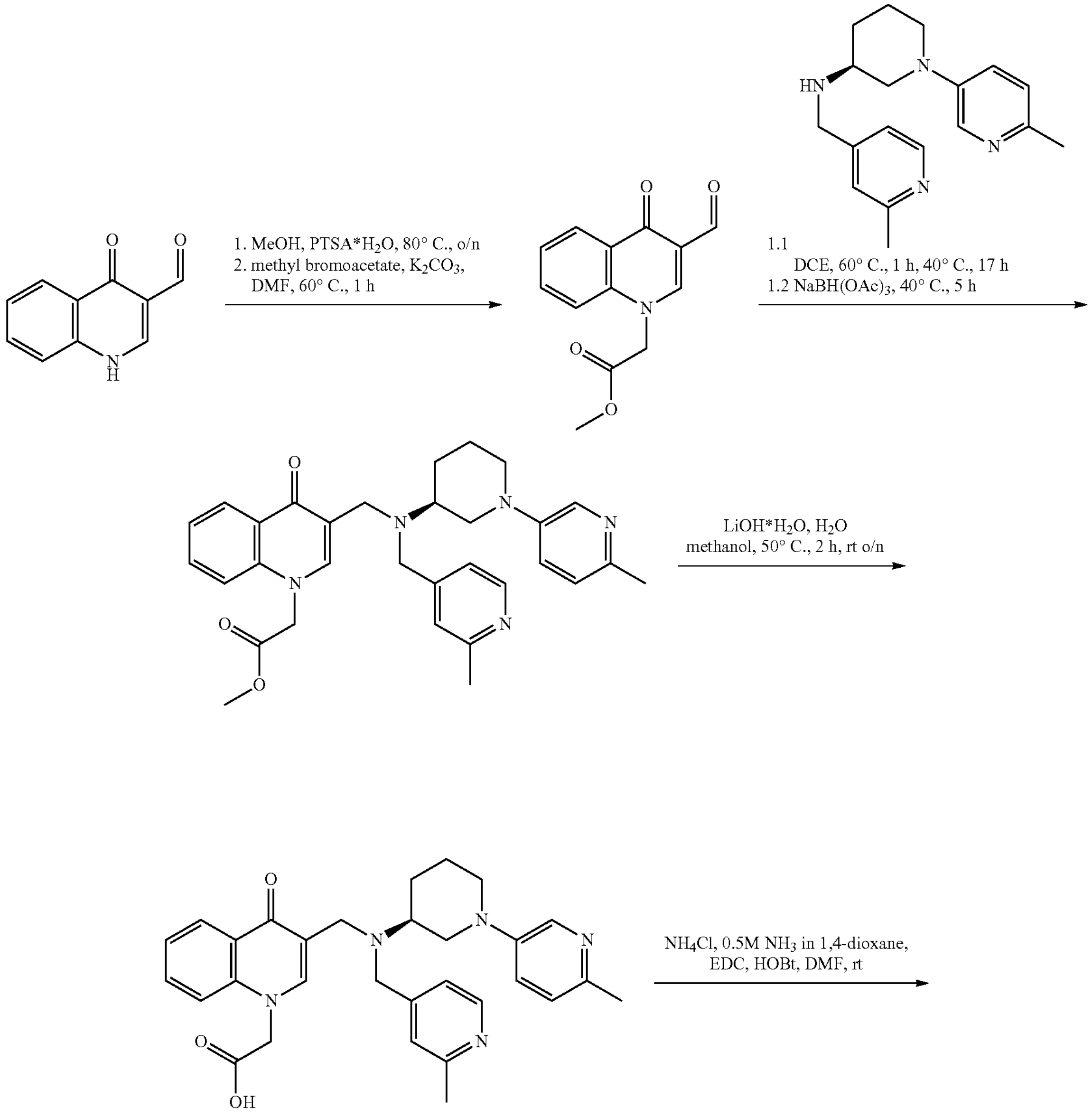

-continued

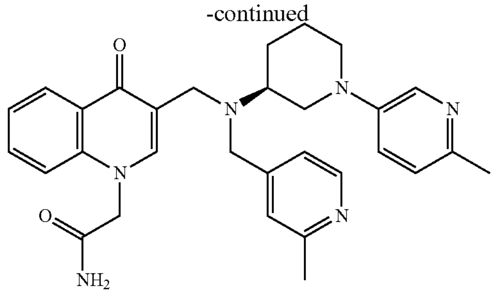

Preparation of methyl 2-(3-formyl-4-oxo-1,4-dihydroquinolin-1-yl)acetate

A mixture of 4-oxo-1,4-dihydroquinoline-3-carbaldehyde (Intermediate 1) (0.2 g, 1.0 eq.), PTSA*$H_2O$ (0.37 g, 2.0 eq.) and MeOH (10.0 mL) was heated at 80° C. overnight. Then, the mixture was concentrated in vacuo. The residue was dissolved in DMF (2.0 mL) and $K_2CO_3$ (0.27 g, 2.0 eq.) was added. The resulting mixture was stirred for 5 min at RT and then methyl bromoacetate (0.14 mL, 1.5 eq.) was added. The resulting mixture was heated for 1 h at 60° C. Afterwards, the mixture was partitioned between DCM and water and the aqueous layer was further washed with DCM. The combined organic layers were washed with brine, dried over anh. $Na_2SO_4$, filtered and concentrated in vacuo. The residue was purified by FCC (SiHP, Hex:EtOAc:DCM) to give the product (0.10 g, 42% yield) as a yellow solid. ESI-MS: 246.1 $[M+H]^+$.

Preparation of methyl 2-[3-({[(3S)-1-(6-methylpyridin-3-yl)piperidin-3-yl][(2-methylpyridin-4-yl)methylpyridin-4-yl)methyl]amino}methyl)-4-oxo-1,4-dihydroquinolin-1-yl]acetate A mixture of (3S)-1-(6-methylpyridin-3-yl)-N-[(2-methylpyridin-4-yl)methyl]piperidin-3-amine (Intermediate 2)(0.115 g, 1.0 eq.), methyl 2-(3-formyl-4-oxo-1,4-dihydroquinolin-1-yl)acetate (0.094 g, 1.0 eq.) in anh. DCE (5.0 mL) was heated for 1 h at 60° C., then at 40° C. for 17 h. Afterwards, the mixture was coaled to RT and $NaBH(OAc)_3$ (0.20 g, 2.5 eq.) was added and the resulting mixture was heated for 5 h at 40° C. Then, the mixture was partitioned between water and DCM. The aq. layer was additionally washed with DCM. The combined organic layers were washed with brine, dried over anh. $Na_2SO_4$, filtered and concentrated in vacuo. The residue was purified by FCC (SiHP-15 μm, DCM:MeOH) to give the product (0.107 g, 53% yield) as a yellow semi-solid. ESI-MS: 526.6 [M+H].

Preparation of 2-[3-({[(3S)-1-(6-methylpyridin-3-yl)piperidin-3-yl][(2-methylpyridin-4-yl)methy]amino}methyl)-4-oxo-1,4-dihydroquinolin-1-yl]acetic acid A mixture of methyl 2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]acetate (0.107 g, 1.0 eq.), LiOH*$H_2O$ (0.03 g, 3.6 eq.), methanol (5.0 mL) and $H_2O$ (1.0 mL) was stirred for 2 h at 50° C. and then overnight at RT. The reaction mixture was concentrated in vacuo. 1 M HCl aa. solution (0.7 mL) was added to the above residue and the sample was purified using RP-FCC (C18HP, $H_2O$:MeCN) to give the product (0.105 g, quant. yield) as a yellow solid. ESI-MS: 512.4 $[M+H]^+$.

Preparation of 2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]acetamide DIPEA (0.18 mL, 5.0 eq.) was added to a mixture of 2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]acetic acid (0.105 g, 1.0 eq.), EDC hydrochloride (0.058 g, 1.5 eq.), HOBt (0.047 g, 1.5 eq.) and DMF (5.0 mL) and was followed by the addition of $NH_4Cl$ (0.022 g, 2.0 eq.) and the resulting mixture was stirred overnight at RT. Then 0.5 M $NH_3$ solution in 1,4-dioxane (1.22 mL, 3.0 eq.) was added and after 160 min additionally EDC hydrochloride (0.058 g, 1.5 eq.) and HOBt (0.047 g, 1.5 eq.) were also added and the reaction mixture was stirred for 5 days at RT. Then, the mixture was concentrated in vacuo and the residue was partitioned between water and DCM. The product was found in the aqueous layer which was then concentrated in vacuo. The residue was purified by RP-FCC (C18HP, $H_2O$:MeCN), FCC (SiHP, DCM:MeOH) and finally prep-HPLC ($H_2O$:MeCN:$NH_3$) to give the product (0.034 g, 33% yield) as a white solid. ESI-MS: 511.4 $[M+H]^+$. $^1H$ NMR (400 MHz, DMSO-$d_6$) δ 8.28 (d, J=5.0 Hz, 1H), 8.19 (dd, J=8.0, 1.6 Hz, 1H), 8.13 (d, J=3.0 Hz, 1H), 8.05 (s, 1H), 7.82 (s, 1H), 7.68 (ddd, J=8.7, 7.0, 1.7 Hz, 1H), 7.47-7.32 (m, 3H), 7.27 (s, 1H), 7.25-7.18 (m, 2H), 7.01 (d, J=8.5 Hz, 1H), 4.96 (s, 2H), 3.87-3.52 (m, 6H), 2.80-2.65 (m, 2H), 2.62-2.53 (m, 1H), 2.39 (s, 3H), 2.32 (s, 3H), 2.05-1.94 (m, 1H), 1.81-1.69 (m, 1H), 1.59-1.37 (m, 2H).

Example 78. 1-Cyclopropyl-6-fluoro-7-[(3R)-3-hydroxypyrrolidin-1-yl]-3-({[(2-methylpyridin-4-yl)methyl][(3S)-1-(pyridin-3-yl)piperidin-3-yl]amino}methyl)-1,4-dihydroquinolin-4-one
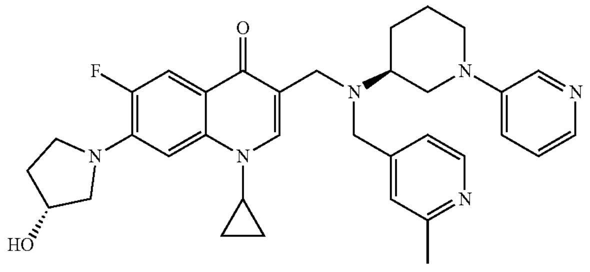 [SMILES: Cc1cc(CN(Cc2cn(C3CC3)c3cc(N4CC[C@@H](O)C4)c(F)cc3c2=O)[C@H]2CCCN(c3cccnc3)C2)ccn1]
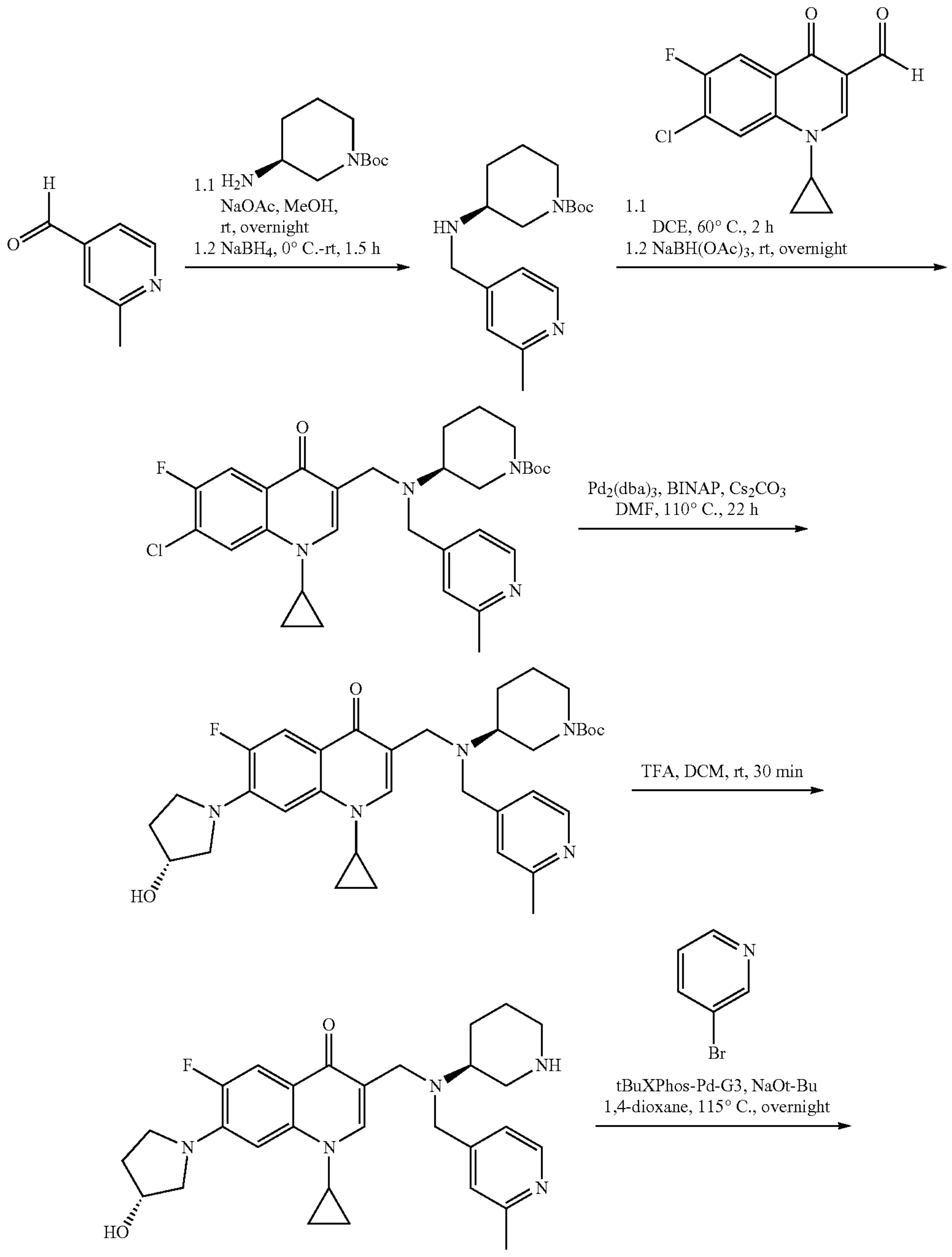

-continued

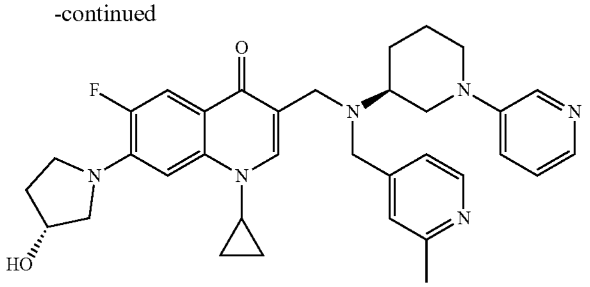

Preparation of tert-butyl (3S)-3-{[(2-methylpyridin-4-yl)methyl]amino}piperidine-1-carboxylate (Intermediate 18)

A dry reaction vessel, flushed with argon, was charged with tert-butyl (3S)-3-aminopiperidine-1-carboxylate (1.8 mL, 1.1 eq.), 2-methylpyridine-4-carbaldehyde (1.0 g, 1.0 eq.) and NaOAc (0.68 g, 1.0 eq.). Then, MeOH (8.0 mL) was added and the resulting mixture was stirred overnight at RT under argon atmosphere. Subsequently, the mixture was cooled to 0° C., $NaBH_4$ (0.34 g, 1.1 eq.) was added in portions and the reaction mixture was left stirring for 1.5 h at RT. Afterwards, the mixture was concentrated in vacuo and the residue was dissolved in DCM. Then, water was added and pH was adjusted to 12 using 12 M NaOH aq. solution. The resulting mixture was washed with DCM (3×). The combined organic layers were washed with brine, dried over anh. $MgSO_4$, filtered and concentrated in vacuo. The residue was purified by two consecutive FCC (SiHP; DCM: MeOH) to give the product (2.3 g, 91% yield) as an orange oil. ESI-MS: 306.5 $[M+H]^+$.

Preparation of tert-butyl (3S)-3-{[(7-chloro-1-cyclopropyl-6-fluoro-4-oxo-1,4-dihydroquinolin-3-yl)methyl][(2-methylpyridin-4-yl)methyl]amino}piperidine-1-carboxylate A mixture of tert-butyl (3S)-3-{[(2-methylpyridin-4-yl)methyl]amino}piperidine-1-carboxylate (Intermediate 18) (0.22 g, 1.1 eq.) and 7-chloro-1-cyclopropyl-6-fluoro-4-oxo-1,4-dihydroquinoline-3-carbaldehyde (Intermediate 9) (0.2 g, 1.0 eq.) and anh. DCE (4.0 mL) were heated for 2 h at 60° C. under inert atmosphere. Then, the mixture was cooled to RT, $NaBH(OAc)_3$ (0.38 g, 3.0 eq.) was added and the resulting mixture was stirred overnight at RT. Subsequently, the reaction mixture was diluted with water and partitioned between NaOH aq. solution and DCM. The organic layer was dried over anh. $MgSO_4$, filtered and concentrated in vacuo. The residue was purified by FCC (SiHP; DCM: MeOH) to give the product (0.19 g, 56% yield) as a white solid. ESI-MS: 577.6 $[M+Na]^+$.

Preparation of tert-butyl (3S)-3-[({1-cyclopropyl-6-fluoro-7-[(3R)-3-hydroxypyrrolidin-1-yl]-4-oxo-1,4-dihydroquinolin-3-yl}methyl)[(2-methylpyridin-4-yl)methyl]amino]piperidine-1-carboxylate A mixture of tert-butyl (3S)-3-{[(7-chloro-1-cyclopropyl-6-fluoro-4-oxo-1,4-dihydroquinolin-3-yl)methyl][(2-methylpyridin-4-yl)methyl]amino}piperidine-1-carboxylate (0.19 g, 1.0 eq.), (3R)pyrrolidin-3-ol (0.043 g, 1.5 eq.), $Cs_2CO_3$ (0.2 g, 1.8 eq.) and anh. DMF (3.0 mL) was purged with argon for 15 min. Then, BINAP (0.041 g, 0.2 eq.) and $Pd_2(dba)_3$ (0.03 g, 0.1 eq.) were added and the resulting mixture was purged with argon for another 5 min. The vessel was sealed and the mixture was heated for 22 h at 110° C. Subsequently, the reaction mixture was filtered through a pad of celite and concentrated in vacuo. The residue was purified by FCC (SiHP; DCM:MeOH) to give the product (0.20 g, 96% yield). ESI-MS: 606.5 $[M+H]^+$.

Preparation of 1-cyclopropyl-6-fluoro-7-[(3R-3-hydroxypyrrolidin-1-yl]-3-({[(2-methylpyridin-4-yl)methyl][(3S)-piperidin-3-yl]amino}methyl)-1,4-dihydroquinolin-4-one (Intermediate 28)

TFA (2.0 mL, 82 eq.) was added to a solution of tert-butyl (3S)-3-[({1-cyclopropyl-6-fluoro-7-[(3R)-3-hydroxypyrrolidin-1-yl]-4-oxo-1,4-dihydroquinolin-3-yl}methyl)[(2-methylpyridin-4-yl)methyl]amino]piperidine-1-carboxylate (0.2 g, 1.0 eq.) in DCM (4.5 mL) and the resulting mixture was stirred for 30 min at RT. Then, the mixture was concentrated in vacuo, triturated with DCM and again concentrated in vacuo (3 cycles). The residue was partitioned between water and DCM, then aqueous layer basified with 1 M NaOH aq. solution and washed with DCM again. The combined organic layers were dried over anh. $MgSO_4$, filtered and concentrated in vacuo to give the product (0.133 g, 71% yield) as a yellow oil. ESI-MS: 506.4 $[M+H]^+$.

Preparation of 1-cyclopropyl-6-fluoro-7-[(3R)-3-hydroxypyrrolidin-1-yl]-3-({[(2-methylpyridin-4-yl)methyl][(3S)-1-(pyridin-3-yl)piperidin-3-yl]amino}methyl)-1,4-dihydroquinolin-4-one A dry reaction flask equipped with a septum was charged with 1-cyclopropyl-6-fluoro-7-[(3S)-3-hydroxypyrrolidin-1-yl]-3-({[(2-methylpyridin-4-yl)methyl][(3S)-piperidin-3-yl]amino}methyl)-1,4-dihydroquinolin-4-one (0.09 g, 1.0 eq.), 3-bromopyridine (0.035 g, 1.5 eq.), NaO t-Bu (0.029 g, 2.0 eq.) and anh. 1,4-dioxane (2.0 mL). The resulting mixture was purged with argon for 10 min and BuXPhos-Pd-G3 (0.012 g, 0.1 eq.) was added under argon atmosphere. The vessel was capped and the reaction mixture was stirred overnight at 115° C. Subsequently, the mixture was diluted with EtOAc and filtered through celite. The filtrate was concentrated in vacuo and the residue was purified by FCC (SiHP; DCM:MeOH) and re-purified by prep-HPLC ($H_2O$: $MeCN:NH_3$) to give the product (0.004 g, 5% yield) as a white solid. ESI-MS: 583.5 $[M+H]^+$. $^1H$ NMR (400 MHz, Methanol-$d_4$) δ 8.30-8.19 (m, 1H), 8.15 (d, J=5.5 Hz, 1H), 7.97-7.86 (m, 1H), 7.82 (s, 1H), 7.76 (d, J=14.8 Hz, 1H), 7.41 (ddd, J=8.6, 3.0, 1.3 Hz, 1H), 7.33-7.15 (m, 3H), 6.91 (d, J=7.7 Hz, 1H), 4.56-4.50 (m, 1H), 4.01-3.91 (m, 1H), 3.90-3.65 (m, 7H), 3.64-3.56 (m, 1H), 3.54-3.46 (m, 1H), 3.45-3.33 (m, 1H), 3.01-2.83 (m, 2H), 2.82-2.64 (m, 1H), 2.34 (s, 3H), 2.21-1.98 (m, 3H), 1.98-1.85 (m, 1H), 1.78-1.58 (m, 2H), 1.41-1.17 (m, 2H), 1.01-0.78 (m, 2H).

Example 79. 1-cyclopropyl-6-fluoro-7-[3-(hydroxymethyl)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride

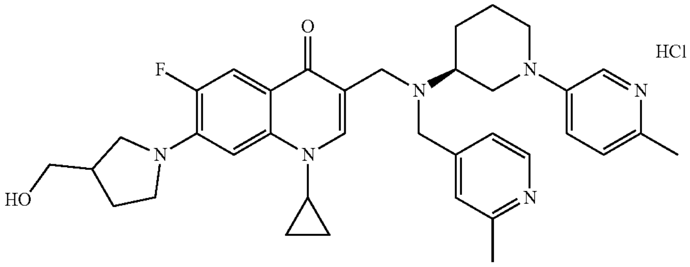

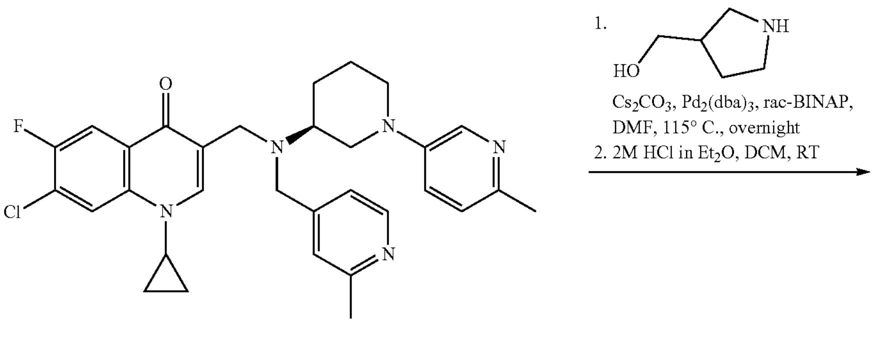

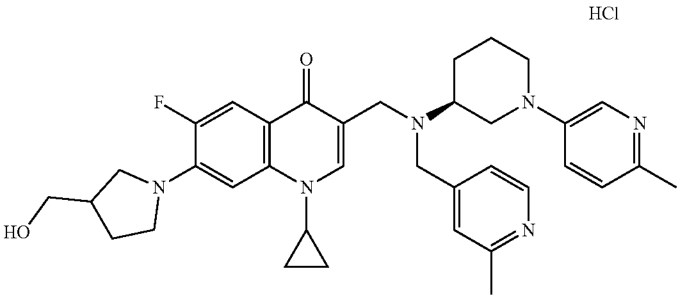

Preparation of 1-cyclopropyl-6-fluoro-7-[3-(hydroxymethyl)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride A solution of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.2 g, 1.0 eq.), (pyrrolidin-3-yl)methanol (0.053 g, 1.5 eq.) and $Cs_2CO_3$ (0.21 g, 1.8 eq.) in anh. DMF (6.0 mL) was purged with argon for 15 min. Then, BINAP (0.044 g, 0.2 eq.) and $Pd_2(dba)_3$ (0.032 g, 0.1 eq.) were added and the reaction mixture was stirred overnight at 110° C. The reaction mixture was filtered through a pad of celite. The filtrate was sonicated with scavenger QuadraPure MPA, filtered through a pad of cotton and concentrated in vacuo. The crude material was purified by FCC (SiHP; DCM: MeOH) and re-purified by prep. HPLC ($H_2O$:MeCN:FA) to give the desired product (0.069 g, 31% yield) as a yellow solid. ESI-MS: 611.5 $[M+H]^+$. The compound was converted to the HCl salt using 2 M HCl in $Et_2O$ (0.06 mL, 1.0 eq. to FB) and DCM as a solvent (5.0 mL) to give the product (0.071 g, 95% yield) as an orange solid. ESI-MS: 611.3 $[M+H]^+$. $^1H$ NMR (400 MHz, Methanol-$d_4$) δ 8.28 (d, J=5.7 Hz, 1H), 8.23 (d, J=3.0 Hz, 1H), 7.99 (dd, J=9.0, 3.0 Hz, 1H), 7.86 (s, 1H), 7.72 (d, J=14.7 Hz, 1H), 7.66-7.52 (m, 3H), 6.92 (d, J=7.6 Hz, 1H), 4.22-4.07 (m, 3H), 4.05-3.84 (m, 2H), 3.82-3.75 (m, 1H), 3.75-3.55 (m, 5H), 3.46-3.37 (m, 2H), 3.22-3.06 (m, 2H), 2.95-2.85 (m, 1H), 2.62-2.51 (m, 4H), 2.46 (s, 3H), 2.27-2.09 (m, 2H), 2.05-1.94 (m, 1H), 1.89-1.63 (m, 3H), 1.38-1.24 (m, 2H), 1.03-0.90 (m, 2H).

Example 80. 7-(aminomethyl)-1-cyclopropyl-6-fluoro-3-({[(3S)-1-(6-methylpyridin-3-yl)piperidin-3 (2-methylpyridin-4-yl)methyl]amino}methyl)-1,4-dihydroquinolin-4-one

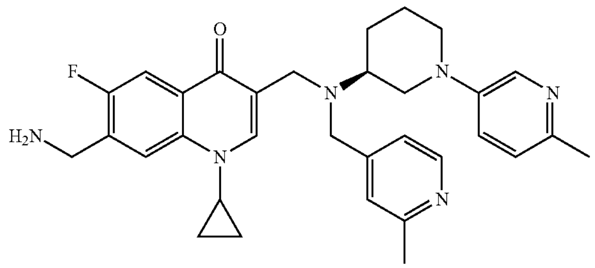

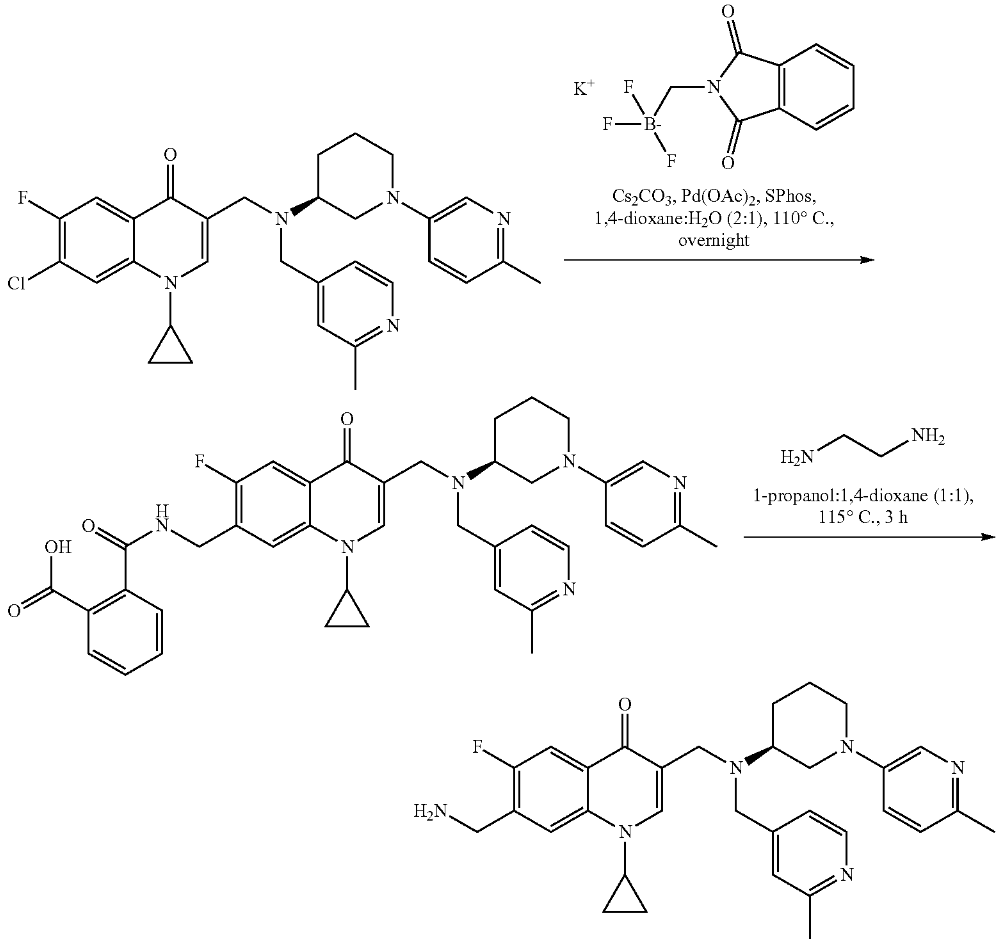

Preparation of 2-({[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]methyl}carbamoyl)benzoic acid A suspension of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Intermediate 3) (0.2 g, 1.0 eq.) and potassium [(1,3-dioxo-2,3-dihydro-1H-isoindol-2-yl)methyl] trifluoroboranuide (0.11 g, 1.2 eq.) in the mixture of 1,4-dioxane and water (4.5 mL, 2:1 v/v) was treated with $Cs_2CO_3$ (0.27 g, 2.4 eq.). The mixture was purged with argon for 15 min. Subsequently, SPhos (0.017 g, 0.12 eq.) and $Pd(OAc)_2$ (0.004 g, 0.052 eq.) were added. After stirring at 100° C. for 19 h, additional portions of SPhos (0.017 g, 0.12 eq.), $Pd(OAc)_2$ (0.004 g, 0.052 eq.) were added. The stirring was continued overnight at 110° C. The mixture was concentrated in vacuo, and the residue was dissolved in EtOAc and washed with $H_2O$ and brine. The organic layer was dried over anh. $Na_2SO_4$, filtered and concentrated in vacuo. The residue was purified by FCC (SiHP; DCM: MeOH) affording the product (0.256 g, 17% yield). ESI-MS: 689.5 $[M+H]^+$.

Preparation of 7-(aminomethyl)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one 1-Propanol (1.0 mL) and ethane-1,2-diamine (0.084 mL, 19.0 eq.) were added to a solution of 2-({[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]methyl}carbamoyl)benzoic acid (0.256 g, 1.0 eq.) in 1,4-dioxane (1.0 mL). After stirring at 115° C. for 3 h under microwave irradiation, the mixture was concentrated in vacuo. The residue was purified by FCC (SiHP; DCM:MeOH) followed by purification by RP-FCC (C18HP; $H_2O$:MeCN) affording the product (0.021 g, 61% yield) as a white solid. ESI-MS: 541.5 $[M+H]^+$. $^1H$ NMR (400 MHz, Methanol-$d_4$) δ 8.18-8.11 (m, 2H), 8.08 (d, J=2.9 Hz, 1H), 8.00 (s, 1H), 7.89 (d, J=10.5 Hz, 1H), 7.35 (dd, J=8.6, 3.0 Hz, 1H), 7.28-7.23 (m, 1H), 7.23-7.18 (m, 1H), 7.11 (d, J=8.6 Hz, 1H), 4.07 (s, 2H), 3.92-3.84 (m, 3H), 3.81 (s, 2H), 3.66-3.56 (m, 1H), 3.56-3.46 (m, 1H), 3.01-2.91 (m, 1H), 2.85 (t, 1=11.1 Hz, 1H), 2.78-2.59 (m, 1H), 2.40 (s, 3H), 2.34 (s, 3H), 2.18-2.07 (m, 1H), 2.02-1.86 (m, 1H), 1.75-1.58 (m, 2H), 1.51-1.26 (m, 2H), 1.04-0.89 (m, 2H).

Example 81. 1-cyclopropyl-6-fluoro-7-[(3S)-3-hydroxypiperidin-1-yl]-3-({[(3S)-1-(5-methylpyrazin-2-yl)piperidin-3-yl][(2-methylpyridin-4-yl)methyl]amino}methyl)-1,4-dihydroquinolin-4-one

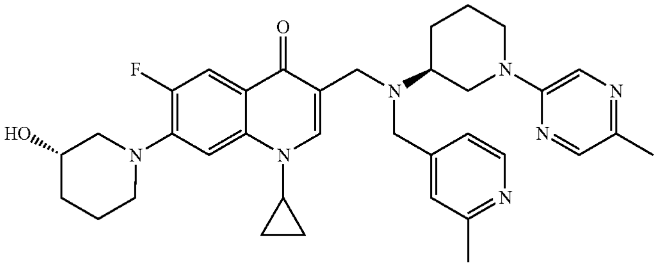

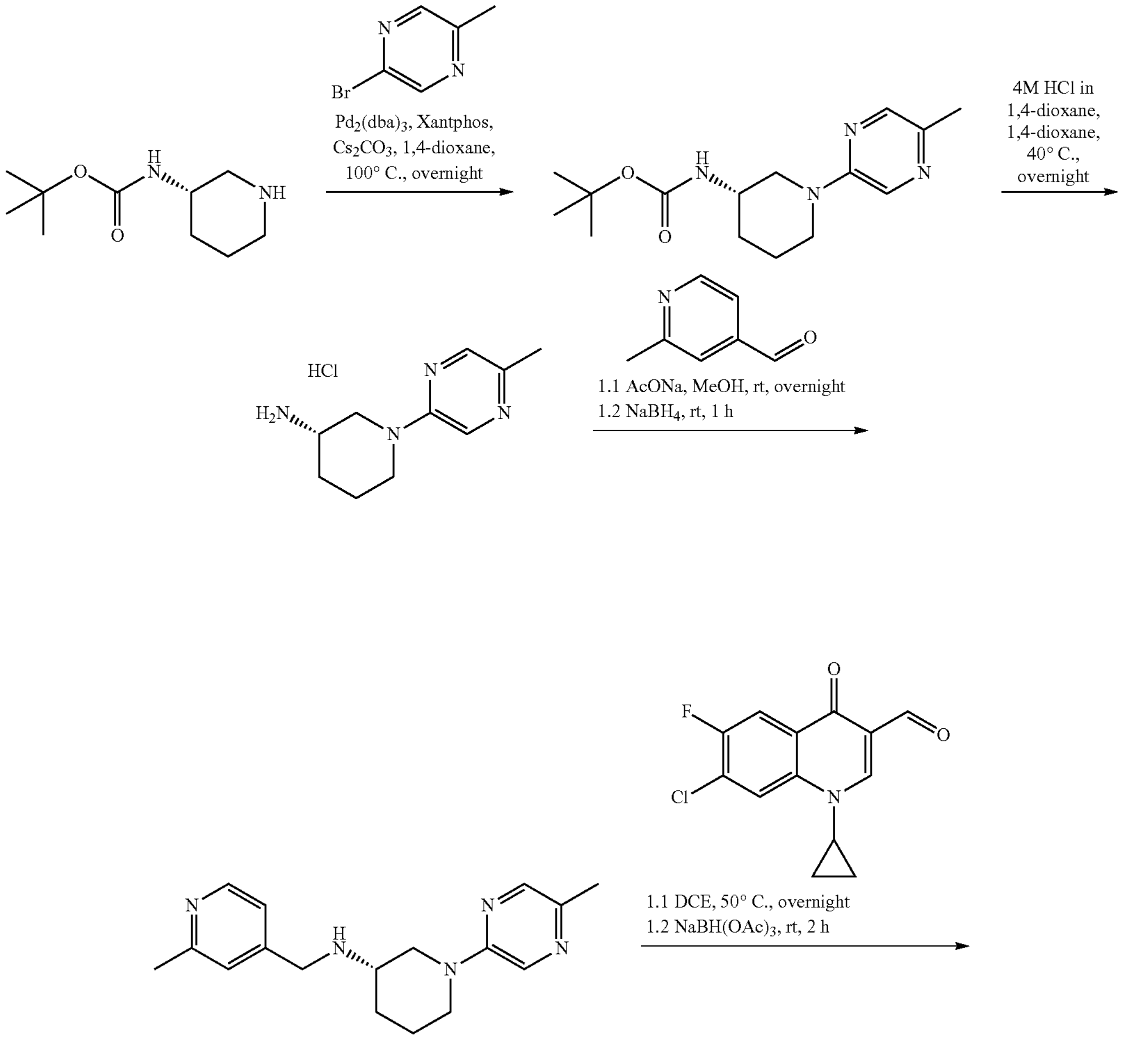

-continued

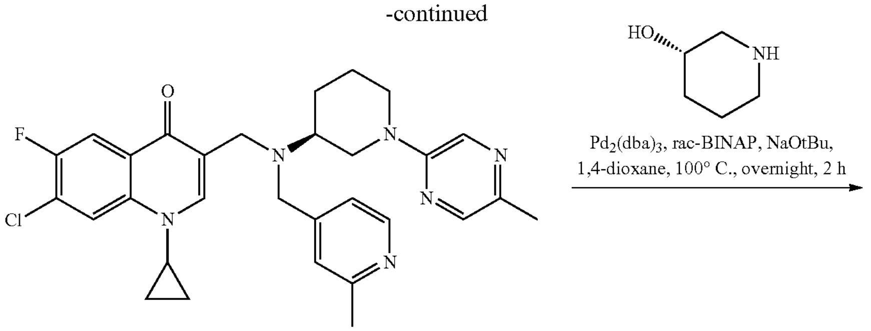

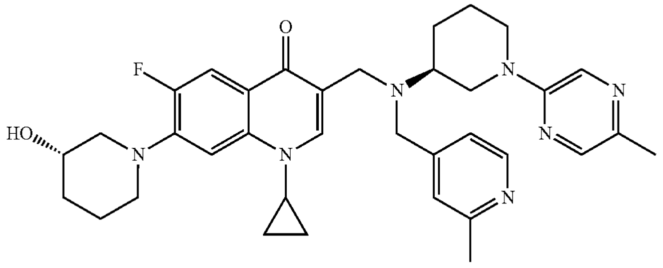

Preparation of tert-butyl N-[(3S)-1-(5-methylpyrazin-2-yl)piperidin-3-yl]carbamate A suspension of tert-butyl N-[(3S)-piperidin-3-yl]carbamate (0.60 g, 1.3 eq.), 2-bromo-5-methylpyrazine (0.4 g, 1.0 eq.), $Cs_2CO_3$ (1.0 g, 1.4 eq.) in anh. 1,4-dioxane (10.0 mL) was purged with nitrogen for 10 min. Then, Xantphos (0.08 g, 0.06 eq.) and $Pd_2(dba)_3$ (0.11 g, 0.05 eq.) were added and the resulting mixture was purged again with nitrogen for 10 min. The vessel was closed and the reaction mixture was heated overnight at 100° C. Subsequently, the mixture was filtered through a pad of celite and the pad was washed with EtOAc. The filtrate was concentrated in vacuo and the residue was purified by FCC (SIHP; Hex:EtOAc) to give the product (0.71 g, 87% yield) as a brown solid. ESI-MS: 293.3 $[M+H]^+$.

Preparation of (S-1-(5-methylpyrazin-2-yl)piperidin-3-amine hydrochloride

4 M HCl solution in 1,4-dioxane (2.5 mL, 5.0 eq.) was added to a solution of tert-butyl N-[(3S)-1-(5-methylpyrazin-2-yl)piperidin-3-yl]carbamate (0.71 g, 1.0 eq.) in 1,4-dioxane (10.0 mL). The resulting mixture was heated overnight at 40° C. Subsequently, the reaction mixture was concentrated in vacuo and the residue was purified by RP-FCC (C18HP; $H_2O$:MeCN) to give the product (0.48 g, 97% yield) as a brown oil. ESI-MS: 193.1 $[M+H]^+$.

Preparation of (3S)-1-(5-methylpyrazin-2-yl)-N-[(2-methylpyridin-4-yl)methyl]piperidin-3-amine A mixture of (3S)-1-(5-methylpyrazin-2-yl)piperidin-3-amine hydrochloride (0.48 g, 1.0 eq.), NaOAc (0.16 g, 1.0 eq.) and 2-methylpyridine-4-carbaldehyde (0.24 mL, 1.1 eq.) in anh. MeOH (10.0 mL) was stirred overnight at RT. Then, $NaBH_4$ (0.10 g, 1.3 eq.) was added and the resulting mixture was stirred for 1 h at RT. Subsequently, the reaction mixture was concentrated in vacuo and the residue was partitioned between NaOH aq. solution and DCM. The organic layer was dried over anh. $Na_2SO_4$, filtered and concentrated in vacuo. The residue was purified by RP-FCC (C18HP; $H_2O$:MeCN). The isolated sample was partitioned between NaOH aq. solution and DCM. The organic layer was dried over anh. $Na_2SO_4$, filtered and concentrated in vacuo. The residue was re-purified by FCC (SiHP; DCM:MeOH) to give the product (0.14 g, 22% yield) as a brown oil. ESI-MS: 298.3 $[M+H]^+$.

Preparation of 7-chloro-1-cyclopropyl-6-fluoro-3-({[(3S)-1-(5-methylpyrazin-2-yl)piperidin-3-yl][(2-methylpyridin-4-yl)methyl]amino}methyl)-1,4-dihydroquinolin-4-one A mixture of (3S)-1-(5-methylpyrazin-2-yl)-N-[(2-methylpyridin-4-yl)methyl]piperidin-3-amine (0.13 g, 1.1 eq.), 7-chloro-1-cyclopropyl-6-fluoro-4-oxo-1,4-dihydroquinoline-3-carbaldehyde (Intermediate 9) (0.11 g, 1.0 eq.) and anh. DCE (3.0 mL) was stirred overnight at 50° C. Then, $NaBH(OAc)_3$ (0.24 g, 2.8 eq.) was slowly added in portions and the resulting mixture was stirred for 2 h at RT. Subsequently, the reaction mixture was partitioned between NaOH aq. solution and DCM. The organic layer was washed with brine, dried over anh. $Na_2SO_4$, filtered and concentrated in vacuo. The residue was purified by FCC (SiHP; DCM:MeOH) to give the product (0.029 g, 11% yield) as a colorless oil. ESI-MS: 547.7 $[M+H]^+$.

Preparation of 1-cyclopropyl-6-fluoro-7-[(3S)-3-hydroxypiperidin-1-yl]-3-({[(3S)-1-(5-methylpyrazin-2-yl)piperidin-3-yl][(2-methylpyridin-4-yl)methyl]amino}methyl)-1,4-dihydroquinolin-4-one NaO t-Bu (0.009 g, 2.1 eq.) was added to a solution of 7-chloro-1-cyclopropyl-6-fluoro-3-({[(3S)-1-(5-methylpyrazin-2-yl)piperidin-3-yl][(2-methylpyridin-4-yl)methyl]amino}methyl)-1,4-dihydroquinolin-4-one (0.03 g, 1.0 eq.) and (3S)-piperidin-3-ol hydrochloride (0.012 g, 2.0 eq.) in 1,4-dioxane (2.0 mL) and the resulting mixture was purged with argon for 15 min. Subsequently, BINAP (0.008 g, 0.3 eq.) and $Pd_2(dba)_3$ (0.004 g, 0.1 eq.) were added and the reaction mixture was stirred overnight at 100° C. Then, additional (3S)-piperidin-3-ol hydrochloride (0.006 g, 1.0 eq.), $Pd_2(dba)_3$ (0.004 g, 0.1 eq.) and BINAP (0.008 g, 0.3 eq.) were added and stirring was continued for 2 h. Afterwards, the reaction mixture was concentrated in vacuo and the residue was purified by FCC (SiHP; DCM:MeOH). The obtained sample was dissolved in MeOH and scavenger QuadraPure MPA (0.5 g) was added. After stirring for 1 h, the scavenger was filtered off and the filtrate was concentrated in vacuo. The residue was additionally purified by RP-FCC (C18HP; $H_2O$:MeCN) to give the product (0.021 g, 77% yield) as a beige solid. ESI-MS: 612.6 $[M+H]^+$. $^1H$ NMR (400 MHz, Methanol-$d_4$) δ8.18 (d, J=5.1 Hz, 1H), 8.09 (d, J=1.5 Hz, 1H), 7.97-7.91 (m, 2H), 7.82 (d, J=13.6 Hz, 1H), 7.41 (d, J=7.4 Hz, 1H), 7.29-7.21 (m, 2H), 4.57-4.48 (m, 1H), 4.27-4.11 (m, 1H), 3.94-3.74 (m, 5H), 3.71-3.62 (m, 1H), 3.54-3.41 (m, 2H), 3.12-2.99 (m, 1H), 2.97-2.69 (m, 4H), 2.36 (s, 3H), 2.35 (s, 3H), 2.23-2.13 (m, 1H), 2.12-2.01 (m, 1H), 2.01-1.87 (m, 2H), 1.87-1.68 (m, 2H), 1.67-1.43 (m, 2H), 1.36-1.21 (m, 2H), 1.03-0.84 (m, 2H).

Example 82. 1-cyclopropyl-6-fluoro-3-({[(3S,5S)-fluoro-1-(5-methylpyrazin-2-yl)piperidin-3-yl][(2-methylpyridin-4-yl)methyl]amino}methyl)-7-[(3S-3-hydroxypiperidin-1-yl]-1,4-dihydroquinolin-4-one

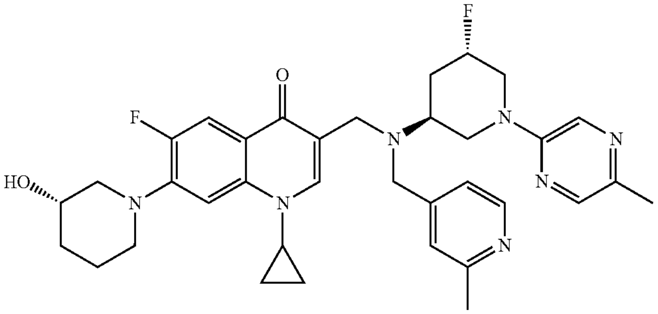

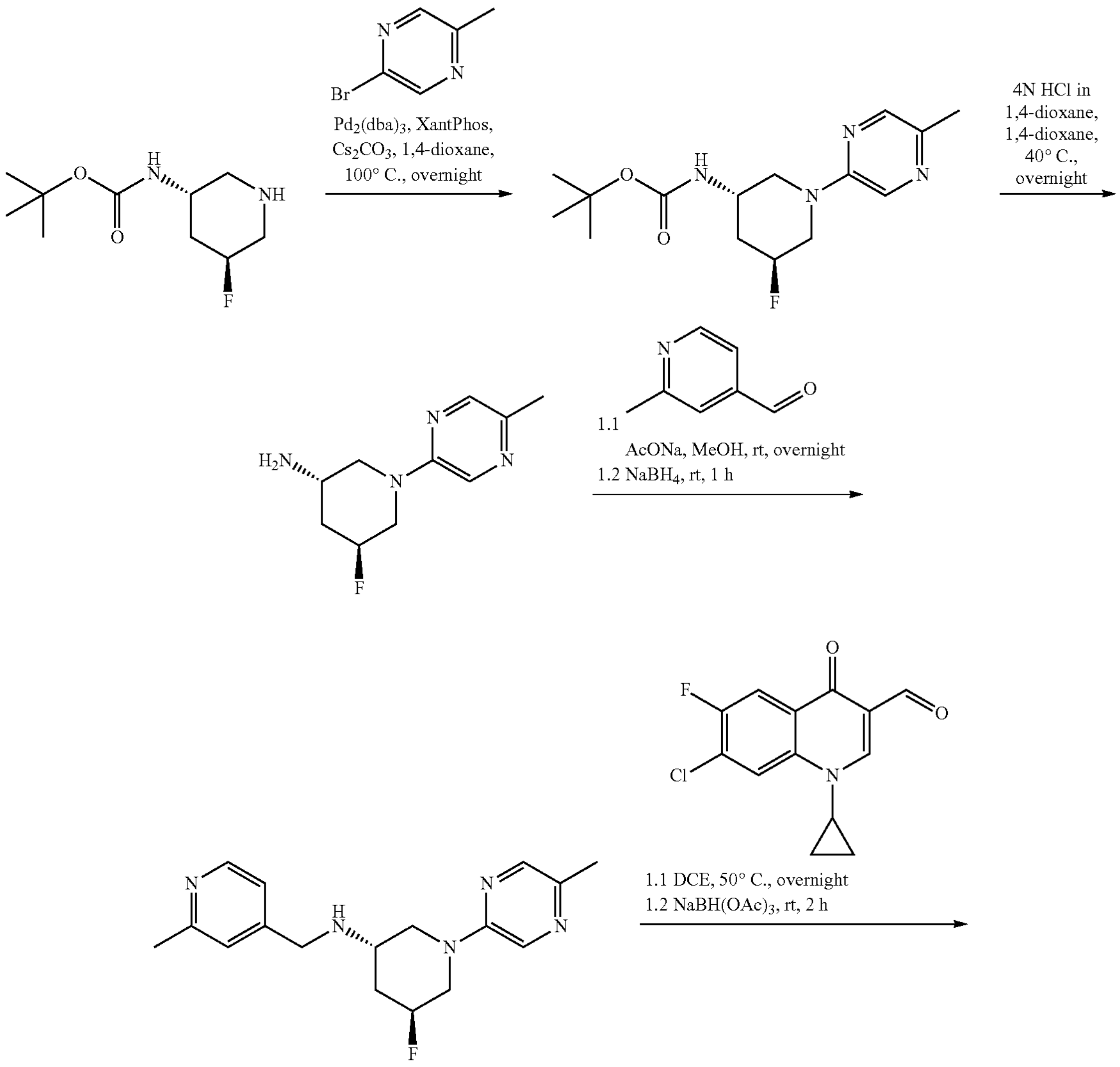

-continued

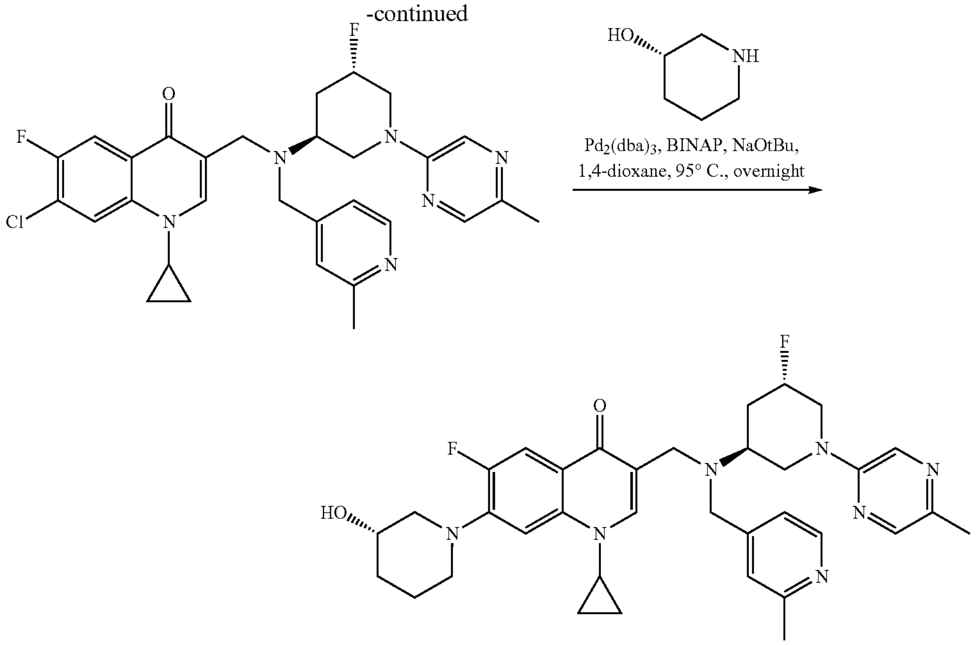

Preparation of tert-butyl N-[(3S,5S)-5-fluoro-1-(5-methylpyrazin-2-yl)piperidin-3-yl]carbamate A suspension of tert-butyl N-[(3S,5S)-5-fluoropiperidin-3-yl]carbamate (0.37 g, 1.0 eq.), 2-bromo-5-methylpyrazine (0.29 g, 1.0 eq.), $Cs_2CO_3$ (0.74 g, 1.4 eq.) and anh. 1,4-dioxane (6.0 mL) was purged with nitrogen for 10 min. Then, Xantphos (0.06 g, 0.06 eq.) and $Pd_2(dba)_3$ (0.08 g, 0.05 eq.) were added and the resulting mixture was purged with nitrogen for an additional 10 min. The vessel was closed and the reaction mixture was heated overnight at 100° C. Subsequently, the mixture was filtered through a pad of celite and concentrated in vacuo. The residue was purified by FCC (SIHP; Hex:EtOAc) to give the product (0.37 g, 69% yield) as a brown oil. ESI-MS: 311.4 $[M+H]^+$.

Preparation of (3S,5S)-5-fluoro-1-(5-methylpyrazin-2-yl)piperidin-3-amine

4 M HCl solution in 1,4-dioxane (1.5 mL, 5.0 eq.) was added to a solution of tert-butyl N-[(3S,5S)-5-fluoro-1-(5-methylpyrazin-2-yl)piperidin-3-yl]carbamate (0.37 g, 1.0 eq.) in 1,4-dioxane (5.0 mL) and the resulting mixture was heated overnight at 40° C. Then, pH was adjusted to 12 using NaOH aq. solution and the mixture was partitioned between DCM and NaOH aq. solution. The organic layer was dried over anh. $Na_2SO_4$, filtered and concentrated in vacuo to give the product (0.22 g, 74% yield) as a brown oil which was used in the next step without further purification. ESI-MS: 211.2 $[M+H]^+$.

Preparation of (3S,5S)-5-fluoro-1-(5-methylpyrazin-2-yl)-N-[(2-methylpyridin-4-yl)methyl]piperidin-3-amine A mixture of (3S,5S)-5-fluoro-1-(5-methylpyrazin-2-yl)piperidin-3-amine (0.22 g, 1.0 eq.), NaOAc (0.06 g, 1.0 eq.), 2-methylpyridine-4-carbaldehyde (0.09 mL, 1.1 eq.) and anh. MeOH (5.0 mL) was stirred overnight at RT. Then, $NaBH_4$ (0.04 g, 1.3 eq.) was added and the resulting mixture was stirred for 1 h at RT. Subsequently, the mixture was concentrated in vacuo and the residue was partitioned between NaOH aq. solution and DCM. The organic layer was dried over anh. $Na_2SO_4$, filtered and concentrated in vacuo. The residue was purified by FCC (SiHP; DCM:MeOH). The unreacted starting amine was isolated and the reaction was performed again in the same manner. Both isolated after purifications samples were combined to give the product (0.12 g, 47% yield) as a brown oil. ESI-MS: 316.3 $[M+H]^+$.

Preparation of 7-chloro-1-cyclopropyl-6-fluoro-3-({[(3S,5S)-5-fluoro-1-(5-methylpyrazin-2-yl)piperidin-3-yl][(2-methylpyridin-4-yl)methyl]amino}methyl)-1,4-dihydroquinolin-4-one A mixture of 7-chloro-1-cyclopropyl-6-fluoro-4-oxo-1,4-dihydroquinoline-3-carbaldehyde (Intermediate 9) (0.1 g, 1.0 eq.), (3S,5S)-5-fluoro-1-(5-methylpyrazin-2-yl)-N-[(2-methylpyridin-4-yl)methyl]piperidin-3-amine (0.131 g, 1.05 eq.) and anh. DCE (3.0 mL) was stirred overnight at 50° C. Then, $NaBH(OAc)_3$ (0.22 g, 2.8 eq.) was added slowly in portions and the resulting mixture was stirred for 2 h at RT. Subsequently, the reaction mixture was partitioned between 2 M NaOH aq. solution and DCM. The organic layer was washed with brine, dried over anh. $Na_2SO_4$, filtered and concentrated in vacuo. The residue was purified by FCC (SiHP; DCM:MeOH) to give the product (0.09 g, 38% yield) as a yellow foam. ESI-MS: 565.8 $[M+H]^+$.

Preparation of 1-cyclopropyl-6-fluoro-3-({[(3S,5S)-5-fluoro-1-(5-methylpyrazin-2-yl)piperidin-3-yl][(2-methylpyridin-4-yl)methyl]amino}methyl)-7-[(3S)-3-hydroxypiperidin-1-yl]-1,4-dihydroquinolin-4-one A suspension of 7-chloro-1-cyclopropyl-6-fluoro-3-({[(3S,5S)-5-fluoro-1-(5-methylpyrazin-2-yl)piperidin-3-yl][(2-methylpyridin-4-yl)methyl]amino}methyl)-1,4-dihydroquinolin-4-one (0.09 g, 1.0 eq.), (3S)-piperidin-3-ol hydrochloride (0.038 g, 2.0 eq.), NaO t-Bu (0.03 g, 2.1 eq.)

and BINAP (0.03 g, 0.3 eq.) in anh. 1,4-dioxane (3.0 mL) was purged with nitrogen for 10 min. Then, $Pd_2(dba)_3$ (0.013 g, 0.1 eq.) was added and the resulting mixture was stirred overnight at 95° C. Subsequently, the reaction mixture was diluted with water and extracted with DCM (3×). The combined organic layers were washed with brine, dried over anh. $MgSO_4$, filtered and concentrated in vacuo. The residue was purified by FCC (SiHP; DCM:MeOH) and re-purified by RP-FCC (C18HP; $H_2O$:MeCN) to give the product (0.043 g, 49% yield) as a white solid. ESI-MS: 630.5 $[M+H]^+$. $^1H$ NMR (400 MHz, Methanol-$d_4$) δ 8.18 (d, J=5.2 Hz, 1H), 8.12 (s, 1H), 7.94 (d, 1=10.4 Hz, 2H), 7.83 (d, J=13.5 Hz, 1H), 7.41 (d, J=7.4 Hz, 1H), 7.28-7.20 (m, 2H), 5.07 (d, J=47.1 Hz, 1H), 4.70 (d, J=12.5 Hz, 1H), 4.49 (t, J=13.2 Hz, 1H), 3.92-3.75 (m, 5H), 3.71-3.62 (m, 1H), 3.53-3.42 (m, 2H), 3.27-3.16 (m, 2H), 3.13-3.02 (m, 2H), 2.99-2.88 (m, 1H), 2.80 (dd, J=11.5, 8.8 Hz, 1H), 2.48-2.39 (m, 1H), 2.38-2.33 (m, 61H), 2.15-1.90 (m, 31H), 1.83-1.69 (m, 1H), 1.56-1.43 (m, 1H), 1.35-1.26 (m, 21H), 1.00-0.91 (m, 21H).

Example 83. 1-cyclopropyl-6-fluoro-3-({[(3S)-1-(5-fluoro-6-methylpyridin-3-yl)piperidin-3-yl][(2-methylpyridin-4-yl)methyl]amino}methyl)-7-(2-hydroxyethoxy-1,4-dihydroquinolin-1,4-one

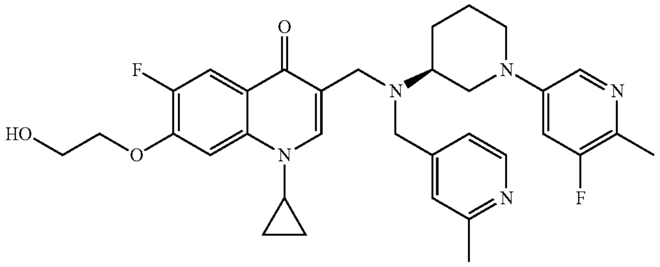

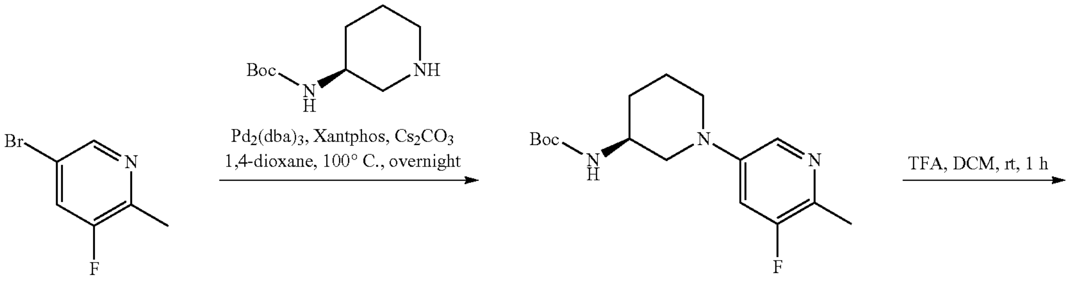

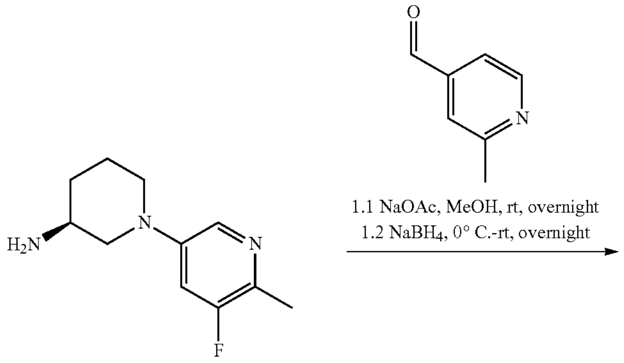

-continued

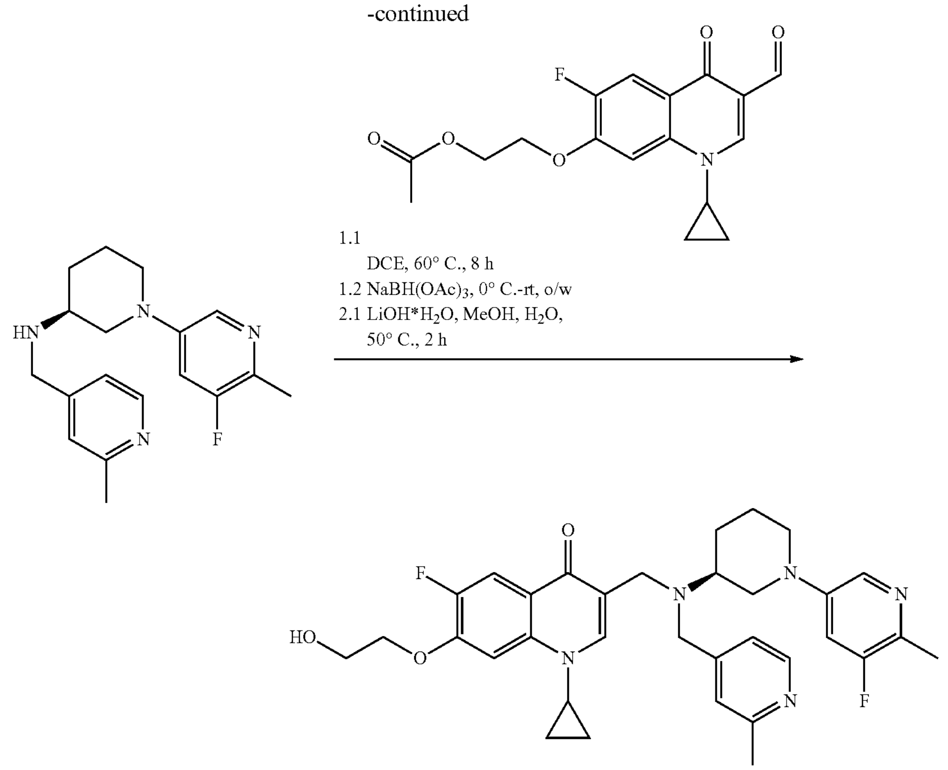

Preparation of tert-butyl N-[(3S)-1-(5-fluoro-6-methylpyridin-3-yl)piperidin-3-yl]carbamate A suspension of tert-butyl N-[(3S)-piperidin-3-yl]carbamate (0.27 g, 1.3 eq.), 5-bromo-3-fluoro-2-methylpyridine (0.2 g, 1.0 eq.) and $Cs_2CO_3$ (0.69 g, 2.0 eq.) in anh. 1,4-dioxane (4.0 mL) was purged with argon for 10 min. Then, Xantphos (0.04 g, 0.06 eq.) and $Pd_2(dba)_3$ (0.05 g, 0.05 eq.) were added and the resulting mixture was additionally purged with argon for 5 min. The vessel was closed and the mixture was heated overnight at 100° C. Subsequently, the reaction mixture was partitioned between water and DCM. The organic layer was dried over anh. $MgSO_4$, filtered and concentrated in vacuo. The residue was purified by FCC (SIHP; DCM:MeOH) to give the product (0.30 g, 89% yield) as a beige solid. ESI-MS: 310.3 $[M+H]^+$.

Preparation of (S-1-(5-fluoro-6-methylpyridin-3-yl) piperidin-3-amine

TFA (2.0 mL, 28.0 eq.) was added to a solution of tert-butyl N-[(3S)-1-(5-fluoro-6-methylpyridin-3-yl)piperidin-3-yl]carbamate (0.30 g, 1.0 eq.) in DCM (6.0 mL) was added and the resulting mixture was left stirring at RT for 1 h. Then, the reaction mixture was concentrated in vacuo, triturated with MeOH and concentrated again in vacuo (3 cycles). The residue was partitioned between water and DCM. The aqueous layer was basified with 1 M NaOH aq. solution and washed with DCM. The organic layer was dried over anh. $MgSO_4$, filtered and concentrated in vacuo to give the product (0.17 g, 84% yield) as a yellowish oil which was used in the next step without further purification. ESI-MS: 210.1 $[M+H]^+$.

Preparation of (3S)-1-(5-fluoro-6-methylpyridin-3-yl)-N-[(2-methylpyridin-4-yl)methyl]piperidin-3-amine A mixture of 2-methylpyridine-4-carbaldehyde (0.092 mL, 1.1 eq.), (3S)-1-(5-fluoro-6-methylpyridin-3-yl)piperidin-3-amine (0.176 g, 1.0 eq.), NaOAc (0.065 g, 1.0 eq.) and MeOH (5.0 mL) was stirred overnight at RT. Then, the reaction mixture was cooled to 0° C., $NaBH_4$ (0.033 g, 1.1 eq.) was added in portions and the resulting mixture was stirred overnight at RT. Subsequently, the reaction mixture was concentrated in vacuo and the residue was purified by FCC (SiHP; DCM:MeOH) to give the product (0.18 g, 71% yield) as a yellowish oil. ESI-MS: 315.2 $[M+H]^+$ Preparation of 1-cyclopropyl-6-fluoro-3-({[(3S)-1-(5-fluoro-6-methylpyridin-3-yl)piperidin-3-yl][(2-methylpyridin-4-yl)methyl]amino}methyl)-7-(2-hydroxyethoxy)-1,4-dihydroquinolin-4-one A mixture of (3S)-1-(5-fluoro-6-methylpyridin-3-yl)-N-[(2-methylpyridin-4-yl)methyl]piperidin-3-amine (0.11 g, 1.0 eq.), 2-[(1-cyclopropyl-6-fluoro-3-formyl-4-oxo-1,4-dihydroquinolin-7-yl)oxy]ethyl acetate (Intermediate 22) (0.15 g, 1.1 eq.) and anh. DCE (12.0 mL) was stirred for 8 h at 60° C. Then, the reaction mixture was cooled to 0° C., $NaBH(OAc)_3$ (0.20 g, 2.8 eq.) was added and the resulting mixture was stirred over the weekend at RT. Afterwards, the mixture was partitioned between sat. $NaHCO_3$ aq. solution and DCM. The organic layer was dried over anh. $Na_2SO_4$, filtered and concentrated in vacuo. The residue was dissolved in a mixture of $H_2O$ and MeOH (10.0 mL, 7:3 v/v) and $LiOH*H_2O$ (0.06 g, 4.0 eq.) was added. The resulting mixture was stirred for 2 h at 50° C. Then, the mixture was concentrated in vacuo and the residue was purified by two consecutive RP-FCC (C18HP; $H_2O$:MeCN) and re-purified by prep-HPLC ($H_2O$:MeCN:$NH_3$) to give the product (0.04 g, 19% yield) as an off-white solid. HR-MS: 590.3 $[M+H]^+$. $^1H$ NMR (400 MHz, Methanol-$d_4$) δ 8.15 (d, J=5.2 Hz, 1H), 7.97-7.91 (m, 2H), 7.89 (d, J=11.6 Hz, 1H), 7.55 (d, J=7.1 Hz, 1H), 7.25 (s, 1H), 7.23-7.18 (m, 1H), 7.15 (dd, J=12.6, 2.5 Hz, 1H), 4.35-4.26 (m, 2H), 4.02-3.96 (m, 2H), 3.95-3.74 (m, 5H), 3.69-3.60 (m, 1H), 3.53-3.43 (m, 1H), 2.98-2.85 (m, 2H), 2.81-2.69 (m, 1H), 2.41-2.23 (m, 6H), 2.18-2.07 (m, 1H), 1.96-1.83 (m, 1H), 1.76-1.57 (m, 2H), 1.37-1.23 (m, 2H), 0.99-0.87 (m, 2H).

Example 84. 1-cyclopropyl-6-fluoro-7-(2-hydroxyethoxy)-3-({[(2-methylpyridin-4-yl)methyl][(3S)-1-(pyridin-3-yl)piperidin-3-yl]amino}methyl)-1,4-dihydroquinolin-4-one hydrochloride

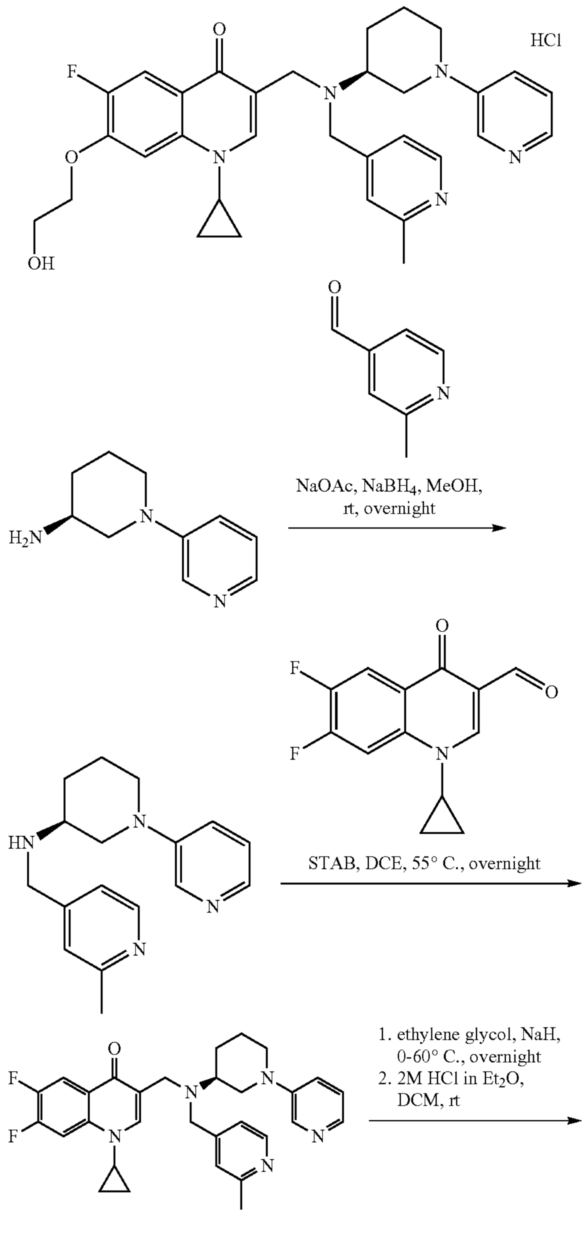

-continued

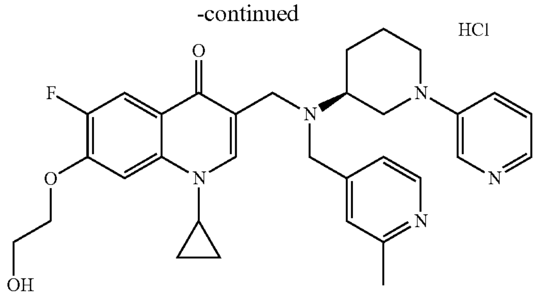

Preparation of (3S)—N-[(2-methylpyridin-4-yl)methyl]-1-(pyridin-3-yl)piperidin-3-amine (Intermediate 23)

A solution of (3S)-1-(pyridin-3-yl)piperidin-3-amine (Intermediate 17) (3.38 g, 1.0 eq.), sodium acetate (1.45 g, 1.0 eq.) and 2-methylpyridine-4-carbaldehyde (2.2 mL, 1.1 eq.) in anh. methanol (100.0 mL) was stirred overnight at RT. Then $NaBH_4$ (0.87 g, 1.3 eq.) was added and the reaction mixture was stirred for 1 h at RT. The crude was concentrated and the residue was partitioned between DCM and NaOH aq. solution. The organic layer was dried over anh. $Na_2SO_4$, filtered and concentrated in vacuo. The residue was purified by FCC (C18HP; $H_2O$:MeCN) to give product (3.94 g, 87% yield) as yellow oil. ESI-MS: 283.4 $[M+H]^+$.

Preparation of 1-cyclopropyl-6,7-fluoro-3-({[(2-methylpyridin-4-yl)methyl][(3S)-1-(pyridin-3-yl)piperidin-3-yl]amino}methyl)-1,4-dihydroquinolin-4-one (Intermediate 24)

A mixture of (3S)—N-[(2-methylpyridin-4-yl)methyl]-1-(pyridin-3-yl)piperidin-3-amine (Intermediate 23) (1.0 g, 1.0 eq.) and 1-cyclopropyl-6,7-difluoro-4-oxo-1,4-dihydroquinoline-3-carbaldehyde (Intermediate 4) (0.9 g, 1.0 eq.) in anh. DCE (13.0 mL) was stirred for 3 h at 55° C. Then, the mixture was cooled in an ice-bath and sodium triacethoxyborohydride (2.1 g, 2.8 eq.) was added in portions and stirring was continued overnight at 55° C. Subsequently, the solvent was evaporated and the residue was diluted with DCM. The organic layer was then washed with water, brine, dried over anh. $Na_2SO_4$, filtered and concentrated in vacuo. The crude product was purified by FCC (SiHP; DCM:MeOH) to give the product (0.75 g, 40% yield) as a yellow solid. ESI-MS: 516.5 $[M+H]^+$.

Preparation of 1-cyclopropyl-6-fluoro-7-(2-hydroxyethoxy-3-({[(2-methylpyridin-4-yl)methyl][(3S)-1-(pyridin-3-yl)piperidin-3-yl]amino}methyl)-1,4-dihydroquinolin-4-one hydrochloride 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one (Intermediate 24) (0.1 g, 1.0 eq.) was dissolved in ethylene glycol (1.9 mL) and the mixture was cooled to 0° C. Then sodium hydride (60% dispersion in mineral oil, 0.04 g, 5.0 eq.) was added in portions. The resulting mixture was stirred overnight at 60° C. This reaction was repeated starting with 0.2 g of Intermediate 24. Subsequently, combined reaction mixtures were partitioned between water and DCM. The organic layer was dried over anh. $Na_2SO_4$, filtered and concentrated in vacuo. The crude was purified by FCC (SiHP; DCM:MeOH) and re-purified by RP-FCC (C18HP; $H_2O$:MeCN) to afford product (0.22 g, 81% yield) as a yellowish solid. The compound (0.2 g) was converted to the HCl salt using 2 M HCl in $Et_2O$ solution (0.17 mL, 1 eq. to FB) and DCM (12.0 mL) as solvent to provide the product (0.2 g, 99% yield) as an orange solid. HR-MS: 558.3 $[M+H]^+$. $^1H$ NMR (400 MHz, Methanol-$d_4$): 8.42 (d, J=2.9 Hz, 1H), 8.33 (d, J=5.9 Hz, 1H), 8.06-7.97 (m, 3H), 7.88 (d, J=11.4 Hz, 1H), 7.76-7.64 (m, 3H), 7.59 (d, J=7.1 Hz, 1H), 4.35-4.28 (m, 2H), 4.26-4.10 (m, 3H), 4.04-3.92 (m, 3H), 3.91-3.80 (m, 2H), 3.56-3.49 (m, 1H), 3.21-3.02 (m, 2H), 2.99-2.89 (m, 1H), 2.52 (s, 3H), 2.27-2.16 (m, 1H), 2.03-1.93 (m, 1H), 1.85-1.62 (m, 2H), 1.39-1.30 (m, 2H), 1.05-0.97 (m, 2H).

Example 85. 1-cyclopropyl-6-fluoro-7-(2-hydroxyethoxy-3-({[(2-methylpyridin-4-yl)methyl][(3S)-1-(pyrazin-2-yl)piperidin-3-yl]amino}methyl)-1,4-dihydroquinolin-4-one hydrochloride

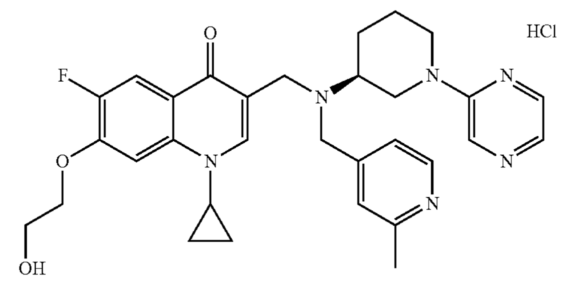

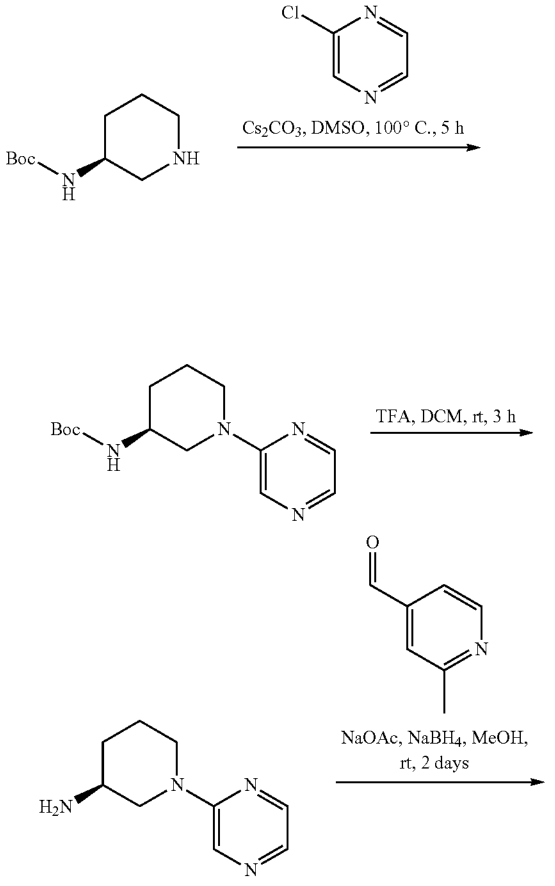

-continued

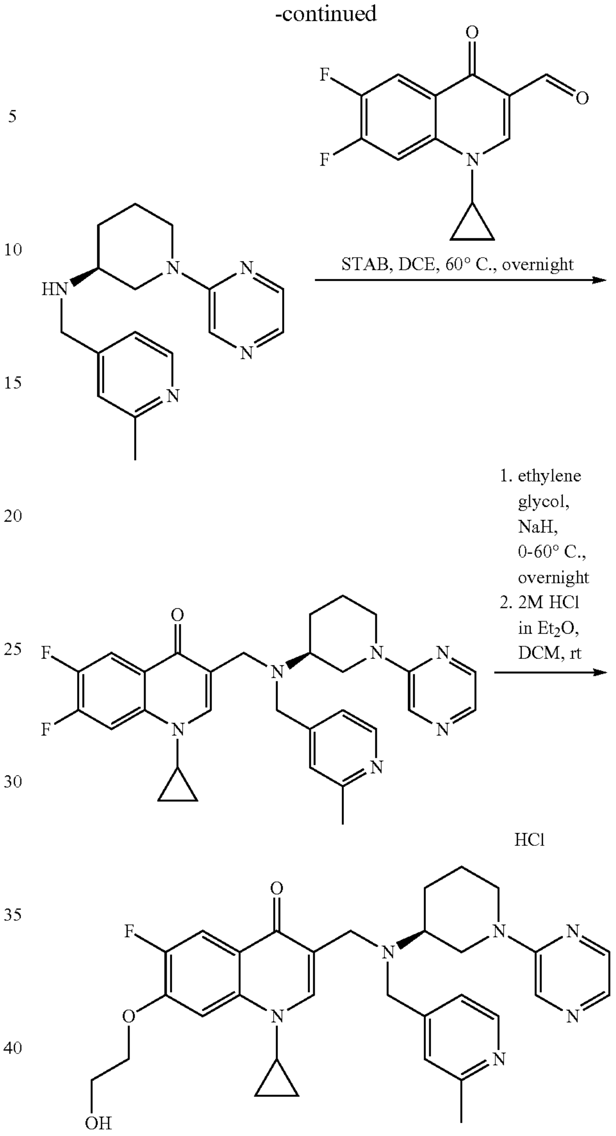

Preparation of tert-butyl N-[(3S)-1-(pyrazin-2-yl)piperidin-3-yl]carbamate $Cs_2CO_3$ (2.8 g, 2.0 eq.) was added to a solution of 2-chloropyrazine (0.5 g, 1.0 eq.) and (S)-3-Boc-aminopiperidine (1.0 g, 1.2 eq.) in DMSO (8.0 mL) and the mixture was stirred 5 h at 100° C. Afterwards, the reaction mixture was cooled to RT, diluted with water and washed with $Et_2O$. The organic layer was washed with brine, dried over $Na_2SO_4$, filtered and concentrated in vacuo. The product was purified by FCC (SiHP; Hex:EtOAc) to give product (0.71 g, 58% yield) as a pale yellow solid. ESI-MS: 279.1 $[M+H]^+$. $^1H$ NMR (400 MHz, Chloroform-d) δ 8.21 (s, 1H), 8.13 (dd, J=2.5, 1.4 Hz, 1H), 7.83 (d, J=2.7 Hz, 1H), 4.69 (s, 1H), 3.96 (d, J=12.8 Hz, 1H), 3.76 (s, 2H), 3.53-3.30 (m, 2H), 2.03-1.93 (m, 1H), 1.84 (ddq, J=13.3, 6.7, 3.5 Hz, 1H), 1.75-1.57 (m, 2H), 1.47 (s, 9H).

Preparation of (3S)-1-(pyrazin-2-yl)piperidin-3-amine

Trifluoroacetic acid (1.9 mL, 10.0 eq.) was added to the solution of tert-butyl N-[(3S)-1-(pyrazin-2-yl)piperidin-3- yl]carbamate (0.7 g, 1.0 eq.) in DCM (12.0 mL) and the reaction mixture was stirred for 3 h at RT. Afterwards, the mixture was concentrated in vacuo and traces of moisture were azeotropically removed with MeOH to give product (0.73 g, 99% yield) as a trifluoroacetate salt. The product was used in the next step without further purification. ESI-MS: 179.0 $[M+H]^+$.

Preparation of (3S)—N-[(2-methylpyridin-4-yl)methyl]-1-(pyrazin-2-yl)piperidin-3-amine (Intermediate 25)

(3S)-1-(pyrazin-2-yl)piperidin-3-amine trifluoroacetate (0.73 g, 1.0 eq.), 2-methylpyridine-4-carbaldehyde (0.27 mL, 1.0 eq.) and sodium acetate (0.20 g, 1.0 eq.) were dissolved in anh. MeOH (8.0 mL) and the mixture was stirred overnight at RT. After that time the mixture was cooled to 0° C. and sodium borohydride (0.19 g, 2.0 eq.) was added and the reaction mixture was stirred overnight at RT. After that time the reaction was concentrated in vacuo and residue was extracted with DCM and aq. NaOH solution (pH was adjusted to 11). The organic layer was washed with brine, dried over $Na_2SO_4$, filtered and concentrated. The crude product was purified by FCC (SiHP; DCM:MeOH) to give product (0.59 g, 83% yield) as a pale yellow oil. ESI-MS: 284.3 $[M+H]^+$.

Preparation of 1-cyclopropyl-6,7-difluoro-3-({[(2-methylpyridin-4-yl)methyl][(3S)-1-(pyrazin-2-yl)piperidin-3-yl]amino}methyl)-1,4-dihydroquinolin-4-one A mixture of 1-cyclopropyl-6,7-difluoro-4-oxo-1,4-dihydroquinoline-3-carbaldehyde (Intermediate 4) (0.47 g, 1.0 eq.) and (3S)—N-[(2-methylpyridin-4-yl)methyl]-1-(pyrazin-2-yl)piperidin-3-amine (Intermediate 25) (0.57 g, 1.1 eq.) in anh. DCE (18.0 mL) was stirred 5 h at 60° C. Then the mixture was cooled to RT and sodium triacethoxyborohydride (1.9 g, 5.0 eq.) was added. Resulting mixture was stirred overnight at 60° C. Then the mixture was diluted with DCM and washed with 0.1M NaOH. Aqueous layer was extracted with DCM. Combined organic layer was washed with brine, dried over $Na_2SO_4$, filtered and concentrated. The residue was purified by FCC (SiHP; DCM:MeOH) to give desired product (0.82 g, 79% yield) as a yellow foam. ESI-MS: 517.5 $[M+H]^+$.

Preparation of 1-cyclopropyl-fluoro-7-(2-hydroxyethoxy)-3-({[(2-methylpyridin-4-yl)methyl][(3S)-1-(pyrazin-2-yl)piperidin-3-yl]amino}methyl)-1,4-dihydroquinolin-4-one hydrochloride Sodium hydride (60% dispersion in mineral oil, 0.29 g, 5.0 eq.) was added in portions to the solution of 1-cyclopropyl-6,7-difluoro-3-({[(2-methylpyridin-4-yl)methyl][(3S)-1-(pyrazin-2-yl)piperidin-3-yl]amino}methyl)-1,4-dihydroquinolin-4-one (0.82 g, 1.0 eq.) in ethane-1,2-diol (14.0 mL) at 0° C. The mixture was stirred at 0° C. for 1 h, warmed to RT and then the mixture was stirred overnight at 60° C. The reaction mixture was quenched by the addition of water. The mixture was diluted with water and washed with DCM. The organic layer was dried over $Na_2SO_4$, filtered and concentrated under reduced pressure. The crude material was purified by FCC (SiHP; DCM:MeOH) and re-purified by RP FCC (C18HP; $H_2O$:MeCN) and re-purified once again using FCC (SiCN column; DCM:MeOH) to give product (0.49 g, 60% yield) as a pale yellow foam. The compound was converted into the HCl salt using 2 M HCl in $Et_2O$ and DCM as a solvent. The mixture was concentrated in vacuo and the compound was freeze-dried to give product (0.5 g, 96% yield) as a yellow solid. ESI-MS: 559.5 $[M+H]^+$. $^1H$ NMR (400 MHz, Methanol-$d_4$) δ 8.53 (d, J=6.0 Hz, 1H), 8.33 (d, J=1.4 Hz, 1H), 8.27 (s, 1H), 8.16 (dd, J=2.7, 1.5 Hz, 1H), 8.01 (s, 1H), 7.97-7.93 (m, 1H), 7.90 (d, J=11.3 Hz, 1H), 7.81 (d, J=2.7 Hz, 1H), 7.68 (d, J=7.1 Hz, 1H), 4.85 (d, J=12.5 Hz, 1H), 4.54 (s, 2H), 4.40-4.32 (m, 2H), 4.32-4.21 (m, 3H), 4.07-3.98 (m, 2H), 3.63 (tt, J=7.1, 3.9 Hz, 1H), 3.44-3.35 (m, 1H), 3.32-3.25 (m, 1H), 3.10 (td, J=13.3, 2.6 Hz, 1H), 2.65 (s, 3H), 2.40-2.30 (m, 1H), 2.12-1.95 (m, 2H), 1.74-1.59 (m, 1H), 1.44-1.32 (m, 2H), 1.20-1.07 (m, 2H).

Example 86. 1-cyclopropyl-6-fluoro-7-[(3S)-3-hydroxypiperidin-1-yl]-3-({[(2-methylpyridin-4-yl)methyl][(3S)-1-(pyridin-3-yl)piperidin-3-yl]amino}methyl)-1,4-dihydroquinolin-4-one hydrochloride

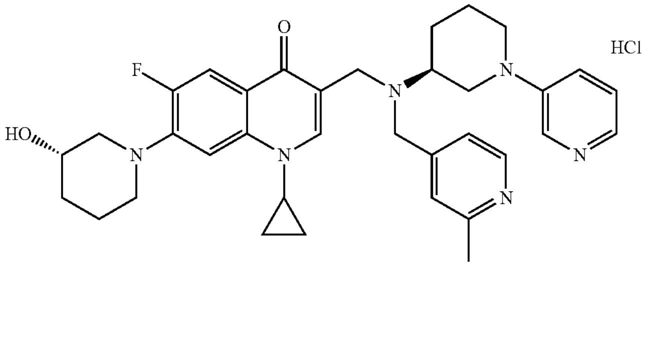

-continued

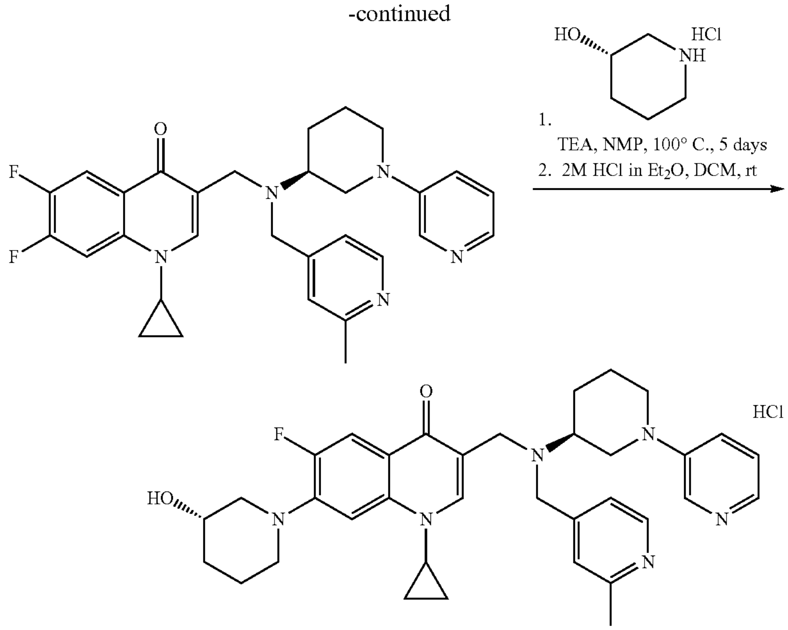

Preparation of 1-cyclopropyl-6-fluoro-7-[(3S)-3-hydroxypiperidin-1-yl]-3-({[(2-methylpyridin-4-yl)methyl][(3S)-1-(pyridin-3-yl)piperidin-3-yl]amino}methyl)-1,4-dihydroquinolin-4-one hydrochloride (3S)-Piperidin-3-ol hydrochloride (0.14 g, 2.5 eq.) and 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one (Intermediate 24) (0.21 g, 1.0 eq.) were dissolved in 1-methyl-2-pyrrolidinone (2.0 mL) and then TEA (0.28 mL, 5.0 eq.) was added. Reaction mixture was heated at 100° C. for 5 days. Then the reaction mixture was diluted with water and washed with EtOAc. The organic layer was washed with brine, dried over $Na_2SO_4$, filtered and concentrated. The crude product was purified by FCC (SIHP; DCM:MeOH) and repurified by RP-FCC (C18HP, MeCN:$H_2O$) to give product (0.17 g, 71% yield) as a beige solid. ESI-MS: 597.5 $[M+H]^+$. The compound was converted into the HCl salt using 2 M HCl in $Et_2O$ and DCM as a solvent. The mixture was concentrated in vacuo and the compound was freeze-dried to give a product (0.14 g, 100% yield) as an orange solid. HR-MS: 597.3 $[M+H]^+$. $^1H$ NMR (400 MHz, Methanol-$d_4$): 8.47 (d, J=2.9 Hz, 1H), 8.36 (d, =6.0 Hz, 1H), 8.15-8.10 (m, 1H), 8.06 (d, =5.3 Hz, 1H), 8.00 (s, 1H), 7.84-7.74 (m, 4H), 7.42 (d, J=7.4 Hz, 1H), 4.29 (d, J=12.0 Hz, 1H), 4.19 (s, 2H), 4.04-3.82 (m, 4H), 3.69-3.62 (m, 1H), 3.54-3.44 (m, 2H), 3.24-3.06 (m, 2H), 3.02-2.92 (m, 2H), 2.88-2.81 (m, 1H), 2.55 (s, 3H), 2.28-2.19 (m, 1H), 2.10-1.91 (m, 3H), 1.86-1.64 (m, 3H), 1.56-1.45 (m, 1H), 1.36-1.28 (m, 2H), 1.04-0.98 (m, 2H).

Example 87. 1-cyclopropyl-6-fluoro-7-[(3S)-3-(hydroxymethyl)pyrrolidin-1 yl]-3-({[(2-methylpyridin-4-yl)methyl][(3S)-1-(pyridin-3-yl)piperidin-3-yl]amino}methyl)-1,4-dihydroquinolin-4-one hydrochloride

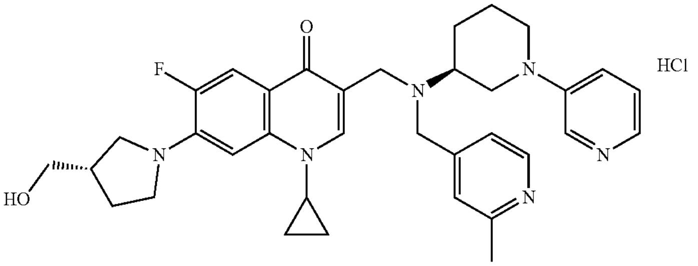

-continued

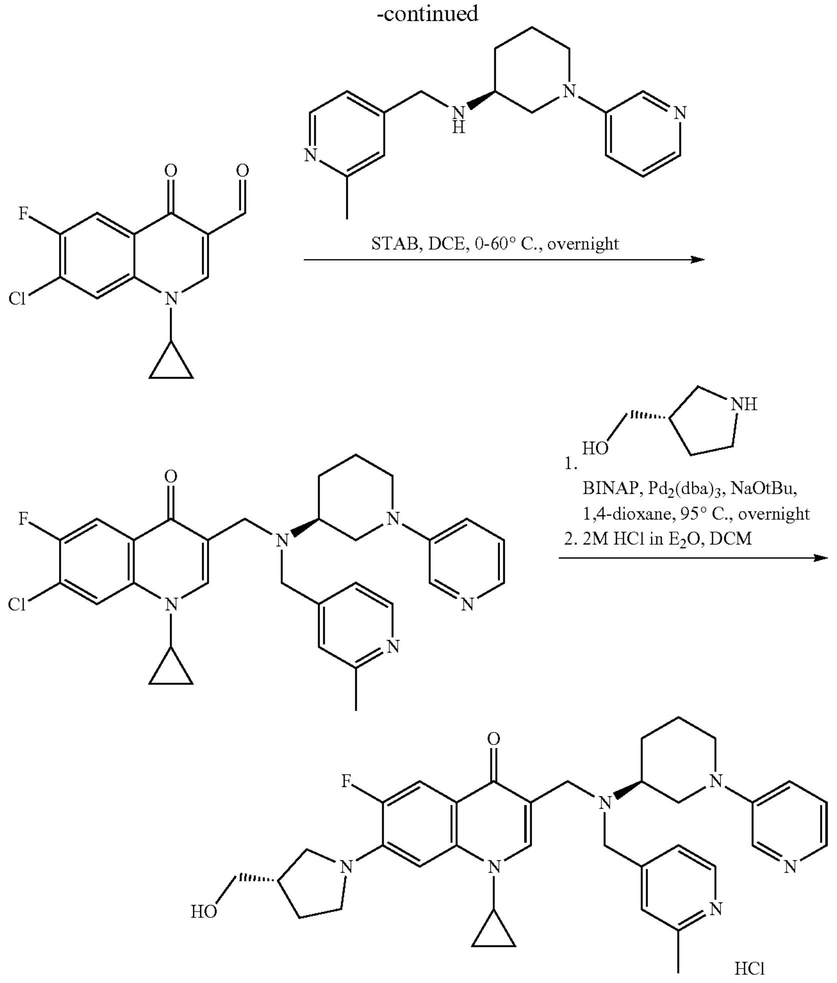

Preparation of 7-chloro-1-cyclopropyl-6-fluoro-3-({[(2-methylpyridin-4-yl)methyl][(3S)-1-(pyridin-3-yl)piperidin-3-yl]amino}methyl)-1,4-dihydroquinolin-4-one (Intermediate 26)

A mixture of (3S)—N-[(2-methylpyridin-4-yl)methyl]-1-(pyridin-3-yl)piperidin-3-amine (Intermediate 23) (1.0 g, 1.0 eq.) and 7-chloro-1-cyclopropyl-6-fluoro-4-oxo-1,4-dihydroquinoline-3-carbaldehyde (Intermediate 9) (1.0 g, 1.1 eq.) in anh. DCE (30.0 mL) was stirred at 60° C. for 3 h. Then, the mixture was cooled in an ice-bath to 0° C. and sodium triacethoxyborohydride (2.1 g, 2.8 eq.) was added in portions. The reaction mixture was stirred overnight at RT, then heated to 40° C. for 1 h. AcOH (0.2 mL, 1.0 eq.) was added and reaction was stirred at RT for 1 h. Then, the mixture was cooled in an ice-bath to 0° C. and sodium triacethoxyborohydride (2.1 g, 2.8 eq.) was added in portions and stirred at 60° C. for 1 h. The solvent was evaporated and the residue was diluted with DCM and washed with sat. $NaHCO_3$ aq. Organic layer was dried over anh. $Na_2SO_4$, filtered and concentrated in vacuo. The crude product was purified by FCC (SiHP; DCM:MeOH) to give the product (0.81 g, 43% yield) as a yellow solid. ESI-MS: 532.5 $[M+H]^+$.

Preparation of 1-cyclopropyl-6-fluoro-7-[(3S)-3-(hydroxymethyl)pyrrolidin-1-yl]-3-({[(2-methylpyridin-4-yl)methyl][(3S)-1-(pyridin-3-yl)piperidin-3-yl]amino}methyl)-1,4-dihydroquinolin-4-one hydrochloride The solution of 7-chloro-1-cyclopropyl-6-fluoro-3-({[(2-methylpyridin-4-yl)methyl][(3S)-1-(pyridin-3-yl)piperidin-3-yl]amino}methyl)-1,4-dihydroquinolin-4-one (Intermediate 26) (0.05 g, 1.0 eq.) and (3S)-pyrrolidin-3-yl]methanol (0.016 g, 1.8 eq.) in anh. 1,4-dioxane (1.0 mL) was purged with argon for 15 min. Then, sodium tert-butoxide (0.018 g, 2.1 eq.), BINAP (0.016 g, 0.3 eq.) and $Pd_2(dba)_3$ (0.008 g, 0.1 eq.) were added. The resulting mixture was heated at 95° C. overnight. The same reaction was repeated twice starting with 0.05 g and 0.28 g of Intermediate 26. Product mixtures from both the batches were combined and filtered through a pad of celite and washed further with MeOH. The filtrate was concentrated in vacuo. The product was purified by FCC (SiHP; DCM:MeOH). The residue was dissolved in MeOH and scavenger QuadraPure MPA (4.0 eq.) was added. The mixture was stirred overnight at RT. Afterwards the mixture was filtered. Filtrate was concentrated in vacuo and the residue was re-purified by FCC (SiHP; DCM:MeOH) to give a product (0.29 g, 73% yield). ESI-MS: 597.5 $[M+H]^+$. The compound was converted to the HCl salt using 2 M HCl in $Et_2O$ (0.2 mL, 1.0 eq. to FB) and DCM as a solvent (3.0 mL) to give the product (0.26 g, 82% yield) as a yellow solid. ESI-MS: 597.3 $[M+H]^+$. $^1H$ NMR (400 MHz, Methanol-$d_4$) δ 8.46 (d, J=2.9 Hz, 1H), 8.32 (d, J=5.8 Hz, 1H), 8.07 (d, J=5.0 Hz, 1H), 8.02 (dd, J=8.6, 2.5 Hz, 1H), 7.91 (s, 1H), 7.78-7.68 (m, 3H), 7.65 (d, J=6.0 Hz, 1H), 6.94 (d, J=7.7 Hz, 1H), 4.33-4.15 (m, 3H), 4.05 (d, J=12.9 Hz, 1H), 3.98-3.83 (m, 2H), 3.78-3.56 (m, 5H), 3.49-3.39 (m, 2H), 3.27-3.12 (m, 2H), 2.98 (td, J=12.6, 2.7 Hz, 1H), 2.62-2.53 (m, 1H), 2.50 (s, 3H), 2.32-2.23 (m, 1H), 2.23-2.12 (m, 1H), 2.06-1.98 (m, 1H), 1.93-1.80 (m, 2H), 1.80-1.67 (m, 1H), 1.37-1.27 (m, 2H), 1.05-0.94 (m, 2H).
Example 88. 1-cyclopropyl-6-fluoro-7-[(3R)-3-(hydroxymethyl)pyrrolidin-1-yl]-3-({[(2-methylpyridin-4-yl)methyl][(3S)-1-(pyridin-3-yl)piperidin-3-yl]amino}methyl)-1,4-dihydroquinolin-4-one hydrochloride
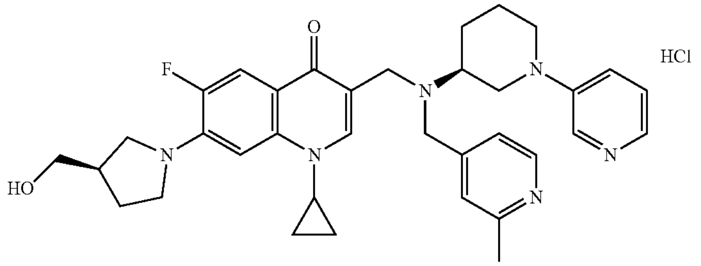
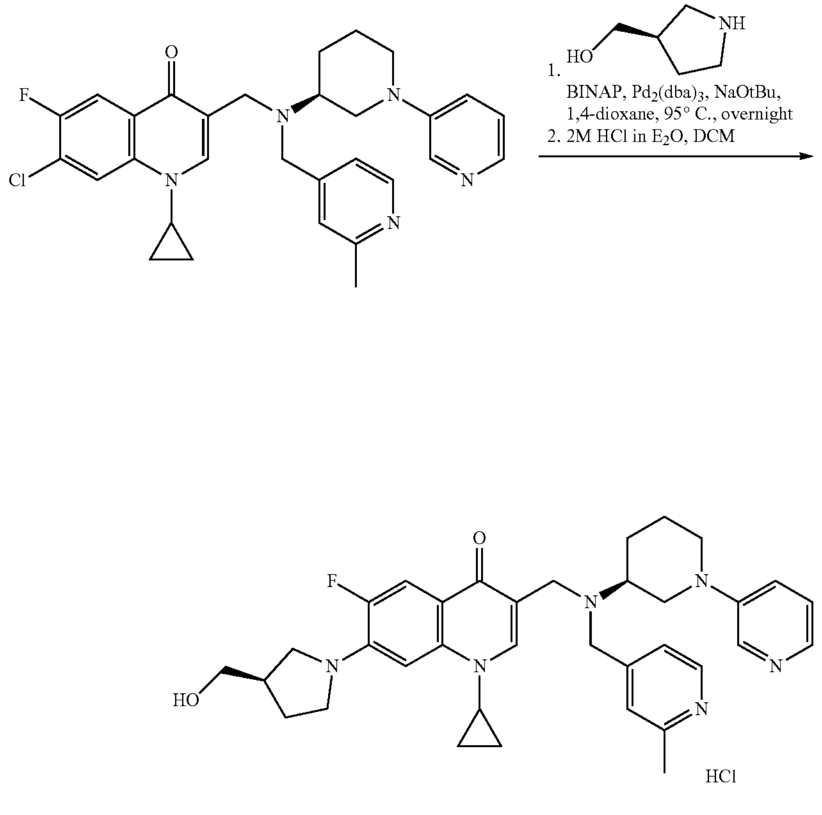

Preparation of 1-cyclopropyl-6-fluoro-7-[(3R-3-(hydroxymethyl)pyrrolidin-1-yl]-3-({[(2-methylpyridin-4-yl)methyl][(3S)-1-(pyridin-3-yl)piperidin-3-yl]amino}methyl)-1,4-dihydroquinolin-4-one hydrochloride The solution of 7-chloro-1-cyclopropyl-6-fluoro-3-({[(2-methylpyridin-4-yl)methyl][(3S)-1-(pyridin-3-yl)piperidin-3-yl]amino}methyl)-1,4-dihydroquinolin-4-one (Intermediate 26) (0.39 g, 1.0 eq.) and [(3R)-pyrrolidin-3-yl]methanol (0.12 g, 1.8 eq.) in anh. 1,4-dioxane (7.0 mL) was purged with argon for 15 min. Then sodium tert-butoxide (0.14 g, 2.1 eq.), BINAP (0.13 g, 0.3 eq.) and $Pd_2(dba)_3$ (0.062 g, 0.1 eq.) were added. The resulting mixture was heated overnight at 95° C. The reaction mixture was filtered though a pad of celite and the filtrate was concentrated under reduced pressure. The residue was dissolved in DCM (100.0 mL) and scavenger QuadraSil MP (1.0 g) was added. The mixture was stirred overnight at RT, scavenger beans were filtered off, washed with DCM and concentrated in vacuo. The crude product was purified by RP-FCC (C18HP; $H_2O$:MeCN) to give desired product (0.31 g, 75% yield) as a yellow solid. ESI-MS: 597.5 $[M+H]^+$. The compound was converted to the HCl salt using 2 M HCl in $Et_2O$ (0.25 mL, 1.0 eq. to FB) and DCM as a solvent (15.0 mL) to give the product (0.32 g, 98% yield) as a yellow solid. ESI-MS: 597.3 $[M+H]^+$. $^1H$ NMR (400 MHz, Methanol-$d_4$): 8.45-8.41 (m, 1H), 8.30 (d, J=5.8 Hz, 1H), 8.04 (d, J=5.2 Hz, 1H), 8.00-7.95 (m, 1H), 7.89 (s, 1H), 7.75-7.65 (m, 3H), 7.64-7.58 (m, 1H), 6.92 (d, J=7.6 Hz, 1H), 4.28-4.15 (m, 3H), 4.08-3.99 (m, 1H), 3.95-3.82 (m, 2H), 3.75-3.57 (m, 5H), 3.47-3.39 (m, 2H), 3.24-3.12 (m, 2H), 3.01-2.91 (m, 1H), 2.59-2.51 (m, 1H), 2.48 (s, 3H), 2.30-2.21 (m, 1H), 2.20-2.11 (m, 1H), 2.05-1.97 (m, 1H), 1.90-1.65 (m, 3H), 1.34-1.26 (m, 2H), 1.02-0.94 (m, 2H).

Example 89. 1-cyclopropyl-6-fluoro-3-({[(3S,5S)-5-fluoro-1-(pyridin-3-yl)piperidin-3-yl][(2-methylpyridin-4-yl)methyl]amino}methyl)-7-(2-hydroxyethoxy)-1,4-dihydroquinolin-4-one hydrochloride

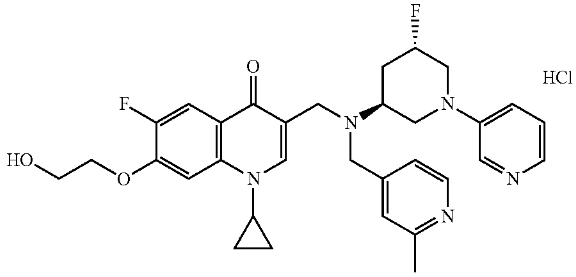

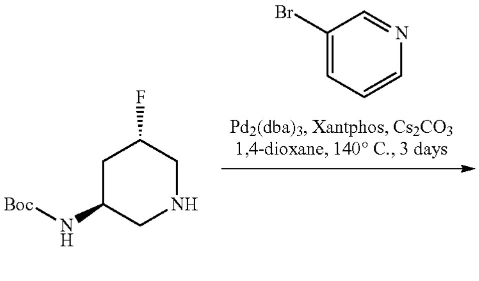

-continued

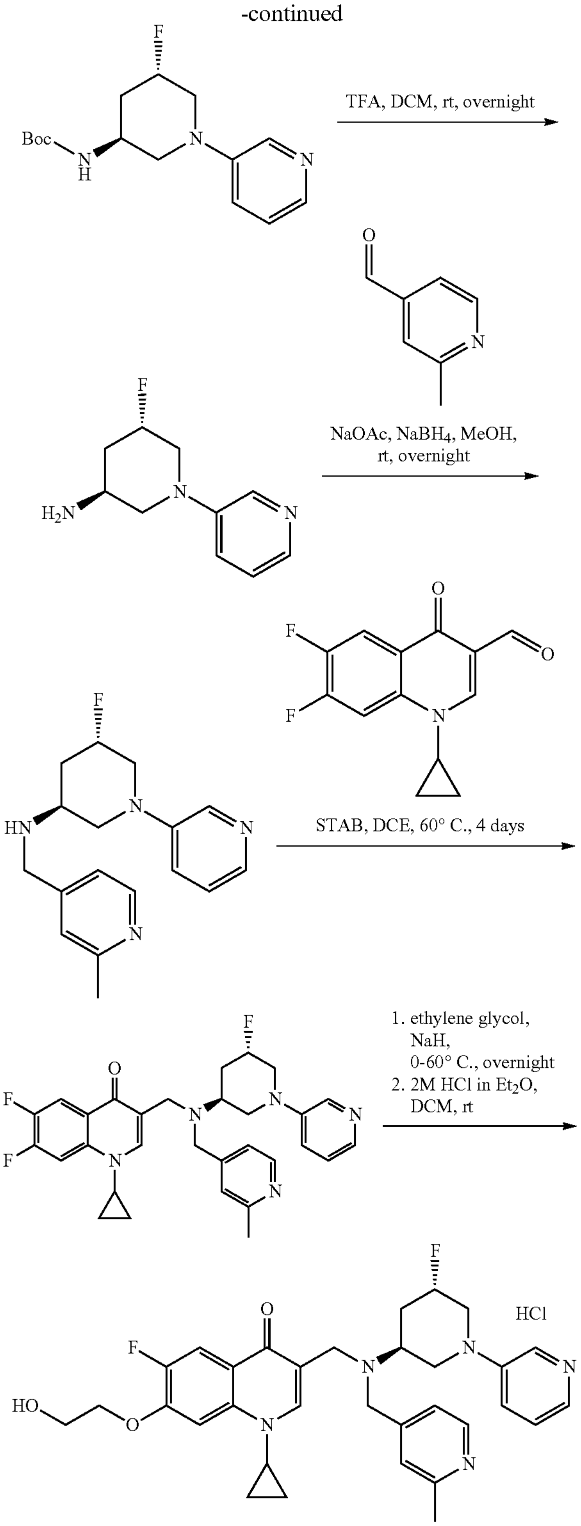

Preparation of tert-butyl N-[(3S,5S)-5-fluoro-1-(pyridin-3-yl)piperidin-3-yl]carbamate A suspension of 3-bromopyridine (1.8 g, 1.0 eq.), tert-butyl N-[(3S,5S)-5-fluoropiperidin-3-yl]carbamate (3.2 g, 1.3 eq.) and cesium carbonate (5.0 g, 1.4 eq.) in anh. 1,4-Dioxane (35.0 mL) was sparged with argon over 20 min and after this time $Pd_2(dba)_3$ (0.52 g, 0.05 eq.) and Xantphos (0.4 g, 0.06 eq.) were added. The reaction tube was closed and reaction mixture was stirred at 140° C. for 2 days. The reaction mixture was cooled to RT and sparged with argon. Then $Pd_2(dba)_3$ (0.52 g, 0.05 eq.) and Xantphos (0.4 g, 0.06 eq.) were added and reaction was stirred at 140° C. overnight. The crude mixture was filtered through a pad of celite. Filtrate was concentrated in vacuo Residue was purified by FCC (SiHP; Hex:EtOAc) to give desired product. The product was dissolved in DCM (50.0 mL) and scavenger QuadraSil MP (0.3 g) was added. Mixture was stirred overnight, scavenger beans were filtrated off, washed with DCM. Solvent was concentrated to give the product (1.05 g, 29% yield) as yellow solid. ESI-MS: 296.1 $[M+H]^+$.

Preparation of (3S,56)-5-fluoro-1-(pyridin-3-yl)piperidin-3-amine trifluoroacetate tert-Butyl N-[(3S,5S)-5-fluoro-1-(pyridin-3-yl)piperidin-3-yl]carbamate (1.05 g, 1.0 eq.) was dissolved in DCM (17.0 mL) and trifluoroacetic acid (2.5 mL, 10.0 eq.) was added dropwise to this solution. The reaction mixture was stirred at RT overnight. Solvent was evaporated and the residue was dissolved in MeOH and concentrated (three cycles) to azeotropically remove traces of moisture. The desired product (1.6 g, quantitative) was obtained as a brown solid. ESI-MS: 196.2 $[M+H]^+$.

Preparation of (3S,5S)-5-fluoro-N-[(2-methylpyridin-4-yl)methyl]-1-(pyridin-3-yl)piperidin-3-amine 2-Methylpyridine-4-carbaldehyde (0.37 mL, 1.0 eq.), (3S,5S)-5-fluoro-1-(pyridin-3-yl)piperidin-3-amine trifluoroacetate (1.19 g, 1.0 eq.) and sodium acetate (0.27 g, 1.0 eq.) were dissolved in anh. methanol (11.0 mL) and the mixture was stirred overnight at RT. After that time the mixture was cooled to 0° C. and sodium borohydride (0.25 g, 2.0 eq.) was added. The reaction was stirred overnight at RT. The reaction mixture was then concentrated in vacuo and residue was partitioned between DCM and aq. NaOH solution (pH was adjusted to 11). The organic layer was washed with brine, dried over $Na_2SO_4$, filtered and concentrated. Crude product was purified by FCC (SiHP; DCM:MeOH) to give product (0.55 g, 55% yield) as a beige solid. ESI-MS: 301.2 $[M+H]^+$.

Preparation of 1-cyclopropyl-6,7-fluoro-3-({[(3S,5S)-5-fluoro-1-(pyridin-3-yl)piperidin-3-yl][(2-methylpyridin-4-yl)methyl]amino}methyl)-1,4-dihydroquinolin-4-one A mixture of 1-cyclopropyl-6,7-difluoro-4-oxo-1,4-dihydroquinoline-3-carbaldehyde (Intermediate 4) (0.61 g, 1.3 eq.) and (3S,5S)-5-fluoro-N-[(2-methylpyridin-4-yl)methyl]-1-(pyridin-3-yl)piperidin-3-amine (0.55 g, 1.0 eq.) in anh. DCE (18.0 mL) was heated at 60° C. for 4 h. Then the mixture was cooled to 0° C. and sodium triacethoxyborohydride (1.55 g, 4.0 eq.) was added in portions. The resulting mixture was stirred for 3 days at RT. 1-cyclopropyl-6,7-difluoro-4-oxo-1,4-dihydroquinoline-3-carbaldehyde (Intermediate 4) (0.23 g, 0.5 eq.) and sodium triacethoxyborohydride (0.78 g, 2.0 eq.) were then added and the reaction mixture was stirred overnight at RT. The reaction mixture was diluted with water and washed with DCM. The organic layer was washed with brine, dried over $Na_2SO_4$ and concentrated in vacuo. Crude product was purified by RP-FCC (C18HP; $H_2O$:MeCN) to give desired product (0.545 g, 51% yield) as a yellowish solid. ESI-MS: 534.3 $[M+H]^+$.

Preparation of 1-cyclopropyl-6-fluoro-3-({[(3S,5S)-5-fluoro-1-(pyridin-3-yl)piperidin-3-yl][(2-methylpyridin-4-yl)methyl]amino}methyl)-7-(2-hydroxyethoxy)-1,4-dihydroquinolin-4-one hydrochloride 1-cyclopropyl-6,7-difluoro-3-({[(3S,5S)-5-fluoro-1-(pyridin-3-yl)piperidin-3-yl][(2-methylpyridin-4-yl)methyl]amino}methyl)-1,4-dihydroquinolin-4-one (0.545 g, 1.0 eq.) was dissolved in ethylene glycol (9.3 mL) and the mixture was cooled to 0° C. Then sodium hydride (60% dispersion in mineral oil, 0.19 g, 5.0 eq.) was added in portions. The resulting mixture was stirred at 60° C. overnight. The reaction mixture was diluted with water and extracted to DCM. The organic layer was dried over anh. $Na_2SO_4$ and concentrated in vacuo. The crude material was purified by RP-FCC (C18HP; $H_2O$:MeCN) to give pure product (0.51 g, 92% yield) as a beige solid. ESI-MS: 576.4 $[M+H]^+$. The compound was converted to the HCl salt using 2 M HCl in $Et_2O$ (0.41 mL, 1.0 eq. to FB) and DCM as a solvent (25.0 mL) to give the product (0.50 g, 97% yield) as a yellow solid. ESI-MS: 576.3 $[M+H]^+$. $^1H$ NMR (400 MHz, Methanol-$d_4$): 8.45-8.38 (m, 1H), 8.34 (d, J=5.9 Hz, 1H), 8.03-7.98 (m, 2H), 7.96-7.87 (m, 2H), 7.76 (s, 1H), 7.70 (d, J=5.9 Hz, 1H), 7.65-7.57 (m, 2H), 5.13 (d, J=46.9 Hz, 1H), 4.31 (t, J=4.6 Hz, 2H), 4.28-4.14 (m, 2H), 4.07 (s, 2H), 4.01-3.97 (m, 2H), 3.92-3.86 (m, 1H), 3.79-3.70 (m, 1H), 3.56-3.50 (m, 1H), 3.39-3.32 (m, 1H), 3.28-3.13 (m, 2H), 2.55 (s, 3H), 2.52-2.41 (m, 1H), 2.14-1.93 (m, 1H), 1.36-1.29 (m, 2H), 1.04-0.94 (m, 2H).

Example 90. 1-cyclopropyl-6-fluoro-3-({[(3S)-1-(5-fluoropyridin-3-yl)piperidin-3-yl][(2-methylpyridin-4-yl)methyl]amino}methyl)-7-(2-hydroxyethoxy)-1,4-dihydroquinolin-4-one hydrochloride

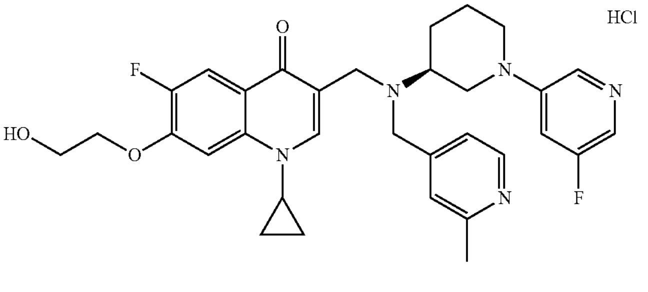 [SMILES: Cc1cc(CN(Cc2cn(C3CC3)c3cc(OCCO)c(F)cc3c2=O)[C@H]2CCCN(c3cncc(F)c3)C2)ccn1 ; Cl]

-continued
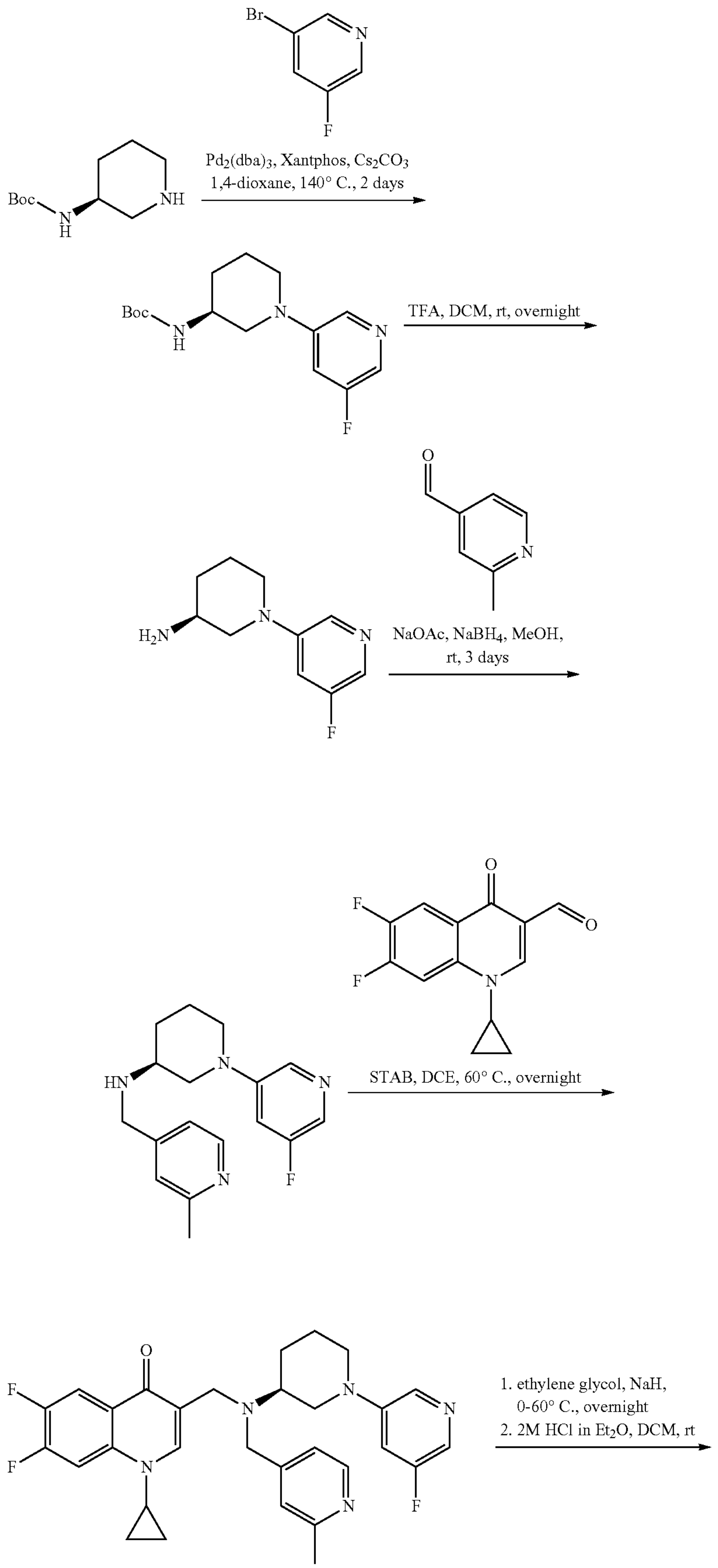

-continued

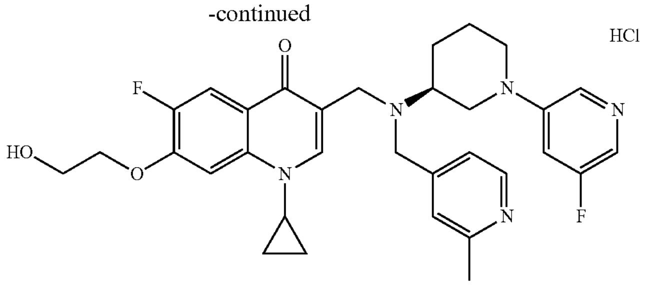

Preparation of tert-butyl N-[(3S)-1-(5-fluoropyridin-3-yl)piperidin-3-yl]carbamate A suspension of 3-bromo-5-fluoropyridine (1.0 g, 1.0 eq.), (S)-3-Boc-aminopiperidine (1.5 g, 1.3 eq.) and cesium carbonate (2.5 g, 1.4 eq.) in anh. 1,4-dioxane (20.0 mL) was sparged with argon for 20 min and then, $Pd_2(dba)_3$ (0.26 g, 0.05 eq.) and Xantphos (0.33 g, 0.1 eq.) were added and the reaction mixture was stirred at 140° C. for 48 h. The crude mixture was filtered through a pad of celite, eluted with methanol. The filtrate was concentrated in vacuo. This crude product was purified on FCC (SiHP; Hex:EtOAc) and the resulting residue was dissolved in EtOAc and scavenger QuadraSil MP (1.0 g) was added. The mixture was stirred 4 h at RT. Scavenger was filtered off and washed with EtOAc. The solvent was evaporated to give the product (1.7 g, 99% yield) as a yellow solid. ESI-MS: 296.4 $[M+H]^+$.

Preparation of (3S)-1-(5-fluoropyridin-3-yl)piperidin-3-amine trifluoroacetate

Trifluoroacetic acid (4.3 mL, 10.0 eq.) was added to a solution of tert-butyl N-[(3S)-1-(5-fluoropyridin-3-yl)piperidin-3-yl]carbamate (1.7 g, 1.0 eq.) in DCM (35.0 mL) and the mixture was stirred overnight at RT. After that time the mixture was concentrated in vacuo and traces of moisture were removed from this residue by azeotropic codistillation with MeOH to give product (1.8 g, 99% yield) as a yellow oil. ESI-MS: 196.1 $[M+H]^+$. The product was used in next step without further purification.

Preparation of (3S)-1-(5-fluoropyridin-3-yl)-N-[(2-methylpyridin-4-yl)methyl]piperidin-3-amine (3S)-1-(5-fluoropyridin-3-yl)piperidin-3-amine trifluoroacetate (1.8 g, 1.0 eq.), 2-methylpyridine-4-carbaldehyde (0.62 mL, 1.0 eq.) and sodium acetate (0.46 g, 1.0 eq.) was dissolved in anh. methanol (20.0 mL) and the mixture was stirred overnight at RT. After that time the mixture was cooled to 0° C. and sodium borohydride (0.42 g, 2.0 eq.) was added. The reaction mixture was stirred 3 days at RT. After that time the reaction was concentrated in vacuo and residue was partitioned between DCM and aqueous NaOH solution (pH was adjusted to 11). The organic layer was washed with brine, dried over $Na_2SO_4$, filtered and concentrated in vacuo. Crude product was purified by FCC (SiHP; DCM:MeOH) to give product (0.95 g, 54% yield) as pale brown oil. ESI-MS: 301.2 $[M+H]^+$.

Preparation of 1-cyclopropyl-6,7-difluoro-3-({[(3S)-1-(5-fluoropyridin-3-yl)piperidin-3-yl][(2-methylpyridin-4-yl)methyl]amino}methyl)-1,4-dihydroquinolin-4-one A mixture of 1-cyclopropyl-6,7-difluoro-4-oxo-1,4-dihydroquinoline-3-carbaldehyde (Intermediate 4) (0.62 g, 1.0 eq.) and (3S)-1-(5-fluoropyridin-3-yl)-N-[(2-methylpyridin-4-yl)methyl]piperidin-3-amine (0.92 g, 1.2 eq.) in anh. 1,2-dichloroethane (25.0 mL) was stirred for 5 h at 60° C. Then the mixture was cooled to RT and sodium triacethoxyborohydride (2.6 g, 5.0 eq.) was added. Resulting mixture was stirred overnight at 60° C. After that time the mixture was diluted with DCM and washed with 0.1 M NaOH aq. solution. The aqueous layer was washed further with DCM. Combined organic layers were washed with brine, dried over $Na_2SO_4$, filtered and concentrated in vacuo. Crude was purified by FCC (SiHP; DCM:MeOH) to give product (0.80 g, 59% yield) as a yellow oil. ESI-MS: 534.5 $[M+H]^+$.

Preparation of 1-cyclopropyl-6-fluoro-3-({[(3S)-1-(5-fluoropyridin-3-yl)piperidin-3-yl][(2-methylpyridin-4-yl)methyl]amino}methyl)-7-(2-hydroxyethoxy)-1,4-dihydroquinolin-4-one hydrochloride Sodium hydride (60% dispersion in mineral oil, 0.29 g, 5.0 eq.) was added in portions to a solution of 1-cyclopropyl-6,7-difluoro-3-({[(3S)-1-(5-fluoropyridin-3-yl)piperidin-3-yl][(2-methylpyridin-4-yl)methyl]amino}methyl)-1,4-dihydroquinolin-4-one (0.80 g, 1.0 eq.) in ethylene glycol (15.0 mL) at 0° C. The mixture was stirred at 0° C. for 1 h and warmed to RT. Then the mixture was stirred overnight at 60° C. After that time the reaction mixture was diluted with water and extracted with DCM. The organic layer was dried over $Na_2SO_4$, filtered and concentrated in vacuo. Crude was purified twice by FCC (SiHP; DCM:MeOH) to give a product (0.77 g, 94% yield) as a yellow foam. ESI-MS: 576.4 $[M+H]^+$. The compound was converted to the HCl salt using 2 M HCl in $Et_2O$ (0.67 mL, 1.0 eq. to FB) and DCM as a solvent (13.0 mL) to give the product (0.76 g, 100% yield) as a yellow solid. ESI-MS: 576.3 $[M+H]^+$. $^1H$ NMR (400 MHz, Methanol-$d_4$) δ 8.40 (d, J=6.0 Hz, 1H), 8.24-8.19 (m, 1H), 8.11 (s, 1H), 7.93-7.84 (m, 3H), 7.80 (d, J=5.9 Hz, 1H), 7.62 (d, J=7.1 Hz, 1H), 7.47 (dt, J=12.2, 2.3 Hz, 1H), 4.37-4.33 (m, 2H), 4.32-4.23 (m, 2H), 4.22-4.14 (m, 1H), 4.10-3.93 (m, 4H), 3.81 (d, J=12.5 Hz, 1H), 3.61-3.54 (m, 1H), 3.24-3.11 (m, 2H), 2.94 (td, J=12.5, 2.6 Hz, 1H), 2.58 (s, 3H), 2.31-2.21 (m, 1H), 2.05-1.95 (m, 1H), 1.91-1.79 (m, 1H), 1.73 (ddt, J=15.8, 12.0, 5.7 Hz, 1H), 1.42-1.31 (m, 2H), 1.11-1.01 (m, 2H).

Example 91. 1-cyclopropyl-6-fluoro-7-[(3R)-3-(hydroxymethyl)pyrrolidin-1-yl]-3-({[(2-methylpyridin-4-yl)methyl][(3S)-1-(pyrazin-2-yl)piperidin-3-yl]amino}methyl)-1,4-dihydroquinolin-4-one hydrochloride

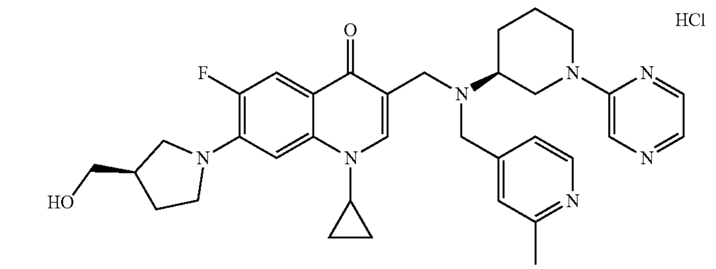

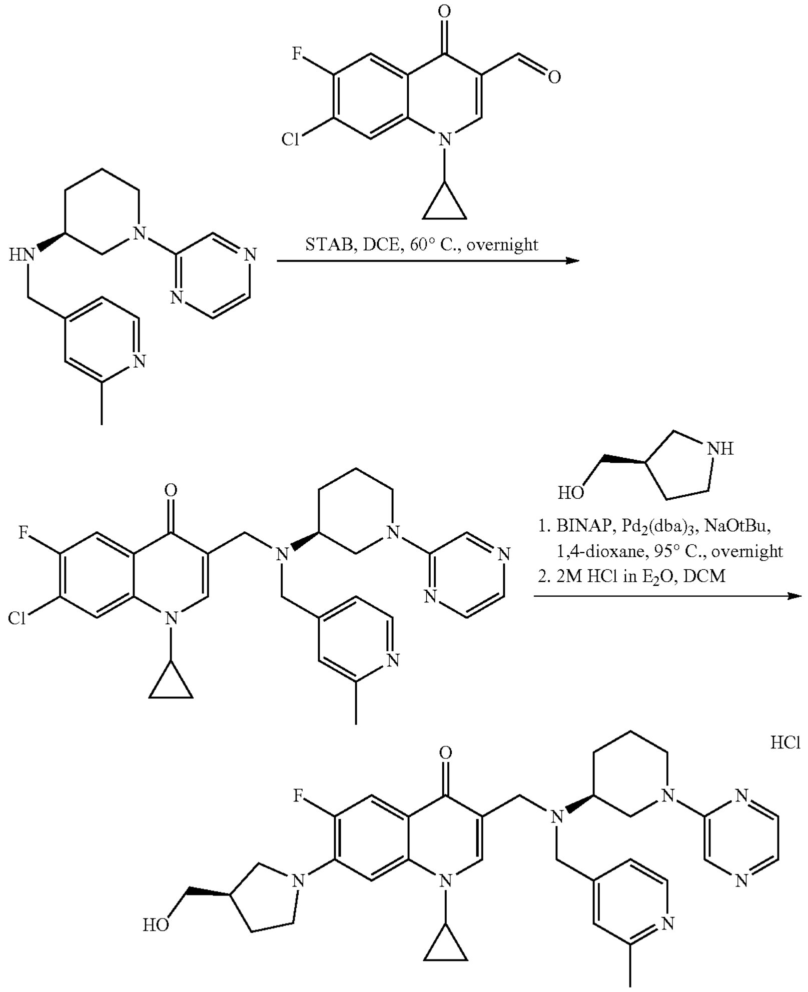

Preparation of 7-chloro-1-cyclopropyl-fluoro-3-({[(2-methylpyridin-4-yl)methyl][(3S)-1-(pyrazin-2-yl)piperidin-3-yl]amino}methyl)-1,4-dihydroquinolin-4-one (Intermediate 27)

A mixture of 7-chloro-1-cyclopropyl-6-fluoro-4-oxo-1,4-dihydroquinoline-3-carbaldehyde (Intermediate 9) (0.51 g, 1.0 eq.) and (3S)—N-[(2-methylpyridin-4-yl)methyl]-1-(pyrazin-2-yl)piperidin-3-amine (Intermediate 25) (0.5 g, 1.0 eq.) in anh. DCE (8.0 mL) was stirred for 3 h at 60° C. Then the mixture was cooled to 0° C. and sodium triacethoxyborohydride (1.05 g, 2.8 eq.) was added. The resulting mixture was stirred overnight at 60° C. After that time the mixture was diluted with DCM and washed with water. The aqueous layer was washed again with DCM. The combined organic layers were washed with brine, dried over $Na_2SO_4$, filtered and concentrated in vacuo. The residue was purified by FCC (SiHP; DCM:MeOH) to give product (0.695 g, 72% yield) as a yellow solid. ESI-MS: 533.7 $[M+H]^+$.

Preparation of 1-cyclopropyl-6-fluoro-7-[(3R-3-(hydroxymethyl)pyrrolidin-1-yl]-3-({[(2-methylpyridin-4-yl)methyl][(3S)-1-(pyrazin-2-yl)piperidin-3-yl]amino}methyl)-1,4-dihydroquinolin-4-one hydrochloride The solution of 7-chloro-1-cyclopropyl-6-fluoro-3-({[(2-methylpyridin-4-yl)methyl][(3S)-1-(pyrazin-2-yl)piperidin-3-yl]amino}methyl)-1,4-dihydroquinolin-4-one (Intermediate 27) (0.20 g, 1.0 eq.) and [(3R)-pyrrolidin-3-yl]methanol (0.07 g, 1.8 eq.) in anh. 1,4-dioxane (4.0 mL) was purged with argon for 15 min. Then sodium tert-butoxide (0.07 g, 2.1 eq.), BINAP (0.07 g, 0.3 eq.) and $Pd_2(dba)_3$ (0.03 g, 0.1 eq.) were added. The resulting mixture was heated overnight at 95° C. The reaction mixture was filtered through a pad of celite and concentrated under reduced pressure. The residue was dissolved in DCM and scavenger QuadraSil MP was added. The mixture was stirred overnight at RT. Scavenger was filtered off and the filtrate was concentrated in vacuo. The residue was purified by FCC (SiHP; DCM:MeOH) and then re-purified by RP-FCC (C18HP; $H_2O$:MeCN) to give a product (0.086 g, 39% yield) as a yellow foam. ESI-MS: 598.7 $[M+H]^+$. The compound was converted to the HCl salt using 2 M HCl in $Et_2O$ (0.7 mL, 1.0 eq. to FB) and DCM as a solvent (5.0 mL) to give the product (0.09 g, 98% yield) as a yellow solid. HR-MS: 598.3 $[M+H]^+$. $^1H$ NMR (400 MHz, Methanol-$d_4$) δ 8.36 (d, J=5.8 Hz, 1H), 8.26 (d, J=1.5 Hz, 1H), 8.09 (dd, J=2.7, 1.5 Hz, 1H), 7.95 (s, 1H), 7.77 (d, J=2.7 Hz, 1H), 7.75-7.61 (m, 3H), 6.95 (d, J=7.6 Hz, 1H), 4.77 (d, J=12.4 Hz, 1H), 4.38-4.01 (m, 5H), 3.77-3.56 (m, 5H), 3.50-3.40 (m, 2H), 3.29-3.12 (m, 2H), 3.03 (t, J=12.6 Hz, 1H), 2.60-2.48 (m, 4H), 2.26 (d, 1=11.5 Hz, 1H), 2.21-2.11 (m, 1H), 2.04-1.79 (m, 3H), 1.65 (q, J=12.8 Hz, 1H), 1.37-1.27 (m, 2H), 1.07-0.97 (m, 2H).

Example 92. 1-cyclopropyl-3-({[(3S)-1-[6-(dimethylamino)pyridin-3-yl]piperidin-3-yl][(2-methylpyridin-4-yl)methyl]amino}methyl)-6-fluoro-7-(2-hydroxyethoxy)-1,4-dihydroquinolin-4-one hydrochloride

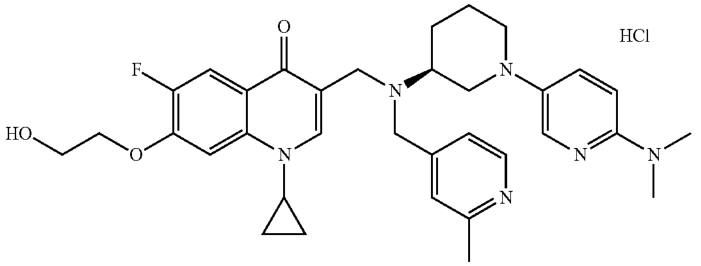

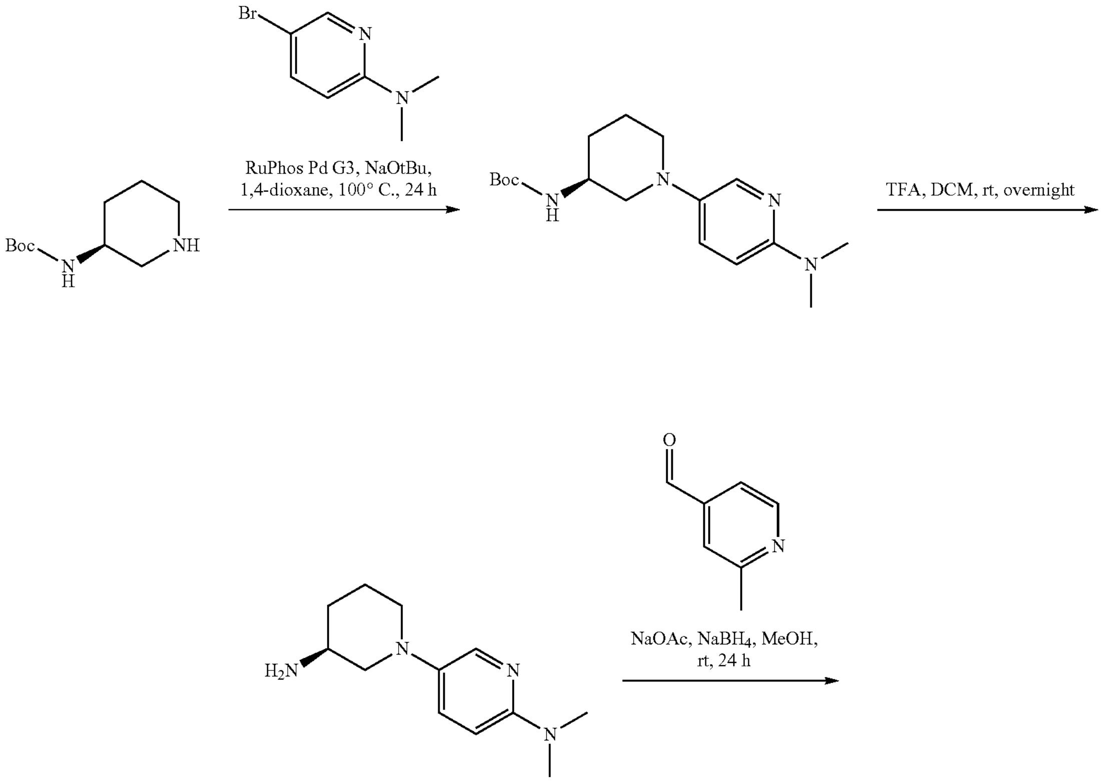

-continued

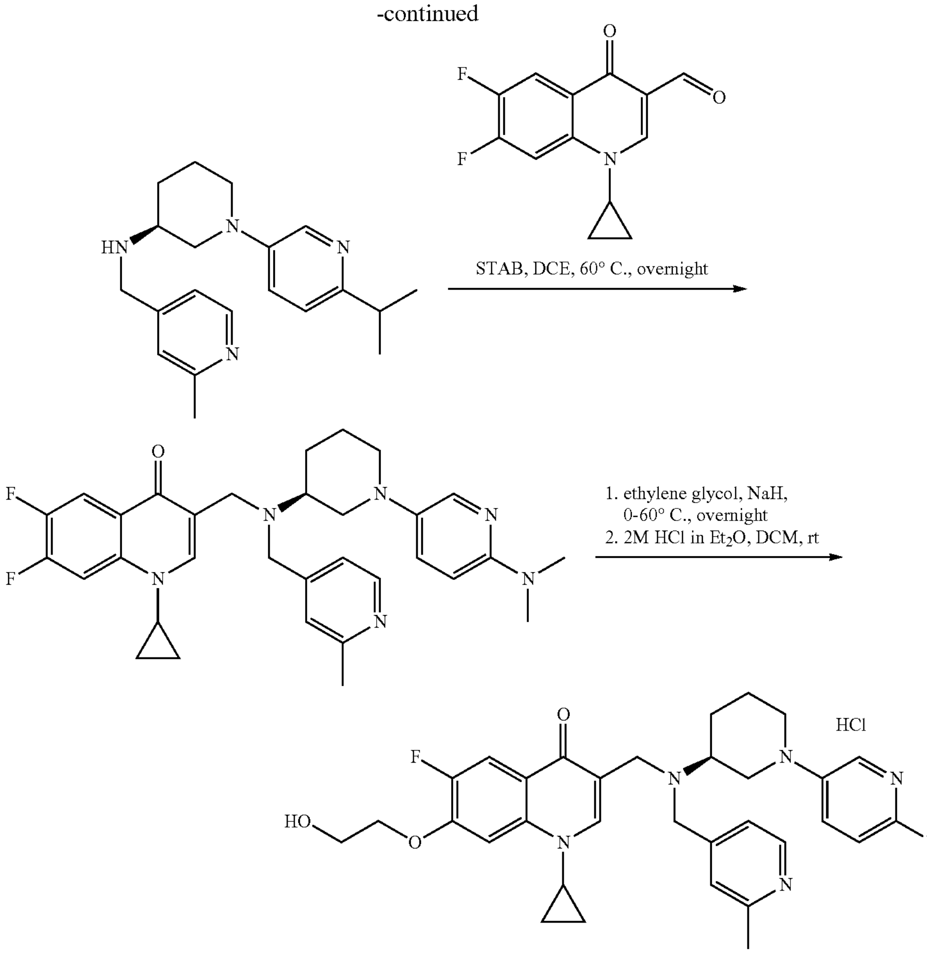

Preparation of 5-[(3S)-3-aminopiperidin-1-yl]-N,N-dimethylpyridin-2-amine trifluoroacetate A solution of (S)-3-Boc-aminopiperidine (0.55 g, 1.1 eq.), 5-bromo-N,N-dimethylpyridin-2-amine (0.50 g, 1.0 eq.) and sodium tert-butoxide (0.30 g, 1.3 eq.) in 1,4-dioxane was purged with argon for 10 min. Subsequently, RuPhos Pd G3 (0.21 g, 0.1 eq.) was added and the reaction mixture was stirred for 24 h at 100° C. The reaction mixture was filtered through a pad of celite and concentrated to dryness under reduced pressure. The residue was diluted with DCM and water. The separated organic layer was dried over anh. $Na_2SO_4$, filtered and concentrated. The crude material was purified by FCC (SiHP, DCM:EtOAc) give product (0.17 g, 21% yield) as a yellow oil. ESI-MS: 321.4 $[M+H]^+$.

Preparation of 5-[(3S)-3-aminopiperidin-1-yl]-N,N-dimethylpyridin-2-amine trifluoroacetate Trifluoroacetic acid (0.4 mL, 10.0 eq.) was added to a solution of tert-butyl N-[(3S)-1-[6-(dimethylamino)pyridin-3-yl]piperidin-3-yl]carbamate (0.17 g, 1.0 eq.) in DCM (10.0 mL) and the mixture was stirred for 3 h at RT. After that time the mixture was concentrated in vacuo and traces of moisture were azeotropically removed with MeOH to give a product (0.17 g, 94% yield) as a yellow oil. ESI-MS: 221.2 $[M+H]^+$. The product was used in next step without further purification.

Preparation of N,N-dimethyl-5-[(3S)-3{[(2-methylpyridin-4-yl)methyl]amino}piperidin-1-yl]pyridin-2-amine 2-methylpyridine-4-carbaldehyde (0.054 mL, 1.0 eq.), 5-[(3S)-3-aminopiperidin-1-yl]-N,N-dimethylpyridin-2-amine trifluoroacetate (0.17 g, 0. 1.0 eq.) and sodium acetate (0.04 g, 1.0 eq.) w dissolved in anh. methanol (5.0 mL) and the mixture was stirred overnight at RT. After that time the mixture was cooled to 0° C. and sodium borohydride (0.037 g, 2.0 eq.) was added. The reaction was stirred for 3 h at RT. The reaction mixture was then concentrated in vacuo and residue was partitioned between DCM and aqueous NaOH solution (pH was adjusted to 11). The organic layer was washed with brine, dried over $Na_2SO_4$, filtered and concentrated in vacuo. The product mixture was purified by FCC (SiHP; DCM:MeOH) to give product (0.16 g, 82% yield) as a yellow oil. ESI-MS: 326.3 $[M+H]^+$.

Preparation of 1-cyclopropyl-3-({[(3S)-1-[6-(dimethylamino)pyridin-3-yl]piperidin-3-yl][(2-methylpyridin-4-yl)methyl]amino}methyl)-6,7-difluoro-1,4-dihydroquinolin-4-one A solution of N,N-dimethyl-5-[(3S)-3-{[(2-methylpyridin-4-yl)methyl]amino}piperidin-1-yl]pyridin-2-amine (0.13 g, 1.0 eq.) and 1-cyclopropyl-6,7-difluoro-4-oxo-1,4-dihydroquinoline-3-carbaldehyde (Intermediate 4) (0.10 g, 1.1 eq.) in anh. DCE (5.0 mL) was stirred at 60° C. for 3 h, then reaction was cooled to 0° C., sodium triacethoxyborohydride (0.42 g, 5.0 eq.) was added and the reaction mixture was stirred overnight at 60° C. After that time reaction mixture was concentrated and the crude material was diluted with DCM and washed with water and brine. The organic layer was combined, dried over $Na_2SO_4$, filtered and concentrated. Crude was purified on FCC (SiHP; DCM:MeOH) to give product (0.16 g, 41% yield) as a yellow oil. ESI-MS: 559.5 $[M+H]^+$.

Preparation of 1-cyclopropyl-3-({[(3S)-1-[6-(dimethylamino)pyridin-3-yl]piperidin-3-yl][(2-methylpyridin-4-yl)methyl]amino}methyl)-6-fluoro-7-(2-hydroxyethoxy)-1,4-dihydroquinolin-4-one hydrochloride Sodium hydride (60% dispersion in mineral oil, 0.034 g, 5.0 eq.) was added in portions to a solution of 1-cyclopropyl-3-({[(3S)-1-[6-(dimethylamino)pyridin-3-yl]piperidin-3-yl][(2-methylpyridin-4-yl)methyl]amino}methyl)-6,7-difluoro-1,4-dihydroquinolin-4-one (0.16 g, 1.0 eq.) in ethylene glycol (2.0 mL). The reaction mixture was stirred at 60° C. overnight. The reaction mixture was quenched with ice-cold water and extracted with DCM (3×). The combined organic layers were washed with water, brine and dried with anh. $Na_2SO_4$, filtered and concentrated in vacuo. The residue was purified by FCC (SiHP; DCM:MeOH) to give product (0.11 g, 63% yield) as a yellow solid. ESI-MS: 601.6 $[M+H]^+$. The compound was converted to the HCl salt using 2 M HCl in $Et_2O$ (0.09 mL, 1.0 eq. to FB) and DCM as a solvent (5.0 mL) to give the product (0.12 g, 99% yield) as a green-yellow solid. HR-MS: 601.3 $[M+H]^+$. $^1H$ NMR (400 MHz, Methanol-$d_4$) δ 8.21 (d, J=5.4 Hz, 1H), 7.95 (s, 1H), 7.87 (dd, J=15.9, 10.3 Hz, 2H), 7.58 (d, J=7.1 Hz, 1H), 7.44-7.31 (m, 3H), 7.05 (d, J=9.7 Hz, 1H), 4.37-4.25 (m, 2H), 4.09-3.66 (m, 7H), 3.54-3.45 (m, 1H), 3.44-3.36 (m, 1H), 3.19 (s, 6H), 3.15-2.98 (m, 1H), 2.86 (s, 1H), 2.69 (s, 1H), 2.39 (s, 3H), 2.15 (d, J=6.9 Hz, 1H), 2.04-1.92 (m, 1H), 1.80-1.67 (m, 2H), 1.36-1.30 (m, 2H), 1.01-0.93 (m, 2H).

Example 93. 1-cyclopropyl-6-fluoro-7-(2-hydroxyethoxy)-3-({[(2-methylpyridin-4-yl)methyl][(3S)-1-[5-(trifluoromethyl)pyridin-3-yl]piperidin-3-yl]amino}methyl)-1,4-dihydroquinolin-4-one hydrochloride

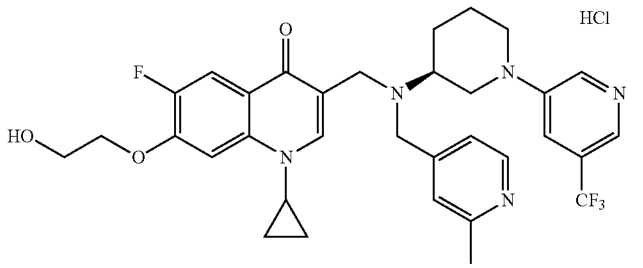 [SMILES: Cc1cc(CN(Cc2cn(C3CC3)c3cc(OCCO)c(F)cc3c2=O)[C@H]2CCCN(c3cncc(C(F)(F)F)c3)C2)ccn1 ; Cl]

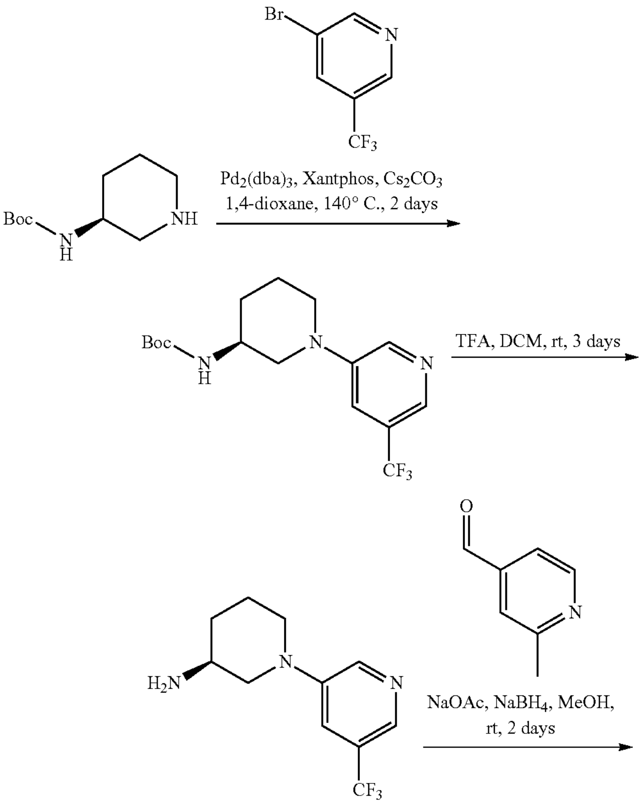

-continued

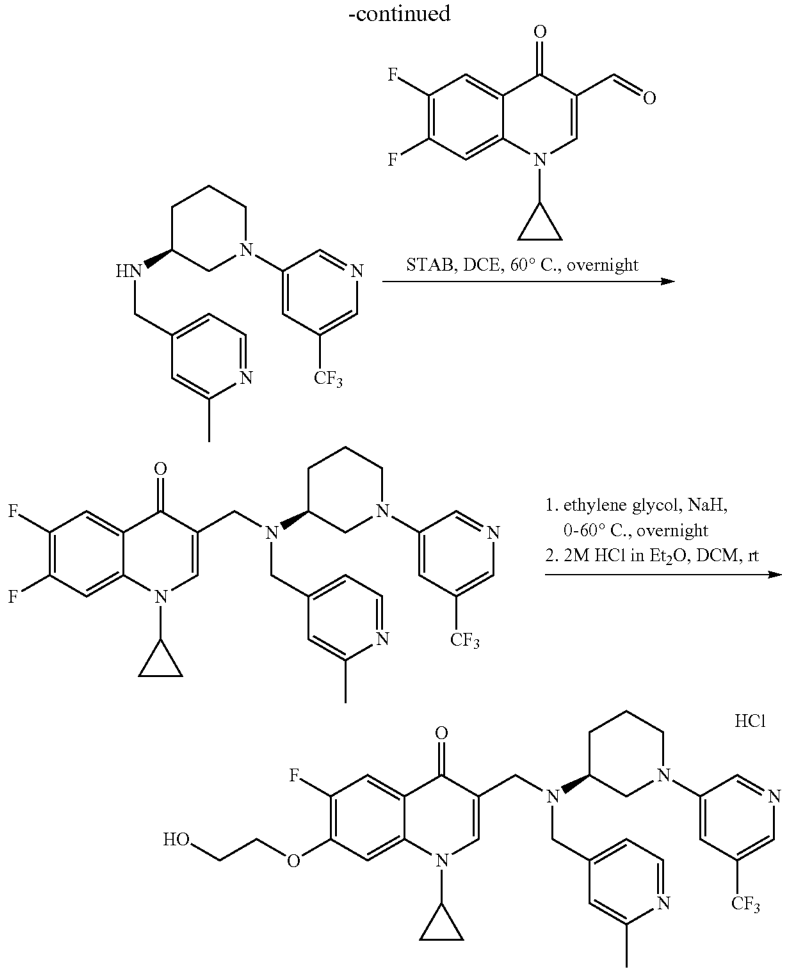

Preparation of tert-butyl N-[(3S)-1-[5-(trifluoromethyl)pyridin-3-yl]piperidin-3-yl]carbamate A suspension of 3-Bromo-5-(trifluoromethyl)pyridine (1.5 g, 1.0 eq.), (S)-3-Boc-aminopiperidine (1.7 g, 1.3 eq.) and $Cs_2CO_3$ (2.9 g, 1.4 eq.) in anh. 1,4-dioxane (20.0 mL) was sparged with argon over 20 min and after this $Pd_2(dba)_3$ (0.30 g, 0.05 eq.) and Xantphos (0.38 g, 0.1 eq.) were added. The reaction tube was closed and reaction was stirred at 140° C. for 2 days. The mixture was filtered through celite pad and concentrated in vacuo. Product was purified on FCC (SIH P; Hex:EtOAc), dissolved in EtOAc and scavenger QuadraSil MP (2.7 g) was added. The mixture was stirred overnight at RT. Scavenger was filtered off and washed with EtOAc. The solvent was concentrated to give the product (1.9 g, 82% yield) as a yellow solid. ESI-MS: 346.1 $[M+H]^+$.

Preparation of (3S)-1-[5-(trifluoromethyl)pyridin-3-yl]piperidin-3-amine trifluoroacetate Trifluoroacetic acid (4.1 mL, 10.0 eq.) was added to a solution of tert-butyl N-[(3S)-1-[5-(trifluoromethyl)pyridin-3-yl]piperidin-3-yl]carbamate (1.9 g, 1.0 eq.) in DCM (35.0 mL) at room temperature and the mixture was stirred for 3 days at RT. After that time the mixture was concentrated in vacuo and traces of moisture were removed by azeotropic distillation with MeOH to give a product (1.7 g, 99% yield) as an orange solid. The product was used in next step without further purification. ESI-MS: 246.2 $[M+H]^+$.

Preparation of (3S)—N-[(2-methylpyridin-4-yl)methyl]-1-[5-(trifluoromethyl)pyridin-3-yl]piperidin-3-amine (3S)-1-[5-(trifluoromethyl)pyridin-3-yl]piperidin-3-amine trifluoroacetate (1.7 g, 1.0 eq.), 2-methylpyridine-4-carbaldehyde (0.60 mL, 1.0 eq.) and sodium acetate (0.44 g, 1.0 eq.) were dissolved in anh. methanol (20.0 mL) and the mixture was stirred overnight at RT. After that time the mixture was cooled to 0° C. and sodium borohydride (0.41 g, 2.0 eq.) was added. The reaction was stirred overnight at RT. After that time the reaction was concentrated in vacuo and residue was extracted with DCM and aqueous NaOH solution (pH was adjusted to 11). The organic layer was washed with brine, dried over $Na_2SO_4$, filtered and concentrated under reduced pressure.

The product mixture was purified by FCC (SiHP; DCM: MeOH) to give product (1.63 g, 79% yield) as a pale yellow solid. ESI-MS: 351.3 $[M+H]^+$.

Preparation of 1-cyclopropyl-6,7-difluoro-3-({[(2-methylpyridin-4-yl)methyl][(3S)-1-[5-(trifluoromethyl)pyridin-3-yl]piperidin-3-yl]amino}methyl)-1,4-dihydroquinolin-4-one A mixture of 1-cyclopropyl-6,7-difluoro-4-oxo-1,4-dihydroquinoline-3-carbaldehyde (Intermediate 4) (0.65 g, 1.0 eq.) and (3S)—N-[(2-methylpyridin-4-yl)methyl]-1-[5-(trifluoromethyl)pyridin-3-yl]piperidin-3-amine (0.98 g, 1.0 eq.) in anh. DCE (25.0 mL) was stirred for 5 h at 50° C. Then the mixture was cooled to RT and sodium triacethoxyborohydride (2.7 g, 5.0 eq.) was added. The resulting mixture was stirred overnight at 60° C. After that time the mixture was diluted with DCM and washed with 0.1 M NaOH aq. solution. The aqueous layer was washed with DCM. The organic layer was washed with brine, dried over $Na_2SO_4$, filtered and concentrated. The product was purified by FCC (SiHP; DCM:MeOH) to give product (1.05 g, 58% yield) as a white foam. ESI-MS: 584.4 $[M+H]^+$.

Preparation of 1-cyclopropyl-6-fluoro-7-(2-hydroxyethoxy-3-({[(2-methylpyridin-4-yl)methyl][(3S)-1-[5-(trifluoromethyl)pyridin-3-yl]piperidin-3-yl]amino}methyl)-1,4-dihydroquinolin-4-one hydrochloride Sodium hydride (60% dispersion in mineral oil, 0.3 g, 5.0 eq.) was added in portions to a solution of 1-cyclopropyl-6,7-difluoro-3-({[(2-methylpyridin-4-yl)methyl][(3S)-1-[5-(trifluoromethyl)pyridin-3-yl]piperidin-3-yl]amino}methyl)-1,4-dihydroquinolin-4-one (1.05 g, 1.0 eq.) in ethylene glycol (15.0 mL) at 0° C. The mixture was stirred at 0° C. for 1 h and warmed to RT. Then the mixture was stirred overnight at 60° C. After that time the reaction was quenched by water addition. The mixture was diluted with water and washed with DCM. The organic layer was dried over $Na_2SO_4$. The product was purified by FCC (SiHP; DCM:MeOH) and re-purified by FCC using HPLC grade solvents (SiHP; DCM:MeOH) to give product (0.68 g, 72% yield) as a white foam. The compound was converted to the HCl salt using 2 M HCl in $Et_2O$ (0.5 mL, 1.0 eq. to FB) and DCM as a solvent (12.0 mL) to give the product (0.63 g, 89% yield) as a pale yellow solid. HRMS: 626.3 $[M+H]^+$. $^1H$ NMR (400 MHz, Methanol-$d_4$) δ 8.53 (d, J=2.8 Hz, 1H), 8.37 (d, J=6.0 Hz, 1H), 8.22 (s, 1H), 8.07 (s, 1H), 7.90 (d, J=11.4 Hz, 1H), 7.82 (s, 1H), 7.76 (d, J=5.5 Hz, 1H), 7.65-7.58 (m, 2H), 4.37-4.30 (m, 2H), 4.30-4.11 (m, 3H), 4.11-3.88 (m, 4H), 3.86-3.78 (m, 1H), 3.60-3.52 (m, 1H), 3.25-3.06 (m, 2H), 2.92 (td, J=12.3, 2.3 Hz, 1H), 2.57 (s, 3H), 2.31-2.19 (m, 1H), 2.06-1.95 (m, 1H), 1.91-1.66 (m, 2H), 1.43-1.32 (m, 2H), 1.11-0.97 (m, 2H).

Example 94. 1-cyclopropyl-6-fluoro-7-[(3S)-3-(hydroxymethyl)pyrrolidin-1-yl]-3-({[(2-methylpyridin-4-yl)methyl][(3S)-1-(pyrazin-2-yl)piperidin-3-yl]amino}methyl)-1,4-dihydroquinolin-4-one hydrochloride

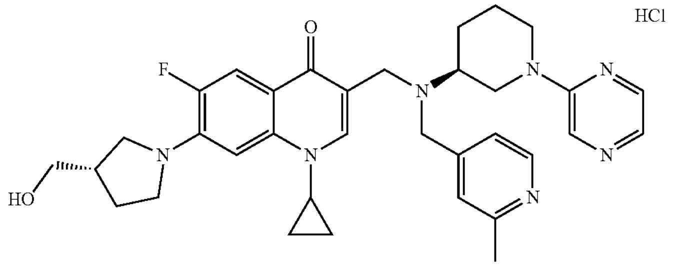

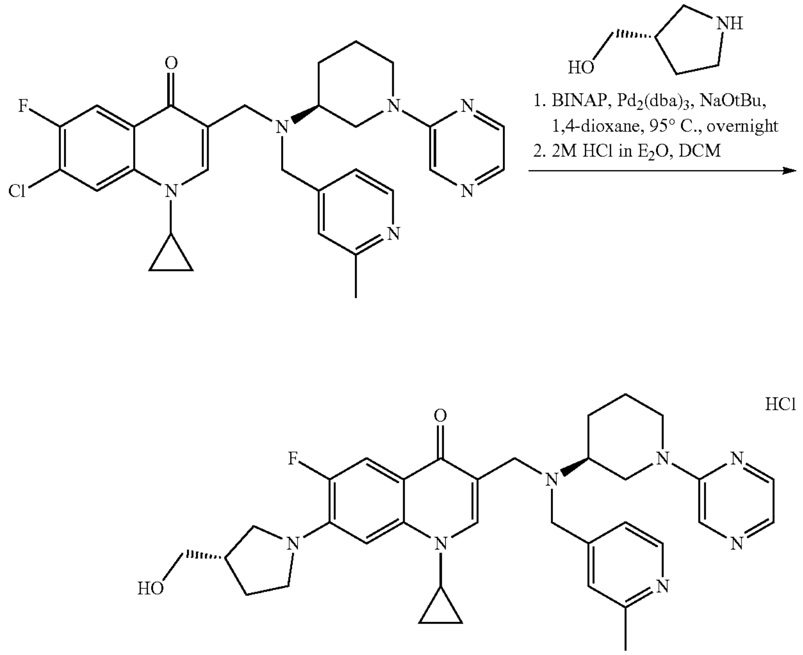

Preparation of 1-cyclopropyl-6-fluoro-7-[(3S)-3-(hydroxymethyl)pyrrolidin-1-yl]-3-({[(2-methylpyridin-4-yl)methyl][(3S)-1-(pyrazin-2-yl)piperidin-3-yl]amino}methyl)-1,4-dihydroquinolin-4-one hydrochloride The solution of 7-chloro-1-cyclopropyl-6-fluoro-3-({[(2-methylpyridin-4-yl)methyl][(3S)-1-(pyrazin-2-yl)piperidin-3-yl]amino}methyl)-1,4-dihydroquinolin-4-one (Intermediate 27) (0.80 g, 1.0 eq.) and (S)-Pyrrolidin-3-ylmethanol (0.27 g, 1.8 eq.) in anh. 1,4-dioxane (15.0 mL) was purged with argon for 15 min. Then sodium tert-butoxide (0.29 g, 2.1 eq.), BINAP (0.27 g, 0.3 eq.) and $Pd_2(dba)_3$ (0.13 g, 0.1 eq.) were added. The resulting mixture was heated overnight at 95° C. The reaction mixture was filtered through a pad of celite and concentrated under reduced pressure. The residue was dissolved in DCM and scavenger QuadraSil MP (4.0 eq.) was added.

The mixture was stirred overnight at RT. Scavenger was filtrated off and the filtrate was concentrated in vacuo. The residue was purified by FCC (SiHP; DCM:MeOH) and then re-purified by RP-FCC (C18HP; H2O:MeCN) to give a product (0.43 g, 48% yield) as a yellow foam. ESI-MS: 598.5 $[M+H]^+$. The compound was converted to the HCl salt using 2 M HCl in $Et_2O$ (0.35 mL, 1.0 eq. to FB) and DCM as a solvent (32.0 mL) to give the product (0.43 g, 94% yield) as a yellow solid. HRMS: 598.3 $[M+H]^+$. $^1H$ NMR (400 MHz, Methanol-$d_4$) δ 8.37 (d, J=6.0 Hz, 1H), 8.28 (d, J=1.5 Hz, 1H), 8.10 (dd, J=2.7, 1.5 Hz, 1H), 7.97 (s, 1H), 7.79 (d, J=2.7 Hz, 1H), 7.77-7.70 (m, 2H), 7.70-7.64 (m, 1H), 6.96 (d, J=7.6 Hz, 1H), 4.79 (d, J=12.3 Hz, 1H), 4.33 (s, 2H), 4.30-4.21 (m, 1H), 4.13 (s, 2H), 3.79-3.57 (m, 5H), 3.52-3.42 (m, 2H), 3.31-3.12 (m, 2H), 3.11-3.00 (m, 1H), 2.62-2.54 (m, 1H), 2.53 (s, 3H), 2.32-2.24 (m, 1H), 2.24-2.12 (m, 1H), 2.05-1.92 (m, 2H), 1.87 (s, 1H), 1.73-1.60 (m, 1H), 1.34 (dd, J=6.9, 1.7 Hz, 2H), 1.03 (dq, J=7.5, 3.8 Hz, 2H).

Example 95. 1-cyclopropyl-6-fluoro-3-({[(3S,5S)-5-fluoro-1-(pyrazin-2-yl)piperidin-3-yl][(2-methylpyridin-4-yl)methyl]amino}methyl)-7-(2-hydroxyethoxy)-1,4-dihydroquinolin-4-one hydrochloride

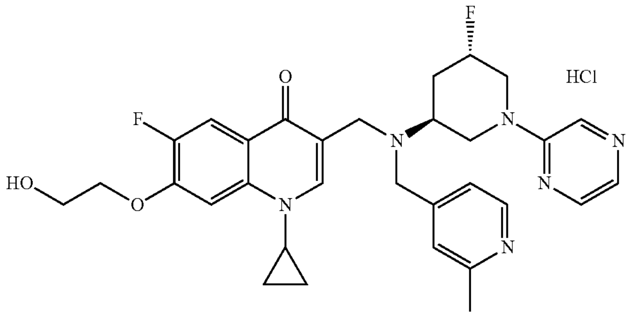 [SMILES: Cc1cc(CN(Cc2cn(C3CC3)c3cc(OCCO)c(F)cc3c2=O)[C@H]2C[C@H](F)CN(c3cnccn3)C2)ccn1 ; Cl]

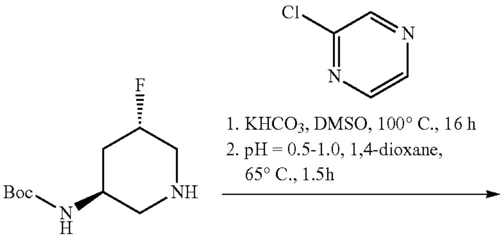

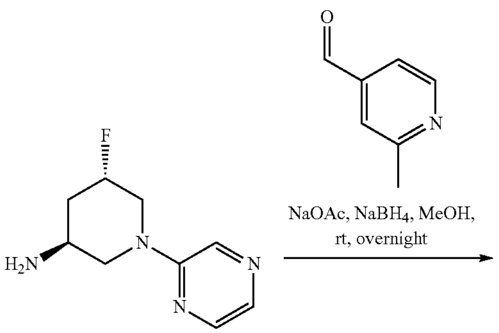

-continued

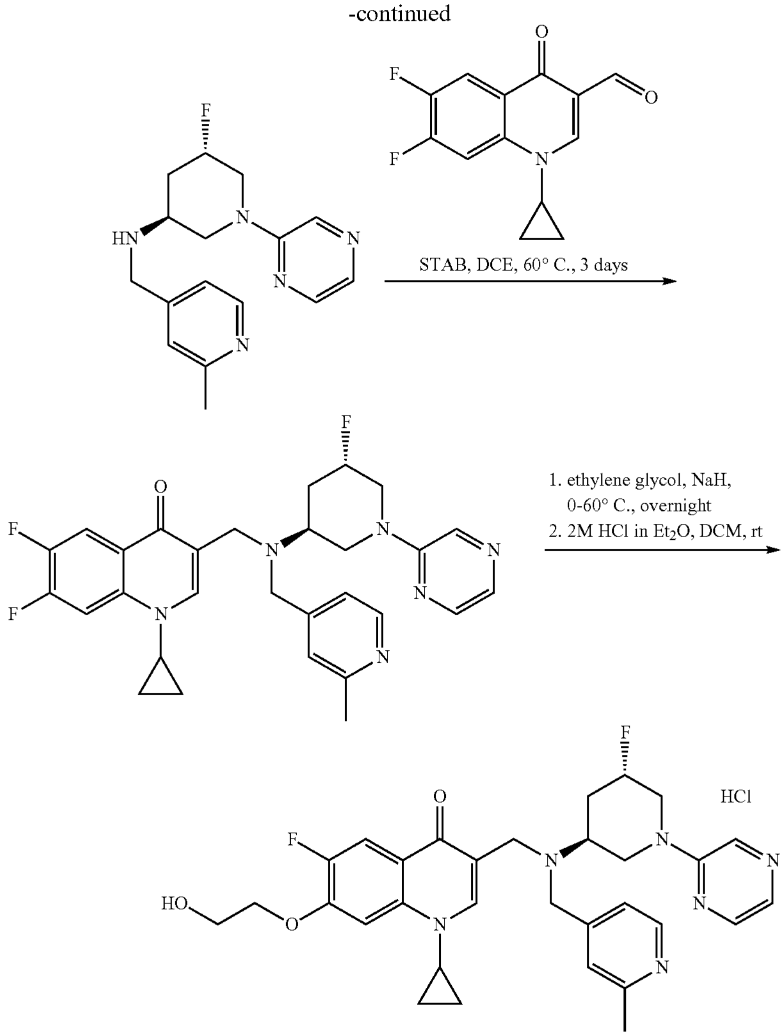

Preparation of (3S,5S)-5-fluoro-1-(pyrazin-2-yl) piperidin-3-amine

2-Chloropyrazine (0.9 g, 1.0 eq.) was added to the mixture of $KHCO_3$ (1.6 g, 2.0 eq.), tert-butyl N-[(3S,5S)-5-fluoropiperidin-3-yl]carbamate (1.9 g, 1.1 eq.) in DMSO (10.0 mL) under inert atmosphere. The reaction mixture was stirred at 100° C. for 16 h. The reaction was cooled to RT and water was added (50.0 mL). The reaction mixture was washed with diethyl ether (3x20.0 mL). The combined organic layers were dried over $Na_2SO_4$ filtered and the volatiles were evaporated to furnish an orange oil (2.2 g). ESI-MS: 297.4 $[M+H]^+$. The orange oil was then dissolved in 1,4-dioxane (20.0 mL). The pH of the mixture was adjusted to between pH=0.5-1.0. The solution was then heated at 65° C. for 1.5 h. The reaction was cooled to RT and the volatiles were evaporated. The crude mixture was then dissolved in water (20.0 mL) and basified using NaOH (solid) until pH>12. The organics were extracted using EtOAc (3x20.0 mL), the organic layer dried over $Na_2SO_4$, filtered and the volatiles were evaporated to obtain the product (0.78 g, 51% yield) as a yellow oil. ESI-MS: 197.1 $[M+H]^+$.

Preparation of (3S,5S)-5-fluoro-N-[(2-methylpyridin-4-yl)methyl]-1-(pyrazin-2-yl)piperidin-3-amine A mixture of (3S,5S)-5-fluoro-1-(pyrazin-2-yl)piperidin-3-amine (0.78 g, 1.0 eq.), 2-methylpyridine-4-carboalde-hyde (0.45 mL, 1.1 eq.), sodium acetate (0.33 g, 1.0 mL) and anh. methanol (20.0 mL) was stirred overnight at RT under $N_2$. Sodium borohydride (0.20 g, 1.3 eq.) was added to the mixture in portions over 10 min. The mixture was then stirred at RT for 1 h. Then MeOH was evaporated and the crude material was dissolved in DCM (50.0 mL) and washed with water (2x20.0 mL). Organic layers were combined, dried over $Na_2SO_4$, filtered and concentrated. Crude product was purified by RP-FCC (C18HP; $H_2O$:MeCN) to give desired product (0.66 g, 55% yield) as a light yellow oil. ESI-MS: 302.4 $[M+H]^+$.

Preparation of 1-cyclopropyl-6,7-difluoro-3-({[(3S, 5S)-5-fluoro-1-(pyrazin-2-yl)piperidin-3-yl][(2-methylpyridin-4-yl)methyl]amino}methyl)-1,4-dihy-droquinolin-4-one A mixture of 1-cyclopropyl-6,7-difluoro-4-oxo-1,4-dihy-droquinoline-3-carbaldehyde (Intermediate 4) (0.72 g, 1.3 eq.) and (3S,5S)-5-fluoro-N-[(2-methylpyridin-4-yl)

methyl]-1-(pyrazin-2-yl)piperidin-3-amine (0.66 g, 1.0 eq.) in anh. DCE (22.0 mL) was heated at 60° C. for 4 h. Then the mixture was cooled to 0° C. and sodium triacethoxyborohydride (1.8 g, 4.0 eq.) was added in portions. The resulting mixture was stirred 2 days at RT. 1-cyclopropyl-6,7-difluoro-4-oxo-1,4-dihydroquinoline-3-carbaldehyde (0.36 g, 0.65 eq.) and sodium triacethoxyborohydride (0.92 g, 2.0 eq.) were added and reaction mixture was stirred overnight at RT. The reaction mixture was quenched with water and washed with DCM. Organic layer was washed with brine, dried over $Na_2SO_4$ and concentrated in vacuo. Crude product was purified by FCC (SiHP, DCM:MeOH), re-purified by FCC (SiHP, EtOAc:MeOH) to give product (0.85 g, 71% yield) as a white solid. ESI-MS: 535.4 $[M+H]^+$.

Preparation of 1-cyclopropyl-6-fluoro-3-({[(3S,5S)-5-fluoro-1-(pyrazin-2-yl)piperidin-3-yl][(2-methylpyridin-4-yl)methyl]amino}methyl)-7-(2-hydroxyethoxy)-1,4-dihydroquinolin-4-one hydrochloride 1-Cyclopropyl-6,7-difluoro-3-({[(3S,5S)-5-fluoro-1-(pyrazin-2-yl)piperidin-3-yl][(2-methylpyridin-4-yl)methyl]amino}methyl)-1,4-dihydroquinolin-4-one (0.85 g, 1.0 eq.) was dissolved in ethylene glycol (15.0 mL) and the mixture was cooled to 0° C. Then sodium hydride (60% dispersion in mineral oil, 0.31 g, 5.0 eq.) was added in portions. The resulting mixture was stirred at 60° C. overnight. The reaction mixture was diluted with water and extracted to DCM. Organic layers were washed with brine, dried over $Na_2SO_4$ and concentrated in vacuo. Crude product was purified by FCC (SiHP; DCM:MeOH) and re-purified by FCC (SiHP; DCM:MeOH) using HPLC grade solvents to give product (0.89 g, 81% yield). ESI-MS: 577.4 $[M+H]^+$. The compound (0.7 g) was converted to the HCl salt using 2 M HCl in $Et_2O$ (0.6 mL, 1.0 eq. to FB) and DCM as a solvent (10.0 mL) to give the product (0.69 g, 90% yield) as a yellow solid. HR-MS: 577.3 $[M+H]^+$. $^1H$ NMR (400 MHz, Methanol-$d_4$) δ 8.45 (d, J=6.1 Hz, 1H), 8.26 (d, J=1.3 Hz, 1H), 8.09 (s, 1H), 8.06 (dd, J=2.7, 1.5 Hz, 1H), 7.97 (s, 1H), 7.93-7.86 (m, 2H), 7.75 (d, J=2.7 Hz, 1H), 7.62 (d, J=7.1 Hz, 1H), 5.09 (d, J=48.4 Hz, 1H), 4.81 (d, J=12.6 Hz, 1H), 4.59 (t, J=13.6 Hz, 1H), 4.36-4.30 (m, 2H), 4.18 (s, 2H), 4.04-3.98 (m, 2H), 3.91-3.80 (m, 2H), 3.56 (tt, J=7.2, 4.0 Hz, 1H), 3.31-3.08 (m, 3H), 2.67 (s, 3H), 2.52-2.40 (m, 1H), 2.18-1.99 (m, 1H), 1.40-1.30 (m, 2H), 1.10-0.93 (m, 2H).

Example 96. 1-cyclopropyl-6-fluoro-7-(2-hydroxyethoxy)-3-({[(2-methylpyridin-4-yl)methyl][(3S)-1-(pyridazin-3-yl)piperidin-3-yl]amino}methyl)-1,4-dihydroquinolin-4-one

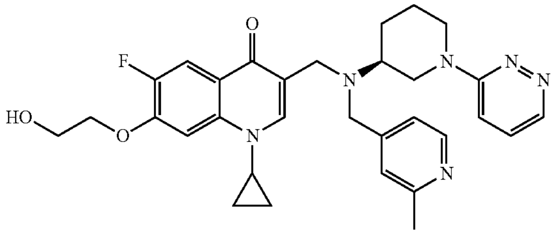

-continued

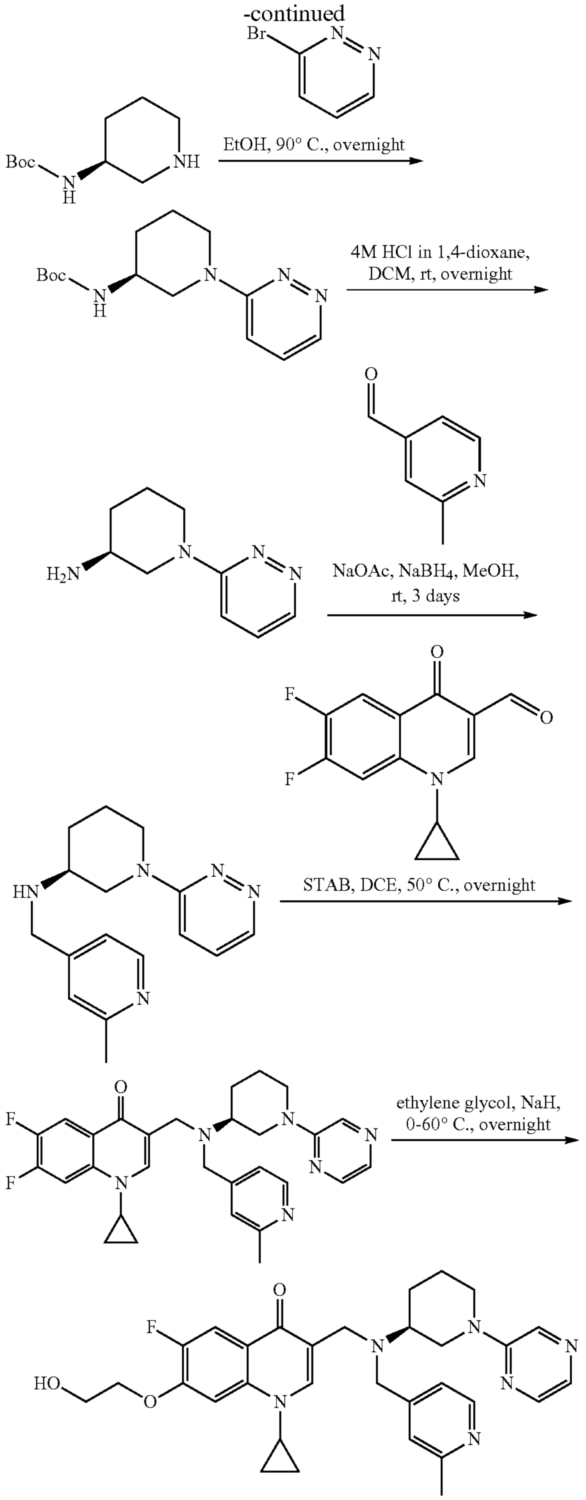

Preparation of tert-butyl N-[(3S)-1-(pyridazin-3-yl)piperidin-3-yl]carbamate A solution of 3-bromopyridazine (1.0 g, 1.0 eq.) and (S)-3-Boc-aminopiperidine (5.0 g, 4.0 eq.) in EtOH (63.0 mL) was heated overnight at 90° C. Solvent was evaporated and the residue was dissolved in DMC and washed with water and brine. The separated organic layer was dried over anh. $Na_2SO_4$, filtered and concentrated in vacuo. Crude product was purified by FCC (SiHP; DCM:MeOH) to give product (1.2 g, 66% yield) as an orange oil. ESI-MS: 279.2 $[M+H]^+$.

Preparation of (3S)-1-(pyridazin-3-yl)piperidin-3-amine hydrochloride tert-Butyl N-[(3S)-1-(pyridazin-3-yl)piperidin-3-yl]carbamate (1.33 g, 1.0 eq.) was dissolved in DCM (8.0 mL) and 4 M hydrogen chloride in 1,4-dioxane (5.9 mL, 5.0 eq.) was added. The reaction mixture was stirred overnight at RT. Solvents were evaporated. The residue was co-concentrated with DCM several times to give product (1.1 g, quantitative yield) as an orange solid. ESI-MS: 179.1 $[M+H]^+$.

Preparation of (3S)—N-[(2-methylpyridin-4-yl)methyl]-1-(pyridazin-3-yl)piperidin-3-amine A solution of (3S)-1-(pyridazin-3-yl)piperidin-3-amine hydrochloride (1.1 g, 1.0 eq.), 2-methylpyridine-4-carbaldehyde (0.70 mL, 1.3 eq.) and sodium acetate (0.61 g, 1.5 eq.) in anh. methanol (16.0 mL) was stirred for 3 days at RT. After that time, the mixture was cooled to 0° C. and sodium borohydride (0.37 g, 2.0 eq.) was added. The reaction was stirred at RT for 1.5 h. Solvent was evaporated. The residue was dissolved in DMC and washed with 1 M NaOH and subsequently with brine. Separated organic layer was dried over anh. $Na_2SO_4$, filtered and concentrated in vacuo. Crude product was purified by FCC (SiHP; DCM:MeOH) to give product (0.97 g, 69% yield) as a yellow oil. ESI-MS: 284.1 $[M+H]^+$.

Preparation of 1-cyclopropyl-6,7-difluoro-3-({[(2-methylpyridin-4-yl)methyl][(3S)-1-(pyridazin-3-yl)piperidin-3-yl]amino}methyl)-1,4-dihydroquinolin-4-one A mixture of 1-cyclopropyl-6,7-difluoro-4-oxo-1,4-dihydroquinoline-3-carbaldehyde (Intermediate 4) (1.12 g, 1.3 eq.) and (3S)—N-[(2-methylpyridin-4-yl)methyl]-1-(pyridazin-3-yl)piperidin-3-amine (0.97 g, 1.0 eq.) in anh. DCE (34.0 mL) was heated overnight at 50° C. Then the mixture was cooled to 0° C. and sodium triacethoxyborohydride (2.9 g, 4.0 eq.) was added. The resulting mixture was stirred for 1.5 h at RT. The reaction mixture was quenched with water and washed with DCM. Separated organic layer was washed with brine, dried over $Na_2SO_4$ and concentrated in vacuo. The crude product was purified by FCC (SiHP, DCM:MeOH) to give product (0.72 g, 40% yield) as a yellow solid. ESI-MS: 517.3 [M+H]r.

Preparation of 1-cyclopropyl-6-fluoro-7-(2-hydroxyethoxy-3-({[(2-methylpyridin-4-yl)methyl][(3S)-1-(pyridazin-3-yl)piperidin-3-yl]amino}methyl)-1,4-dihydroquinolin-4-one 1-cyclopropyl-6,7-difluoro-3-({[(2-methylpyridin-4-yl)methyl][(3S)-1-(pyridazin-3-yl)piperidin-3-yl]amino}methyl)-1,4-dihydroquinolin-4-one (0.72 g, 1.0 eq.) was dissolved in ethylene glycol (14.0 mL) and mixture was cooled to 0° C. Then sodium hydride (60% dispersion in mineral oil, 0.27 g, 5.0 eq.) was added in portions. The resulting mixture was stirred at 60° C. overnight. The reaction mixture was diluted with water and extracted to DCM. Organic layers were washed with brine, dried over $Na_2SO_4$ and concentrated in vacuo. The crude product was purified by RP-FCC (C18HP; $H_2O$:MeCN) and re-purified twice by FCC (SiHP; DCM:MeOH to give product (0.13 g, 15% yield) as a white solid. ESI-MS: 559.5 $[M+H]^+$. $^1H$ NMR (400 MHz, Methanol-$d_4$) δ 8.43 (dd, J=4.4, 1.2 Hz, 1H), 8.17 (d, J=5.2 Hz, 1H), 7.98 (s, 1H), 7.91 (d, J=11.6 Hz, 1H), 7.57 (d, J=7.2 Hz, 1H), 7.39-7.35 (m, 1H), 7.31-7.28 (m, 1H), 7.28-7.26 (m, 1H), 7.25-7.21 (m, 1H), 4.74-4.68 (m, 1H), 4.33-4.26 (m, 3H), 4.02-3.98 (m, 2H), 3.90-3.86 (m, 2H), 3.84-3.78 (m, 2H), 3.53-3.47 (m, 1H), 3.14-3.06 (m, 1H), 2.99-2.91 (m, 1H), 2.90-2.82 (m, 1H), 2.36 (s, 3H), 2.22-2.14 (m, 1H), 1.96-1.89 (m, 1H), 1.87-1.76 (m, 1H), 1.66-1.54 (m, 1H), 1.36-1.29 (m, 2H), 0.99-0.93 (m, 2H).

Example 97. 3-({[(3S)-1-(6-chloropyridin-3-yl)piperidin-3-yl][(2-methylpyridin-4-yl)methyl]amino}methyl)-1-cyclopropyl-6-fluoro-7-(2-hydroxyethoxy)-1,4-dihydroquinolin-4-one hydrochloride

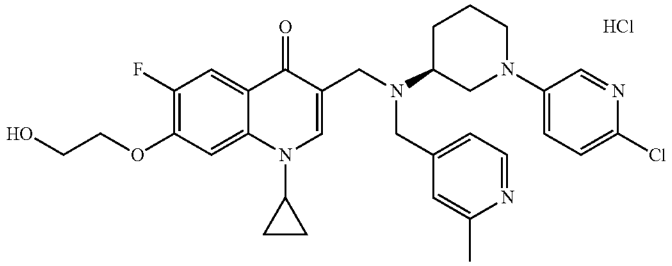

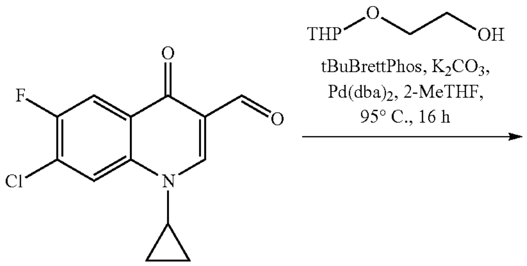

-continued
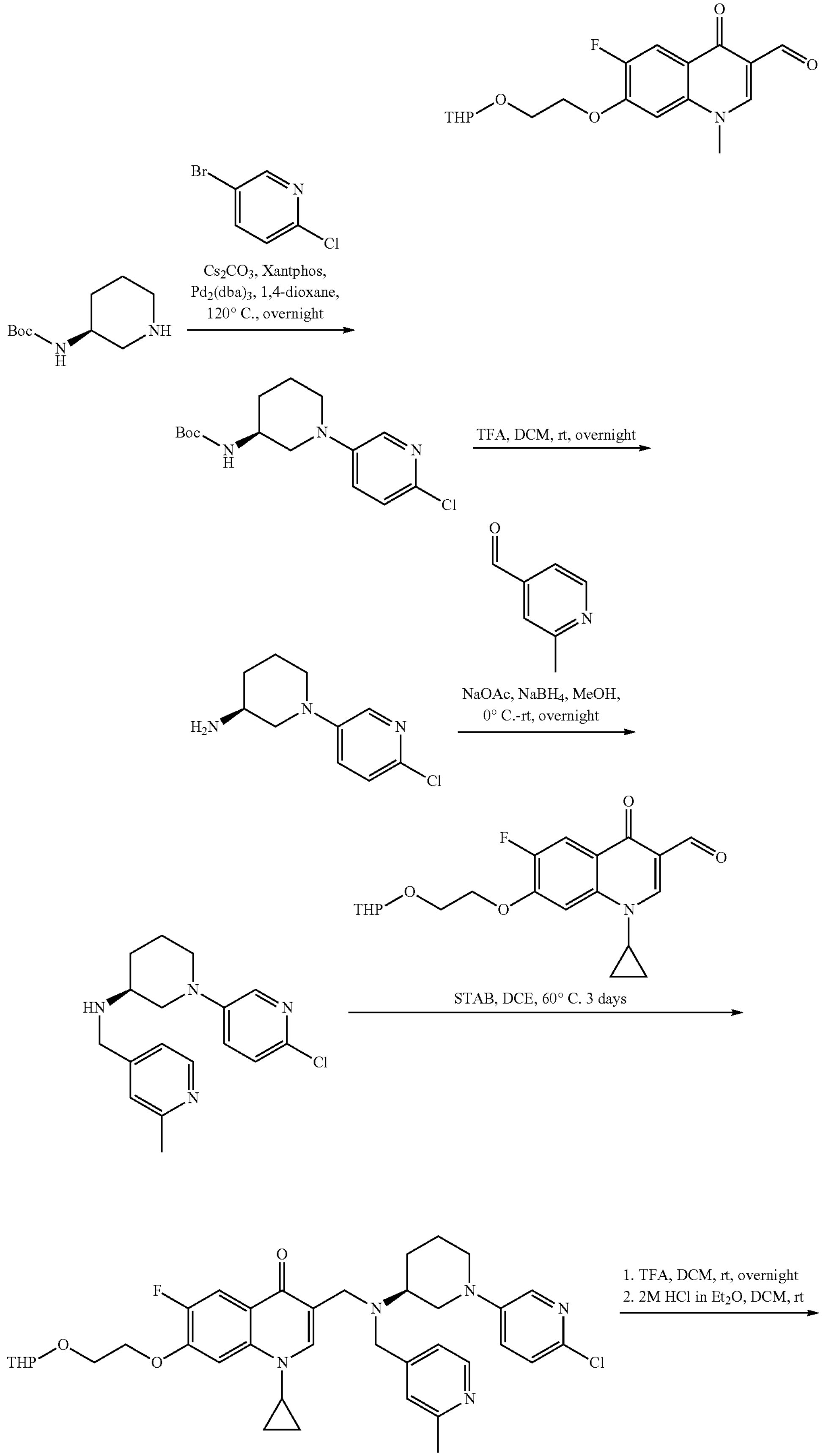

-continued

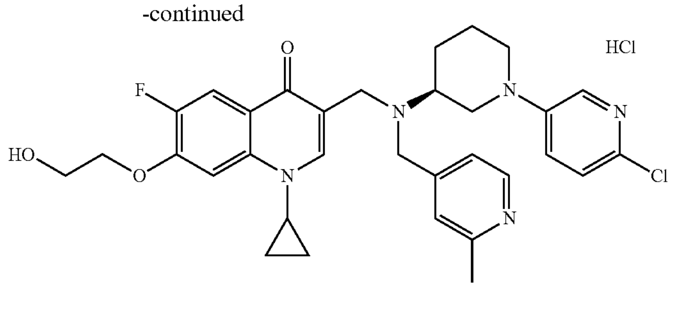

Preparation of tert-butyl N-[(3S)-1-(6-chloropyridin-3-yl)piperidin-3-yl]carbamate A solution of(S)-3-Boc-aminopiperidine (1.04 g, 1.0 eq.), 5-bromo-2-chloropyridine (1.0 g, 1.0 eq.) and $Cs_2CO_3$ (3.4 g, 2.0 eq.) in 1,4-dioxane (20.0 mL) was purged with argon for 10 min. Then Xantphos (0.3 g, 0.10 eq.) and $Pd_2(dba)_3$ (0.24 g, 0.05 eq.) were added and the reaction mixture was stirred overnight at 120° C. Two identical reactions starting with 0.1 g of 5-bromo-2-chloropyridine were also carried out at the same time. The crude reaction mixtures of all these batches were combined. diluted with DCM and washed with water. Aqueous layer was washed with DCM and the organic layer was washed with brine, dried over $Na_2SO_4$, filtered and concentrated in vacuo. The mixture obtained was purified by FCC (SiHP; Hex:EtOAc). Product was dissolved in EtOAc and 4.0 eq of scavenger QuadraSil MP were added. The mixture was stirred overnight at RT. After that time the mixture was filtered. Filtrate was concentrated in vacuo to give product (1.09 g, 56% yield) as a yellow solid. ESI-MS: 312.1 $[M+H]^+$.

Preparation of (3S)-1-(6-chloropyridin-3-yl)piperidin-3-amine trifluoroacetate

Trifluoroacetic acid (2.6 mL, 10.0 eq.) was added to a solution od tert-butyl N-[(3S)-1-(6-chloropyridin-3-yl)piperidin-3-yl]carbamate (1.09 g, 1.0 eq.) in DCM (15.0 mL). The mixture was stirred overnight at RT. After that time the mixture was concentrated in vacuo after dilution with DCM. The product (1.1 g, 89% yield) was used in next step without further purification. ESI-MS: 212.1 $[M+H]^+$.

Preparation of (3S)-1-(6-chloropyridin-3-yl)-N-[(2-methylpyridin-4-yl)methyl]piperidin-3-amine (3S)-1-(6-chloropyridin-3-yl)piperidin-3-aminetrifluoroacetate (1.1 g, 1.0 eq.), 2-methylpyridine-4-carbaldehyde (0.47 mL, 1.4 eq.) and sodium acetate (0.25 g, 1.0 eq.) were dissolved in anh. MeOH (15.0 mL) and the mixture was stirred overnight at RT. After that time the mixture was cooled to 0° C. and sodium borohydride (0.23 g, 2.0 eq.) was added. The reaction was stirred at RT for 2 h. After that time the reaction was concentrated in vacuo and residue was partitioned between DCM and water. The organic layer was washed with brine, dried over $Na_2SO_4$, filtered and concentrated. The product mixture was purified by FCC (SiHP; DCM:MeOH) to give a product (0.82 g, 81% yield) as a yellow oil. ESI-MS: 317.9 [M+2]+.

Preparation of 1-cyclopropyl-6-fluoro-7-[2-(oxan-2-yloxy)ethoxy]-4-oxo-1,4-dihydroquinoline-3-carbaldehyde 7-chloro-1-cyclopropyl-6-fluoro-4-oxo-1,4-dihydroquinoline-3-carbaldehyde (Intermediate 9)(1.0 g, 1.0 eq.), dipotassium carbonate (1.02 g, 2.0 eq.), tBuBrettPhos (0.045 g, 0.025 eq.) and $Pd(dba)_2$ (0.027 g, 0.013 eq.) were dissolved in 2-methyltetrahydrofuran (10.0 mL) under nitrogen atmosphere. Then, 2-(Tetrahydro-2H-pyran-2-yloxy)ethanol (0.60 mL, 1.2 eq.) was added. The reaction mixture was stirred at 95° C. for 16 h. After completion of the reaction, 10 mL of water was added to the reaction mixture. It was stirred for 15 min and 10 mL of 2-MeTHF was added. Then, the biphasic mixture was poured into a separatory funnel and organic phase was collected. The aqueous phase was washed with 2-MeTHF (3×10 mL). Combined organic layers were dried over sodium sulphate, filtered and concentrated to half of its volume. 20 mL of n-heptane was added and the 2-MeTHF was evaporated under reduced pressure. During evaporation, yellow solids precipitated. Solid was filtered and dried on vacuum to give a product (0.49 g, 33% yield). ESI-MS: 376.5 $[M+H]^+$.

Preparation of 3-({[(3S)-1-(6-chloropyridin-3-yl)piperidin-3-yl][(2-methylpyridin-4-yl)methyl]amino}methyl)-1-cyclopropyl-6-fluoro-7-[2-(oxan-2-yloxy)ethoxy]-1,4-dihydroquinolin-4-one A mixture of 1-cyclopropyl-6-fluoro-7-[2-(oxan-2-yloxy)ethoxy]-4-oxo-1,4-dihydroquinoline-3-carbaldehyde (0.09 g, 1.0 eq.) and (3S)-1-(6-chloropyridin-3-yl)-N-[(2-methylpyridin-4-yl)methyl]piperidin-3-amine (0.097 g, 1.4 eq.) in anh. DCE (2.0 mL) was stirred for 1 h at RT. Then STAB (0.221 g, 5.0 eq.) was added and the mixture was stirred over weekend at RT. After that time the mixture was diluted with DCM and washed with water. Aqueous layer was extracted with DCM. The organic layer was washed with brine, dried over $Na_2SO_4$, filtered and evaporated. The product was purified by FCC (SiHP; DCM:MeOH) to give product (0.124 g, 70% yield). ESI-MS: 676.7 $[M+H]^+$.

Preparation of 3-({[(3S)-1-(6-chloropyridin-3-yl)piperidin-3-yl][(2-methylpyridin-4-yl)methyl]amino}methyl)-1-cyclopropyl-6-fluoro-7-(2-hydroxyethoxy)-1,4-dihydroquinolin-4-one hydrochloride Trifluoroacetic acid (0.055 mL, 5.0 eq.) was added to a solution of 3-({[(3S)-1-(6-chloropyridin-3-yl)piperidin-3-yl][(2-methylpyridin-4-yl)methyl]amino}methyl)-1-cyclopropyl-6-fluoro-7-[2-(oxan-2-yloxy)ethoxy]-1,4-dihydroquinolin-4-one (0.124 g, 1.0 eq.) in DCM (1.5 mL) and the mixture was stirred overnight at RT. After that time the mixture was concentrated in vacuo. The residue was dissolved in water, basified with saturated $NaHCO_3$, and extracted with DCM. The organic layer was washed with brine, dried over $Na_2SO_4$, filtered and concentrated in vacuo. The product mixture was purified by FCC (SiHP;

DCM:MeOH) and the residue was dissolved in MeOH, scavenger QuadraSip MP was added and the mixture was stirred for 48 h at RT. After that time the mixture was filtered off and filtrate was concentrated in vacuo. The residue was re-purified by FCC (SiHP; DCM:MeOH) to give product (0.065 g, yield 72%) as a colorless oil. ESI-MS: 592.6 $[M+H]^+$. The compound was converted to the HCl salt using 2 M HCl in $Et_2O$ (0.05 mL, 1.0 eq. to FB) and DCM as a solvent (1.0 mL) to give the product (0.056 g, 85% yield) as a white solid. $^1$H NMR (400 MHz, Methanol-$d_4$) δ 8.39 (d, J=6.0 Hz, 1H), 8.08 (s, 1H), 8.03 (d, J=3.1 Hz, 1H), 7.90 (d, J=11.4 Hz, 1H), 7.81 (br s, 1H), 7.76 (br d, 1H), 7.63 (d, J=7.1 Hz, 1H), 7.46 (dd, J=8.9, 3.2 Hz, 1H), 7.25 (d, J=8.9 Hz, 1H), 4.37-4.30 (m, 2H), 4.30-4.19 (m, 2H), 4.12-3.91 (m, 5H), 3.69-3.62 (m, 1H), 3.60-3.52 (m, 1H), 3.27-3.17 (m, 1H), 3.14-3.03 (m, 1H), 2.91-2.81 (m, 1H), 2.57 (s, 3H), 2.26-2.19 (m, 1H), 2.04-1.95 (m, 1H), 1.88-1.66 (m, 2H), 1.41-1.33 (m, 2H), 1.11-1.00 (m, 2H).

Example 98. 1-cyclopropyl-6-fluoro-7-[(3S)-3-hydroxypiperidin-1-yl]-3-({[(2-methylpyridin-4-yl)methyl][(3S)-1-(pyrazin-2-yl)piperidin-3-yl]amino}methyl)-1,4-dihydroquinolin-4-one hydrochoride

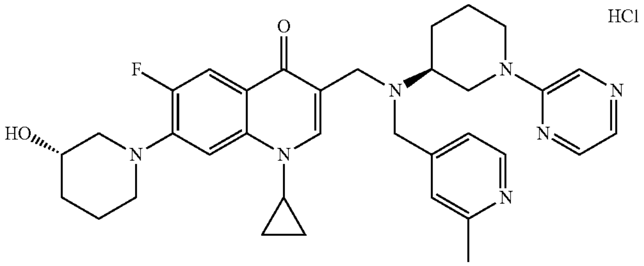

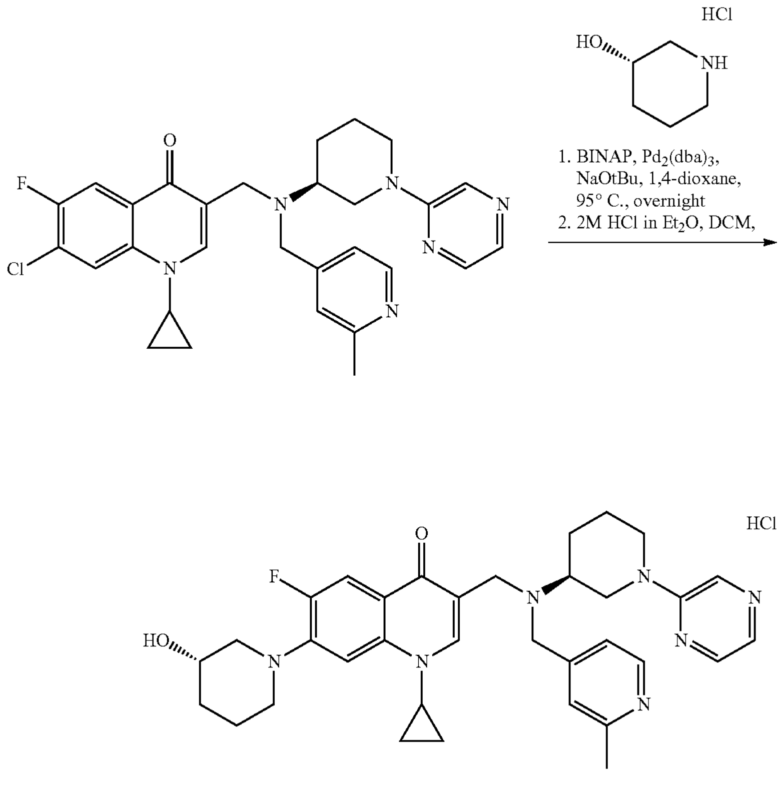

Preparation of 1-cyclopropyl-6-fluoro-7-[(3S)-3-hydroxypiperidin-1-yl]-3-({[(2-methylpyridin-4-yl)methyl][(3S)-1-(pyrazin-2-yl)piperidin-3-yl]amino}methyl)-1,4-dihydroquinolin-4-one hydrochloride 7-chloro-1-cyclopropyl-6-fluoro-3-({[(2-methylpyridin-4-yl)methyl][(3S)-1-(pyrazin-2-yl)piperidin-3-yl]amino}methyl)-1,4-dihydroquinolin-4-one (Intermediate 27) (0.8 g, 1.0 eq.), (3S)-Piperidin-3-ol, HCl (0.36 g, 1.8 eq.) and sodium tert-butoxide (0.29 g, 2.1 eq.) were dissolved in anh. 1,4-dioxane (15.0 mL) and purged with argon for 15 min. Then BINAP (0.27 g, 0.3 eq.) and $Pd_2(dba)_3$ (0.13 g, 0.1 eq.) were added and reaction was stirred overnight at 95° C. Reaction mixture was cooled to RT and filtered through a pad of celite. The filtrate was concentrated and then residue was dissolved in DCM and washed with water. Organic layers were collected, dried over anh. $Na_2SO_4$, filtered and evaporated. Product was purified by FCC (SHiP, DCM: MeOH). The Residue was dissolved in anh. DCM and 4.0 eq. of Scavenger QuadraSip MP was added. The mixture was stirred overnight at RT. After that time the mixture was filtered off. Filtrate was concentrated under reduced pressure and the product was re-purified by FCC (SHiP, DCM: MeOH) to obtain the product (0.58 g, 66% yield) as a beige solid. ESI-MS: 598.5 $[M+H]^+$. The compound was converted to the HCl salt using 2 M HCl in $Et_2O$ (0.5 mL, 1.0 eq. to FB) and DCM as a solvent (43.0 mL) to give the product (0.59 g, yield 97%) as a yellow solid. HR-MS: 598.3 $[M+H]^+$. $^1H$ NMR (400 MHz, Methanol-$d_4$) δ 8.40 (d, J=5.9 Hz, 1H), 8.26 (d, J=1.5 Hz, 1H), 8.11-8.07 (m, 1H), 8.05 (s, 1H), 7.86-7.69 (m, 4H), 7.45 (d, J=7.4 Hz, 1H), 4.76 (d, J=12.4 Hz, 1H), 4.38-4.20 (m, 3H), 4.15-3.96 (m, 2H), 3.93-3.82 (m, 1H), 3.68 (dd, J=11.7, 3.9 Hz, 1H), 3.59-3.44 (m, 2H), 3.29-3.06 (m, 2H), 3.06-2.94 (m, 2H), 2.86 (dd, J=11.7, 8.6 Hz, 1H), 2.56 (s, 3H), 2.31-2.19 (m, 1H), 2.13-2.02 (m, 1H), 2.02-1.86 (m, 3H), 1.83-1.69 (m, 1H), 1.69-1.58 (m, 1H), 1.58-1.46 (m, 1H), 1.43-1.27 (m, 2H), 1.11-0.98 (m, 2H).

Example 99. N-{5-[(3S)-3-{[(1-cyclopropyl-6,7-difluoro-4-oxo-1,4-dihydroquinolin-3-yl)methyl][(2-methoxypyridin-4-yl)methyl]amino}piperidin-1-yl]pyridin-2-yl}acetamide

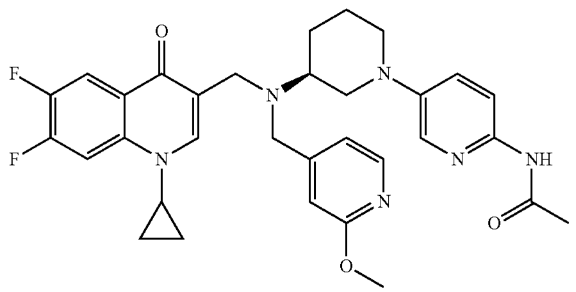

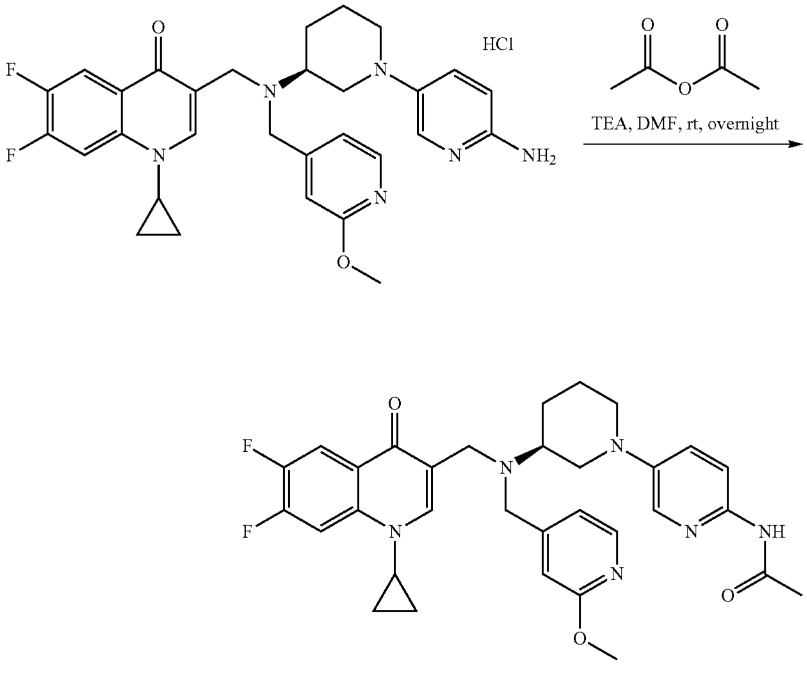

Preparation of N-{5-[(3S)-3-{[(1-cyclopropyl-6,7-difluoro-4-oxo-1,4-dihydroquinolin-3-yl)methyl][(2-methoxypyridin-4-yl)methyl]amino}piperidin-1-yl]pyridin-2-yl}acetamide TEA (0.21 mL, 6.0 eq.) was added to a mixture of 3-({[(3S)-1-(6-aminopyridin-3-yl)piperidin-3-yl][(2-methoxypyridin-4-yl)methyl]amino}methyl)-1-cyclopropyl-6,7-difluoro-1,4-dihydroquinolin-4-one hydrochloride (Example 4) (0.15 g, 1.0 eq.) in DMF (1.0 mL) placed in an ice bath and was followed by dropwise addition of $Ac_2O$ (0.029 mL, 1.2 eq.). The resulting mixture was stirred overnight at RT. The reaction mixture was concentrated in vacuo and then concentrated again after dilution with n-heptane. The residue was purified by FCC (SiHP; DCM:MeOH) to give the product (0.12 g, 76% yield). ESI-MS: 589.4 [M+H]r. $^1H$ NMR (400 MHz, DMSO-$d_6$) δ 10.19 (s, 1H), 8.04-7.94 (m, 4H), 7.92 (s, 1H), 7.88 (d, J=9.0 Hz, 1H), 7.35 (dd, J=9.1, 3.1 Hz, 1H), 6.95 (dd, J=5.2, 1.3 Hz, 1H), 6.77 (s, 1H), 3.84-3.69 (m, 6H), 3.69-3.57 (m, 2H), 3.59-3.52 (m, 1H), 3.53-3.44 (m, 1H), 2.81-2.69 (m, 2H), 2.57 (td, J=12.6, 3.3 Hz, 1H), 2.03 (s, 3H), 1.98-1.88 (m, 1H), 1.84-1.69 (m, 1H), 1.59-1.42 (m, 2H), 1.29-1.14 (m, 2H), 0.97-0.81 (m, 2H).

Example 100. 1-cyclopropyl-3-({[(3S)-1-(6-cyclopropylpyridin-3-yl)piperidin-3-yl][(2-methylpyridin-4-yl)methyl]amino}methyl)-6-fluoro-7-(2-hydroxyethoxy)-1,4-dihydroquinolin-4-one

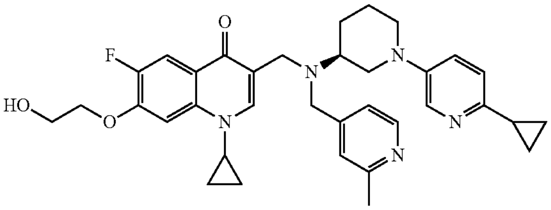 [SMILES: Cc1cc(CN(Cc2cn(C3CC3)c3cc(OCCO)c(F)cc3c2=O)[C@H]2CCCN(c3ccc(C4CC4)nc3)C2)ccn1]

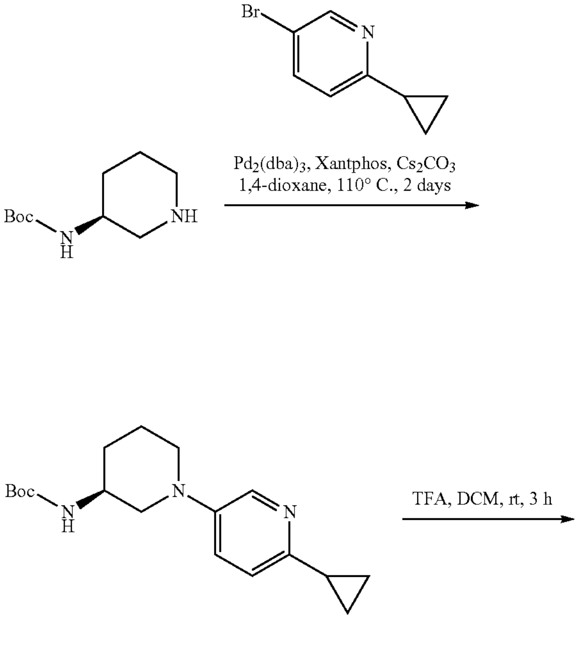

-continued

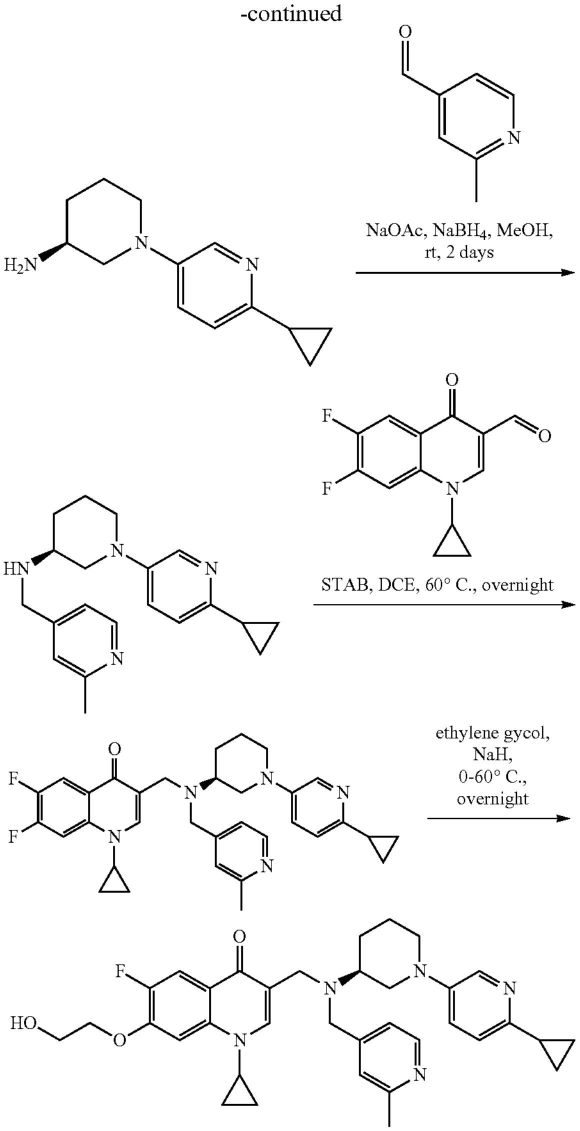

Preparation of tert-butyl N-[(3S)-1-(6-cyclopropylpyridin-3-yl)piperidin-3-yl]carbamate (S)-3-Boc-aminopiperidine (0.46 g, 1.5 eq.) was added to the mixture of 5-Bromo-2-cyclopropylpyridine (0.3 g, 1.0 eq.) and cesium carbonate (0.67 g, 1.4 eq.) in anh. 1,4-dioxane (15.0 mL). The mixture was purged with argon for 10 min. Subsequently, Xantphos (0.053 g, 0.06 eq.) and $Pd_2(dba)_3$ (0.07 g, 0.05 eq.) were added, vessel was closed and the reaction mixture was stirred at 110° C. over the weekend. After that time, the reaction mixture was filtered through a pad of celite and concentrated under reduced pressure. The residue was diluted with DCM and washed with water, brine, dried over anh. $Na_2SO_4$, filtered and concentrated in vacuo. Product was purified by FCC (SiHP; Hex:EtOAc) to give the product (0.14 g, 29% yield) as a clear oil. ESI-MS: 318.5 $[M+H]^+$.

Preparation of (3S)-1-(6-cyclopropylpyridin-3-yl)piperidin-3-amine

Trifluoroacetic acid (0.33 mL, 10.0 eq.) was added to a solution of tert-butyl N-[(3S)-1-(6-cyclopropylpyridin-3-yl)

piperidin-3-yl]carbamate (0.14 g, 1.0 eq.) in DCM (5.0 mL) and the reaction was stirred for 3 h at RT. After that time, the mixture was concentrated in vacuo. The residue was diluted with DCM and washed with 5 M NaOH, brine, dried over anh. sodium sulfate and concentrated under reduced pressure. The crude product (0.093 g, 97% yield) was used in next step without any purification. ESI-MS: 218.0 $[M+H]^+$.

Preparation of (3S)-1-(6-cyclopropylpyridin-3-yl)-N-[(2-methylpyridin-4-yl)methyl]piperidin-3-amine (3S)-1-(6-cyclopropylpyridin-3-yl)piperidin-3-amine (0.16 g, 1.0 eq.), 2-methylpyridine-4-carbaldehyde (0.08 mL, 1.0 eq.) and sodium acetate (0.06 g, 1.0 eq.) were dissolved in anh. methanol (3.0 mL) and the mixture was stirred overnight at RT. After that time the mixture was cooled to 0° C. and sodium borohydride (0.054 g, 2.0 eq.) was added. The reaction was stirred overnight at RT. The reaction mixture was then concentrated in vacuo and residue was extracted with DCM and aqueous NaOH solution (pH was adjusted to 11). The organic layer was washed with brine, dried over $Na_2SO_4$, filtered and evaporated. Product was purified by RP-FCC (C18HP; $H_2O$:MeCN) to give product (0.17 g, 72% yield) as a yellow oil. ESI-MS: 323.4 $[M+H]^+$.

Preparation of 1-cyclopropyl-3-({[(3S)-1-(6-cyclopropylpyridin-3-yl)piperidin-3-yl][(2-methylpyridin-4-yl)methyl]amino}methyl)-6,7-difluoro-1,4-dihydroquinolin-4-one A solution of 1-cyclopropyl-6,7-difluoro-4-oxo-1,4-dihydroquinoline-3-carbaldehyde (Intermediate 4) (0.13 g, 1.0 eq.) and (3S)-1-(6-cyclopropylpyridin-3-yl)-N-[(2-methylpyridin-4-yl)methyl]piperidin-3-amine (0.16 g, 1.0 eq.) was stirred in anh. DCE (6.0 mL) at 60° C. for 1 h. Then the solution was cooled to RT and STAB (0.54 g, 5.0 eq.) was added. The heating at 60° C. was continued overnight. The reaction mixture was diluted with DCM, washed with water, brine, dried over anh. sodium sulfate, filtered and evaporated. The residue was purified by FCC (SiHP; DCM: MeOH) give product (0.13 g, 44% yield) as a clear oil. ESI-MS: 556.5 $[M+H]^+$.

Preparation of 1-cyclopropyl-3-({[(3S)-1-(6-cyclopropylpyridin-3-yl)piperidin-3-yl][(2-methylpyridin-4-yl)methyl]amino}methyl)-6-fluoro-7-(2-hydroxyethoxy)-1,4-dihydroquinolin-4-one A mixture of 1-cyclopropyl-3-({[(3S)-1-(6-cyclopropylpyridin-3-yl)piperidin-3-yl][(2-methylpyridin-4-yl)methyl]amino}methyl)-6,7-difluoro-1,4-dihydroquinolin-4-one (0.13 g, 1.0 eq.), sodium hydride (60% dispersion in mineral oil, 0.027 g, 5.0 eq.) and ethylene glycol (2.0 mL) was stirred at 60° C. overnight. The reaction mixture was cooled to RT, diluted with water, basified using 5 M NaOH and extracted to DCM. The organic layer was washed with brine, dried over anh. $Na_2SO_4$, filtered and concentrated in vacuo. The residue was purified by FCC (SiHP; DCM: MeOH) give the product (0.08 g, 59% yield) as white solid. ESI-MS: 598.6 $[M+H]^+$. $^1H$ NMR (400 MHz, DMSO-$d_6$) δ 8.28 (d, J=5.0 Hz, 1H), 8.09 (d, J=2.8 Hz, 1H), 7.84 (s, 1H), 7.79 (d, J=11.7 Hz, 1H), 7.51 (d, J=7.2 Hz, 1H), 7.23-7.14 (m, 3H), 7.05 (d, J=8.5 Hz, 1H), 5.03 (t, J=5.4 Hz, 1H), 4.24 (t, J=4.8 Hz, 2H), 3.85-3.69 (m, 5H), 3.65-3.47 (m, 4H), 2.79-2.69 (m, 2H), 2.62-2.54 (m, 1H), 2.37 (s, 3H), 2.00-1.90 (m, 2H), 1.79-1.71 (m, 1H), 1.58-1.41 (m, 2H), 1.28-1.18 (m, 2H), 0.94-0.71 (m, 6H).

Example 101. 3-({[(3S)-1-[6-(2-hydroxyethoxy)pyridin-3-yl]piperidin-3-yl][(2-methylpyridin-4-yl)methyl]amino}methyl)-1-methyl-1,4-dihydroquinolin-4-one

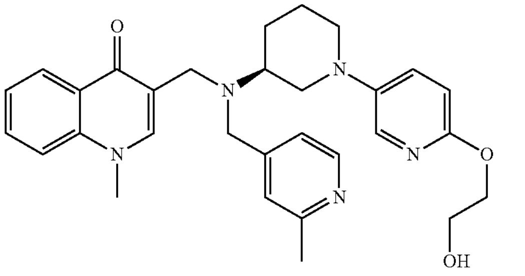

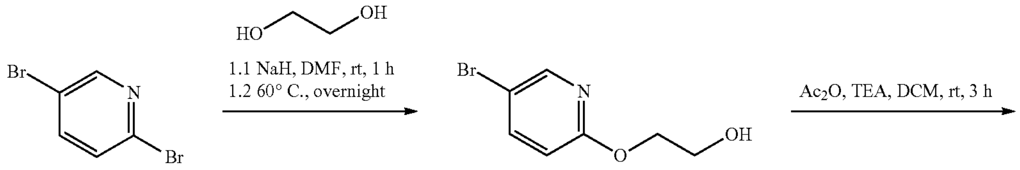

-continued

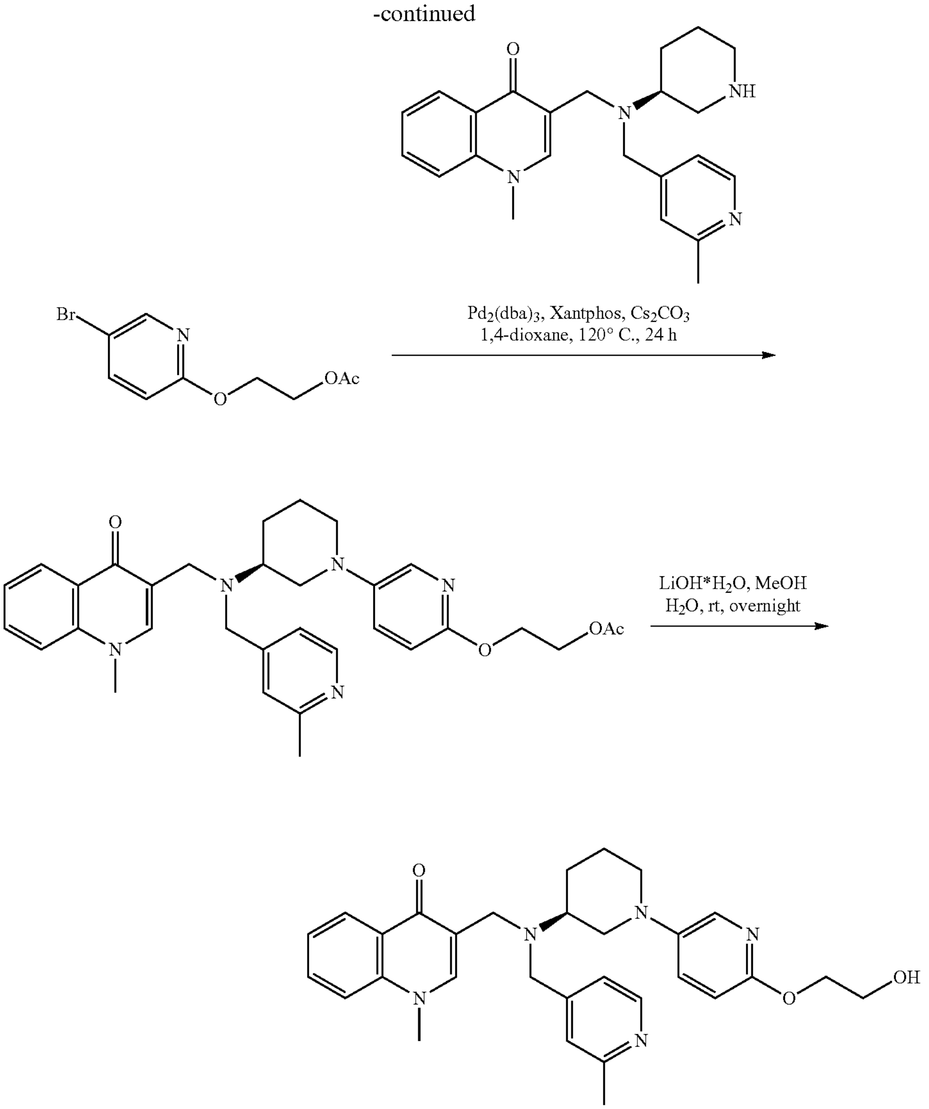

Preparation of 2-[(5-bromopyridin-2-yl)oxy]ethan-1-ol

A suspension of 2,5-dibromopyridine (1.0 g, 1.0 eq.), ethane-1,2-diol (1.2 mL, 5.0 eq.) and NaH (60% dispersion in mineral oil, 0.20 g, 1.2 eq.) was stirred in anh. DMF (12.0 mL) for 1 h at RT, then reaction mixture was stirred overnight at 60° C. Then solvent was evaporated in vacuo and crude product was purified by FCC (SiHP; Hex:EtOAc) to give the product (0.68 g, 74% yield) as a colorless oil. ESI-MS: 219.9 [M+2]+.

Preparation of (5-bromopyridin-2-yl)methyl acetate $Ac_2O$ (0.35 mL, 1.2 eq.) was added to a solution of 2-[(5-bromopyridin-2-yl)oxy]ethan-1-ol (0.68 g, 1.0 eq.) and TEA (1.7 mL, 4.0 eq.) in anh. DCM (15.0 mL). The reaction mixture was stirred for 3 h at RT, then crude mixture was concentrated in vacuo and purified by FCC (SiHP; Hex:EtOAc) to give the product (0.65 g, 76% yield) as a colorless oil. ESI-MS: 262.1 $[M+2H]^+$.

Preparation of 2-({5-[(3S)-3-{[(1-methyl-4-oxo-1,4-dihydroquinolin-3-yl)methyl][(2-methylpyridin-4-yl)methyl]amino}piperidin-1-yl]pyridin-2-yl}oxy)ethyl acetate A suspension of 2-[(5-bromopyridin-2-yl)oxy]ethyl acetate (0.2 g, 1.0 eq.), 1-methyl-3-({[(2-methylpyridin-4-yl)methyl][(3S)-piperidin-3-yl]amino}methyl)-1,4-dihydroquinolin-4-one (Intermediate 5) (0.29 g, 1.1 eq.) and $Cs_2CO_3$ (0.48 g, 2.0 eq.) in 1,4-dioxane (5.0 mL) was purged with argon for 10 min. Then $Pd_2(dba)_3$ (0.033 g, 0.05 eq.) and Xantphos (0.018 g, 0.06 eq.) were added and the reaction mixture was purged with argon for a few minutes. The reaction mixture was stirred at 120° C. for 24 h and then filtered through a pad of celite, washed with DCM and concentrated in vacuo. The residue was stirred for 4 h with scavenger QuadraPure MPA in DCM, filtered, evaporated in vacuo and purified by FCC (SiHP; DCM:MeOH) to give the product (0.138 g, 33% yield) as a yellow solid. ESI-MS: 556.7 $[M+H]^+$.

Preparation of 3-({[(3S)-1-[6-(2-hydroxyethoxy)pyridin-3-yl]piperidin-3-yl][(2-methylpyridin-4-yl)methyl]amino}methyl)-1-methyl-1,4-dihydroquinolin-4-one 2-({5-[(3S)-3-{[(1-methyl-4-oxo-1,4-dihydroquinolin-3-yl)methyl][(2-methylpyridin-4-yl)methyl]amino}piperidin-1-yl]pyridin-2-yl}oxy)ethyl acetate (0.138 g, 1.0 eq.) was suspended in water (1.0 mL) and methanol (5.0 mL). Then lithium hydroxide monohydrate (0.031 g, 3.0 eq.) was added and the reaction mixture was stirred overnight at RT. The crude mixture was concentrated in vacuo. The residue was purified on FCC (C18HP; $H_2O$:MeCN) to give the product (0.096 g, 76% yield) as white solid. ESI-MS: 514.4 $[M+H]^+$.

$^1H$ NMR (400 MHz, DMSO-$d_6$) 8.28 (d, =5.0, 1H), 8.19 (dd, J=8.1, 1.6 Hz, 1H), 8.01 (s, 1H), 7.76 (d, J=3.0 Hz, 1H), 7.75-7.68 (m, 1H), 7.62 (d, J=8.4 Hz, 1H), 7.42 (dd, J=9.0, 3.1 Hz, 1H), 7.40-7.34 (m, 1H), 7.27-7.20 (m, 2H), 6.67 (d, J=9.0 Hz, 1H), 4.78 (s, 1H), 4.21-4.11 (m, 2H), 3.85 (s, 3H), 3.80-3.54 (m, 7H), 3.43 (d, J=11.5 Hz, 1H), 2.81-2.61 (m, 2H), 2.37 (s, 3H), 2.03-1.91 (m, 1H), 1.83-1.70 (m, 1H), 1.57-1.37 (m, 2H).

Example 102. 5-[(3S)-3-{[(7-Chloro-1-cyclopropyl-6-fluoro-4-oxo-1,4-dihydroquinolin-3-yl)methyl][2-methylpyridin-4-yl)methyl]amino}piperidin-1-yl]pyridine-2-carboxylic acid

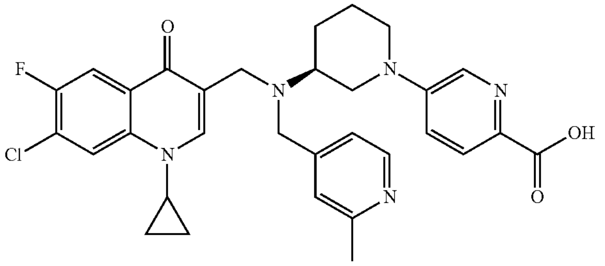 [SMILES: Cc1cc(CN(Cc2cn(C3CC3)c3cc(Cl)c(F)cc3c2=O)[C@H]2CCCN(c3ccc(C(=O)O)nc3)C2)ccn1]

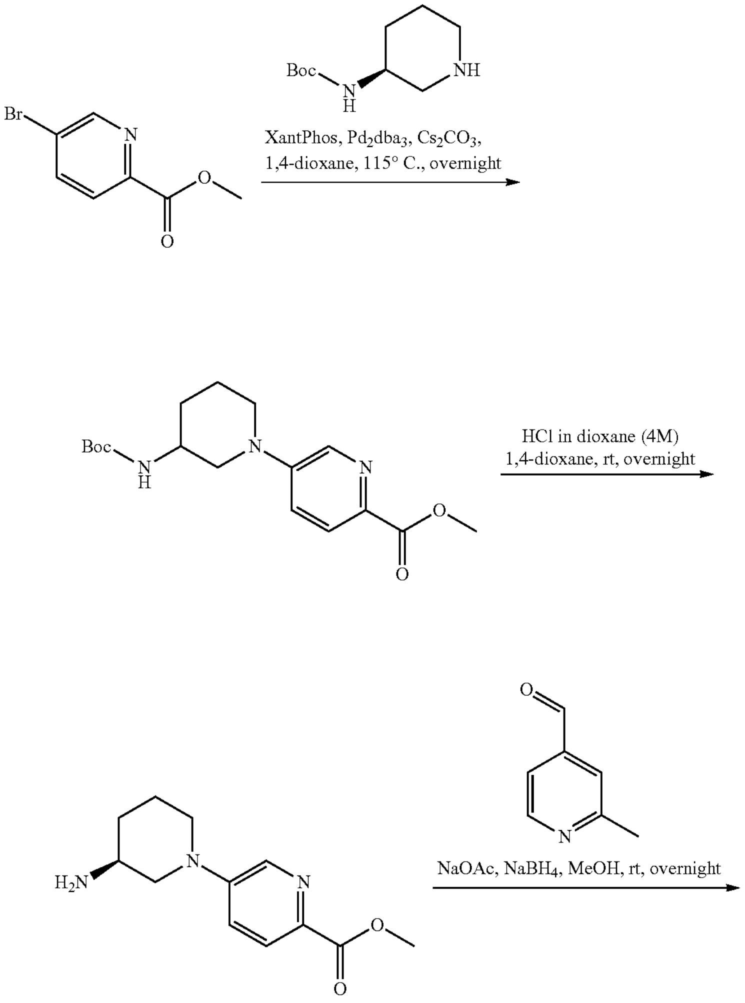

-continued

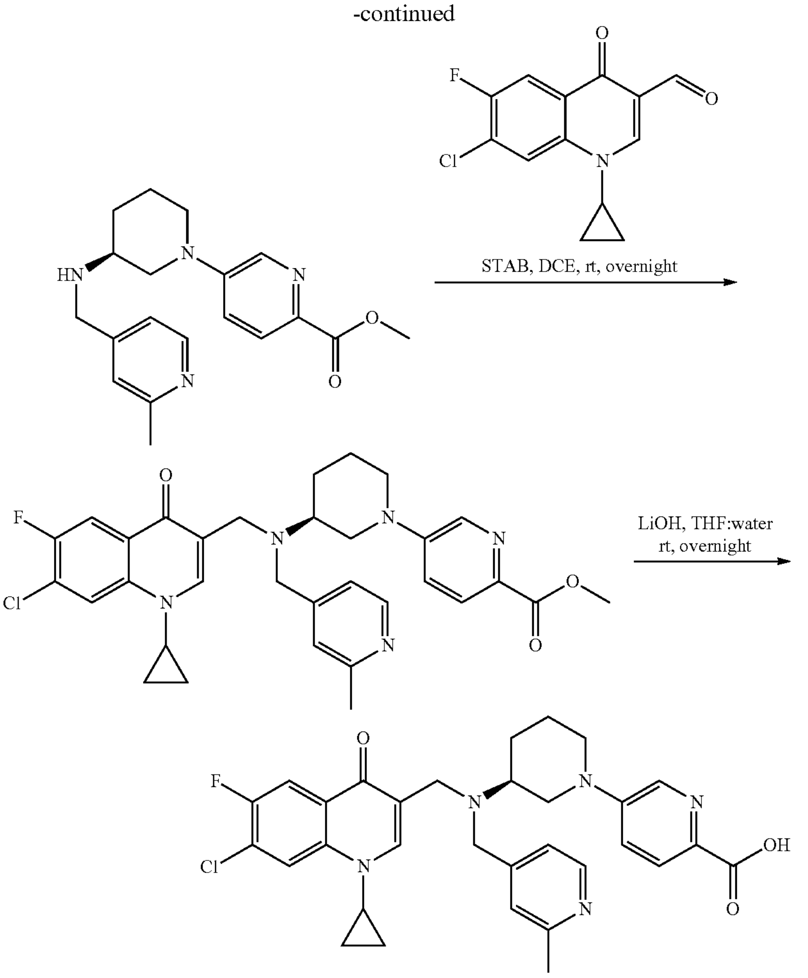

Preparation of Methyl 5-[(3S)-3-{[(tert-butoxy)carbonyl]amino}piperidin-1-yl]pyridine-2-carboxylate (S)-3-Boc-aminopiperidine (0.48 g, 1.3 eq.), methyl 5-bromopyridine-2-carboxylate (0.03 g, 1.0 eq.) and cesium carbonate (1.2 g, 2.0 eq.) were suspended in anh. 1,4-dioxane (5.0 mL). and the mixture was purged with argon for 10 min. Then $Pd_2(dba)_3$ (0.085 g, 0.05 eq.) and Xantphos (0.064 g, 0.06 eq.) were added. The reaction mixture was purged one more time with argon for 10 minutes and reaction was heated at 115° C. overnight. The mixture was filtered through a pad of celite and the filtrate was concentrated in vacuo. DCM was added and washed with water and brine. The organic layer was dried over anh. $MgSO_4$, filtered and concentrated in vacuo. The crude was purified by FCC (SiHP, DCM:MeOH), to give a product (0.206 g, 39% yield). ESI-MS: 336.5 $[M+H]^+$.

Preparation of Methyl 5-[(3S)-3-aminopiperidin-1-yl]pyridine-2-carboxylate 4.0 M HCl in 1,4-dioxane (0.81 mL, 8.0 eq.) was added to solution of methyl 5-[(3S)-3-{[(tert-butoxy)carbonyl]amino}piperidin-1-yl]pyridine-2-carboxylate (0.157 g, 1.0 eq.) in 1,4-dioxane (4.0 mL). The reaction mixture was stirred at RT over the weekend. The solvent was evaporated under reduced pressure. Subsequently, the crude material was partitioned between NaOH aq and DCM. The organic layer was dried over anh. $Na_2SO_4$, filtered and concentrated to dryness to give product (0.085 g, 85% yield). ESI-MS: 236.2 $[M+H]^+$.

Preparation of methyl 5-[(3S)-3-{[(2-methylpyridin-4-yl)methyl]amino}piperidin-1-yl]pyridine-2-carboxylate Methyl 5-[(3S)-3-aminopiperidin-1-yl]pyridine-2-carboxylate (0.080 g, 1.0 eq.), 2-methylpyridine-4-carbaldehyde (0.038 mL, 1.1 eq.) and sodium acetate (0.027 g, 1.0 eq.) were dissolved in anh. methanol (5.0 mL) and the reaction mixture was stirred at RT overnight. Then the mixture was cooled to 0° C. and sodium borohydride (0.014 g, 1.1 eq.) was added in portions and the reaction mixture was stirred at RT for 1 h. Methanol was evaporated. Product was purified by FCC (SiHP; DCM:MeOH) to give product (0.046 g, 38% yield). ESI-MS: 341.3 $[M+H]^+$.

Preparation of methyl 5-[(3S)-3-{[(7-Chloro-1-cyclopropyl-6-fluoro-4-oxo-1,4-dihydroquinolin-3-yl)methyl][(2-methylpyridin-4-yl)methyl]amino}piperidin-1-yl]pyridine-2-carboxylate 7-Chloro-1-cyclopropyl-6-fluoro-4-oxo-1,4-dihydroquinoline-3-carbaldehyde (Intermediate 9) (0.044 g, 1.1 eq.)

and methyl 5-[(3S)-3-{[(2-methylpyridin-4-yl)methyl]amino}piperidin-1-yl]pyridine-2-carboxylate (0.046 g, 1.0 eq.) were dissolved in anh. DCE (3.0 mL). The resulting mixture was stirred at RT overnight. Then sodium triacethoxyborohydride (0.074 g, 2.8 eq.) was added and the mixture was stirred for another 24 h at RT. The reaction mixture was diluted with DCM, washed subsequently with sat. aq. sodium bicarbonate, water, brine, dried over anh. $MgSO_4$ and concentrated in vacuo. The residue was purified by FCC (C18HP; $H_2O$:MeCN) to give product (0.026 g, 36% yield). $^1H$ NMR (400 MHz, DMSO-$d_6$) δ 8.34 (d, J=3.0 Hz, 1H), 8.27 (d, J=5.0 Hz, 1H), 8.15 (d, J=6.2 Hz, 1H), 7.97 (d, J=9.5 Hz, 1H), 7.91 (s, 1H), 7.79 (d, J=8.9 Hz, 1H), 7.29 (dd, J=9.0, 3.0 Hz, 1H), 7.21 (s, 1H), 7.16 (d, J=5.4 Hz, 1H), 4.10 (d, J=12.8 Hz, 1H), 3.91 (d, J=13.1 Hz, 1H), 3.79 (s, 2H), 3.77 (d, J=2.8 Hz, 2H), 3.65 (s, 2H), 3.56-3.50 (m, 1H), 3.03 (d, J=12.0 Hz, 1H), 2.86 (t, J=12.4 Hz, 1H), 2.36 (s, 3H), 1.98 (d, J=12.3 Hz, 1H), 1.78 (d, J=13.3 Hz, 1H), 1.67 (q, J=11.3 Hz, 2H), 1.45 (d, J=13.1 Hz, 2H), 1.25-1.19 (m, 2H), 0.95-0.85 (qm, J2H).

Preparation of 5-[(3S)-3-{[(7-Chloro-1-cyclopropyl-6-fluoro-4-oxo-1,4-dihydroquinolin-3-yl)methyl][(2-methylpyridin-4-yl)methyl]amino}piperidin-1-yl]pyridine-2-carboxylic acid Lithium hydroxide monohydrate (0.003 g, 4.5 eq.) was added to a solution of methyl 5-[(3S)-3-{[(7-chloro-1-cyclopropyl-6-fluoro-4-oxo-1,4-dihydroquinolin-3-yl)methyl][(2-methylpyridin-4-yl)methyl]amino}piperidin-1-yl]pyridine-2-carboxylate (0.018 g, 1.0 eq.) in THF (3.0 mL) and water (1.0 mL). The resulting mixture was stirred at RT overnight. The reaction mixture was diluted with DCM and washed with conc. aq. HCl. The crude was purified by FCC (C18HP, $H_2O$:MeCN) to give product (0.005 g, 31% yield). ESI-MS: 576.6 $[M+H]^+$. $^1H$ NMR (400 MHz, Methanol-$d_4$) δ 8.27 (s, 1H), 8.16 (t, J=6.3 Hz, 2H), 8.01 (d, J=9.5 Hz, 1H), 7.97 (s, 1H), 7.94 (d, J=8.9 Hz, 1H), 7.44 (dd, J=8.7, 2.4 Hz, 1H), 7.26 (s, 1H), 7.22 (d, J=5.3 Hz, 1H), 4.16 (d, J=11.9 Hz, 1H), 3.92 (s, 1H), 3.86 (s, 2H), 3.79 (s, 2H), 3.48 (quint, J=7.3, 3.4 Hz, 1H), 3.10 (t, J=12.1 Hz, 1H), 2.97-2.87 (m, 2H), 2.35 (s, 3H), 2.15 (d, J=11.8 Hz, 1H), 1.93 (d, J=12.8 Hz, 1H), 1.82-1.71 (m, 1H), 1.70-1.61 (m, 1H), 1.33-1.27 (m, 2H), 0.94 (dt, J=6.2, 3.4 Hz, 2H).

Example 103. 5-[(3S)-3-{[(7-Chloro-1-cyclopropyl-6-fluoro-4-oxo-1,4-dihydroquinolin-3-yl)methyl][(2-methylpyridin-4-yl)methyl]amino}piperidin-1-yl]pyridine-2-carboxamide

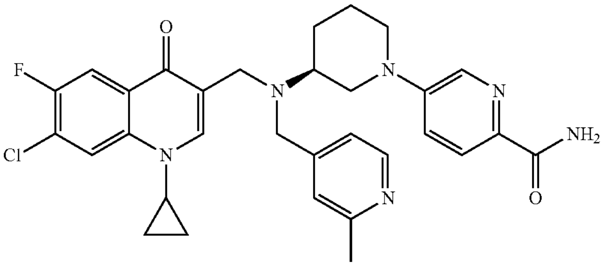

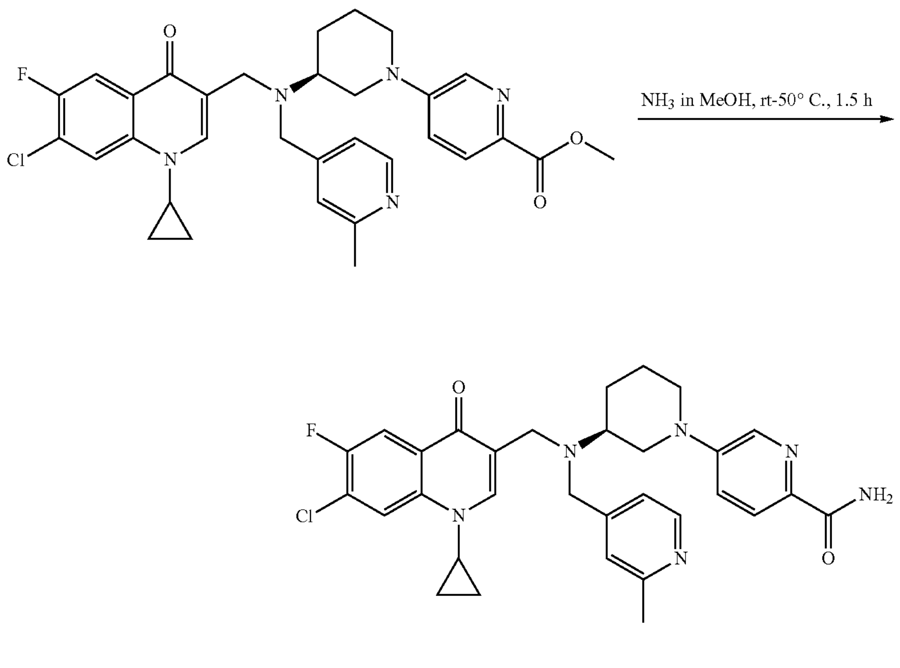

Preparation of 5-[(3S)-3-{[(7-Chloro-1-cyclopropyl-6-fluoro-4-oxo-1,4-dihydroquinolin-3-yl)methyl][(2-methylpyridin-4-yl)methyl]amino}piperidin-1-yl]pyridine-2-carboxamide A mixture of methyl 5-[(3S)-3-{[(7-chloro-1-cyclopropyl-6-fluoro-4-oxo-1,4-dihydroquinolin-3-yl)methyl][(2-methylpyridin-4-yl)methyl]amino}piperidin-1-yl]pyridine-2-carboxylate (0.029 g, 1.0 eq.) in 7.0 N ammonia solution in MeOH (5.0 mL) was stirred at RT overnight. Then the mixture was heated to 50° C. for 1.5 h. The solvent was evaporated and the crude material was purified by FCC (C18HP, $H_2O$:MeCN) to give the product (0.021 g, 84% yield). ESI-MS: 575.7 $[M+H]^+$. $^1H$ NMR (400 MHz, Methanol-$d_4$) δ 8.26 (d, J=2.9 Hz, 1H), 8.17 (dd, J=8.8, 5.7 Hz, 2H), 8.02 (d, J=9.4 Hz, 1H), 7.98 (s, 1H), 7.88 (d, J=8.8 Hz, 1H), 7.35 (dd, J=8.9, 2.9 Hz, 1H), 7.26 (s, 1H), 7.22 (d, J=5.1 Hz, 1H), 4.13 (d, J=12.3 Hz, 1H), 3.89 (s, 1H), 3.86 (d, J=2.7 Hz, 2H), 3.80 (s, 2H), 3.52-3.45 (m, 1H), 3.06 (t, J=12.1 Hz, 1H), 2.95-2.85 (m, 2H) J, 2.36 (s, 3H), 2.15 (d, J=11.9 Hz, 1H), 1.92 (d, J=12.2 Hz, 1H), 1.81-1.71 (m, 1H), 1.70-1.59 (m, 1H) J, 1.34-1.27 (m, 2H), 0.99-0.90 (m, 2H).

Preparation of Compound-Linker Constructs

Example 4A. N-{5-[(3S)-3-{[(1-cyclopropyl-6,7-difluoro-4-oxo-1,4-dihydroquinolin-3-yl)methyl][(2-methoxypyridin-4-yl)methyl]amino}piperidin-1-yl]pyridin-2-yl}-4,7,10,13,16-pentaoxanonadec-18-ynamide

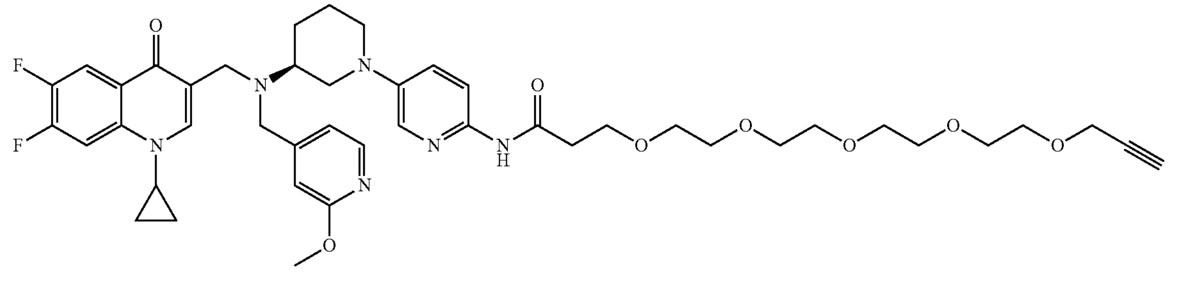

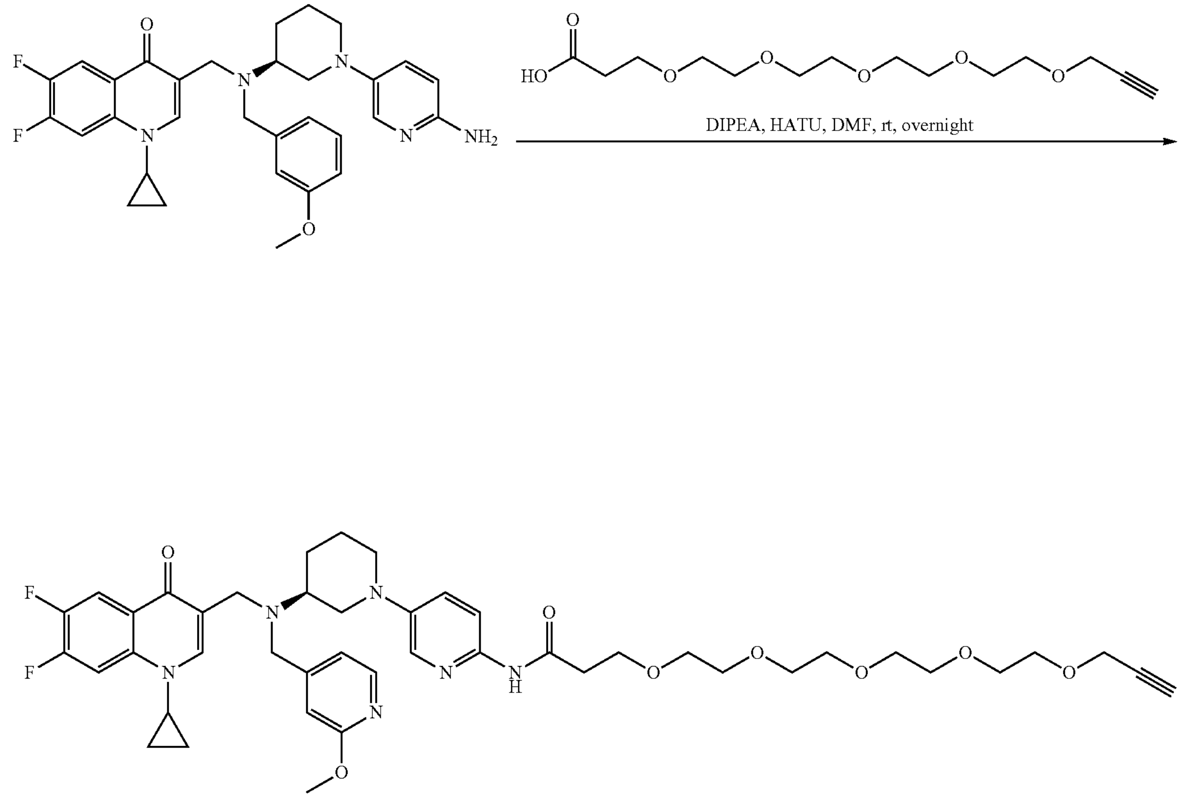

Preparation of N-{5-[(3S)-3-{[(1-cyclopropyl-6,7-difluoro-4-oxo-1,4-dihydroquinolin-3-yl)methyl][(2-methoxypyridin-4-yl)methyl]amino}piperidin-1-j]pyridin-2-yl}-4,7,10,13,16-pentaoxanonadec-18-ynamide HATU (0.06 g, 1.3 eq.), DIPEA (0.06 ml, 3.0 eq.), 3-({[(3S)-1-(6-aminopyridin-3-yl)piperidin-3-yl][(2-methoxypyridin-4-yl)methyl]amino}methyl)-1-cyclopropyl-6,7-difluoro-1,4-dihydroquinolin-4-one hydrochloride (Example 4) (0.07 g, 1.0 eq.), 4,7,10,13,16-pentaoxanonadec-18-ynoic acid (0.04 g, 1.0 eq.) taken in anh. DMF (1.5 mL)) were stirred overnight at RT. Then reaction mixture was concentrated in vacuo. The residue was re-dissolved in DCM and extracted with water. Organic layer was washed with brine, dried over $Na_2SO_4$ and evaporated. Crude product was purified by FCC (SiHP; DCM:MeOH) and re-purified by FCC ($NH_2$ column, DCM:MeOH) to give product (0.06 g, 60% yield) as a colorless oil. ESI-MS: 833.8 $[M+H]^+$. $^1H$ NMR (400 MHz, Methanol-$d_4$) δ 8.10-8.04 (m, 2H), 8.00-7.89 (m, 4H), 7.43 (dd, J=9.1, 3.0 Hz, 1H), 6.95 (dd, J=5.3, 1.2 Hz, 1H), 6.79 (s, 1H), 4.18 (d, J=2.4 Hz, 2H), 3.88-3.82 (m, 5H), 3.82-3.78 (m, 5H), 3.68-3.56 (m, 16H), 3.53-3.47 (m, 1H), 3.02-2.93 (m, 1H), 2.90-2.82 (m, 2H), 2.77-2.70 (m, 1H), 2.70-2.65 (m, 2H), 2.17-2.10 (m, 1H), 1.97-1.91 (m, 1H), 1.74-1.63 (m, 2H), 1.36-1.27 (m, 3H), 1.02-0.96 (m, 2H).

Example 10A. {4-[(2S)-2-[(2S)-2-(3-{2-[2-(2-azidoethoxy)ethoxy]ethoxy}propanamido)-3-methyl-butanamido]-5-(carbamoylamino)pentanamido]phenyl}methyl N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)carbamate

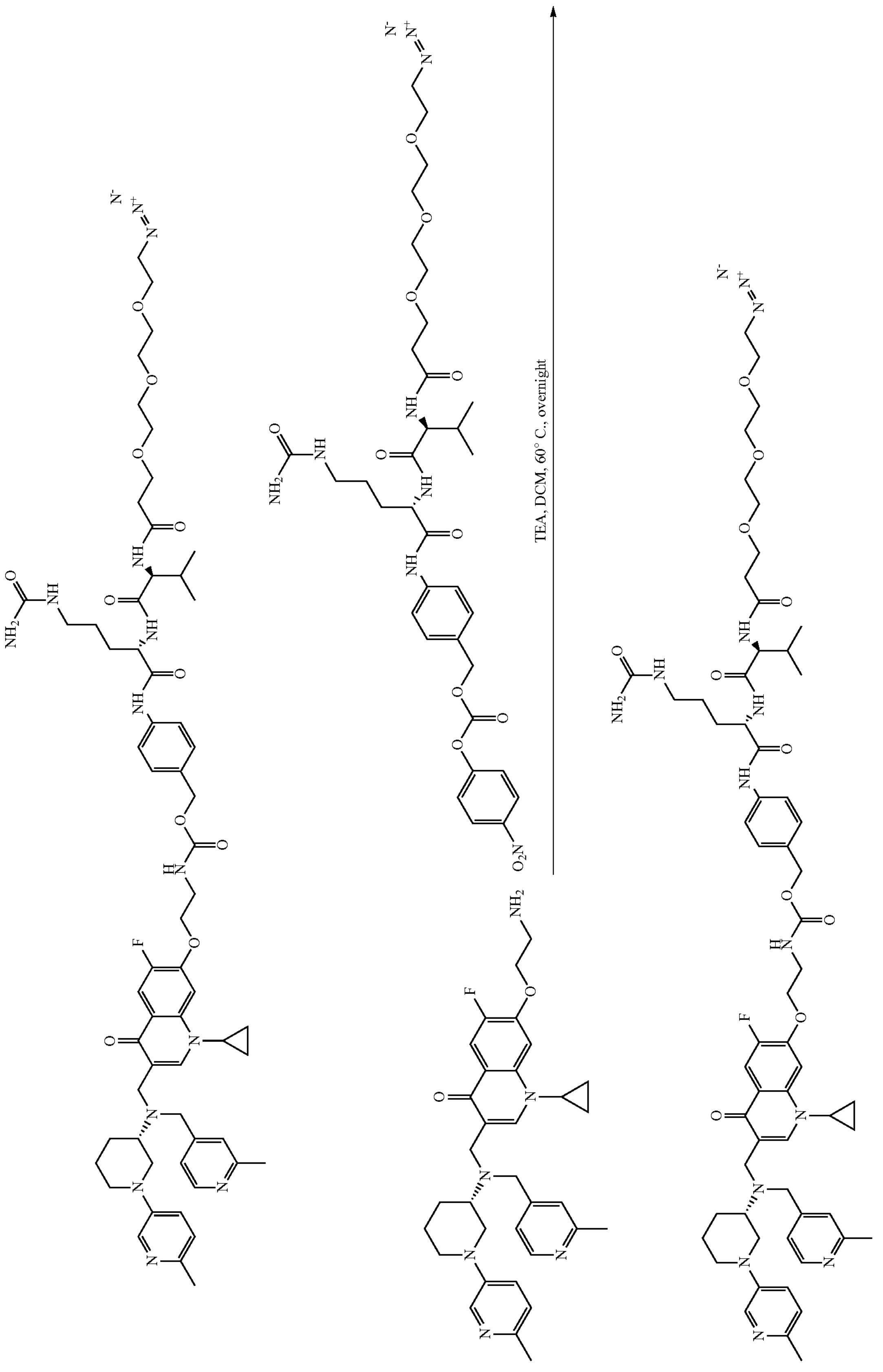
TEA, DCM, 60° C., overnight

Preparation of {4-(2S)-2-[(2S)-2-(3-{2-[2-(2-azidoethoxy)ethoxy}propanamido)-3-methyl-butanamido]-5-(carbamoylamino)pentanamido]phenyl}methyl N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)carbamate A mixture of 7-(2-aminoethoxy)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Example 10)(0.018 g, 1.2 eq.), {4-[(2S)-2-[(2S)-2-(3-{2-[2-(2-azidoethoxy)ethoxy]ethoxy}propanamido)-3-methyl-butanamido]-5-(carbamoylamino)pentanamido]phenyl}methyl 4-nitrophenyl carbonate (0.02 g, 1.0 eq.) and TEA (0.007 mL, 1.9 eq.) in DCM (1.0 mL) was stirred overnight at 60° C. Subsequently the mixture was concentrated in vacuo and the residue was purified by FCC (SiHP; DCM:MeOH) and freeze-dried to give product (0.018 g, 54% yield) as off white solid. ESI-MS: 1205.9 [M+H]$^+$. HR-MS: 1205.6 [M+H]$^+$.

Example 11A. 2-[2-(2-aminoethoxy)ethoxy]-N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)-N-methylacetamide

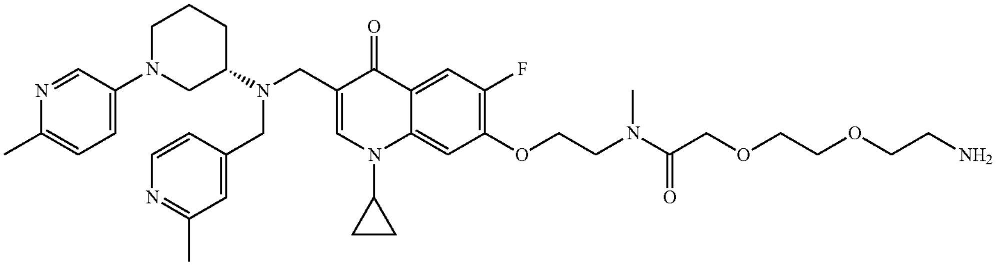

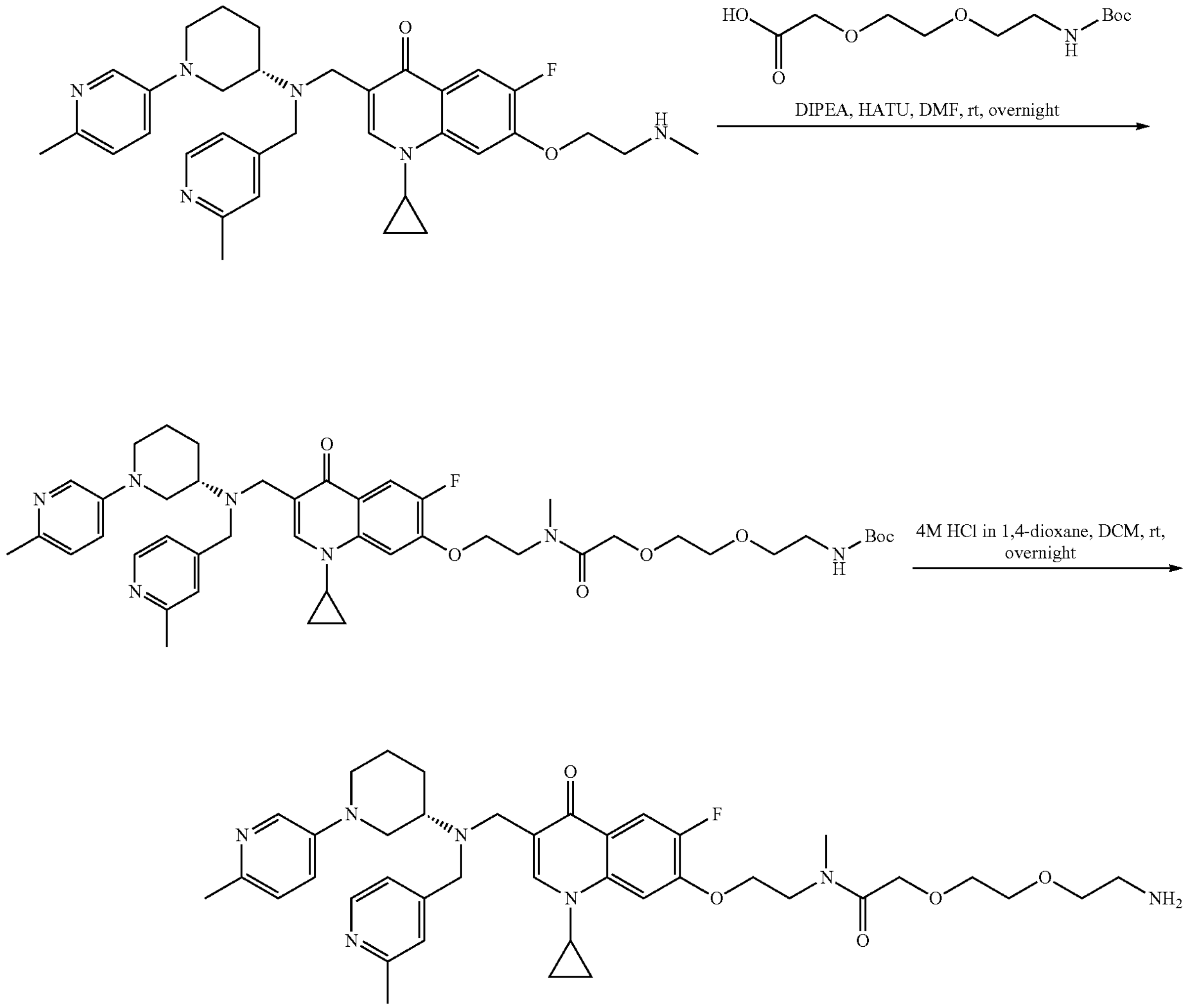

Preparation of tert-butyl N-[2-(2-{[2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)(methyl)carbamoyl]methoxy}ethoxy)ethyl]carbamate A mixture of HATU (0.11 g, 1.3 eq.), DIPEA (0.11 ml, 3.0 eq.), 1-cyclopropyl-6-fluoro-7-[2-(methylamino)ethoxy]-3-({[(3S)-1-(6-methylpyridin-3-yl)piperidin-3-yl][(2-methylpyridin-4-yl)methyl]amino}methyl)-1,4-dihydroquinolin-4-one (Example 11) (0.13 g, 1.0 eq.), 2-[2-(2-{[(tert-butoxy)carbonyl]amino}ethoxy)ethoxy]acetic acid (0.062 g, 1.1 eq.) in DMF anh (3.0 mL) were stirred overnight at RT. Then reaction mixture was evaporated in vacuo. The residue was re-dissolved in DCM and washed with water. Organic layer was washed with 1 M NaOH, brine, dried over $Na_2SO_4$ and evaporated. Crude product was purified by FCC (SiHP; DCM:MeOH) and repurified by FCC ($NH_2$ column, DCM:MeOH) to give product (0.11 g, 57% yield) as a white solid. ESI-MS: 830.8 [M+H]+.

Preparation of 2-[2-(2-aminoethoxy)ethoxy]-N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydro-quinolin-7-yl]oxy}ethyl)-N-methylacetamide tert-Butyl N-[2-(2-{[(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)(methyl)carbamoyl]methoxy}ethoxy)ethyl]carbamate (0.078 g, 1.0 eq.) was dissolved in dichloromethane (1.0 mL) and 4 M hydrogen chloride in 1,4-dioxane (0.32 ml, 15.0 eq.) was added. The reaction mixture was stirred overnight at RT. Reaction mixture was evaporated. The residue was re-dissolved in water and basified with 2 M NaOH. After washing this aqueous layer with DCM, the organic layer was washed with brine, dried over $Na_2SO_4$ and concentrated in vacuo. Crude product was purified by flash FCC ($NH_2$ column, DCM:MeOH) to give product (0.026 g, 39% yield) as a white solid. ESI-MS: 730.7 $[M+H]^+$. $^1H$ NMR (400 MHz, DMSO-$d_6$) δ 8.28 (d, J=5.0 Hz, 1H), 8.13 (d, J=2.9 Hz, 1H), 7.87-7.84 (m, 1H), 7.81 (dd, J=11.5, 5.5 Hz, 1H), 7.51 (dd, 1=12.7, 7.1 Hz, 1H), 7.25-7.20 (m, 2H), 7.17 (d, J=5.1 Hz, 1H), 7.03 (d, J=8.5 Hz, 1H), 4.39 (t, J=5.0 Hz, 1H), 4.35 (t, J=5.7 Hz, 1H), 4.31 (s, 1H), 4.18 (s, 1H), 3.83-3.71 (m, 5H), 3.62 (s, 2H), 3.60-3.48 (m, 6H), 3.38-3.35 (m, 2H), 3.06 (s, 2H), 2.92 (s, 1H), 2.80-2.72 (m, 2H), 2.65-2.60 (m, 2H), 2.60-2.55 (m, 1H), 2.54-2.52 (m, 1H), 2.38 (s, 3H), 2.33 (s, 3H), 2.01-1.94 (m, 1H), 1.81-1.72 (m, 1H), 1.59-1.43 (m, 3H), 1.28-1.22 (m, 2H), 0.95-0.83 (m, 2H).

Example 11B. 3-{2-[2-(2-aminoethoxy)ethoxy]ethoxy}-N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)-N-methylpropanamide

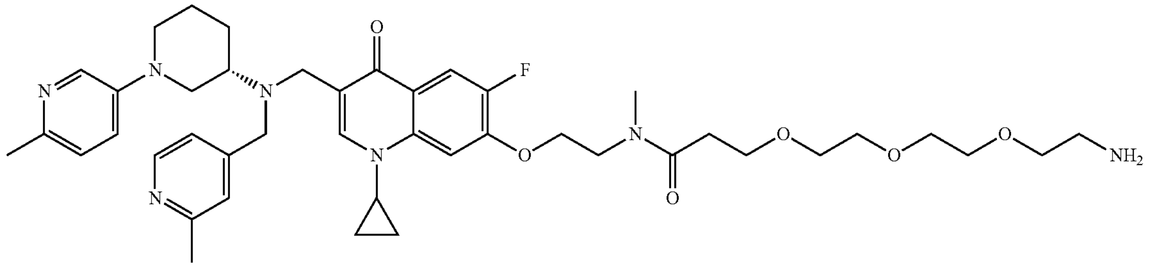

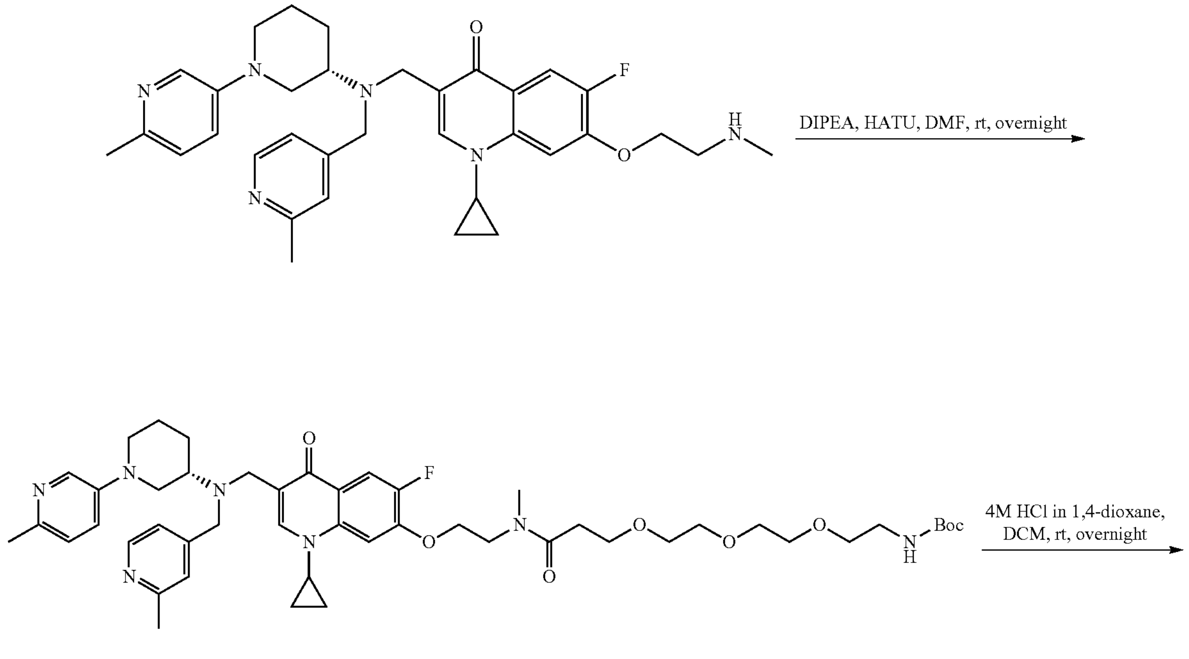

-continued

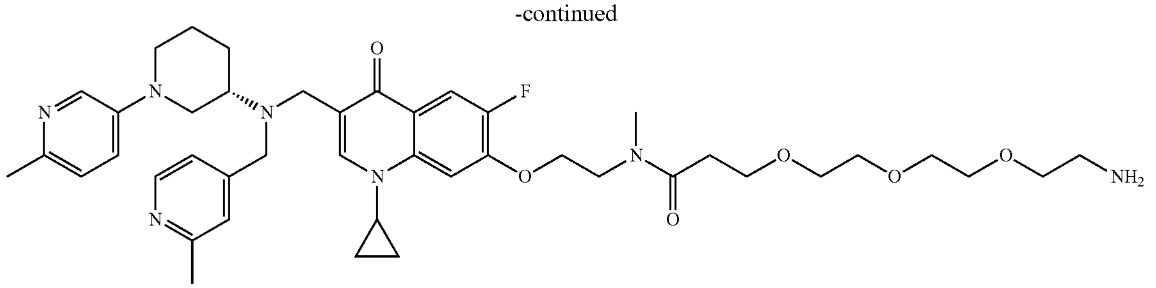

Preparation of tert-butyl N-{2-[2-(2-{2-[(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)(methyl)carbamoyl]ethoxy}ethoxy)ethoxy]ethyl}carbamate A mixture of HATU (0.08 g, 1.3 eq.), DIPEA (0.09 ml, 3.0 eq.), 1-cyclopropyl-6-fluoro-7-[2-(methylamino)ethoxy]-3-({[(3S)-1-(6-methylpyridin-3-yl)piperidin-3-yl][(2-methylpyridin-4-yl)methyl]amino}methyl)-1,4-dihydroquinolin-4-one (Example 11)(0.10 g, 1.0 eq.), 3-{2-[2-(2-{[(tert-butoxy)carbonyl]amino}ethoxy)ethoxy]ethoxy}propanoic acid (0.06 g, 1.1 eq.) in DMF anh (3.0 mL)) was stirred overnight at RT. Then reaction mixture was evaporated in vacuo. The residue was re-dissolved in DCM and extracted with water. Organic layer was washed with 1 M NaOH, brine, dried over $Na_2SO_4$ and evaporated. The crude mixture was purified by FCC (SiHP; DCM: MeOH) and re-purified by FCC ($NH_2$ column, DCM:MeOH) to give product (0.10 g, 67% yield) as a white solid. ESI-MS: 888.9 $[M+H]^+$.

Preparation of 3-{2-[2-(2-aminoethoxy)ethoxy]ethoxy}-N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)-N-methylpropanamide tert-butyl N-{2-[2-(2-{2-[(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)(methyl)carbamoyl]ethoxy}ethoxy)ethoxy]ethyl}carbamate (0.10 g, 1.0 eq.) was dissolved in DCM (1.5 mL) and 4 M hydrogen chloride in 1,4-dioxane (0.41 ml, 15.0 eq.) was added. Reaction mixture was stirred overnight at RT. Reaction mixture was first concentrated and then again after dilution with DCM (3 cycles). Crude was dissolved in water and basified with 2 M NaOH. This was washed with DCM and then the organic layer was washed with brine, dried over $Na_2SO_4$ and concentrated in vacuo to give product (0.05 g, 59% yield) as a white solid. ESI-MS: 788.7 $[M+H]^+$. $^1H$ NMR (400 MHz, DMSO-$d_6$) δ 8.28 (d, J=5.1 Hz, 1H), 8.13 (d, J=2.8 Hz, 1H), 7.87-7.84 (m, 1H), 7.81 (dd, J=11.5, 3.1 Hz, 1H), 7.52 (dd, J=11.8, 7.3 Hz, 1H), 7.24-7.20 (m, 2H), 7.17 (d, J=5.1 Hz, 1H), 7.03 (d, J=8.6 Hz, 1H), 4.38 (t, J=5.0 Hz, 1H), 4.32 (t, J=5.6 Hz, 1H), 3.86-3.71 (m, 5H), 3.67-3.56 (m, 5H), 3.52-3.45 (m, 9H), 3.38-3.36 (m, 2H), 3.12 (s, 2H), 2.92 (s, 1H), 2.80-2.70 (m, 3H), 2.69-2.64 (m, 2H), 2.62-2.55 (m, 2H), 2.55-2.52 (m, 1H), 2.38 (s, 3H), 2.33 (s, 3H), 2.00-1.93 (m, 1H), 1.80-1.72 (m, 1H), 1.59-1.44 (m, 2H), 1.30-1.19 (m, 3H), 0.93-0.83 (m, 2H).

Example 11C. 7-[(1-amino-15-methyl-3,6,9,12-tetraoxa-15-azaheptadecan-17-yl)oxy]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one

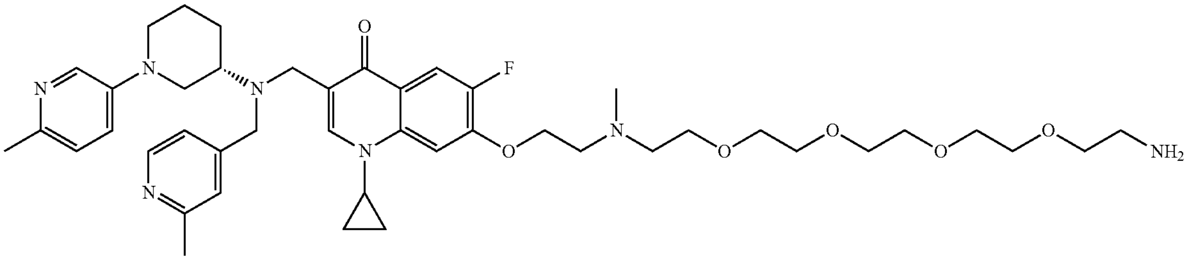

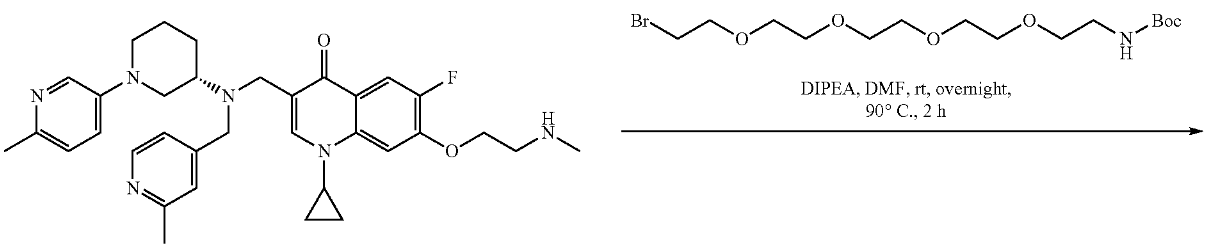

-continued

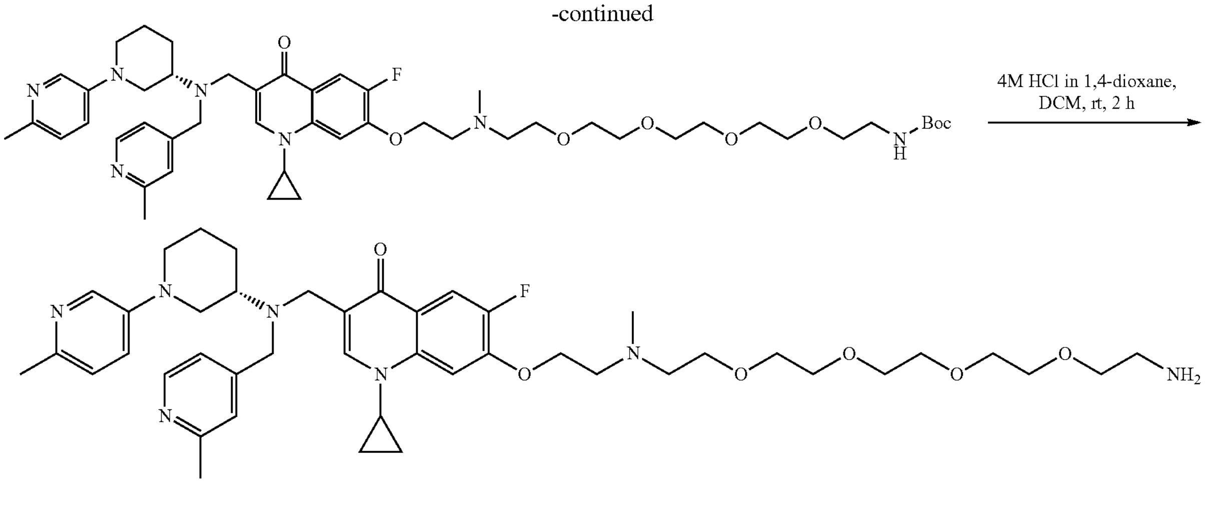

Preparation of tert-butyl N-(17-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}-15-methyl-3,6,9,12-tetraoxa-15-azaheptadecan-1-yl)carbamate A mixture of DIPEA (0.04 ml, 2.0 eq.), 1-cyclopropyl-6-fluoro-7-[2-(methylamino)ethoxy]-3-hydroquinolin-4-one (Example 11) (0.07 g, 1.0 eq.), tert-butyl N-(14-bromo-3,6,9,12-tetraoxatetradecan-1-yl)carbamate (0.05 g, 1.1 eq.) in anh. DMF (1.0 mL) was stirred overnight at RT, then it was heated at 90° C. for 2 h. The reaction mixture was concentrated in vacuo. The residue was re-dissolved in DCM and water and product was extracted into DCM. Organic layer was washed with 1 M NaOH, brine, dried over $Na_2SO_4$ and evaporated. Crude product was purified by FCC (SIHP; DCM:MeOH) and re-purified by FCC (NH2 column, DCM:MeOH) to give product (0.035 g, 33% yield) as a colorless oil. ESI-MS: 904.8 $[M+H]^+$.

Preparation of 7-[(1-amino-15-methyl-3,6,9,12-tetraoxa-15-azaheptadecan-17-yl)oxy]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one tert-Butyl N-(17-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}-15-methyl-3,6,9,12-tetraoxa-15-azaheptadecan-1-yl)carbamate (0.03 g, 1.0 eq.) was dissolved in dichloromethane (2.0 mL) and 4 M hydrogen chloride in 1,4-dioxane (0.12 ml, 15.0 eq.) was added. Reaction mixture was stirred at RT for 2 h. Reaction mixture was evaporated. Crude was dissolved in water and basified with 2 M NaOH. This aqueous layer was washed with DCM and then the organic layer was washed with brine, dried over $Na_2SO_4$ and evaporated in vacuo to give product (0.03 g, 93% yield) as a colorless oil. ESI-MS: 804.7 $[M+H]^+$. $^1H$ NMR (400 MHz, DMSO-$d_6$) δ 8.28 (d, J=5.0 Hz, 1H), 8.13 (d, J=3.0 Hz, 1H), 7.85 (s, 1H), 7.79 (d, J=11.6 Hz, 1H), 7.51 (d, J=7.4 Hz, 1H), 7.24-7.20 (m, 2H), 7.19-7.15 (m, 1H), 7.02 (d, J=8.5 Hz, 1H), 4.30 (t, J=5.7 Hz, 2H), 3.82-3.66 (m, 5H), 3.63-3.56 (m, 4H), 3.55-3.46 (m, 16H), 3.40 (t, J=5.6 Hz, 3H), 2.87 (t, J=5.7 Hz, 2H), 2.80-2.70 (m, 4H), 2.65-2.55 (m, 4H), 2.54-2.52 (m, 2H), 2.38 (s, 3H), 2.35-2.30 (m, 7H), 2.00-1.94 (m, 1H), 1.80-1.73 (m, 1H), 1.57-1.46 (m, 2H), 1.27-1.21 (m, 3H), 0.94-0.85 (m, 2H).

Example 11 D. 1-amino-N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)-N-methyl-3,6,9,12,15,18,21-heptaoxatetracosan-24-amide

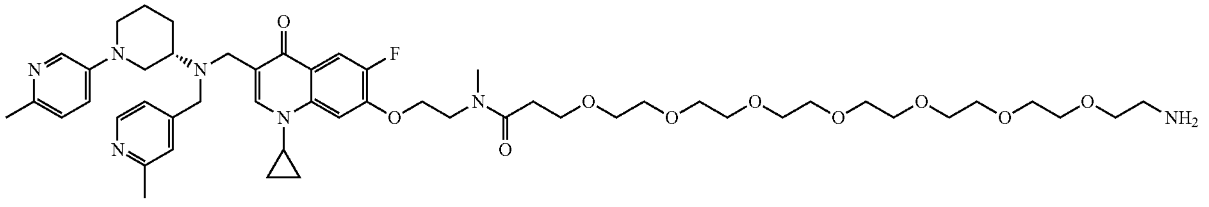

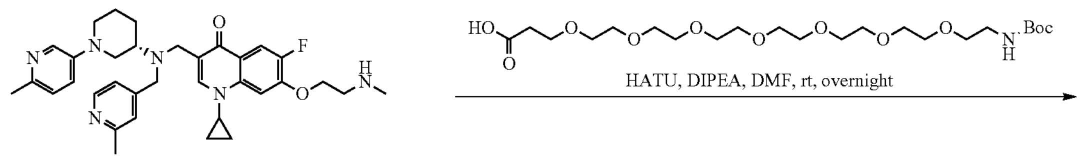

-continued

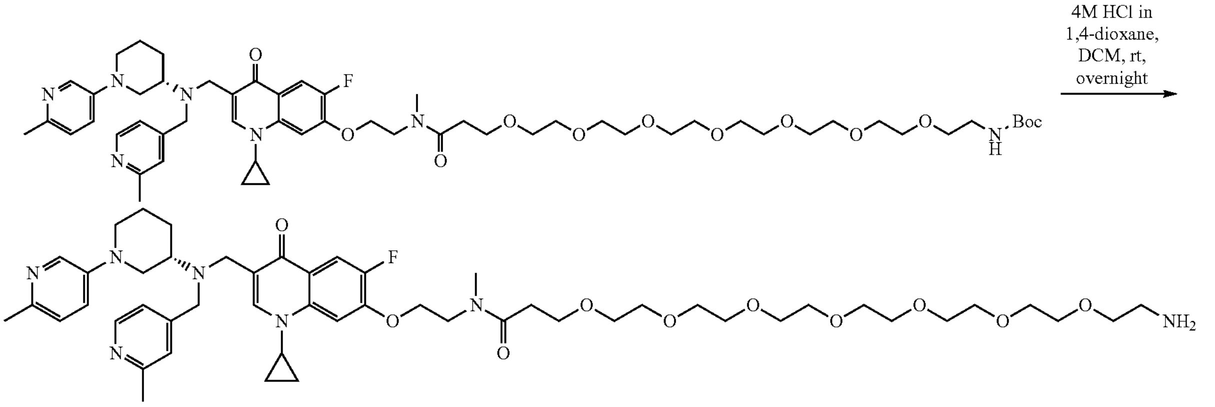

Preparation of tert-butyl N-{23-[(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)(methyl)carbamoyl]-3,6,9,12,15,18,21-heptaoxatricosan-1-yl}arbamate HATU (0.057 g, 1.3 eq.), DIPEA (0.061 ml, 3.0 eq.), 1-cyclopropyl-6-fluoro-7-[2-(methylamino)ethoxy]-3-({[(3S)-1-(6-methylpyridin-3-yl)piperidin-3-yl][(2-methylpyridin-4-yl)methyl]amino}methyl)-1,4-dihydroquinolin-4-one (0.07 g, 1.0 eq.) and 1-{[(tert-butoxy)carbonyl]amino}-3,6,9,12,15,18,21-heptaoxatetracosan-24-oic acid (0.064 g, 1.1 eq.) were mixed in anh. DMF (2.0 mL). The reaction mixture were stirred overnight at RT. Solvent was concentrated under reduced pressure. The residue was dissolved in DCM and wash with water, 1 M NaOH. brine. dried over anh. $Na_2SO_4$. filtered and concentrated in vacuo. The crude product was purified by FCC (SiHP; DCM:MeOH), re-purified by FCC ($NH_2$ column, DCM:MeOH) to give product (0.075 g, 60% yield) as a white solid. ESI-MS: 1064.8 $[M+H]^+$.

Preparation of 1-amino-N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)-N-methyl-3,6,9,12,15,18,21-heptaoxatetracosan-24-amide tert-Butyl N-{23-[(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)(methyl)carbamoyl]-3,6,9,12,15,18,21-heptaoxatricosan-1-yl}carbamate (0.075 g, 1.0 eq.) was dissolved in DCM (1.0 mL). 4 M HCl in 1,4-dioxane (0.26 ml, 15.0 eq.) was added and the reaction mixture was stirred overnight at RT. Volatiles were evaporated in vacuo. The residue was dissolved in water and basified with 2 M NaOH. Organics were washed with DCM and Organic layer was washed with brine, dried over anh. $Na_2SO_4$, filtered and concentrated in vacuo. Crude product was purified twice by FCC (NH2 column, DCM:MeOH) to give product (0.032 g, 47% yield) as a yellow oil. ESI-MS: 964.6 $[M+H]^+$. $^1H$ NMR (400 MHz, Acetonitrile-$d_3$) δ 8.30 (d, J=5.1 Hz, 1H), 8.16 (d, J=3.0 Hz, 1H), 7.89 (dd, J=11.7, 3.2 Hz, 1H), 7.86-7.85 (m, 1H), 7.50 (dd, J=19.9, 7.2 Hz, 1H), 7.25-7.23 (m, 1H), 7.22-7.16 (m, 2H), 7.02 (d, J=8.5 Hz, 1H), 4.38-4.32 (m, 2H), 3.88-3.80 (m, 3H), 3.80-3.78 (m, 2H), 3.76-3.70 (m, 2H), 3.70-3.67 (m, 2H), 3.61-3.50 (m, 25H), 3.44-3.37 (m, 3H), 3.16 (s, 2H), 2.99 (s, 1H), 2.86-2.79 (m, 2H), 2.78-2.75 (m, 1H), 2.75-2.71 (m, 2H), 2.67-2.59 (m, 3H), 2.42 (s, 3H), 2.38 (s, 3H), 2.10-2.04 (m, 2H), 1.87-1.80 (m, 1H), 1.63-1.55 (m, 2H), 1.32-1.25 (m, 2H), 0.96-0.88 (m, 2H).

Example 11E. 1-[(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)(methyl)carbamoyl]-3,6,9,12,15,18,21-heptaoxatetracosan-24-oic acid

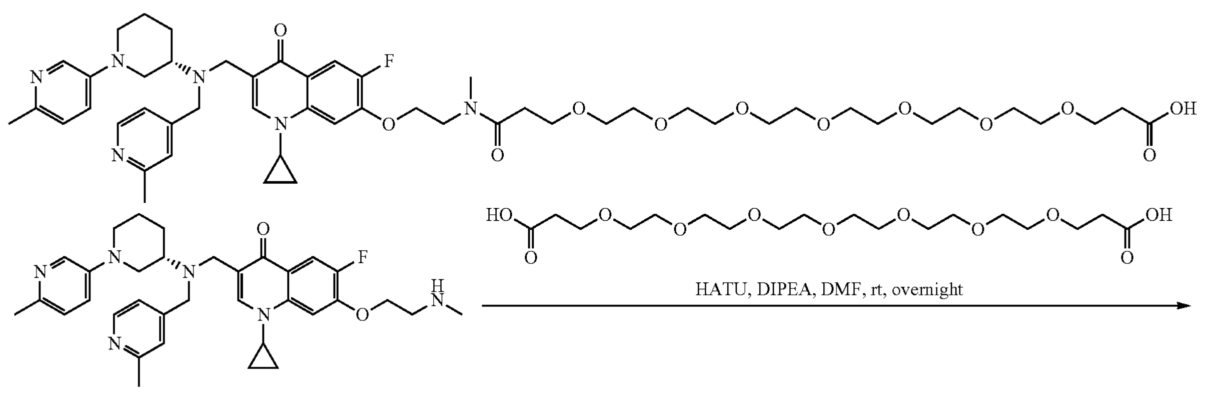

-continued

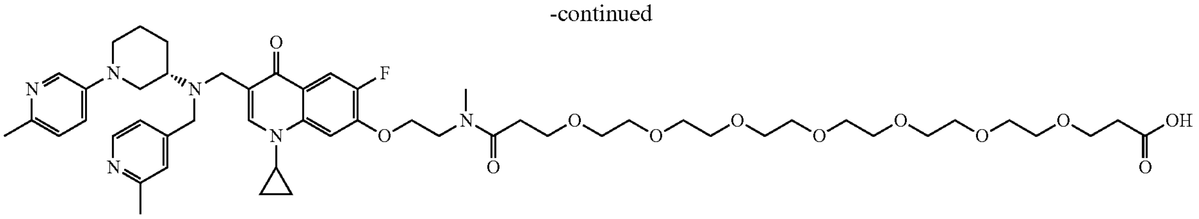

Preparation of 1-[(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)(methyl)carbamoyl]-3,6,9,12,15,18,21-heptaoxatetracosan-24-oic acid HATU (0.057 g, 1.3 eq.), DIPEA (0.061 ml, 3.0 eq.), 1-cyclopropyl-6-fluoro-7-[2-(methylamino)ethoxy]-3-({[(3S)-1-(6-methylpyridin-3-yl)piperidin-3-yl][(2-methylpyridin-4-yl)methyl]amino}methyl)-1,4-dihydroquinolin-4-one (0.07 g, 1.0 eq.) and 4,7,10,13,16,19,22-heptaoxapentacosanedioic acid (0.05 g, 1.0 eq.) were mixed in anh. DMF (2.0 mL). The reaction mixture were stirred overnight at RT. Solvent was concentrated under reduced pressure. The residue was dissolved in DCM and wash with water, 1 M NaOH, brine, dried over anh. $Na_2SO_4$, filtered and concentrated in vacuo. The crude product was purified by prep-HPLC ($H_2O$:MeCN:FA) to give product as the formic salt. The obtained sample was dissolved in water, basified by 1 M NaOH and extracted to DCM. Organic layer was washed with brine, dried over anh. $Na_2SO_4$, filtered and concentrated in vacuo to give a product (0.05 g, 41% yield) as a yellow oil. ESI-MS: 993.7 $[M+H]^+$. $^1H$ NMR (400 MHz, Methanol-$d_4$) δ 8.18 (t, J=4.7 Hz, 1H), 8.08 (t, J=3.0 Hz, 1H), 7.96-7.88 (m, 2H), 7.58-7.49 (m, 1H), 7.34-7.29 (m, 1H), 7.26-7.23 (m, 1H), 7.22-7.18 (m, 1H), 7.10 (dd, J=8.5, 4.5 Hz, 1H), 4.46-4.37 (m, 2H), 4.00-3.94 (m, 1H), 3.92-3.71 (m, 10H), 3.67-3.54 (m, 19H), 3.52-3.46 (m, 1H), 3.36-3.33 (m, 4H), 3.28-3.24 (m, 2H), 3.09-3.04 (m, 1H), 3.02-2.92 (m, 2H), 2.90-2.81 (m, 2H), 2.75-2.66 (m, 2H), 2.61-2.46 (m, 2H), 2.43-2.39 (m, 3H), 2.39-2.35 (m, 3H), 2.17-2.09 (m, 1H), 1.96-1.89 (m, 1H), 1.73-1.61 (m, 2H), 1.37-1.29 (m, 3H), 0.98-0.91 (m, 2H).

Example 11F. [4-(4,7,10,13,16-pentaoxanonadec-18-ynamido)phenyl]methyl N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)-N-methylcarbamate

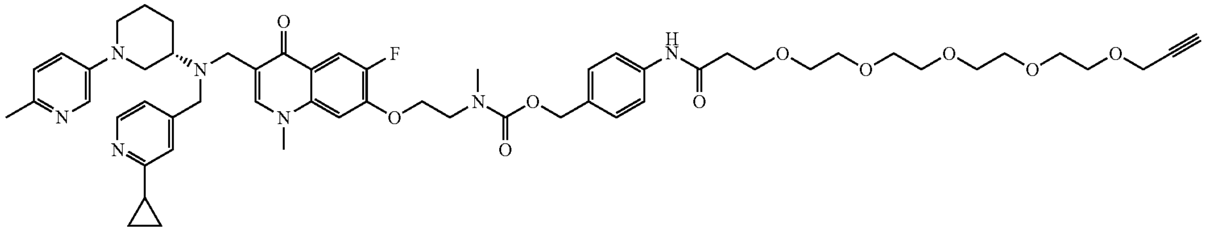 [SMILES: C#CCOCCOCCOCCOCCOCCC(=O)Nc1ccc(COC(=O)N(C)CCOc2cc3c(cc2F)c(=O)c(CN(Cc2ccnc(C4CC4)c2)[C@H]2CCCN(c4ccc(C)nc4)C2)cn3C)cc1]

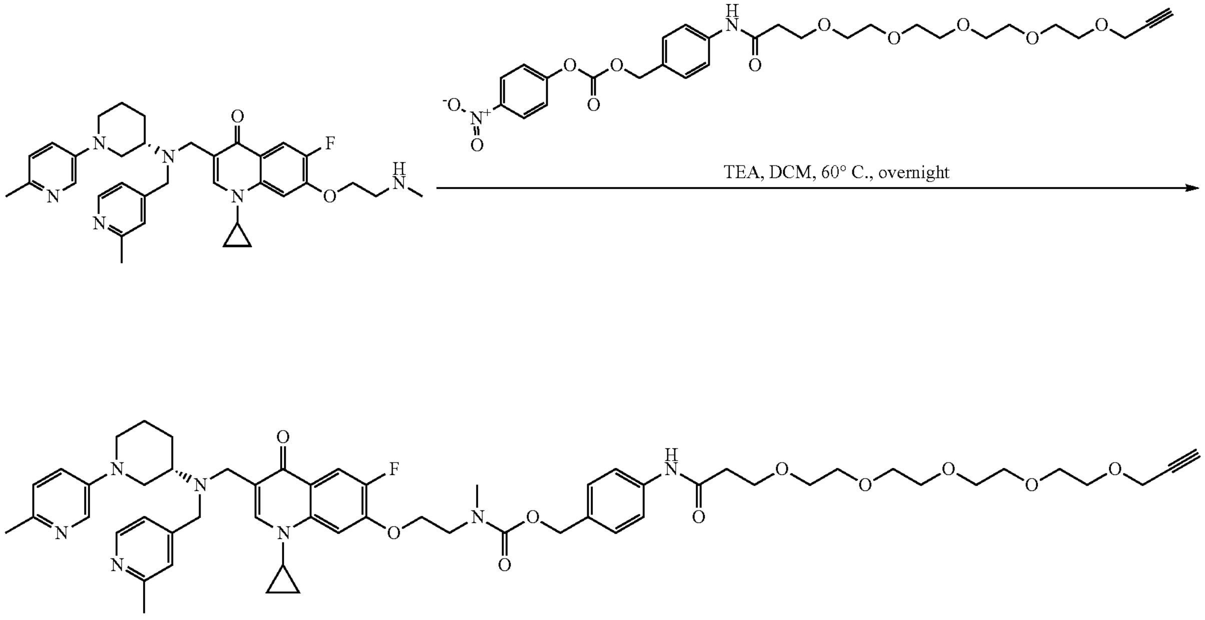

Preparation of [4-(4,7,10,13,16-pentaoxanonadec-18-ynamido)phenyl]methyl N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)-N-methylcarbamate 1-cyclopropyl-6-fluoro-7-[2-(methylamino)ethoxy]-3-({[(3S)-1-(6-methylpyridin-3-yl)piperidin-3-yl][(2-methylpyridin-4-yl)methyl]amino}methyl)-1,4-dihydroquinolin-4-one (Example 11) (0.03 g, 1.0 eq.), 4-nitrophenyl [4-(4,7,10,13,16-pentaoxanonadec-18-ynamido)phenyl]methyl carbonate (Intermediate 29) (0.03 g, 1.0 eq.) and TEA (0.014 ml, 2.0 eq.) were dissolved in anh. DCM (1.0 mL) and reaction was stirred overnight at 60° C. Reaction mixture was concentrated in vacuo. The residue was purified twice by FCC (SiHP; DCM:MeOH) to obtain product (0.024 g, 46% yield) as a beige solid. ESI-MS: 1020.9 $[M+H]^+$. $^1H$ NMR (400 MHz, Methanol-$d_4$) δ 8.17 (d, J=5.2 Hz, 1H), 8.10 (d, J=2.9 Hz, 1H), 7.97-7.88 (m, 2H), 7.59-7.53 (m, 1H), 7.51-7.40 (m, 2H), 7.38-7.30 (m, 2H), 7.26 (s, 1H), 7.25-7.21 (m, 2H), 7.13 (d, J=8.6 Hz, 1H), 5.12-5.01 (m, 2H), 4.43-4.34 (m, 2H), 4.17 (d, J=2.4 Hz, 2H), 3.92-3.77 (m, 9H), 3.66-3.59 (m, 10H), 3.58-3.54 (m, 5H), 3.52-3.35 (m, 2H), 3.16-3.08 (m, 3H), 3.01-2.94 (m, 1H), 2.90-2.86 (m, 1H), 2.85 (t, J=2.4 Hz, 1H), 2.75-2.67 (m, 1H), 2.65-2.57 (m, 2H), 2.42 (s, 3H), 2.37 (s, 3H), 2.18-2.12 (m, 1H), 1.97-1.91 (m, 1H), 1.73-1.63 (m, 2H), 1.36-1.30 (m, 2H), 1.29-1.23 (m, 1H), 0.96-0.86 (m, 2H).

Example 11G. 3-[2-(2-{2-[(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)(methyl)carbamoyl]ethoxy}ethoxy)ethoxy]propanoic acid formate

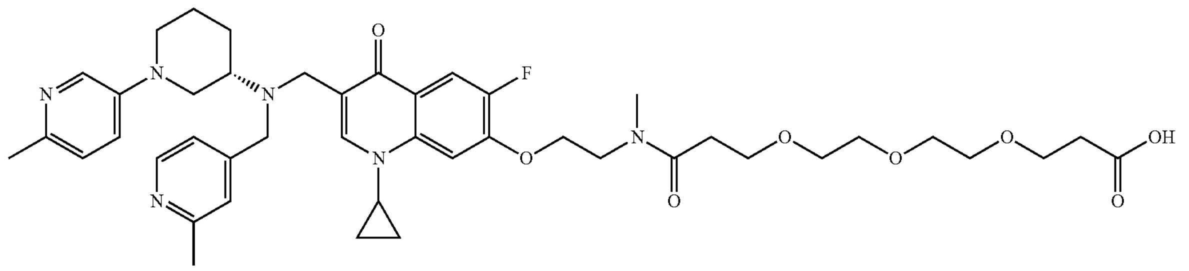 [SMILES: Cc1ccc(N2CCC[C@H](N(Cc3ccnc(C)c3)Cc3cn(C4CC4)c4cc(OCCN(C)C(=O)CCOCCOCCOCCC(=O)O)c(F)cc4c3=O)C2)cn1]

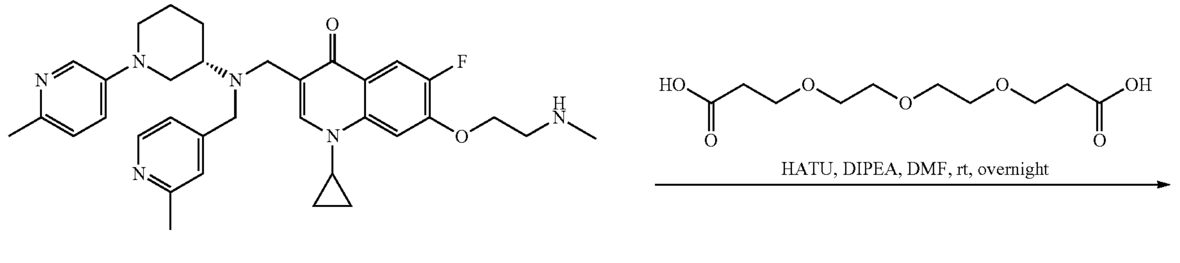

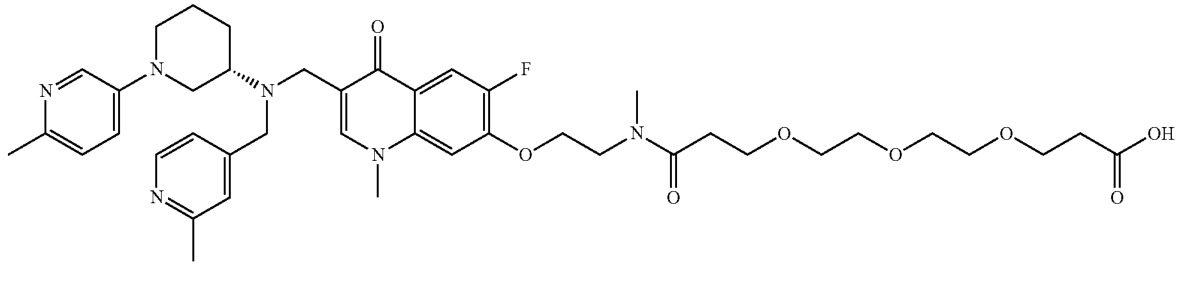

Preparation of 3-[2-(2-{2-[(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)(methyl)carbamoyl]ethoxy}ethoxy)ethoxy]propanoic acid formate HATU (0.057 g, 1.3 eq.), DIPEA (0.061 ml, 3.0 eq.), 1-cyclopropyl-6-fluoro-7-[2-(methylamino)ethoxy]-3-({[(3S)-1-(6-methylpyridin-3-yl)piperidin-3-yl][(2-methylpyridin-4-yl)methyl]amino}methyl)-1,4-dihydroquinolin-4-one (Example 11) (0.07 g, 1.0 eq.) and 3-{2-[2-(2-carboxyethoxy)ethoxy]ethoxy}propanoic acid (0.03 g, 1.0 eq.) were mixed in anh. DMF (1.5 mL). The reaction mixture were stirred overnight at RT. Solvent was concentrated under reduced pressure. The residue was dissolved in DCM and washed with water, brine, dried over anh. $Na_2SO_4$, filtered and concentrated in vacuo. The crude product was purified by prep-HPLC ($H_2O$:MeCN:FA) to give product as a formate salt (0.045 g, 45% yield) as a yellow oil. ESI-MS: 817.6 $[M+H]^+$. $^1H$ NMR (400 MHz, DMSO-$d_6$) δ12.71 (s, 1H), 8.30-8.25 (m, 1H), 8.14 (s, 1H), 8.14-8.11 (m, 1H), 7.86-7.76 (m, 2H), 7.55-7.46 (m, 1H), 7.25-7.18 (m, 2H), 7.19-7.14 (m, 1H), 7.05-6.99 (m, 1H), 4.40-4.34 (m, 1H), 4.34-4.28 (m, 1H), 3.86-3.70 (m, 5H), 3.66-3.55 (m, 6H), 3.52-3.42 (m, 6H), 3.13-3.08 (m, 2H), 2.92-2.89 (m, 1H), 2.80-2.66 (m, 4H), 2.63-2.52 (m, 6H), 2.45-2.41 (m, 1H), 2.39-2.35 (m, 3H), 2.35-2.30 (m, 3H), 2.01-1.93 (m, 1H), 1.80-1.71 (m, 1H), 1.58-1.43 (m, 2H), 1.28-1.21 (m, 2H), 0.94-0.82 (m, 2H).

Example 11H. {4-[(2S)-2-[(2S)-2-(3-{2-[2-(2-azidoethoxy)ethoxy]ethoxy}propanamido)-3-methyl-butanamido]-5-(carbamoylamino)pentanamido]phenyl}methyl N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)-N-methylcarbamate

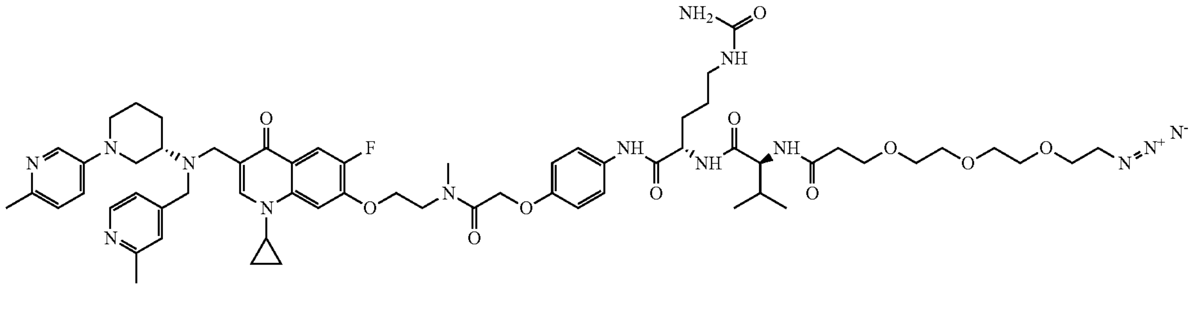

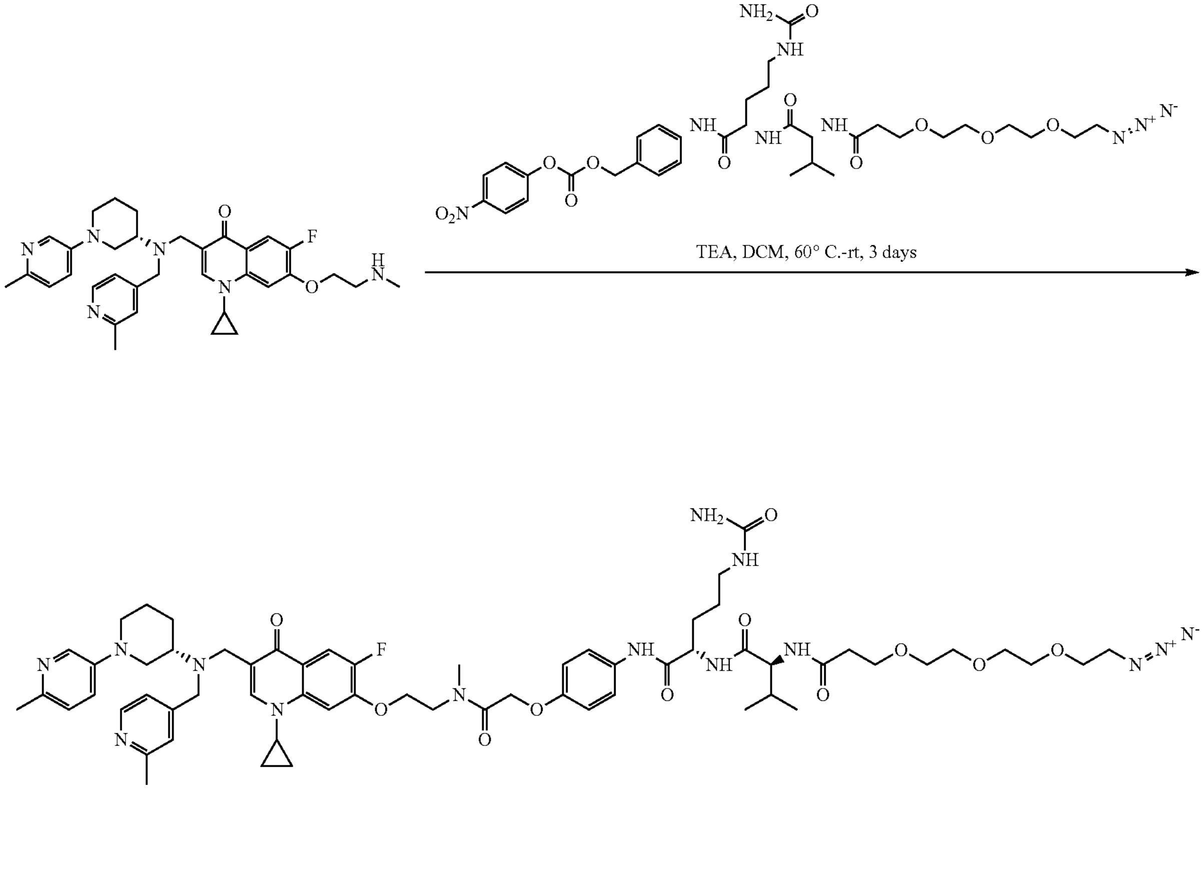

Preparation of {4-[(2S)-2-[(2S)-2-(3-{2-[2-(2-azidoethoxy)ethoxy]ethoxy}propanamido)-3-methyl-butanamido]-5-(carbamoylamino)pentanamido]phenyl}methyl N-(2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl)-N-methylcarbamate A mixture of 1-cyclopropyl-6-fluoro-7-[2-(methylamino)ethoxy]-3-({[(3S)-1-(6-methylpyridin-3-yl)piperidin-3-yl][(2-methylpyridin-4-yl)methyl]amino}methyl)-1,4-dihydroquinolin-4-one (Example 11) (0.019 g, 1.2 eq.), {4-[(2S)-2-[(2S)-2-(3-{2-[2-(2-azidoethoxy)ethoxy]ethoxy}propanamido)-3-methyl-butanamido]-5-(carbamoylamino)pentanamido]phenyl}methyl 4-nitrophenyl carbonate (0.02 g, 1.0 eq.), triethylamine (0.01 ml, 2.8 eq.) and DCM (1.0 mL) was stirred overnight at 60° C. and then stirred for two days at RT. Subsequently, the mixture was concentrated in vacuo and the residue was purified by FCC (SiHP; DCM:MeOH) to give product (0.017 g, 54% yield) as a white solid. ESI-MS: 1220.3 $[M+H]^+$.

Example 12A. {4-[(2S)-2-[(2S)-2-(3-{2-[2-(2-azidoethoxy)ethoxy]ethoxy}propanamido)-3-methyl-butanamido]-5-(carbamoylamino)pentanamido]phenyl}methyl N-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]carbamate

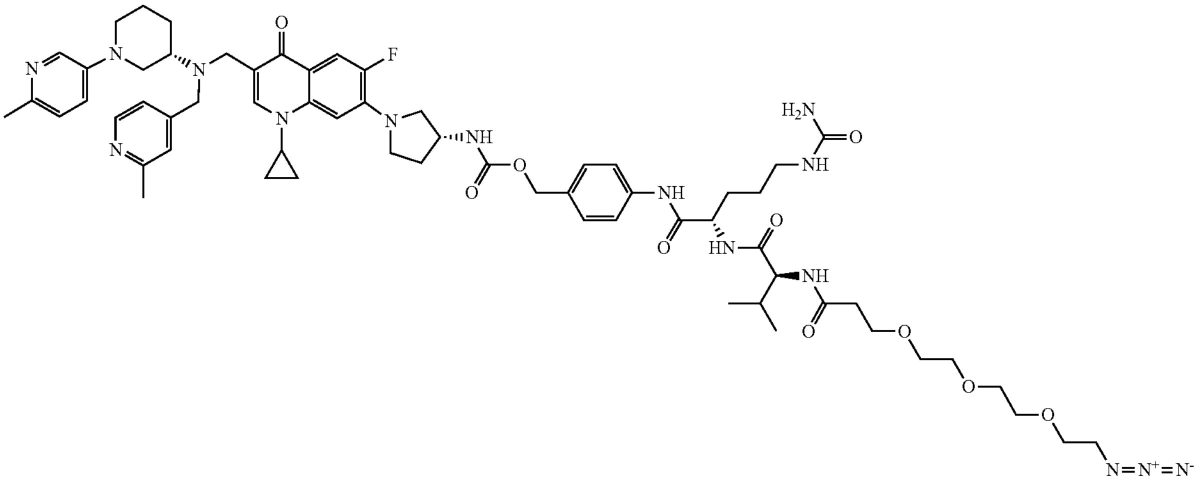

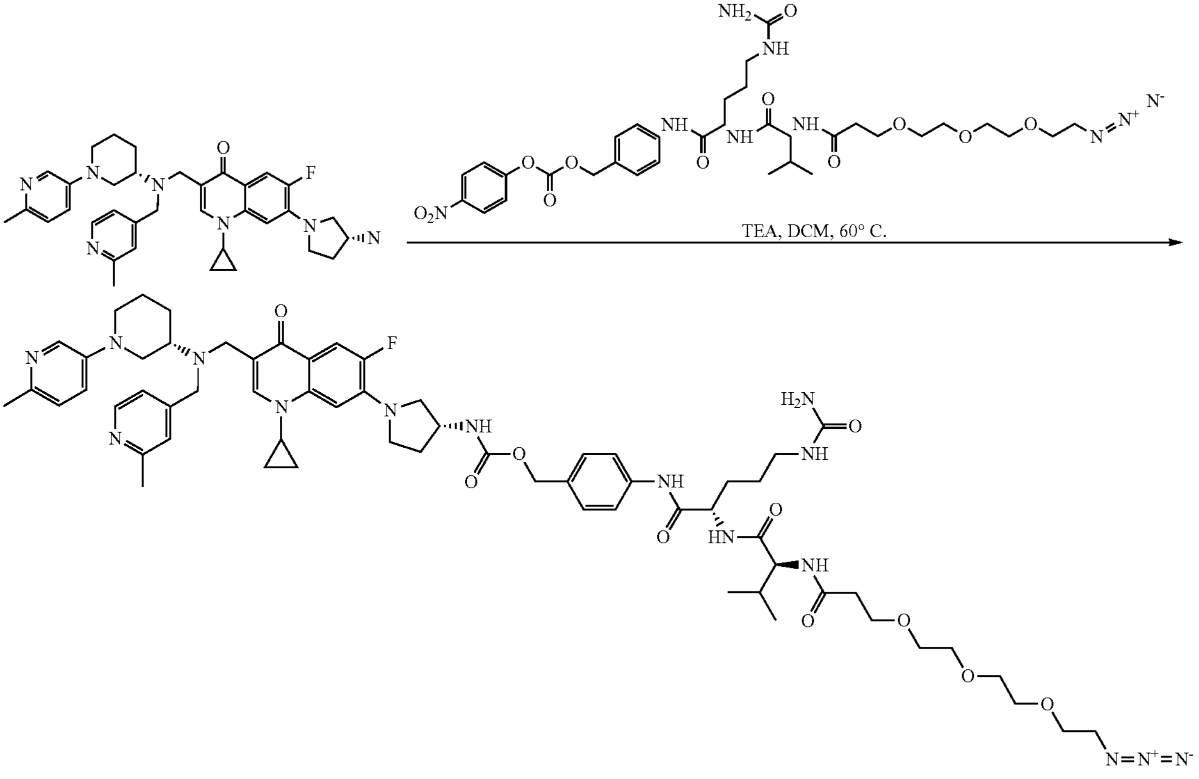

Preparation of {4-[(2S)-2-[(2S)-2-(3-{2-[2-(2-azidoethoxy)ethoxy]ethoxy}propanamido-3 methyl-butanamido]-5-(carbamoylamino)pentanamido] phenyl}methyl N-[(3R-1-[1-cyclopropyl-6-fluoro-3-({[(3S-1-(6 methylpyridin-)piperidin-3-yl][(2-methylpyridin-4-yl)methyl]amino}methyl)-4-oxo-1, 4-dihydroquinolin-7-yl]pyrrolidin-3-yl]carbamate {4-[(2S)-2-[(2S)-2-(3-{2-[2-(2-azidoethoxy)ethoxy] ethoxy}propanamido-3-methylbutanamido]-5-(carbamoylamino)pentanamido]phenyl}methyl 4-nitrophenyl carbonate (0.02 g, 1.0 eq.) and 7-[(3R)-3-aminopyrrolidin-1-yl]-1-cyclopropyl-6-fluoro-3-({[(3S)-1-(6-methylpyridin-3-yl) piperidin-3-yl][2-methylpyridin-4-yl)methyl] amino}methyl)-1,4-dihydroquinolin-4-one (Example 12) (0.019 g, 1.2 eq.) were suspended in DCM (1.0 mL). Subsequently, TEA (0.007 ml, 1.9 eq.) was added and the reaction mixture was stirred overnight at 60° C. The reaction mixture was concentrated in vacuo and the residue was purified twice by FCC (SiHP; DCM:MeOH) to give product (0.016 g, 46% yield) as a yellow solid. ESI-MS: 1230.9 $[M+H]^+$. HR-MS: 1230.7 $[M+H]^+$.

Example 15A. 1-amino-N-{[(3R)-1-[1-cyclopropyl-6-fluoro-3-({[(3S)-1-(6-methylpyridin-3-yl)piperidin-3-yl][(2-methylpyridin-4-yl)methyl] amino}methyl)-4-oxo-1,4-dihydroquinolin-7-yl] pyrrolidin-3-yl]methyl}-3,6,9,12-tetraoxapentadecan-15-amide

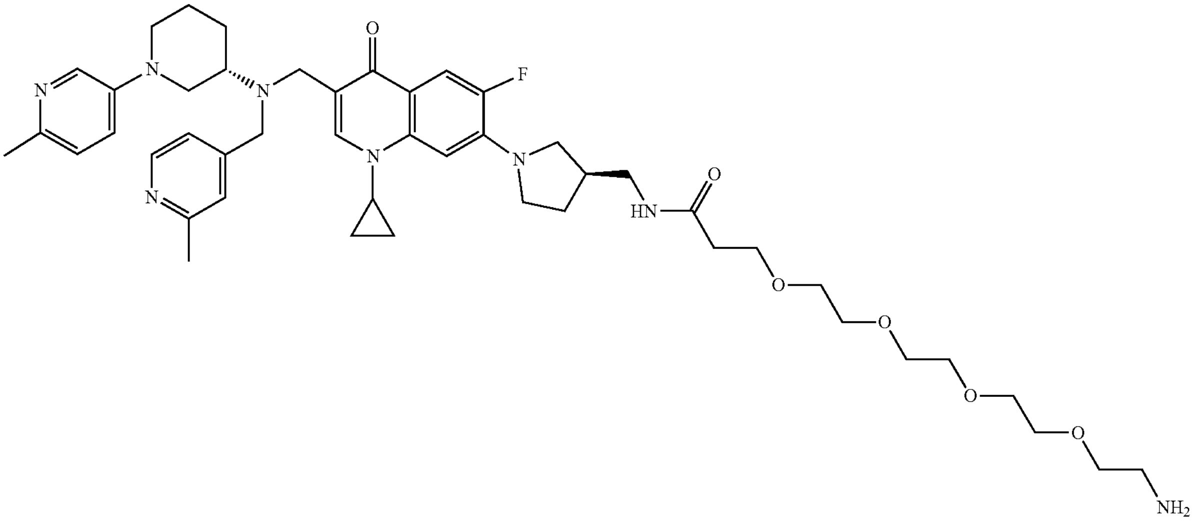

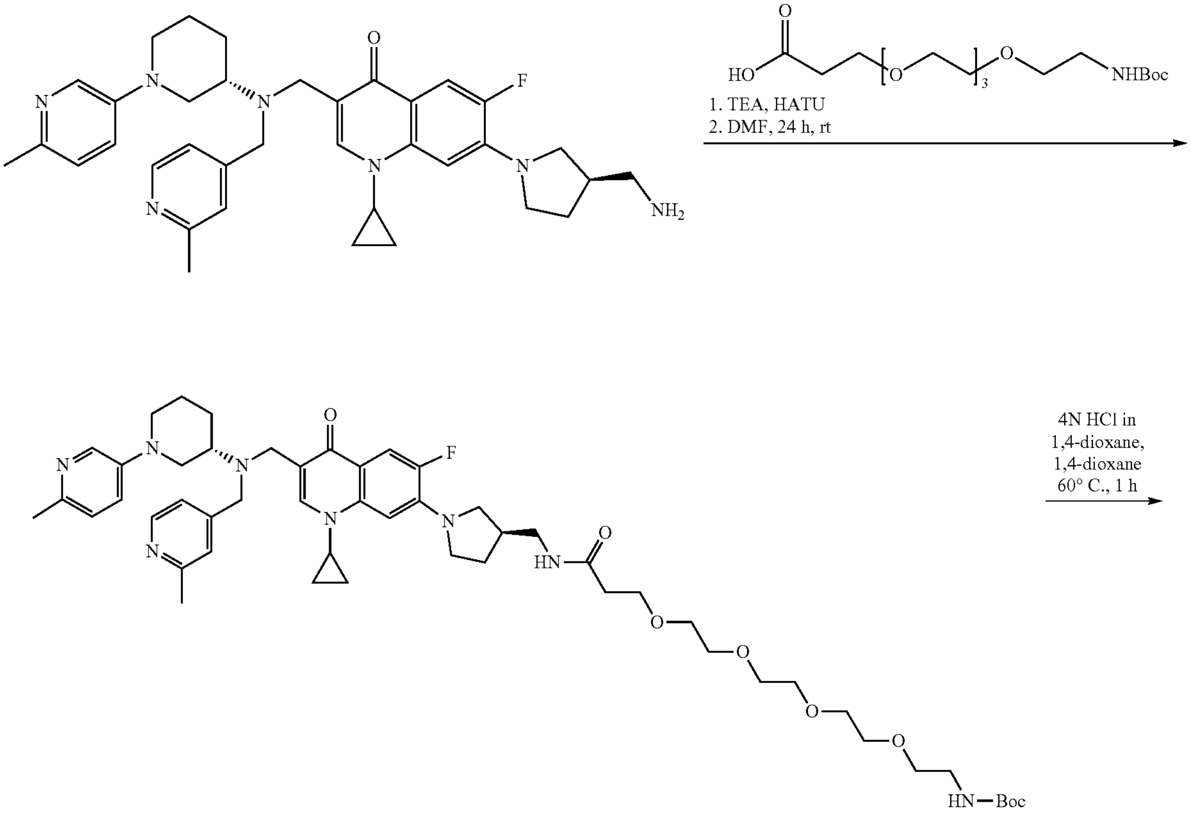

-continued

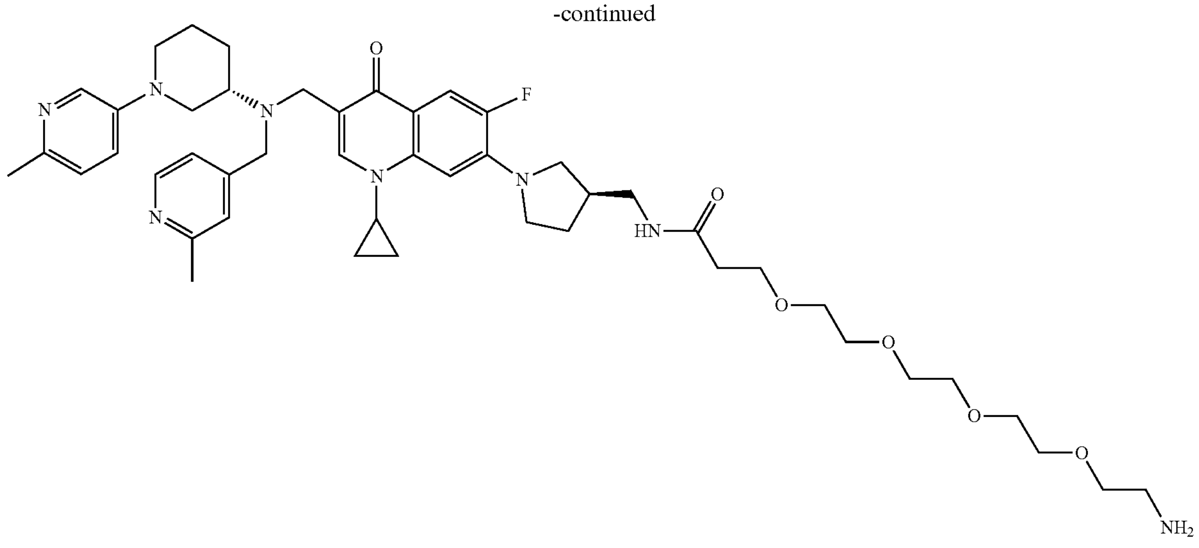

Preparation of tert-butyl N-[14-({[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]methyl}carbamoyl)-3,6,9,12-tetraoxatetradecan-1-yl]carbamate 1-{[(tert-butoxy)carbonyl]amino}-3,6,9,12-tetraoxapentadecan-15-oic acid (0.207 g, 1.5 eq) and HATU (0.172 g, 1.2 eq.) were dissolved in dry DMF (5.0 ml) then 7-[(3R)-3-(aminomethyl)pyrrolidin-1-yl]-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (Example 15) (0.230 g, 1.0 eq.) and TEA (0.160 ml, 3.0 eq.) were added, reaction was stirred at RT for 24 h. Crude was evaporated and extracted (DCM/NaOH aq). Organic layers were combined, dried over $Na_2SO_4$, filtered and evaporated. Product was purified by FCC (SiHP; DCM:MeOH). The titled compound was obtained (0.30 g, yield 84%) as a brown oil. ESI-MS: 957.9 $[M+H]^+$ Preparation of 1-amino-N-{[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]methyl}-3,6,9,12-tetraoxapentadecan-15-amide Tert-butyl N-[14-({[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]methyl}carbamoyl)-3,6,9,12-tetraoxatetradecan-1-yl]carbamate (0.300 g, 1.0 eq.) was dissolved in 1,4-dioxane (8.0 ml) and 4N HCl in 1,4-dioxane (1.18 ml, 15.0 eq.) was added. Reaction mixture was stirred for 1 h at 60° C., after completion of reaction solvent was evaporated and crude was extracted (DCM/NaOH (aq)). The organic layers were combined, dried over $MgSO_4$ and evaporated. The residue was purified by RP-FCC (C18HP; $H_2O$:MeCN) to give the titled compound (0.190 g, yield 71%) as a beige solid, ESI-MS: 858.6 $[M+H]^+$. $^1H$ NMR (400 MHz, Pyridine-d5) δ 8.83 (t, J=5.9 Hz, 1H), 8.59 (dd, J=10.4, 3.9 Hz, 2H), 8.41 (d, J=14.6 Hz, 1H), 7.87 (s, 1H), 7.35 (d, J=5.6 Hz, 2H), 7.29 (dd, J=8.5, 3.1 Hz, 1H), 7.05 (d, J=8.5 Hz, 1H), 6.80 (d, J=7.6 Hz, 1H), 4.07 (d, J=21.2 Hz, 3H), 3.92 (q, J=8.3, 7.2 Hz, 2H), 3.85 (d, J=4.2 Hz, 2H), 3.76-3.34 (m, 21H), 3.24 (td, J=6.8, 3.6 Hz, 1H), 3.19-3.03 (m, 1H), 2.99 (t, J=5.4 Hz, 2H), 2.86 (t, J=11.2 Hz, 1H), 2.72 (t, J=6.2 Hz, 2H), 2.67-2.58 (m, 1H), 2.57 (s, 3H), 2.51 (s, 4H), 2.16-1.91 (m, 2H), 1.80-1.62 (m, 2H), 1.52 (q, J=11.9 Hz, 2H), 1.09 (q, J=6.3, 5.6 Hz, 2H), 0.90 (p, J=4.8 Hz, 2H).

Example 19A. {4-[(2S)-2-[(2S)-2-(3-{2-[2-(2-azidoethoxy)ethoxy]ethoxy}propanamido)-3-methyl-butanamido]-(carbamoylamino)pentanamido] phenyl}methy N-{1-[1-cyclopropyl-6-fluoro-3-({([(3S)-1-(6-methylpyridin-3-yl)piperidin-3-yl][(2-methylpyridin-4-yl)methyl]amino}methyl)-4-oxo-1,4-dihydroquinolin-7-yl]piperidin-4-yl}-N-methylcarbamate
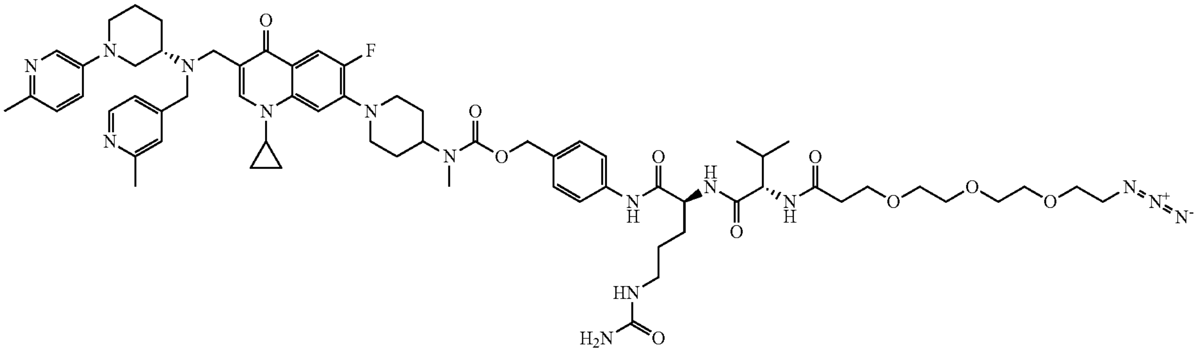 [SMILES: Cc1ccc(N2CCC[C@H](N(Cc3ccnc(C)c3)Cc3cn(C4CC4)c4cc(N5CCC(N(C)C(=O)OCc6ccc(NC(=O)[C@H](CCCNC(N)=O)NC(=O)[C@@H](NC(=O)CCOCCOCCOCCN=[N+]=[N-])C(C)C)cc6)CC5)c(F)cc4c3=O)C2)cn1]
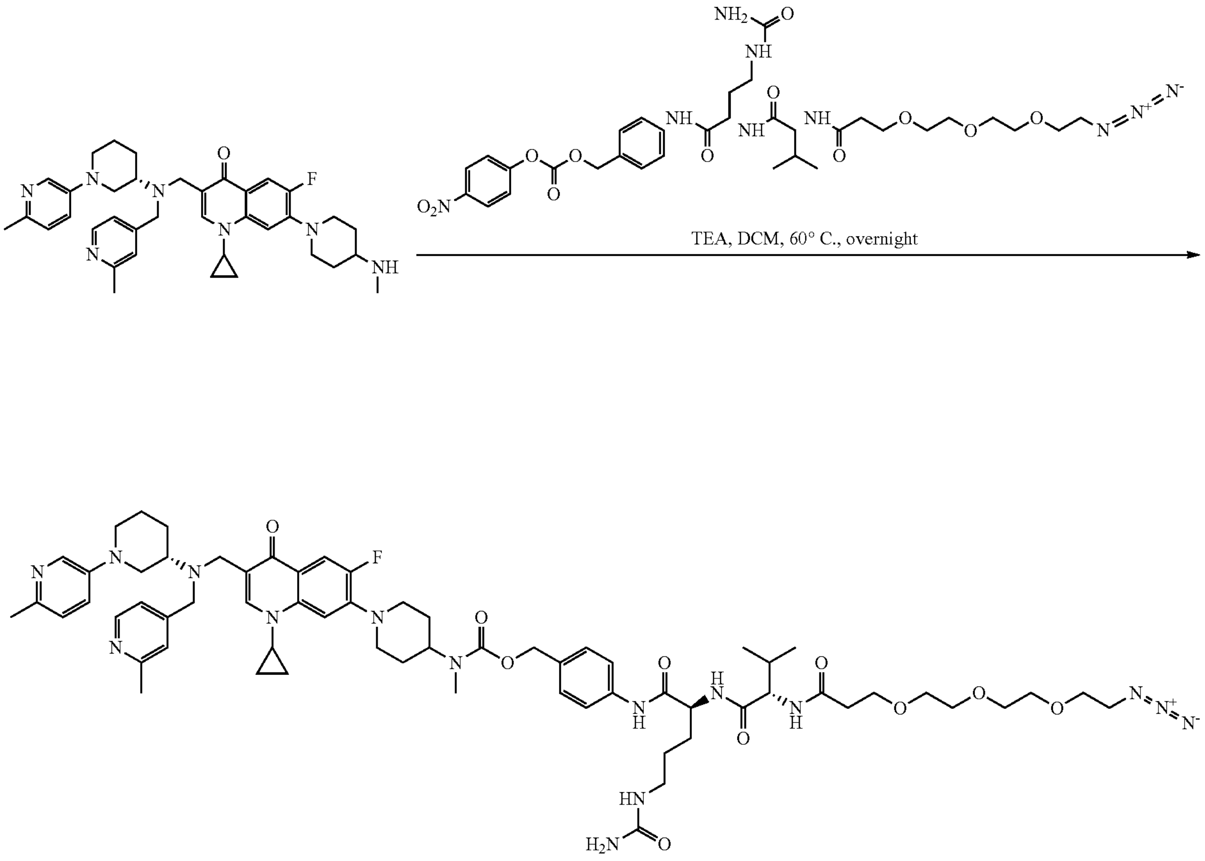

Preparation of {4-[(2S)-2-[(2S)-2-(3-{2-[2-(2-azidoethoxy)ethoxy]ethoxy}propanamido)-3-methyl-butanamido]-5-(carbamoylamino)pentanamido]phenyl}methyl N-{1-[1-cyclopropyl-6-fluoro-3-({([(3S)-1-(6-methylpyridin-3-yl)piperidin-3-yl][(2-methylpyridin-4-yl)methyl]amino}methyl)-4-oxo-1,4-dihydroquinolin-7-yl]piperidin-4-yl}-N-methylcarbamate {4-[(2S)-2-[(2S)-2-(3-{2-[2-(2-azidoethoxy)ethoxy]ethoxy}propanamido)-3-methylbutanamido]-5-(carbamoylamino)pentanamido]phenyl}methyl 4-nitrophenyl carbonate (0.02 g, 1.0 eq.) and 1-cyclopropyl-6-fluoro-7-[4-(methylamino)piperidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride (Example 19) (0.016 g, 1.0 eq.) were suspended in DCM (1.0 mL). Subsequently, TEA (0.007 mL, 2.0 eq.) was added and the reaction mixture was stirred overnight at 60° C. Solvent was evaporated in vacuo and the residue was purified by FCC (SiHP; DCM:MeOH) to give product (0.017 g, 50% yield) as a yellow solid. ESI-MS: 1258.9 $[M+H]^+$. HR-MS: 1258.9 $[M+H]^+$.

Example 31A. (3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl 4,7,10,13,16-pentaoxanonadec-18-ynoate

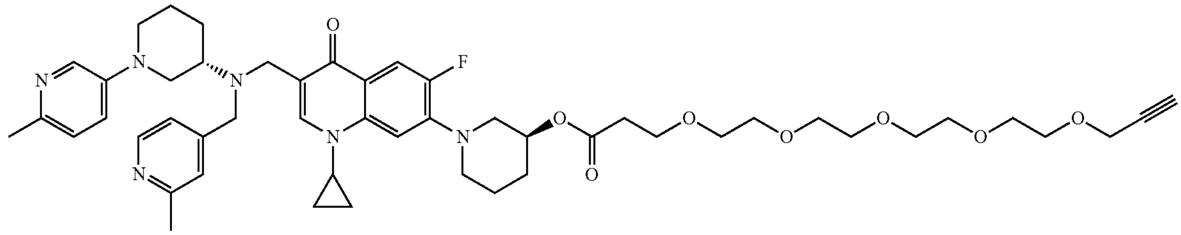 [SMILES: C#CCOCCOCCOCCOCCOCCC(=O)O[C@H]1CCCN(c2cc3c(cc2F)c(=O)c(CN(Cc2ccnc(C)c2)[C@H]2CCCN(c4ccc(C)nc4)C2)cn3C2CC2)C1]

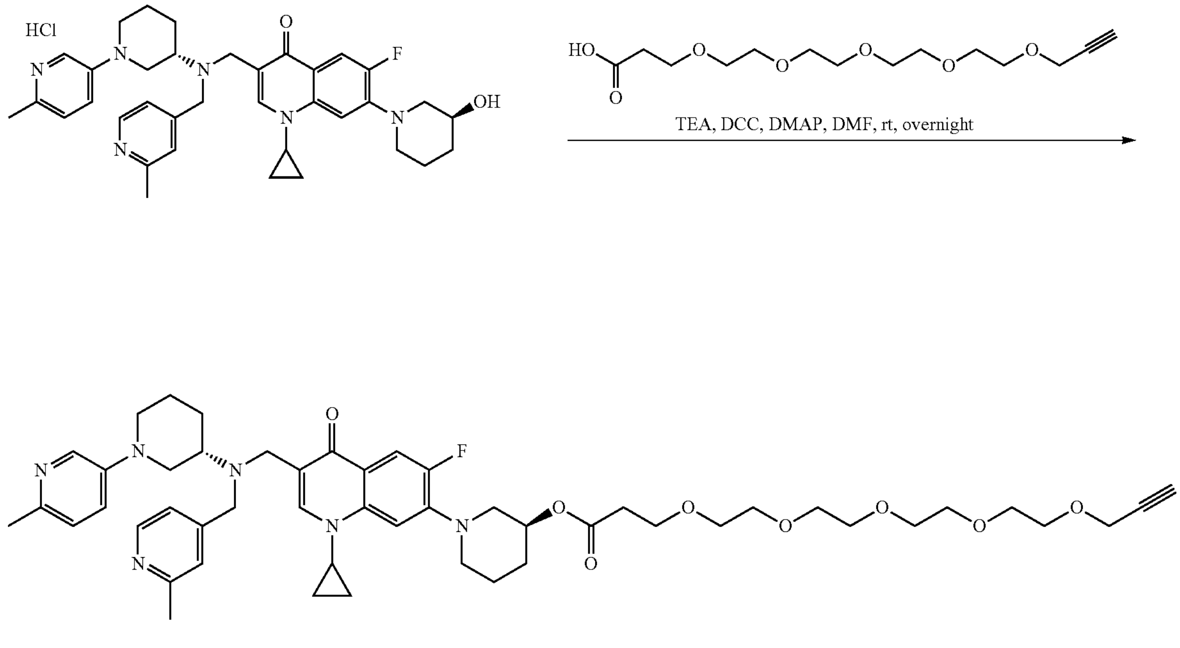

Preparation of (3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl 4,7,10,13,16-pentaoxanonadec-18-ynoate A solution of 1-cyclopropyl-6-fluoro-7-[(3S)-3-hydroxypiperidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride (Example 31) (0.107 g, 1.0 eq.) and TEA (0.023 mL, 1.0 eq.) in anh. DMF (1.0 mL) was stirred at RT for 10 min. A solution of 4,7,10,13,16-pentaoxanonadec-18-ynoic acid (0.05 g, 1.0 eq.), DMAP (0.002 g, 0.1 eq.) and DCC (0.037 g, 0.179 mmol, 1.091 eq.) in DCM (1.0 mL) was stirred for 10 min. Then both solutions were combined and the reaction mixture was stirred overnight at RT. Then reaction mixture was concentrated in vacuo. DCM was added and the residue was washed with water. Organic layer was dried over anh. $Na_2SO_4$, filtered and concentrated under reduced pressure. Crude product was purified twice by FCC (SiHP; DCM: MeOH) to give product (0.022 g, 14% yield) as a colorless oil. ESI-MS: 897.7 $[M+H]^+$. $^1H$ NMR (400 MHz, Methanol-$d_4$) δ 8.19 (d, J=5.3 Hz, 1H), 8.10 (d, J=2.8 Hz, 1H), 7.93 (s, 1H), 7.83 (d, J=13.7 Hz, 1H), 7.47 (d, J=7.5 Hz, 1H), 7.36 (dd, J=8.6, 3.0 Hz, 1H), 7.26 (s, 1H), 7.24 (d, J=5.2 Hz, 1H), 7.13 (d, J=8.6 Hz, 1H), 5.08-5.01 (m, 1H), 4.18 (d, J=2.4 Hz, 2H), 3.91-3.85 (m, 3H), 3.82-3.78 (m, 2H), 3.74 (t, J=6.2 Hz, 2H), 3.68-3.56 (m, 17H), 3.52-3.42 (m, 2H), 3.31-3.23 (m, 2H), 3.00-2.93 (m, 1H), 2.90-2.83 (m, 2H), 2.75-2.66 (m, 1H), 2.60 (t, J=6.2 Hz, 2H), 2.42 (s, 3H), 2.37 (s, 3H), 2.18-2.12 (m, 1H), 2.08-1.98 (m, 2H), 1.97-1.91 (m, 1H), 1.83-1.73 (m, 2H), 1.72-1.61 (m, 2H), 1.38-1.30 (m, 3H), 0.97-0.88 (m, 2H).

Example 31B. (3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl N-{[4-(4,7,10,13,16-pentaoxanonadec-18-ynamido)phenyl]methyl}carbamate

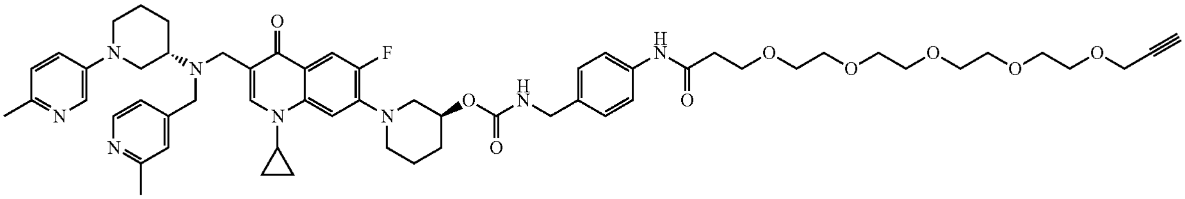 [SMILES: C#CCOCCOCCOCCOCCOCCC(=O)Nc1ccc(CNC(=O)O[C@H]2CCCN(c3cc4c(cc3F)c(=O)c(CN(Cc3ccnc(C)c3)[C@H]3CCCN(c5ccc(C)nc5)C3)cn4C3CC3)C2)cc1]

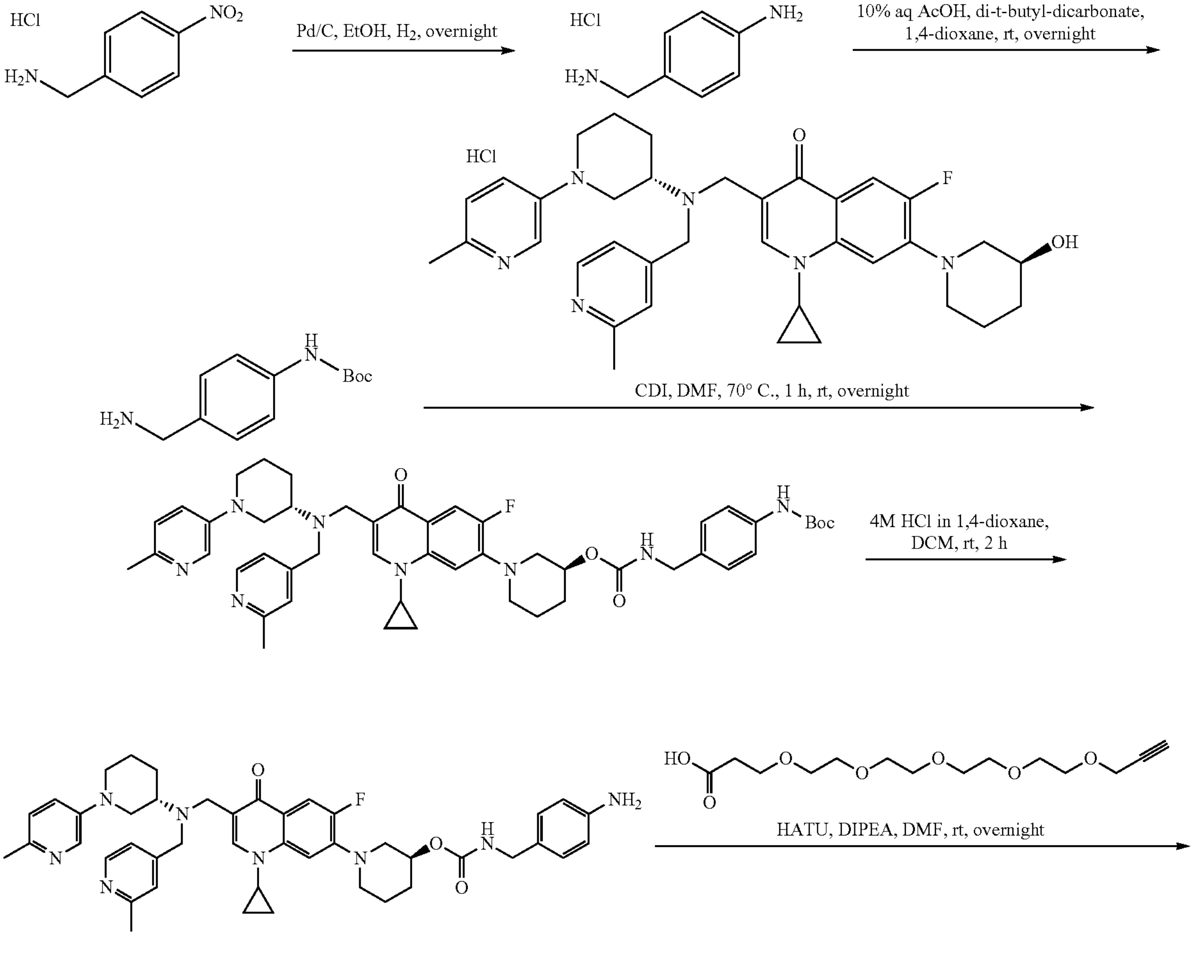

-continued

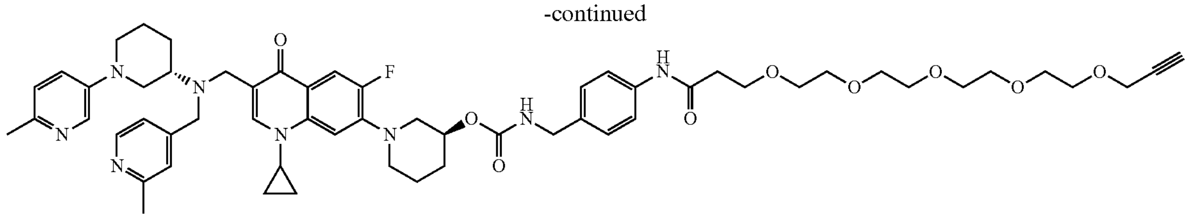

Preparation of 4-(aminomethyl)aniline hydrochloride

A solution of 1-(4-nitrophenyl)methanamine hydrochloride (1.5 g, 1.0 eq.) in EtOH (30.0 mL) was purged with argon and Pd/C (0.17 g, 0.2 eq.) was added. Reaction was run under hydrogen atmosphere overnight at RT. The reaction mixture was filtered through a pad of celite and the filtrate was concentrated to give product (1.15 g, 82% yield). $^{1}H$ NMR (400 MHz, DMSO-$d_6$) δ 8.22 (s, 2H), 7.12 (d, J=8.4 Hz, 2H), 6.56 (d, J=8.5 Hz, 2H), 5.33 (s, 2H), 3.78 (s, 2H).

Preparation of tert-butyl N-[4-(aminomethyl)phenyl]carbamate

A solution of di-t-butyl-dicarbonate (1.5 g, 1.1 eq.) in 1,4-dioxane (55.0 mL) was added to a solution of 4-(aminomethyl)aniline hydrochloride (1.15 g, 1.0 eq.) in 10% aq acetic acid (55.0 mL). The reaction mixture was stirred overnight at RT. Water was added and the mixture was washed with $Et_2O$. The aqueous phase was basified with 2 N NaOH to pH 14 and extracted with $Et_2O$. The organic layer was washed with water, dried over $Na_2SO_4$ and concentrated in vacuo. Crude product was purified by FCC ($NH_2$, DCM:MeOH) to give product (0.48 g, 33% yield) as a yellow solid. 1H NMR (400 MHz, Methanol-d4) δ 7.37 (d, J=8.4 Hz, 2H), 7.25 (d, J=8.5 Hz, 2H), 3.73 (s, 2H), 3.37 (s, 1H), 1.53 (s, 9H).

Preparation of (3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl N-[(4-{[(tert-butoxy)carbonyl]amino}phenyl)methyl]carbamate A solution of CDI (0.027 g, 1.1 eq.), 1-cyclopropyl-6-fluoro-7-[(3S)-3-hydroxypiperidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride (Example 31) (0.1 g, 1.0 eq.) in DMF (2.0 mL) was stirred at 70° C. for 1 h. Then tert-butyl N-[4-(aminomethyl)phenyl]carbamate (0.035 g, 1.0 eq.) was added and stirred overnight at RT. Solvent was evaporated under reduced pressure. Subsequently, residue was partitioned between DCM and water. Organic layer was washed with brine, dried over $Na_2SO_4$ and concentrated in vacuo. Crude product was purified twice by FCC (SiHP; DCM:MeOH) to give product (0.041 g, 26% yield). ESI-MS: 859.5 $[M+H]^+$.

Preparation of (3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl N-[(4-aminophenyl)methyl]carbamate hydrochloride (3S)-1-[1-Cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl N-[(4-{[(tert-butoxy)carbonyl]amino}phenyl)methyl]carbamate (0.04 g, 1.0 eq.) was dissolved in DCM (1.0 mL) and 4 M hydrogen chloride in 1,4-dioxane (0.29 mL, 30.0 eq.) was added. Reaction mixture was stirred at RT for 2 h. Solvents were evaporated under reduced pressure. The residue was diluted with DCM and concentrated in vacuo (3 cycles) to give product (0.035 g, quant.). ESI-MS: 759.6 $[M+H]^+$.

Preparation of (3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl N-{[4-(4,7,13,16-pentaoxanonadec-18-ynamido)phenyl]methyl}carbamate A mixture of HATU (0.018 g, 1.3 eq.), DIPEA (0.019 mL, 3.0 eq.), 4,7,10,13,16-pentaoxanonadec-18-ynoic acid (0.011 g, 1.0 eq.), (3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]piperidin-3-yl N-[(4-aminophenyl)methyl]carbamate hydrochloride (0.031 g, 1.0 eq.) in anh. DMF (1.0 mL) was stirred overnight at RT. Solvent was evaporated. Subsequently, residue was partitioned between DCM and water. The organic layer was washed with brine, dried over anh. $Na_2SO_4$, filtered and concentrated in vacuo. Crude product was purified by FCC (SiHP; DCM:MeOH) to give product (0.02 g, 51% yield) as a white solid. ESI-MS: 1045.9 $[M+H]^+$. $^{1}H$ NMR (400 MHz, Methanol-$d_4$) δ 8.17 (d, J=5.1 Hz, 1H), 8.10-8.07 (m, 1H), 7.92-7.88 (m, 1H), 7.82 (d, J=13.7 Hz, 1H), 7.55-7.49 (m, 2H), 7.46-7.39 (m, 1H), 7.36 (dd, J=8.6, 3.0 Hz, 1H), 7.28-7.20 (m, 4H), 7.12 (d, J=8.6 Hz, 1H), 4.27-4.23 (m, 1H), 4.17 (d, J=2.4 Hz, 2H), 3.92-3.76 (m, 8H), 3.68-3.53 (m, 20H), 3.48-3.41 (m, 2H), 3.31-3.21 (m, 2H), 3.02-2.92 (m, 1H), 2.90-2.83 (m, 2H), 2.76-2.66 (m, 1H), 2.66-2.55 (m, 2H), 2.42 (s, 3H), 2.35 (s, 3H), 2.18-2.10 (m, 1H), 2.10-1.90 (m, 3H), 1.82-1.59 (m, 4H), 1.36-1.24 (m, 3H), 0.96-0.84 (m, 2H).

Example 47A. 2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl 4,7,10,13,16-pentaoxanonadec-18-ynoate

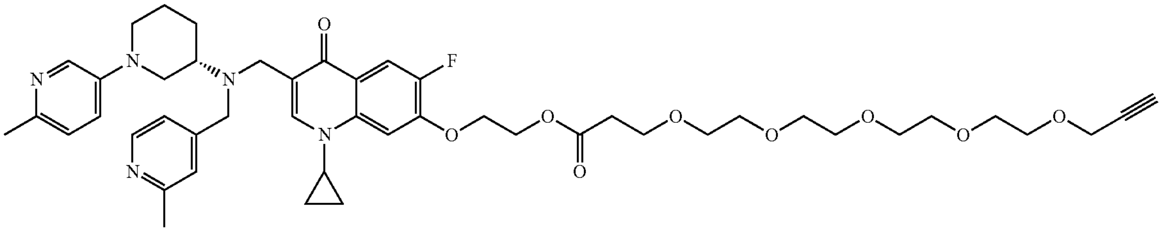 [SMILES: C#CCOCCOCCOCCOCCOCCC(=O)OCCOc1cc2c(cc1F)c(=O)c(CN(Cc1ccnc(C)c1)[C@H]1CCCN(c3ccc(C)nc3)C1)cn2C1CC1]

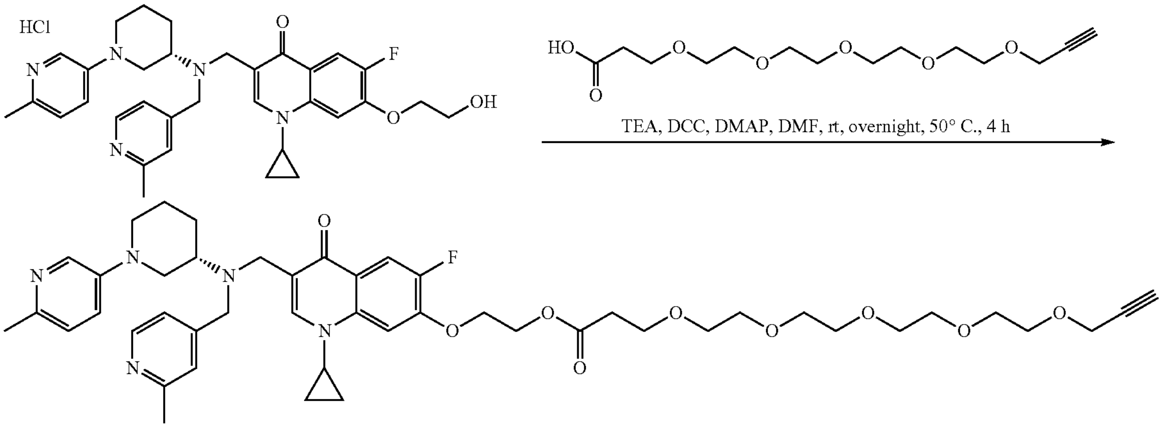

Preparation of 2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl 4,7,10,13,16-pentaoxanonadec-18-ynoate A solution of DMAP (0.002 g, 0.13 eq.), DCC (0.03 g, 1.1 eq.) and 4,7,10,13,16-pentaoxanonadec-18-ynoic acid (0.04 g, 1.0 eq.) in anh. DCM (2.0 mL) was stirred at RT. Then, 1-cyclopropyl-6-fluoro-7-(2-hydroxyethoxy)-3-({[(3S)-1-(6-methylpyridin-3-yl)piperidin-3-yl][(2-methylpyridin-4-yl)methyl]amino}methyl)-1,4-dihydroquinolin-4-one hydrochloride (Example 47) (0.088 g, 1.1 eq.) in DMF (1.0 mL) was added and reaction mixture was stirred overnight at RT and 4 h at 50° C. After that time, the mixture was concentrated in vacuo. The residue was redissolved in water washed well with DCM. Organic layer was dried over anh. $Na_2SO_4$, filtered and concentrated under reduced pressure. Crude product was purified twice by FCC (SiHP; DCM: MeOH) to give product (0.02 g, 17% yield) as a yellow oil. ESI-MS: 858.7 $[M+H]^+$. $^1H$ NMR (400 MHz, Methanol-$d_4$) δ 8.19 (d, J=5.2 Hz, 1H), 8.10 (d, J=2.9 Hz, 1H), 7.97 (s, 1H), 7.93 (d, J=11.5 Hz, 1H), 7.57 (d, J=7.1 Hz, 1H), 7.37 (dd, J=8.6, 3.0 Hz, 1H), 7.28 (s, 1H), 7.26-7.23 (m, 1H), 7.14 (d, J=8.6 Hz, 1H), 4.59-4.55 (m, 2H), 4.50-4.46 (m, 2H), 4.21-4.17 (m, 2H), 3.92-3.86 (m, 3H), 3.82-3.75 (m, 4H), 3.69-3.58 (m, 17H), 3.54-3.48 (m, 1H), 3.01-2.93 (m, 1H), 2.90-2.86 (m, 1H), 2.86-2.83 (m, 1H), 2.75-2.68 (m, 1H), 2.66 (t, J=6.1 Hz, 2H), 2.42 (s, 3H), 2.38 (s, 3H), 2.18-2.12 (m, 1H), 1.97-1.91 (m, 1H), 1.73-1.64 (m, 2H), 1.36-1.31 (m, 2H), 0.98-0.93 (m, 2H).

Example 47B. 2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl N-{[4-(3-{2-[2-(2-{[(tert-butoxy)carbonyl]amino}ethoxy)ethoxy]ethoxy}propanamido)phenyl]methyl}carbamate

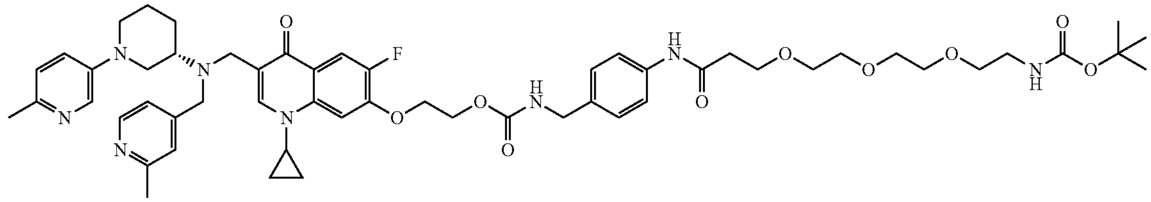 [SMILES: Cc1ccc(N2CCC[C@H](N(Cc3ccnc(C)c3)Cc3cn(C4CC4)c4cc(OCCOC(=O)NCc5ccc(NC(=O)CCOCCOCCOCCNC(=O)OC(C)(C)C)cc5)c(F)cc4c3=O)C2)cn1]

-continued

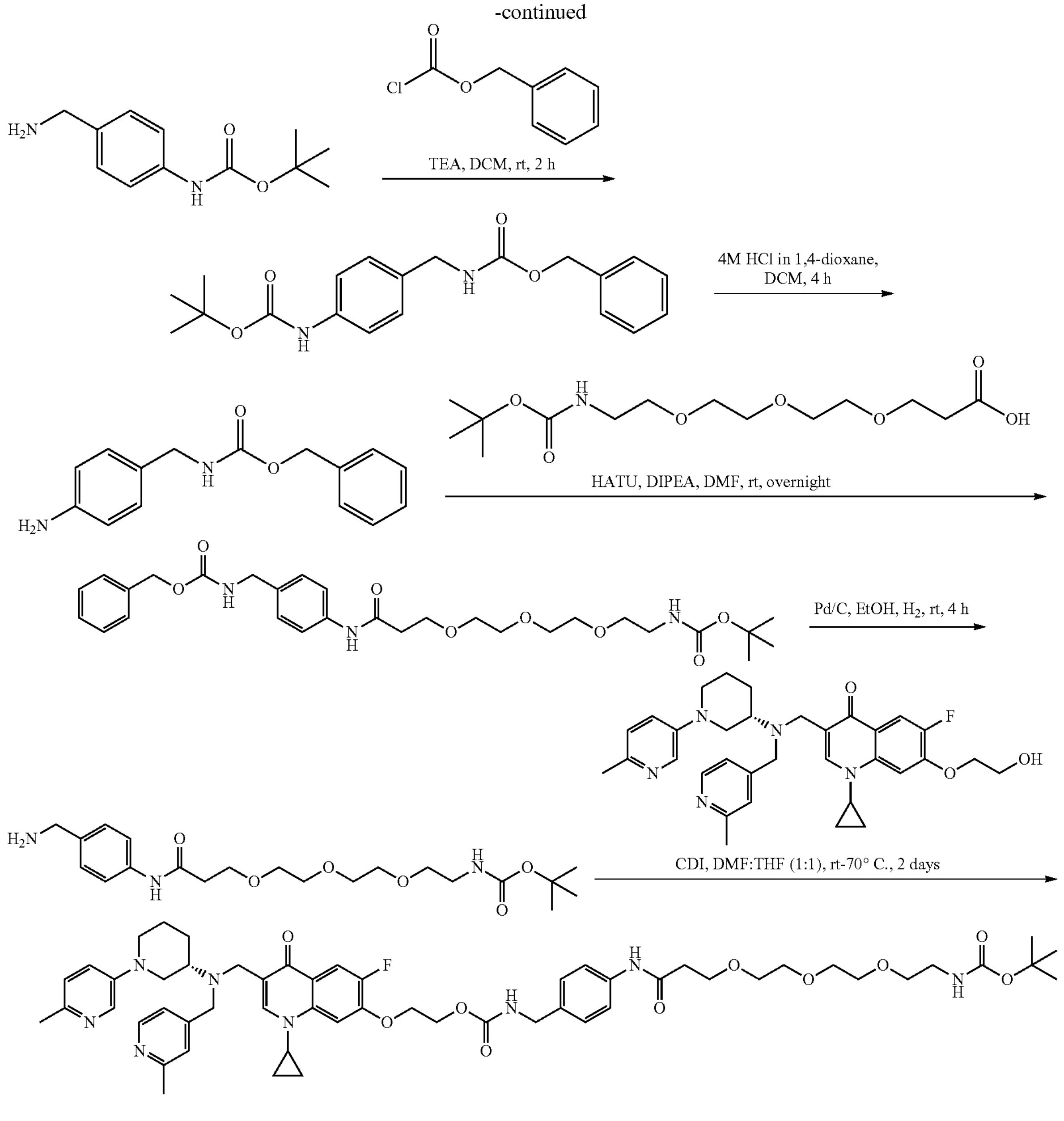

Preparation of benzyl N-[(4-{[(tert-butoxy)carbonyl]amino}phenyl)methyl]carbamate TEA was added (0.35 mL, 1.1 eq.) to a solution of tert-butyl N-[4-(aminomethyl)phenyl]carbamate (0.5 g, 1.0 eq.) in DCM (7.0 mL) kept at 0° C. Then, benzyl carbonochloridate (0.32 mL, 1.0 eq.) was added dropwise and reaction mixture was stirred at RT for 2 h. Reaction mixture was diluted with water and washed with DCM. Organic layer was washed with brine, dried over anh. $Na_2SO_4$, filtered and concentrated under reduced pressure. Crude product was purified by FCC (SiHP; Hex:AcOEt) to give product (0.79 g, 93% yield) as a white solid. ESI-MS: 379.1 [M+Na]+.

Preparation of benzyl N-[(4-aminophenyl)methyl]carbamate hydrochloride

Benzyl N-[(4-{[(tert-butoxy)carbonyl]amino}phenyl)methyl]carbamate (0.79 g, 1.0 eq.) was dissolved in DCM (8.0 mL) and 4 M HCl in 1,4-dioxane (7.8 mL, 15.0 eq.) was added. Reaction mixture was stirred at RT for 4 h. The mixture was concentrated in vacuo. The residue was diluted with DCM and concentrated (3 cycles) to give product (0.7 g, quant. yield) as a yellow solid. ESI-MS: 257.0 $[M+H]^+$.

Preparation of benzyl N-[4-(3-{2-[2-(2{[(tert-butoxy)carbonyl]aminoethoxy)ethoxy]ethoxy}propanamido)phenyl]methyl}carbamate A mixture of HATU (0.323 g, 1.3 eq.), DIPEA (0.34 mL, 3.0 eq.), benzyl N-[(4-aminophenyl)methyl]carbamate hydrochloride (0.21 g, 1.0 eq.) and 3-{2-[2-(2-{[(tert-butoxy)carbonyl]amino}ethoxy)ethoxy]ethoxy}propanoic acid (0.19 mL, 1.0 eq.) in anh. DMF (4.0 mL) was stirred overnight at RT. After that time reaction mixture was concentrated in vacuo. The residue was redissolved in DCM and washed well with water. The combined organic layers were washed with brine, dried over anh. $Na_2SO_4$, filtered and concentrated under reduced pressure. Crude product was purified by FCC (SiHP; DCM:MeOH) to give product (0.36 g, 97% yield) as an orange oil. ESI-MS: 558.3 $[M-H]^-$.

Preparation of tert-buty N-(2-{2-[2-(2-{[4-(aminomethyl)phenyl]carbamoyl}ethoxy)ethoxy]ethoxy}ethyl)carbamate Benzyl N-{[4-(3-{2-[2-(2-{[(tert-butoxy)carbonyl]amino}ethoxy)ethoxy]ethoxy}propanamido)phenyl]methyl}carbamate (0.36 g, 1.0 eq.) was dissolved in EtOH (20.0 mL). Argon was bubbled through the solution for a few minutes, then palladium on carbon (0.047 g, 0.7 eq.) was added. Reaction was run under hydrogen atmosphere at RT for 4 h. Reaction mixture was filtered through a pad of Celite and the filtrate was concentrated to give product (0.265 g, 95% yield) as a yellow oil. ESI-MS: 426.3 $[M+H]^+$.

Preparation of 2-{[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]oxy}ethyl N-{[4-(3-{2-[2-(2-{[(tert-butoxy)carbonyl]amino}ethoxy)ethoxy]ethoxy}propanamido)phenyl]methyl}carbamate A solution of 1-cyclopropyl-6-fluoro-7-(2-hydroxyethoxy)-3-({[(3S)-1-(6-methylpyridin-3-yl)piperidin-3-yl][(2-methylpyridin-4-yl)methyl]amino}methyl)-1,4-dihydroquinolin-4-one hydrochloride (Example 47) (0.06 g, 1.0 eq.) and CDI (0.018 g, 1.1 eq.) in DMF (1.0 mL) and THF (1.0 mL) was stirred at RT for 1 h. Then, tert-butyl N-(2-{2-[2-(2-{[4-(aminomethyl)phenyl]carbamoyl}ethoxy)ethoxy]ethoxy}ethyl)carbamate (0.044 g, 1.0 eq.) was added and the reaction mixture was stirred overnight at RT. Then, it was heated at 60° C. for 3 h and again overnight at 70° C. Solvents were evaporated under reduced pressure. DCM was added and washed with water. Organic layer was washed with brine, dried over anh. $Na_2SO_4$, filtered and concentrated under reduced pressure. Crude product was purified twice by FCC (SiHP; DCM:MeOH) to give product (0.016 g, 15% yield). ESI-MS: 1023.8 $[M+H]^+$. $^1H$ NMR (400 MHz, Methanol-$d_4$) δ 8.17 (d, J=5.5 Hz, 1H), 8.09 (d, J=2.8 Hz, 1H), 7.95 (s, 1H), 7.91 (d, J=11.5 Hz, 1H), 7.55 (d, J=6.9 Hz, 1H), 7.51 (d, J=8.4 Hz, 2H), 7.36 (dd, J=8.5, 2.9 Hz, 1H), 7.29-7.19 (m, 4H), 7.13 (d, J=8.6 Hz, 1H), 4.56-4.49 (m, 2H), 4.49-4.37 (m, 2H), 4.29-4.16 (m, 2H), 3.93-3.71 (m, 7H), 3.67-3.56 (m, 7H), 3.55-3.49 (m, 2H), 3.49-3.41 (m, 3H), 3.22-3.14 (m, 2H), 3.01-2.93 (m, 1H), 2.91-2.83 (m, 1H), 2.75-2.67 (m, 1H), 2.65-2.49 (m, 2H), 2.42 (s, 3H), 2.36 (s, 3H), 2.18-2.10 (m, 1H), 1.98-1.91 (m, 1H), 1.76-1.58 (m, 2H), 1.43 (s, 9H), 1.37-1.25 (m, 4H), 0.98-0.89 (m, 2H).

Example 55A. [4-(4,7,10,13,16-pentaoxanonadec-18-ynamido)phenyl]methyl N-[(3R-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]-N-methylcarbamate

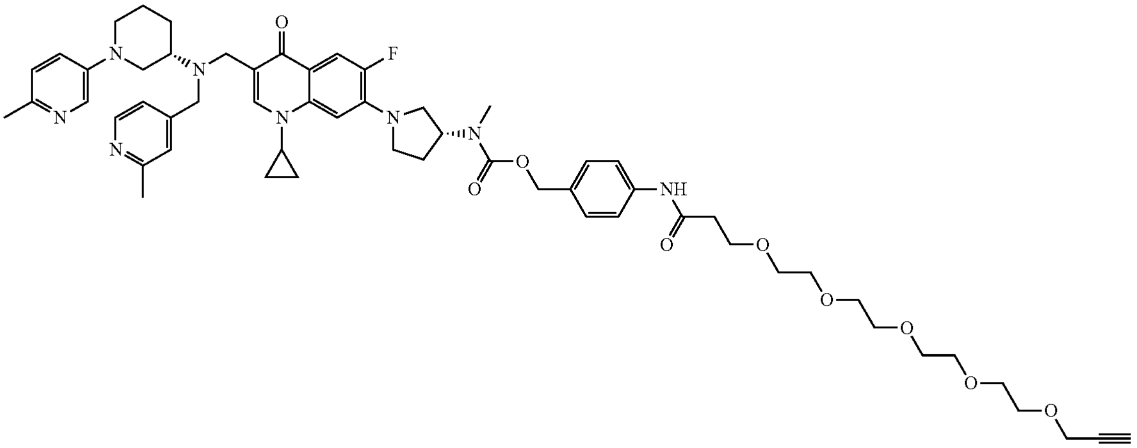 [SMILES: C#CCOCCOCCOCCOCCOCCC(=O)Nc1ccc(COC(=O)N(C)[C@@H]2CCN(c3cc4c(cc3F)c(=O)c(CN(Cc3ccnc(C)c3)[C@H]3CCCN(c5ccc(C)nc5)C3)cn4C3CC3)C2)cc1]

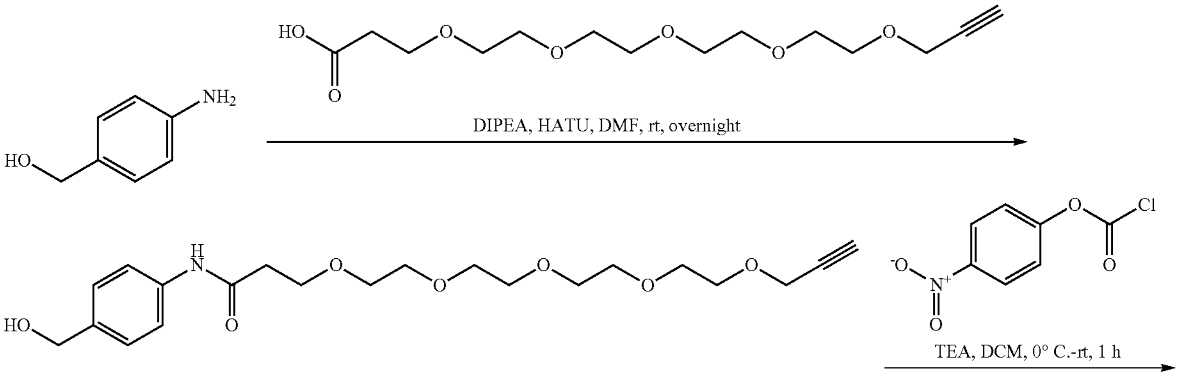

-continued

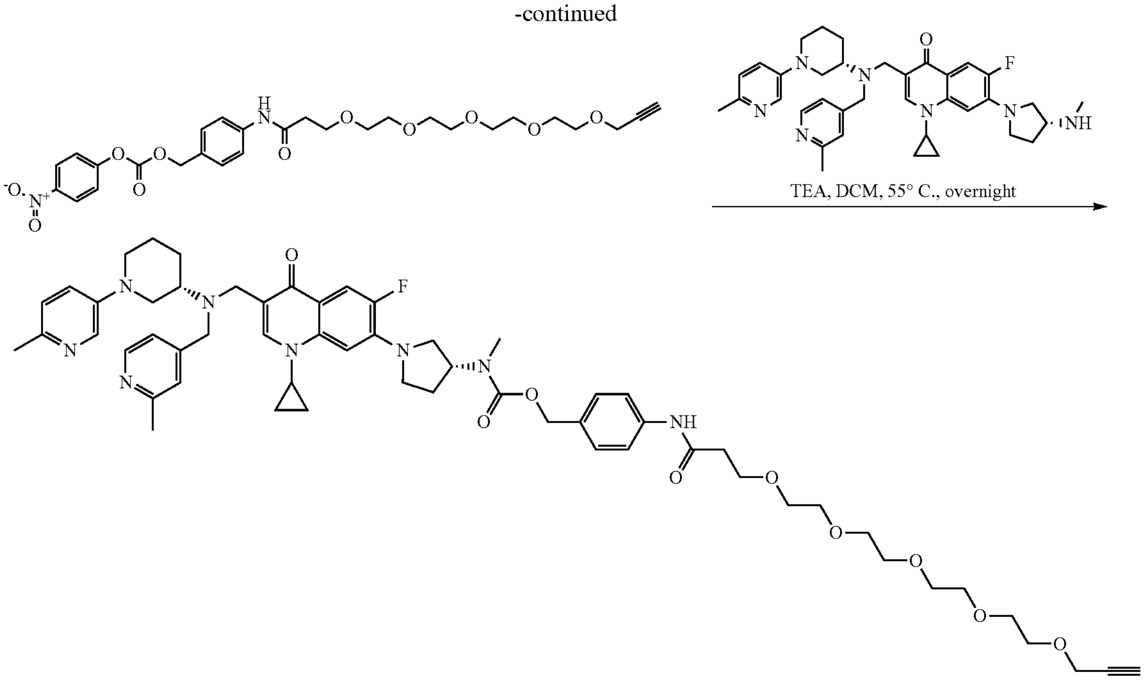

Preparation of N-[4-(hydroxymethyl)phenyl]-4,7,10,13,16-pentaoxanonadec-18-ynamide A mixture of 4-aminobenzyl alcohol (0.15 g, 1.0 eq.), 4,7,10,13,16-pentaoxanonadec-18-ynoic acid (0.37 g, 1.0 eq.) and HATU (0.70 g, 1.5 eq.) was stirred in anh. DMF (9.0 mL) for 10 min. Then DIPEA (0.85 ml, 4.0 eq.) was added and the mixture was stirred overnight at RT. After that time the mixture was diluted with water and washed with EtOAc. The organic layer was washed with brine, dried over anh. $Na_2SO_4$, filtered and concentrated in vacuo. Product was purified by FCC (SiHP, DCM:MeOH) to obtain product (0.24 g, 48% yield) as an orange oil. ESI-MS: 410.2 $[M+H]^+$.

Preparation of 4-nitrophenyl [4-(4,7,10,13,16-pentaoxanonadec-18-ynamido)phenyl]methyl carbonate (Intermediate 29)

TEA (0.16 ml, 2.0 eq.) was added to a solution of N-[4-(hydroxymethyl)phenyl]-4,7,10,13,16-pentaoxanonadec-18-ynamide (0.24 g, 1.0 eq.) in anh. DCM (4.0 mL) kept at 0° C. Then, 4-nitrophenyl chloroformate (0.08 mL, 1.0 eq.) was added dropwise and reaction mixture was stirred at RT for 1 h. Reaction mixture was diluted with water and washed with DCM. Organic layer was washed with brine, dried over anh. $Na_2SO_4$, filtered and concentrated under reduced pressure. Product was purified by FCC (SiHP, DCM:MeOH) to give product (0.15 g, 44% yield) as beige oil. ESI-MS: 575.3 $[M+H]^+$.

Preparation of [4-(4,7,10,13,16-pentaoxanonadec-18-ynamido)phenyl]methyl N-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]-N-methylcarbamate 1-cyclopropyl-6-fluoro-7-[(3R)-3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride (Example 55) (0.04 g, 1.0 eq.), 4-nitrophenyl [4-(4,7,10,13,16-pentaoxanonadec-18-ynamido)phenyl]methyl carbonate (Intermediate 29) (0.04 g, 1.0 eq.) and TEA (0.02 ml, 2.0 eq.) were dissolved in anh. DCM (2.0 mL) and the reaction mixture was stirred overnight at 55° C. Reaction mixture was diluted with DCM and washed with water and brine. Organic layer was dried over anh. $Na_2SO_4$, filtered and concentrated in vacuo. The residue was purified by FCC (SiHP; DCM:MeOH) to obtain product (0.03 g, 46% yield) as a beige solid. ESI-MS: 1045.8 $[M+H]^+$. $^1$HNMR (400 MHz, Methanol-$d_4$) δ 8.17 (d, J=5.2 Hz, 1H), 8.10 (d, J=2.9 Hz, 1H), 7.85 (s, 1H), 7.78 (d, J=14.7 Hz, 1H), 7.60 (d, J=8.4 Hz, 2H), 7.40-7.33 (m, 3H), 7.26 (s, 1H), 7.23 (d, J=5.5 Hz, 1H), 7.14 (d, J=8.6 Hz, 1H), 6.98-6.91 (m, 1H), 5.14 (s, 2H), 4.17 (d, 1=2.4 Hz, 2H), 3.93-3.73 (m, 8H), 3.73-3.67 (m, 1H), 3.67-3.60 (m, 11H), 3.58 (s, 6H), 3.43-3.36 (m, 1H), 3.00-2.94 (m, 4H), 2.90-2.82 (m, 2H), 2.76-2.66 (m, 1H), 2.64 (t, J=6.0 Hz, 2H), 2.42 (s, 3H), 2.36 (s, 3H), 2.30-2.19 (m, 2H), 2.19-2.07 (m, 1H), 1.98-1.90 (m, 1H), 1.72-1.59 (m, 2H), 1.38-1.22 (m, 4H), 0.99-0.83 (m, 3H).

Example 55B. tert-Butyl N-{2-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]-5,8,11,14-tetraoxa-2-azahexadecan-16-yl}carbamate

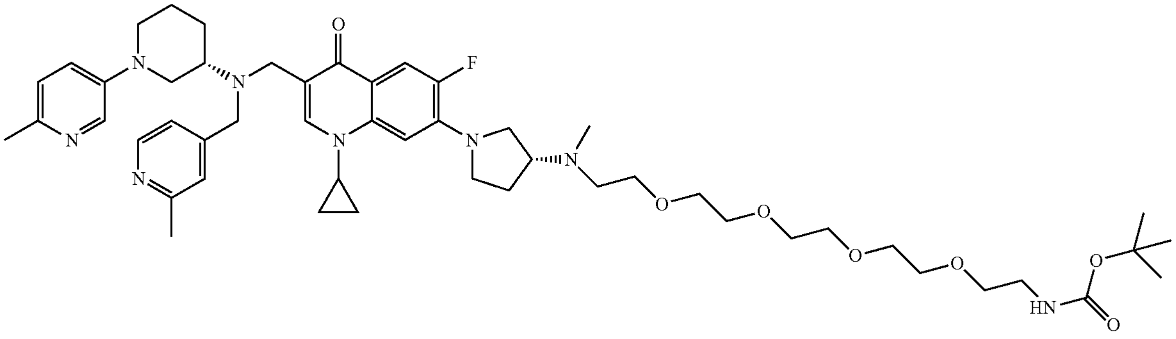 [SMILES: Cc1ccc(N2CCC[C@H](N(Cc3ccnc(C)c3)Cc3cn(C4CC4)c4cc(N5CC[C@@H](N(C)CCOCCOCCOCCOCCNC(=O)OC(C)(C)C)C5)c(F)cc4c3=O)C2)cn1]

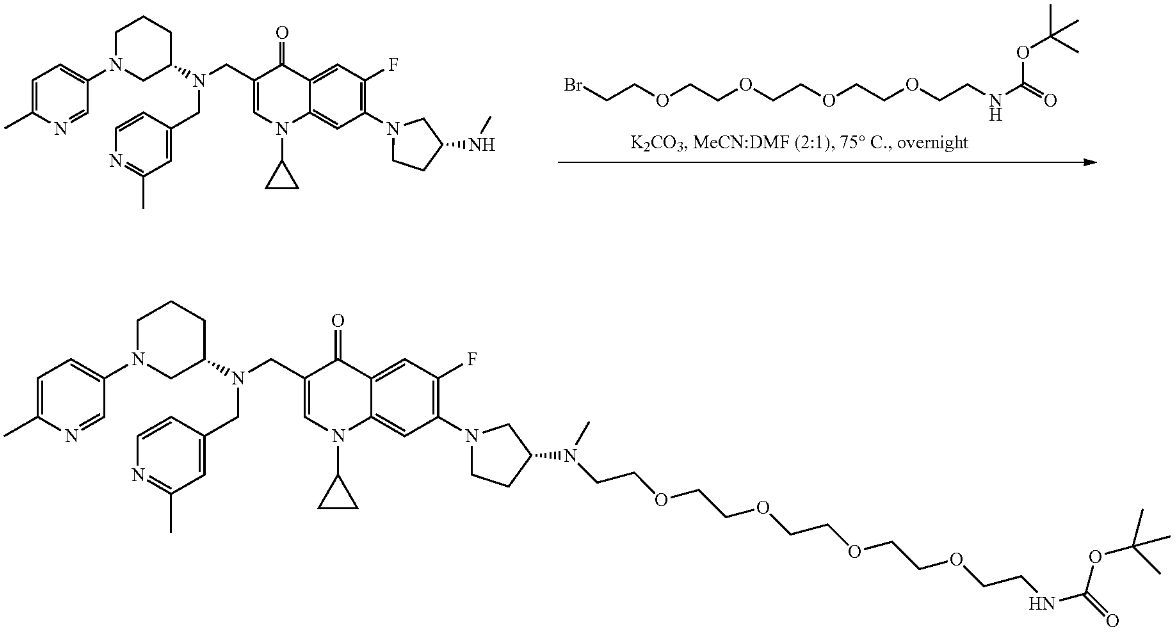

Preparation of tert-butyl N-{2-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]-5,8,11,14-tetraoxa-2-azahexadecan-16-yl}carbamate 1-cyclopropyl-6-fluoro-7-[(3R)-3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride (Example 55) (0.05 g, 1.0 eq.), tert-butyl N-(14-bromo-3,6,9,12-tetraoxatetradecan-1-yl)carbamate (0.06 g, 2.0 eq.) and $K_2CO_3$ (0.03 g, 3.0 eq.) were taken in a mixture of MeCN and DMF (1.5 mL; 2:1). The reaction mixture was stirred overnight at 75° C. Reaction mixture was diluted with water and washed with EtOAc. Organic layer was washed brine, dried over anh. $Na_2SO_4$, filtered and concentrated in vacuo. The residue was purified twice by FCC (SiHP; DCM:MeOH) to obtain product (0.013 g, 19% yield) as a beige solid. ESI-MS: 929.8 $[M+H]^+$. $^1H$ NMR (400 MHz, Methanol-$d_4$) δ 8.18 (d, J=5.2 Hz, 1H), 8.10 (d, =3.0 Hz, 1H), 7.85 (s, 1H), 7.79 (d, J=14.7 Hz, 1H), 7.36 (dd, J=8.6, 3.0 Hz, 1H), 7.26 (s, 1H), 7.23 (d, J=5.3 Hz, 1H), 7.13 (d, J=8.6 Hz, 1H), 6.94 (d, J=7.6 Hz, 1H), 3.92-3.76 (m, 7H), 3.73-3.58 (m, 17H). 3.57-3.52 (m, 1H), 3.50 (t, J=5.6 Hz, 2H), 3.45-3.41 (m, 1H), 3.22 (t, J=5.6 Hz, 2H), 2.99-2.91 (m, 1H), 2.87 (d, J=11.2 Hz, 1H), 2.84-2.77 (m, 2H), 2.74-2.65 (m, 1H), 2.46-2.39 (m, 6H), 2.37 (s, 3H), 2.34-2.27 (m, 1H), 2.18-2.11 (m, 1H), 2.02-1.90 (m, 2H), 1.72-1.62 (m, 2H), 1.44 (s, 9H), 1.33-1.27 (m, 3H), 0.93-0.87 (m, 2H).

Example 55C. tert-Butyl N-(2-{2-[2-(2-{[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl](methyl)carbamoyl}ethoxy)ethoxy]ethoxy}ethyl)carbamate

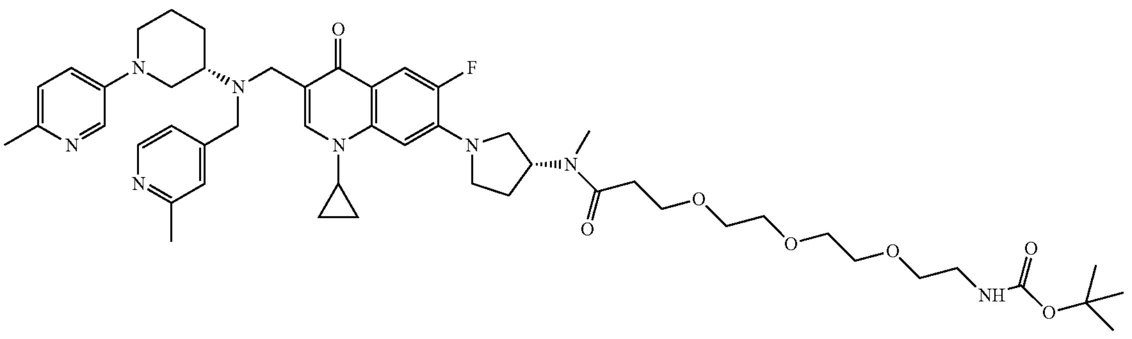 [SMILES: Cc1ccc(N2CCC[C@H](N(Cc3ccnc(C)c3)Cc3cn(C4CC4)c4cc(N5CC[C@@H](N(C)C(=O)CCOCCOCCOCCNC(=O)OC(C)(C)C)C5)c(F)cc4c3=O)C2)cn1]

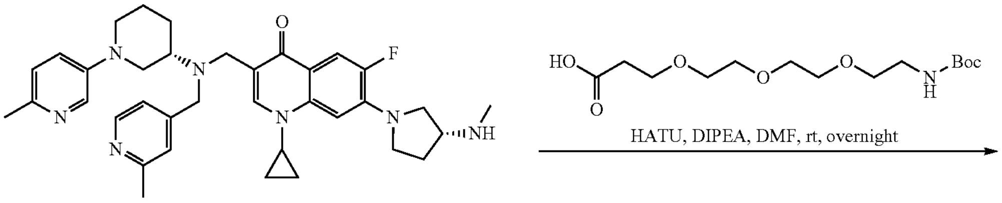

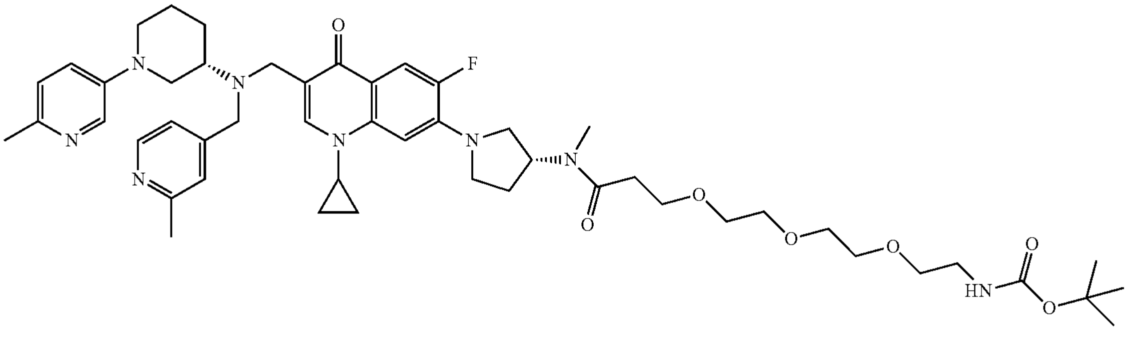

Preparation of tert-butyl N-(2-{2-[2-(2-{[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl](methyl)carbamoyl}ethoxy)ethoxy]ethoxy}ethyl)carbamate HATU (0.044 g, 1.5 eq.), 1-cyclopropyl-6-fluoro-7-[(3R)-3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride (Example 55) (0.05 g, 1.0 eq.) and 3-{2-[2-(2-{[(tert-butoxy)carbonyl]amino}ethoxy)ethoxy]ethoxy}propanoic acid (0.03 g, 1.2 eq.) were stirred in anh. DMF (1.0 mL) for 10 min. Then DIPEA (0.054 ml, 4.0 eq.) was added. The reaction mixture were stirred overnight at RT. The reaction mixture was diluted with water and extracted to EtOAc. Organic layer was washed with brine, dried over anh. $Na_2SO_4$, filtered and concentrated in vacuo. The crude product was purified twice by FCC (SiHP; DCM:MeOH) and re-purified by RP-FCC (C18HP; $H_2O$:MeCN) to give product (0.037 g, 49% yield) as an off-white solid. ESI-MS: 913.9 $[M+H]^+$.

Example 55D. 3-{2-[2-(2-aminoethoxy)ethoxy]ethoxy}-N-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]-N-methylpropanamide formate

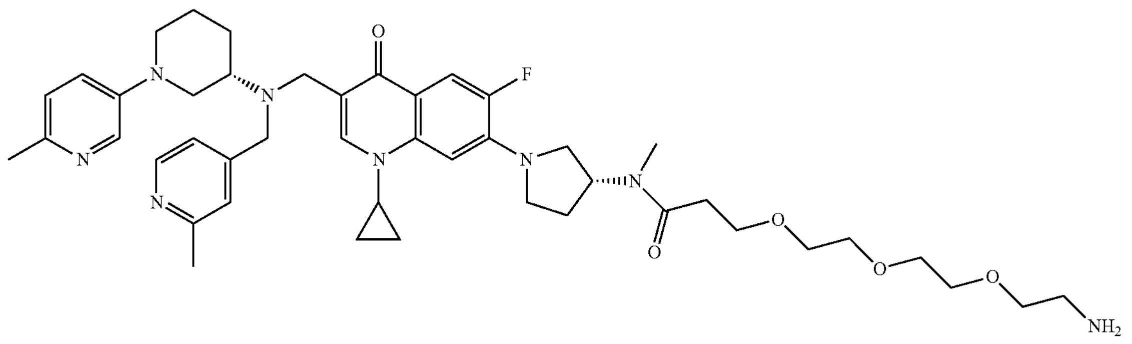 [SMILES: Cc1ccc(N2CCC[C@H](N(Cc3ccnc(C)c3)Cc3cn(C4CC4)c4cc(N5CC[C@@H](N(C)C(=O)CCOCCOCCOCCN)C5)c(F)cc4c3=O)C2)cn1]

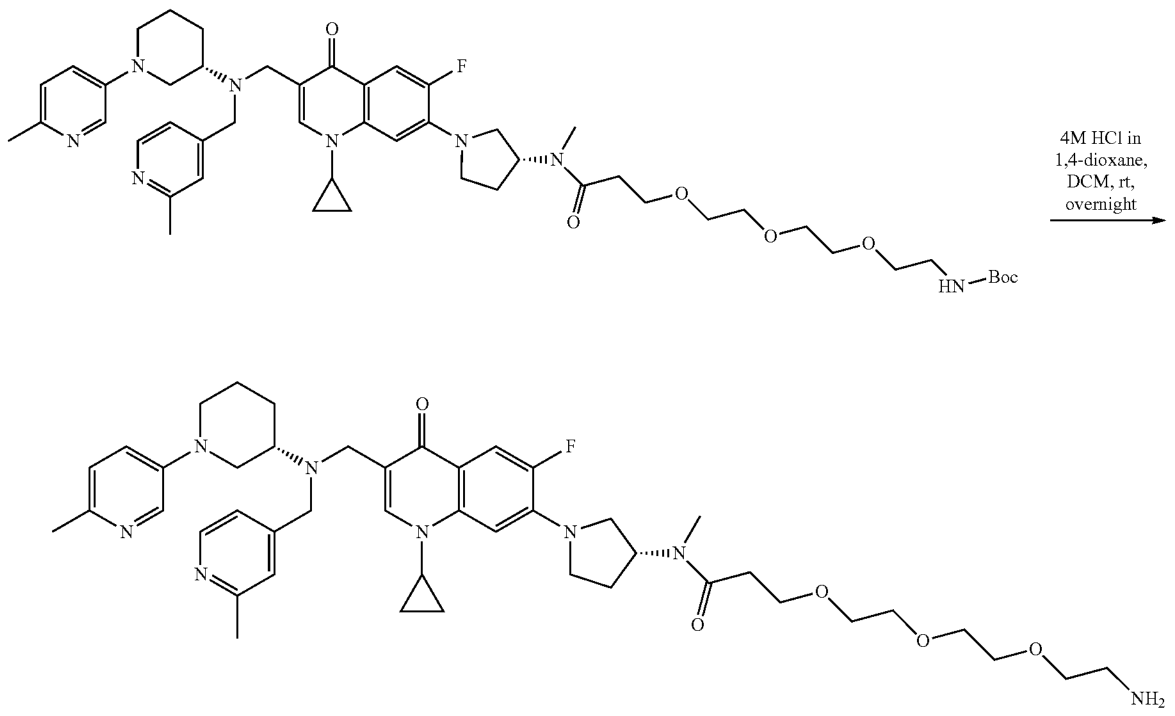

Preparation of 3-{2-[2-(2-aminoethoxy)ethoxy]ethoxy}-N-[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]-N-methylpropanamide fromate tert-Butyl N-(2-{2-[2-(2-{[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl](methyl)carbamoyl}ethoxy)ethoxy]ethoxy}ethyl)carbamate (Example 55C) (0.037 g, 1.0 eq.) was dissolved in DCM (2.0 mL). 4 M HCl in 1,4-dioxane (0.14 mL, 15.0 eq.) was added and the reaction mixture was stirred for 1 h at RT. Volatiles were evaporated in vacuo. The residue was partitioned between sat. $NaHCO_3$ and DCM. Organic layer was concentrated in vacuo. Crude product was purified by prep-HPLC ($H_2O$:MeCN:FA) to give product as formate salt (0.005 g, 14% yield) as a pale orange solid. ESI-MS: 813.2 $[M+H]^+$.

Example 58A. [4-(4,7,10,13,16-pentaoxanonadec-18-ynamido)phenyl]methyl N-[(3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]-N-methylcarbamate

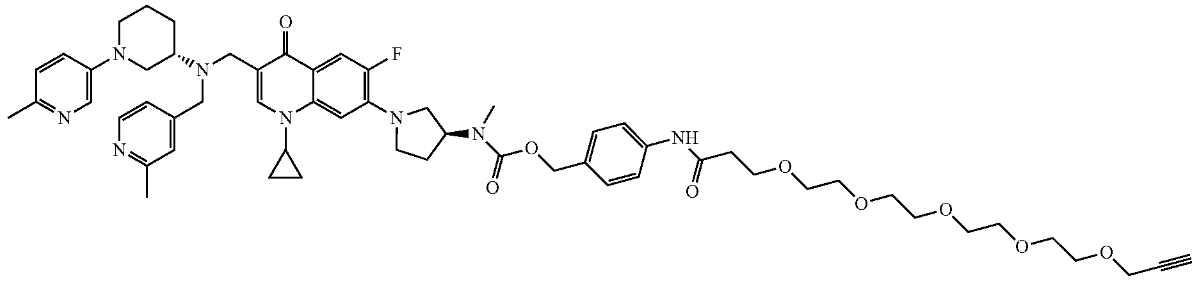 [SMILES: C#CCOCCOCCOCCOCCOCCC(=O)Nc1ccc(COC(=O)N(C)[C@H]2CCN(c3cc4c(cc3F)c(=O)c(CN(Cc3ccnc(C)c3)[C@H]3CCCN(c5ccc(C)nc5)C3)cn4C3CC3)C2)cc1]

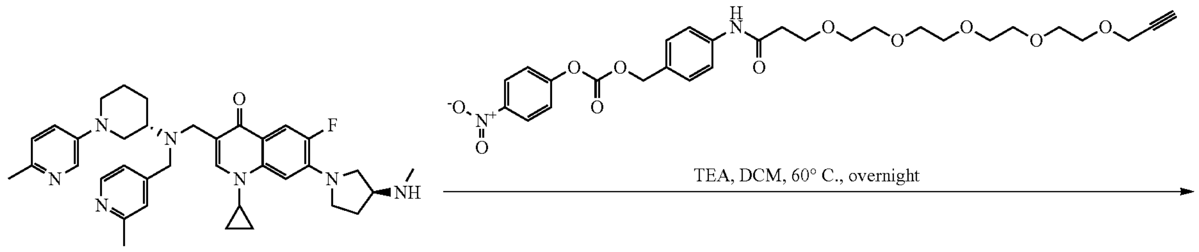

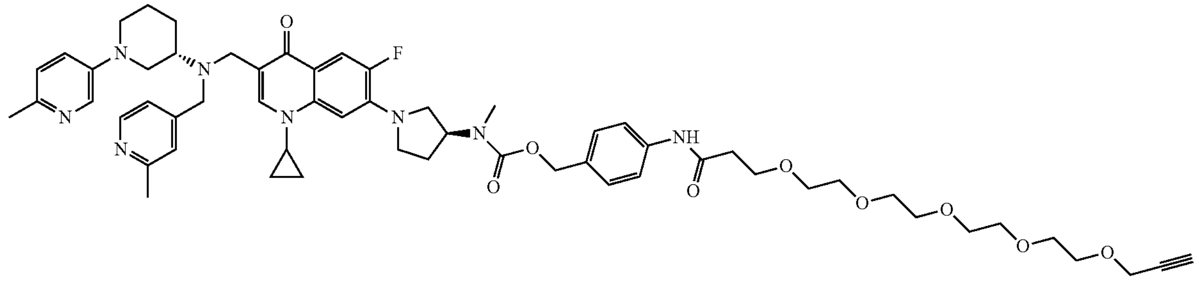

Preparation of [4-(4,7,10,13,16-pentaoxanonadec-18-ynamido)phenyl]methyl N-[(3S)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinol-7-yl]pyrrolidin-3-yl]-N-methylcarbamate 1-cyclopropyl-6-fluoro-7-[(3S)-3-(methylamino)pyrrolidin-1-yl]-3-({[(3S)-1-(6-methylpyridin-3-yl)piperidin-3-yl][(2-methylpyridin-4-yl)methyl]amino}methyl)-1,4-dihydroquinolin-4-one hydrochloride (Example 58) (0.03 g, 1.0 eq.), 4-nitrophenyl [4-(4,7,10,13,16-pentaoxanonadec-18-ynamido)phenyl]methyl carbonate (Intermediate 29) (0.03 g, 1.0 eq.) and TEA (0.013 ml, 2.0 eq.) was dissolved in anh. DCM (1.5 mL) and reaction was stirred overnight at 60° C. Reaction mixture was diluted with DCM. Organics were washed with water and brine, dried over $Na_2SO_4$, filtered and concentrated in vacuo. The residue was purified twice by FCC (SiHP; DCM:MeOH) to obtain product (0.02 g, 40% yield) as a beige solid. HR-MS: 1045.5 $[M+H]^+$. $^1H$ NMR (400 MHz, Methanol-$d_4$) δ8.17 (d, J=5.2 Hz, 1H), 8.10 (d, J=3.0 Hz, 1H), 7.85 (s, 1H), 7.78 (d, J=14.7 Hz, 1H), 7.63-7.56 (m, 2H), 7.40-7.33 (m, 3H), 7.25 (s, 1H), 7.22 (d, J=5.4 Hz, 1H), 7.13 (d, J=8.6 Hz, 1H), 6.99-6.89 (m, 1H), 5.14 (s, 2H), 4.17 (d, J=2.4 Hz, 2H), 3.92-3.75 (m, 8H), 3.75-3.68 (m, 1H), 3.67-3.59 (m, 13H), 3.59-3.56 (m, 6H), 3.43-3.36 (m, 1H), 3.00-2.93 (m, 4H), 2.89-2.82 (m, 2H), 2.74-2.66 (m, 1H), 2.63 (t, J=6.0 Hz, 2H), 2.42 (s, 3H), 2.36 (s, 3H), 2.29-2.20 (m, 2H), 2.17-2.11 (m, 1H), 1.97-1.90 (m, 1H), 1.74-1.61 (m, 2H), 1.35-1.24 (m, 3H), 0.94-0.88 (m, 2H).

Example 68A. {4-[(2S)-2-[(2S)-2-(3-{2-[2-(2-azido-ethoxy)ethoxy]ethoxy}propanamido)-3-methyl-butanamido]-5-(carbamoylamino)pentanamido]phenyl}methyl 5-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-octahydro-1H-pyrrolo[3,2-c]pyridine-1-carboxylate
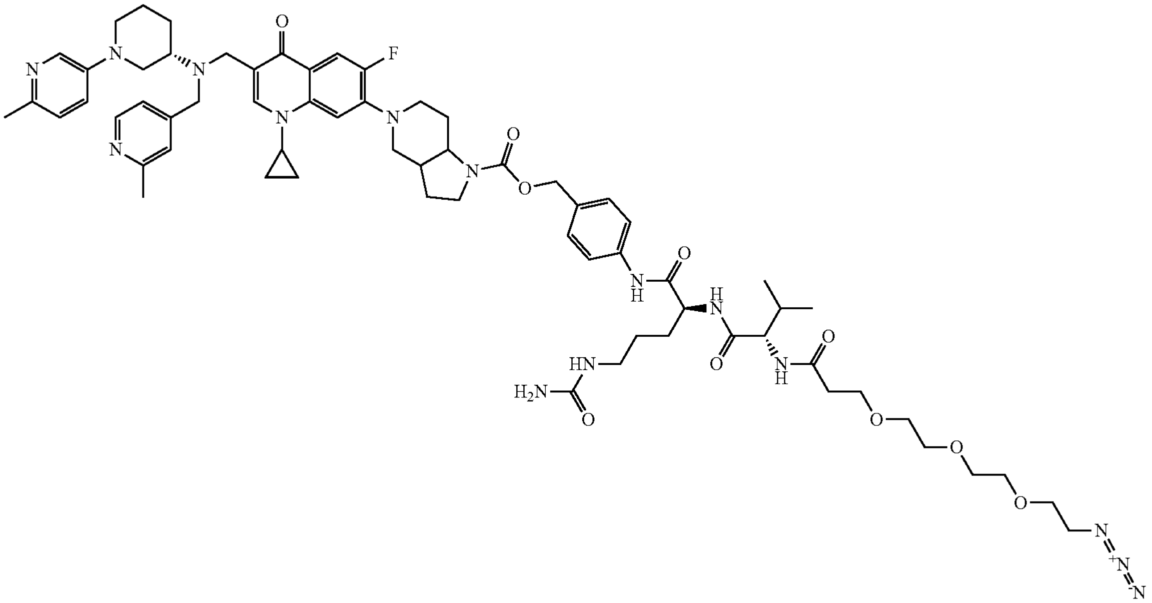
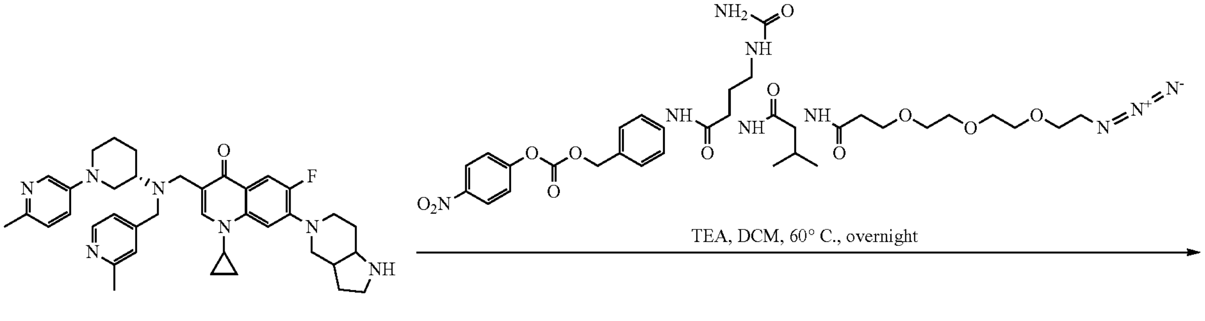

-continued

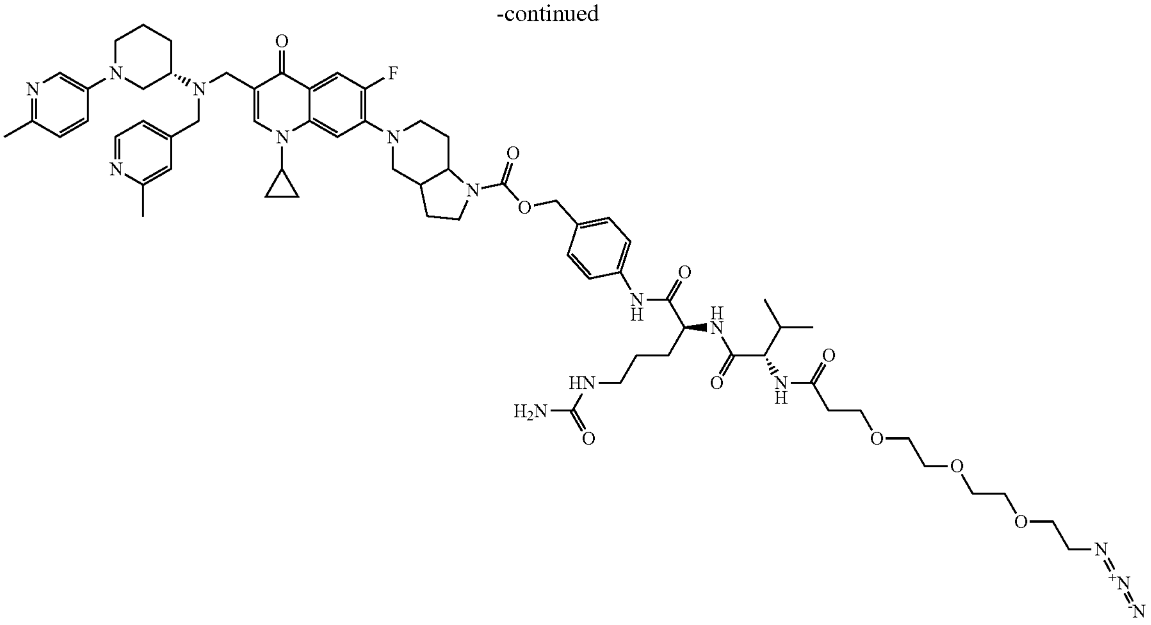

Preparation of {4-[(2S)-2-[(2S)-2-(3-{2-[2-(2-azidoethoxy)ethoxy]ethoxy}propanamido)-3-methyl-butanamido]-5-(carbamoylamino)pentanamido]phenyl}methyl 5-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-octahydro-1H-pyrrolo[3,2-c]pyridine-1-carboxylate {4-[(2 S)-2-[(2S)-2-(3-{2-[2-(2-azidoethoxy)ethoxy]ethoxy}propanamido)-3-methylbutanamido]-5-(carbamoylamino)pentanamido]phenyl}methyl 4-nitrophenyl carbonate (0.02 g, 1.0 eq.) and 1-cyclopropyl-6-fluoro-3-({[(3S)-1-(6-methylpyridin-3-yl)piperidin-3-yl][(2-methylpyridin-4-yl)methyl]amino}methyl)-7-{octahydro-1H-pyrrolo[3,2-c]pyridin-5-yl}-1,4-dihydroquinolin-4-one (Example 68) (0.019 g, 1.2 eq.) were suspended in DCM (1.0 mL). Subsequently, TEA (0.018 mL, 5.0 eq.) was added and the reaction mixture was stirred at 60° C. overnight. Solvent was concentrated in vacuo and the residue was purified by prep-H PLC (($H_2O$:MeCN) to give product (0.022 g, 66% yield) as a yellow solid. ESI-MS: 1270.9 $[M+H]^+$. HR-MS: 1270.7 $[M+H]^+$.

Example 84A. 2-{[1-cyclopropyl-6-fluoro-3-({[(2-methylpyridin-4-yl)methyl][(3S)-1-(pyridin-3-yl)piperidin-3-yl]amino}methyl)-4-oxo-1,4-dihydroquinolin-7-yl]oxy}ethyl N-{[4-(4,7,10,13,16-pentaoxanonadec-18-ynamido)phenyl]methyl}carbamate

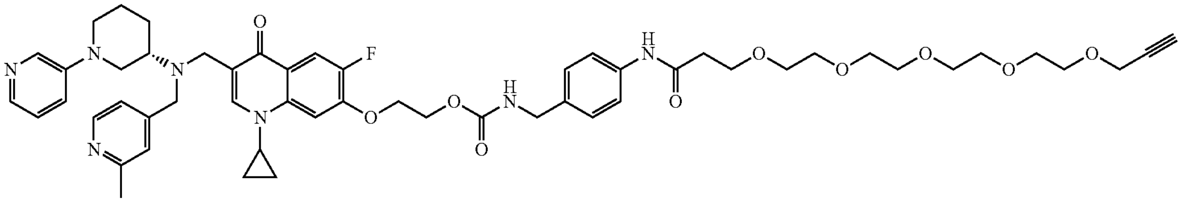 [SMILES: C#CCOCCOCCOCCOCCOCCC(=O)Nc1ccc(CNC(=O)OCCOc2cc3c(cc2F)c(=O)c(CN(Cc2ccnc(C)c2)[C@H]2CCCN(c4cccnc4)C2)cn3C2CC2)cc1]

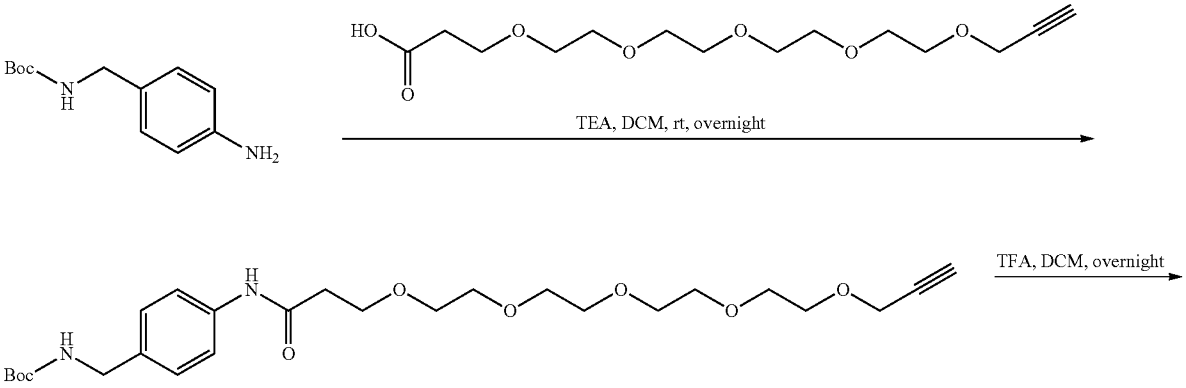

-continued

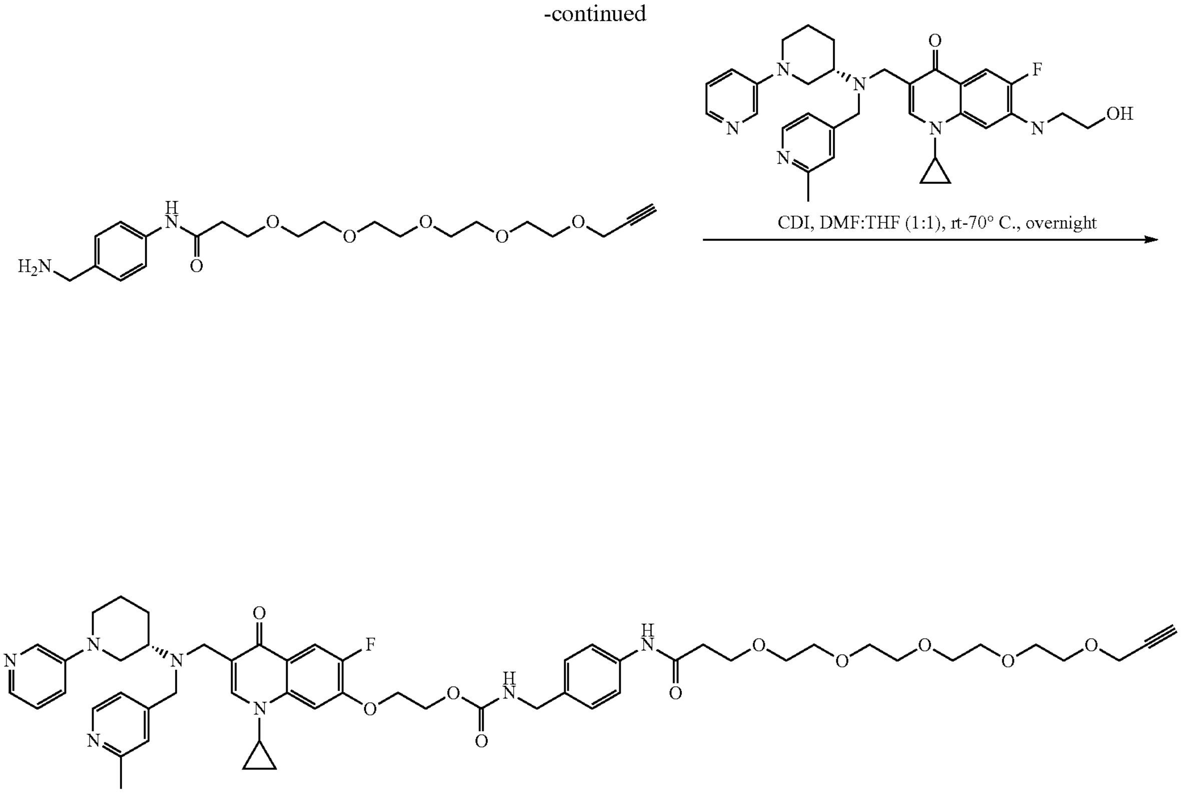

Preparation of tert-buty N-{[4-(4,7,10,13,16-pentaoxanonadec-18-ymamido)phenyl]methyl}carbamate tert-Butyl N-[(4-aminophenyl)methyl]carbamate (0.15 g, 1.0 eq.), 4,7,10,13,16-pentaoxanonadec-18-ynoic acid (0.2 g, 1.0 eq.) and HATU (0.38 g, 1.5 eq.) were stirred in DMF (6.5 mL) for 10 min. Then DIPEA (0.46 mL, 4.0 eq.) was added and the mixture was stirred overnight at RT. After that time, the mixture was diluted with water and extracted with EtOAc. The organic layer was washed with brine, dried over anh. $Na_2SO_4$, filtered and concentrated under reduced pressure. Product mixture was purified by FCC (SiHP; DCM:MeOH) to obtain product (0.223 g, 63% yield) as orange oil. ESI-MS: 509.3 $[M+H]^+$.

Preparation of N-[4-(aminomethyl)phenyl]-4,7,10,13,16-pentaoxanonadec-18-ynamide tert-Butyl N-{[4-(4,7,10,13,16-pentaoxanonadec-18-ynamido)phenyl]methyl}carbamate (0.22 g, 1.0 eq.) was dissolved in DCM (2.0 mL) and trifluoroacetic acid (0.32 mL, 10.0 eq.) was added dropwise. The reaction mixture was stirred overnight at RT. Solvent was evaporated under reduced pressure. The residue was diluted with MeOH (×2) for azeotropic removal of traces of moisture. The residue was dissolved in DCM and washed with brine. Organic layer was dried over anh. $Na_2SO_4$ and concentrated under reduced pressure to obtain the product (0.175 g, 99% yield) as a beige oil. This was used without further purification in the next step. ESI-MS: 409.4 $[M+H]^+$.

Preparation of 2-{[1-cyclopropyl-6-fluoro-3-({[(2-methylpyridin-4-yl)methyl][(3S)-1-(pyridin-3-yl)piperidin-3-yl]amino}methyl)-4-oxo-1,4-dihydroquinolin-7-yl]oxy}ethyl N-{[4-(4,7,10,13,16-pentaoxanonadec-18-ynamido)phenyl]methyl}carbamate A solution of 1-cyclopropyl-6-fluoro-7-(2-hydroxyethoxy)-3-({[(2-methylpyridin-4-yl)methyl][(3S)-1-(pyridin-3-yl)piperidin-3-yl]amino}methyl)-1,4-dihydroquinolin-4-one hydrochloride (Example 84)(0.08 g, 1.0 eq.) and CDI (0.024 g, 1.1 eq.) in a mixture of DMF (1.0 mL) and THF (1.0 mL) was stirred at RT for 1.5 h. Then, N-[4-(aminomethyl)phenyl]-4,7,10,13,16-pentaoxanonadec-18-ynamide (0.056 g, 1.0 eq.) was added. The reaction mixture was stirred at 70° C. overnight. Reaction mixture was diluted with water and extracted with DCM. Organic layers were washed with brine, dried over anh. $Na_2SO_4$, filtered and concentrated under reduced pressure. Crude product was purified by FCC (SiHP, DCM:MeOH), re-purified by RP-FCC (C18HP; $H_2O$:MeCN) to give product (0.016 g, 12% yield) as a beige solid. ESI-MS: 992.7 $[M+H]^+$. HRMS: 992.5 $[M+H]^+$.

General Procedure for a Further Derivatization of the Functional Handle of the Linker
Example 15B. N-{[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]methyl}-1-[3-(2,5-dioxo-2,5-dihydro-1H-pyrrol-1-yl)propanamido]-3,6,9,12-tetraoxapentadecan-15-amide
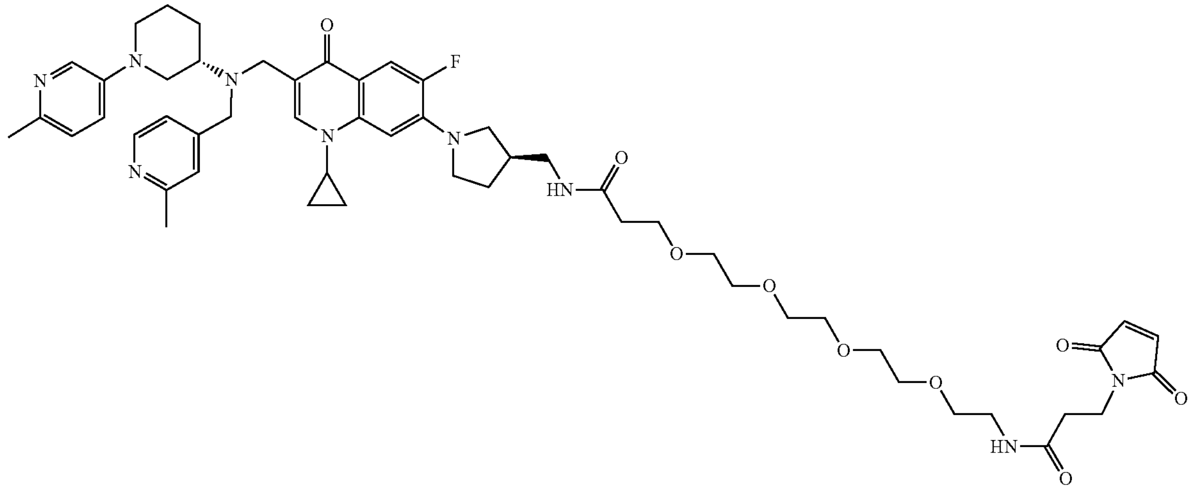
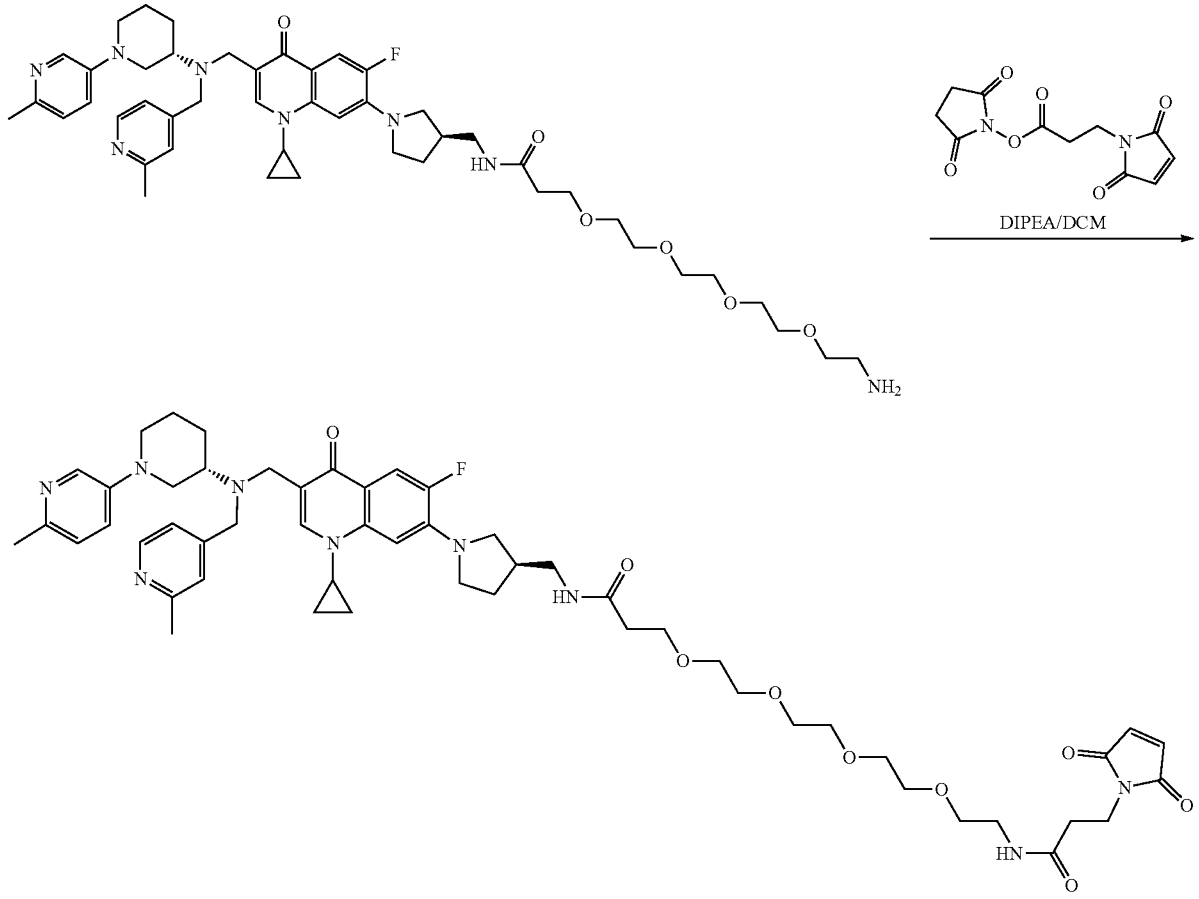

Preparation of N-{[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]methyl}-1-[3-(2,5-dioxo-2,5-dihydro-1H-pyrrol-1-yl)propanamido]-3,6,9,12-tetraoxapentadecan-15-amide To a solution of 1-amino-N-{[(3R)-1-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]pyrrolidin-3-yl]methyl}-3,6,9,12-tetraoxapentadecan-15-amide (0.10 g, 1.0 eq.) in DCM (10.0 mL) DIPEA (0.10 mL, 5.0 eq) then 2,5-dioxo-1-pyrrolidinyl 3-(2,5-dioxo-1H-pyrrol-1-yl)propionate (0.047 g, 1.5 eq.) is added. The resulting solution is stirred overnight at RT. The solvents are evaporated and the residue is purified by RP-FCC to give the titled compound (0.065 g, yield 54%), ESI-MS: 1009.2 $[M+H]^+$.

General Procedure for Preparation of ADC linker construct 15B could be desalted in 0.1 M sodium hydrogen carbonate buffer (pH 8.0) to give the corresponding ADC of 15B.

Biological Assays and Data:

As stated above, the compounds of formula (I) as such, but also in the form of the compound-linker constructs and conjugates of the invention are STING modulators and are useful in treating diseases by STING activity regulation. The biological activity of the compounds, constructs and conjugates of the present invention can be determined by any appropriate test to determine the activity of the compound as STING modulator, as well as cell lines and in vivo models.

Fluorescence Thermal Shift Assay

Compounds, constructs and conjugates of the present invention were tested for binding to human STING in Fluorescence Thermal Shift assay. STING was preincubated with the compounds for 20 minutes in 50 mM Hepes, 150 mM NaCl, pH 7.5 in 15 or 16 μl volume, following by adding 4 μl of SyproOrange dye dilution (ThermoFisher, cat no. S-6651). Final STING concentration was 0.1 mg/mL.

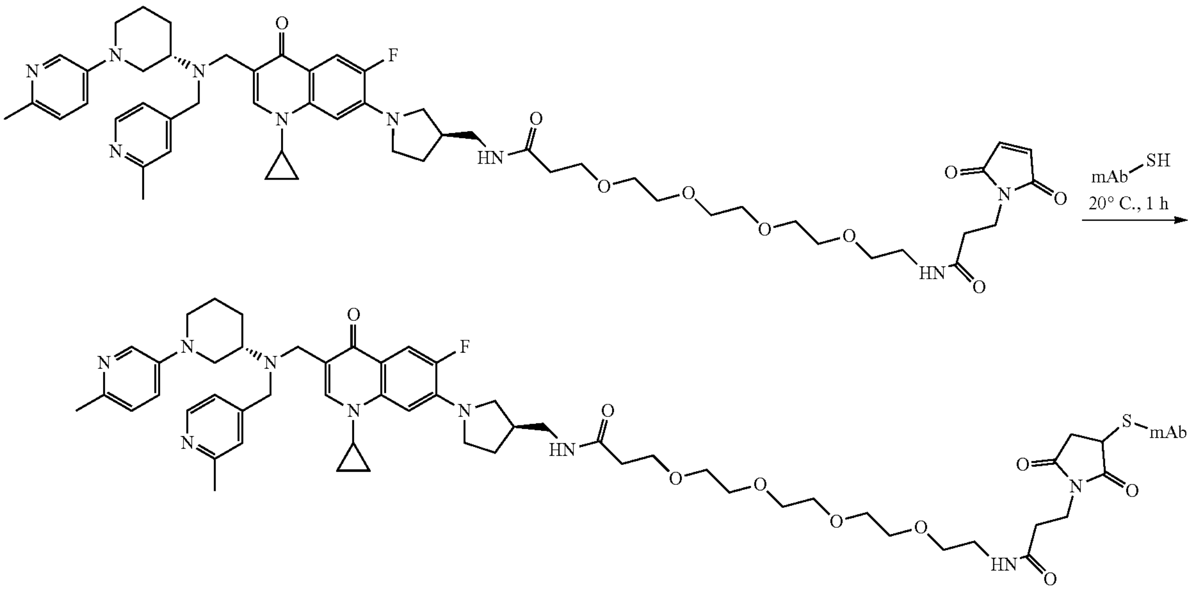

The antibody or the fragments of the antibodies can be conjugated to compound-linker constructs such as compound-linker constructs according to Example 15B according to the procedures described in Br. J. Cancer (1994), 70, 35-41 and Br. J. Cancer (1994), 70, 1126-1130 as follows: the thiol group in the cysteine residues present in the antibodies can be used as conjugation sites, otherwise such thiol groups can be created on lysine residues treating the (or fAb) with a suitable basic solution (like ad eg 0.1 M sodium hydrogen carbonate buffer at pH 8.0) containing 2M of EDTA. To this solution, 2-iminothiolane hydrochloride at a suitable concentration (like ad eg 1 mM) is added and left reacting for 30 min. The unreacted reagent will be desalted using a suitable gel filtration column (like ad eg Sephadex G-25). This procedure will yield the mAb-(SH)n. Aliquots can be taken from this solution and immediately titrated with 4,4'dithiopyridine (DTDP) to determine number of thiols generated. The compound-linker construct according to Example 15B is added to the mAb-SH in 10 M excess and reacted for a suitable time (ad eg 1 h). Excessive compound- Thermal unfolding was performed in Real-Time PCR QuantStudio 6 Flex System (Applied Biosystems), from 25 to 99° C., with continuous ramp mode and ramp rate 0.033° C./s. The data were analyzed using Protein Thermal Shift Software (ThermoFisher).

Using the Fluorescence Thermal Shift assay described above, Examples 1-35, 37, 45-47, 49, 55-58, 66-68, 75, 78, 82, 85, 86, 95, 98, 99 exhibited ΔTm [° C.] values in the following ranges: +=ΔTm ≤10° C.; ++=10<ΔTm <20° C.; +++=ΔTm ≥20° C. For the following examples ΔTm [° C.] of FTS assay are:

| Examples | hSTING FTS binding assay (ΔT C. °) |
|---|---|
| 1 | + |
| 2 | +++ |
| 3 | + |
| 4 | +++ |
| 5 | +++ |
| 6 | ++ |

-continued

| Examples | hSTING FTS binding assay (ΔT C. °) |
|---|---|
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | + |
| 19 | +++ |
| 20 | +++ |
| 21 | +++ |
| 22 | +++ |
| 23 | ++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 37 | +++ |
| 45 | +++ |
| 46 | ++ |
| 47 | +++ |
| 49 | + |
| 55 | +++ |
| 56 | +++ |
| 57 | +++ |
| 58 | +++ |
| 66 | +++ |
| 67 | +++ |

-continued

| Examples | hSTING FTS binding assay (ΔT C. °) |
|---|---|
| 68 | +++ |
| 75 | +++ |
| 78 | +++ |
| 82 | ++ |
| 85 | ++ |
| 86 | +++ |

THP-1 Dual Reporter Assay

Compounds of the present invention were tested for their activity using THP-1 dual cells (Invivogen, cat no. thpd-nfis) allowing for simultaneous study of NF-κB pathway and the interferon regulatory factor (IRF) pathway. THP-1 dual cells contain luciferase reporter gene under the control of an ISG54 (interferon-stimulated gene) minimal promoter in conjunction with five interferon-stimulated response elements and a secreted embryonic alkaline phosphatase reporter gene under the control an IFN (interferon)-β minimal promoter fused to five copies of the NF-κB consensus transcriptional response element with three copies of the c-Rel binding site. Following 18 h of stimulation with STING agonist, medium was collected and transferred onto fresh cell culture plate. To verify activity of the IRF pathway, luminescence activity was measured with standard laboratory plate reader immediately after addition 10 μl of the medium to 40 or 50 μl of luminescence reagent (Invivogen, cat. No. rep-qlc2). To verify activity of NF-κB pathway, 10 or 20 μl of the medium was mixed with 80 μl of a detection medium (Invivogen, cat. No. rep-qb2) and incubated for 1 or 2 hours at 37° C. in a humidified atmosphere containing 5% $CO_2$. Next, absorbance at 630 or 655 nm was recorded using standard laboratory plate reader. Compounds of the present disclosure, as exemplified above, showed EC50 values in the following ranges: +=$EC_{50}$≥10 μM; ++=1 μM <$EC_{50}$<10 μM; +++=$EC_{50}$≥1 μM.

| Examples | Structure | THP1 Dual EC50 (μM) IRF | THP1 Dual EC50 (μM) NFkB |
|---|---|---|---|
| 1 | 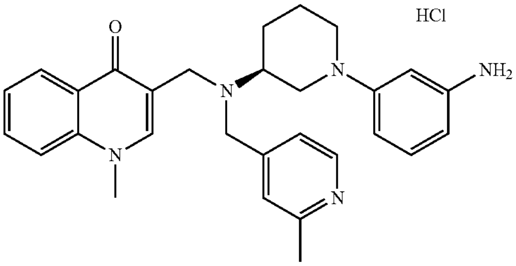 [SMILES: Cc1cc(CN(Cc2cn(C)c3ccccc3c2=O)[C@H]2CCCN(c3cccc(N)c3)C2)ccn1 ; Cl] HCl | ++ | ++ |
| 2 | 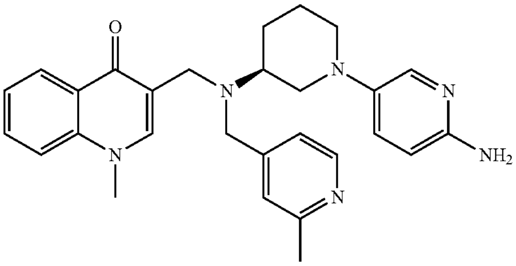 [SMILES: Cc1cc(CN(Cc2cn(C)c3ccccc3c2=O)[C@H]2CCCN(c3ccc(N)nc3)C2)ccn1] | +++ | +++ |

-continued
| Examples | Structure | THP1 Dual EC50 (μM) IRF | THP1 Dual EC50 (μM) NFkB |
|---|---|---|---|
| 3 | 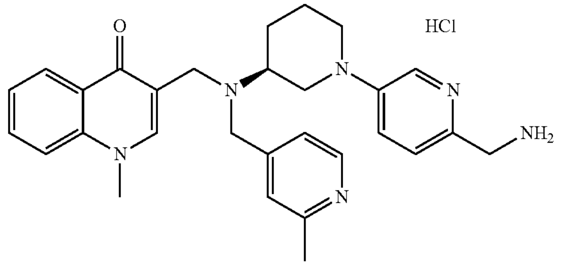 [SMILES: Cc1cc(CN(Cc2cn(C)c3ccccc3c2=O)[C@H]2CCCN(c3ccc(CN)nc3)C2)ccn1 ; Cl] | +++ | ++ |
| 4 | 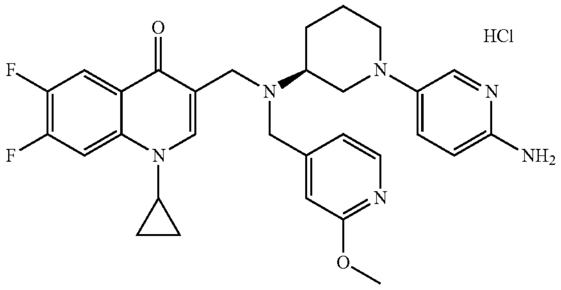 [SMILES: COc1cc(CN(Cc2cn(C3CC3)c3cc(F)c(F)cc3c2=O)[C@H]2CCCN(c3ccc(N)nc3)C2)ccn1 ; Cl] | +++ | +++ |
| 5 | 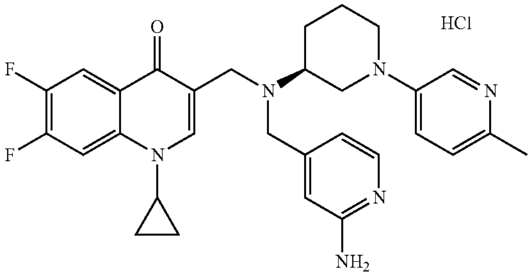 [SMILES: Cc1ccc(N2CCC[C@H](N(Cc3ccnc(N)c3)Cc3cn(C4CC4)c4cc(F)c(F)cc4c3=O)C2)cn1 ; Cl] | +++ | +++ |
| 6 | 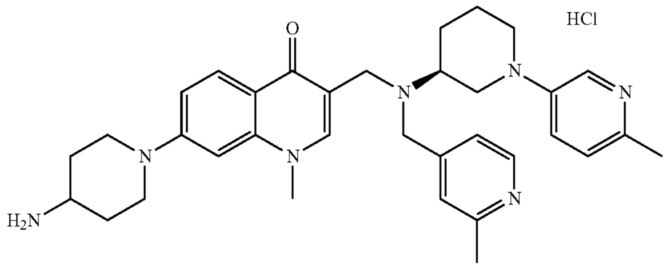 [SMILES: Cc1ccc(N2CCC[C@H](N(Cc3ccnc(C)c3)Cc3cn(C)c4cc(N5CCC(N)CC5)ccc4c3=O)C2)cn1 ; Cl] | ++ | ++ |
| 7 | 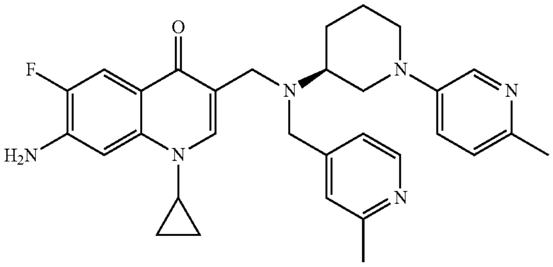 [SMILES: Cc1ccc(N2CCC[C@H](N(Cc3ccnc(C)c3)Cc3cn(C4CC4)c4cc(N)c(F)cc4c3=O)C2)cn1] | +++ | +++ |

-continued
| Exam-ples | Structure | THP1 Dual EC50 (μM) IRF | THP1 Dual EC50 (μM) NFkB |
|---|---|---|---|
| 8 | 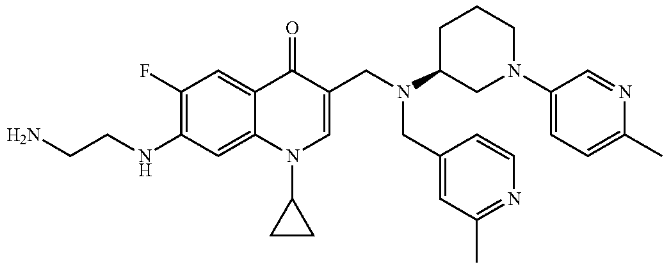 [SMILES: Cc1ccc(N2CCC[C@H](N(Cc3ccnc(C)c3)Cc3cn(C4CC4)c4cc(NCCN)c(F)cc4c3=O)C2)cn1] | +++ | +++ |
| 9 | 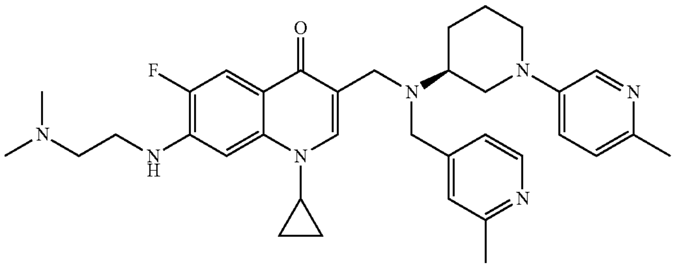 | +++ | +++ |
| 10 | 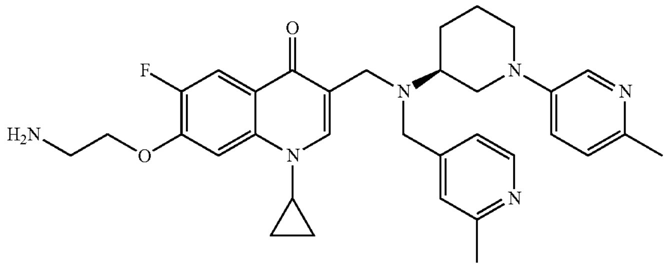 [SMILES: Cc1ccc(N2CCC[C@H](N(Cc3ccnc(C)c3)Cc3cn(C4CC4)c4cc(OCCN)c(F)cc4c3=O)C2)cn1] | +++ | +++ |
| 11 | 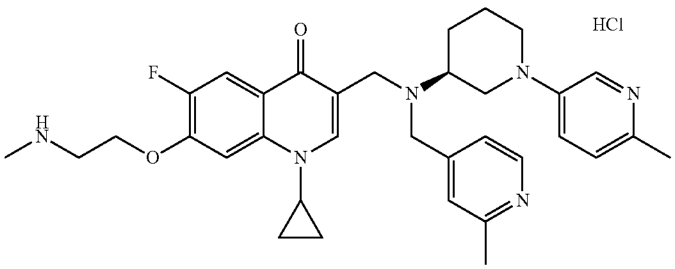 HCl | +++ | +++ |
| 12 | 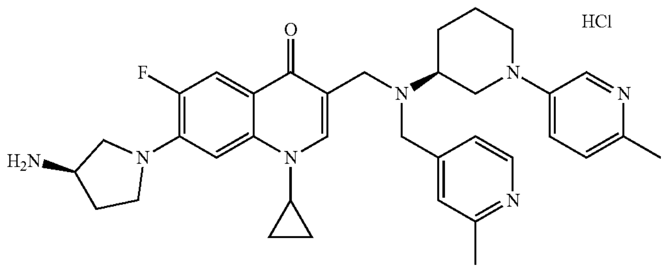 [SMILES: Cc1ccc(N2CCC[C@H](N(Cc3ccnc(C)c3)Cc3cn(C4CC4)c4cc(N5CC[C@@H](N)C5)c(F)cc4c3=O)C2)cn1 ; Cl] HCl | +++ | +++ |

-continued
| Examples | Structure | THP1 Dual EC50 (μM) IRF | THP1 Dual EC50 (μM) NFkB |
|---|---|---|---|
| 13 | 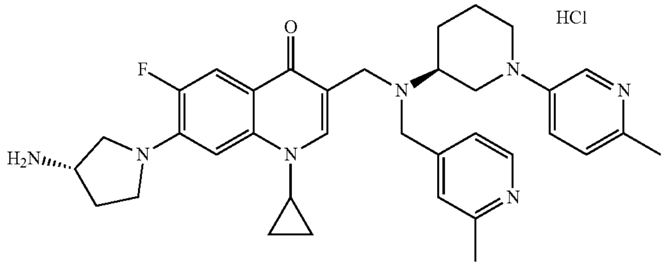 [SMILES: Cc1ccc(N2CCC[C@H](N(Cc3ccnc(C)c3)Cc3cn(C4CC4)c4cc(N5CC[C@H](N)C5)c(F)cc4c3=O)C2)cn1 ; Cl] HCl | +++ | +++ |
| 14 | 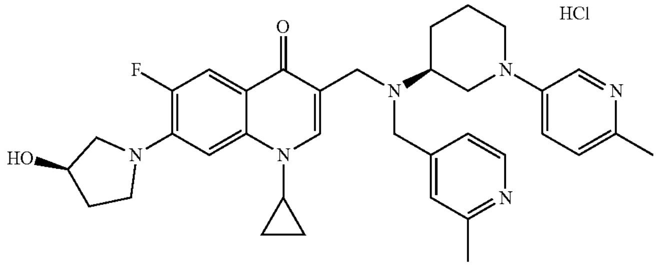 [SMILES: Cc1ccc(N2CCC[C@H](N(Cc3ccnc(C)c3)Cc3cn(C4CC4)c4cc(N5CC[C@@H](O)C5)c(F)cc4c3=O)C2)cn1 ; Cl] HCl | +++ | +++ |
| 15 | 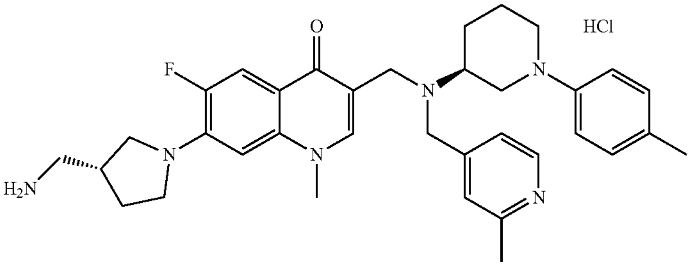 [SMILES: Cc1ccc(N2CCC[C@H](N(Cc3ccnc(C)c3)Cc3cn(C)c4cc(N5CC[C@H](CN)C5)c(F)cc4c3=O)C2)cc1 ; Cl] HCl | +++ | +++ |
| 16 | 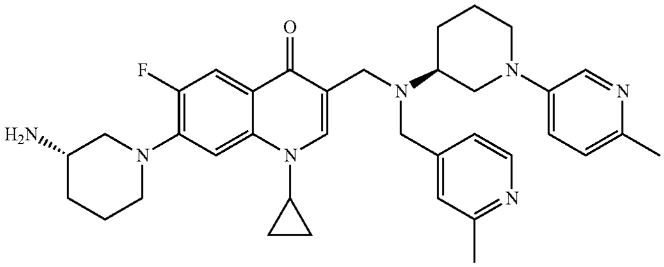 [SMILES: Cc1ccc(N2CCC[C@H](N(Cc3ccnc(C)c3)Cc3cn(C4CC4)c4cc(N5CCC[C@H](N)C5)c(F)cc4c3=O)C2)cn1] | +++ | +++ |
| 17 | 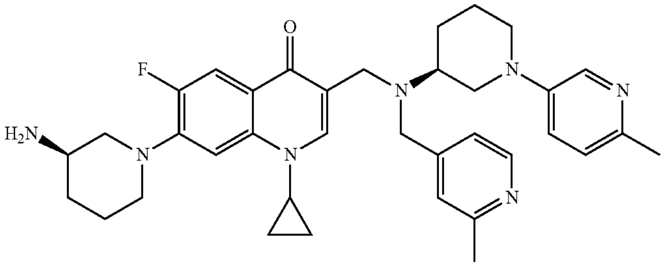 [SMILES: Cc1ccc(N2CCC[C@H](N(Cc3ccnc(C)c3)Cc3cn(C4CC4)c4cc(N5CCC[C@@H](N)C5)c(F)cc4c3=O)C2)cn1] | +++ | +++ |

-continued
| Examples | Structure | THP1 Dual EC50 (μM) IRF | THP1 Dual EC50 (μM) NFkB |
|---|---|---|---|
| 18 | 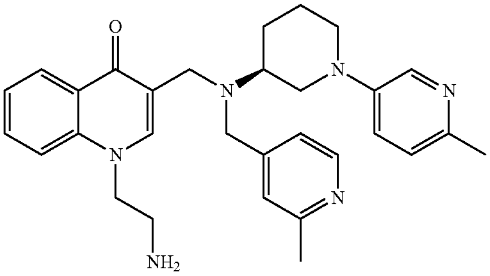 [SMILES: Cc1ccc(N2CCC[C@H](N(Cc3ccnc(C)c3)Cc3cn(CCN)c4ccccc4c3=O)C2)cn1] | ++ | ++ |
| 19 | 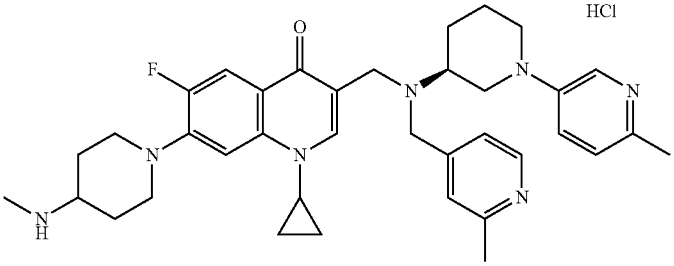 HCl | +++ | +++ |
| 20 | 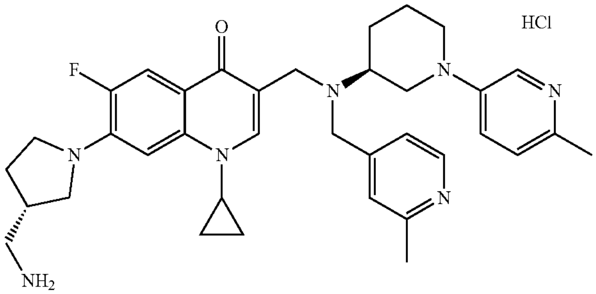 [SMILES: Cc1ccc(N2CCC[C@H](N(Cc3ccnc(C)c3)Cc3cn(C4CC4)c4cc(N5CC[C@@H](CN)C5)c(F)cc4c3=O)C2)cn1 ; Cl] HCl | +++ | +++ |
| 21 | 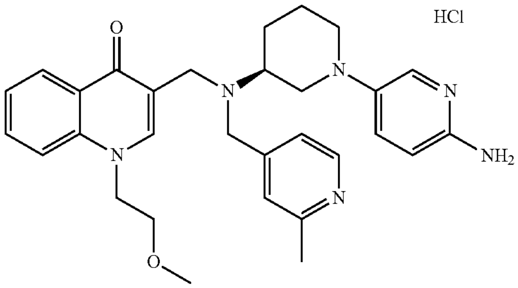 [SMILES: COCCn1cc(CN(Cc2ccnc(C)c2)[C@H]2CCCN(c3ccc(N)nc3)C2)c(=O)c2ccccc21 ; Cl] HCl | +++ | +++ |
| 22 | 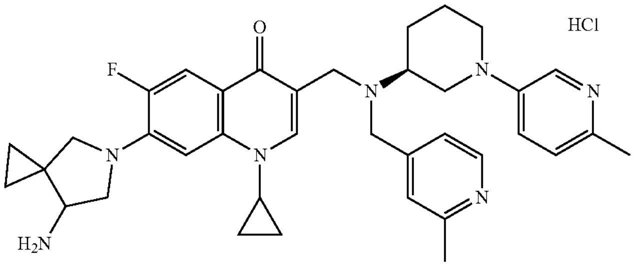 [SMILES: Cc1ccc(N2CCC[C@H](N(Cc3ccnc(C)c3)Cc3cn(C4CC4)c4cc(N5CC(N)C6(CC6)C5)c(F)cc4c3=O)C2)cn1 ; Cl] HCl | +++ | +++ |

-continued
| Examples | Structure | THP1 Dual EC50 (μM) IRF | THP1 Dual EC50 (μM) NFkB |
|---|---|---|---|
| 23 | 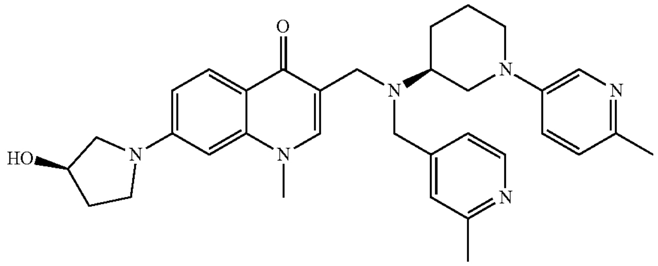 [SMILES: Cc1ccc(N2CCC[C@H](N(Cc3ccnc(C)c3)Cc3cn(C)c4cc(N5CC[C@@H](O)C5)ccc4c3=O)C2)cn1] | +++ | +++ |
| 24 | 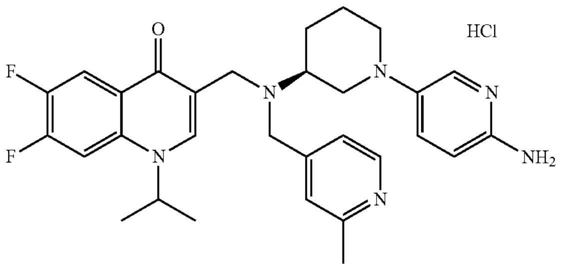 [SMILES: Cc1cc(CN(Cc2cn(C(C)C)c3cc(F)c(F)cc3c2=O)[C@H]2CCCN(c3ccc(N)nc3)C2)ccn1 ; Cl] | +++ | +++ |
| 25 | 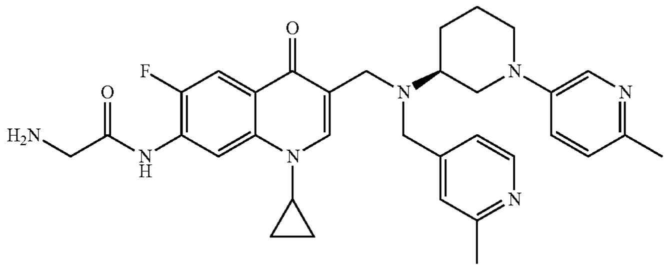 [SMILES: Cc1ccc(N2CCC[C@H](N(Cc3ccnc(C)c3)Cc3cn(C4CC4)c4cc(NC(=O)CN)c(F)cc4c3=O)C2)cn1] | +++ | +++ |
| 26 | 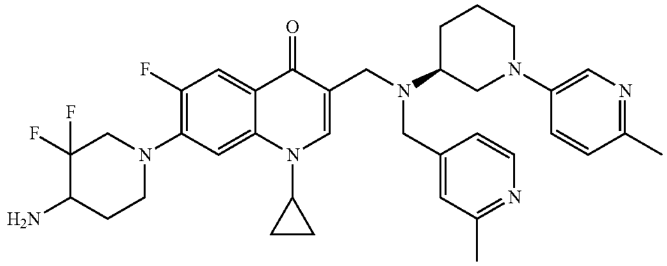 [SMILES: Cc1ccc(N2CCC[C@H](N(Cc3ccnc(C)c3)Cc3cn(C4CC4)c4cc(N5CCC(N)C(F)(F)C5)c(F)cc4c3=O)C2)cn1] | +++ | +++ |
| 27 | 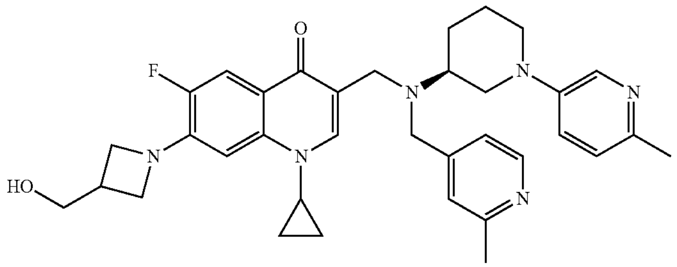 [SMILES: Cc1ccc(N2CCC[C@H](N(Cc3ccnc(C)c3)Cc3cn(C4CC4)c4cc(N5CC(CO)C5)c(F)cc4c3=O)C2)cn1] | +++ | +++ |

-continued
| Examples | Structure | THP1 Dual EC50 (μM) IRF | THP1 Dual EC50 (μM) NFkB |
|---|---|---|---|
| 28 | 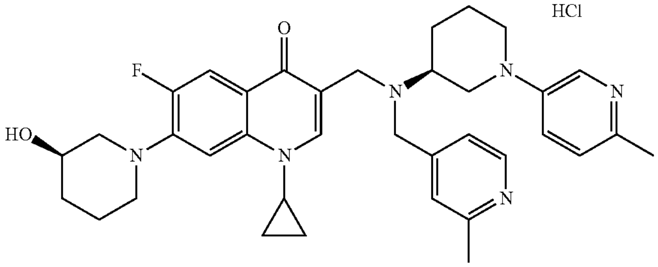 [SMILES: Cc1ccc(N2CCC[C@H](N(Cc3ccnc(C)c3)Cc3cn(C4CC4)c4cc(N5CCC[C@@H](O)C5)c(F)cc4c3=O)C2)cn1 ; Cl] HCl | +++ | +++ |
| 29 | 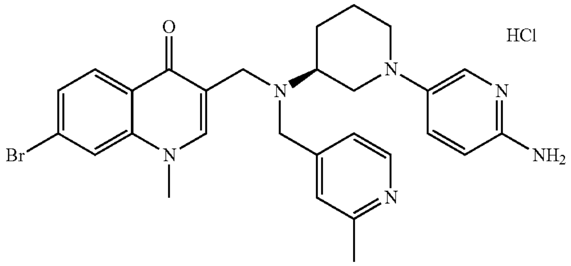 [SMILES: Cc1cc(CN(Cc2cn(C)c3cc(Br)ccc3c2=O)[C@H]2CCCN(c3ccc(N)nc3)C2)ccn1 ; Cl] HCl | +++ | +++ |
| 30 | 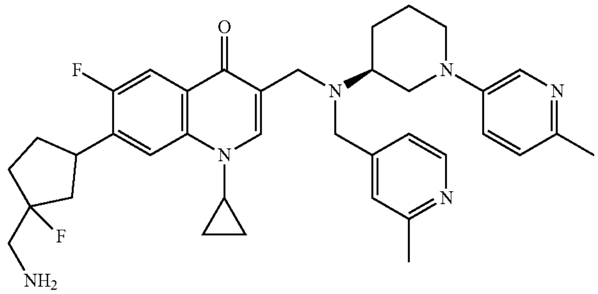 [SMILES: Cc1ccc(N2CCC[C@H](N(Cc3ccnc(C)c3)Cc3cn(C4CC4)c4cc(C5CCC(F)(CN)C5)c(F)cc4c3=O)C2)cn1] | +++ | +++ |
| 31 | 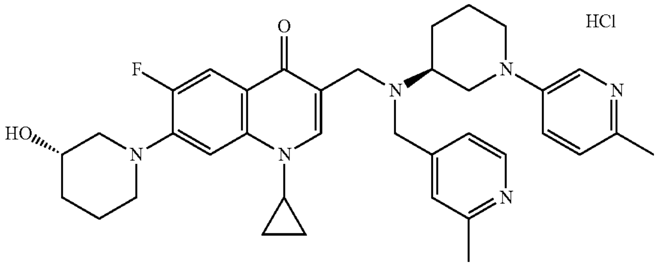 [SMILES: Cc1ccc(N2CCC[C@H](N(Cc3ccnc(C)c3)Cc3cn(C4CC4)c4cc(N5CCC[C@H](O)C5)c(F)cc4c3=O)C2)cn1 ; Cl] HCl | +++ | +++ |
| 32 | 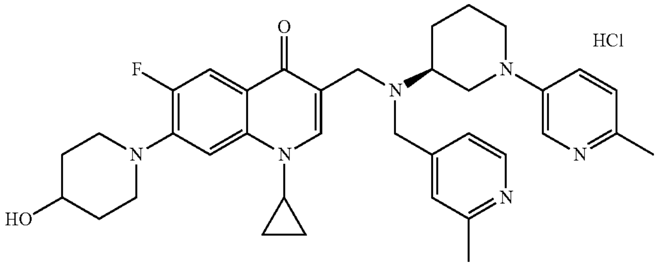 [SMILES: Cc1ccc(N2CCC[C@H](N(Cc3ccnc(C)c3)Cc3cn(C4CC4)c4cc(N5CCC(O)CC5)c(F)cc4c3=O)C2)cn1 ; Cl] HCl | +++ | +++ |

-continued
| Examples | Structure | THP1 Dual EC50 (µM) IRF | THP1 Dual EC50 (µM) NFkB |
|---|---|---|---|
| 33 | 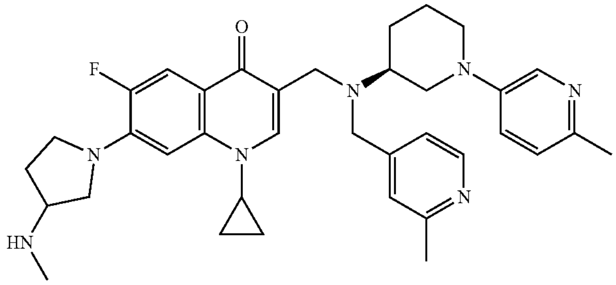 [SMILES: CNC1CCN(c2cc3c(cc2F)c(=O)c(CN(Cc2ccnc(C)c2)[C@H]2CCCN(c4ccc(C)nc4)C2)cn3C2CC2)C1] | +++ | +++ |
| 34 | 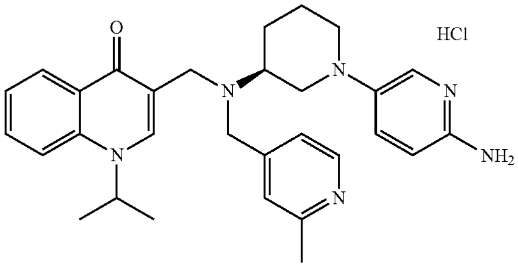 [SMILES: Cc1cc(CN(Cc2cn(C(C)C)c3ccccc3c2=O)[C@H]2CCCN(c3ccc(N)nc3)C2)ccn1 ; Cl] HCl | +++ | +++ |
| 35 | 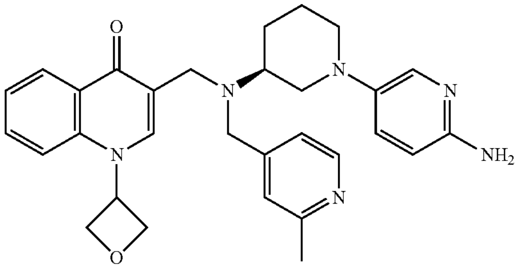 [SMILES: Cc1cc(CN(Cc2cn(C3COC3)c3ccccc3c2=O)[C@H]2CCCN(c3ccc(N)nc3)C2)ccn1] | +++ | +++ |
| 36 | 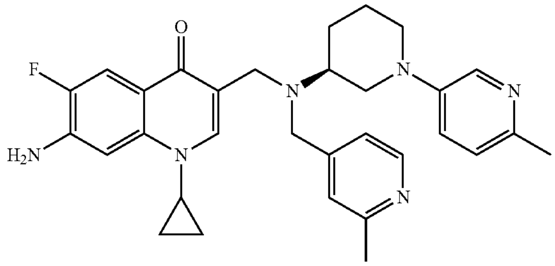 [SMILES: Cc1ccc(N2CCC[C@H](N(Cc3ccnc(C)c3)Cc3cn(C4CC4)c4cc(N)c(F)cc4c3=O)C2)cn1] | +++ | +++ |
| 37 | 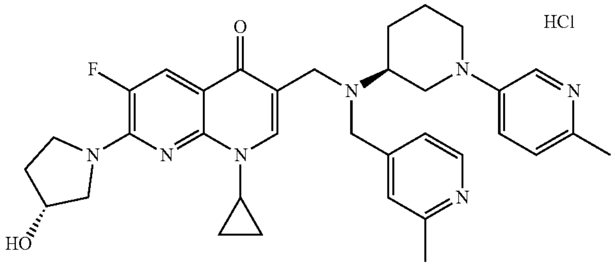 [SMILES: Cc1ccc(N2CCC[C@H](N(Cc3ccnc(C)c3)Cc3cn(C4CC4)c4nc(N5CC[C@@H](O)C5)c(F)cc4c3=O)C2)cn1 ; Cl] HCl | +++ | +++ |

-continued
| Examples | Structure | THP1 Dual EC50 (μM) IRF | THP1 Dual EC50 (μM) NFkB |
|---|---|---|---|
| 38 | 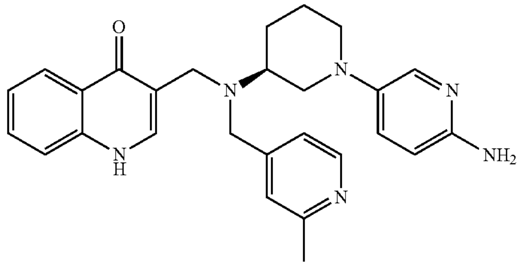 | +++ | +++ |
| 39 | 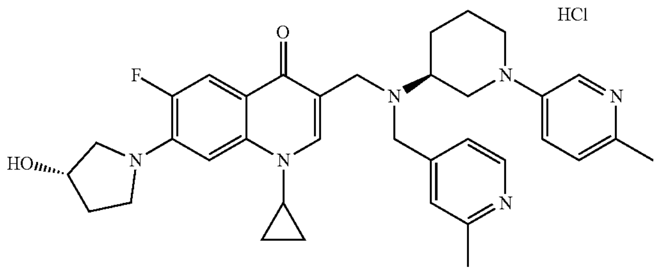 [SMILES: Cc1ccc(N2CCC[C@H](N(Cc3ccnc(C)c3)Cc3cn(C4CC4)c4cc(N5CC[C@H](O)C5)c(F)cc4c3=O)C2)cn1 ; Cl] | +++ | +++ |
| 40 | 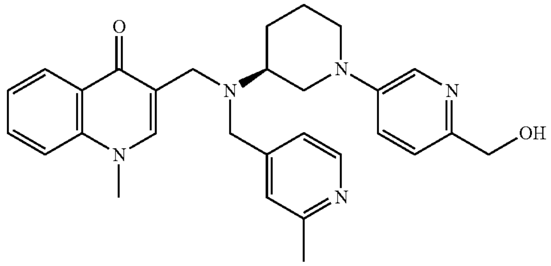 [SMILES: Cc1cc(CN(Cc2cn(C)c3ccccc3c2=O)[C@H]2CCCN(c3ccc(CO)nc3)C2)ccn1] | ++ | ++ |
| 41 | 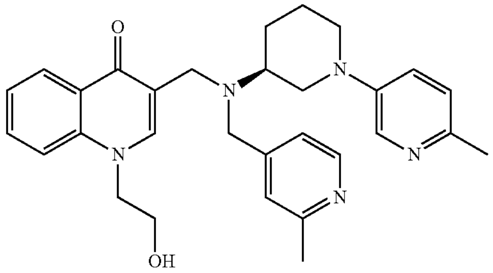 [SMILES: Cc1ccc(N2CCC[C@H](N(Cc3ccnc(C)c3)Cc3cn(CCO)c4ccccc4c3=O)C2)cn1] | ++ | ++ |
| 42 | 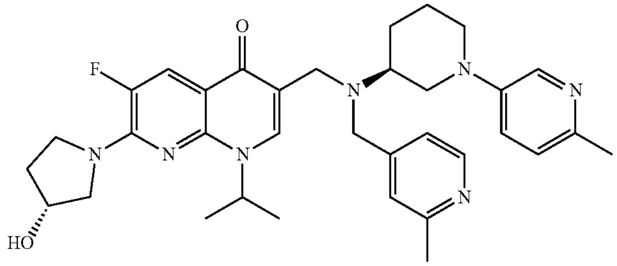 [SMILES: Cc1ccc(N2CCC[C@H](N(Cc3ccnc(C)c3)Cc3cn(C(C)C)c4nc(N5CC[C@@H](O)C5)c(F)cc4c3=O)C2)cn1] | +++ | +++ |

-continued
| Examples | Structure | THP1 Dual EC50 (μM) IRF | THP1 Dual EC50 (μM) NFkB |
|---|---|---|---|
| 43 | 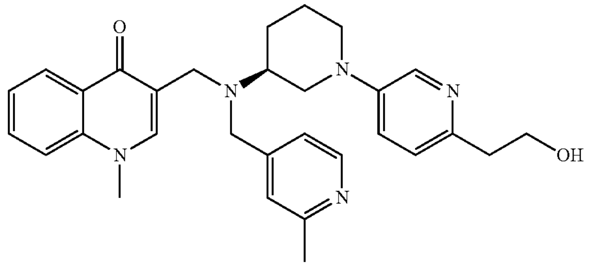 [SMILES: Cc1cc(CN(Cc2cn(C)c3ccccc3c2=O)[C@H]2CCCN(c3ccc(CCO)nc3)C2)ccn1] | ++ | ++ |
| 44 | 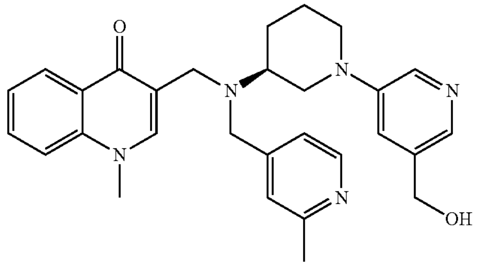 [SMILES: Cc1cc(CN(Cc2cn(C)c3ccccc3c2=O)[C@H]2CCCN(c3cncc(CO)c3)C2)ccn1] | + | + |
| 45 | 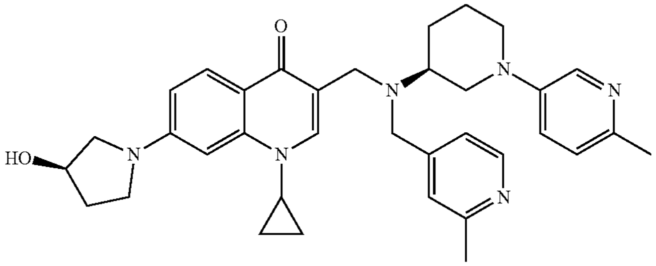 [SMILES: Cc1ccc(N2CCC[C@H](N(Cc3ccnc(C)c3)Cc3cn(C4CC4)c4cc(N5CC[C@@H](O)C5)ccc4c3=O)C2)cn1] | +++ | +++ |
| 46 | 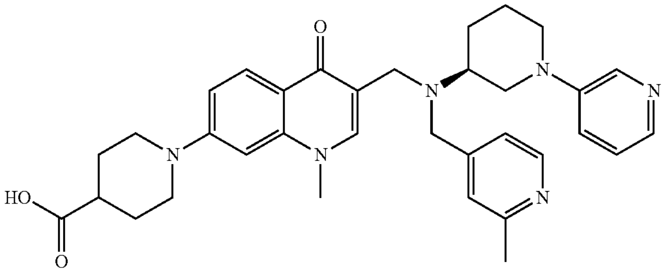 [SMILES: Cc1cc(CN(Cc2cn(C)c3cc(N4CCC(C(=O)O)CC4)ccc3c2=O)[C@H]2CCCN(c3cccnc3)C2)ccn1] | + | + |
| 47 | 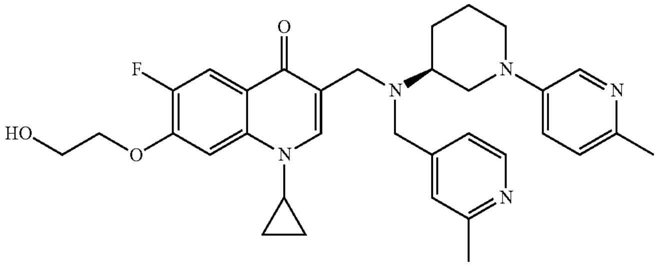 [SMILES: Cc1ccc(N2CCC[C@H](N(Cc3ccnc(C)c3)Cc3cn(C4CC4)c4cc(OCCO)c(F)cc4c3=O)C2)cn1] | + + + | + + + |

-continued
| Examples | Structure | THP1 Dual EC50 (μM) IRF | THP1 Dual EC50 (μM) NFkB |
|---|---|---|---|
| 48 | 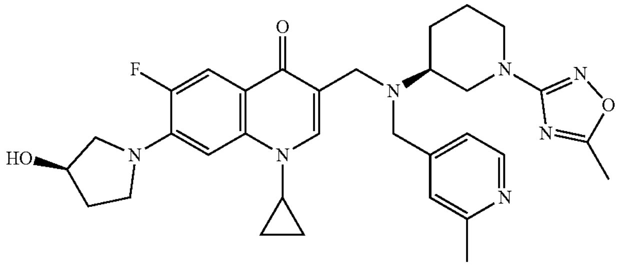 [SMILES: Cc1cc(CN(Cc2cn(C3CC3)c3cc(N4CC[C@@H](O)C4)c(F)cc3c2=O)[C@H]2CCCN(c3noc(C)n3)C2)ccn1] | +++ | ++ |
| 49 | 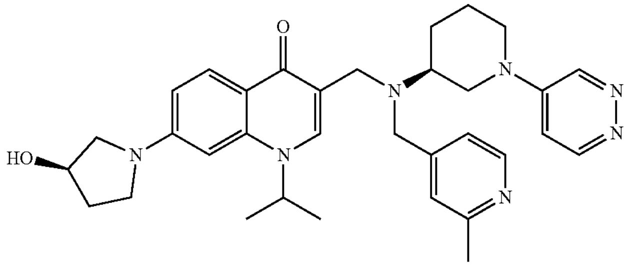 [SMILES: Cc1cc(CN(Cc2cn(C(C)C)c3cc(N4CC[C@@H](O)C4)ccc3c2=O)[C@H]2CCCN(c3ccnnc3)C2)ccn1] | + | + |
| 50 | 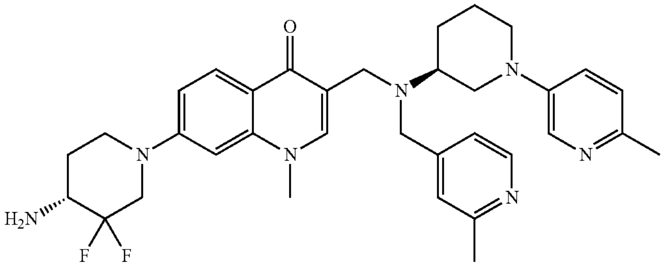 [SMILES: Cc1ccc(N2CCC[C@H](N(Cc3ccnc(C)c3)Cc3cn(C)c4cc(N5CC[C@@H](N)C(F)(F)C5)ccc4c3=O)C2)cn1] | +++ | +++ |
| 51 | 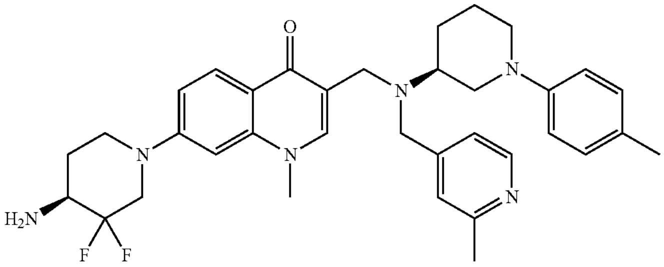 [SMILES: Cc1ccc(N2CCC[C@H](N(Cc3ccnc(C)c3)Cc3cn(C)c4cc(N5CC[C@H](N)C(F)(F)C5)ccc4c3=O)C2)cc1] | +++ | ++ |
| 52 | 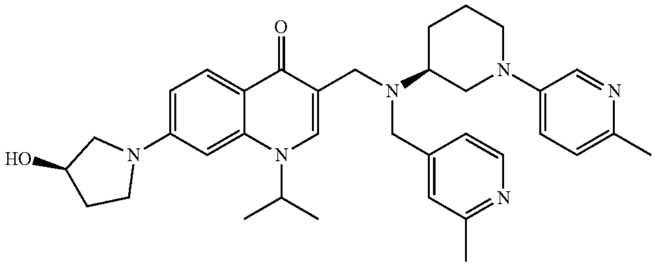 [SMILES: Cc1ccc(N2CCC[C@H](N(Cc3ccnc(C)c3)Cc3cn(C(C)C)c4cc(N5CC[C@@H](O)C5)ccc4c3=O)C2)cn1] | +++ | +++ |

-continued
| Examples | Structure | THP1 Dual EC50 (μM) IRF | THP1 Dual EC50 (μM) NFkB |
|---|---|---|---|
| 53 | 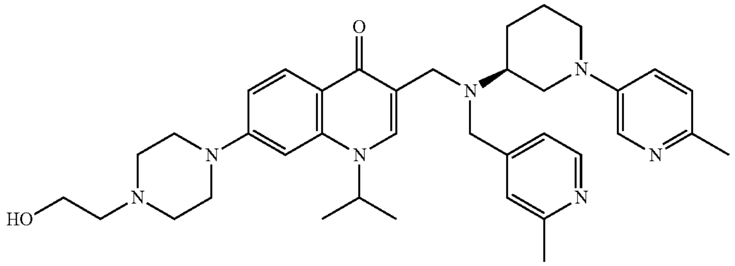 [SMILES: Cc1ccc(N2CCC[C@H](N(Cc3ccnc(C)c3)Cc3cn(C(C)C)c4cc(N5CCN(CCO)CC5)ccc4c3=O)C2)cn1] | +++ | +++ |
| 54 | 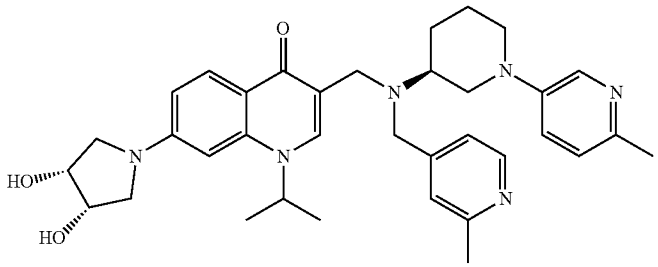 [SMILES: Cc1ccc(N2CCC[C@H](N(Cc3ccnc(C)c3)Cc3cn(C(C)C)c4cc(N5C[C@@H](O)[C@@H](O)C5)ccc4c3=O)C2)cn1] | +++ | ++ |
| 55 | 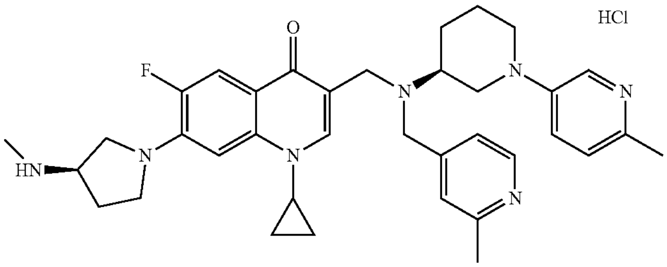 HCl | +++ | +++ |
| 56 | 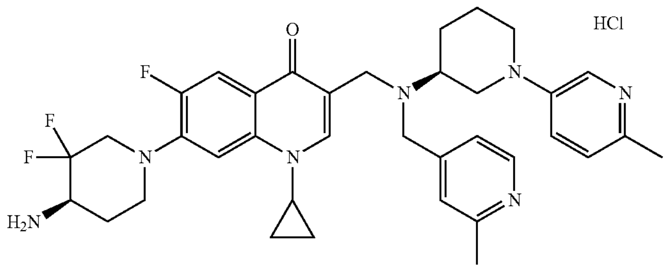 [SMILES: Cc1ccc(N2CCC[C@H](N(Cc3ccnc(C)c3)Cc3cn(C4CC4)c4cc(N5CC[C@@H](N)C(F)(F)C5)c(F)cc4c3=O)C2)cn1 ; Cl] HCl | +++ | +++ |
| 57 | 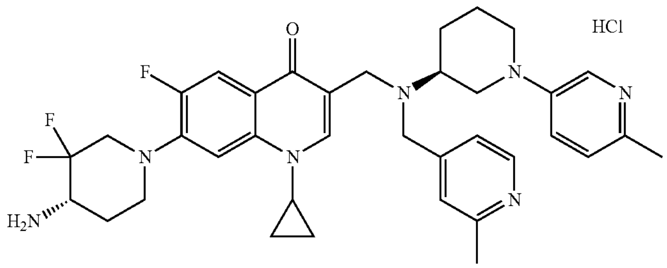 [SMILES: Cc1ccc(N2CCC[C@H](N(Cc3ccnc(C)c3)Cc3cn(C4CC4)c4cc(N5CC[C@H](N)C(F)(F)C5)c(F)cc4c3=O)C2)cn1 ; Cl] HCl | +++ | +++ |

-continued
| Examples | Structure | THP1 Dual EC50 (μM) IRF | THP1 Dual EC50 (μM) NFkB |
|---|---|---|---|
| 58 | 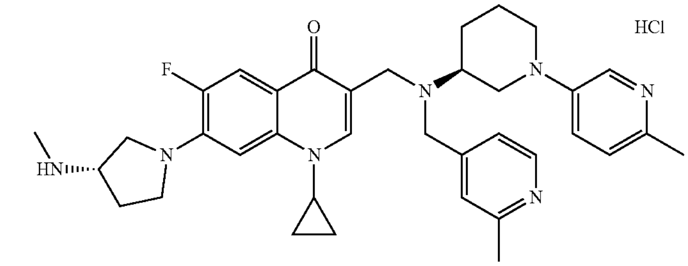 HCl | +++ | +++ |
| 59 | 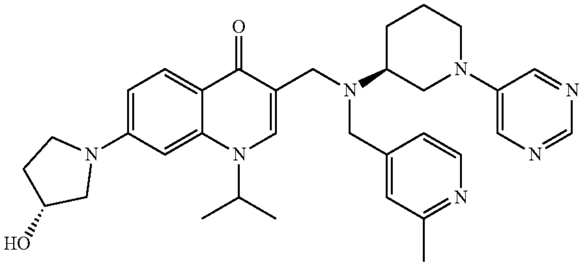 [SMILES: Cc1cc(CN(Cc2cn(C(C)C)c3cc(N4CC[C@@H](O)C4)ccc3c2=O)[C@H]2CCCN(c3cncnc3)C2)ccn1] | + | + |
| 60 | 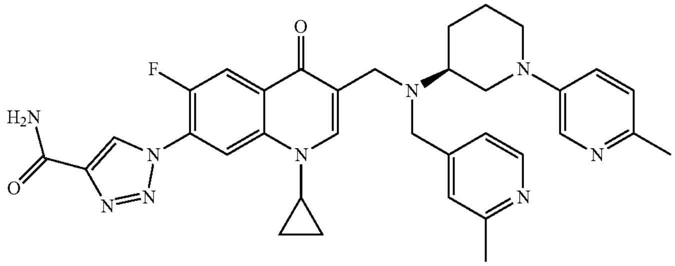 [SMILES: Cc1ccc(N2CCC[C@H](N(Cc3ccnc(C)c3)Cc3cn(C4CC4)c4cc(-n5cc(C(N)=O)nn5)c(F)cc4c3=O)C2)cn1] | +++ | +++ |
| 61 | 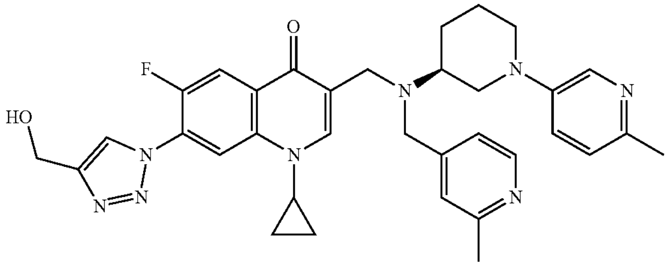 [SMILES: Cc1ccc(N2CCC[C@H](N(Cc3ccnc(C)c3)Cc3cn(C4CC4)c4cc(-n5cc(CO)nn5)c(F)cc4c3=O)C2)cn1] | +++ | +++ |
| 62 | 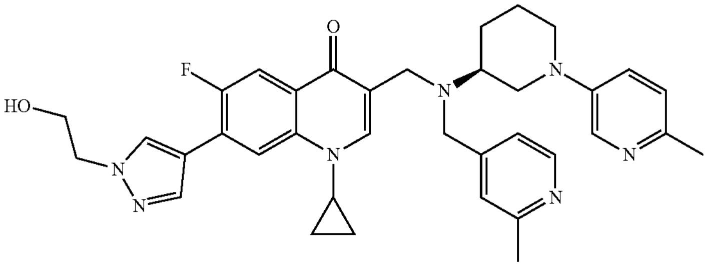 [SMILES: Cc1ccc(N2CCC[C@H](N(Cc3ccnc(C)c3)Cc3cn(C4CC4)c4cc(-c5cnn(CCO)c5)c(F)cc4c3=O)C2)cn1] | +++ | +++ |

-continued
| Examples | Structure | THP1 Dual EC50 (μM) IRF | THP1 Dual EC50 (μM) NFkB |
|---|---|---|---|
| 63 | 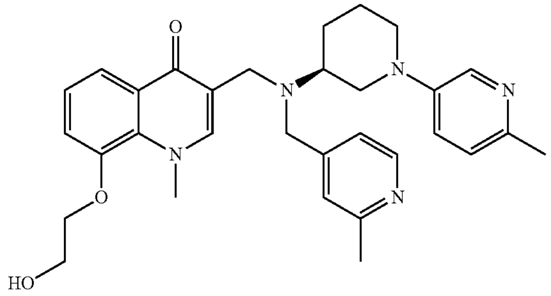 [SMILES: Cc1ccc(N2CCC[C@H](N(Cc3ccnc(C)c3)Cc3cn(C)c4c(OCCO)cccc4c3=O)C2)cn1] | +++ | +++ |
| 64 | 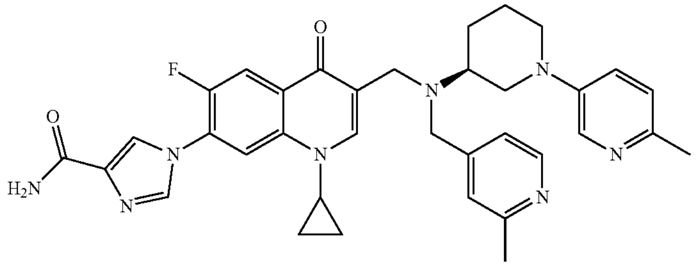 [SMILES: Cc1ccc(N2CCC[C@H](N(Cc3ccnc(C)c3)Cc3cn(C4CC4)c4cc(-n5cnc(C(N)=O)c5)c(F)cc4c3=O)C2)cn1] | +++ | +++ |
| 65 | 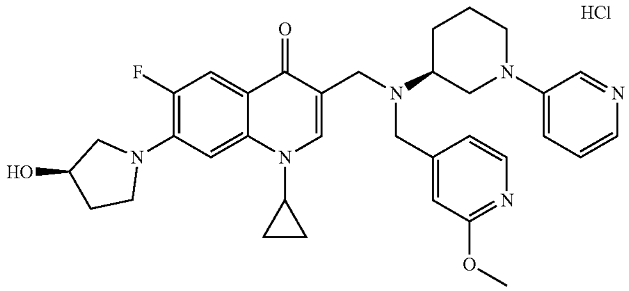 [SMILES: COc1cc(CN(Cc2cn(C3CC3)c3cc(N4CC[C@@H](O)C4)c(F)cc3c2=O)[C@H]2CCCN(c3cccnc3)C2)ccn1 ; Cl] | +++ | +++ |
| 66 | 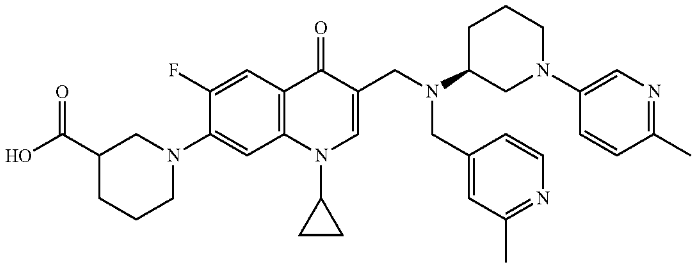 [SMILES: Cc1ccc(N2CCC[C@H](N(Cc3ccnc(C)c3)Cc3cn(C4CC4)c4cc(N5CCCC(C(=O)O)C5)c(F)cc4c3=O)C2)cn1] | ++ | ++ |
| 67 | 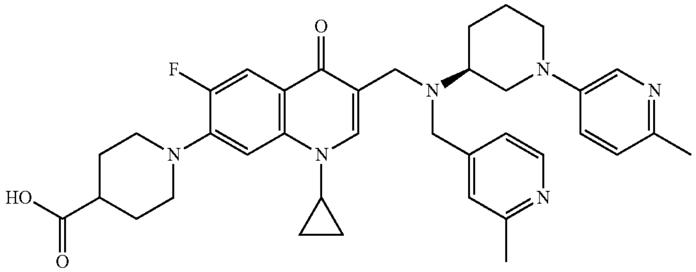 [SMILES: Cc1ccc(N2CCC[C@H](N(Cc3ccnc(C)c3)Cc3cn(C4CC4)c4cc(N5CCC(C(=O)O)CC5)c(F)cc4c3=O)C2)cn1] | ++ | ++ |

-continued
| Examples | Structure | THP1 Dual EC50 (μM) IRF | THP1 Dual EC50 (μM) NFkB |
|---|---|---|---|
| 68 | 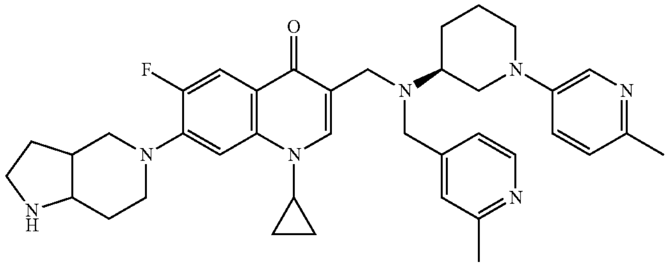 [SMILES: Cc1ccc(N2CCC[C@H](N(Cc3ccnc(C)c3)Cc3cn(C4CC4)c4cc(N5CCC6NCCC6C5)c(F)cc4c3=O)C2)cn1] | +++ | +++ |
| 69 | 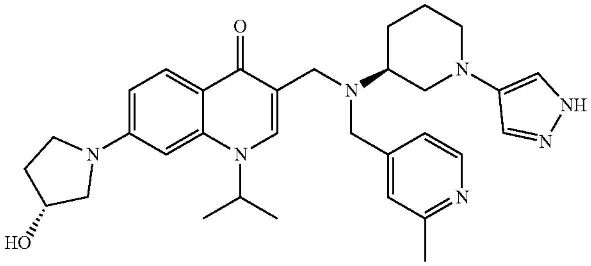 [SMILES: Cc1cc(CN(Cc2cn(C(C)C)c3cc(N4CC[C@@H](O)C4)ccc3c2=O)[C@H]2CCCN(c3cn[nH]c3)C2)ccn1] | ++ | ++ |
| 70 | 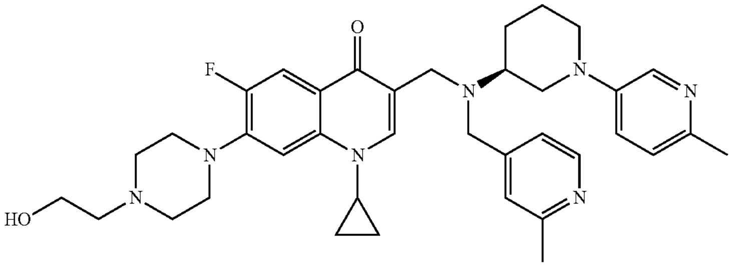 [SMILES: Cc1ccc(N2CCC[C@H](N(Cc3ccnc(C)c3)Cc3cn(C4CC4)c4cc(N5CCN(CCO)CC5)c(F)cc4c3=O)C2)cn1] | +++ | +++ |
| 71 | 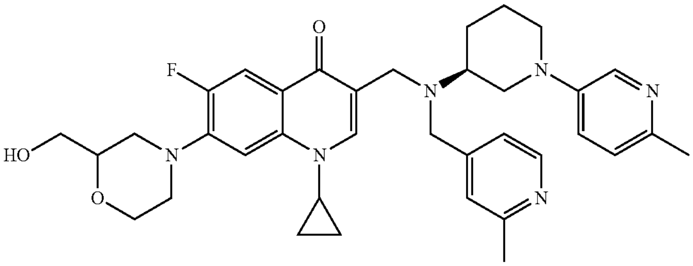 [SMILES: Cc1ccc(N2CCC[C@H](N(Cc3ccnc(C)c3)Cc3cn(C4CC4)c4cc(N5CCOC(CO)C5)c(F)cc4c3=O)C2)cn1] | +++ | +++ |
| 72 | 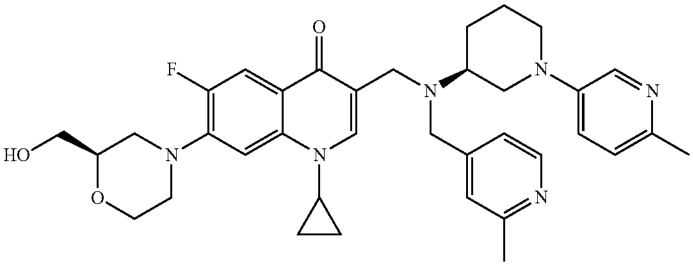 [SMILES: Cc1ccc(N2CCC[C@H](N(Cc3ccnc(C)c3)Cc3cn(C4CC4)c4cc(N5CCO[C@@H](CO)C5)c(F)cc4c3=O)C2)cn1] | +++ | +++ |

-continued
| Exam-ples | Structure | THP1 Dual EC50 (μM) IRF | THP1 Dual EC50 (μM) NFkB |
|---|---|---|---|
| 73 | 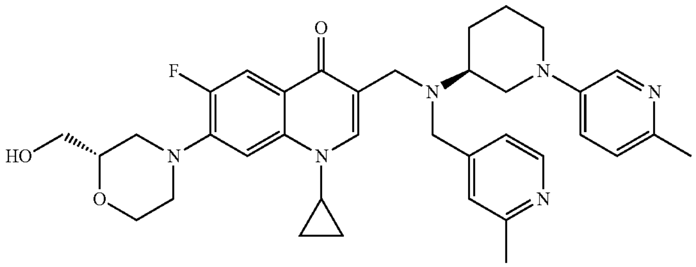 | +++ | +++ |
| 74 | 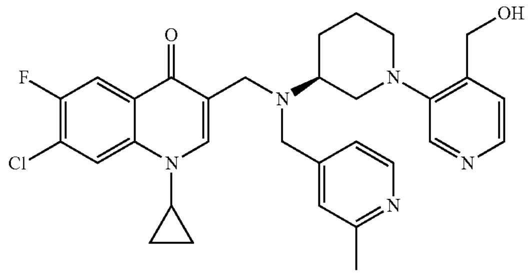 [SMILES: Cc1cc(CN(Cc2cn(C3CC3)c3cc(Cl)c(F)cc3c2=O)[C@H]2CCCN(c3cnccc3CO)C2)ccn1] | ++ | ++ |
| 75 | 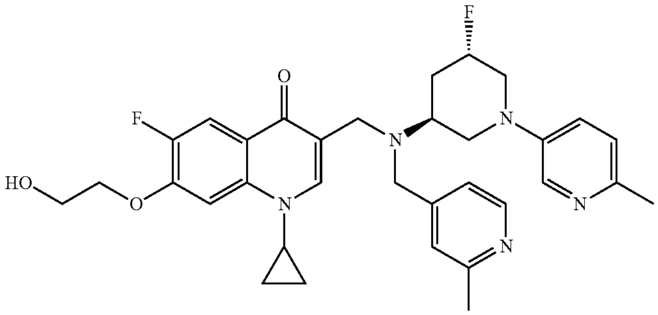 [SMILES: Cc1ccc(N2C[C@@H](F)C[C@H](N(Cc3ccnc(C)c3)Cc3cn(C4CC4)c4cc(OCCO)c(F)cc4c3=O)C2)cn1] | +++ | +++ |
| 76 | 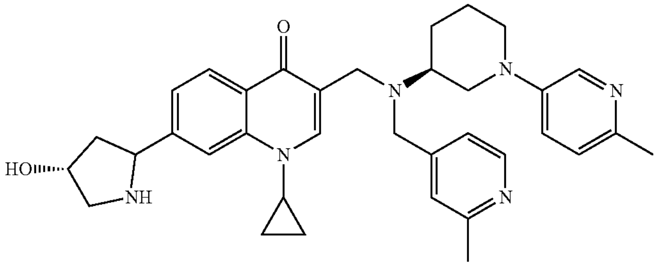 [SMILES: Cc1ccc(N2CCC[C@H](N(Cc3ccnc(C)c3)Cc3cn(C4CC4)c4cc(C5C[C@@H](O)CN5)ccc4c3=O)C2)cn1] | ++ | ++ |
| 77 | 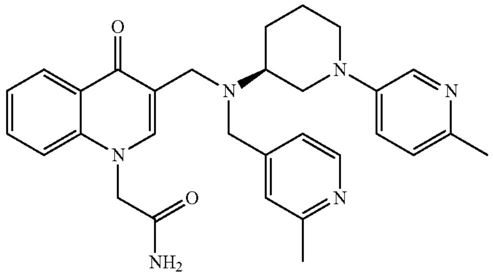 [SMILES: Cc1ccc(N2CCC[C@H](N(Cc3ccnc(C)c3)Cc3cn(CC(N)=O)c4ccccc4c3=O)C2)cn1] | ++ | ++ |

-continued
| Examples | Structure | THP1 Dual EC50 (μM) IRF | THP1 Dual EC50 (μM) NFkB |
| --- | --- | --- | --- |
| 78 | 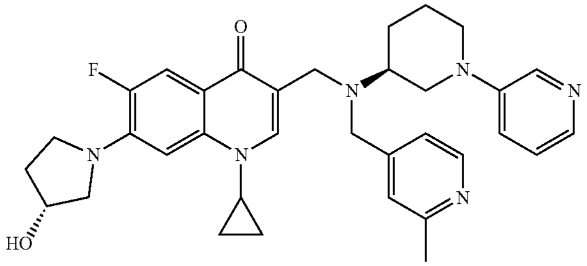 [SMILES: Cc1cc(CN(Cc2cn(C3CC3)c3cc(N4CC[C@@H](O)C4)c(F)cc3c2=O)[C@H]2CCCN(c3cccnc3)C2)ccn1] | +++ | +++ |
| 79 | 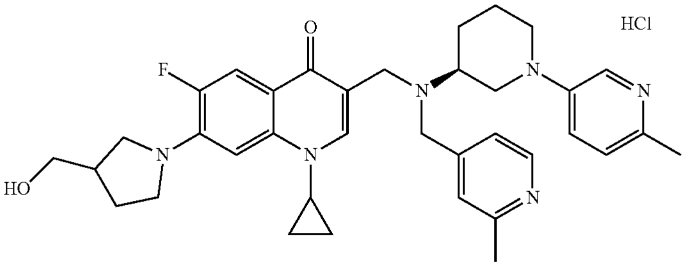 [SMILES: Cc1ccc(N2CCC[C@H](N(Cc3ccnc(C)c3)Cc3cn(C4CC4)c4cc(N5CCC(CO)C5)c(F)cc4c3=O)C2)cn1 ; Cl] HCl | +++ | +++ |
| 80 | 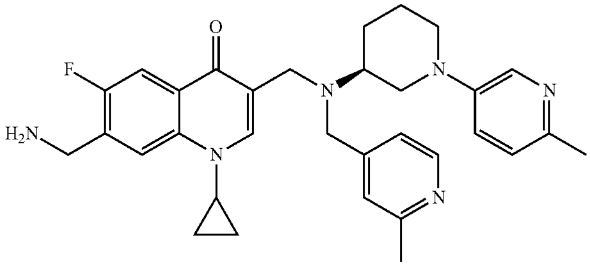 [SMILES: Cc1ccc(N2CCC[C@H](N(Cc3ccnc(C)c3)Cc3cn(C4CC4)c4cc(CN)c(F)cc4c3=O)C2)cn1] | +++ | +++ |
| 81 | 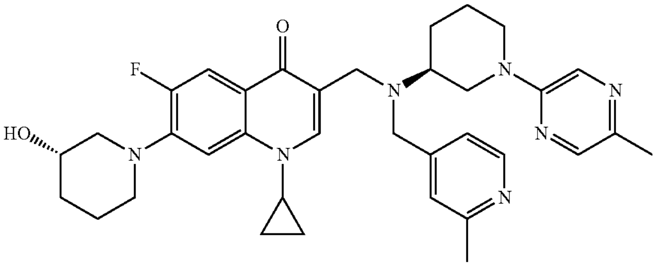 [SMILES: Cc1cnc(N2CCC[C@H](N(Cc3ccnc(C)c3)Cc3cn(C4CC4)c4cc(N5CCC[C@H](O)C5)c(F)cc4c3=O)C2)cn1] | +++ | +++ |
| 82 | 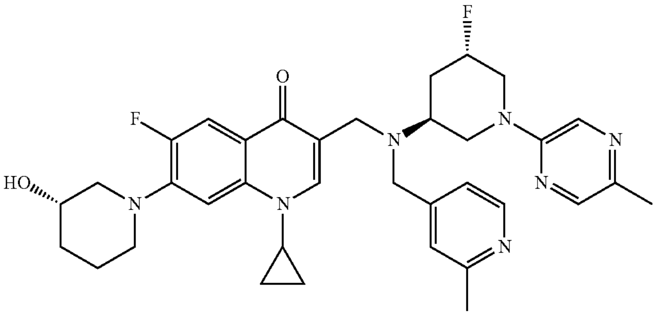 [SMILES: Cc1cnc(N2C[C@@H](F)C[C@H](N(Cc3ccnc(C)c3)Cc3cn(C4CC4)c4cc(N5CCC[C@H](O)C5)c(F)cc4c3=O)C2)cn1] | +++ | +++ |

-continued
| Examples | Structure | THP1 Dual EC50 (μM) IRF | THP1 Dual EC50 (μM) NFkB |
|---|---|---|---|
| 83 | 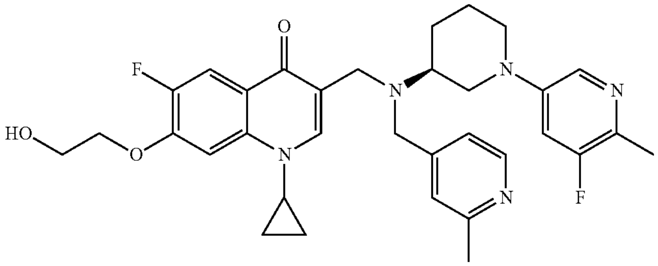 [SMILES: Cc1cc(CN(Cc2cn(C3CC3)c3cc(OCCO)c(F)cc3c2=O)[C@H]2CCCN(c3cnc(C)c(F)c3)C2)ccn1] | +++ | +++ |
| 84 | 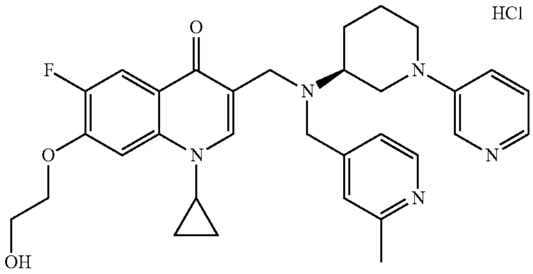 [SMILES: Cc1cc(CN(Cc2cn(C3CC3)c3cc(OCCO)c(F)cc3c2=O)[C@H]2CCCN(c3cccnc3)C2)ccn1 ; Cl] HCl | +++ | +++ |
| 85 | 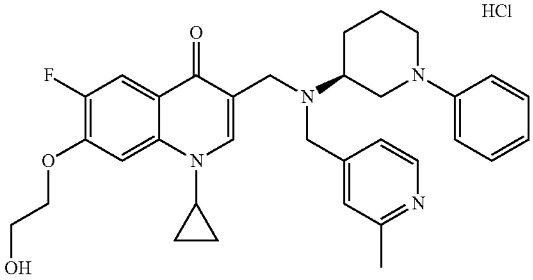 [SMILES: Cl ; Cc1cc(CN(Cc2cn(C3CC3)c3cc(OCCO)c(F)cc3c2=O)[C@H]2CCCN(c3ccccc3)C2)ccn1] HCl | +++ | +++ |
| 86 | 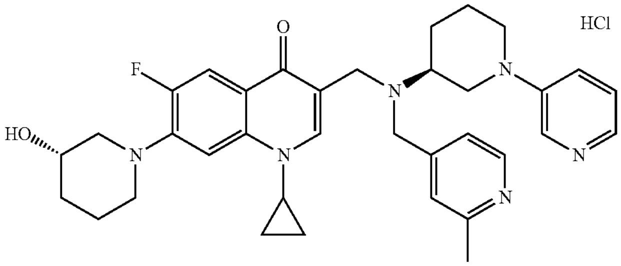 [SMILES: Cc1cc(CN(Cc2cn(C3CC3)c3cc(N4CCC[C@H](O)C4)c(F)cc3c2=O)[C@H]2CCCN(c3cccnc3)C2)ccn1 ; Cl] HCl | +++ | +++ |
| 87 | 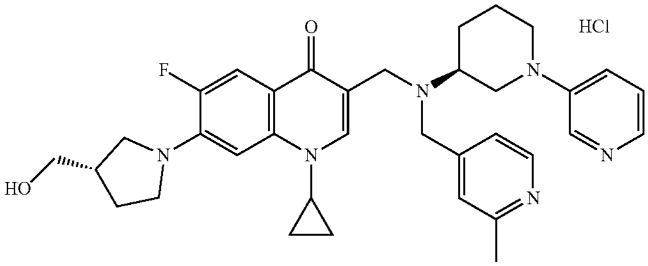 [SMILES: Cc1cc(CN(Cc2cn(C3CC3)c3cc(N4CC[C@H](CO)C4)c(F)cc3c2=O)[C@H]2CCCN(c3cccnc3)C2)ccn1 ; Cl] HCl | +++ | +++ |

-continued
| Exam-ples | Structure | THP1 Dual EC50 (μM) IRF | THP1 Dual EC50 (μM) NFkB |
|---|---|---|---|
| 88 | 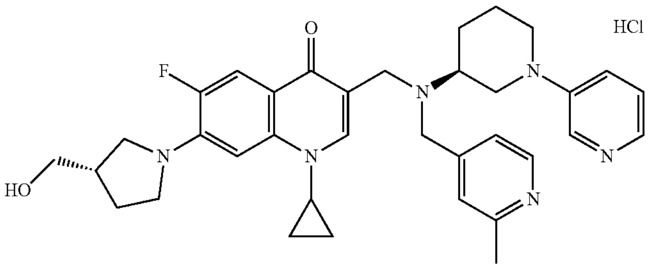 [SMILES: Cc1cc(CN(Cc2cn(C3CC3)c3cc(N4CC[C@H](CO)C4)c(F)cc3c2=O)[C@H]2CCCN(c3cccnc3)C2)ccn1 ; Cl] | +++ | +++ |
| 89 | 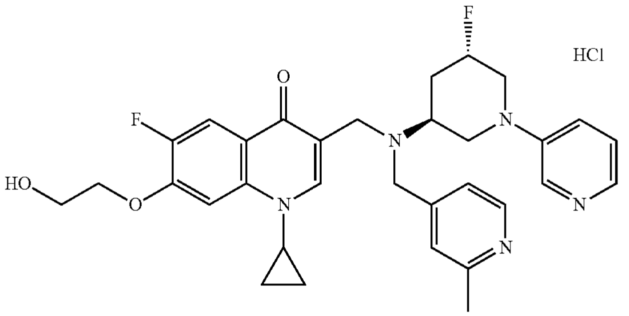 [SMILES: Cc1cc(CN(Cc2cn(C3CC3)c3cc(OCCO)c(F)cc3c2=O)[C@H]2C[C@H](F)CN(c3cccnc3)C2)ccn1 ; Cl] | +++ | +++ |
| 90 | 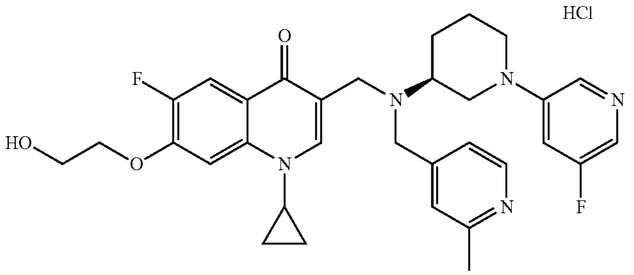 [SMILES: Cl ; Cc1cc(CN(Cc2cn(C3CC3)c3cc(OCCO)c(F)cc3c2=O)[C@H]2CCCN(c3cncc(F)c3)C2)ccn1] | +++ | +++ |
| 91 | 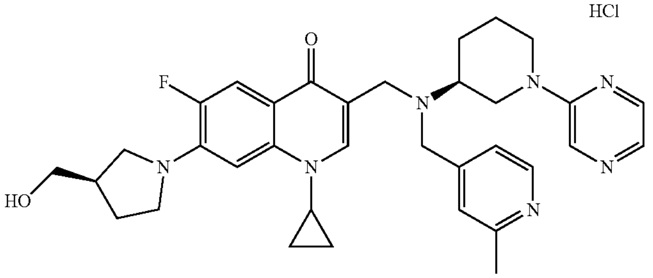 [SMILES: Cl ; Cc1cc(CN(Cc2cn(C3CC3)c3cc(N4CC[C@@H](CO)C4)c(F)cc3c2=O)[C@H]2CCCN(c3cnccn3)C2)ccn1] | +++ | +++ |
| 92 | 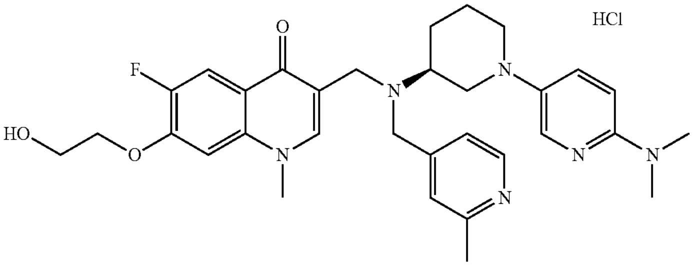 [SMILES: Cc1cc(CN(Cc2cn(C)c3cc(OCCO)c(F)cc3c2=O)[C@H]2CCCN(c3ccc(N(C)C)nc3)C2)ccn1 ; Cl] | +++ | +++ |

-continued
| Examples | Structure | THP1 Dual EC50 (μM) IRF | THP1 Dual EC50 (μM) NFkB |
|---|---|---|---|
| 93 | 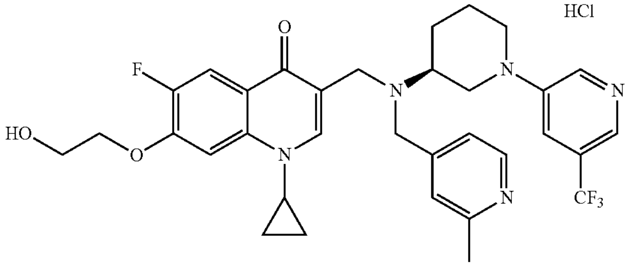 [SMILES: Cc1cc(CN(Cc2cn(C3CC3)c3cc(OCCO)c(F)cc3c2=O)[C@H]2CCCN(c3cncc(C(F)(F)F)c3)C2)ccn1 ; Cl] HCl | +++ | +++ |
| 94 | 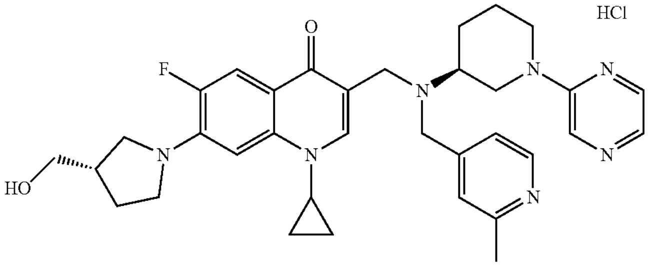 [SMILES: Cc1cc(CN(Cc2cn(C3CC3)c3cc(N4CC[C@H](CO)C4)c(F)cc3c2=O)[C@H]2CCCN(c3cnccn3)C2)ccn1 ; Cl] HCl | +++ | +++ |
| 95 | 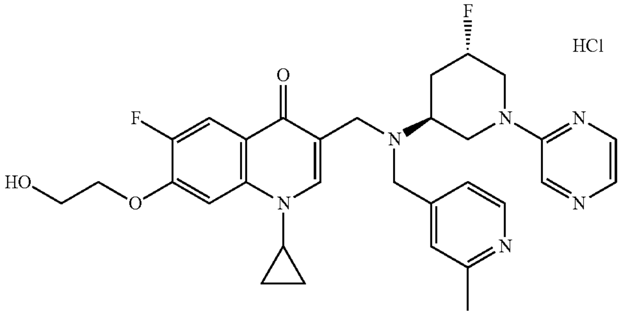 [SMILES: Cc1cc(CN(Cc2cn(C3CC3)c3cc(OCCO)c(F)cc3c2=O)[C@H]2C[C@H](F)CN(c3cnccn3)C2)ccn1 ; Cl] HCl | +++ | +++ |
| 96 | 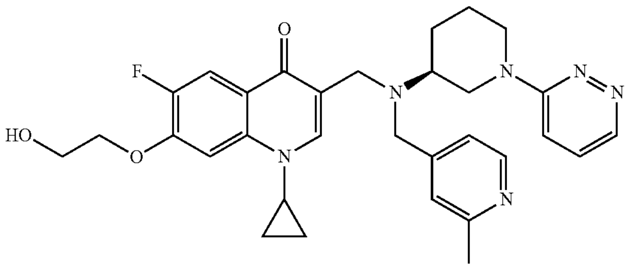 [SMILES: Cc1cc(CN(Cc2cn(C3CC3)c3cc(OCCO)c(F)cc3c2=O)[C@H]2CCCN(c3cccnn3)C2)ccn1] | ++ | + |
| 97 | 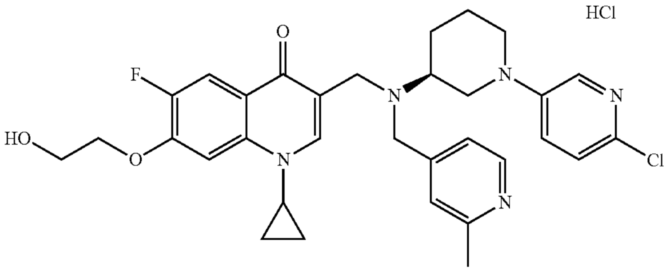 [SMILES: Cc1cc(CN(Cc2cn(C3CC3)c3cc(OCCO)c(F)cc3c2=O)[C@H]2CCCN(c3ccc(Cl)nc3)C2)ccn1 ; Cl] HCl | +++ | +++ |

-continued
| Examples | Structure | THP1 Dual EC50 (μM) IRF | THP1 Dual EC50 (μM) NFkB |
|---|---|---|---|
| 98 | 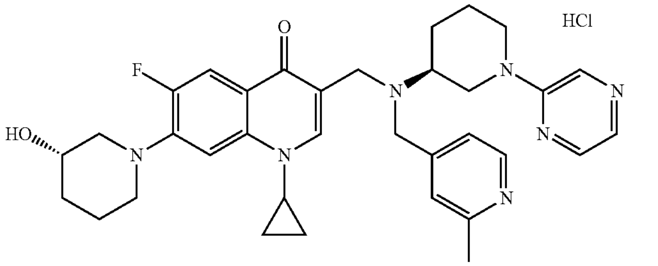 [SMILES: Cc1cc(CN(Cc2cn(C3CC3)c3cc(N4CCC[C@H](O)C4)c(F)cc3c2=O)[C@H]2CCCN(c3cnccn3)C2)ccn1 ; Cl] | +++ | +++ |
| 99 | 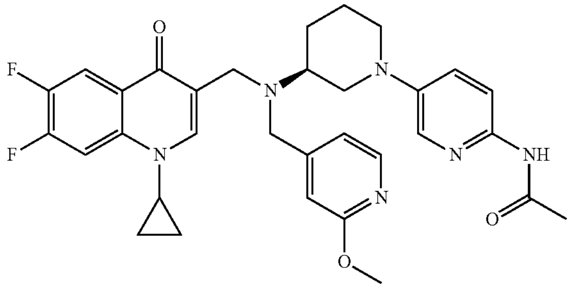 [SMILES: COc1cc(CN(Cc2cn(C3CC3)c3cc(F)c(F)cc3c2=O)[C@H]2CCCN(c3ccc(NC(C)=O)nc3)C2)ccn1] | +++ | +++ |
| 100 | 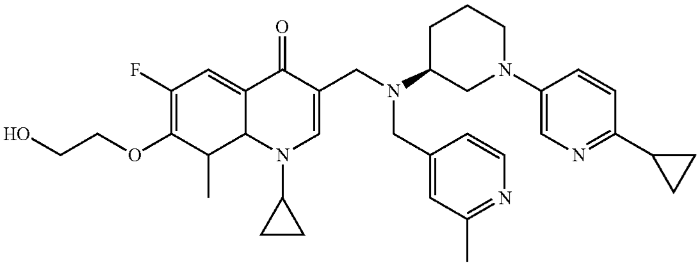 [SMILES: Cc1cc(CN(CC2=CN(C3CC3)C3C(=CC(F)=C(OCCO)C3C)C2=O)[C@H]2CCCN(c3ccc(C4CC4)nc3)C2)ccn1] | +++ | +++ |
| 101 | 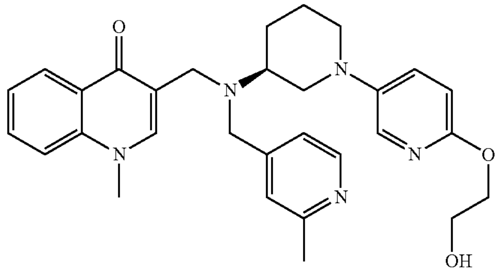 [SMILES: Cc1cc(CN(Cc2cn(C)c3ccccc3c2=O)[C@H]2CCCN(c3ccc(OCCO)nc3)C2)ccn1] | ++ | ++ |
| 102 | 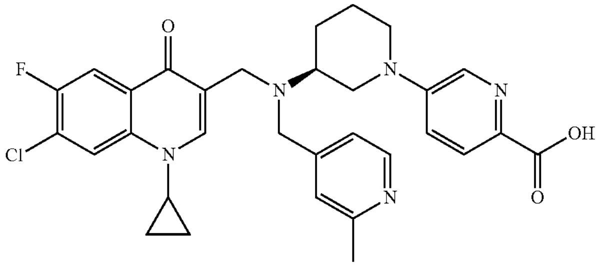 [SMILES: Cc1cc(CN(Cc2cn(C3CC3)c3cc(Cl)c(F)cc3c2=O)[C@H]2CCCN(c3ccc(C(=O)O)nc3)C2)ccn1] | ++ | ++ |

-continued
| Exam-ples | Structure | THP1 Dual EC50 (μM) IRF | THP1 Dual EC50 (μM) NFkB |
|---|---|---|---|
| 103 | 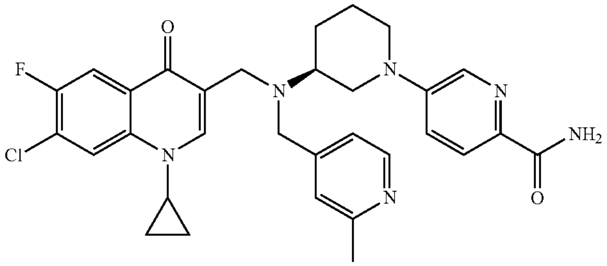 [SMILES: Cc1cc(CN(Cc2cn(C3CC3)c3cc(Cl)c(F)cc3c2=O)[C@H]2CCCN(c3ccc(C(N)=O)nc3)C2)ccn1] | +++ | +++ |
| 15A | 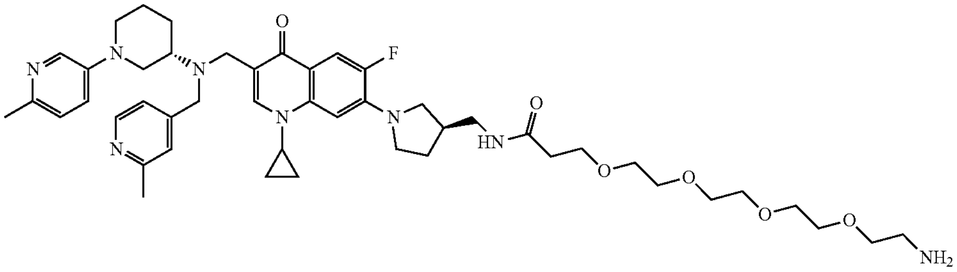 [SMILES: Cc1ccc(N2CCC[C@H](N(Cc3ccnc(C)c3)Cc3cn(C4CC4)c4cc(N5CC[C@H](CNC(=O)CCOCCOCCOCCOCCN)C5)c(F)cc4c3=O)C2)cn1] | ++ | ++ |
| 11A | 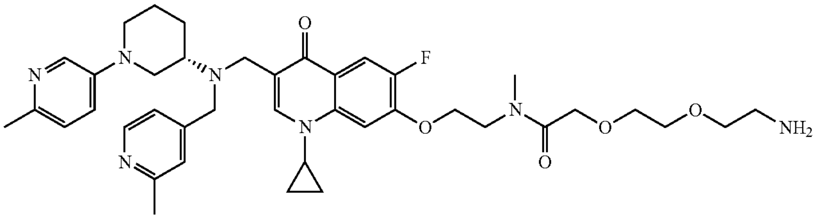 [SMILES: Cc1ccc(N2CCC[C@H](N(Cc3ccnc(C)c3)Cc3cn(C4CC4)c4cc(OCCN(C)C(=O)COCCOCCN)c(F)cc4c3=O)C2)cn1] | ++ | ++ |
| 11B | 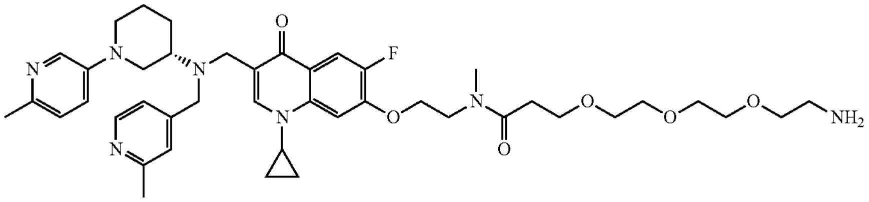 [SMILES: Cc1ccc(N2CCC[C@H](N(Cc3ccnc(C)c3)Cc3cn(C4CC4)c4cc(OCCN(C)C(=O)CCOCCOCCOCCN)c(F)cc4c3=O)C2)cn1] | ++ | ++ |
| 11C | 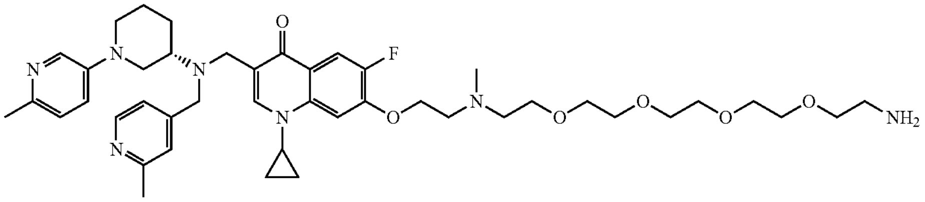 [SMILES: Cc1ccc(N2CCC[C@H](N(Cc3ccnc(C)c3)Cc3cn(C4CC4)c4cc(OCCN(C)CCOCCOCCOCCOCCN)c(F)cc4c3=O)C2)cn1] | ++ | ++ |
| 4A | 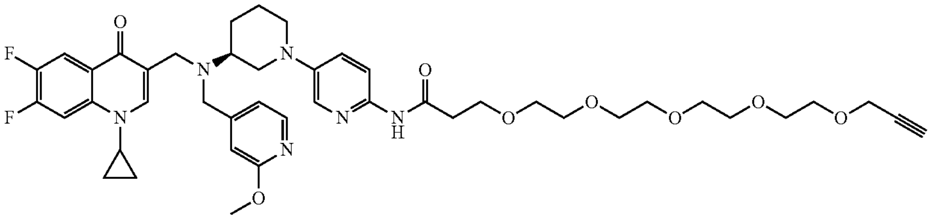 [SMILES: C#CCOCCOCCOCCOCCOCCC(=O)Nc1ccc(N2CCC[C@H](N(Cc3ccnc(OC)c3)Cc3cn(C4CC4)c4cc(F)c(F)cc4c3=O)C2)cn1] | +++ | +++ |

-continued
| Examples | Structure | THP1 Dual EC50 (μM) IRF | THP1 Dual EC50 (μM) NFkB |
|---|---|---|---|
| 55A | 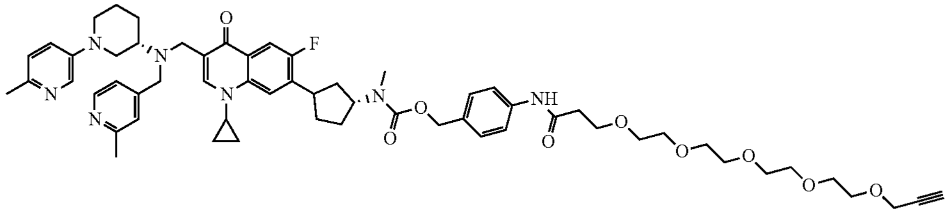 [SMILES: C#CCOCCOCCOCCOCCOCCC(=O)Nc1ccc(COC(=O)N(C)[C@@H]2CCC(c3cc4c(cc3F)c(=O)c(CN(Cc3ccnc(C)c3)[C@H]3CCCN(c5ccc(C)nc5)C3)cn4C3CC3)C2)cc1] | +++ | +++ |
| 11D | 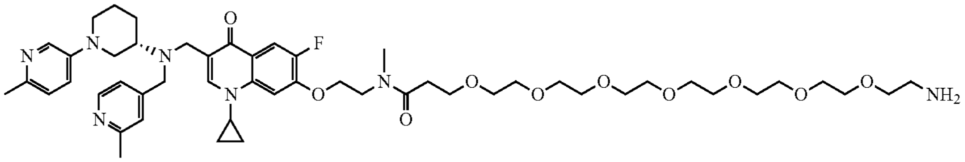 [SMILES: Cc1ccc(N2CCC[C@H](N(Cc3ccnc(C)c3)Cc3cn(C4CC4)c4cc(OCCN(C)C(=O)CCOCCOCCOCCOCCOCCOCCOCCN)c(F)cc4c3=O)C2)cn1] | ++ | ++ |
| 11E | 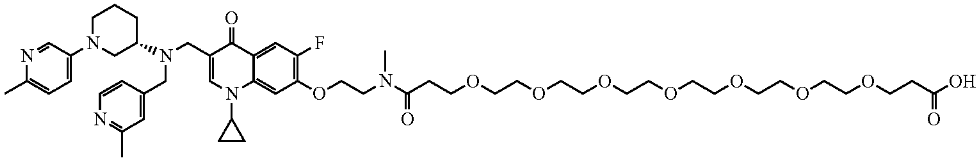 [SMILES: Cc1ccc(N2CCC[C@H](N(Cc3ccnc(C)c3)Cc3cn(C4CC4)c4cc(OCCN(C)C(=O)CCOCCOCCOCCOCCOCCOCCOCCC(=O)O)c(F)cc4c3=O)C2)cn1] | ++ | ++ |
| 11F | 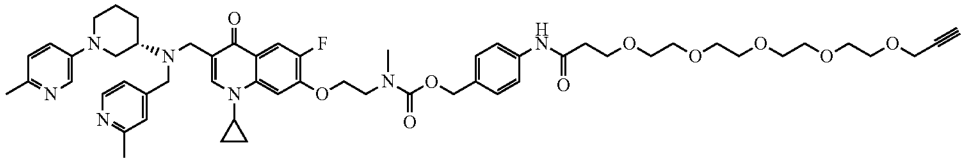 [SMILES: C#CCOCCOCCOCCOCCOCCC(=O)Nc1ccc(COC(=O)N(C)CCOc2cc3c(cc2F)c(=O)c(CN(Cc2ccnc(C)c2)[C@H]2CCCN(c4ccc(C)nc4)C2)cn3C2CC2)cc1] | +++ | +++ |
| 11G | HCOOH 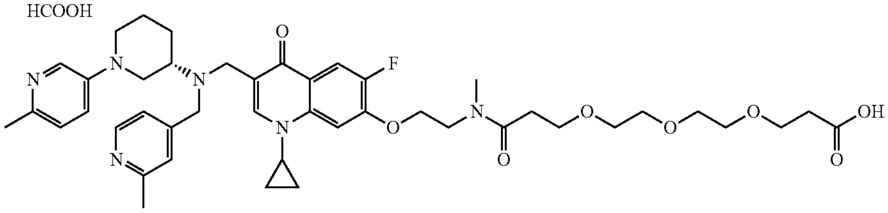 [SMILES: "HCOOH" ; Cc1ccc(N2CCC[C@H](N(Cc3ccnc(C)c3)Cc3cn(C4CC4)c4cc(OCCN(C)C(=O)CCOCCOCCOCCC(=O)O)c(F)cc4c3=O)C2)cn1] | ++ | ++ |
| 55B | 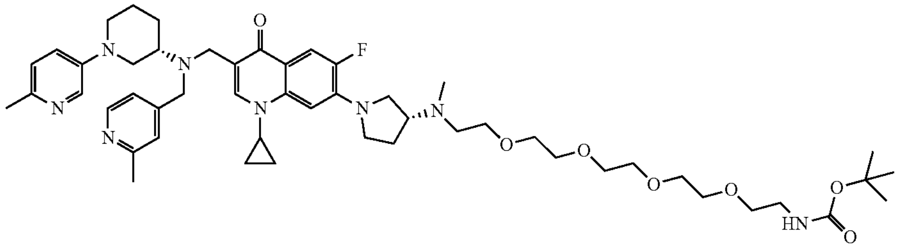 [SMILES: Cc1ccc(N2CCC[C@H](N(Cc3ccnc(C)c3)Cc3cn(C4CC4)c4cc(N5CC[C@@H](N(C)CCOCCOCCOCCOCCNC(=O)OC(C)(C)C)C5)c(F)cc4c3=O)C2)cn1] | +++ | +++ |
| 58A | 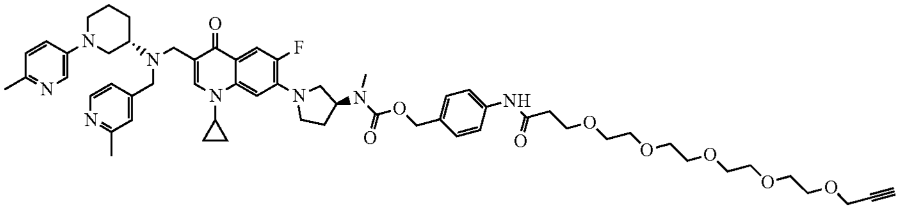 [SMILES: C#CCOCCOCCOCCOCCOCCC(=O)Nc1ccc(COC(=O)N(C)[C@H]2CCN(c3cc4c(cc3F)c(=O)c(CN(Cc3ccnc(C)c3)[C@H]3CCCN(c5ccc(C)nc5)C3)cn4C3CC3)C2)cc1] | +++ | +++ |

-continued
| Examples | Structure | THP1 Dual EC50 (μM) IRF | THP1 Dual EC50 (μM) NFkB |
|---|---|---|---|
| 55C | 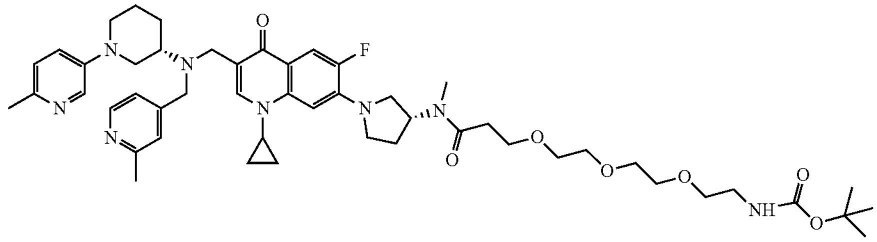 [SMILES: Cc1ccc(N2CCC[C@H](N(Cc3ccnc(C)c3)Cc3cn(C4CC4)c4cc(N5CC[C@@H](N(C)C(=O)CCOCCOCCOCCNC(=O)OC(C)(C)C)C5)c(F)cc4c3=O)C2)cn1] | +++ | +++ |
| 55D | HCOOH 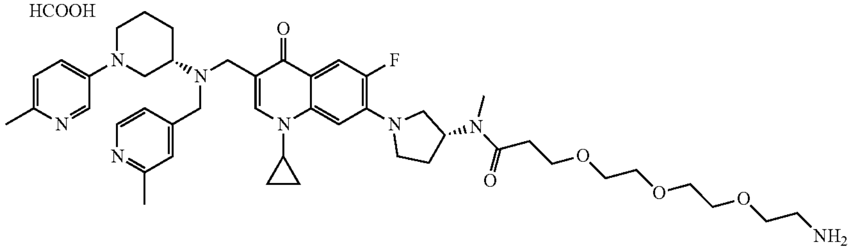 [SMILES: "HCOOH" ; Cc1ccc(N2CCC[C@H](N(Cc3ccnc(C)c3)Cc3cn(C4CC4)c4cc(N5CC[C@@H](N(C)C(=O)CCOCCOCCOCCN)C5)c(F)cc4c3=O)C2)cn1] | ++ | ++ |
| 11H | 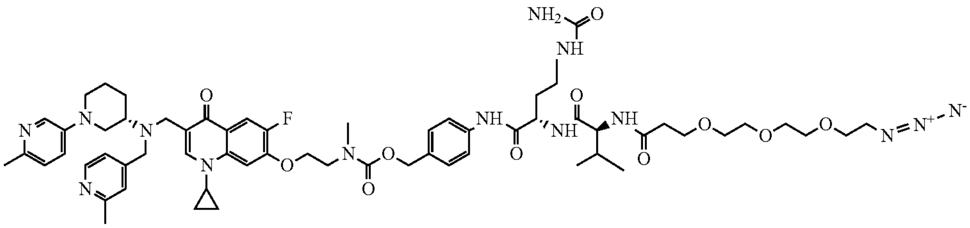 [SMILES: Cc1ccc(N2CCC[C@H](N(Cc3ccnc(C)c3)Cc3cn(C4CC4)c4cc(OCCN(C)C(=O)OCc5ccc(NC(=O)[C@H](CCCNC(N)=O)NC(=O)[C@@H](NC(=O)CCOCCOCCOCC/N=[NH+]\[NH-])C(C)C)cc5)c(F)cc4c3=O)C2)cn1] | + | + |
| 12A | 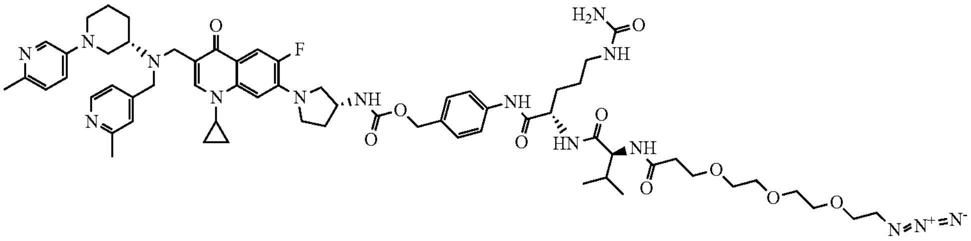 [SMILES: Cc1ccc(N2CCC[C@H](N(Cc3ccnc(C)c3)Cc3cn(C4CC4)c4cc(N5CC[C@@H](NC(=O)OCc6ccc(NC(=O)[C@H](CCCNC(N)=O)NC(=O)[C@@H](NC(=O)CCOCCOCCOCCN=[N+]=[N-])C(C)C)cc6)C5)c(F)cc4c3=O)C2)cn1] | ++ | + |
| 31A | 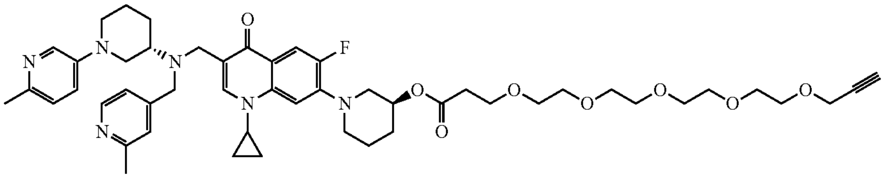 [SMILES: C#CCOCCOCCOCCOCCOCCC(=O)O[C@H]1CCCN(c2cc3c(cc2F)c(=O)c(CN(Cc2ccnc(C)c2)[C@H]2CCCN(c4ccc(C)nc4)C2)cn3C2CC2)C1] | +++ | +++ |
| 47A | 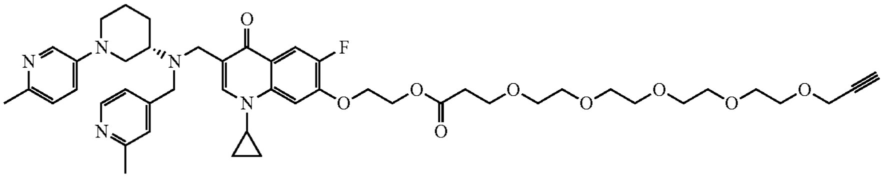 [SMILES: C#CCOCCOCCOCCOCCOCCC(=O)OCCOc1cc2c(cc1F)c(=O)c(CN(Cc1ccnc(C)c1)[C@H]1CCCN(c3ccc(C)nc3)C1)cn2C1CC1] | +++ | +++ |

-continued
| Examples | Structure | THP1 Dual EC50 (μM) IRF | THP1 Dual EC50 (μM) NFkB |
|---|---|---|---|
| 47B | 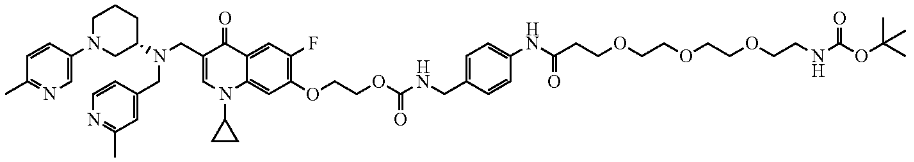 [SMILES: Cc1ccc(N2CCC[C@H](N(Cc3ccnc(C)c3)Cc3cn(C4CC4)c4cc(OCCOC(=O)NCc5ccc(NC(=O)CCOCCOCCOCCNC(=O)OC(C)(C)C)cc5)c(F)cc4c3=O)C2)cn1] | +++ | +++ |
| 68A | 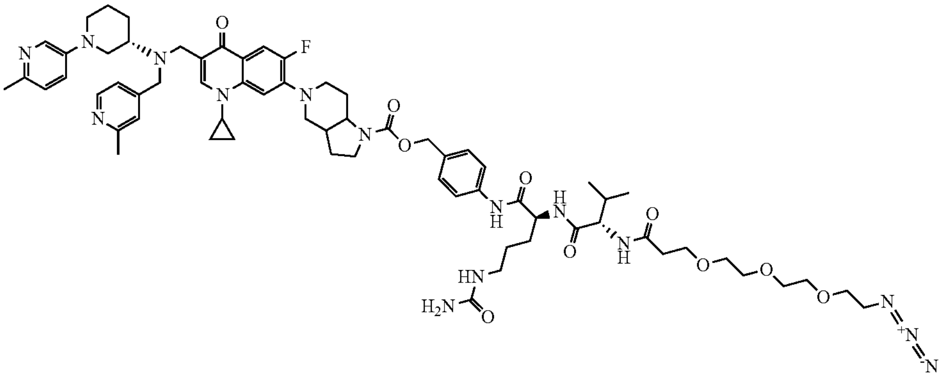 | ++ | + |
| 19A | 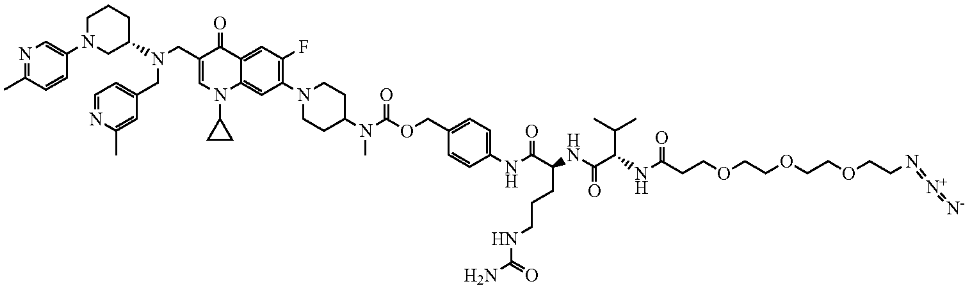 [SMILES: Cc1ccc(N2CCC[C@H](N(Cc3ccnc(C)c3)Cc3cn(C4CC4)c4cc(N5CCC(N(C)C(=O)OCc6ccc(NC(=O)[C@H](CCCNC(N)=O)NC(=O)[C@@H](NC(=O)CCOCCOCCOCCN=[N+]=[N-])C(C)C)cc6)CC5)c(F)cc4c3=O)C2)cn1] | ++ | ++ |
| 10A | 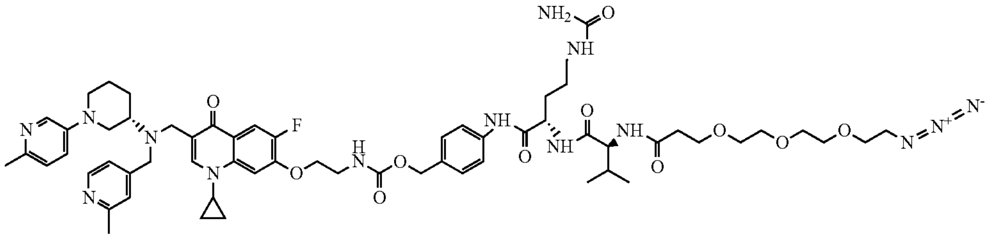 [SMILES: Cc1ccc(N2CCC[C@H](N(Cc3ccnc(C)c3)Cc3cn(C4CC4)c4cc(OCCNC(=O)OCc5ccc(NC(=O)[C@H](CCCNC(N)=O)NC(=O)[C@@H](NC(=O)CCOCCOCCOCCN=[N+]=[N-])C(C)C)cc5)c(F)cc4c3=O)C2)cn1] | + | + |
| 31B | 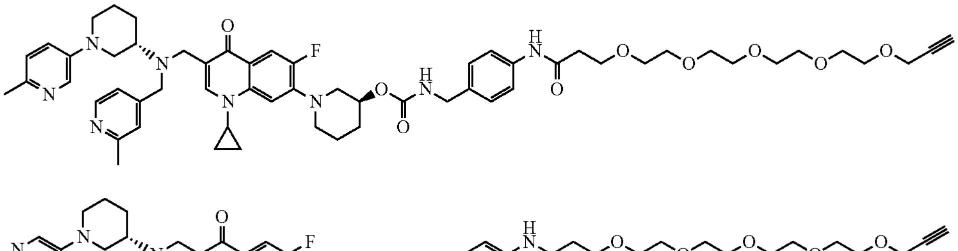 | +++ | +++ |
| 84A | 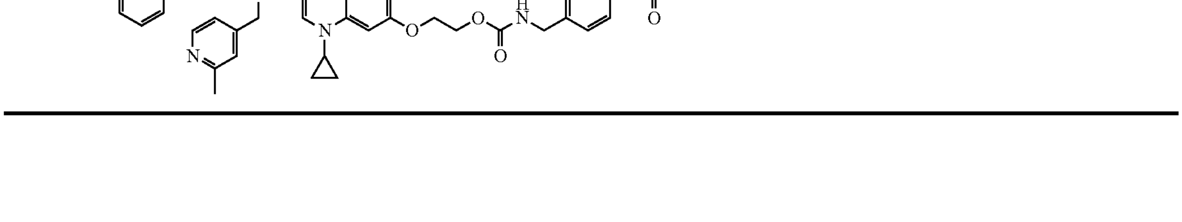 | +++ | +++ |

In Vivo Anti-Tumor Efficacy

Figure 1B:
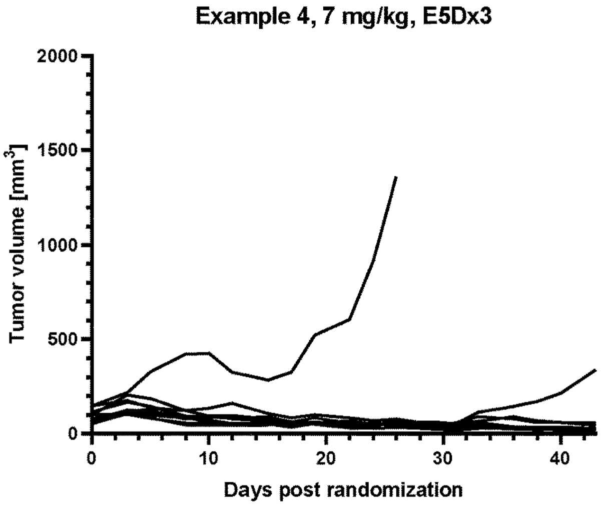
Figure 1C:
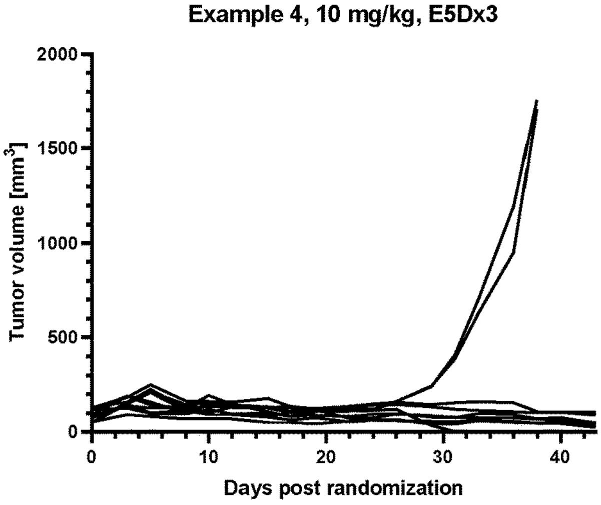
Figure 2A:
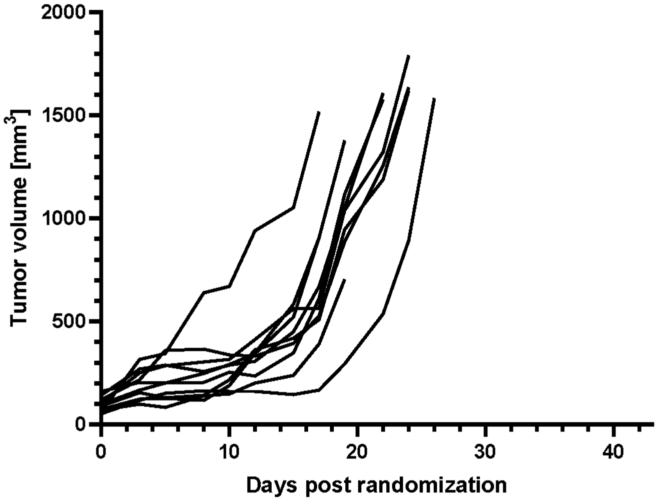
FIG. 2A-FIG. 2C show the efficacy of Example 31 in CT26 murine colon carcinoma allograft in Balb/C female mice.
Figure 2B:
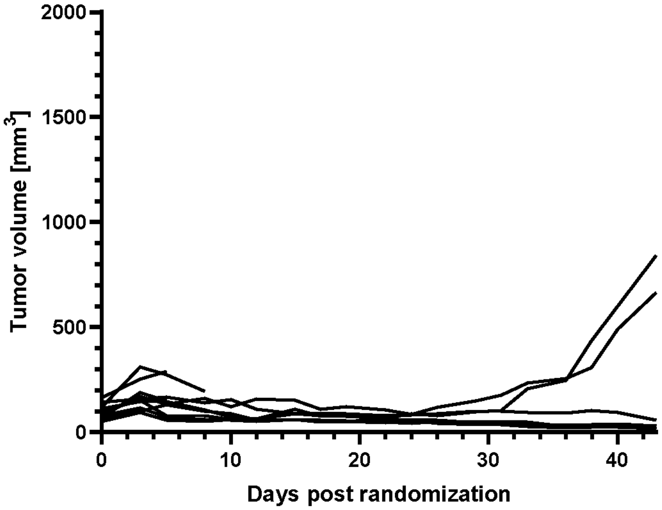
Figure 2C:
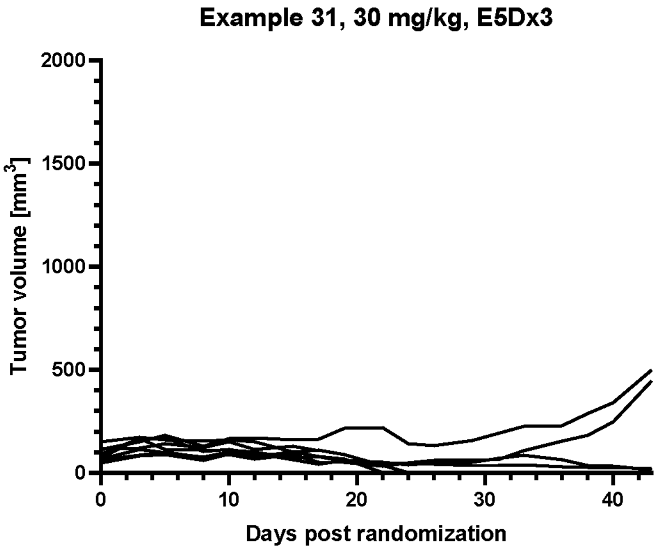
Figure 3A:
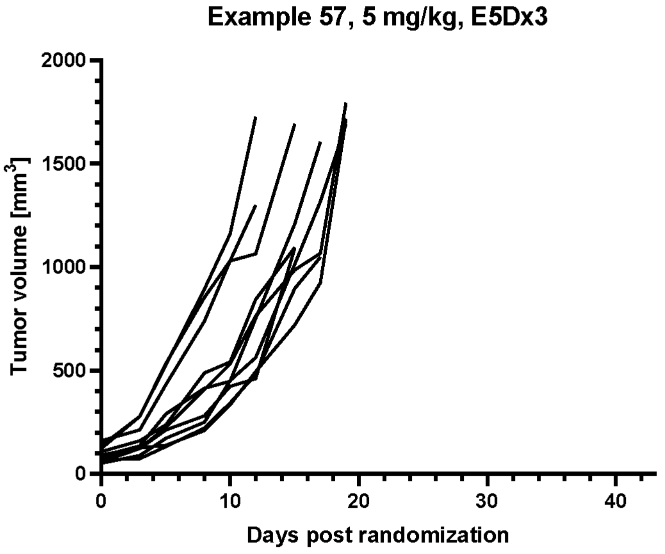
FIG. 3A-FIG. 3C show the efficacy of Example 57 in CT26 murine colon carcinoma allograft in Balb/C female mice.
Figure 3B:
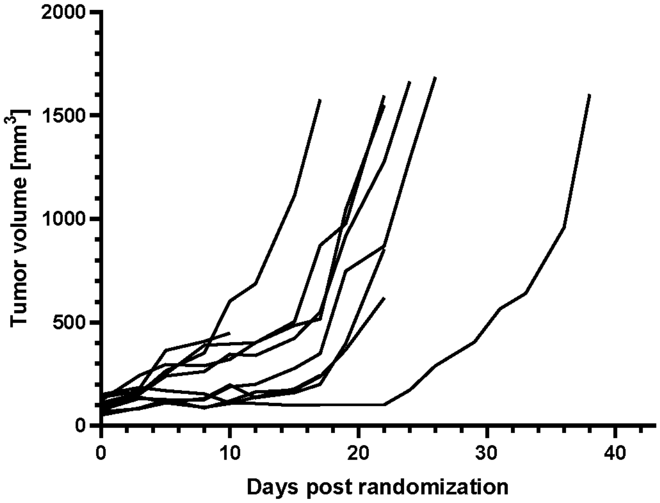
Figure 3C:
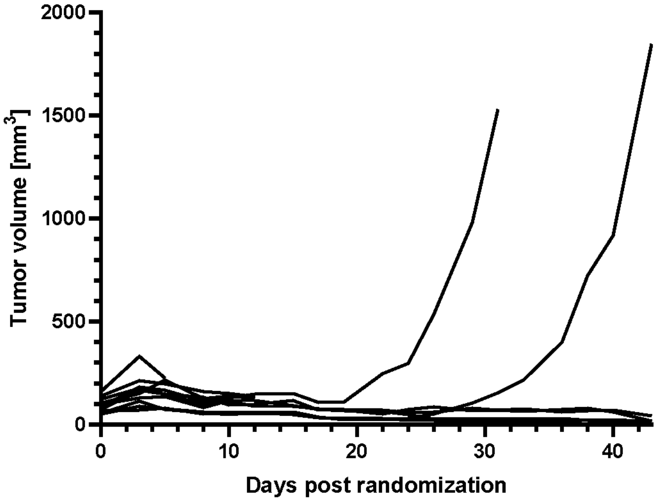

The efficacy of Example 4, Example 31 and Example 57 was evaluated in established CT26 murine colon carcinoma allografts in female Balb/C mice. Compounds were formulated in 5% ethanol with 10% Captisol in PBS and administered intravenously, once every fifth day on three occasions. The solution was prepared fresh prior to each administration. CT26 tumors responded prominently to the treatment with Example 4, Example 31 and Example 57. Both dose levels of Example 4, 7 and 10 mg/kg, were efficacious and caused tumor growth delay or significant decrease of the tumor size compared to the control group or day volume at randomization, respectively (FIG. 1A-FIG. 1C). By the end of the study there was one complete response among animals treated at 10 mg/kg of Example 4. Treatment with Example 31 resulted in slight tumor growth delay when treated at 7 mg/kg when compared to the control group (FIG. 2A-FIG. 2C). Both 15 mg/kg and 30 mg/kg of Example 31 were prominently efficacious, and treatment with the higher dose resulted in two complete responses by the end of the study on day 43. CT26 tumors responded to treatment with Example 57 in a dose dependent manner with moderately efficacious dose at 10 mg/kg and full efficacious dose at 20 mg/kg (FIG. 3A-FIG. 3C). In the group treated at 5 mg/kg only a minimal tumor growth delay was observed when compared to the control group. By the end of the study, on day 43, there was one complete response recorded in group treated at 20 mg/kg of Example 57.

In particular, the present invention relates to the following items:

1. A compound-linker construct comprising
(i) a compound of formula (I); and
(ii) a linker $L^1$
wherein the compound of formula (I) is a compound of the following formula (I)

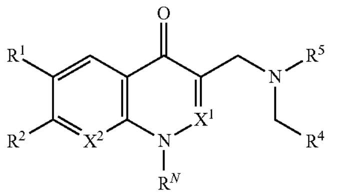

or a salt, stereoisomer, tautomer, or N-oxide thereof, wherein $X^1$ is CH or N;

$X^2$ is $CR^3$ or N;

$R^1$, $R^2$ and $R^3$ are independently H, OH, $NR^CR^D$, CN, halogen, $C_1$-$C_4$-alkyl, $NR^CR^D$—$C_1$-$C_4$-alkyl, $C_1$-$C_4$-alkoxy, aryloxy, benzyloxy, C(═O)$R^E$, $NR^F$C(═O)$R^E$, $NR^F$—($C_1$-$C_4$-alkylene) C(═O)$R^E$, $NR^F$—($C_1$-$C_4$-alkylene)-$NR^CR^D$, O—($C_1$-$C_4$-alkylene)-$NR^CR^D$, or 4- to 6-membered saturated, partially or fully unsaturated, or aromatic carbocyclyl, carbocyclyl-$C_1$-$C_2$-alkyl, heterocyclyl, heterocyclyloxy, or heterocyclyl-$C_1$-$C_2$-alkyl, or 8- to 10-membered saturated, partially or fully unsaturated, or aromatic carbobicyclyl or heterobicyclyl, wherein the aforementioned heterocyclic or heterobicyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents $R^X$;

$R^5$ is a 5- or 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents $R^Y$;

and wherein $R^N$ is H, $C_1$-$C_4$-alkyl, HO(C═O)—$C_1$-$C_4$-alkyl, $NR^CR^D$—$C_1$-$C_4$-alkyl, $C_1$-$C_2$-alkoxy-$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, $NR^CR^D$—$C_1$-$C_4$-alkyl, phenyl, benzyl, $OR^G$, or $NR^HR^I$; or a 5- or 6-membered saturated, partially or fully unsaturated heterocyclyl, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^F$;

$R^F$ is H, $C_1$-$C_2$-alkyl, $C_3$-$C_6$-cycloalkyl, phenyl, benzyl, or C(═O)$NR^HR^I$;

$R^G$ is H, $C_1$-$C_2$-alkyl, or 5- or 6-membered aromatic carbocyclyl, carbocyclyl-$C_1$-$C_2$alkyl, heterocyclyl, or heterocyclyl-$C_1$-$C_2$alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is OH, $NR^CR^D$, halogen, CN, $NO_2$, $C_1$-$C_2$-alkyl, $C_1$-$C_2$haloalkyl, $NR^CR^D$—$C_1$-$C_4$-alkyl, $R^CO$—$C_1$-$C_4$-alkyl, $C_1$-$C_2$alkoxy, C(═O)$R^E$, or two $R^X$ form ═O, or two $R^X$ together with the carbon atom to which they are bonded form a 3- to 5-membered saturated, partially or fully unsaturated, or aromatic carbocyclic ring;

$R^Y$ is halogen, CN, OH, $C_1$-$C_2$-alkyl, HO—$C_1$-$C_2$alkyl, $C_3$-$C_6$-cycloalkyl, $C_1$-$C_2$-alkoxy, $NR^CR^D$, S(═O)$_2$ $NR^CR^D$, C(═O)$R^E$, or 5- or 6-membered saturated, partially or fully unsaturated, or aromatic carbocyclyl, carbocyclyl-$C_1$-$C_2$alkyl, heterocyclyl, and heterocyclyl-$C_1$-$C_2$alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form ═O; or two $R^Y$ attached to identical or neighboring carbon atoms may form a 3-membered carbocyclic ring;

with the proviso that either any one of $R^1$, $R^2$, or $R^3$ is $NR^CR^D$, $NR^CR^D$—$C_1$-$C_4$-alkyl, $NR^F$—($C_1$-$C_4$-alkylene)-$NR^CR^D$, O—($C_1$-$C_4$-alkylene)-$NR^CR^D$, or 8- to 10-membered saturated, partially or fully unsaturated, or aromatic carbobicyclyl or heterobicyclyl, wherein the aforementioned heterobicyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or any one of $R^1$, $R^2$, or $R^3$ is $NR^F$C(═O)$R^E$, wherein $R^E$ is $NR^CR^D$—$C_1$-$C_4$-alkyl;

or $R^N$ is $NR^CR^D$—$C_1$-$C_4$-alkyl, or $C_1$-$C_2$-alkoxy-$C_1$-$C_4$-alkyl;

or any one of the substituents $R^1$, $R^2$, $R^3$, $R^4$, $R^5$, $R^N$ carries a substituent $R^X$, wherein $R^X$ is OH, $NR^CR^D$, $NR^CR^D$—$C_1$-$C_4$-alkyl, or $R^CO$—$C_1$-$C_4$-alkyl.

2. The compound-linker construct according to item 1, wherein a covalent bond between the compound of formula (I) and the linker $L^1$ is established by the reaction of a functional group of the compound of formula (I) with a functional group handle of the linker $L^1$; and wherein preferably the functional group of the compound of formula (I) is attached to or part of the substituents $R^2$, $R^4$, $R^5$, or $R^N$ so that the linker $L^1$ will be covalently bonded to the compound of formula (I) according to any one of the following structures:

(I-$R^2$-$L^1$)

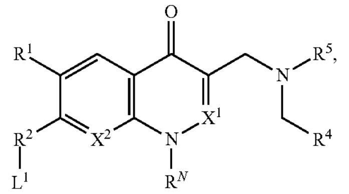

(I-$R^N$-$L^1$)

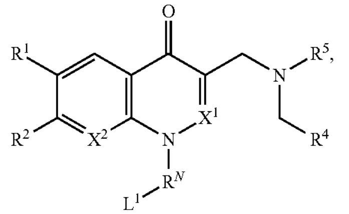

(I-$R^4$-$L^1$)

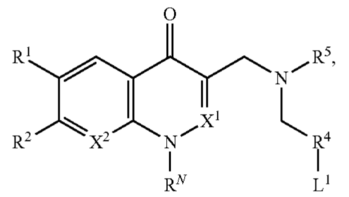

(I-$R^5$-$L^1$)

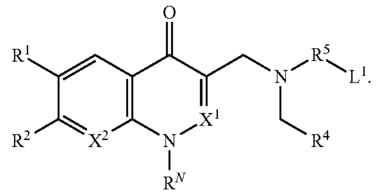

3. The compound-linker construct according to item 1 or 2, wherein the linker $L^1$ comprises (i) a chain $L^C$ of 2 to 100 atoms selected from carbon, nitrogen, oxygen, and sulfur atoms, which may be interrupted by 5- to 10-membered aryl and heteroaryl groups and/or 3- to 8-membered saturated carbocyclyl or heterocyclyl groups, wherein the aforementioned heteroaryl and heterocyclic groups comprise one or more, same or different heteroatoms selected from O, N or S, wherein said N- and/or S-atoms are independently oxidized or non-oxidized, and wherein each substitutable carbon or heteroatom in the chain is independently unsubstituted or substituted with one or more same or different substituents selected from halogen, OH, ═O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

and preferably a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, ═O, $C_1$-$C_5$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$haloalkoxy;

(ii) a functional group handle $H^{1A}$, which is covalently bonded to the compound of formula (I);

(iii) a functional group handle $H^{1B}$ suitable for forming a covalent bond to a targeting moiety T.

4. The compound-linker construct according to any one of items 1 to 3, wherein the linker $L^1$ has the structure $H^{1A}$-$L^C$-$H^{1B}$ and is selected from the group consisting of:

($L^1$-1)

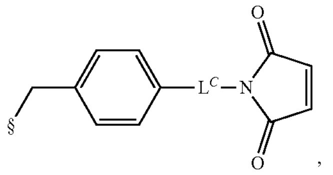

, ($L^1$-2)

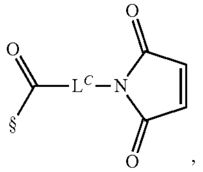

, ($L^1$-3)

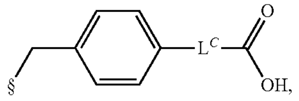

($L^1$-4)

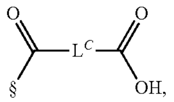

($L^1$-5)

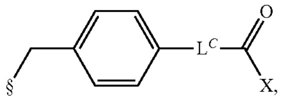

and

-continued ($L^1$-6)

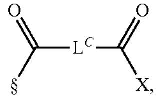

wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_2$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy; and § marks the connection to the compound of formula (I); and X represents a leaving group selected from (X-1)

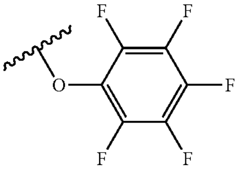

and (X-2)

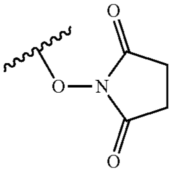

and wherein preferably LC is selected from the group consisting of ($L^C$-1)

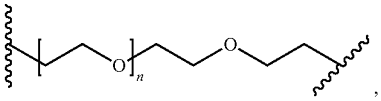

, ($L^C$-2)

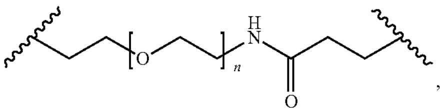

, ($L^C$-3)

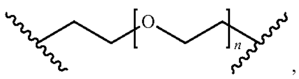

, ($L^C$-4)

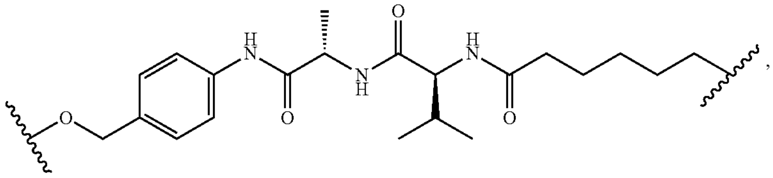

,

-continued
(L^C-5)
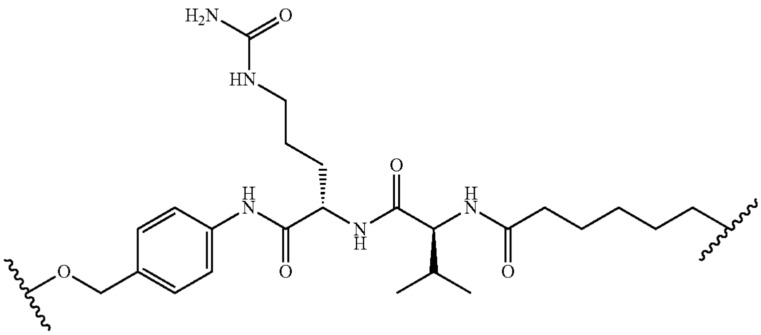
,
(L^C-6)
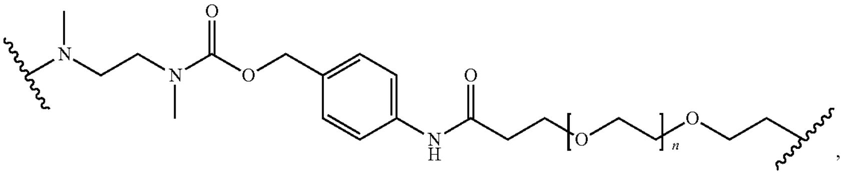
,
(L^C-7)
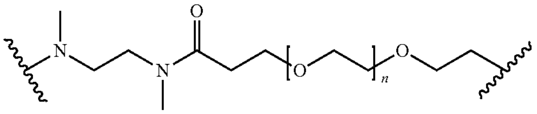
,
(L^C-8)
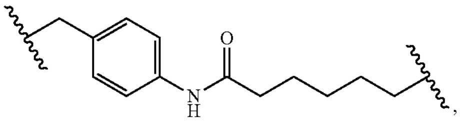
, and
(L^C-9)
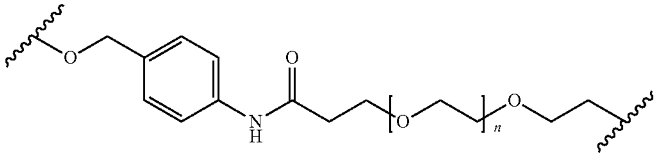
.
5. The compound-linker construct according to any one of items 1 to 4, wherein the linker $L^1$ is selected from the group consisting of:
($L^1$-a)
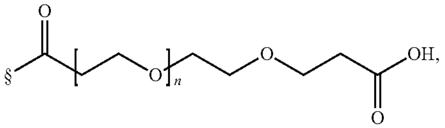
($L^1$-b)
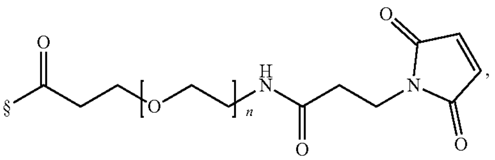
,
($L^1$-c)
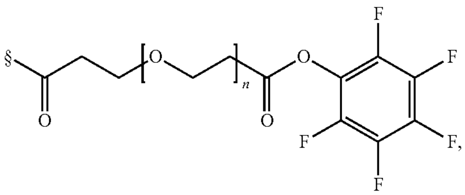
($L^1$-d)
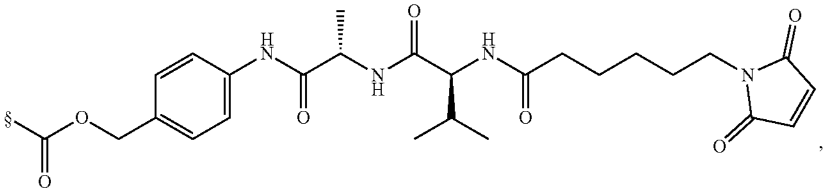
, -continued
(L1-e)
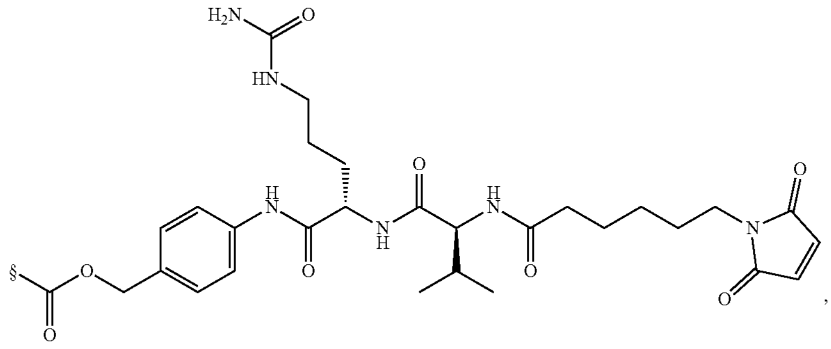
,
(L1-f)
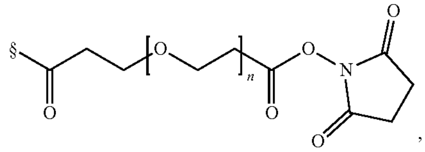
,
(L1-g)
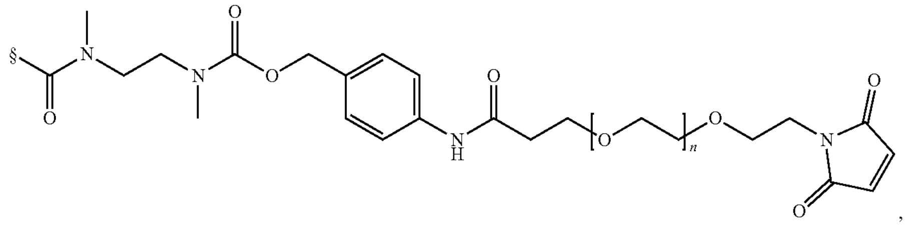
,
(L1-h)
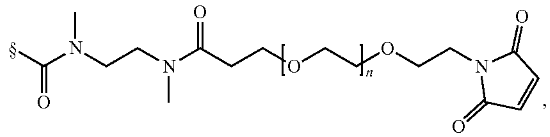
,
(L1-i)
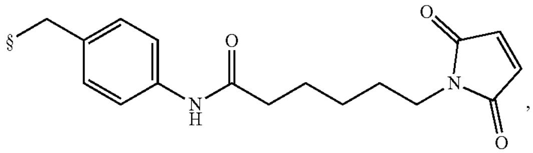
,
(L1-j)
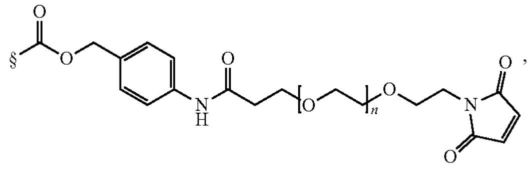
, and
(L1-k)
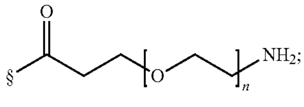
;

wherein

§ marks the connection to the compound of formula (I).

6. A conjugate comprising (i) a compound of formula (I);

(ii) a linker $L^2$; and (iii) a targeting moiety T wherein the compound of formula I is a compound of the following formula (I)

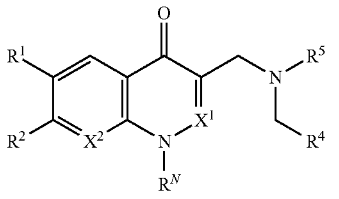

or a salt, stereoisomer, tautomer, or N-oxide thereof, wherein $X^1$ is CH or N;

$X^2$ is $CR^3$ or N;

$R^1$, $R^2$ and $R^3$ are independently H, OH, $NR^CR^D$, CN, halogen, $C_1$-$C_4$-alkyl, $NR^CR^D$—$C_1$-$C_4$-alkyl, $C_1$-$C_4$-alkoxy, aryloxy, benzyloxy, C(═O)$R^E$, $NR^F$C(═O)$R^E$, $NR^F$—($C_1$-$C_4$-alkylene) C(═O)$R^E$, $NR^F$—($C_1$-$C_4$-alkylene)-$NR^CR^D$, O—($C_1$-$C_4$-alkylene)-$NR^CR^D$, or 4- to 6-membered saturated, partially or fully unsaturated, or aromatic carbocyclyl, carbocyclyl-$C_1$-$C_2$-alkyl, heterocyclyl, heterocyclyloxy, or heterocyclyl-$C_1$-$C_2$-alkyl, or 8- to 10-membered saturated, partially or fully unsaturated, or aromatic carbobicyclyl or heterobicyclyl, wherein the aforementioned heterocyclic or heterobicyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents $R^X$;

$R^5$ is a 5- or 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents $R^Y$;

and wherein $R^N$ is H, $C_1$-$C_4$-alkyl, HO(C═O)—$C_1$-$C_4$-alkyl, $NR^CR^D$—$C_1$-$C_4$-alkyl, $C_1$-$C_2$-alkoxy-$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, $NR^CR^D$—$C_1$-$C_4$-alkyl, phenyl, benzyl, $OR^G$, or $NR^HR^I$; or a 5- or 6-membered saturated, partially or fully unsaturated heterocyclyl, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^F$;

$R^F$ is H, $C_1$-$C_2$-alkyl, $C_3$-$C_6$-cycloalkyl, phenyl, benzyl, or C(═O)$NR^HR^I$;

$R^G$ is H, $C_1$-$C_2$-alkyl, or 5- or 6-membered aromatic carbocyclyl, carbocyclyl-$C_1$-$C_2$alkyl, heterocyclyl, or heterocyclyl-$C_1$-$C_2$alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is OH, $NR^CR^D$, halogen, CN, $NO_2$, $C_1$-$C_2$-alkyl, $C_1$-$C_2$haloalkyl, $NR^CR^D$—$C_1$-$C_4$-alkyl, $R^C$O—$C_1$-$C_4$-alkyl, $C_1$-$C_2$-alkoxy, C(═O)$R^E$, or two $R^X$ form ═O, or two $R^X$ together with the carbon atom to which they are bonded form a 3- to 5-membered saturated, partially or fully unsaturated, or aromatic carbocyclic ring;

$R^Y$ is halogen, CN, OH, $C_1$-$C_2$-alkyl, HO—$C_1$-$C_2$-alkyl, $C_3$-$C_6$-cycloalkyl, $C_1$-$C_2$-alkoxy, $NR^CR^D$, S(═O)$_2$ $NR^CR^D$, C(═O)$R^E$, or 5- or 6-membered saturated, partially or fully unsaturated, or aromatic carbocyclyl, carbocyclyl-$C_1$-$C_2$-alkyl, heterocyclyl, and heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form ═O; or two $R^Y$ attached to identical or neighboring carbon atoms may form a 3-membered carbocyclic ring;

with the proviso that either any one of $R^1$, $R^2$, or $R^3$ is $NR^CR^D$, $NR^CR^D$—$C_1$-$C_4$-alkyl, $NR^F$—($C_1$-$C_4$-alkylene)-$NR^CR^D$, O—($C_1$-$C_4$-alkylene)-$NR^CR^D$, or 8- to 10-membered saturated, partially or fully unsaturated, or aromatic carbobicyclyl or heterobicyclyl, wherein the aforementioned heterobicyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or any one of $R^1$, $R^2$, or $R^3$ is $NR^FC$(═O)$R^E$, wherein $R^E$ is $NR^CR^D$—$C_1$-$C_4$-alkyl;

or $R^N$ is $NR^CR^D$—$C_1$-$C_4$-alkyl, or $C_1$-$C_2$-alkoxy-$C_1$-$C_4$-alkyl;

or any one of the substituents $R^1$, $R^2$, $R^3$, $R^4$, $R^5$, $R^N$ carries a substituent $R^X$, wherein $R^X$ is OH, $NR^CR^D$, $NR^CR^D$—$C_1$-$C_4$-alkyl, or $R^CO$—$C_1$-$C_4$-alkyl.

7. The conjugate according to item 6, wherein a covalent bond between the compound of formula (I) and the linker $L^2$ is established by the reaction of a functional group of the compound of formula (I) with a functional group handle of the linker $L^2$ and wherein a covalent bond between the targeting moiety T and the linker $L^2$ is established by the reaction of a functional group of the targeting moiety T with a functional group handle of the linker $L^2$; and wherein preferably the functional group of the compound of formula (I) is attached to or part of the substituents $R^2$, $R^4$, $R^5$, or $R^N$ so that the linker $L^2$, to which the targeting moiety is covalently bonded on one end, will on the other end be covalently bonded to the compound of formula (I) according to any one of the following structures:

(I-$R^2$-$L^2$-T)

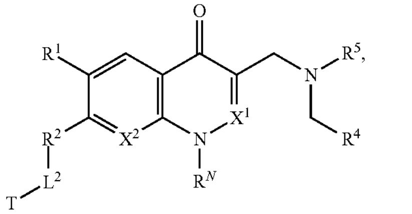

-continued (I-$R^N$-$L^2$-T)

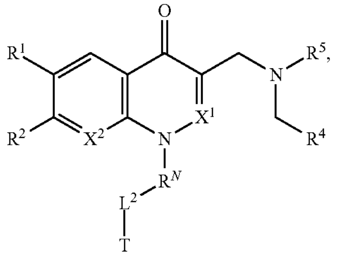

(I-$R^4$-$L^2$-T)

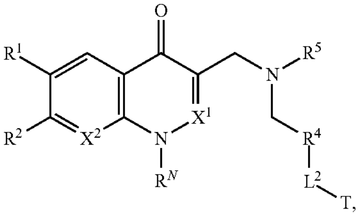

(I-$R^5$-$L^2$-T)

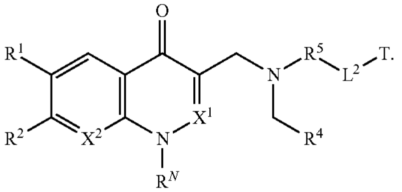

8. The conjugate according to item 6 or 7, wherein the linker $L^2$ Comprises (i) a chain $L^C$ of 2 to 100 atoms selected from carbon, nitrogen, oxygen, and sulfur atoms, which may be interrupted by 5- to 10-membered aryl and heteroaryl groups and/or 3- to 8-membered saturated carbocyclyl or heterocyclyl groups, wherein the aforementioned heteroaryl and heterocyclic groups comprise one or more, same or different heteroatoms selected from O, N or S, wherein said N- and/or S-atoms are independently oxidized or non-oxidized, and wherein each substitutable carbon or heteroatom in the chain is independently unsubstituted or substituted with one or more same or different substituents selected from halogen, OH, ═O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

and preferably a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, ═O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$haloalkoxy;

(ii) a functional group handle $H^{1A}$, which is covalently bonded to the compound of formula (I);

(iii) a functional group handle $H^{2B}$, which is covalently bonded to the targeting moiety T.

9. The conjugate according to any one of items 6 to 8, wherein the linker $L^2$ has the structure $H^{1A}L^C$-$H^{2B}$ and is selected from the group consisting of:

(L²-1)

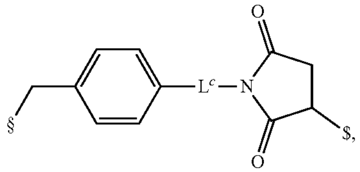

(L²-2)

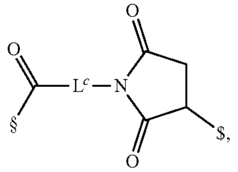

(L²-3)

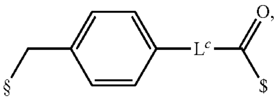

and

-continued (L²-4)

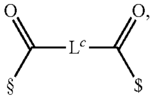

wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

§ marks the connection to the compound of formula (I); and $ marks the connection to the targeting moiety T.

and wherein preferably LC is selected from the group consisting of ($L^C$-1)

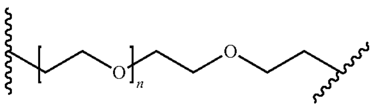

, ($L^C$-2)

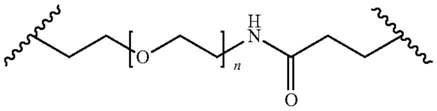

, ($L^C$-3)

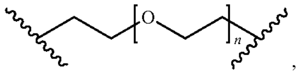

, ($L^C$-4)

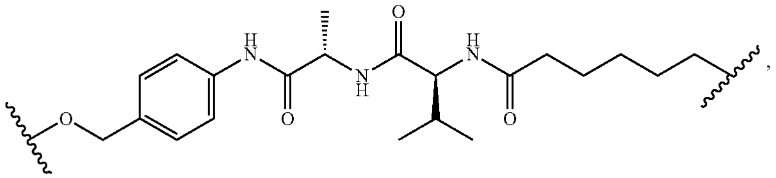

, ($L^C$-5)

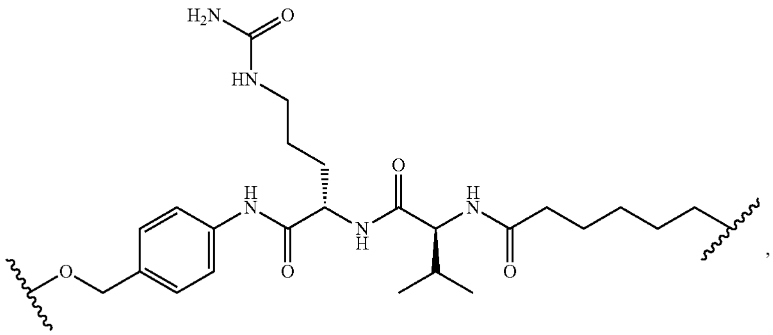

, ($L^C$-6)

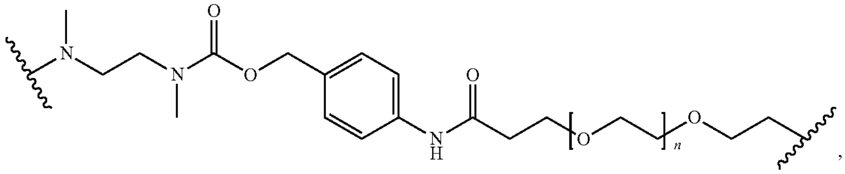

,

-continued ($L^C$-7)

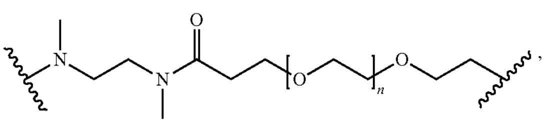

, ($L^C$-8)

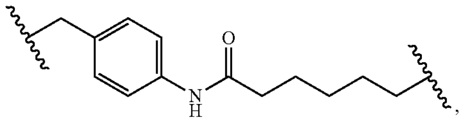

, and ($L^C$-9)

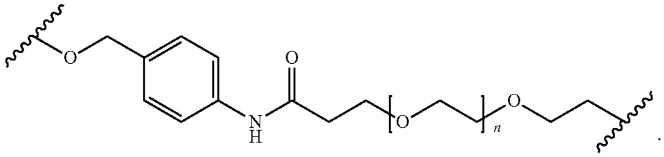

.

10. The conjugate of any one of items 6 to 9, wherein the targeting moiety T comprises an antibody, an antibody fragment, a nucleic acid based molecule, a carbohydrate, a peptide, or a modified peptide, in particular an antibody or an antigen-binding fragment, which is designed to target the Human Epidermal Growth Factor Receptor (EGFR), a plasminogen activator, a cytotoxic T-lymphocyte associated antigen (CTLA), vascular endothelial growth factor (VEGF), neurotrophic factors, a nerve growth factor, platelet-derived growth factor (PDGF), transforming growth factor (TGF), EpCAM, $FLT_3$, PSMA, PSCA, STEAP, CEA, folate receptor, the $CD_{33}/CD_{30}/CD_{79}/CD_{22}$ receptors, the $SLC_{34}A_2$ gene product, the mesothelin protein, the $EphA_2$ tyrosine kinase, the $Muc_1/Muc_{16}$ cell-surface antigens, ALK, AFP, brc-abl, caspase-8, $CD_{20}$, $CD_{40}$, $CD_{123}$, $CDK_4$, c-kit, cMET, $ErbB_2/Her_2$, $ErbB_3/Her_3$, $ErbB_4/Her_4$, $Her_2$, $OX_{40}$, $p_{53}$, PAP, $PAX_3$, $PAX_5$, Ras, and Rho.

11. The compound-linker construct of any one of items 1 to 5, or the conjugate of any one of items 6 to 10, wherein the functional group of the compound of formula (I), which is attached to or part of the substituents $R^2$, $R^4$, $R^5$, or $R^N$, and which forms the covalent bond to the functional group handle $H^{1A}$ of the linker $L^1$ or $L^2$, is selected from the following options: either $R^2$ is $NHR^D$, $NHR^D$—$C_1$-$C_4$-alkyl, NH—($C_1$-$C_4$-alkylene)-$NR^CR^D$, $NR^F$—($C_1$-$C_4$-alkylene)-$NHR^D$, O—($C_1$-$C_4$-alkylene)-$NHR^D$, or 8- to 10-membered saturated heterobicyclyl, wherein the aforementioned heterobicyclic ring comprises at least one nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or $R^2$ is $NR^FC(=O)R^E$, wherein $R^E$ is $NHR^D$—$C_1$-$C_4$-alkyl;

or $R^N$ is $NHR^D$—$C_1$-$C_4$-alkyl;

or any one of the substituents $R^2$, $R^4$, $R^5$, $R^N$ carries a substituent $R^X$, wherein $R^X$ is OH, $NHR^D$, $NHR^D$—$C_1$-$C_4$-alkyl, or HO—$C_1$-$C_4$-alkyl;

and preferably either $R^2$ is $NH_2$, $NH_2$—$C_1$-$C_2$-alkyl, NH—($C_1$-$C_3$-alkylene)-$NH_2$, NH—($C_1$-$C_3$-alkylene)-$NHCH_3$, NH—($C_1$-$C_3$-alkylene)-$N(CH_3)_2$, O—($C_1$-$C_3$-alkylene)-$NH_2$, or O—($C_1$-$C_3$-alkylene)-$NHCH_3$;

or $R^2$ is $NHC(=O)R^E$, wherein $R^E$ is $NH_2$—$C_1$-$C_4$-alkyl;

or $R^N$ is $NH_2$—$C_1$-$C_3$-alkyl;

or any one of the substituents $R^2$, $R^4$, or $R^5$ carries a substituent $R^X$, wherein $R^X$ is OH, $NH_2$, $NHCH_3$, $NH_2$—$C_1$-$C_2$-alkyl, or HO—$C_1$-$C_2$alkyl.

12. The compound-linker construct of any one of items 1 to 5 or 11, or the conjugate of any one of items 6 to 10 or 11, wherein in the compound of formula (I)

$X^1$ is CH;

$X^2$ is $CR^3$ with $R^3$ being H;

$R^1$ is H or F;

$R^2$ is H, OH, $NR^CR^D$, CN, halogen, $NR^CR^D$—$C_1$-$C_4$-alkyl, $NR^FC(=O)R^E$, $NR^F$—($C_1$-$C_4$-alkylene) C(=O) $R^E$, $NR^F$—($C_1$-$C_4$-alkylene)-$NR^CR^D$, O—($C_1$-$C_4$-alkylene)-$NR^CR^D$, or 4- to 6-membered saturated heterocyclyl, or 8- to 10-membered saturated heterobicyclyl, wherein the aforementioned heterocyclic or heterobicyclic rings comprise a nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is pyridinyl, wherein each substitutable carbon atom in the cyclic ring is independently unsubstituted or substituted by one or more, same or different substituents $R^X$;

$R^5$ is piperidine, wherein each substitutable carbon or heteroatom in the piperidine ring is independently unsubstituted or substituted by one or more, same or different substituents $R^Y$; and $R^N$ is H, $C_1$-$C_4$-alkyl, HO(C=O)—$C_1$-$C_3$-alkyl, $NHR^D$—$C_1$-$C_6$-alkyl, $C_1$-$C_2$alkoxy-$C_1$-$C_6$-alkyl, or cyclopropyl;

wherein preferably $R^C$ is H or $C_1$-$C_2$-alkyl;

$R^D$ is H or $C_1$-$C_2$-alkyl;

$R^E$ is $NH_2$—$C_1$-$C_4$-alkyl;

$R^F$ is H;

$R^X$ is halogen, OH, $NH_2$, $NHCH_3$, $C_1$-$C_2$-alkyl, $C_1$-$C_2$alkoxy, $NH_2$—$C_1$-$C_2$-alkyl, HO—$C_1$-$C_2$-alkyl, or two $R^X$ together with the carbon atom to which they are bonded form a 3-membered saturated carbocyclic ring;

$R^Y$ is halogen, OH, $NH_2$, or a 5- or 6-membered aromatic heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

with the proviso that either $R^2$ is $NH_2$, $NH_2$—$C_1$-$C_2$-alkyl, NH—($C_1$-$C_3$-alkylene)-$NH_2$, NH—($C_1$-$C_3$-alkylene)-$NHCH_3$, NH—($C_1$-$C_3$-alkylene)-$N(CH_3)_2$, O—($C_1$-$C_3$-alkylene)-$NH_2$, or O—($C_1$-$C_3$-alkylene)-$NHCH_3$; or $R^2$ is NHC(═O)$R^E$, wherein $R^E$ is $NH_2$—$C_1$-$C_4$-alkyl;

or $R^N$ is $NH_2$—$C_1$-$C_3$-alkyl;

or any one of the substituents $R^2$, $R^4$, or $R^5$ carries a substituent $R^X$, wherein $R^X$ is OH, $NH_2$, $NHCH_3$, $NH_2$—$C_1$-$C_2$-alkyl, or HO—$C_1$-$C_2$alkyl.

13. A pharmaceutical composition comprising a pharmaceutically effective amount of the compound-linker construct of any one of items 1 to 5, 11 or 12, or the conjugate of any one of items 6 to 10, 11 or 12 and optionally a pharmaceutically acceptable carrier, diluent or excipient.

14. A compound-linker construct of any one of items 1 to 5, 11 or 12, or the conjugate of any one of items 6 to 10, 11 or 12, or a pharmaceutical composition according to item 13 for use in medicine.

15. A compound-linker construct of any one of items 1 to 5, 11 or 12, or the conjugate of any one of items 6 to 10, 11 or 12, or a pharmaceutical composition according to item 13 for use in the treatment of a disease selected from the group consisting of cancer, precancerous syndromes, and infectious diseases; or for use in an immunogenic composition or as vaccine adjuvant.

16. A compound-linker construct of any one of items 1 to 5, 11 or 12, or the conjugate of any one of items 6 to 10, 11 or 12, or a pharmaceutical composition according to item 13 for use in the treatment of a disease selected from the group consisting of inflammatory diseases, allergic diseases, and autoimmune diseases.

The invention claimed is:

1. A compound-linker construct comprising (i) a compound of formula (I); and (ii) a linker $L^1$ wherein the compound of formula (I) is a compound of the following formula (I)

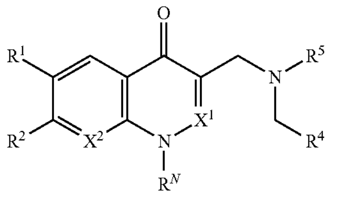

or a salt, stereoisomer, tautomer, or N-oxide thereof, wherein $X^1$ is CH or N;

$X^2$ is $CR^3$ or N;

$R^1$, $R^2$ and $R^3$ are independently H, OH, $NR^CR^D$, CN, halogen, $C_1$-$C_4$-alkyl, $NR^CR^D$—$C_1$-$C_4$-alkyl, $C_1$-$C_4$-alkoxy, aryloxy, benzyloxy, C(═O)$R^E$, $NR^F$C(═O)$R^E$, $NR^F$—($C_1$-$C_4$-alkylene)-C(═O)$R^E$, $NR^F$—($C_1$-$C_4$-alkylene)-$NR^CR^D$, O—($C_1$-$C_4$-alkylene)-$NR^CR^D$, or 4- to 6-membered saturated, partially or fully unsaturated, or aromatic carbocyclyl, carbocyclyl-$C_1$-$C_2$-alkyl, heterocyclyl, heterocyclyloxy, or heterocyclyl-$C_1$-$C_2$-alkyl, or 8- to 10-membered saturated, partially or fully unsaturated, or aromatic carbobicyclyl or heterobicyclyl, wherein the aforementioned heterocyclic or heterobicyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents $R^X$;

$R^5$ is selected from the group consisting of ($R^5$-1)

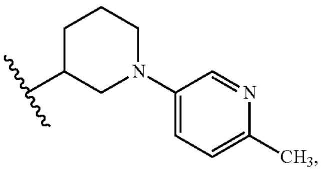

($R^5$-2)

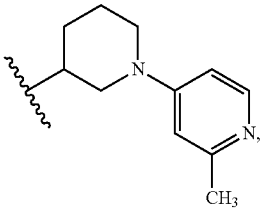

($R^5$-3)

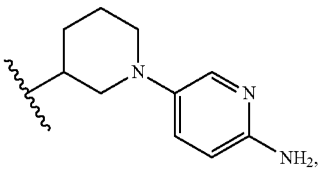

-continued
($R^5$-4)
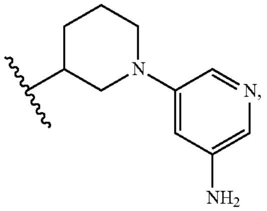
($R^5$-5)
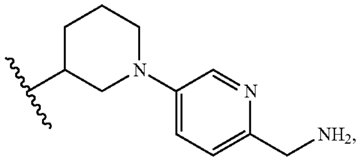
($R^5$-6)
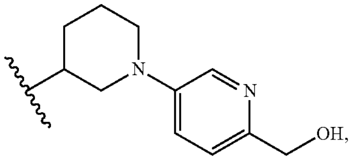
($R^5$-8)
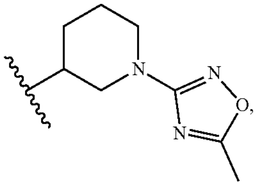
($R^5$-10)
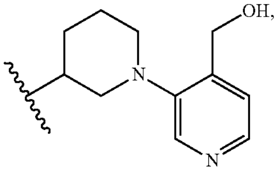
($R^5$-11)
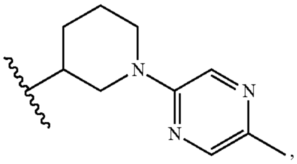
($R^5$-12)
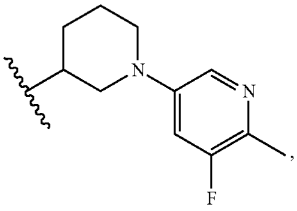
($R^5$-13)
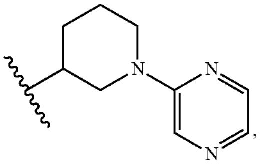
-continued
($R^5$-14)
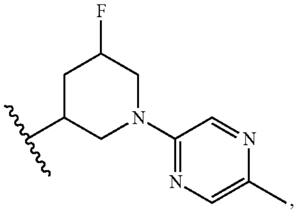
($R^5$-15)
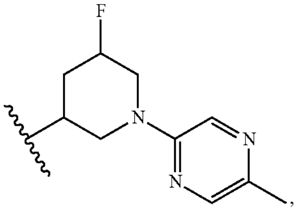
($R^5$-16)
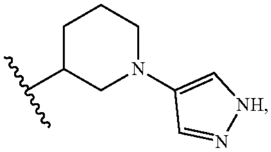
($R^5$-18)
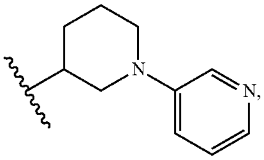
($R^5$-19)
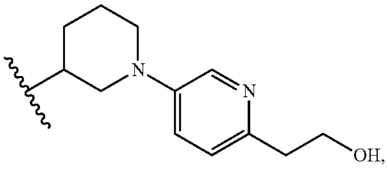
($R^5$-20)
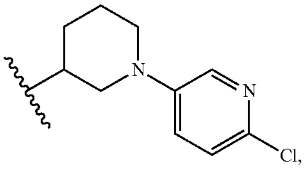
($R^5$-21)
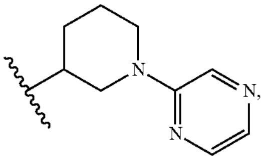
($R^5$-23)
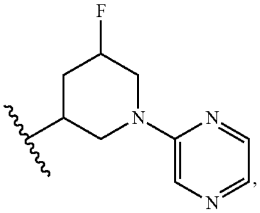

-continued (R5-24)

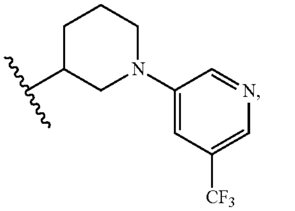

(R5-25)

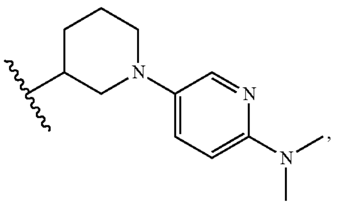

(R5-26)

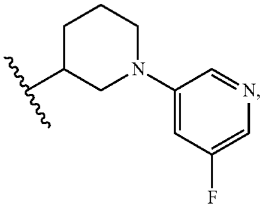

(R5-27)

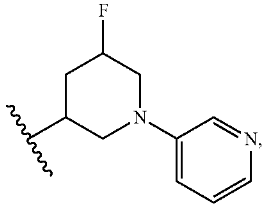

and (R5-28)

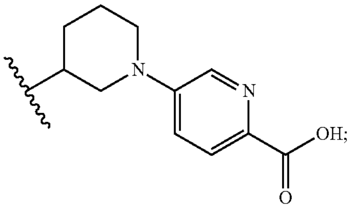

and wherein $R^N$ is H, $C_1$-$C_4$-alkyl, HO(C═O)—$C_1$-$C_4$-alkyl, $NR^CR^D$—$C_1$-$C_4$-alkyl, $C_1$-$C_2$-alkoxy-$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, $NR^CR^D$—$C_1$-$C_4$-alkyl, phenyl, benzyl, $OR^G$, or $NR^HR^I$; or a 5- or 6-membered saturated, partially or fully unsaturated heterocyclyl, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^F$;

$R^F$ is H, $C_1$-$C_2$-alkyl, $C_3$-$C_6$-cycloalkyl, phenyl, benzyl, or C(═O) $NR^HR^I$;

$R^G$ is H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is OH, $NR^CR^D$, halogen, CN, $NO_2$, $C_1$-$C_2$-alkyl, $C_1$-$C_2$-haloalkyl, $NR^CR^D$—$C_1$-$C_4$-alkyl, $R^CO$—$C_1$-$C_4$-alkyl, $C_1$-$C_2$-alkoxy, C(═O)$R^E$, or two $R^X$ form ═O, or two $R^X$ together with the carbon atom to which they are bonded form a 3- to 5-membered saturated, partially or fully unsaturated, or aromatic carbocyclic ring;

with the proviso that at least one of the following conditions is met:

any one of $R^1$, $R^2$, or $R^3$ is independently $NR^CR^D$, $NR^CR^D$—$C_1$-$C_4$-alkyl, $NR^F$—($C_1$-$C_4$-alkylene)-$NR^CR^D$, O—($C_1$-$C_4$-alkylene)-$NR^CR^D$, and $R^C$ is H;

or any one of $R^1$, $R^2$, or $R^3$ is $NR^F$C(═O)$R^E$, wherein $R^E$ is $NR^CR^D$—$C_1$-$C_4$-alkyl, and $R^C$ is H; or $R^N$ is $NR^CR^D$—$C_1$-$C_4$-alkyl and $R^C$ is H;

or any one of the substituents $R^1$, $R^2$, $R^3$, $R^4$, $R^5$, $R^N$ carries a substituent $R^X$, wherein $R^X$ is OH, $NR^CR^D$, $NR^CR^D$—$C_1$-$C_4$-alkyl, or $R^CO$—$C_1$-$C_4$-alkyl, and $R^C$ is H;

wherein a covalent bond between the compound of formula (I) and the linker $L^1$ is established by the reaction of a functional group of the compound of formula (I) with a functional group handle of the linker $L^1$; and wherein the functional group of the compound of formula (I) is attached to or part of the substituents $R^2$, $R^4$, $R^5$, or $R^N$ so that the linker $L^1$ is covalently bonded to the compound of formula (I) according to any one of the following structures;

(I-$R^2$-$L^1$)

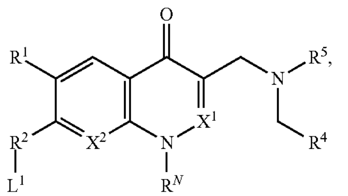

(I-$R^N$-$L^1$)

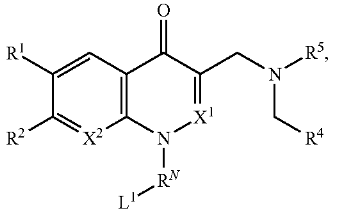

(I-$R^4$-$L^1$)

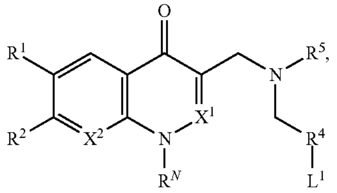

or (I-$R^5$-$L^1$)

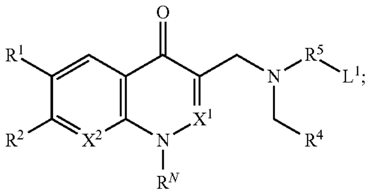

wherein the linker $L^1$ has the structure $H^{1A}$-$L^C$-$H^{1B}$;

$L^C$ is a chain of 2 to 100 atoms selected from carbon, nitrogen, oxygen, and sulfur atoms, which may be interrupted by 5- to 10-membered aryl and heteroaryl groups and/or 3- to 8-membered saturated carbocyclyl or heterocyclyl groups, wherein the aforementioned heteroaryl and heterocyclic groups comprise one or more, same or different heteroatoms selected from O, N or S, wherein said N- and/or S-atoms are independently oxidized or non-oxidized, and wherein each substitutable carbon or heteroatom in the chain is independently unsubstituted or substituted with one or more same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

$H^{1A}$ is a first functional group handle which is covalently bonded to the compound of formula (I); and $H^{1B}$ is a second functional group handle suitable for forming a covalent bond to a targeting moiety T.

2. The compound-linker construct according to claim 1, wherein the linker $L^1$ is covalently bonded to the compound of formula (I) according to (I-$R^5$-$L^1$)

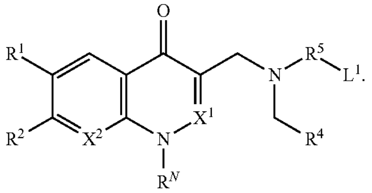

3. The compound-linker construct according to claim 1, wherein the linker $L^1$ is selected from the group consisting of:

($L^1$-1)

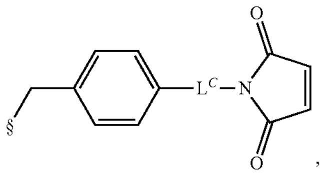

($L^1$-2)

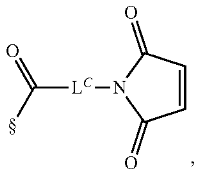

($L^1$-3)

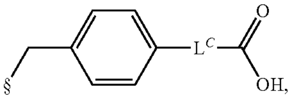

($L^1$-4)

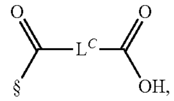

($L^1$-5)

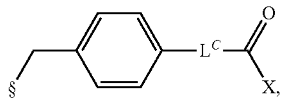

($L^1$-6)

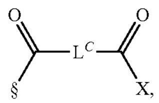

($L^1$-7)

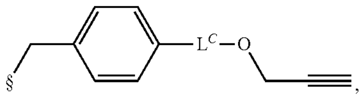

($L^1$-8)

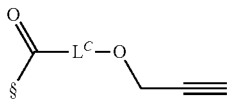

-continued (L1-9)

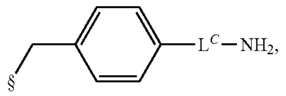

(L1-10)

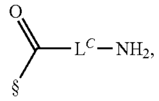

(L1-11)

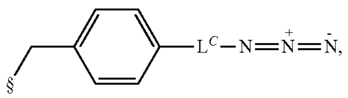

(L1-12)

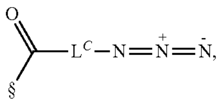

(L1-13)

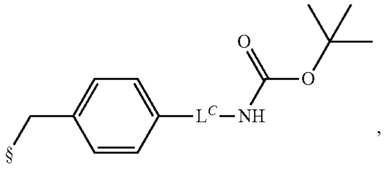

, (L1-14)

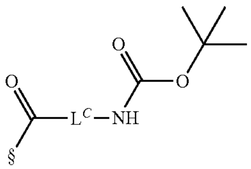

, (L1-15)

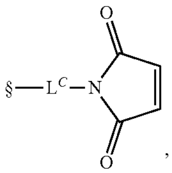

, (L1-16)

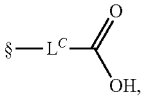

(L1-17)

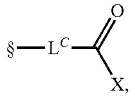

-continued (L1-18)

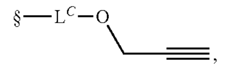

(L1-19)

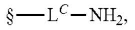

(L1-20)

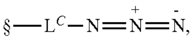

and (L1-21)

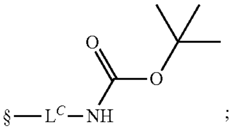

;

wherein $L^C$ is a chain $L^C$ of units selected from the group consisting of a linear or branched polyethylene glycol chain, a sequence of amino acids, and a linear or branched $C_1$-$C_{10}$-alkyl chain, and any combinations thereof, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy; and § marks the connection to the compound of formula (I); and X represents a leaving group selected from (X-1)

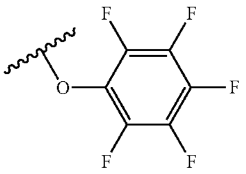

and (X-2)

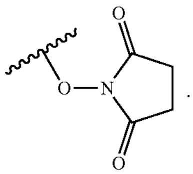

.

4. The compound-linker construct according claim 1, wherein the linker $L^1$ is selected from the group consisting of:

(L1-a)

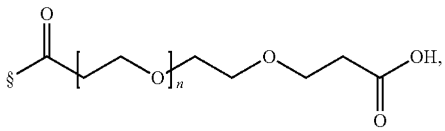

(L1-b)

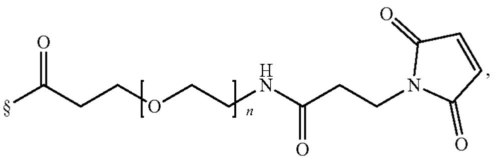

-continued
(L1-c)
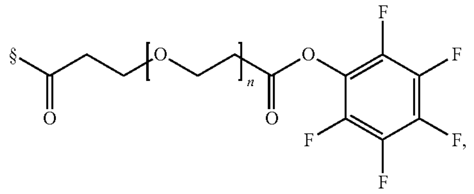
(L1-d)
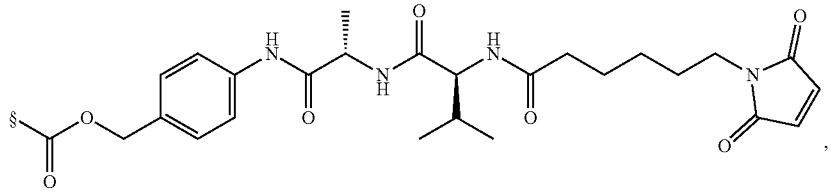
,
(L1-e)
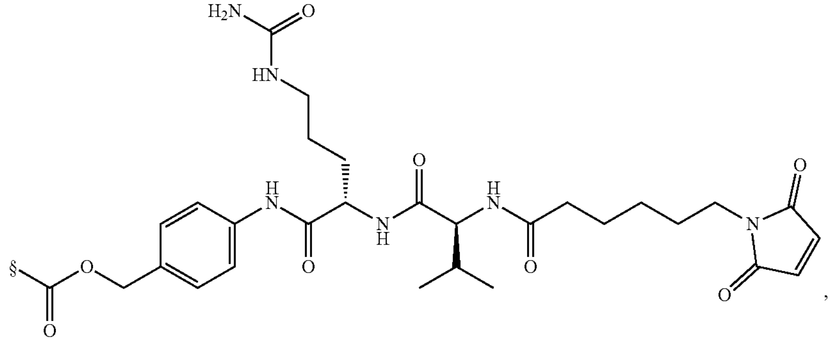
,
(L1-f)
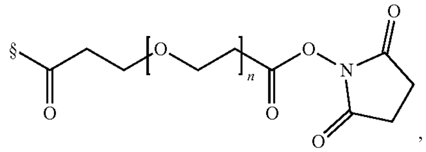
,
(L1-g)
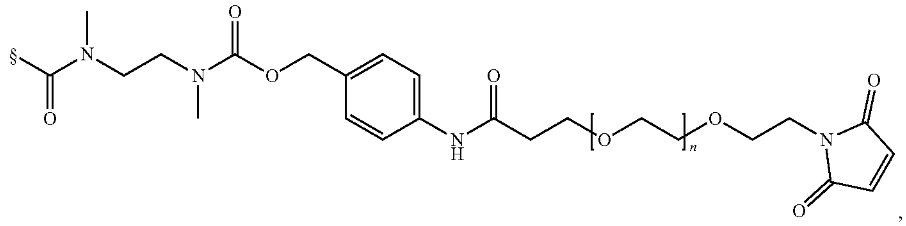
,
(L1-h)
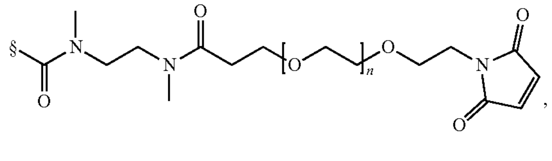
,
(L1-i)
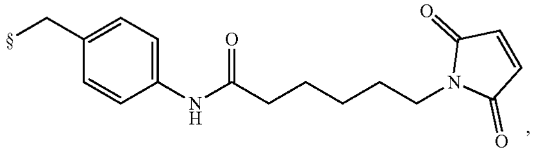
,
(L1-j)
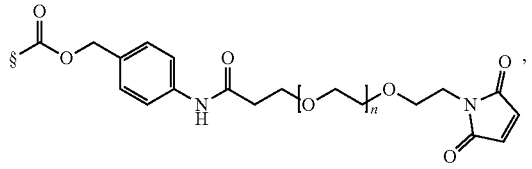
, and
(L1-k)
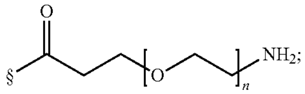
;

wherein

§ marks the connection to the compound of formula (I).

5. A conjugate comprising (i) a compound of formula (I);

(ii) a linker $L^2$; and (iii) a targeting moiety T;

wherein the compound of formula (I) is a compound of the following formula (I)

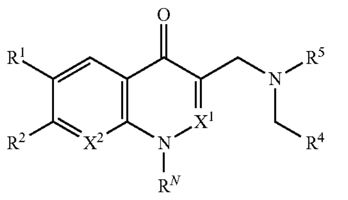

or a salt, stereoisomer, tautomer, or N-oxide thereof, wherein $X^1$ is CH or N;

$X^2$ is $CR^3$ or N;

$R^1$, $R^2$ and $R^3$ are independently H, OH, $NR^CR^D$, CN, halogen, $C_1$-$C_4$-alkyl, $NR^CR^D$—$C_1$-$C_4$-alkyl, $C_1$-$C_4$-alkoxy, aryloxy, benzyloxy, C(=O)$R^E$, $NR^F$C(=O)$R^E$, $NR^F$—($C_1$-$C_4$-alkylene)-C(=O)$R^E$, $NR^F$—($C_1$-$C_4$-alkylene)-$NR^CR^D$, O—($C_1$-$C_4$-alkylene)-$NR^CR^D$, or 4- to 6-membered saturated, partially or fully unsaturated, or aromatic carbocyclyl, carbocyclyl-$C_1$-$C_2$-alkyl, heterocyclyl, heterocyclyloxy, or heterocyclyl-$C_1$-$C_2$-alkyl, or 8- to 10-membered saturated, partially or fully unsaturated, or aromatic carbobicyclyl or heterobicyclyl, wherein the aforementioned heterocyclic or heterobicyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents $R^X$;

$R^5$ is selected from consisting of ($R^5$-1)

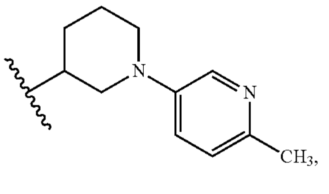

-continued ($R^5$-2)

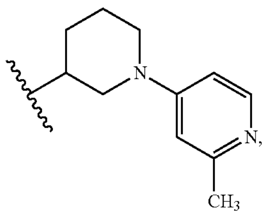

($R^5$-3)

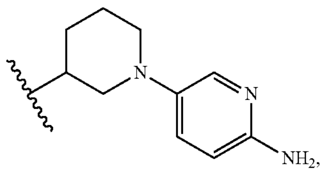

($R^5$-4)

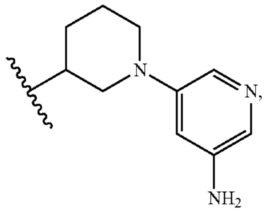

($R^5$-5)

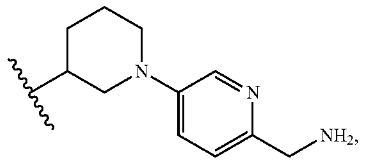

($R^5$-6)

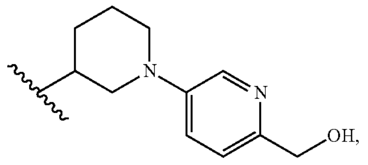

($R^5$-8)

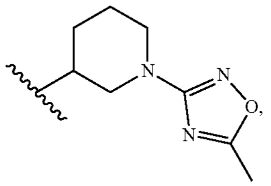

($R^5$-10)

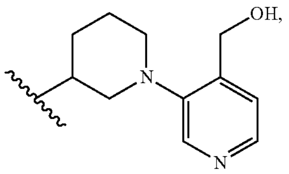

($R^5$-11)

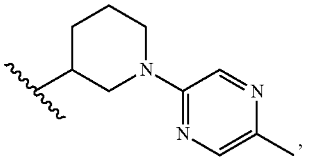

-continued
(R$^5$-12)
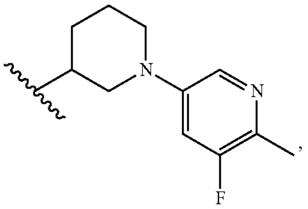
(R$^5$-13)
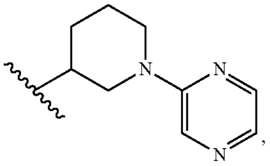
(R$^5$-14)
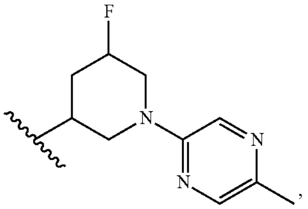
(R$^5$-15)
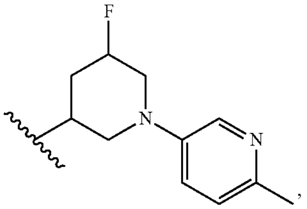
(R$^5$-16)
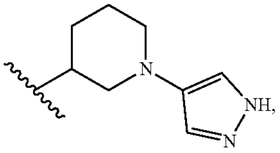
(R$^5$-18)
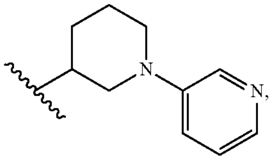
(R$^5$-19)
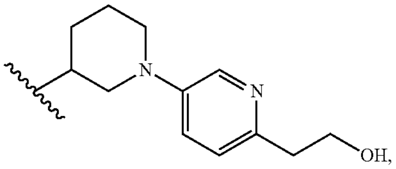
(R$^5$-20)
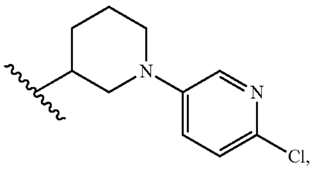
-continued
(R$^5$-22)
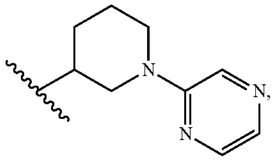
(R$^5$-23)
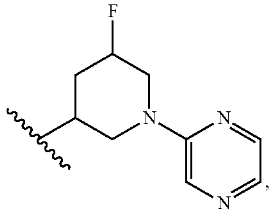
(R$^5$-24)
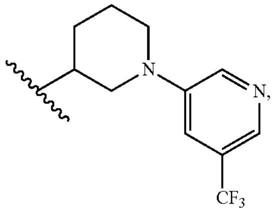
(R$^5$-25)
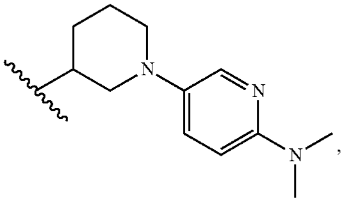
(R$^5$-26)
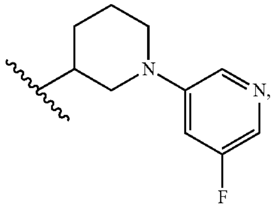
(R$^5$-27)
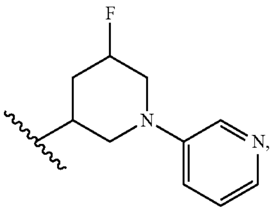
and
(R$^5$-28)
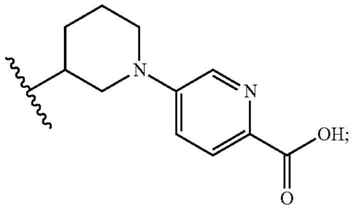
and wherein
$R^N$ is H, $C_1$-$C_4$-alkyl, HO(C═O)—$C_1$-$C_4$-alkyl, $NR^CR^D$—$C_1$-$C_4$-alkyl, $C_1$-$C_2$-alkoxy-$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, $NR^CR^D$—$C_1$-$C_4$-alkyl, phenyl, benzyl, $OR^G$, or $NR^HR^I$; or a 5- or 6-membered saturated, partially or fully unsaturated heterocyclyl, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^F$;

$R^F$ is H, $C_1$-$C_2$-alkyl, $C_3$-$C_6$-cycloalkyl, phenyl, benzyl, or C(=O) $NR^HR^I$;

$R^G$ is H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is OH, $NR^CR^D$, halogen, CN, $NO_2$, $C_1$-$C_2$-alkyl, $C_1$-$C_2$-haloalkyl, $NR^CR^D$—$C_1$-$C_4$-alkyl, $R^CO$—$C_1$-$C_4$-alkyl, $C_1$-$C_2$-alkoxy, C(=O)$R^E$, or two $R^X$ form =O, or two $R^X$ together with the carbon atom to which they are bonded form a 3- to 5-membered saturated, partially or fully unsaturated, or aromatic carbocyclic ring;

with the proviso that at least one of the following conditions is met;

any one of $R^1$, $R^2$, or $R^3$ is independently $NR^CR^D$, $NR^CR^D$—$C_1$-$C_4$-alkyl, $NR^F$—($C_1$-$C_4$-alkylene)-$NR^CR^D$, O—($C_1$-$C_4$-alkylene)-$NR^CR^D$, and $R^C$ is H;

or any one of $R^1$, $R^2$, or $R^3$ is $NR^FC$(=O)$R^E$, wherein $R^E$ is $NR^CR^D$—$C_1$-$C_4$-alkyl and $R^C$ is H;

or $R^N$ is $NR^CR^D$—$C_1$-$C_4$-alkyl and $R^C$ is H;

or any one of the substituents $R^1$, $R^2$, $R^3$, $R^4$, $R^5$, $R^N$ carries a substituent $R^X$, wherein $R^X$ is OH, $NR^CR^D$, $NR^CR^D$—$C_1$-$C_4$-alkyl, or $R^CO$—$C_1$-$C_4$-alkyl, and $R^C$ is H;

wherein a covalent bond between the compound of formula (I) and the linker $L^2$ is established by the reaction of a functional group of the compound of formula (I) with a first functional group handle $H^{1A}$ of the linker $L^2$ and wherein a covalent bond between the targeting moiety T and the linker $L^2$ is established by the reaction of a functional group of the targeting moiety T with a second functional group handle $H^{2B}$ of the linker $L^2$;

wherein the functional group of the compound of formula (I) is attached to or part of the substituents $R^2$, $R^4$, $R^5$, or $R^N$ so that the linker $L^1$, is covalently bonded to the compound of formula (I) at one end according to any one of the following structures:

(I-$R^2$-$L^2$-T)

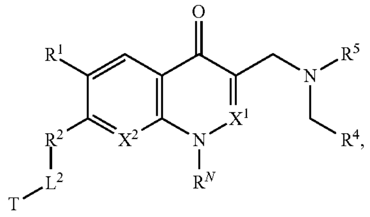

(I-$R^N$-$L^2$-T)

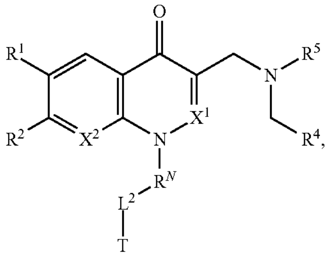

(I-$R^4$-$L^2$-T)

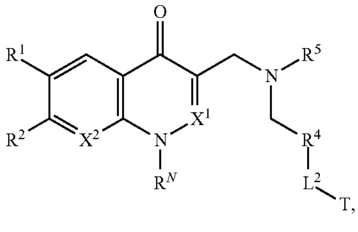

or (I-$R^5$-$L^2$-T)

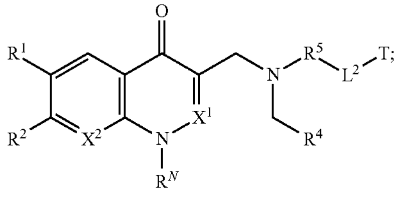

wherein the linker $L^2$ comprises (i) a chain $L^C$ of 2 to 100 atoms selected from carbon, nitrogen, oxygen, and sulfur atoms, which may be interrupted by 5- to 10-membered aryl and heteroaryl groups and/or 3- to 8-membered saturated carbocyclyl or heterocyclyl groups, wherein the aforementioned heteroaryl and heterocyclic groups comprise one or more, same or different heteroatoms selected from O, N or S, wherein said N- and/or S-atoms are independently oxidized or non-oxidized, and wherein each substitutable carbon or heteroatom in the chain is independently unsubstituted or substituted with one or more same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

(i) the functional group handle $H^{1A}$, which is covalently bonded to the compound of formula (I); and (iii) the functional group handle $H^{2B}$, which is covalently bonded to the targeting moiety T.

6. The conjugate according to claim 5, wherein the linker $L^2$ has the structure $H^{1A}$-$L^C$-$H^{2B}$ and is selected from the group consisting of:

($L^2$-1)

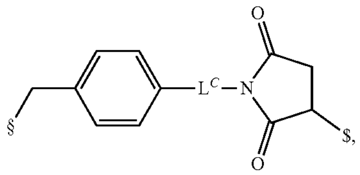

($L^2$-2)

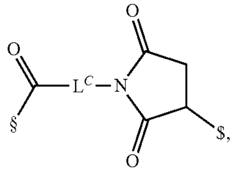

($L^2$-3)

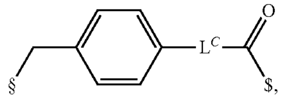

($L^2$-4)

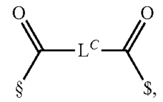

($L^2$-5)

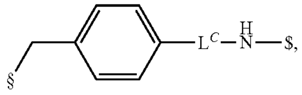

($L^2$-6)

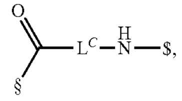

($L^2$-7)

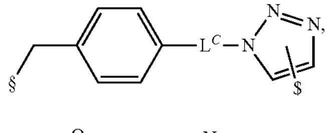

($L^2$-8)

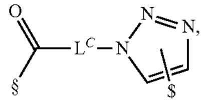

-continued ($L^2$-9)

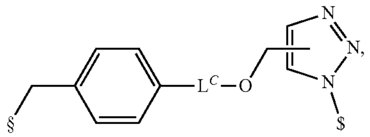

($L^2$-10)

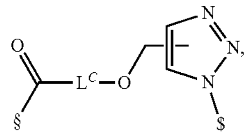

($L^2$-11)

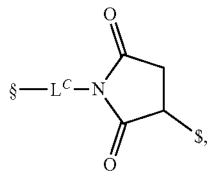

($L^2$-12)

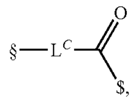

($L^2$-13)

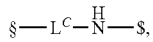

($L^2$-14)

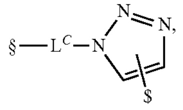

and ($L^2$-15)

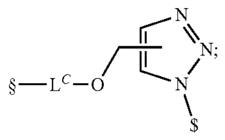

wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

§ marks the connection to the compound of formula (I); and $ marks the connection to the targeting moiety T.

7. The conjugate of claim 5, wherein the targeting moiety T comprises an antibody, an antibody fragment, a nucleic acid based molecule, a carbohydrate, a peptide, or a modified peptide.

8. The compound-linker construct of claim 1, wherein the functional group of the compound of formula (I), which forms the covalent bond to the first functional group handle $H^{1A}$ of the linker $L^1$, is selected from one of the following options:

$R^2$ is $NHR^D$, $NHR^D$—$C_1$-$C_4$-alkyl, NH—($C_1$-$C_4$-alkylene)-$NR^CR^D$, $NR^F$—($C_1$-$C_4$-alkylene)-$NHR^D$, O—($C_1$-$C_4$-alkylene)-$NHR^D$;

or $R^2$ is $NR^FC(=O)R^E$, wherein $R^E$ is $NHR^D$—$C_1$-$C_4$-alkyl;

or $R^N$ is $NHR^D$—$C_1$-$C_4$-alkyl;

or any one of the substituents $R^2$, $R^4$, $R^5$, $R^N$ carries a substituent $R^X$, wherein $R^X$ is OH, $NHR^D$, $NHR^D$—$C_1$-$C_4$-alkyl, or HO—$C_1$-$C_4$-alkyl.

9. The compound-linker construct of claim 1, wherein in the compound of formula (I)

$X^1$ is CH;

$X^2$ is $CR^3$ with $R^3$ being H;

$R^1$ is H or F;

$R^2$ is H, OH, $NR^CR^D$, CN, halogen, $NR^CR^D$—$C_1$-$C_4$-alkyl, $NR^FC(=O)R^E$, $NR^F$—($C_1$-$C_4$-alkylene)-C(=O)$R^E$, $NR^F$—($C_1$-$C_4$-alkylene)-$NR^CR^D$, O—($C_1$-$C_4$-alkylene)-$NR^CR^D$, or 4- to 6-membered saturated heterocyclyl, or 8- to 10-membered saturated heterobicyclyl, wherein the aforementioned heterocyclic or heterobicyclic rings comprise a nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is pyridinyl, wherein each substitutable carbon atom in the cyclic ring is independently unsubstituted or substituted by one or more, same or different substituents $R^X$;

$R^N$ is H, $C_1$-$C_4$-alkyl, HO(C=O)—$C_1$-$C_3$-alkyl, $NHR^D$—$C_1$-$C_3$-alkyl, $C_1$-$C_2$-alkoxy-$C_1$-$C_3$-alkyl, or cyclopropyl;

wherein $R^C$ is H or $C_1$-$C_2$-alkyl;

$R^D$ is H or $C_1$-$C_2$-alkyl;

$R^E$ is $NH_2$—$C_1$-$C_4$-alkyl;

$R^F$ is H;

$R^X$ is halogen, OH, $NH_2$, $NHCH_3$, $C_1$-$C_2$-alkyl, $C_1$-$C_2$-alkoxy, $NH_2$—$C_1$-$C_2$-alkyl, HO—$C_1$-$C_2$-alkyl, or two $R^X$ together with the carbon atom to which they are bonded form a 3-membered saturated carbocyclic ring;

with the proviso that at least one of the following conditions is met:

$R^2$ is $NH_2$, $NH_2$—$C_1$-$C_2$-alkyl, NH—($C_1$-$C_3$-alkylene)-$NH_2$, NH—($C_1$-$C_3$-alkylene)-$NHCH_3$, NH—($C_1$-$C_3$-alkylene)-$N(CH_3)_2$, O—($C_1$-$C_3$-alkylene)-$NH_2$, or O—($C_1$-$C_3$-alkylene)-$NHCH_3$;

or $R^2$ is NHC(=O)$R^E$, wherein $R^E$ is $NH_2$—$C_1$-$C_4$-alkyl;

or $R^N$ is $NH_2$—$C_1$-$C_3$-alkyl;

or any one of the substituents $R^2$, $R^4$, or $R^5$ carries a substituent $R^X$, wherein $R^X$ is OH, $NH_2$, $NHCH_3$, $NH_2$—$C_1$-$C_2$-alkyl, or HO—$C_1$-$C_2$-alkyl.

10. A pharmaceutical composition comprising a pharmaceutically effective amount of the compound-linker construct of claim 1 and optionally a pharmaceutically acceptable carrier, diluent or excipient.

11. The compound-linker construct according to claim 1, wherein $L^C$ of the linker $L^1$ comprises units selected from the group consisting of a linear or branched polyethylene glycol chain, a sequence of amino acids, and a linear or branched $C_1$-$C_{10}$-alkyl chain, and wherein each substitutable carbon or heteroatom of the aforementioned units is unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy.

12. The compound-linker construct according to claim 3, wherein $L^C$ is selected from the group consisting of ($L^C$-1)

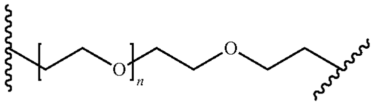

, ($L^C$-2)

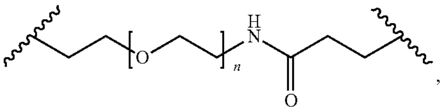

, ($L^C$-3)

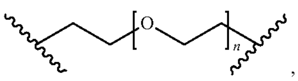

, ($L^C$-4)

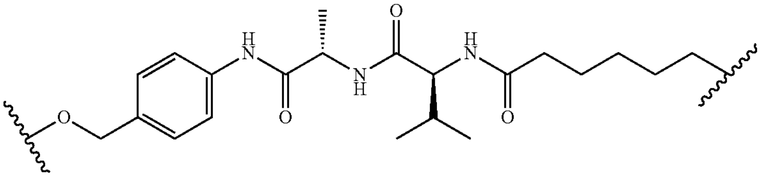

,

-continued (L^C-5)

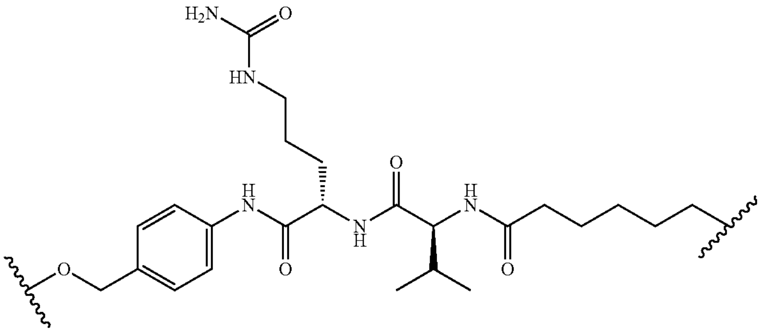

, (L^C-6)

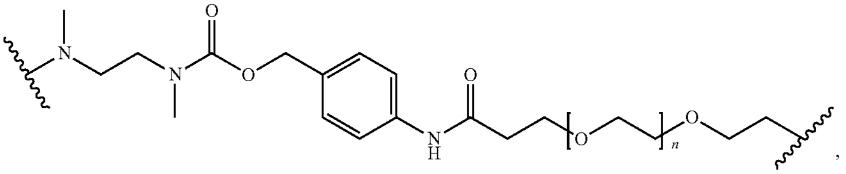

, (L^C-7)

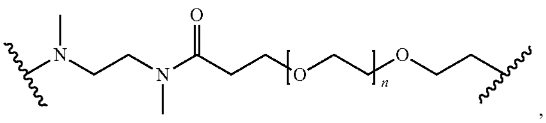

, (L^C-8)

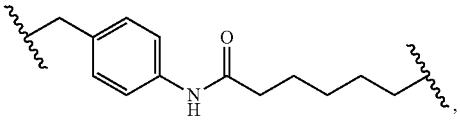

, (L^C-9)

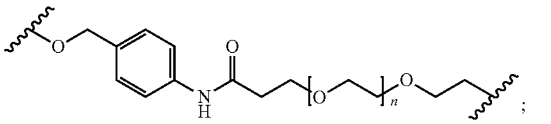

;

(L^C-10)

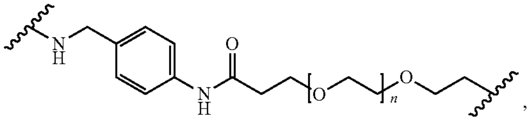

, and (L^C-11)

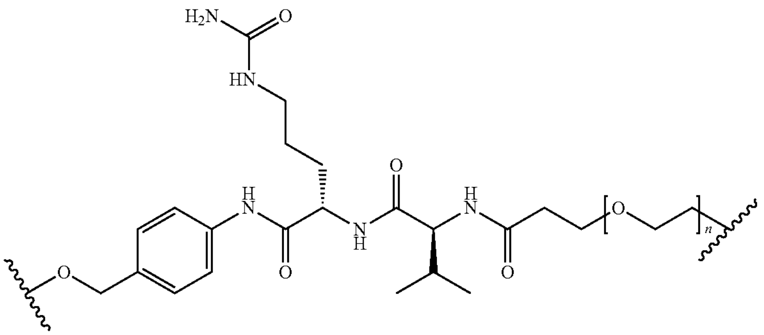

;

wherein n is 0, 1, 2, 3, 4, 5, 6, 7, or 8.

13. The conjugate according to claim 5, wherein the linker $L^2$ comprises a chain $L^C$ of units selected from the group consisting of a linear or branched polyethylene glycol chain, a sequence of amino acids, and a linear or branched $C_1$-$C_{10}$-alkyl chain, wherein each substitutable carbon or heteroatom of the afore mentioned units is unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy.

14. The conjugate of claim 6, wherein $L^C$ is selected from the group consisting of (L^C-1)

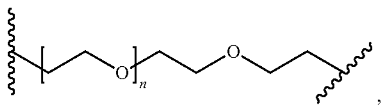

, (L^C-2)

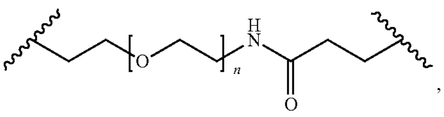

,

-continued ($L^C$-3)

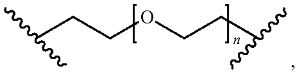

, ($L^C$-4)

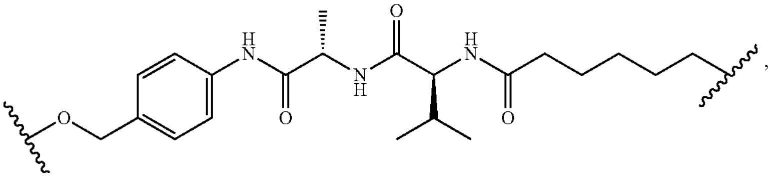

, ($L^C$-5)

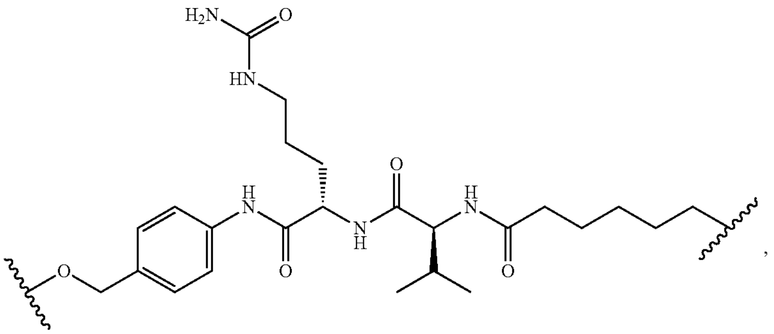

, ($L^C$-6)

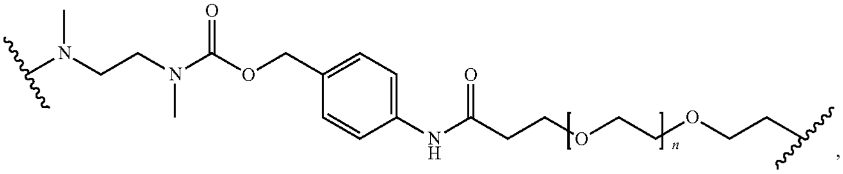

, ($L^C$-7)

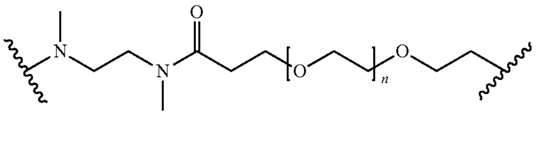

, ($L^C$-8)

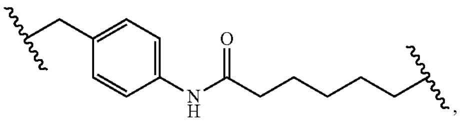

, ($L^C$-9)

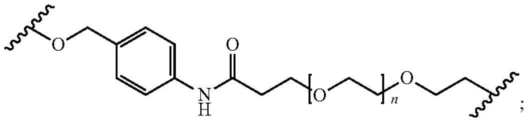

;

($L^C$-10)

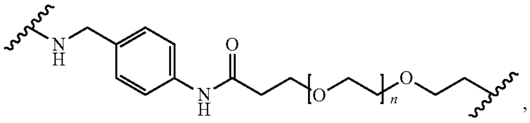

, and ($L^C$-11)

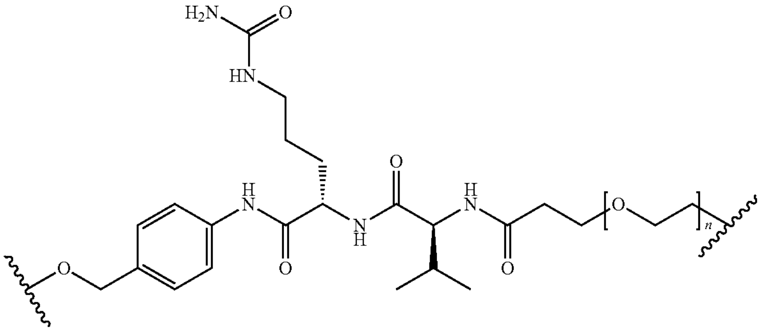

;

wherein n is 0, 1, 2, 3, 4, 5, 6, 7, or 8.

15. The conjugate according to claim 7, wherein the targeting moiety T is an antibody or an antigen-binding fragment, which is designed to target any one or more of the following: the Human Epidermal Growth Factor Receptor (EGFR), a plasminogen activator, a cytotoxic T-lymphocyte associated antigen (CTLA), vascular endothelial growth factor (VEGF), fibroblast growth factor receptor (FGFR), platelet-derived growth factor (PDGF), transforming growth factor (TGF), neurotrophic factors, a nerve growth factor, platelet-derived growth factor (PDGF), interleukin receptors, transforming growth factor (TGF), estrogen receptor, progesterone receptor, c-Kit, cMET, ErbB2/Her2, ErbB3/Her3, ErbB4/Her4, CD3, CD20, CD22, CD30, CD33, CD40, CD47, CD79, CD123, CD133, CD166, CD137, the mesothelin protein, EpCAM, FLT3, PSMA, PSCA, STEAP, CEA, folate receptor, the CD39/CD73 receptors, adenosine receptors, SLC34A2 gene product, the EphA2 tyrosine kinase, the Muc1/Muc16 cell-surface antigens, ALK, AFP, bcr-Abl, or PAP.

16. The conjugate of claim 5, wherein the functional group of the compound of formula (I), which forms the covalent bond to the functional group handle $H^{1A}$ of the linker $L^2$, is selected from one of the following options:

$R^2$ is $NHR^D$, $NHR^D$—$C_1$-$C_4$-alkyl, NH—($C_1$-$C_4$-alkylene)-$NR^CR^D$, $NR^F$—($C_1$-$C_4$-alkylene)-$NHR^D$, O—($C_1$-$C_4$-alkylene)-$NHR^D$;

or $R^2$ is $NR^FC$(=O)$R^E$, wherein $R^E$ is $NHR^D$—$C_1$-$C_4$-alkyl;

or $R^N$ is $NHR^D$—$C_1$-$C_4$-alkyl;

or any one of the substituents $R^2$, $R^4$, $R^5$, $R^N$ carries a substituent $R^X$, wherein $R^X$ is OH, $NHR^D$, $NHR^D$—$C_1$-$C_4$-alkyl, or HO—$C_1$-$C_4$-alkyl.

17. The conjugate of claim 5, wherein in the compound of formula (I)

$X^1$ is CH;

$X^2$ is $CR^3$ with $R^3$ being H;

$R^1$ is H or F;

$R^2$ is H, OH, $NR^CR^D$, CN, halogen, $NR^CR^D$—$C_1$-$C_4$-alkyl, $NR^FC$(=O)$R^E$, $NR^F$—($C_1$-$C_4$-alkylene)-C(=O)$R^E$, $NR^F$—($C_1$-$C_4$-alkylene)-$NR^CR^D$, O—($C_1$-$C_4$-alkylene)-$NR^CR^D$, or 4- to 6-membered saturated heterocyclyl, or 8- to 10-membered saturated heterobicyclyl, wherein the aforementioned heterocyclic or heterobicyclic rings comprise a nitrogen atom and optionally one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is pyridinyl, wherein each substitutable carbon atom in the cyclic ring is independently unsubstituted or substituted by one or more, same or different substituents $R^X$;

$R^N$ is H, $C_1$-$C_4$-alkyl, HO(C=O)—$C_1$-$C_3$-alkyl, $NHR^D$—$C_1$-$C_3$-alkyl, $C_1$-$C_2$-alkoxy-$C_1$-$C_3$-alkyl, or cyclopropyl;

wherein $R^C$ is H or $C_1$-$C_2$-alkyl;

$R^D$ is H or $C_1$-$C_2$-alkyl;

$R^E$ is $NH_2$—$C_1$-$C_4$-alkyl;

$R^F$ is H;

$R^X$ is halogen, OH, $NH_2$, $NHCH_3$, $C_1$-$C_2$-alkyl, $C_1$-$C_2$-alkoxy, $NH_2$—$C_1$-$C_2$-alkyl, HO—$C_1$-$C_2$-alkyl, or two $R^X$ together with the carbon atom to which they are bonded form a 3-membered saturated carbocyclic ring;

with the proviso that at least one of the conditions is met:

$R^2$ is $NH_2$, $NH_2$—$C_1$-$C_2$-alkyl, NH—($C_1$-$C_3$-alkylene)-$NH_2$, NH—($C_1$-$C_3$-alkylene)-$NHCH_3$, NH—($C_1$-$C_3$-alkylene)-$N(CH_3)_2$, O—($C_1$-$C_3$-alkylene)-$NH_2$, or O—($C_1$-$C_3$-alkylene)-$NHCH_3$;

or $R^2$ is NHC(=O)$R^E$, wherein $R^E$ is $NH_2$—$C_1$-$C_4$-alkyl;

or $R^N$ is $NH_2$—$C_1$-$C_3$-alkyl;

or any one of the substituents $R^2$, $R^4$, or $R^5$ carries a substituent $R^X$, wherein $R^X$ is OH, $NH_2$, $NHCH_3$, $NH_2$—$C_1$-$C_2$-alkyl, or HO—$C_1$-$C_2$-alkyl.

18. A pharmaceutical composition comprising a pharmaceutically effective amount of the conjugate of claim 5 and optionally a pharmaceutically acceptable carrier, diluent or excipient.

19. A compound-linker construct comprising (i) a compound of formula (I); and (ii) a linker $L^1$ wherein the compound of formula (I) is a compound of the following formula (I)

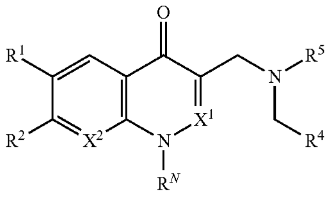

or a salt, stereoisomer, tautomer, or N-oxide thereof, wherein $X^1$ is CH;

X is CH or N;

$R^1$ is H or F $R^2$ is H, OH, $NR^CR^D$, CN, halogen, $C_1$-$C_4$-alkyl, $NR^CR^D$—$C_1$-$C_4$-alkyl, $C_1$-$C_4$-alkoxy, aryloxy, benzyloxy, C(=O)$R^E$, $NR^FC$(=O)$R^E$, $NR^F$—($C_1$-$C_4$-alkylene)-C(=O)$R^E$, $NR^F$—($C_1$-$C_4$-alkylene)-$NR^CR^D$, O—($C_1$-$C_4$-alkylene)-$NR^CR^D$, or 4- to 6-membered saturated, partially or fully unsaturated, or aromatic carbocyclyl, carbocyclyl-$C_1$-$C_2$-alkyl, heterocyclyl, heterocyclyloxy, or heterocyclyl-$C_1$-$C_2$-alkyl, or 8- to 10-membered saturated, partially or fully unsaturated, or aromatic carbobicyclyl or heterobicyclyl, wherein the aforementioned heterocyclic or heterobicyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is pyridinyl, wherein each substitutable carbon atom in the cyclic ring is independently unsubstituted or substituted by one or more, same or different substituents $R^X$;

$R^5$ is piperidine, wherein each substitutable carbon or heteroatom in the piperidine ring is independently unsubstituted or substituted by one or more, same or different substituents $R^Y$;

$R^N$ is H, $C_1$-$C_4$-alkyl, HO(C=O)—$C_1$-$C_3$-alkyl, $NHR^D$—$C_1$-$C_3$-alkyl, $C_1$-$C_2$-alkoxy-$C_1$-$C_3$-alkyl, or cyclopropyl;

$R^X$ is halogen, OH, $NH_2$, $NHCH_3$, $C_1$-$C_2$-alkyl, $C_1$-$C_2$-alkoxy, $NH_2$—$C_1$-$C_2$-alkyl, HO—$C_1$-$C_2$-alkyl, or two $R^X$ together with the carbon atom to which they are bonded form a 3-membered saturated carbocyclic ring;

$R^Y$ is halogen, OH, $NH_2$, or a 5- or 6-membered aromatic heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl;

$R^E$ is H, $C_1$-$C_2$-alkyl, $NR^CR^D$—$C_1$-$C_4$-alkyl, phenyl, benzyl, $OR^G$, or $NR^HR^I$; or a 5- or 6-membered saturated, partially or fully unsaturated heterocyclyl, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^F$;

$R^F$ is H, $C_1$-$C_2$-alkyl, $C_3$-$C_6$-cycloalkyl, phenyl, benzyl, or C(═O) $NR^HR^I$;

$R^G$ is H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized;

with the proviso that at least one of the following conditions is met:

$R^2$ is $NR^CR^D$, $NR^CR^D$—$C_1$-$C_4$-alkyl, $NR^F$—($C_1$-$C_4$-alkylene)-$NR^CR^D$, O—($C_1$-$C_4$-alkylene)-$NR^CR^D$, and $R^C$ is H;

or $R^2$ is $NR^FC$(═O)$R^E$, wherein $R^E$ is $NR^CR^D$—$C_1$-$C_4$-alkyl, and $R^C$ is H;

or $R^N$ is $NHR^D$—$C_1$-$C_4$-alkyl;

or any one of the substituents $R^2$, $R^4$, or $R^5$ carries a substituent $R^X$, wherein $R^X$ is OH, $NHR^D$, $NHR^D$—$C_1$-$C_4$-alkyl, or HO—$C_1$-$C_4$-alkyl;

wherein a covalent bond between the compound of formula (I) and the linker $L^1$ is established by the reaction of a functional group of the compound of formula (I) with a functional group handle of the linker $L^1$; and wherein the functional group of the compound of formula (I) is attached to or part of the substituents $R^2$, $R^4$, $R^5$, or $R^N$ so that the linker $L^1$ is covalently bonded to the compound of formula (I) according to any one of the following structures:

(I-$R^2$-$L^1$)

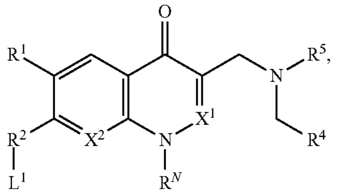

(I-$R^N$-$L^1$)

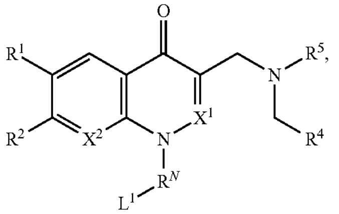

(I-$R^4$-$L^1$)

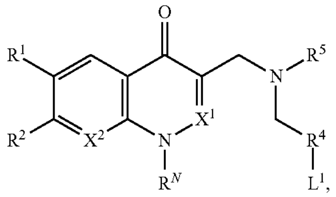

or (I-$R^5$-$L^1$)

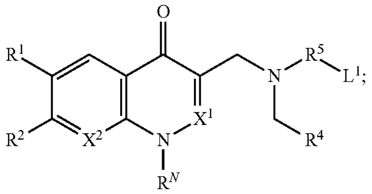

wherein the linker $L^1$ has the structure $H^{1A}$-$L^C$-$H^{1B}$;

$L^C$ is a chain of 2 to 100 atoms selected from carbon, nitrogen, oxygen, and sulfur atoms, which may be interrupted by 5- to 10-membered aryl and heteroaryl groups and/or 3- to 8-membered saturated carbocyclyl or heterocyclyl groups, wherein the aforementioned heteroaryl and heterocyclic groups comprise one or more, same or different heteroatoms selected from O, N or S, wherein said N- and/or S-atoms are independently oxidized or non-oxidized, and wherein each substitutable carbon or heteroatom in the chain is independently unsubstituted or substituted with one or more same or different substituents selected from halogen, OH, ═O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy;

$H^{1A}$ is a first functional group handle which is covalently bonded to the compound of formula (I); and $H^{1B}$ is a second functional group handle suitable for forming a covalent bond to a targeting moiety T.

20. The compound-linker construct of claim 19, wherein $R^2$ is H, Br, F, $C_1$, $NH_2$, ($R^2$-1)

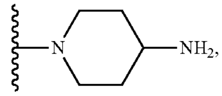

-continued
(R$^2$-2)
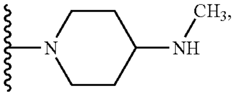
(R$^2$-3)
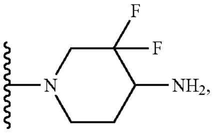
(R$^2$-4)
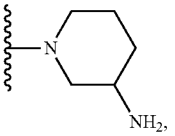
(R$^2$-5)
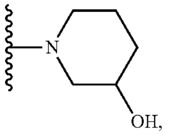
(R$^2$-6)
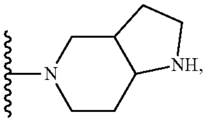
(R$^2$-7)
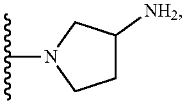
(R$^2$-8)
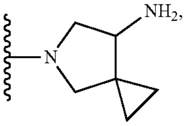
(R$^2$-9)
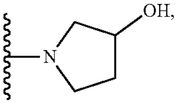
(R$^2$-10)
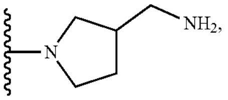
(R$^2$-11)
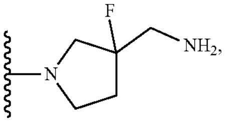
(R$^2$-12)
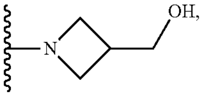
(R$^2$-13)
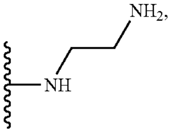
-continued
(R$^2$-14)
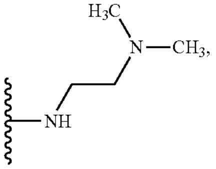
(R$^2$-15)
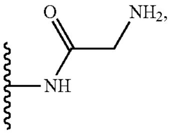
(R$^2$-16)
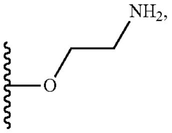
(R$^2$-17)
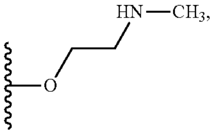
(R$^2$-18)
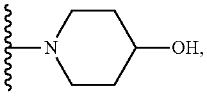
(R$^2$-19)
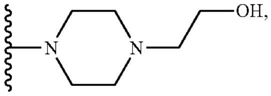
(R$^2$-20)
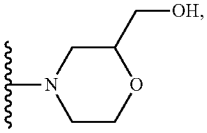
(R$^2$-21)
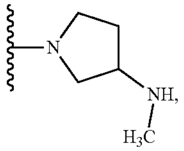
(R$^2$-22)
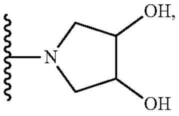
(R$^2$-23)
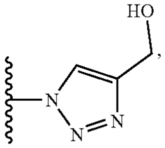
(R$^2$-24)
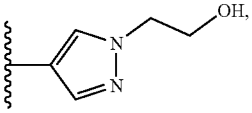

-continued (R$^2$-25)

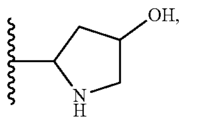

(R$^2$-26)

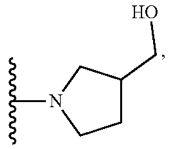

(R$^2$-27)

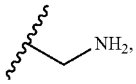

or (R$^2$-28)

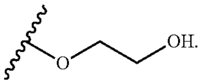

21. The compound-linker construct of claim 20, wherein $R^2$ is H, Br, F, $C_1$, or $NH_2$.

22. The compound-linker construct of claim 20, wherein $R^4$ is methylpyridinyl, aminopyridinyl or methoxypyridinyl.

23. The compound-linker construct of claim 22, or the salt, stereoisomer, tautomer, or N-oxide thereof, wherein $R^4$ is methylpyridinyl.

24. The compound-linker construct of claim 22, wherein $R^N$ is H, $C_1$-$C_4$-alkyl, HO(C═O)—$C_1$-$C_3$-alkyl, $NH_2$—$C_1$-$C_3$-alkyl, $C_1$-$C_2$-alkoxy-$C_1$-$C_3$-alkyl, or cyclopropyl.

25. The compound-linker construct of claim 24, or the salt, stereoisomer, tautomer, or N-oxide thereof, wherein $R^N$ is methyl or cyclopropyl.

26. The compound-linker construct of claim 24, wherein $R^5$ is selected from the group consisting of (R$^5$-1)

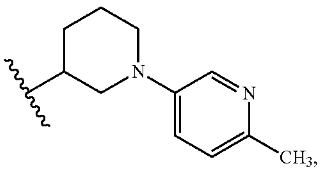

(R$^5$-2)

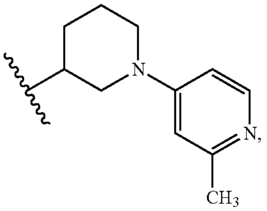

(R$^5$-3)

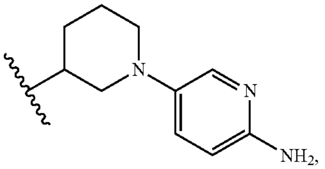

-continued (R$^5$-4)

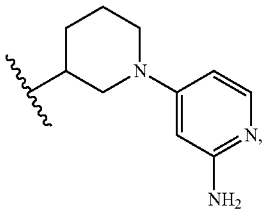

(R$^5$-5)

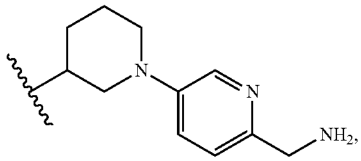

(R$^5$-6)

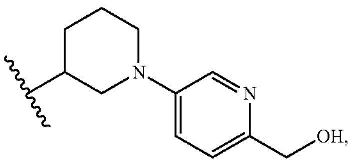

(R$^5$-8)

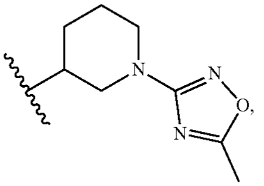

(R$^5$-10)

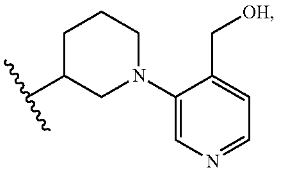

(R$^5$-11)

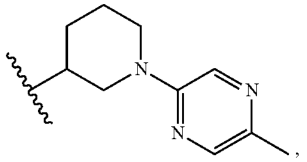

(R$^5$-12)

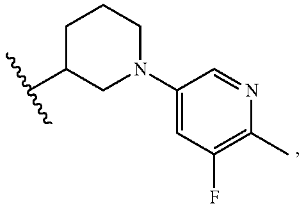

(R$^5$-13)

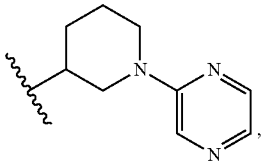

-continued
(R5-14)
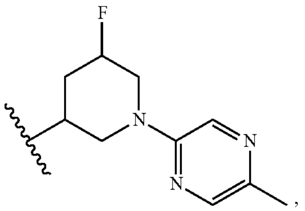
(R5-15)
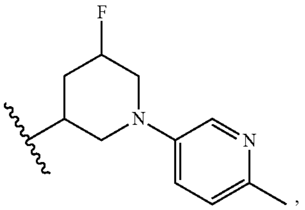
(R5-16)
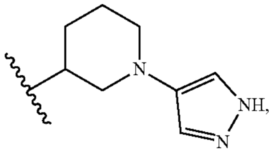
(R5-18)
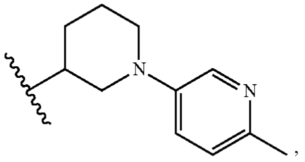
(R5-19)
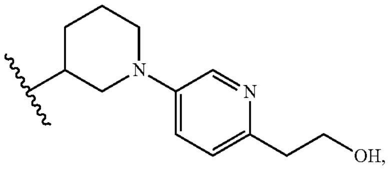
(R5-20)
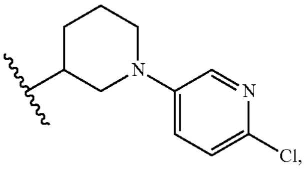
(R5-22)
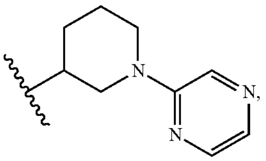
(R5-23)
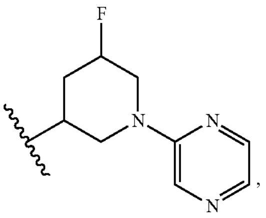
-continued
(R5-24)
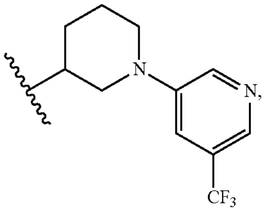
(R5-25)
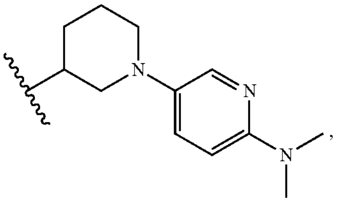
(R5-26)
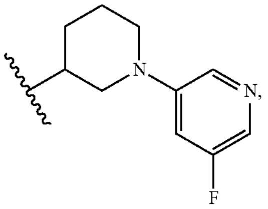
(R5-27)
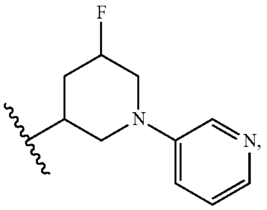
and
(R5-28)
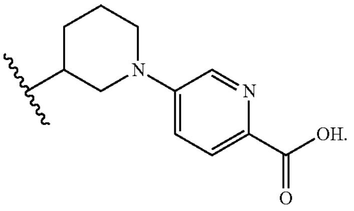
27. The compound-linker construct of claim 26, wherein $R^5$ is
(R5-3)
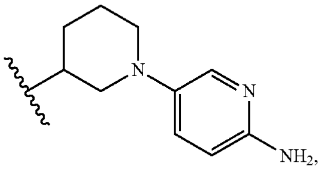

-continued
(R5-4)
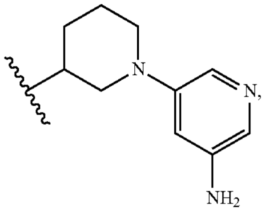
(R5-5)
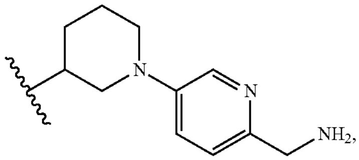
(R5-6)
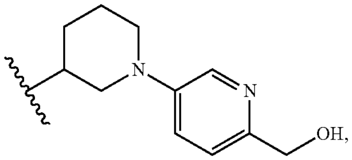
(R5-10)
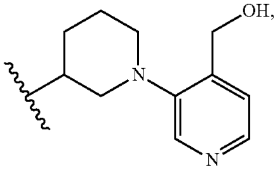
(R5-19)
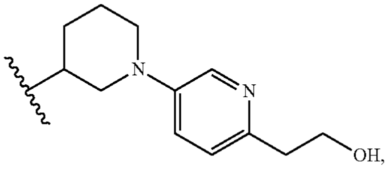
or
(R5-28)
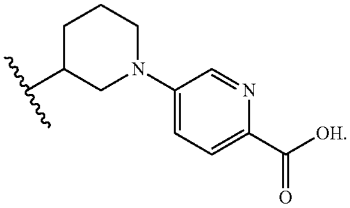
28. The compound-linker construct of claim 26, wherein the linker $L^1$ is selected from the group consisting of:
($L^1$-1)
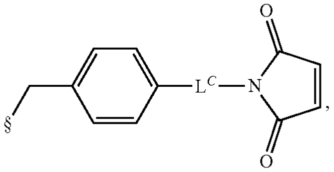
-continued
($L^1$-2)
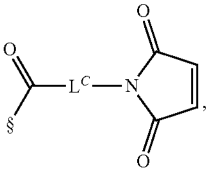
($L^1$-3)
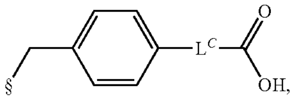
($L^1$-4)
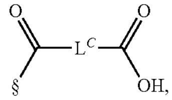
($L^1$-5)
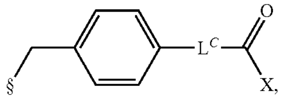
($L^1$-6)
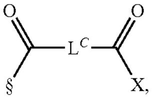
($L^1$-7)
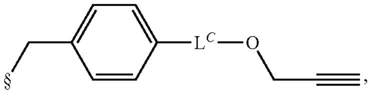
($L^1$-8)
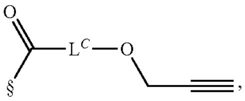
($L^1$-9)
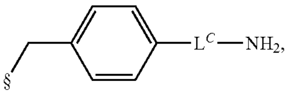
($L^1$-10)
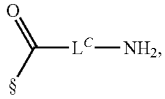
($L^1$-11)
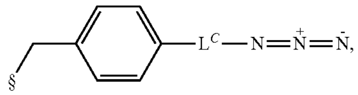
($L^1$-12)
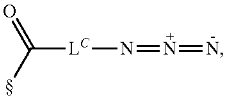
($L^1$-13)
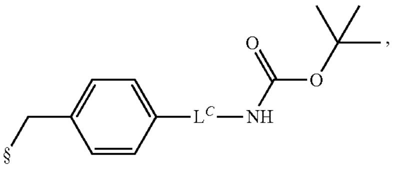

-continued ($L^1$-14)

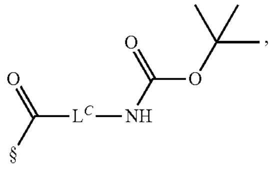

($L^1$-15)

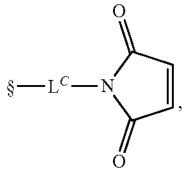

($L^1$-16)

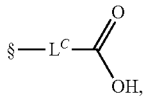

($L^1$-17)

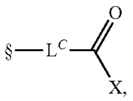

($L^1$-18)

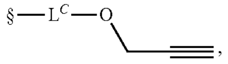

($L^1$-19)

§—$L^C$—$NH_2$, ($L^1$-20)

§—$L^C$—$N{=}\overset{+}{N}{=}\overset{-}{N}$, and ($L^1$-21)

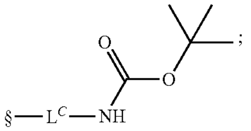

wherein $L^C$ is a chain $L^C$ of units selected from a linear or branched polyethylene glycol chain, a sequence of amino acids, and a linear or branched $C_1$-$C_{10}$-alkyl chain, wherein each substitutable carbon or heteroatom of the afore mentioned units may be unsubstituted or substituted with one or more, same or different substituents selected from halogen, OH, =O, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, and $C_1$-$C_6$-haloalkoxy; and § marks the connection to the compound of formula (I); and X represents a leaving group selected from (X-1)

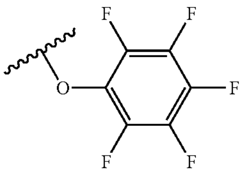

and (X-2)

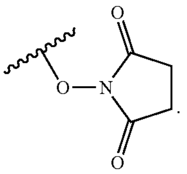

* * * * *